United States Patent
Cao et al.

(10) Patent No.: US 12,060,346 B2
(45) Date of Patent: *Aug. 13, 2024

(54) INHIBITORS OF APOL1 AND METHODS OF USING SAME

(71) Applicant: Vertex Pharmaceuticals Incorporated, Boston, MA (US)

(72) Inventors: Jingrong Cao, Newton, MA (US); Jon H. Come, Cambridge, MA (US); Leslie A. Dakin, Framingham, MA (US); Francois Denis, Boston, MA (US); Warren A. Dorsch, Waltham, MA (US); Anne Fortier, Jamaica Plain, MA (US); Martine Hamel, Boston, MA (US); Elaine B. Krueger, Milton, MA (US); Brian Ledford, Norton, MA (US); Suganthini S. Nanthakumar, Newton, MA (US); Olivier Nicolas, Montreal (CA); Camil Sayegh, Boston, MA (US); Timothy J. Senter, Arlington, MA (US); Tiansheng Wang, Concord, MA (US); Michael Brodney, Newton, MA (US); Kan-Nian Hu, Brighton, MA (US); Peter Rose, Littleton, MA (US); Kevin Gagnon, Burlington, MA (US); Yi Shi, Natick, MA (US); Muna Shrestha, Belmont, MA (US); Ales Medek, Winchester, MA (US); Faith Witkos, Attleboro, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/106,569

(22) Filed: Feb. 7, 2023

(65) Prior Publication Data

US 2023/0271945 A1 Aug. 31, 2023

Related U.S. Application Data

(62) Division of application No. 16/717,099, filed on Dec. 17, 2019, now Pat. No. 11,618,746.

(60) Provisional application No. 62/780,667, filed on Dec. 17, 2018.

(51) Int. Cl.
C07D 403/12 (2006.01)
C07D 405/14 (2006.01)

(52) U.S. Cl.
CPC ......... *C07D 403/12* (2013.01); *C07D 405/14* (2013.01); *C07B 2200/05* (2013.01); *C07B 2200/13* (2013.01)

(58) Field of Classification Search
CPC ............................ C07D 403/12; C07D 405/14
See application file for complete search history.

(56) References Cited

U.S. PATENT DOCUMENTS

| | | |
|---|---|---|
| 6,518,273 B1 | 2/2003 | Chapman et al. |
| 6,605,633 B1 | 8/2003 | Paquet et al. |
| 11,618,746 B2 | 4/2023 | Cao et al. |
| 11,801,234 B2 | 10/2023 | Mallalieu et al. |
| 11,866,446 B2 | 1/2024 | Ahn et al. |
| 2001/0039286 A1 | 11/2001 | Dinnell et al. |
| 2004/0006237 A1 | 1/2004 | Dolitzky et al. |
| 2004/0138287 A1 | 7/2004 | Barth et al. |
| 2005/0100902 A1 | 5/2005 | Barth et al. |
| 2008/0153861 A1 | 6/2008 | Bissantz et al. |
| 2008/0249128 A1 | 10/2008 | Oberboersch et al. |
| 2010/0317661 A1 | 12/2010 | Wang et al. |
| 2013/0237532 A1 | 9/2013 | Kim et al. |
| 2018/0118681 A1 | 5/2018 | Ross et al. |
| 2021/0246121 A1 | 8/2021 | Lai et al. |
| 2021/0275496 A1 | 9/2021 | Mallalieu et al. |
| 2022/0106327 A1 | 10/2022 | Ahn et al. |
| 2022/0340523 A1 | 10/2022 | Dakin et al. |
| 2023/0011118 A1 | 1/2023 | Dakin et al. |
| 2023/0014907 A1 | 1/2023 | Dakin et al. |
| 2023/0119114 A1 | 4/2023 | Daniel et al. |
| 2023/0201201 A1 | 6/2023 | Skorecki et al. |
| 2023/0203000 A1 | 6/2023 | Dakin et al. |
| 2023/0250087 A1 | 8/2023 | Gagnon et al. |
| 2023/0271945 A1 | 8/2023 | Cao et al. |

FOREIGN PATENT DOCUMENTS

| | | |
|---|---|---|
| EP | 0924209 A1 | 6/1999 |
| EP | 0934941 | 8/1999 |
| EP | 2905278 A1 | 8/2015 |
| FR | 2315272 A1 | 1/1977 |
| WO | WO 2001/017965 A2 | 3/2001 |
| WO | WO 2001/038305 A2 | 5/2001 |
| WO | WO 2002/028831 A1 | 4/2002 |

(Continued)

OTHER PUBLICATIONS

Balasubramanian, M. et al. (1970) "Studies on Conformation: Part X—Addition of Grignard Reagents to 4-Piperidones." *Indian J. Chem.*, vol. 8, May 1, 1970, pp. 420-422.

(Continued)

*Primary Examiner* — Deepak R Rao
(74) *Attorney, Agent, or Firm* — Finnegan, Henderson, Farabow, Garrett & Dunner LLP

(57) ABSTRACT

The disclosure provides at least one entity chosen from compounds of formula (I), solid state forms of the same, compositions comprising the same, and methods of using the same, including use in treating focal segmental glomerulosclerosis (FSGS) and/or non-diabetic kidney disease (NDKD).

53 Claims, 59 Drawing Sheets

(56) References Cited

FOREIGN PATENT DOCUMENTS

| | | |
|---|---|---|
| WO | WO 2002/092568 A1 | 11/2002 |
| WO | WO 2003/104180 A1 | 12/2003 |
| WO | WO 2004/058717 A1 | 7/2004 |
| WO | WO 2005/021505 A1 | 3/2005 |
| WO | WO 2005/115983 A1 | 4/2005 |
| WO | WO 2005/092854 A1 | 10/2005 |
| WO | WO 2007/061763 A2 | 5/2007 |
| WO | WO 2008/092231 A1 | 8/2008 |
| WO | WO 2008/155132 A1 | 12/2008 |
| WO | WO 2011/060035 A1 | 11/2010 |
| WO | WO 2011/060217 A1 | 11/2010 |
| WO | WO 2010/137351 A1 | 12/2010 |
| WO | WO 2012/025155 A1 | 3/2012 |
| WO | WO 2014/085154 A1 | 6/2014 |
| WO | WO 2015/048301 A1 | 4/2015 |
| WO | WO 2015/147639 A1 | 10/2015 |
| WO | WO 2016/055517 A1 | 4/2016 |
| WO | WO 2016/078770 A1 | 5/2016 |
| WO | WO 2017/033093 A1 | 3/2017 |
| WO | WO 2017/137334 A1 | 8/2017 |
| WO | WO 2019/213148 A1 | 11/2019 |
| WO | WO 2019/226611 A1 | 11/2019 |
| WO | WO 2020/131807 A1 | 6/2020 |
| WO | WO 2020/186220 A1 | 9/2020 |
| WO | WO 2021/216665 A1 | 4/2021 |
| WO | WO 2021/127337 A1 | 6/2021 |
| WO | WO 2021/154997 A1 | 8/2021 |
| WO | WO 2021/158666 A1 | 8/2021 |
| WO | WO 2021/178768 A1 | 9/2021 |
| WO | WO 2021/224927 A1 | 9/2021 |
| WO | WO 2021/220178 A1 | 11/2021 |
| WO | WO 2021/252849 A1 | 12/2021 |
| WO | WO 2021/252859 A1 | 12/2021 |
| WO | WO 2021/252863 A1 | 12/2021 |
| WO | WO 2022/047031 A1 | 3/2022 |
| WO | WO 2023/028237 A1 | 3/2023 |
| WO | WO 2023/101981 A1 | 6/2023 |
| WO | WO 2023/154309 A1 | 8/2023 |
| WO | WO 2023/154310 A1 | 8/2023 |
| WO | WO 2023/154314 A1 | 8/2023 |
| WO | WO 2023/154344 A1 | 8/2023 |

OTHER PUBLICATIONS

Bartolucci, S. et al. (2015), "Iridium-Catalyzed Direct Synthesis of Tryptamine Derivatives from Indoles: Exploiting N-Protected Amino Alcohols as Alkylating Agents," *J. Org. Chem*, 2015, 80, 3217-3222.

Campbell K.N., et al. (1949) "Studies on γ-Pyrones. II. Synthesis of 4-Piperidinols from Pyrones," J. Org. Chem. 15(2), 337-342.

Casy, A.F., et al. (1972) "Diastereoisomeric esters of 1,2-dimethyl-4-phenylpiperidin-4-ol and related compounds," J. Chem. Soc., Perkin Trans. 1, 726-731.

Casy, A.F. et al. (1976), "Reversed ester analogues of pethidine: isomeric 4-acetoxy-1,2,6-trimethyl-4-phenyrpiperidines." *JPP*, vol. 28, No. 2, pp. 106-110.

Database Registry (2002), Chembridge Corporation: 4-Piperidinol, 4-(2-methoxyphenyl)-1-methyl-2,6-diphenyl-II XP093022694, Database accession No. 471293-86-4 compound with Registry No. 471293-86-4.

Database Registry (2016), Aurora Fine Chemicals: "Piperidine, 4-[(I, 3-diethyl-IH-pyrazol-5-yl)methyl]-2, 6-dimethyl," XP093022702, Database accession No. 1993174-76-7 compounds with Registry Nos. 1993174-76-7, 1993166-16-7 and 1993166-02-1.

Database Registry (2018), Aurora Fine Chemicals: "4-Piperidinol, 1,2,6-trimethyl-4-(2-methylphenyl)-", XP093022693, Database accession No. 2182802-01-1 compound with Registry No. 2182802-01-1.

Database Registry (2021), "2'-Cyclopropyl-7,8-dihydro-6'-methylspiro [I,6-naphthyridine-5(6H), 4'-piperidine]," XP093024331, retrieved from STN Database accession No. 2645191-67-7 abstract.

Database Registry (2021), "2'-Cyclopropyl-6,7-dihydro-6,6'-dimethyls piro[I,7-naphthyridine-8(5H), 4'-piperidine]," XP093024335, retrieved from STN Database accession No. 2644543-73-5 abstract.

Database Registry (2021), Anonymous: "Name not yet assigned", XP093024338, retrieved from STN Database accession No. 2642534-36-7 abstract.

Database Registry (2021), Anonymous: "2'-Cyclopropyl-3,4-dihydro-6'-methylspiro [isoquinoline-1(2H),4'-piperidin]-7-ol," XP093024340, retrieved from STN Database accession No. 2631256-91-0 abstract.

Database Registry (2021), Anonymous: "2-Cyclopropyl-7',8'-dihydro-2', 6-dimethyl spiro[piperidine-4,5'(3'H)-pyrido[4,3-d]py rimidin]-4' (6'H)-one", XP093024343, retrieved from STN Database accession No. 2631119-41-8 abstract.

Database Registry (2021), Anonymous: "Name not yet assigned", XP093024344, retrieved from STN Database accession No. 2630494-88-9 abstract.

Database Registry (2021), Anonymous: "2'-Cyclopropyl-6,7-dihydro-6'-methylspiro [I,7-naphthyridine-8(5H), 4' piperidine]-6-methanol," XP093024346, retrieved from STN Database accession No. 2626788-69-8 abstract.

Database Registry (2021), Anonymous: "rel-(2'R,6'R)-3,4-Dihydro-7-methoxy-2',6'-dimethylspiro[2,6-naphthyridine1(2H), 4'-p iperidine]," XP093024348, retrieved from STN Database accession No. 2625380-27-8 abstract.

Database Registry (2021), Anonymous: "2'-Cyclopropyl-3,4-dihydro-3,6'-dimethyls piro[2,6-naphthyridine-1(2H), 4'piperidine]," XP093024352, retrieved from STN Database accession No. 2620609-98-3 abstract.

Database Registry (2021), Anonymous: "2'-Cyclopropyl-6,7-dihydro-6'-methylspiro [I,7-naphthyridine-8(5H), 4' piperidine]-5-methanol," XP093024350, retrieved from STN Database accession No. 2617381-98-1 abstract.

Database Registry (2011), Aurora Fine Chemicals: "Spiro[isobenzofuran-1(3H), 4'-piperidine]-3-carboxamide, N, N-dimethyl-1'-[(5-methyl-2-furanyl)methyl]-2,2,2-trifluoroacetate (1:1)", XP093038422, retrieved from STN Database accession No. 2649946-46-1 abstract.

Database Registry (2018), Aurora Fine Chemicals: "Spiro[isobenzofuran-1(3H), 4'-piperidine]-3-carboxamide, N, N-dimethyl-1'-[(5-methyl-2-furanyl)methy1)-, 2,2,2-trifluoroacetate (1:1)", XP093038441, retrieved from STN Database accesion No. 2185363-22-6 abstract.

Database Registry (2018), Aurora Fine Chemicals: "Spiro[isobenzofuran-1(3H),4'-piperidine]-3-carboxamide, N, N-dimethyl-1'-(2-thiazolylmethyl)-", XP093038443, retrieved from STN Database accession No. 2185335-69-5 abstract.

Database Registry (2018), Aurora Fine Chemicals: "Spiro[isobenzofuran-1(3H),4'-piperidine]-3-carboxamide, N, N-climethyl-1'-(3-thienylmethy1)-", XP093038444, retrieved from STN Database accession No. 2184532-71-4 abstract.

Database Registry (2018), Aurora Fine Chemicals: "Spiro[isobenzofuran-1(3H),4'-piperidine]-3-carboxamide, N, N-climethy1-1'-[(1-methy1-1H-imidazo1-2-yl) methyl]-", XP093038484, retrieved from Database accession No. 2182642-77-7.

Dummer, P.D. et al. (2015), "APOL1 kidney disease risk variants—an evolving landscape," *Semin Nephrol.* 35(3):222-236. HHS Public Access Author Manuscript; available in PMC May 1, 2016 (25 pages).

Harish, B. et al. (2017) "N-Heterocyclic carbene (NHC)-catalysed atom economical construction of 2,3-disubstituted indoles," *Chem. Commun*, 2017, 53, 3338-3341.

Harper N.J. et al. (1960) "Some isomeric hydroxypiperidines." J. Am. Chem. Soc., Jan. 1, 1960, pp. 2704-2711.

Harriman, G.C.B., et al. (2000) "Synthesis of 4-substituted 4-arylpiperidines," Tet. Lett. 41(46), 8853-8856.

Jones, A.J. et al. (1973), "Carbon-13 Magnetic Resonance: the Stereochemistry of 1,2- and 1,3-Dimethyl-4-phenylpiperidine Derivatives." Can. J. Chem., vol. 41, No. 11, pp. 1782-1789.

Kagabu, S. et al. (2009), "N-Thiophenylethyl-2,2-dichloro-1-cyclopropanecarboxamides: modification of the amide part of carpropamid and examination of fungicidal activity," J. Pestic. Sci. 34(3) 161-172.

(56) References Cited

OTHER PUBLICATIONS

Kozikowski, A.P. et al. (1993), "Chemistry, binding affinities, and behavioral properties of a new class of "antineophobic" mitochondrial DBI receptor complex (mDRC) ligands," *J. Med. Chem.* 36(20):2908-2920.
Lennox, A. (2018) "Electrochemical Aminoxyl-Mediated α-Cyanation of Secondary Piperidines for Pharmaceutical Building Block Diversification" J. Am. Chem. Soc. 140, 11227-11231.
Lin, J. et al. (2021), "Oncogene APOL1 promotes proliferation and inhibits apoptosis via activating NOTCH1 signaling pathway in pancreatic cancer," *Cell Death and Disease* 12:760 (11 pages).
Manimekalai, A. et al. (2007), "Benzyl group conformation in 4-benzyl-4-hydroxypiperidines," *J. Struct. Chem.*, vol. 48, No. 6, pp. 1036-1045.
Meyers, A.L. et al. (1985), "alpha.-Amino carbanions. Preparation, metalation, and alkylation of enamidines. Synthesis of piperidine and pyrrolidine natural products and homologation of carbonyl compounds," *J. Org. Chem.*, vol. 50, No. 7, pp. 1019-1026.
Nitta, A. et al. (2008) "(3R)-3-Amino-4-(2,4,5-trifluorophenyl)-N-{4-[6-(2-methoxyethoxy)benzothiazol-2-yl]tetrahydropyran-4-yl}butanamide as a potent dipeptidyl peptidase IV inhibitor for the treatment of type 2 diabetes," Bioorg. Med. Chem. Lett. 18(2008), 5435-5438.
Nitta, A. et al. (2012) "Pyrrolidinyl phenylurea derivatives as novel CCR3 antagonists," Bioorg. Med. Chem. Lett. 22(2012), 6876-6881.
Pedregal, A. et al. (2012) "Development of LC-MS/MS-Based Receptor Occupancy Tracers and Positron Emission Tomography Radioligands for the Nociceptin/Orphanin FQ (NOP) Receptor," J. Med. Chem. 55, 4955-4967.
Prostakov, N.S. et al. (1975) "Synthesis of 3-Alkyl-2, 4, 6-Triphenylpyridines and 1, 3-Diphenyl-4- and -2-Azafluorenes." Chem Heterocycl Compd, vol. 11, pp. 971-975.
Takai, K. et al., (2014) "Discovery of N-substituted 7-azaindoline derivatives as potent, orally available M1 and M4 muscarinic acetylcholine receptors selective agonist," Bioorg. Med. Chem. Lett. 24(2014), 3189-3193.
Takasawa, R. et al. (2011), "Discovery of a new type inhibitor of human glyoxalase I by myricetin-based 4-point pharmacophore," *Bioorganic Med. Chem. Lett.* 21:4337-4342.
Trotter, B.W. et al. (2001) "2-Arylindole-3-acetamides: FPP-Competitive Inhibitors of Farnesyl Protein Transferase," Bioorg. Med. Chem. Lett. 11(2001) 865-869.
Turnu, F. et al. (2019) "Catalytic Tandem Friedel-Crafts Alkylation/C4-C3 Ring-Contraction Reaction: An Efficient Route for the Synthesis of Indolyl Cyclopropanecarbaldehydes and Ketones," *Org. Lett.* 21:7329-7332, (4 pages).
U.S. Appl. No. 17/923,508, filed Nov. 11, 2022 by Skorecki, et al.
U.S. Appl. No. 18/001,371, filed Dec. 9, 2022 by Gagnon, et al.
U.S. Appl. No. 18/071,153, filed Nov. 29, 2022, by Dakin et. al.
Vajgel, G. et al. (2020), "A single APOL1 nephropathy variant increases risk of advanced lupus nephritis in Brazilians," *J Rheumatol.* 47(8):1209-1217. HHS Public Access Author Manuscript; available in PMC Aug. 1, 2021 (18 pages).
Van Wijngaarden, I. et al. (1987) "2-Phenylpyrroles as conformationally restricted benzamide analogs. A new class of potential antipsychotics," J. Med. Chem. 30(11), 2099-2104.
Valles, D.A. et al. (2021), "[alpha], [alpha]-C—H Bond Difunctionalization of Unprotected Alicyclic Amines," *Org. Lett.*, vol. 23, No. 16, pp. 6367-6371.
*Vertex Announces Positive Results From Phase 2 Study of VX-147 in APOL1-Mediated Focal Segmental Glomerulosclerosis*, Vertex (Dec. 1, 2021), https://news.vrtx.com/press-release/vertex-announces-positive-results-phase-2-study-vx-147-apol1-mediated-focal-segmental (6 pages).
Winters, M.P. et al. (2008), "Carboxylic acid bioisosteres acylsulfonamides, acylsulfamides, and sulfonylureas as novel antagonists of the CXCR2 receptor," *Bioorganic Med. Chem. Lett.* 18:1926-1930.
CAplus Registry No. RN 847480-40-4.
Horner, et al. DE 1266763 (abstract) retrieved from STN Accession No. 1968:506703, CAPLUS, Apr. 25, 1968.
International Search Report and Written Opinion for International Application No. PCT/US2019/066746, mailed Mar. 9, 2020 (11 pages).
Johansson, H. et al. (2013), "3-Substituted 2-phenyl-indoles: privileged structures for medicinal chemistry" RSC Adv, 3, 945-960.
U.S. Appl. No. 18/106,569, filed Feb. 7, 2023, by Dakin et. al.
Kang H. et al. (2018), "Potent aromatase inhibitors and molecular mechanism of inhibitory action," European Journal of Medicinal Chemistry, 143, 426-437.
Naik M. et al. (2014), "2-Phenylindole and arylsulfonamide: novel scaffolds bactericidal against *Mycobacterium tuberculosis*" ACS Med. Chem. Lett. 2014, 5, 9, 1005-1009.
Shaw D. et al. (2001), "2-Aryl Indole NK1 Antagonists: Optimisation of the Amide Substituent," Bioorg. Med. Chem. Lett., 11, 3031-3034.
U.S. Appl. No. 18/504,559, filed Nov. 8, 2023.
Zhang, G.-N. et al. (2019), "An Efficient Synthesis of N-Aryl-2-(Indol-3-yl)-Acetamides via Multi-Component Reactions," Heterocycles, 98(4), 535-543.
Brittain H. G. et al., (2001) "X-Ray Diffraction III: Pharmaceutical Applications of X-ray Powder Diffraction," Spectroscopy, 16(7), pp. 14-18.
Joshi, K.C. et al. (1978), "Synthesis and CNS Activity of Some Fluorine Containing 3-Indolylglyoxamides and Tryptamines" Agric. Biol. Chem., 42(9), pp. 1723-1726.
Notice of Allowance and Fee(s) Due for U.S. Appl. No. 17/161,474, mailed Mar. 5, 2024, Examiner Samantha L Shterengarts.
The United States Pharmacopeia, Jan. 1, 1995, 23rd Revision, USP 23/NF 18, General Chapter on X-ray diffraction, pp. 1843-1844.

INHIBITORS OF APOL1 AND METHODS OF USING SAME

This application is a divisional of U.S. application Ser. No. 16/717,099, filed on Dec. 17, 2019, which claims the benefit of U.S. Provisional Application No. 62/780,667, filed on Dec. 17, 2018, the contents of which are incorporated herein by reference in their entirety.

This disclosure provides compounds that may inhibit apolipoprotein L1 (APOL1) and methods of using those compounds to treat focal segmental glomerulosclerosis (FSGS) and/or non-diabetic kidney disease (NDKD). In some embodiments, the FSGS and/or NDKD is associated with at least one of the 2 common APOL1 genetic variants (G1: S342G:I384 M and G2: N388del:Y389del).

FSGS is a disease of the podocyte (glomerular visceral epithelial cells) responsible for proteinuria and progressive decline in kidney function. NDKD is a disease characterized by hypertension and progressive decline in kidney function. Human genetics support a causal role for the G1 and G2 APOL1 variants in inducing kidney disease. Individuals with 2 APOL1 risk alleles are at increased risk of developing primary (idiopathic) FSGS, human immunodeficiency virus (HIV)-associated FSGS, and NDKD. Currently, FSGS and NDKD are managed with symptomatic treatment (including blood pressure control using blockers of the renin angiotensin system), and patients with FSGS and heavy proteinuria may be offered high dose steroids. Corticosteroids induce remission in a minority of patients and are associated with numerous side effects. These patients, in particular individuals of recent sub-Saharan African ancestry with 2 APOL1 risk alleles, experience rapid disease progression leading to end-stage renal disease (ESRD). Thus, there is an unmet medical need for treatment for FSGS and NDKD.

One aspect of the disclosure provides at least one entity chosen from compounds of Formulae (I), (II), (IIIa), (IIIb), and (IIIc), pharmaceutically acceptable salts of any of those compounds, solvates of any of the foregoing, and deuterated derivatives of any of the foregoing, which can be employed in the treatment of diseases mediated by APOL1, such as FSGS and NDKD. For example, the at least one entity can be chosen from compounds of Formula (I):

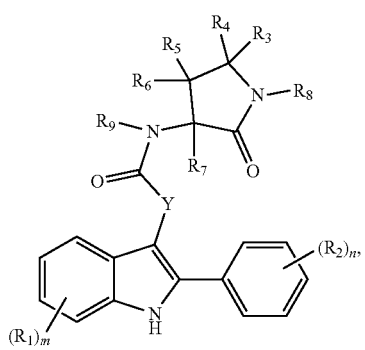

(I)

wherein:
(i) each $R_1$ is independently chosen from
halogen groups,
hydroxy,
thiol,
amino,
cyano,
—OC(O)$C_1$-$C_6$ linear, branched, and cyclic alkyl groups,
—C(O)O$C_1$-$C_6$ linear, branched, and cyclic alkyl groups,
—NHC(O)$C_1$-$C_6$ linear, branched, and cyclic alkyl groups,
—C(O)NH$C_1$-$C_6$ linear, branched, and cyclic alkyl groups,
—NHC(O)aryl groups,
—C(O)NHaryl groups,
—NHC(O)heteroaryl groups,
—C(O)NHheteroaryl groups,
—NHS(O)$_2$$C_1$-$C_6$ linear, branched, and cyclic alkyl groups,
—S(O)$_2$NH$C_1$-$C_6$ linear, branched, and cyclic alkyl groups,
—NHS(O)$_2$aryl groups,
—S(O)$_2$NHaryl groups,
—NHS(O)$_2$heteroaryl groups,
—S(O)$_2$NHheteroaryl groups,
—NHC(O)NH$C_1$-$C_6$ linear, branched, and cyclic alkyl groups,
—NHC(O)NHaryl groups,
—NHC(O)NHheteroaryl groups,
$C_1$-$C_6$ linear, branched, and cyclic alkyl groups,
$C_2$-$C_6$ linear, branched, and cyclic alkenyl groups,
$C_1$-$C_6$ linear, branched, and cyclic hydroxyalkyl groups,
$C_1$-$C_6$ linear, branched, and cyclic alkoxy groups,
$C_1$-$C_6$ linear, branched, and cyclic thioalkyl groups,
$C_1$-$C_6$ linear, branched, and cyclic haloalkyl groups,
$C_1$-$C_6$ linear, branched, and cyclic haloaminoalkyl groups,
$C_1$-$C_6$ linear, branched, and cyclic halothioalkyl groups,
$C_1$-$C_6$ linear, branched, and cyclic haloalkoxy groups,
benzyloxy, benzylamino, or benzylthio groups,
3 to 6-membered heterocycloalkenyl groups,
3 to 6-membered heterocycloalkyl groups, and
5 and 6-membered heteroaryl groups; or
two $R_1$ groups, together with the carbon atoms to which they are attached, form a $C_4$-$C_8$ cycloalkyl group, an aryl group, or a heteroaryl group;
(ii) each $R_2$ is independently chosen from
halogen groups,
hydroxy,
thiol,
amino,
cyano,
—NHC(O)$C_1$-$C_6$ linear, branched, and cyclic alkyl groups,
—C(O)NH$C_1$-$C_6$ linear, branched, and cyclic alkyl groups,
—NHC(O)aryl groups,
—C(O)NHaryl groups,
—NHC(O)heteroaryl groups,
—C(O)NHheteroaryl groups,
—NHS(O)$_2$$C_1$-$C_6$ linear, branched, and cyclic alkyl groups,
—S(O)$_2$NH$C_1$-$C_6$ linear, branched, and cyclic alkyl groups,
—NHS(O)$_2$aryl groups,
—S(O)$_2$NHaryl groups,
—NHS(O)$_2$heteroaryl groups,
—S(O)$_2$NHheteroaryl groups,
—NHC(O)NH$C_1$-$C_4$ linear, branched, and cyclic alkyl groups, —NHC(O)NH aryl groups,
—NHC(O)NH heteroaryl groups,
$C_1$-$C_4$ linear, branched, and cyclic alkyl groups,
$C_2$-$C_4$ linear, branched, and cyclic alkenyl groups,
$C_1$-$C_4$ linear, branched, and cyclic hydroxyalkyl groups,
$C_1$-$C_4$ linear, branched, and cyclic alkoxy groups,
$C_1$-$C_4$ linear, branched, and cyclic thioalkyl groups,
$C_1$-$C_4$ linear, branched, and cyclic haloalkyl groups,
$C_1$-$C_4$ linear, branched, and cyclic haloaminoalkyl groups,
$C_1$-$C_4$ linear, branched, and cyclic halothioalkyl groups, and
$C_1$-$C_4$ linear, branched, and cyclic haloalkoxy groups;
(iii) m is chosen from 0, 1, 2, 3, and 4;
(iv) n is chosen from 0, 1, 2, 3, 4, and 5;
(v) Y is chosen from divalent $C_1$-$C_8$ linear and branched alkyl groups, divalent $C_1$-$C_8$ linear and branched alkoxy groups, divalent $C_1$-$C_8$ linear and branched aminoalkyl groups, and divalent $C_1$-$C_8$ linear and branched thioalkyl groups, wherein the divalent alkyl groups, divalent alkoxy groups, divalent aminoalkyl groups, and divalent thioalkyl groups are optionally substituted with at least one group chosen from
$C_1$-$C_6$ alkyl groups,
aryl groups,
heteroaryl groups,
halogen groups,
hydroxy, and
amino;
(vi) each of $R_3$ and $R_4$ is independently chosen from
hydrogen,
hydroxy,
thiol,
amino,
halogen groups,
$C_1$-$C_6$ linear, branched, and cyclic hydroxyalkyl groups,
$C_1$-$C_6$ linear, branched, and cyclic alkoxy groups,
$C_1$-$C_6$ linear, branched, and cyclic thioalkyl groups,
$C_1$-$C_6$ linear, branched, and cyclic haloalkyl groups,
$C_1$-$C_6$ linear, branched, and cyclic haloaminoalkyl groups,
$C_1$-$C_6$ linear, branched, and cyclic halothioalkyl groups,
$C_1$-$C_6$ linear, branched, and cyclic haloalkoxy groups, or
$R_3$ and $R_4$, together with the carbon atom to which they are attached, form a $C_3$-$C_6$ cycloalkyl group or carbonyl group;
(vii) each of $R_5$ and $R_6$ is independently chosen from
hydrogen,
thiol,
amino,
halogen groups,
hydroxy,
$C_1$-$C_6$ linear, branched, and cyclic hydroxyalkyl groups,
$C_1$-$C_6$ linear, branched, and cyclic alkoxy groups,
$C_1$-$C_6$ linear, branched, and cyclic thioalkyl groups,
$C_1$-$C_6$ linear, branched, and cyclic haloalkyl groups,
$C_1$-$C_6$ linear, branched, and cyclic haloaminoalkyl groups,
$C_1$-$C_6$ linear, branched, and cyclic halothioalkyl groups,
$C_1$-$C_6$ linear, branched, and cyclic haloalkoxy groups,
—OC(O)$C_1$-$C_6$ linear, branched, and cyclic alkyl groups,
—C(O)O$C_1$-$C_6$ linear, branched, and cyclic alkyl groups,
—NHC(O)$C_1$-$C_6$ linear, branched, and cyclic alkyl groups,
—C(O)NH$C_1$-$C_6$ linear, branched, and cyclic alkyl groups,
—NHC(O)aryl groups,
—C(O)NHaryl groups,
—NHC(O)heteroaryl groups,
—C(O)NHheteroaryl groups,
—NHS(O)$_2$$C_1$-$C_6$ linear, branched, and cyclic alkyl groups,
—S(O)$_2$NH$C_1$-$C_6$ linear, branched, and cyclic alkyl groups,
—NHS(O)$_2$aryl groups,
—S(O)$_2$NHaryl groups,
—NHS(O)$_2$heteroaryl groups,
—S(O)$_2$NHheteroaryl groups,
—NHC(O)NH$C_1$-$C_6$ linear, branched, and cyclic alkyl groups,
—NHC(O)NH aryl groups, and
—NHC(O)NH heteroaryl groups;
(viii) each of $R_7$, $R_8$, and $R_9$ is independently chosen from
hydrogen,
$C_1$-$C_6$ linear, branched, and cyclic alkyl groups,
$C_1$-$C_6$ linear, branched, and cyclic hydroxyalkyl groups,
$C_1$-$C_6$ linear, branched, and cyclic alkoxy groups,
$C_1$-$C_6$ linear, branched, and cyclic thioalkyl groups,
$C_1$-$C_6$ linear, branched, and cyclic haloalkyl groups,
$C_1$-$C_6$ linear, branched, and cyclic haloaminoalkyl groups,
$C_1$-$C_6$ linear, branched, and cyclic halothioalkyl groups, and
$C_1$-$C_6$ linear, branched, and cyclic haloalkoxy groups.

In one aspect of the disclosure, the compounds of Formula I can be chosen from compounds of Formula (I):
wherein:
(i) each $R_1$ is independently chosen from
halogen groups,
hydroxy,
cyano,
$C_1$-$C_4$ linear, branched, and cyclic alkyl groups,
$C_2$-$C_4$ linear, branched, and cyclic alkenyl groups,
$C_1$-$C_4$ linear, branched, and cyclic hydroxyalkyl groups,
$C_1$-$C_4$ linear, branched, and cyclic alkoxy groups,
$C_1$-$C_4$ linear, branched, and cyclic haloalkyl groups,
$C_1$-$C_4$ linear, branched, and cyclic haloalkoxy groups,
benzyloxy groups,
3 to 6-membered heterocycloalkenyl groups,
3 to 6-membered heterocycloalkyl groups, and
5 and 6-membered heteroaryl groups;
(ii) each $R_2$ is independently chosen from
halogen groups,
cyano,
$C_1$-$C_4$ linear, branched, and cyclic alkoxy groups,
$C_1$-$C_4$ linear, branched, and cyclic haloalkoxy groups,
$C_1$-$C_4$ linear, branched, and cyclic alkyl groups, and
$C_1$-$C_4$ linear, branched, and cyclic haloalkyl groups;
(iii) m is chosen from 0 to 4;
(iv) n is chosen from 0 to 5;

(v) Y is chosen from divalent $C_1$-$C_8$ linear and branched alkyl groups, wherein the divalent alkyl groups are optionally substituted with at least one group chosen from
$C_1$-$C_4$ alkyl groups,
halogen groups, and
hydroxy;
(vi) each of $R_3$ and $R_4$ is independently chosen from
hydrogen,
$C_1$-$C_3$ linear, branched, and cyclic alkyl groups,
$C_1$-$C_3$ linear, branched, and cyclic hydroxyalkyl groups, and
$C_1$-$C_3$ linear, branched, and cyclic haloalkyl groups, or
$R_3$ and $R_4$, together with the carbon atom to which they are attached, form a $C_3$-$C_6$ cycloalkyl group or carbonyl group;
(vii) each of $R_5$ and $R_6$ is independently chosen from
hydrogen,
hydroxy,
$C_1$-$C_4$ linear, branched, and cyclic alkyl groups,
$C_1$-$C_4$ linear, branched, and cyclic haloalkyl groups, and
—OC(O)$C_1$-$C_4$ linear, branched, and cyclic alkyl groups; and
(viii) each of $R_7$, $R_8$, and $R_9$ is independently chosen from
hydrogen,
$C_1$-$C_4$ linear, branched, and cyclic alkyl groups, and
$C_1$-$C_4$ linear, branched, and cyclic haloalkyl groups.

In one aspect of the disclosure, the compounds of Formula I are chosen from Compounds 1 to 135 such that the at least one entity is chosen from Compounds 1 to 135, pharmaceutically acceptable salts of any of those compounds, solvates of any of the foregoing, and deuterated derivatives of any of the foregoing.

In some embodiments, the disclosure provides pharmaceutical compositions comprising at least one entity chosen from compounds of Formulae (I), (II), (IIIa), (IIIb), and (IIIc), pharmaceutically acceptable salts of any of those compounds, solvates of any of the foregoing, and deuterated derivatives of any of the foregoing. In some embodiments, the pharmaceutical compositions may comprise at least one compound chosen from Compounds 1 to 135, pharmaceutically acceptable salts of any of those compounds, solvates of any of the foregoing, and deuterated derivatives of any of the foregoing. These compositions may further include at least one additional active pharmaceutical ingredient and/or at least one carrier.

Another aspect of the disclosure provides methods of treating FSGS and/or NDKD comprising administering to a subject in need thereof, at least one entity chosen from compounds of Formulae (I), (II), (IIIa), (IIIb), and (IIIc), pharmaceutically acceptable salts of any of those compounds, solvates of any of the foregoing, and deuterated derivatives of any of the foregoing or a pharmaceutical composition comprising the at least one entity. In some embodiments, the methods comprise administering at least one entity chosen from Compounds 1 to 135, pharmaceutically acceptable salts of any of those compounds, solvates of any of the foregoing, and deuterated derivatives of any of the foregoing.

In some embodiments, the methods of treatment include administration of at least one additional active agent to the subject in need thereof, either in the same pharmaceutical composition as the at least one entity chosen from compounds of Formulae (I), (II), (IIIa), (IIIb), and (IIIc), pharmaceutically acceptable salts of any of those compounds, solvates of any of the foregoing, and deuterated derivatives of any of the foregoing, or as separate compositions. In some embodiments, the methods comprise administering at least one entity chosen from Compounds 1 to 135, pharmaceutically acceptable salts of any of those compounds, solvates of any of the foregoing, and deuterated derivatives of any of the foregoing with at least one additional active agent either in the same pharmaceutical composition or in a separate composition.

Also provided are methods of inhibiting APOL1, comprising administering to a subject in need thereof, at least one entity chosen from compounds of Formulae (I), (II), (IIIa), (IIIb), and (IIIc), pharmaceutically acceptable salts of any of those compounds, solvates of any of the foregoing, and deuterated derivatives of any of the foregoing or a pharmaceutical composition comprising the at least one entity. In some embodiments, the methods of inhibiting APOL1 comprise administering at least one entity chosen from Compounds 1 to 135, pharmaceutically acceptable salts of any of those compounds, solvates of any of the foregoing, and deuterated derivatives of any of the foregoing or a pharmaceutical composition comprising the at least one entity.

DEFINITIONS

Figure 1:
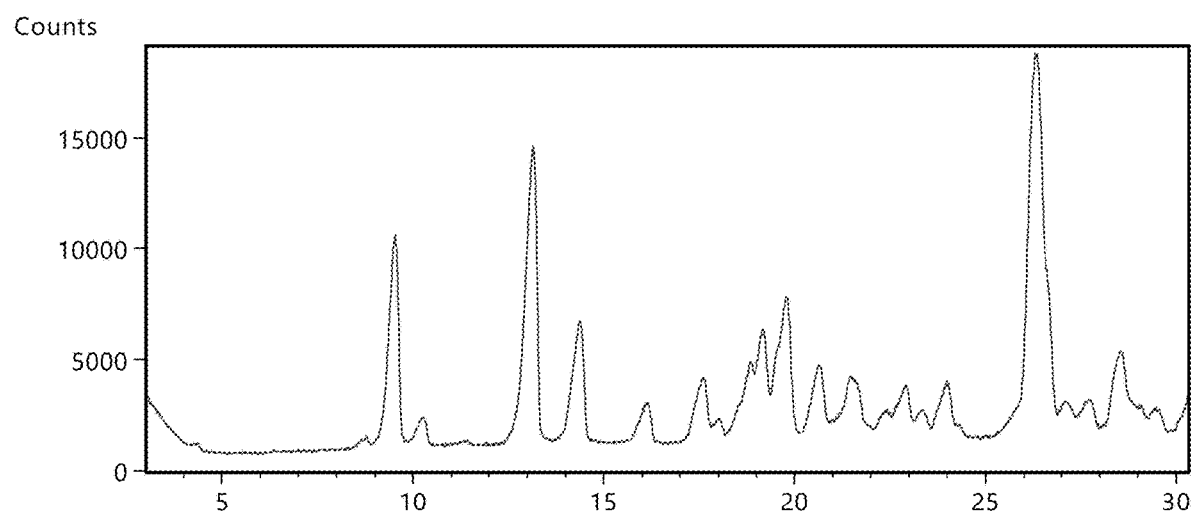
FIG. 1 depicts an XRPD diffractogram of Form A of Compound 2.

The term "APOL1" as used herein means apolipoprotein L1 protein and the term "APOL1" means apolipoprotein L1 gene.

The term "FSGS" as used herein means focal segmental glomerulosclerosis, which is a disease of the podocyte (glomerular visceral epithelial cells) responsible for proteinuria and progressive decline in kidney function, and associated with 2 common APOL1 genetic variants (G1: S342G: I384 M and G2: N388del:Y389del).

The term "NDKD" as used herein means non-diabetic kidney disease, which is characterized by severe hypertension and progressive decline in kidney function, and associated with 2 common APOL1 genetic variants (G1: S342G: I384 M and G2: N388del:Y389del).

The term "compound," when referring to a compound of this disclosure, refers to a collection of molecules having an identical chemical structure unless otherwise indicated as a collection of stereoisomers (for example, a collection of racemates, a collection of cis/trans stereoisomers, or a collection of (E) and (Z) stereoisomers), except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this disclosure will depend upon a number of factors including the isotopic purity of reagents used to make the compound and the efficiency of incorporation of isotopes in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

As used herein, "optionally substituted" is interchangeable with the phrase "substituted or unsubstituted." In general, the term "substituted", whether preceded by the term "optionally" or not, refers to the replacement of hydrogen radicals in a given structure with the radical of a specified substituent. Unless otherwise indicated, an "optionally substituted" group may have a substituent at each substitutable position of the group, and when more than one position in any given structure may be substituted with more than one substituent chosen from a specified group, the substituent may be either the same or different at every position. Combinations of substituents envisioned by this disclosure are those that result in the formation of stable or chemically feasible compounds.

The term "isotopologue" refers to a species in which the chemical structure differs from only in the isotopic composition thereof. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$ or $^{14}C$ are within the scope of this disclosure.

Unless otherwise indicated, structures depicted herein are also meant to include all isomeric forms of the structure, e.g., racemic mixtures, cis/trans isomers, geometric (or conformational) isomers, such as (Z) and (E) double bond isomers, and (Z) and (E) conformational isomers. Therefore, geometric and conformational mixtures of the present compounds are within the scope of the disclosure. Unless otherwise stated, all tautomeric forms of the compounds of the disclosure are within the scope of the disclosure.

The term "tautomer," as used herein, refers to one of two or more isomers of compound that exist together in equilibrium, and are readily interchanged by migration of an atom, e.g., a hydrogen atom, or group within the molecule.

"Stereoisomer" as used herein refers to enantiomers and diastereomers.

As used herein, "deuterated derivative" refers to a compound having the same chemical structure as a reference compound, but with one or more hydrogen atoms replaced by a deuterium atom ("D" or "$^2H$"). It will be recognized that some variation of natural isotopic abundance occurs in a synthesized compound depending on the origin of chemical materials used in the synthesis. The concentration of naturally abundant stable hydrogen isotopes, notwithstanding this variation is small and immaterial as compared to the degree of stable isotopic substitution of deuterated derivatives described herein. Thus, unless otherwise stated, when a reference is made to a "deuterated derivative" of compound of the disclosure, at least one hydrogen is replaced with deuterium at well above its natural isotopic abundance (which is typically about 0.015%). In some embodiments, the deuterated derivatives of the disclosure have an isotopic enrichment factor for each deuterium atom, of at least 3500 (52.5% deuterium incorporation at each designated deuterium) at least 4500, (67.5% deuterium incorporation), at least 5000 (75% deuterium incorporation) at least 5500 (82.5% deuterium incorporation), at least 6000 (90% deuterium incorporation), at least 6333.3 (95% deuterium incorporation, at least 6466.7 (97% deuterium incorporation, or at least 6600 (99% deuterium incorporation).

The term "isotopic enrichment factor" as used herein means the ratio between the isotopic abundance and the natural abundance of a specified isotope.

The term "alkyl" or "aliphatic" as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic that has a single point of attachment to the rest of the molecule. Unless otherwise specified, alkyl groups contain 1 to 20 alkyl carbon atoms. In some embodiments, alkyl groups contain 1 to 10 aliphatic carbon atoms. In some embodiments, alkyl groups contain 1 to 8 aliphatic carbon atoms. In some embodiments, alkyl groups contain 1 to 6 alkyl carbon atoms, and in some embodiments, alkyl groups contain 1 to 4 alkyl carbon atoms, and in yet other embodiments alkyl groups contain 1 to 3 alkyl carbon atoms. Nonlimiting examples of alkyl groups include, but are not limited to, linear or branched, and substituted or unsubstituted alkyl. Suitable cycloaliphatic groups include cycloalkyl, bicyclic cycloalkyl (e.g., decalin), bridged bicycloalkyl such as norbornyl or [2.2.2]bicyclo-octyl, or bridged tricyclic such as adamantyl. In some embodiments, alkyl groups are substituted. In some embodiments, alkyl groups are unsubstituted. In some embodiments, alkyl groups are straight-chain. In some embodiments, alkyl groups are branched.

The terms "cycloalkyl," "carbocycle," "cycloaliphatic," or "cyclic alkyl" refer to a spirocyclic or monocyclic $C_{3-8}$ hydrocarbon or a spirocyclic, bicyclic, bridged bicyclic, tricyclic, or bridged tricyclic $C_{8-14}$ hydrocarbon that is completely saturated or that contains one or more units of unsaturation, but which is not aromatic, wherein any individual ring in said bicyclic ring system has 3 to 7 members. In some embodiments, cyclogroups are substituted. In some embodiments, cyclogroups are unsubstituted.

The term "heteroalkyl," or "heteroaliphatic" as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "alkenyl" as used herein, means a straight-chain (i.e., unbranched), branched, substituted or unsubstituted hydrocarbon chain that contains one or more units of saturation, or a monocyclic hydrocarbon or bicyclic hydrocarbon that contains one or more units of unsaturation, but which is not aromatic (referred to herein as, "cyclic alkenyl"). In some embodiments, alkenyl groups are substituted. In some embodiments, alkenyl groups are unsubstituted. In some embodiments, alkenyl groups are straight-chain. In some embodiments, alkenyl groups are branched.

The term "heterocycle", "heterocyclyl", "heterocycloaliphatic", or "heterocyclic" as used herein means non-aromatic, monocyclic, bicyclic, or tricyclic ring systems in which one or more ring members is an independently chosen heteroatom. In some embodiments, the "heterocycle", "heterocyclyl", "heterocycloaliphatic", or "heterocyclic" group has 3 to 14 ring members in which one or more ring members is a heteroatom independently chosen from oxygen, sulfur, nitrogen, and phosphorus. In some embodiments, each ring in a bicyclic or tricyclic ring system contains 3 to 7 ring members. In some embodiments the heterocycle has at least one unsaturated carbon-carbon bond. In some embodiments, the heterocycle has at least one unsaturated carbon-nitrogen bond. In some embodiments, the heterocycle has one heteroatom independently chosen from oxygen, sulfur, nitrogen, and phosphorus. In some embodiments, the heterocycle has one heteroatom that is a nitrogen atom. In some embodiments, the heterocycle has one heteroatom that is an oxygen atom. In some embodiments, the heterocycle has two heteroatoms that are each independently selected from nitrogen and oxygen. In some embodiments, the heterocycle has three heteroatoms that are each independently selected from nitrogen and oxygen. In some embodiments, heterocycles are substituted. In some embodiments, heterocycles are unsubstituted.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units or degrees of unsaturation. Unsaturation is the state in which not all of the available valance bonds in a compound are satisfied by substituents and thus the compound contains double or triple bonds.

The term "alkoxy", or "thioalkyl", as used herein, refers to an alkyl group, as previously defined, wherein one carbon of the alkyl group is replaced by an oxygen ("alkoxy") or sulfur ("thioalkyl") atom, respectively, provided that the oxygen and sulfur atoms are linked between two carbon atoms. A "cyclic alkoxy" refers to a monocyclic, spirocyclic, bicyclic, bridged bicyclic, tricyclic, or bridged tricyclic hydrocarbon that contains at least one alkoxy group, but is not aromatic. Non-limiting examples of cyclic alkoxy groups include tetrahydropyranyl, tetrahydrofuranyl, oxetanyl, 8-oxabicyclo[3.2.1]octanyl, and oxepanyl. In some embodiments, "alkoxy" and/or "thioalkyl" groups are substituted. In some embodiments, "alkoxy" and/or "thioalkyl" groups are unsubstituted.

The terms "haloalkyl" and "haloalkoxy," as used herein, means a linear or branched alkyl or alkoxy, as the case may be, which is substituted with one or more halogen atoms. Non-limiting examples of haloalkyl groups include —$CHF_2$, —$CH_2F$, —$CF_3$, —$CF_2$—, and perhaloalkyls, such as —$CF_2CF_3$. Non-limiting examples of haloalkoxy groups include —$OCHF_2$, —$OCH_2F$, —$OCF_3$, —$OCF_2$—.

The term "halogen" includes F, Cl, Br, and I, i.e., fluoro, chloro, bromo, and iodo, respectively.

The term "aminoalkyl" means an alkyl group which is substituted with or contains an amino group.

As used herein, an "amino" refers to a group which is a primary, secondary, or tertiary amine.

As used herein, a "carbonyl" group refers to C=O.

As used herein, a "cyano" or "nitrile" group refer to —C≡N.

As used herein, a "hydroxy" group refers to —OH.

As used herein, a "thiol" group refers to —SH.

As used herein, "tert" and "t-" each refer to tertiary.

As used herein, "aromatic groups" or "aromatic rings" refer to chemical groups that contain conjugated, planar ring systems with delocalized pi electron orbitals comprised of [4n+2]p orbital electrons, wherein n is an integer ranging from 0 to 6. Nonlimiting examples of aromatic groups include aryl and heteroaryl groups.

The term "aryl" used alone or as part of a larger moiety as in "arylalkyl", "arylalkoxy", or "aryloxyalkyl", refers to monocyclic, bicyclic, and tricyclic ring systems having a total of five to fourteen ring members, wherein at least one ring in the system is aromatic and wherein each ring in a bicyclic or tricyclic ring system contains 3 to 7 ring members. The term "aryl" also refers to heteroaryl ring systems as defined herein below. Nonlimiting examples of aryl groups include phenyl rings. In some embodiments, aryl groups are substituted. In some embodiments, aryl groups are unsubstituted.

The term "heteroaryl", used alone or as part of a larger moiety as in "heteroarylalkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in a bicyclic or tricyclic ring system contains 3 to 7 ring members. In some embodiments, heteroaryl groups are substituted. In some embodiments, heteroaryl groups have one or more heteroatoms chosen from nitrogen, oxygen, and sulfur. In some embodiments, heteroaryl groups have one heteroatom. In some embodiments, heteroaryl groups have two heteroatoms. In some embodiments, heteroaryl groups are monocyclic ring systems having five ring members. In some embodiments, heteroaryl groups are monocyclic ring systems having six ring members. In some embodiments, heteroaryl groups are unsubstituted.

Non-limiting examples of useful protecting groups for nitrogen-containing groups, such as amine groups, include, for example, t-butyl carbamate (Boc), benzyl (Bn), tetrahydropyranyl (THP), 9-fluorenylmethyl carbamate (Fmoc) benzyl carbamate (Cbz), acetamide, trifluoroacetamide, triphenylmethylamine, benzylideneamine, and p-toluenesulfonamide. Methods of adding (a process generally referred to as "protecting") and removing (process generally referred to as "deprotecting") such amine protecting groups are well-known in the art and available, for example, in P. J. Kocienski, Protecting Groups, Thieme, 1994, which is hereby incorporated by reference in its entirety and in Greene and Wuts, *Protective Groups in Organic Synthesis, 3rd Edition* (John Wiley & Sons, New York, 1999) and *4th Edition* (John Wiley & Sons, New Jersey, 2014).

Non-limiting examples of suitable solvents that may be used in this disclosure include, but are not limited to, water, methanol (MeOH), ethanol (EtOH), dichloromethane or "methylene chloride" ($CH_2C_2$), toluene, acetonitrile (MeCN), dimethylformamide (DMF), dimethyl sulfoxide (DMSO), methyl acetate (MeOAc), ethyl acetate (EtOAc), heptanes, isopropyl acetate (IPAc), tert-butyl acetate (t-BuOAc), isopropyl alcohol (IPA), tetrahydrofuran (THF), 2-methyl tetrahydrofuran (2-Me THF), methyl ethyl ketone (MEK), tert-butanol, diethyl ether ($Et_2O$), methyl-tert-butyl ether (MTBE), 1,4-dioxane, and N-methyl pyrrolidone (NMP).

Non-limiting examples of suitable bases that may be used in this disclosure include, but are not limited to, 1,8-diazabicyclo[5.4.0]undec-7-ene (DBU), potassium tert-butoxide (KOtBu), potassium carbonate ($K_2CO_3$), N-methylmorpholine (NMM), triethylamine ($Et_3N$; TEA), diisopropyl-ethyl amine (i-$Pr_2EtN$; DIPEA), pyridine, potassium hydroxide (KOH), sodium hydroxide (NaOH), lithium hydroxide (LiOH) and sodium methoxide (NaOMe; $NaOCH_3$).

The disclosure includes pharmaceutically acceptable salts of the disclosed compounds. A salt of a compound is formed between an acid and a basic group of the compound, such as an amino functional group, or a base and an acidic group of the compound, such as a carboxyl functional group.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this disclosure. Suitable pharmaceutically acceptable salts are, for example, those disclosed in S. M. Berge, et al. *J. Pharmaceutical Sciences*, 1977, 66, 1 to 19.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In some embodiments, pharmaceutically acceptable acid addition salts include those formed with mineral acids such as hydrochloric acid and hydrobromic acid, and those formed with organic acids such as maleic acid.

Pharmaceutically acceptable salts derived from appropriate bases include alkali metal, alkaline earth metal, ammonium, and $N^+(C_{1-4}alkyl)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other suitable, non-limiting examples of pharmaceutically acceptable salts include besylate and glucosamine salts.

The terms "patient" and "subject" are used interchangeably and refer to an animal including a human.

The terms "effective dose" and "effective amount" are used interchangeably herein and refer to that amount of compound that produces the desired effect for which it is administered (e.g., improvement in symptoms of FSGS and/or NDKD, lessening the severity of FSGS and/NDKD or a symptom of FSGS and/or NDKD, and/or reducing progression of FSGS and/or NDKD or a symptom of FSGS and/or NDKD). The exact amount of an effective dose will depend on the purpose of the treatment and will be ascertainable by one skilled in the art using known techniques (see, e.g., Lloyd (1999) The Art, Science and Technology of Pharmaceutical Compounding).

As used herein, the term "treatment" and its cognates refer to slowing or stopping disease progression. "Treatment" and its cognates as used herein, include, but are not limited to the following: complete or partial remission, lower risk of kidney failure (e.g. ESRD), and disease-related complications (e.g. edema, susceptibility to infections, or thromboembolic events). Improvements in or lessening the severity of any of these symptoms can be readily assessed according to methods and techniques known in the art or subsequently developed.

The terms "about" and "approximately", when used in connection with doses, amounts, or weight percent of ingredients of a composition or a dosage form, include the value of a specified dose, amount, or weight percent or a range of the dose, amount, or weight percent that is recognized by one of ordinary skill in the art to provide a pharmacological effect equivalent to that obtained from the specified dose, amount, or weight percent.

The at least one entity chosen from compounds of Formulae (I), (II), (IIIa), (IIIb), and (IIIc), pharmaceutically acceptable salts of any of those compounds, solvates of any of the foregoing, and/or deuterated derivatives of any of the foregoing may be administered once daily, twice daily, or three times daily, for example, for the treatment of FSGS. In some embodiments, the compounds of Formulae (I), (II), (IIIa), (IIIb), and (IIIc) are chosen from Compounds 1 to 135, pharmaceutically acceptable salts of any of those compounds, solvates of any of the foregoing, and deuterated derivatives of any of the foregoing. In some embodiments, at least one entity chosen from compounds of Formulae (I), (II), (IIIa), (IIIb), and (IIIc), pharmaceutically acceptable salts of any of those compounds, solvates of any of the foregoing, and/or deuterated derivatives of any of the foregoing is administered once daily. In some embodiments, at least one entity chosen from Compounds 1 to 135, pharmaceutically acceptable salts of any of those compounds, solvates of any of the foregoing, and deuterated derivatives of any of the foregoing is administered once daily. In some embodiments, at least one entity chosen from compounds of Formulae (I), (II), (IIIa), (IIIb), and (IIIc), pharmaceutically acceptable salts of any of those compounds, solvates of any of the foregoing, and/or deuterated derivatives of any of the foregoing is administered twice daily. In some embodiments, at least one entity chosen from Compounds 1 to 135, pharmaceutically acceptable salts of any of those compounds, solvates of any of the foregoing, and/or deuterated derivatives of any of the foregoing is administered twice daily. In some embodiments, at least one entity chosen from compounds of Formulae (I), (II), (IIIa), (IIIb), and (IIIc), pharmaceutically acceptable salts of any of those compounds, solvates of any of the foregoing, and/or deuterated derivatives of any of the foregoing are administered three times daily. In some embodiments, at least one entity chosen from Compounds 1 to 135, pharmaceutically acceptable salts of any of those compounds, solvates of any of the foregoing, and/or deuterated derivatives of any of the foregoing is administered three times daily.

In some embodiments, 2 mg to 1500 mg, 5 mg to 1000 mg, 10 mg to 500 mg, 20 mg to 300 mg, 20 mg to 200 mg, 30 mg to 150 mg, 50 mg to 150 mg, 60 mg to 125 mg, or 70 mg to 120 mg, 80 mg to 115 mg, 90 mg to 110 mg, 95 mg to 110 mg, or 100 mg to 105 mg of at least one entity chosen from compounds of Formulae (I), (II), (IIIa), (IIIb), and (IIIc), pharmaceutically acceptable salts of any of those compounds, solvates of any of the foregoing, and deuterated derivatives of any of the foregoing are administered once daily, twice daily, or three times daily. In some embodiments, 2 mg to 1500 mg, 5 mg to 1000 mg, 10 mg to 500 mg, 20 mg to 300 mg, 20 mg to 200 mg, 30 mg to 150 mg, 50 mg to 150 mg, 60 mg to 125 mg, or 70 mg to 120 mg, 80 mg to 115 mg, 90 mg to 110 mg, 95 mg to 110 mg, or 100 mg to 105 mg of at least one entity chosen from Compounds 1 to 135, pharmaceutically acceptable salts of any of those compounds, solvates of any of the foregoing, and deuterated derivatives of any of the foregoing are administered once daily, twice daily, or three times daily.

One of ordinary skill in the art would recognize that, when an amount of compound is disclosed, the relevant amount of a pharmaceutically acceptable salt form of the compound is an amount equivalent to the concentration of the free base of the compound. The amounts of the compounds, pharmaceutically acceptable salts, solvates, and deuterated derivatives disclosed herein are based upon the free base form of the reference compound. For example, "10 mg of at least one compound chosen from compounds of Formula (I) and pharmaceutically acceptable salts thereof" includes 10 mg of compound of Formula (I) and a concentration of a pharmaceutically acceptable salt of compounds of Formula (I) equivalent to 10 mg of compounds of Formula (I).

As used herein, the term "ambient conditions" means room temperature, open air condition and uncontrolled humidity condition.

As used herein, the terms "crystalline form" and "Form" interchangeably refer to a crystal structure (or polymorph) having a particular molecular packing arrangement in the crystal lattice. Crystalline forms can be identified and distinguished from each other by one or more characterization techniques including, for example, X-ray powder diffraction (XRPD), single crystal X-ray diffraction, solid state nuclear magnetic resonance (SSNMR), differential scanning calorimetry (DSC), dynamic vapor sorption (DVS), and/or thermogravimetric analysis (TGA). Accordingly, as used herein, the terms "crystalline Form [X] of Compound ([Y])" and "crystalline Form [C] of a [pharmaceutically acceptable] salt of Compound ([Y])" refer to unique crystalline forms that can be identified and distinguished from each other by one or more characterization techniques including, for example, X-ray powder diffraction (XRPD), single crystal X-ray diffraction, SSNMR, differential scanning calorimetry (DSC), dynamic vapor sorption (DVS), and/or thermogravimetric analysis (TGA). In some embodiments, the novel crystalline forms are characterized by an X-ray powder diffractogram having one or more signals at one or more specified two-theta values (° 2θ).

As used herein, the terms "solvate" refers to a crystal form comprising one or more molecules of compound of the present disclosure and, incorporated into the crystal lattice, one or more molecules of a solvent or solvents in stoichiometric or nonstoichiometric amounts. When the solvent is water, the solvate is referred to as a "hydrate".

As used herein, the term "SSNMR" refers to the analytical characterization method of solid state nuclear magnetic resonance. SSNMR spectra can be recorded at ambient conditions on any magnetically active isotope present in the sample. The typical examples of active isotopes for small molecule active pharmaceutical ingredients include $^1$H, $^2$H, $^{13}$C, $^{19}$F, $^{31}$P, $^{15}$N, $^{14}$N, $^{35}$Cl, $^{11}$B, $^7$Li, $^{17}$O, $^{23}$Na, $^{79}$Br, and $^{195}$Pt.

As used herein, the term "XRPD" refers to the analytical characterization method of X-ray powder diffraction. XRPD patterns can be recorded at ambient conditions in transmission or reflection geometry using a diffractometer.

As used herein, the terms "X-ray powder diffractogram," "X-ray powder diffraction pattern," "XRPD pattern" interchangeably refer to an experimentally obtained pattern plotting signal positions (on the abscissa) versus signal intensities on the ordinate). For an amorphous material, an X-ray powder diffractogram may include one or more broad signals; and for a crystalline material, an X-ray powder diffractogram may include one or more signals, each identified by its angular value as measured in degrees 2θ (° 2θ), depicted on the abscissa of an X-ray powder diffractogram, which may be expressed as "a signal at . . . degrees two-theta," "a signal at [a] two-theta value(s) of . . . " and/or "a signal at at least . . . two-theta value(s) chosen from . . . ."

A "signal" or "peak" as used herein refers to a point in the XRPD pattern where the intensity as measured in counts is at a local maximum. One of ordinary skill in the art would recognize that one or more signals (or peaks) in an XRPD pattern may overlap and may, for example, not be apparent to the naked eye. Indeed, one of ordinary skill in the art would recognize that some art-recognized methods are capable of and suitable for determining whether a signal exists in a pattern, such as Rietveld refinement.

As used herein, "a signal at . . . degrees two-theta," "a signal at [a] two-theta value[ ] of . . . " and/or "a signal at at least . . . two-theta value(s) chosen from . . . ." refer to X-ray reflection positions as measured and observed in X-ray powder diffraction experiments (° 2θ).

The repeatability of the angular values is in the range of ±0.2° 2θ, i.e., the angular value can be at the recited angular value +0.2 degrees two-theta, the angular value −0.2 degrees two-theta, or any value between those two end points (angular value +0.2 degrees two-theta and angular value −0.2 degrees two-theta).

The terms "signal intensities" and "peak intensities" interchangeably refer to relative signal intensities within a given X-ray powder diffractogram. Factors that can affect the relative signal or peak intensities include sample thickness and preferred orientation (e.g., the crystalline particles are not distributed randomly).

The term "X-ray powder diffractogram having a signal at . . . two-theta values" as used herein refers to an XRPD pattern that contains X-ray reflection positions as measured and observed in X-ray powder diffraction experiments (° 2θ).

As used herein, the term "amorphous" refers to a solid material having no long range order in the position of its molecules. Amorphous solids are generally supercooled liquids in which the molecules are arranged in a random manner so that there is no well-defined arrangement, e.g., molecular packing, and no long range order.

For example, an amorphous material is a solid material having no sharp characteristic signal(s) in its X-ray power diffractogram (i.e., is not crystalline as determined by XRPD). Instead, one or more broad peaks (e.g., halos) appear in its diffractogram. Broad peaks are characteristic of an amorphous solid. See, e.g., US 2004/0006237 for a comparison of diffractograms of an amorphous material and crystalline material. In addition, the widths of signals in $^{13}$C NMR and $^{19}$F NMR spectra of amorphous material are typically substantially broader than those in $^{13}$C NMR and $^{19}$F NMR spectra of crystalline material.

As used herein, an X-ray powder diffractogram is "substantially similar to that in [a particular] Figure" when at least 90%, such as at least 95%, at least 98%, or at least 99%, of the signals in the two diffractograms overlap. In determining "substantial similarity," one of ordinary skill in the art will understand that there may be variation in the intensities and/or signal positions in XRPD diffractograms even for the same crystalline form. Thus, those of ordinary skill in the art will understand that the signal maximum values in XRPD diffractograms (in degrees two-theta (° 2θ) referred to herein) generally mean that value reported ±0.2 degrees 2θ of the reported value, an art-recognized variance.

As used herein, an SSNMR spectrum is "substantially similar to that in [a particular] Figure" when at least 90%, such as at least 95%, at least 98%, or at least 99%, of the signals in the two spectra overlap. In determining "substantial similarity," one of ordinary skill in the art will understand that there may be variation in the intensities and/or signal positions in SSNMR spectra even for the same crystalline form. Thus, those of ordinary skill in the art will understand that the signal maximum values in SSNMR spectra (in ppm) referred to herein generally mean that value reported ±0.2 ppm of the reported value, an art-recognized variance.

As used herein, a crystalline form is "substantially pure" when it accounts for an amount by weight equal to or greater than 90% of the sum of all solid form(s) in a sample as determined by a method in accordance with the art, such as quantitative XRPD. In some embodiments, the solid form is "substantially pure" when it accounts for an amount by weight equal to or greater than 95% of the sum of all solid form(s) in a sample. In some embodiments, the solid form is "substantially pure" when it accounts for an amount by weight equal to or greater than 99% of the sum of all solid form(s) in a sample.

As used herein, the term "DSC" refers to the analytical method of Differential Scanning Calorimetry.

As used herein, the term "TGA" refers to the analytical method of Thermo Gravimetric (or thermogravimetric) Analysis.

Compounds and Compositions

In some embodiments, at least one entity of the disclosure is chosen from compounds of Formula (I):

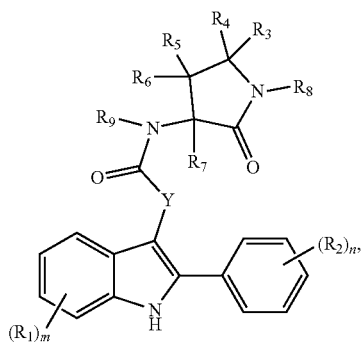

(I)

pharmaceutically acceptable salts thereof, solvates of any of the foregoing, and deuterated derivatives of any of the foregoing, wherein:

(i) each $R_1$ is independently chosen from
halogen groups,
hydroxy,
thiol,
amino,
cyano,
—OC(O)$C_1$-$C_6$ linear, branched, and cyclic alkyl groups,
—C(O)O$C_1$-$C_6$ linear, branched, and cyclic alkyl groups,
—NHC(O)$C_1$-$C_6$ linear, branched, and cyclic alkyl groups,
—C(O)NH$C_1$-$C_6$ linear, branched, and cyclic alkyl groups,
—NHC(O)aryl groups,
—C(O)NHaryl groups,
—NHC(O)heteroaryl groups,
—C(O)NHheteroaryl groups,
—NHS(O)$_2$$C_1$-$C_6$ linear, branched, and cyclic alkyl groups,
—S(O)$_2$NH$C_1$-$C_6$ linear, branched, and cyclic alkyl groups,
—NHS(O)$_2$aryl groups,
—S(O)$_2$NHaryl groups,
—NHS(O)$_2$heteroaryl groups,
—S(O)$_2$NHheteroaryl groups,
—NHC(O)NH$C_1$-$C_6$ linear, branched, and cyclic alkyl groups,
—NHC(O)NHaryl groups,
—NHC(O)NHheteroaryl groups,
$C_1$-$C_6$ linear, branched, and cyclic alkyl groups,
$C_2$-$C_6$ linear, branched, and cyclic alkenyl groups,
$C_1$-$C_6$ linear, branched, and cyclic hydroxyalkyl groups,
$C_1$-$C_6$ linear, branched, and cyclic alkoxy groups,
$C_1$-$C_6$ linear, branched, and cyclic thioalkyl groups,
$C_1$-$C_6$ linear, branched, and cyclic haloalkyl groups,
$C_1$-$C_6$ linear, branched, and cyclic haloaminoalkyl groups,
$C_1$-$C_6$ linear, branched, and cyclic halothioalkyl groups,
$C_1$-$C_6$ linear, branched, and cyclic haloalkoxy groups,
benzyloxy, benzylamino, or benzylthio groups,
3 to 6-membered heterocycloalkenyl groups,
3 to 6-membered heterocycloalkyl groups, and
5 and 6-membered heteroaryl groups; or
two $R_1$ groups, together with the carbon atoms to which they are attached, form a $C_4$-$C_8$ cycloalkyl group, an aryl group, or a heteroaryl group;

(ii) each $R_2$ is independently chosen from
halogen groups,
hydroxy,
thiol,
amino,
cyano,
—NHC(O)$C_1$-$C_6$ linear, branched, and cyclic alkyl groups,
—C(O)NH$C_1$-$C_6$ linear, branched, and cyclic alkyl groups,
—NHC(O)aryl groups,
—C(O)NHaryl groups,
—NHC(O)heteroaryl groups,
—C(O)NHheteroaryl groups,
—NHS(O)$_2$$C_1$-$C_6$ linear, branched, and cyclic alkyl groups,
—S(O)$_2$NH$C_1$-$C_6$ linear, branched, and cyclic alkyl groups,
—NHS(O)$_2$aryl groups,
—S(O)$_2$NHaryl groups,
—NHS(O)$_2$heteroaryl groups,
—S(O)$_2$NHheteroaryl groups,
—NHC(O)NH$C_1$-$C_4$ linear, branched, and cyclic alkyl groups,
—NHC(O)NH aryl groups,
—NHC(O)NH heteroaryl groups,
$C_1$-$C_4$ linear, branched, and cyclic alkyl groups,
$C_2$-$C_4$ linear, branched, and cyclic alkenyl groups,
$C_1$-$C_4$ linear, branched, and cyclic hydroxyalkyl groups,
$C_1$-$C_4$ linear, branched, and cyclic alkoxy groups,
$C_1$-$C_4$ linear, branched, and cyclic thioalkyl groups,
$C_1$-$C_4$ linear, branched, and cyclic haloalkyl groups,
$C_1$-$C_4$ linear, branched, and cyclic haloaminoalkyl groups,
$C_1$-$C_4$ linear, branched, and cyclic halothioalkyl groups, and
$C_1$-$C_4$ linear, branched, and cyclic haloalkoxy groups;

(iii) m is chosen from 0, 1, 2, 3, and 4;
(iv) n is chosen from 0, 1, 2, 3, 4, and 5;
(v) Y is chosen from divalent $C_1$-$C_8$ linear and branched alkyl groups, divalent $C_1$-$C_8$ linear and branched alkoxy groups, divalent $C_1$-$C_8$ linear and branched aminoalkyl groups, and divalent $C_1$-$C_8$ linear and branched thioalkyl groups, wherein the divalent alkyl groups, divalent alkoxy groups, divalent aminoalkyl groups, and divalent thioalkyl groups are optionally substituted with at least one group chosen from
$C_1$-$C_6$ alkyl groups,
aryl groups,
heteroaryl groups,
halogen groups,
hydroxy, and
amino;
(vi) each of $R_3$ and $R_4$ is independently chosen from
hydrogen,
hydroxy,
thiol,
amino,
halogen groups,
$C_1$-$C_6$ linear, branched, and cyclic hydroxyalkyl groups,
$C_1$-$C_6$ linear, branched, and cyclic alkoxy groups,
$C_1$-$C_6$ linear, branched, and cyclic thioalkyl groups,
$C_1$-$C_6$ linear, branched, and cyclic haloalkyl groups,
$C_1$-$C_6$ linear, branched, and cyclic haloaminoalkyl groups,
$C_1$-$C_6$ linear, branched, and cyclic halothioalkyl groups,
$C_1$-$C_6$ linear, branched, and cyclic haloalkoxy groups, or
$R_3$ and $R_4$, together with the carbon atom to which they are attached, form a $C_3$-$C_6$ cycloalkyl group or carbonyl group;
(vii) each of $R_5$ and $R_6$ is independently chosen from
hydrogen,
thiol,
amino,
halogen groups,
hydroxy,
$C_1$-$C_6$ linear, branched, and cyclic hydroxyalkyl groups,
$C_1$-$C_6$ linear, branched, and cyclic alkoxy groups,
$C_1$-$C_6$ linear, branched, and cyclic thioalkyl groups,
$C_1$-$C_6$ linear, branched, and cyclic haloalkyl groups,
$C_1$-$C_6$ linear, branched, and cyclic haloaminoalkyl groups,
$C_1$-$C_6$ linear, branched, and cyclic halothioalkyl groups,
$C_1$-$C_6$ linear, branched, and cyclic haloalkoxy groups,
—OC(O)$C_1$-$C_6$ linear, branched, and cyclic alkyl groups,
—C(O)O$C_1$-$C_6$ linear, branched, and cyclic alkyl groups,
—NHC(O)$C_1$-$C_6$ linear, branched, and cyclic alkyl groups,
—C(O)NH$C_1$-$C_6$ linear, branched, and cyclic alkyl groups,
—NHC(O)aryl groups,
—C(O)NHaryl groups,
—NHC(O)heteroaryl groups,
—C(O)NHheteroaryl groups,
—NHS(O)$_2$$C_1$-$C_6$ linear, branched, and cyclic alkyl groups,
—S(O)$_2$NH$C_1$-$C_6$ linear, branched, and cyclic alkyl groups,
—NHS(O)$_2$aryl groups,
—S(O)$_2$NHaryl groups,
—NHS(O)$_2$heteroaryl groups,
—S(O)$_2$NHheteroaryl groups,
—NHC(O)NH$C_1$-$C_6$ linear, branched, and cyclic alkyl groups,
—NHC(O)NH aryl groups, and
—NHC(O)NH heteroaryl groups; and
(viii) each of $R_7$, $R_8$, and $R_9$ is independently chosen from
hydrogen,
$C_1$-$C_6$ linear, branched, and cyclic alkyl groups,
$C_1$-$C_6$ linear, branched, and cyclic hydroxyalkyl groups,
$C_1$-$C_6$ linear, branched, and cyclic alkoxy groups,
$C_1$-$C_6$ linear, branched, and cyclic thioalkyl groups,
$C_1$-$C_6$ linear, branched, and cyclic haloalkyl groups,
$C_1$-$C_6$ linear, branched, and cyclic haloaminoalkyl groups,
$C_1$-$C_6$ linear, branched, and cyclic halothioalkyl groups, and
$C_1$-$C_6$ linear, branched, and cyclic haloalkoxy groups.

In some embodiments, at least one entity of the disclosure is chosen from compounds of Formula (I):

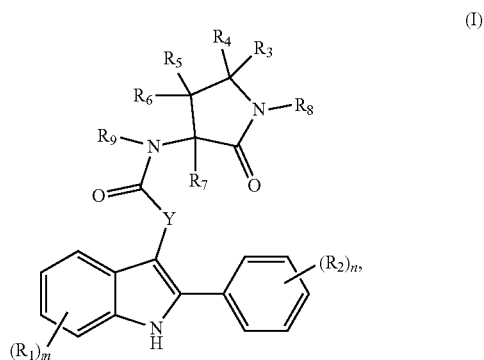

(I)

pharmaceutically acceptable salts thereof, solvates of any of the foregoing, and deuterated derivatives of any of the foregoing, wherein:
(i) each $R_1$ is independently chosen from
halogen groups,
hydroxy,
cyano,
$C_1$-$C_4$ linear, branched, and cyclic alkyl groups,
$C_2$-$C_4$ linear, branched, and cyclic alkenyl groups,
$C_1$-$C_4$ linear, branched, and cyclic hydroxyalkyl groups,
$C_1$-$C_4$ linear, branched, and cyclic alkoxy groups,
$C_1$-$C_4$ linear, branched, and cyclic haloalkyl groups,
$C_1$-$C_4$ linear, branched, and cyclic haloalkoxy groups,
benzyloxy groups,
3 to 6-membered heterocycloalkenyl groups,
3 to 6-membered heterocycloalkyl groups, and
5 and 6-membered heteroaryl groups;
(ii) each $R_2$ is independently chosen from
halogen groups,
cyano,
$C_1$-$C_4$ linear, branched, and cyclic alkoxy groups,
$C_1$-$C_4$ linear, branched, and cyclic haloalkoxy groups,
$C_1$-$C_4$ linear, branched, and cyclic alkyl groups, and
$C_1$-$C_4$ linear, branched, and cyclic haloalkyl groups;
(iii) m is chosen from 0, 1, 2, 3, and 4;
(iv) n is chosen from 0, 1, 2, 3, 4, and 5;
(v) Y is chosen from divalent $C_1$-$C_8$ linear and branched alkyl groups, wherein the divalent alkyl groups are optionally substituted with at least one group chosen from
$C_1$-$C_4$ alkyl groups,
halogen groups, and
hydroxy;

(vi) each of $R_3$ and $R_4$ is independently chosen from
hydrogen,
$C_1$-$C_3$ linear, branched, and cyclic alkyl groups,
$C_1$-$C_3$ linear, branched, and cyclic hydroxyalkyl groups, and
$C_1$-$C_3$ linear, branched, and cyclic haloalkyl groups, or
$R_3$ and $R_4$, together with the carbon atom to which they are attached, form a $C_3$-$C_6$ cycloalkyl group or carbonyl group;
(vii) each of $R_5$ and $R_6$ is independently chosen from
hydrogen,
hydroxy,
$C_1$-$C_4$ linear, branched, and cyclic alkyl groups,
$C_1$-$C_4$ linear, branched, and cyclic haloalkyl groups, and
—OC(O)$C_1$-$C_4$ linear, branched, and cyclic alkyl groups; and
(viii) each of $R_7$, $R_8$, and $R_9$ is independently chosen from
hydrogen,
$C_1$-$C_4$ linear, branched, and cyclic alkyl groups, and
$C_1$-$C_4$ linear, branched, and cyclic haloalkyl groups.

In some embodiments, each of $R_3$ and $R_4$ is hydrogen.
In some embodiments, each of $R_5$ and $R_6$ is independently chosen from hydrogen and hydroxy.
In some embodiments, one of $R_5$ and $R_6$ is hydrogen and the other is hydroxy.
In some embodiments, each $R_1$ is independently chosen from halogen groups.
In some embodiments, each $R_1$ is fluoro.
In some embodiments, each $R_2$ is independently chosen from halogen groups and methyl.
In some embodiments, each $R_2$ is independently chosen from fluoro and methyl.
In some embodiments, each $R_2$ is independently fluoro.
In some embodiments, each $R_2$ is independently methyl.
In some embodiments, m is 0, 1, or 2.
In some embodiments, m is 0.
In some embodiments, m is 1 or 2.
In some embodiments, m is 1.
In some embodiments, m is 2.
In some embodiments, n is 0, 1, or 2.
In some embodiments, n is 0.
In some embodiments, n is 1 or 2.
In some embodiments, n is 1.
In some embodiments, n is 2.
In some embodiments, Y is divalent ethyl optionally substituted with at least one group chosen from $C_1$-$C_4$ alkyl groups, halogen groups, and hydroxy.
In some embodiments, Y is —CH$_2$CH$_2$—, also referred to herein as "divalent ethyl".
In some embodiments, Y is —CH$_2$CH(CH$_3$)—.
In some embodiments, Y is divalent ethyl substituted with one or two groups chosen from halogen groups and hydroxy.
In some embodiments, Y is divalent ethyl substituted with one halogen.
In some embodiments, Y is divalent ethyl substituted with one fluoro.
In some embodiments, Y is divalent ethyl substituted with one chloro.
In some embodiments, Y is divalent ethyl substituted with two halogen groups.
In some embodiments, Y is divalent ethyl substituted with two fluoro groups.
In some embodiments, Y is divalent ethyl substituted with two chloro groups.
In some embodiments, Y is divalent ethyl substituted with one fluoro and one chloro.

In some embodiments, Y is divalent ethyl substituted with one hydroxy.
In some embodiments, m is 2, n is 1, and Y is divalent ethyl. In some embodiments, m is 2, n is 1, one of $R_5$ and $R_6$ is hydrogen and the other is hydroxy, and Y is divalent ethyl. In some embodiments, m is 2, n is 1, each $R_1$ is independently chosen from halogen groups, $R_2$ is chosen from halogen groups, and Y is divalent ethyl. In some embodiments, m is 2, n is 1, each $R_1$ is independently chosen from halogen groups, $R_2$ is chosen from halogen groups, one of $R_5$ and $R_6$ is hydrogen and the other is hydroxyl, and Y is divalent ethyl.
In some embodiments, m is 0, n is 1, and Y is divalent ethyl. In some embodiments, m is 0, n is 1, one of $R_5$ and $R_6$ is hydrogen and the other is hydroxy, and Y is divalent ethyl. In some embodiments, m is 0, n is 1, $R_2$ is chosen from halogen groups, and Y is divalent ethyl. In some embodiments, m is 0, n is 1, $R_2$ is chosen from halogen groups, one of $R_5$ and $R_6$ is hydrogen and the other is hydroxy, and Y is divalent ethyl.

In some embodiments, the at least one entity is chosen from compounds of Formula (II):

pharmaceutically acceptable salts thereof, solvates of any of the foregoing, and deuterated derivatives of any of the foregoing, wherein:
(i) each $R_1$ is independently chosen from
halogen groups,
cyano,
methyl,
cyclopropyl,
isopropyl,
$C_2$-$C_3$ linear and branched alkenyl groups,
hydroxypropyl groups,
methoxy,
dihydrofuran groups, and
furan groups;
(ii) each $R_2$ is independently chosen from
fluoro,
cyano, and
methyl;
(iii) m is chosen from 0, 1, 2, and 3;
(iv) n is chosen from 0, 1, and 2; and
(v) Y is divalent ethyl optionally substituted with at least one group chosen from
fluoro,
methyl, and
hydroxy.

In some embodiments, the at least one entity of the disclosure is chosen from compounds of Formula (IIIa), compounds of Formula (IIIb), compounds of Formula (IIIc):

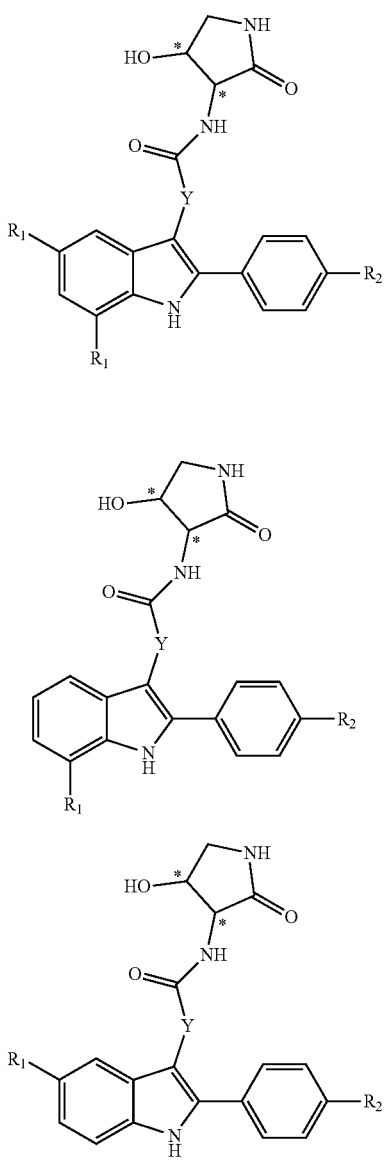

(IIIa)

(IIIb)

(IIIc)

pharmaceutically acceptable salts of any of the foregoing, solvates of any of the foregoing, and deuterated derivatives of any of the foregoing, wherein:

(i) each $R_1$ is independently chosen from
fluoro,
chloro,
bromo,
cyano,
methyl,
cyclopropyl,
ethyl,
hydroxypropyl,
isopropyl,
propen-2-yl,
dihydrofuran,
furan, and
methoxy;

(ii) each $R_2$ is independently chosen from
fluoro,
bromo,
cyano, and
methyl; and (iii) Y is divalent ethyl optionally substituted with at least one group chosen from
fluoro,
methyl, and
hydroxy.

In some embodiments, the at least one entity of the disclosure is chosen from Compounds 1 to 135 depicted in Table 1. A wavy line in a compound in Table 1 (i.e., ⌇) depicts a bond between two atoms and indicates a position of mixed stereochemistry for a collection of molecules, such as a racemic mixture, cis/trans isomers, or (E)/(Z) isomers. An asterisk adjacent to an atom (e.g.,

) in a compound in Table 1, indicates a chiral position in the molecule.

TABLE 1

Compounds 1 to 135

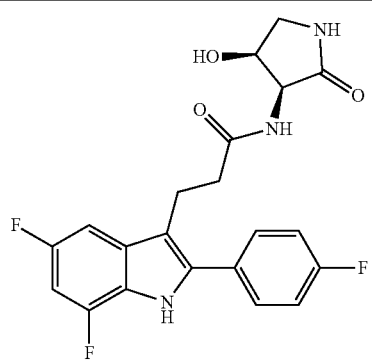

1

TABLE 1-continued
Compounds 1 to 135
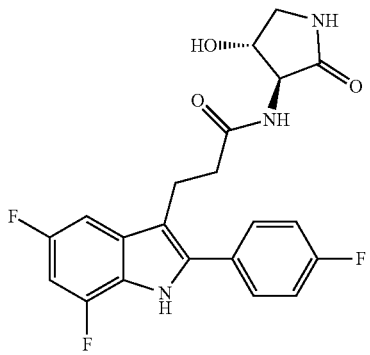 2
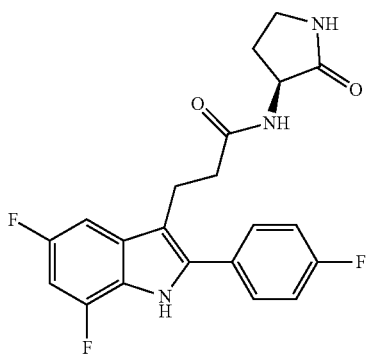 3
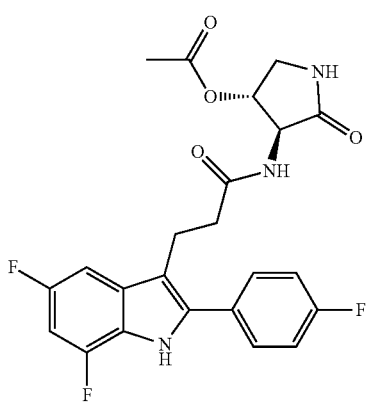 [SMILES: CC(=O)O[C@@H]1CNC(=O)[C@H]1NC(=O)CCc1c(-c2ccc(F)cc2)[nH]c2c(F)cc(F)cc12] 4
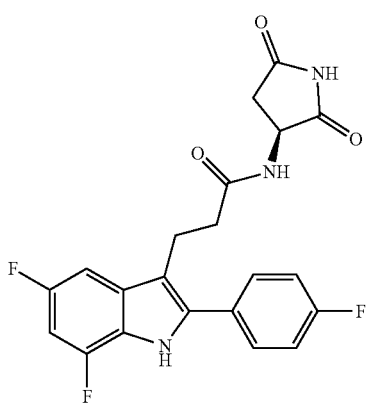 [SMILES: O=C1C[C@H](NC(=O)CCc2c(-c3ccc(F)cc3)[nH]c3c(F)cc(F)cc23)C(=O)N1] 5

TABLE 1-continued
Compounds 1 to 135
6
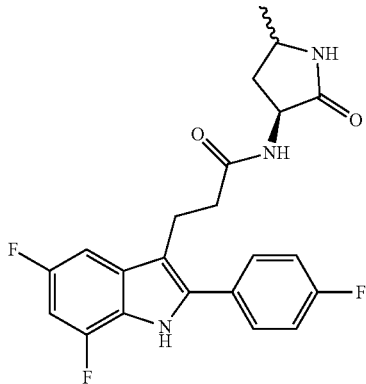 [SMILES: CC1C[C@H](NC(=O)CCc2c(-c3ccc(F)cc3)[nH]c3c(F)cc(F)cc23)C(=O)N1]
7
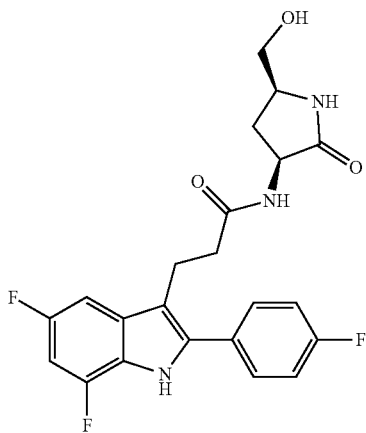 [SMILES: O=C(CCc1c(-c2ccc(F)cc2)[nH]c2c(F)cc(F)cc12)N[C@H]1C[C@@H](CO)NC1=O]
8
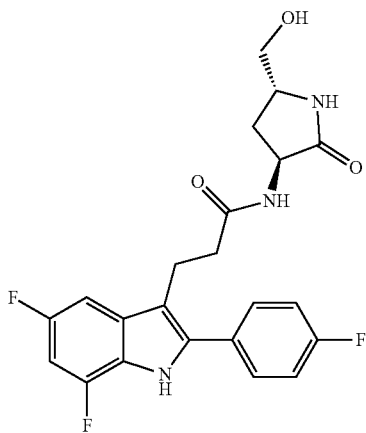 [SMILES: O=C(CCc1c(-c2ccc(F)cc2)[nH]c2c(F)cc(F)cc12)N[C@H]1C[C@H](CO)NC1=O]

TABLE 1-continued
Compounds 1 to 135
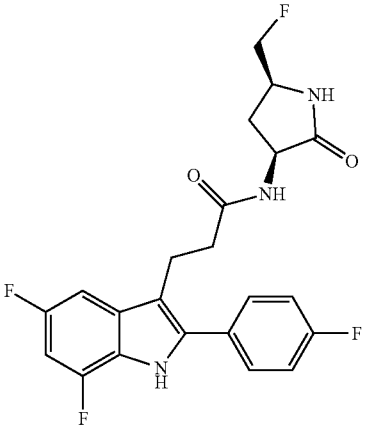 [SMILES: O=C(CCc1c(-c2ccc(F)cc2)[nH]c2c(F)cc(F)cc12)N[C@H]1C[C@@H](CF)NC1=O]
9
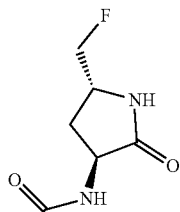
10
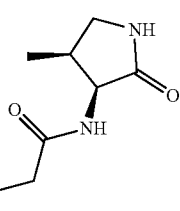
11
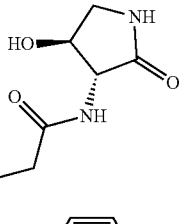
12

TABLE 1-continued
Compounds 1 to 135
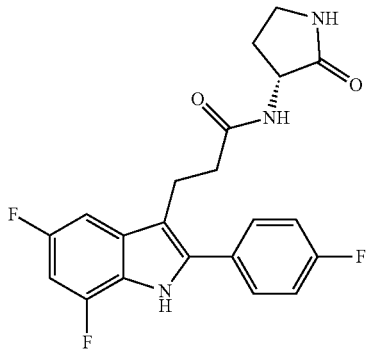 [SMILES: O=C(CCc1c(-c2ccc(F)cc2)[nH]c2c(F)cc(F)cc12)N[C@@H]1CCNC1=O]
13
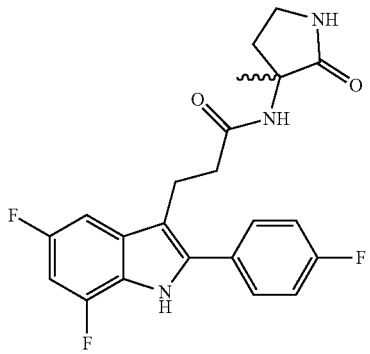 [SMILES: CC1(NC(=O)CCc2c(-c3ccc(F)cc3)[nH]c3c(F)cc(F)cc23)CCNC1=O]
14
15
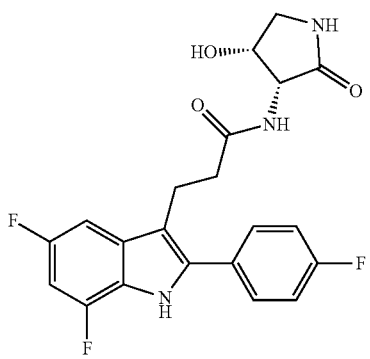 [SMILES: O=C(CCc1c(-c2ccc(F)cc2)[nH]c2c(F)cc(F)cc12)N[C@H]1C(=O)NC[C@H]1O]
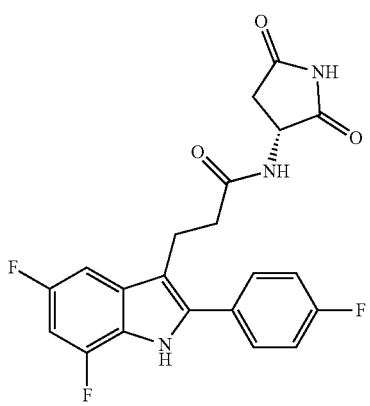 [SMILES: O=C1C[C@@H](NC(=O)CCc2c(-c3ccc(F)cc3)[nH]c3c(F)cc(F)cc23)C(=O)N1]
16

TABLE 1-continued
Compounds 1 to 135
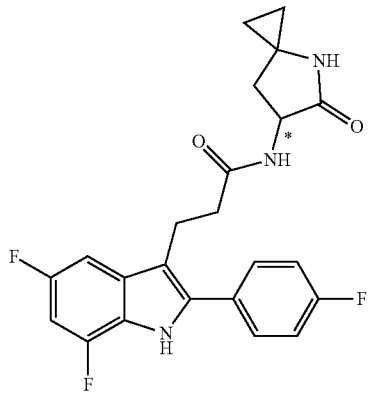 [SMILES: O=C(CCc1c(-c2ccc(F)cc2)[nH]c2c(F)cc(F)cc12)NC1CC2(CC2)NC1=O]
17
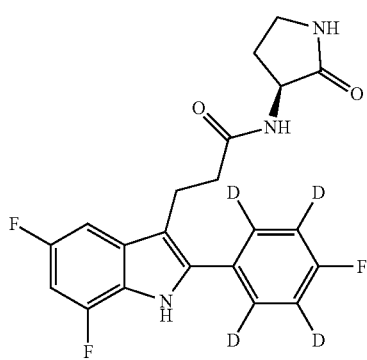 [SMILES: [2H]c1c([2H])c(-c2[nH]c3c(F)cc(F)cc3c2CCC(=O)N[C@H]2CCNC2=O)c([2H])c([2H])c1F]
18
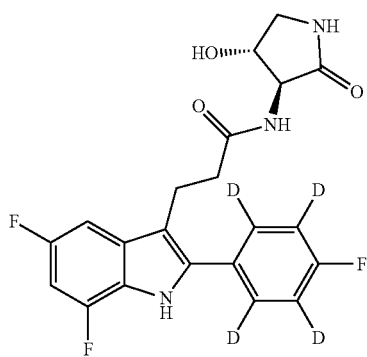 [SMILES: [2H]c1c([2H])c(-c2[nH]c3c(F)cc(F)cc3c2CCC(=O)N[C@@H]2C(=O)NC[C@H]2O)c([2H])c([2H])c1F]
19
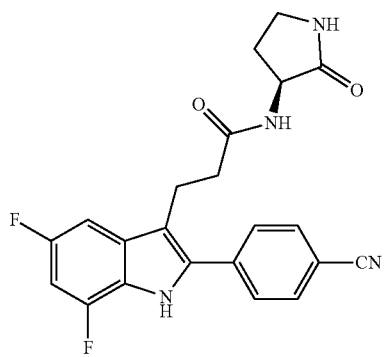 [SMILES: N#Cc1ccc(-c2[nH]c3c(F)cc(F)cc3c2CCC(=O)N[C@H]2CCNC2=O)cc1]
20

TABLE 1-continued
Compounds 1 to 135
| | |
|---|---|
| 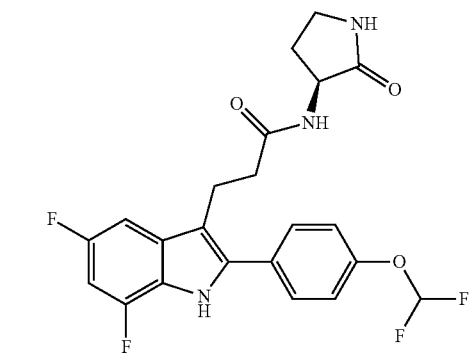 [SMILES: O=C(CCc1c(-c2ccc(OC(F)F)cc2)[nH]c2c(F)cc(F)cc12)N[C@H]1CCNC1=O] | 21 |
| 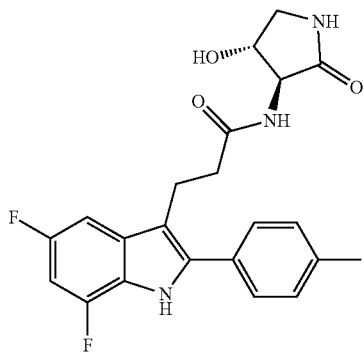 [SMILES: Cc1ccc(-c2[nH]c3c(F)cc(F)cc3c2CCC(=O)N[C@@H]2C(=O)NC[C@H]2O)cc1] | 22 |
| 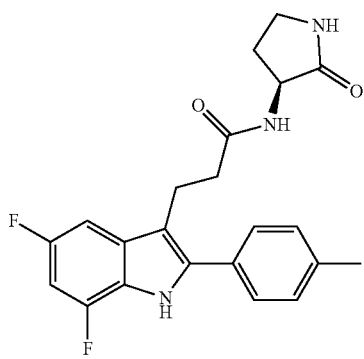 [SMILES: Cc1ccc(-c2[nH]c3c(F)cc(F)cc3c2CCC(=O)N[C@H]2CCNC2=O)cc1] | 23 |
| 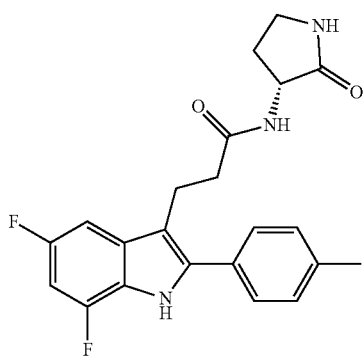 [SMILES: Cc1ccc(-c2[nH]c3c(F)cc(F)cc3c2CCC(=O)N[C@@H]2CCNC2=O)cc1] | 24 |

TABLE 1-continued
Compounds 1 to 135
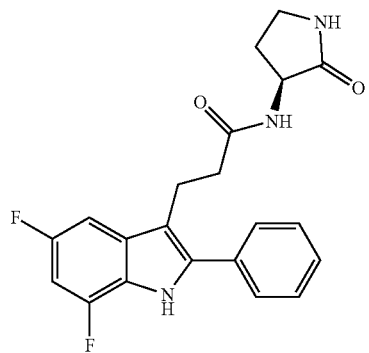 [SMILES: O=C(CCc1c(-c2ccccc2)[nH]c2c(F)cc(F)cc12)N[C@H]1CCNC1=O]
25
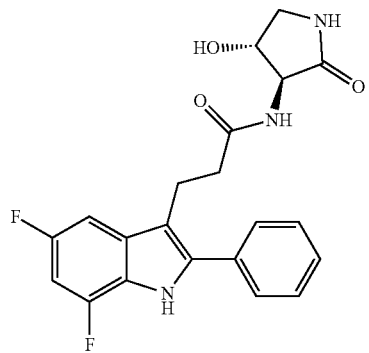 [SMILES: O=C(CCc1c(-c2ccccc2)[nH]c2c(F)cc(F)cc12)N[C@@H]1C(=O)NC[C@H]1O]
26
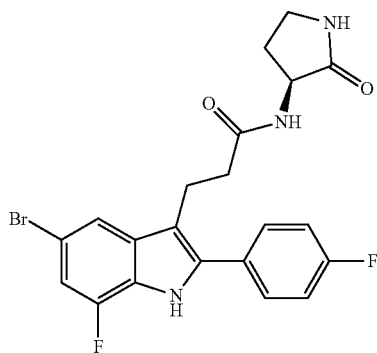
27
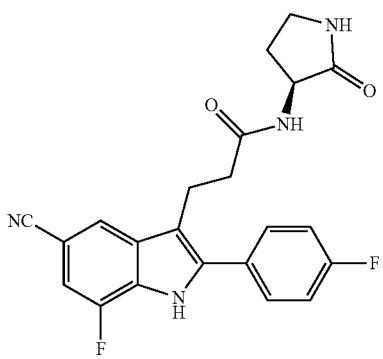 [SMILES: N#Cc1cc(F)c2[nH]c(-c3ccc(F)cc3)c(CCC(=O)N[C@H]3CCNC3=O)c2c1]
28

TABLE 1-continued
Compounds 1 to 135
| | |
|---|---|
| 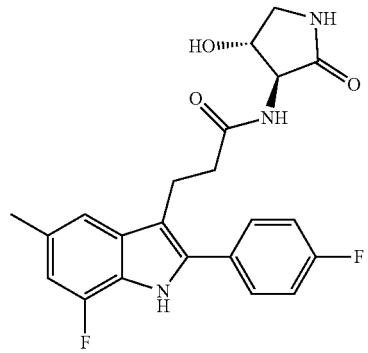 [SMILES: Cc1cc(F)c2[nH]c(-c3ccc(F)cc3)c(CCC(=O)N[C@@H]3C(=O)NC[C@H]3O)c2c1] | 29 |
| 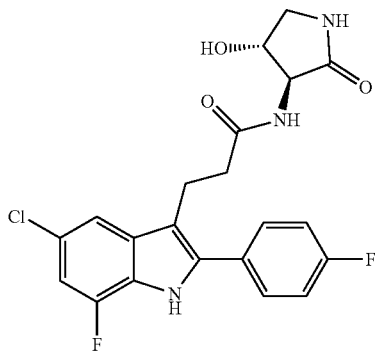 [SMILES: O=C(CCc1c(-c2ccc(F)cc2)[nH]c2c(F)cc(Cl)cc12)N[C@@H]1C(=O)NC[C@H]1O] | 30 |
| 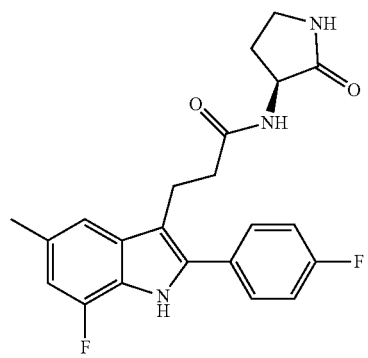 [SMILES: Cc1cc(F)c2[nH]c(-c3ccc(F)cc3)c(CCC(=O)N[C@H]3CCNC3=O)c2c1] | 31 |
| 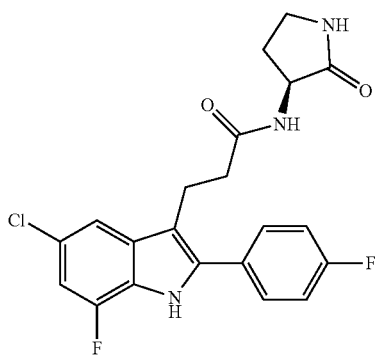 [SMILES: O=C(CCc1c(-c2ccc(F)cc2)[nH]c2c(F)cc(Cl)cc12)N[C@H]1CCNC1=O] | 32 |

TABLE 1-continued
Compounds 1 to 135
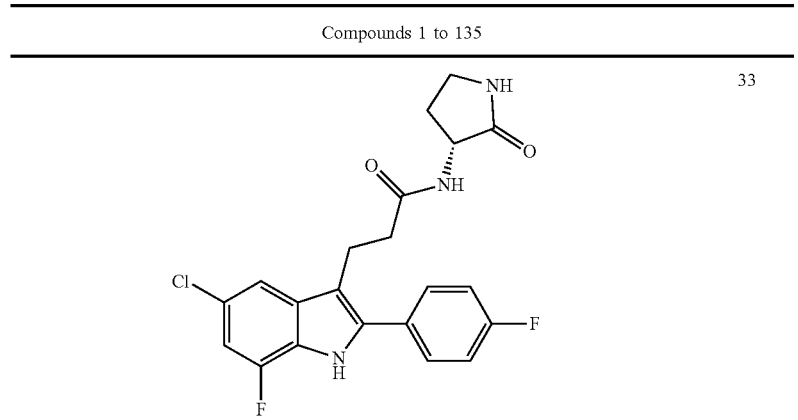
33
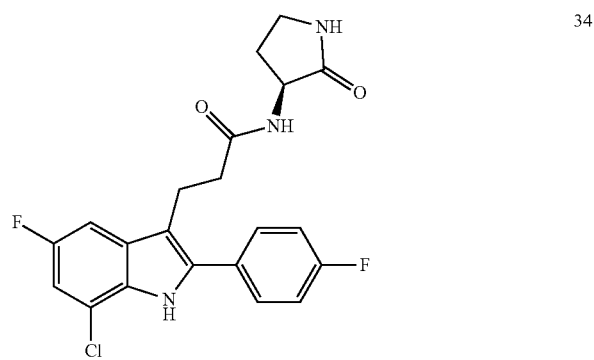
34
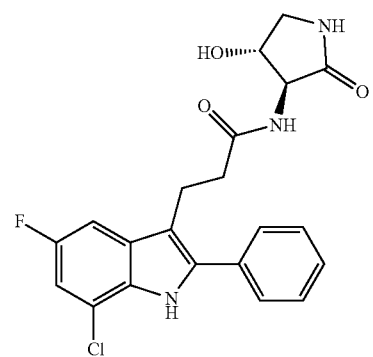
35
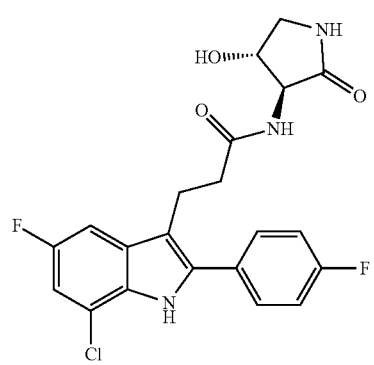 [SMILES: O=C(CCc1c(-c2ccc(F)cc2)[nH]c2c(Cl)cc(F)cc12)N[C@@H]1C(=O)NC[C@H]1O]
36

TABLE 1-continued
Compounds 1 to 135
| | |
|---|---|
| 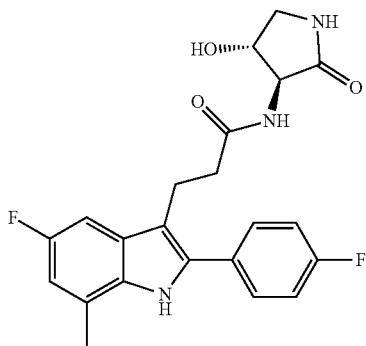 [SMILES: Cc1cc(F)cc2c(CCC(=O)N[C@@H]3C(=O)NC[C@H]3O)c(-c3ccc(F)cc3)[nH]c12] | 37 |
| 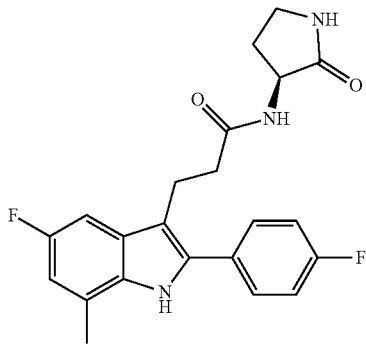 [SMILES: Cc1cc(F)cc2c(CCC(=O)N[C@H]3CCNC3=O)c(-c3ccc(F)cc3)[nH]c12] | 38 |
| 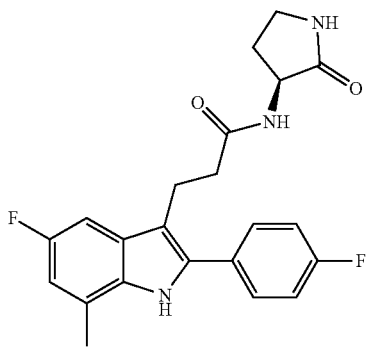 [SMILES: Cc1cc(F)cc2c(CCC(=O)N[C@H]3CCNC3=O)c(-c3ccc(F)cc3)[nH]c12] | 39 |
| 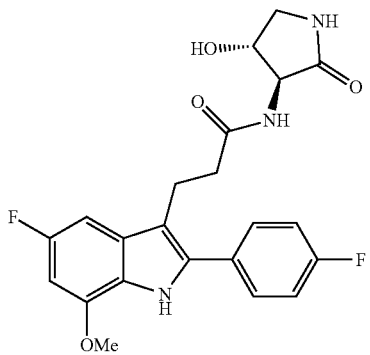 [SMILES: COc1cc(F)cc2c(CCC(=O)N[C@@H]3C(=O)NC[C@H]3O)c(-c3ccc(F)cc3)[nH]c12] | 40 |

TABLE 1-continued
Compounds 1 to 135
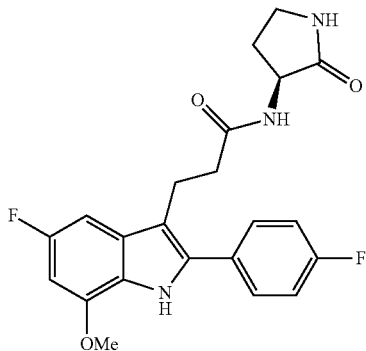 [SMILES: COc1cc(F)cc2c(CCC(=O)N[C@H]3CCNC3=O)c(-c3ccc(F)cc3)[nH]c12]
41
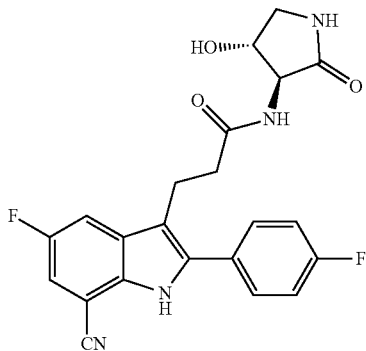 [SMILES: N#Cc1cc(F)cc2c(CCC(=O)N[C@@H]3C(=O)NC[C@H]3O)c(-c3ccc(F)cc3)[nH]c12]
42
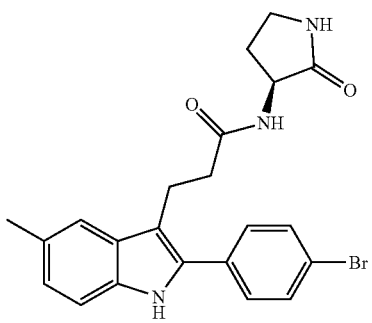 [SMILES: Cc1ccc2[nH]c(-c3ccc(Br)cc3)c(CCC(=O)N[C@H]3CCNC3=O)c2c1]
43
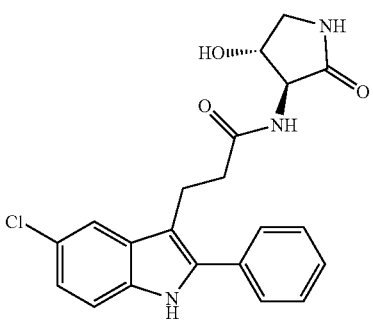 [SMILES: O=C(CCc1c(-c2ccccc2)[nH]c2ccc(Cl)cc12)N[C@@H]1C(=O)NC[C@H]1O]
44

TABLE 1-continued

Compounds 1 to 135

| | |
|---|---|
| [Structure: 5-chloro-2-(4-fluorophenyl)-1H-indol-3-yl propanamide linked to (3S,4S)-4-hydroxy-2-oxopyrrolidin-3-yl] | 45 |
| [Structure: 5-fluoro-2-(4-fluorophenyl)-1H-indol-3-yl propanamide linked to (3S,4S)-4-hydroxy-2-oxopyrrolidin-3-yl] | 46 |
| [Structure: 5-fluoro-2-(4-fluorophenyl)-1H-indol-3-yl propanamide linked to 2-oxopyrrolidin-3-yl (racemic)] | 47 |
| [Structure: 5-fluoro-2-(4-fluorophenyl)-1H-indol-3-yl propanamide linked to 2-oxopyrrolidin-3-yl (racemic)] | 48 |
| [Structure: 5-fluoro-2-(4-fluorophenyl)-1H-indol-3-yl propanamide linked to (S)-2-oxopyrrolidin-3-yl] | 49 |

TABLE 1-continued
Compounds 1 to 135
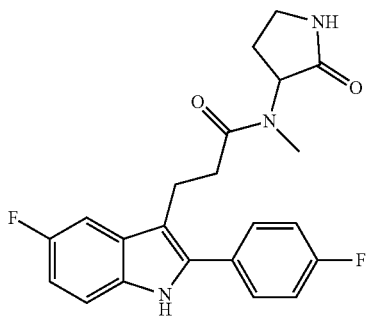 [SMILES: CN(C(=O)CCc1c(-c2ccc(F)cc2)[nH]c2ccc(F)cc12)C1CCNC1=O] 50
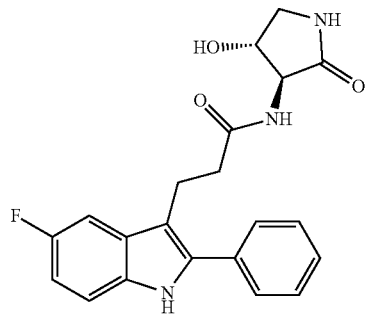 [SMILES: O=C(CCc1c(-c2ccccc2)[nH]c2ccc(F)cc12)N[C@@H]1C(=O)NC[C@H]1O] 51
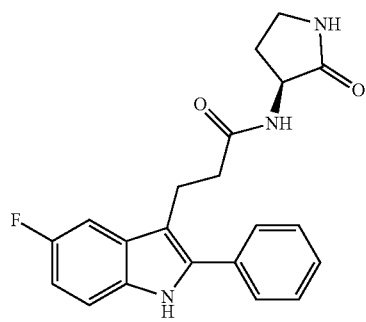 [SMILES: O=C(CCc1c(-c2ccccc2)[nH]c2ccc(F)cc12)N[C@H]1CCNC1=O] 52
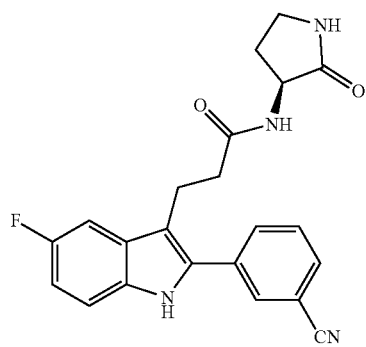 [SMILES: N#Cc1cccc(-c2[nH]c3ccc(F)cc3c2CCC(=O)N[C@H]2CCNC2=O)c1] 53

TABLE 1-continued
Compounds 1 to 135
| | |
|---|---|
| 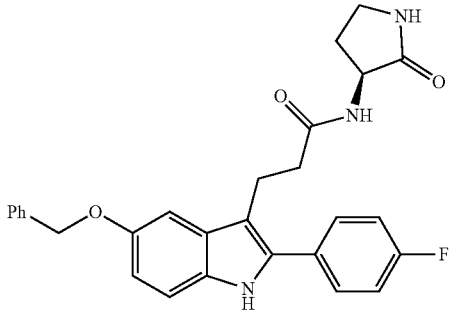 [SMILES: O=C(CCc1c(-c2ccc(F)cc2)[nH]c2ccc(OCc3ccccc3)cc12)N[C@H]1CCNC1=O] | 54 |
| 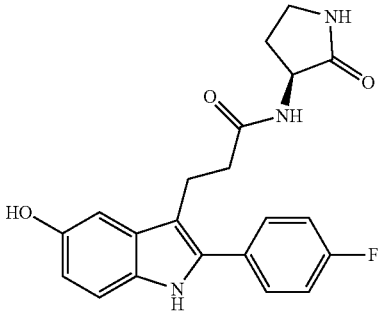 [SMILES: O=C(CCc1c(-c2ccc(F)cc2)[nH]c2ccc(O)cc12)N[C@H]1CCNC1=O] | 55 |
| 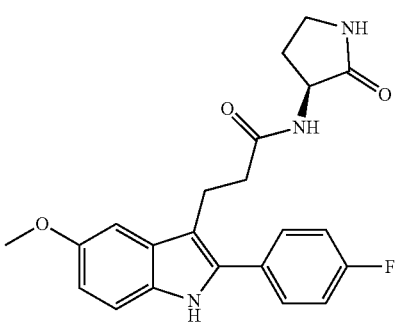 [SMILES: COc1ccc2[nH]c(-c3ccc(F)cc3)c(CCC(=O)N[C@H]3CCNC3=O)c2c1] | 56 |
| 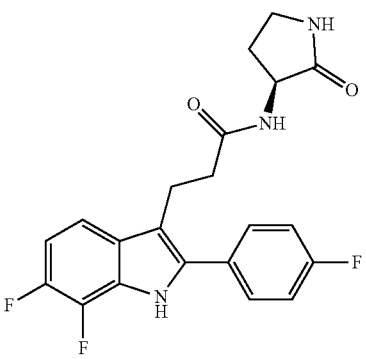 [SMILES: O=C(CCc1c(-c2ccc(F)cc2)[nH]c2c(F)c(F)ccc12)N[C@H]1CCNC1=O] | 57 |

TABLE 1-continued
Compounds 1 to 135
| | |
|---|---|
| 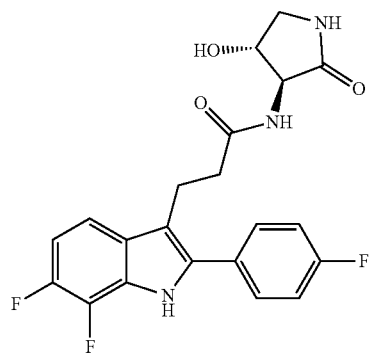 [SMILES: O=C(CCc1c(-c2ccc(F)cc2)[nH]c2c(F)c(F)ccc12)N[C@@H]1C(=O)NC[C@H]1O] | 58 |
|  | 59 |
| 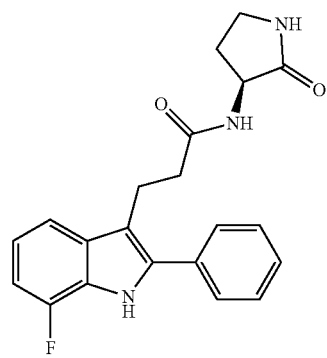 [SMILES: O=C(CCc1c(-c2ccccc2)[nH]c2c(F)cccc12)N[C@H]1CCNC1=O] | 60 |
| 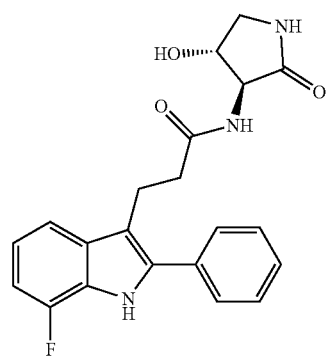 [SMILES: O=C(CCc1c(-c2ccccc2)[nH]c2c(F)cccc12)N[C@@H]1C(=O)NC[C@H]1O] | 61 |

TABLE 1-continued

Compounds 1 to 135

| | |
|---|---|
| (structure) | 62 |
| (structure) | 63 |
| (structure) | 64 |
| (structure) | 65 |

TABLE 1-continued
Compounds 1 to 135
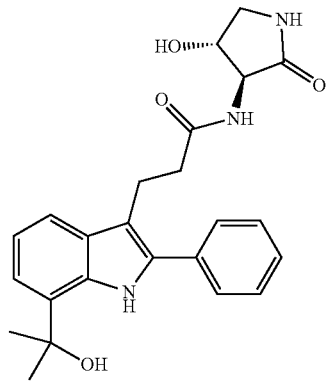 [SMILES: CC(C)(O)c1cccc2c(CCC(=O)N[C@@H]3C(=O)NC[C@H]3O)c(-c3ccccc3)[nH]c12] 66
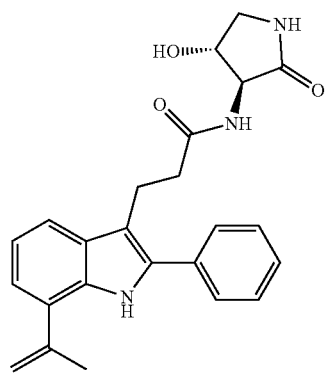 [SMILES: C=C(C)c1cccc2c(CCC(=O)N[C@@H]3C(=O)NC[C@H]3O)c(-c3ccccc3)[nH]c12] 67
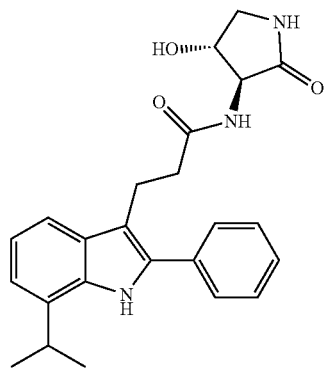 [SMILES: CC(C)c1cccc2c(CCC(=O)N[C@@H]3C(=O)NC[C@H]3O)c(-c3ccccc3)[nH]c12] 68
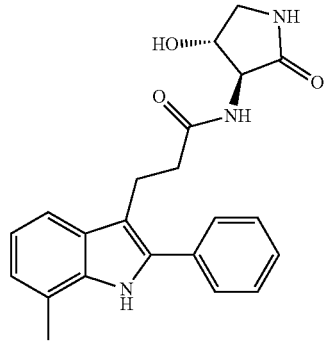 [SMILES: Cc1cccc2c(CCC(=O)N[C@@H]3C(=O)NC[C@H]3O)c(-c3ccccc3)[nH]c12] 69

TABLE 1-continued
Compounds 1 to 135
| | |
|---|---|
| 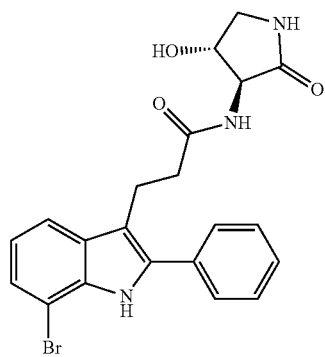 | 70 |
| 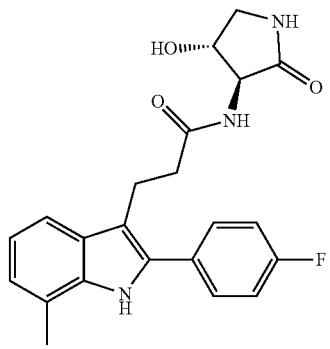 [SMILES: Cc1cccc2c(CCC(=O)N[C@@H]3C(=O)NC[C@H]3O)c(-c3ccc(F)cc3)[nH]c12] | 71 |
| 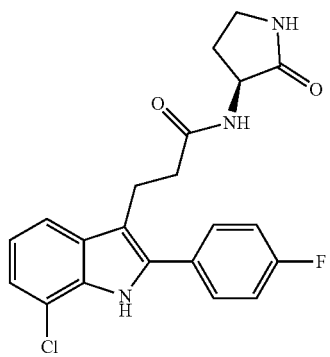 | 72 |
| 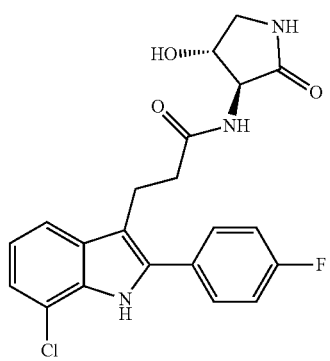 [SMILES: O=C(CCc1c(-c2ccc(F)cc2)[nH]c2c(Cl)cccc12)N[C@@H]1C(=O)NC[C@H]1O] | 73 |

TABLE 1-continued
Compounds 1 to 135
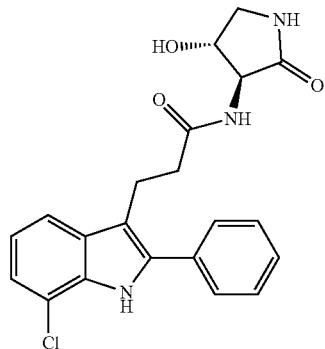
74
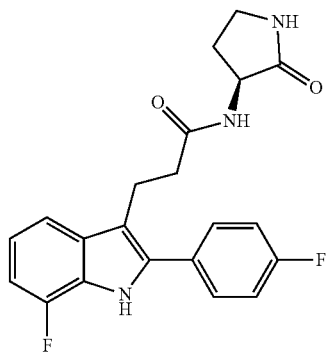 [SMILES: O=C(CCc1c(-c2ccc(F)cc2)[nH]c2c(F)cccc12)N[C@H]1CCNC1=O]
75
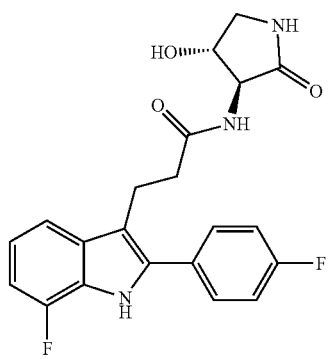 [SMILES: O=C(CCc1c(-c2ccc(F)cc2)[nH]c2c(F)cccc12)N[C@@H]1C(=O)NC[C@H]1O]
76
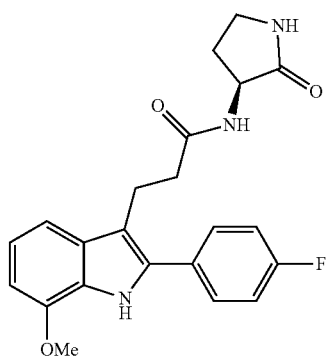 [SMILES: COc1cccc2c(CCC(=O)N[C@H]3CCNC3=O)c(-c3ccc(F)cc3)[nH]c12]
77

TABLE 1-continued
Compounds 1 to 135
| | |
|---|---|
| 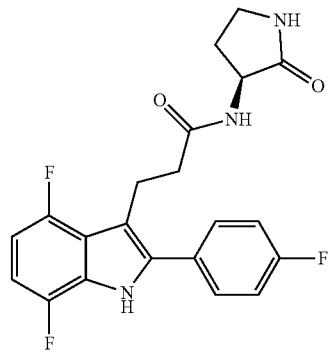 [SMILES: O=C(CCc1c(-c2ccc(F)cc2)[nH]c2c(F)ccc(F)c12)N[C@H]1CCNC1=O] | 78 |
| 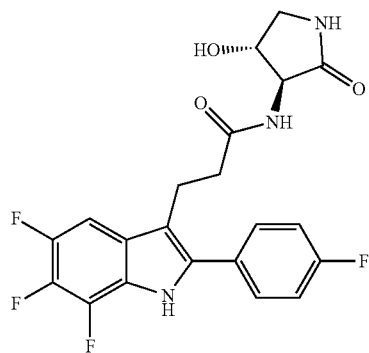 [SMILES: O=C(CCc1c(-c2ccc(F)cc2)[nH]c2c(F)c(F)c(F)cc12)N[C@@H]1C(=O)NC[C@H]1O] | 79 |
| 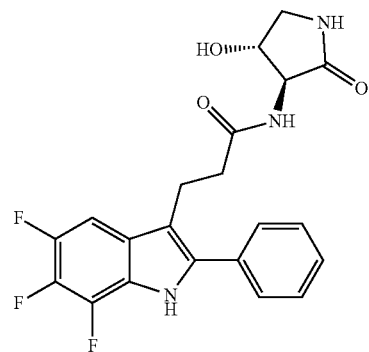 [SMILES: O=C(CCc1c(-c2ccccc2)[nH]c2c(F)c(F)c(F)cc12)N[C@@H]1C(=O)NC[C@H]1O] | 80 |
| 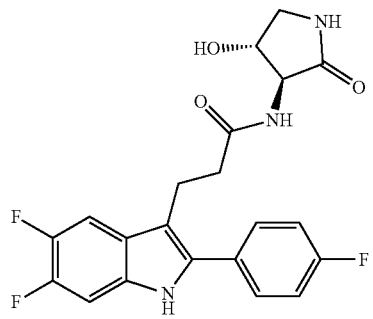 [SMILES: O=C(CCc1c(-c2ccc(F)cc2)[nH]c2cc(F)c(F)cc12)N[C@@H]1C(=O)NC[C@H]1O] | 81 |

TABLE 1-continued
Compounds 1 to 135
| | |
|---|---|
| 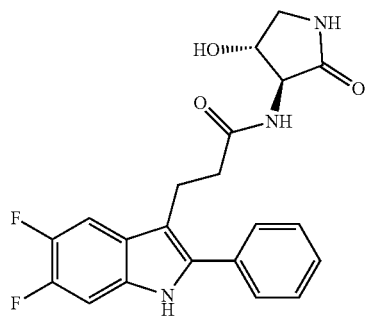 [SMILES: O=C(CCc1c(-c2ccccc2)[nH]c2cc(F)c(F)cc12)N[C@@H]1C(=O)NC[C@H]1O] | 82 |
| 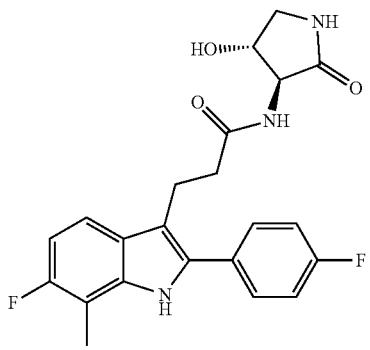 [SMILES: Cc1c(F)ccc2c(CCC(=O)N[C@@H]3C(=O)NC[C@H]3O)c(-c3ccc(F)cc3)[nH]c12] | 83 |
| 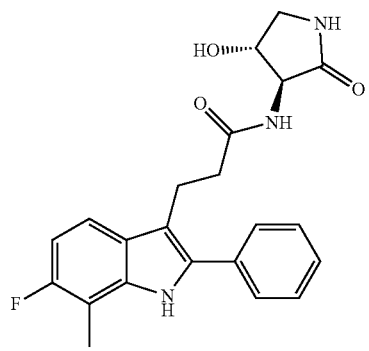 [SMILES: Cc1c(F)ccc2c(CCC(=O)N[C@@H]3C(=O)NC[C@H]3O)c(-c3ccccc3)[nH]c12] | 84 |
| 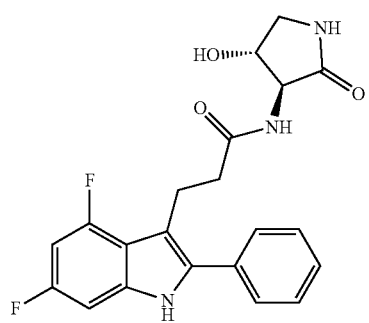 [SMILES: O=C(CCc1c(-c2ccccc2)[nH]c2cc(F)cc(F)c12)N[C@@H]1C(=O)NC[C@H]1O] | 85 |

TABLE 1-continued
Compounds 1 to 135
| | |
|---|---|
| 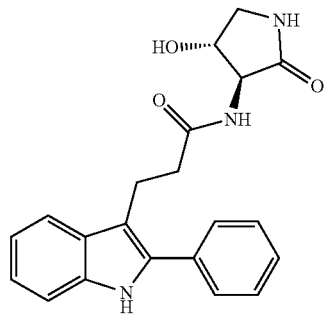 [SMILES: O=C(CCc1c(-c2ccccc2)[nH]c2ccccc12)N[C@@H]1C(=O)NC[C@H]1O] | 86 |
| 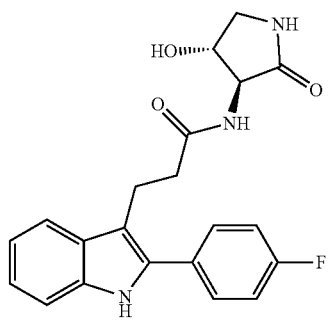 [SMILES: O=C(CCc1c(-c2ccc(F)cc2)[nH]c2ccccc12)N[C@@H]1C(=O)NC[C@H]1O] | 87 |
| 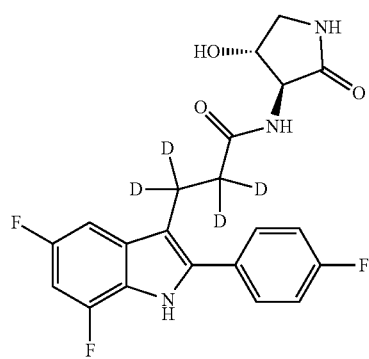 [SMILES: [2H]C([2H])(C(=O)N[C@@H]1C(=O)NC[C@H]1O)C([2H])([2H])c1c(-c2ccc(F)cc2)[nH]c2c(F)cc(F)cc12] | 88 |
| 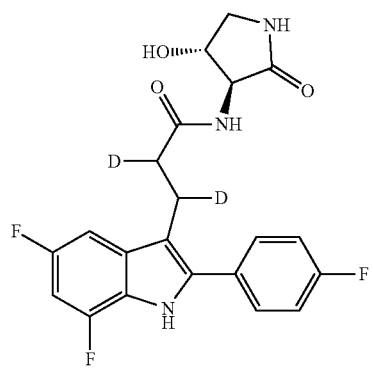 [SMILES: [2H]C(C(=O)N[C@@H]1C(=O)NC[C@H]1O)C([2H])c1c(-c2ccc(F)cc2)[nH]c2c(F)cc(F)cc12] | 89 |

TABLE 1-continued
Compounds 1 to 135
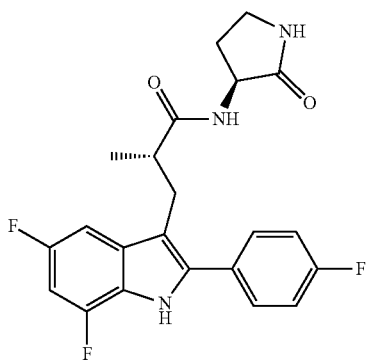 [SMILES: C[C@@H](Cc1c(-c2ccc(F)cc2)[nH]c2c(F)cc(F)cc12)C(=O)N[C@H]1CCNC1=O]
90
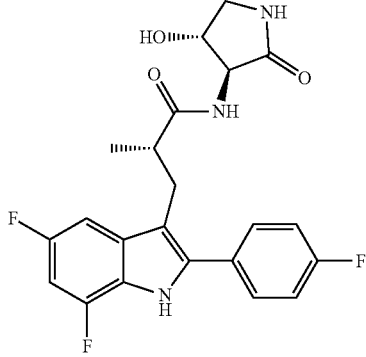 [SMILES: C[C@@H](Cc1c(-c2ccc(F)cc2)[nH]c2c(F)cc(F)cc12)C(=O)N[C@@H]1C(=O)NC[C@H]1O]
91
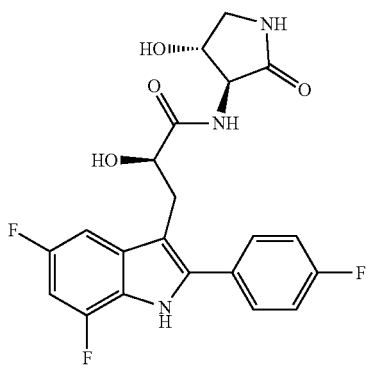 [SMILES: O=C(N[C@@H]1C(=O)NC[C@H]1O)[C@H](O)Cc1c(-c2ccc(F)cc2)[nH]c2c(F)cc(F)cc12]
92
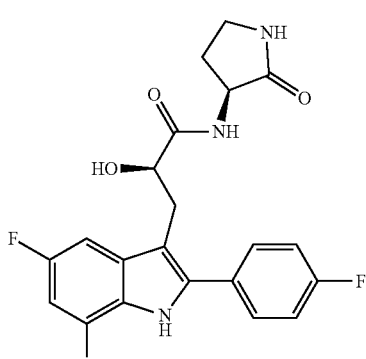
93

TABLE 1-continued
Compounds 1 to 135
| | |
|---|---|
| 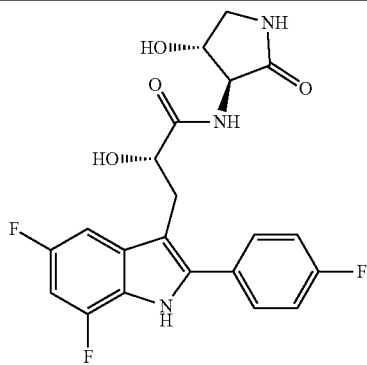 | 94 |
| 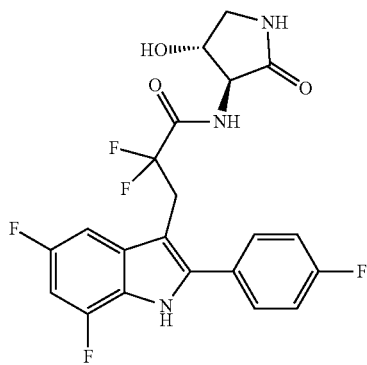 [SMILES: O=C1NC[C@@H](O)[C@@H]1NC(=O)C(F)(F)Cc1c(-c2ccc(F)cc2)[nH]c2c(F)cc(F)cc12] | 95 |
| 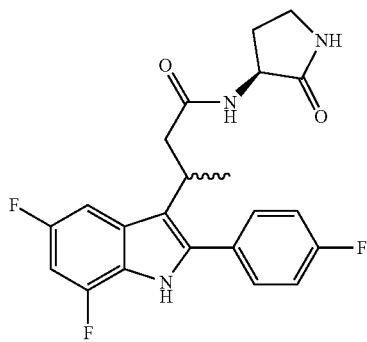 [SMILES: CC(CC(=O)N[C@H]1CCNC1=O)c1c(-c2ccc(F)cc2)[nH]c2c(F)cc(F)cc12] | 96 |
| 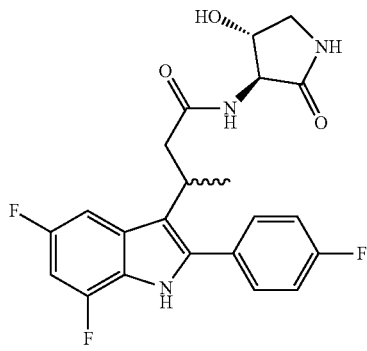 [SMILES: CC(CC(=O)N[C@@H]1C(=O)NC[C@H]1O)c1c(-c2ccc(F)cc2)[nH]c2c(F)cc(F)cc12] | 97 |

TABLE 1-continued
Compounds 1 to 135
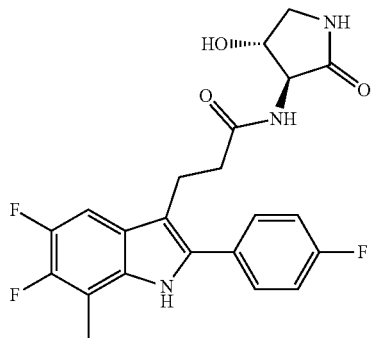 [SMILES: Cc1c(F)c(F)cc2c(CCC(=O)N[C@@H]3C(=O)NC[C@H]3O)c(-c3ccc(F)cc3)[nH]c12]
98
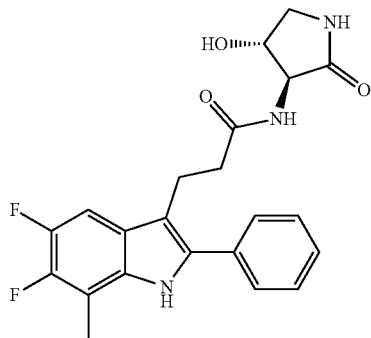 [SMILES: Cc1c(F)c(F)cc2c(CCC(=O)N[C@@H]3C(=O)NC[C@H]3O)c(-c3ccccc3)[nH]c12]
99
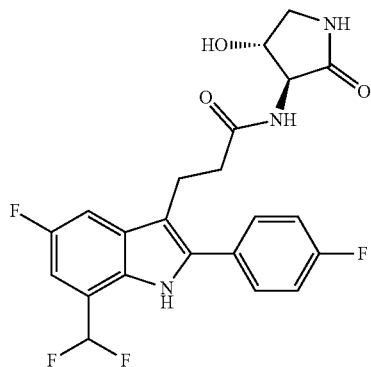 [SMILES: O=C(CCc1c(-c2ccc(F)cc2)[nH]c2c(C(F)F)cc(F)cc12)N[C@@H]1C(=O)NC[C@H]1O]
100
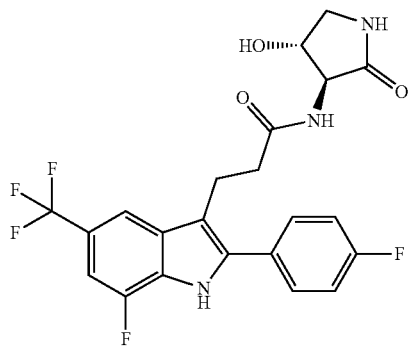 [SMILES: O=C(CCc1c(-c2ccc(F)cc2)[nH]c2c(F)cc(C(F)(F)F)cc12)N[C@@H]1C(=O)NC[C@H]1O]
101

TABLE 1-continued
Compounds 1 to 135
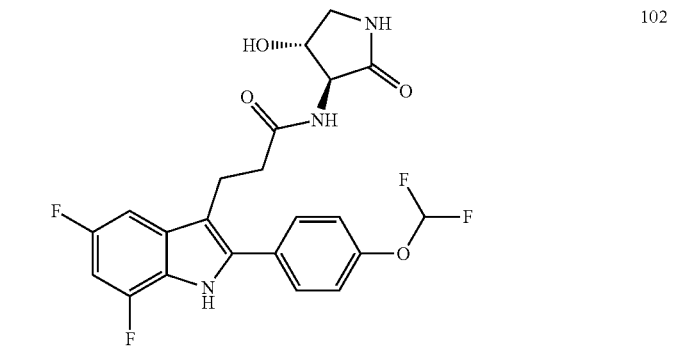
102
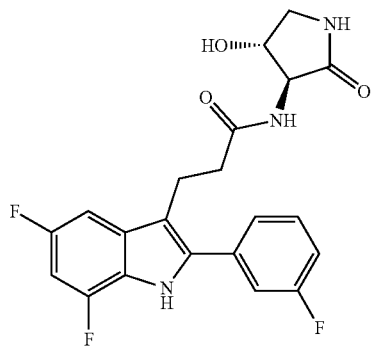 [SMILES: O=C(CCc1c(-c2cccc(F)c2)[nH]c2c(F)cc(F)cc12)N[C@@H]1C(=O)NC[C@H]1O]
103
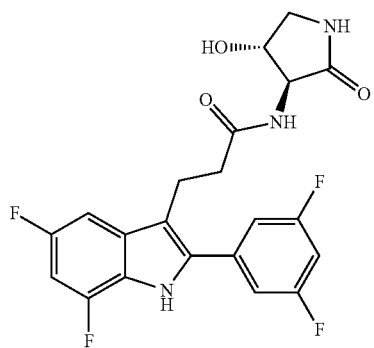 [SMILES: O=C(CCc1c(-c2cc(F)cc(F)c2)[nH]c2c(F)cc(F)cc12)N[C@@H]1C(=O)NC[C@H]1O]
104
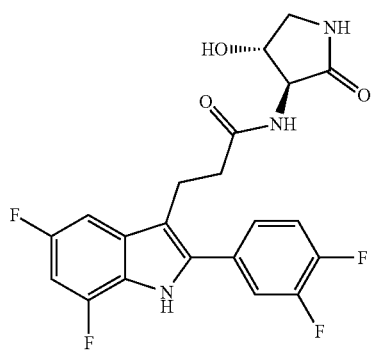 [SMILES: O=C(CCc1c(-c2ccc(F)c(F)c2)[nH]c2c(F)cc(F)cc12)N[C@@H]1C(=O)NC[C@H]1O]
105

TABLE 1-continued
Compounds 1 to 135
| | |
|---|---|
| 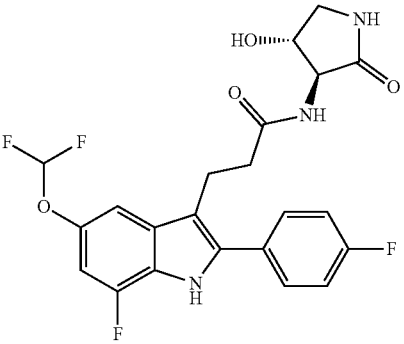 | 106 |
| 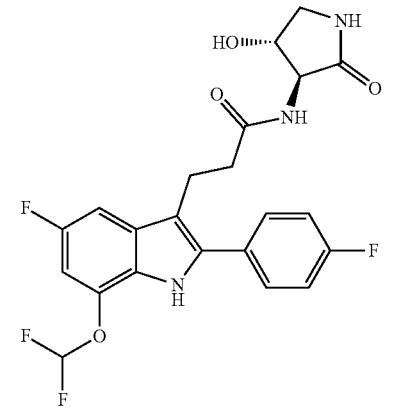 [SMILES: O=C(CCc1c(-c2ccc(F)cc2)[nH]c2c(OC(F)F)cc(F)cc12)N[C@@H]1C(=O)NC[C@H]1O] | 107 |
| 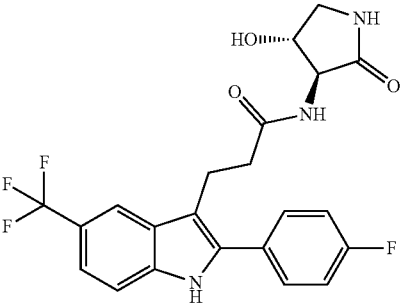 [SMILES: O=C(CCc1c(-c2ccc(F)cc2)[nH]c2ccc(C(F)(F)F)cc12)N[C@@H]1C(=O)NC[C@H]1O] | 108 |
| 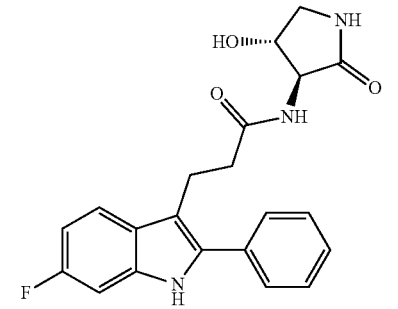 [SMILES: O=C(CCc1c(-c2ccccc2)[nH]c2cc(F)ccc12)N[C@@H]1C(=O)NC[C@H]1O] | 109 |

TABLE 1-continued
Compounds 1 to 135
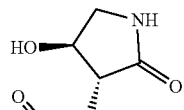
110
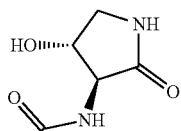
111
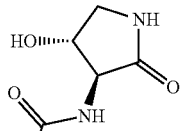
112
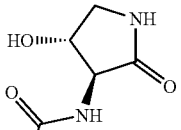
113

TABLE 1-continued
Compounds 1 to 135
114
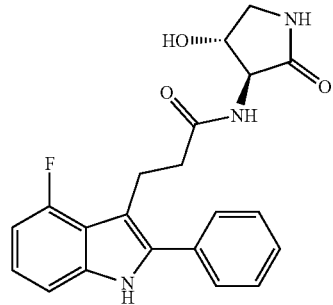 [SMILES: O=C(CCc1c(-c2ccccc2)[nH]c2cccc(F)c12)N[C@@H]1C(=O)NC[C@H]1O]
115
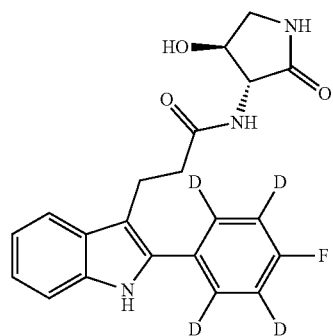 [SMILES: [2H]c1c([2H])c(-c2[nH]c3ccccc3c2CCC(=O)N[C@H]2C(=O)NC[C@@H]2O)c([2H])c([2H])c1F]
116
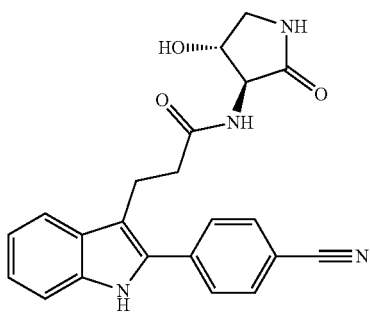 [SMILES: N#Cc1ccc(-c2[nH]c3ccccc3c2CCC(=O)N[C@@H]2C(=O)NC[C@H]2O)cc1]
117
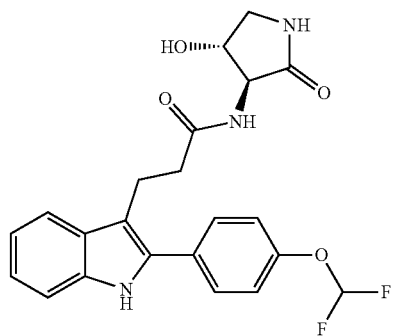 [SMILES: O=C(CCc1c(-c2ccc(OC(F)F)cc2)[nH]c2ccccc12)N[C@@H]1C(=O)NC[C@H]1O]

TABLE 1-continued
Compounds 1 to 135
| | |
|---|---|
| 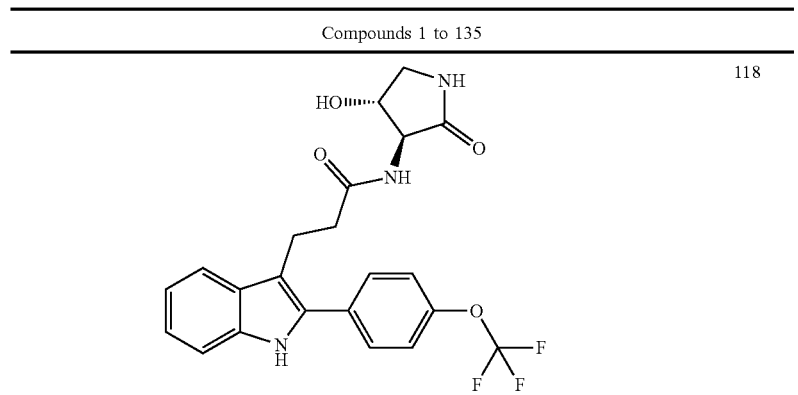 | 118 |
| 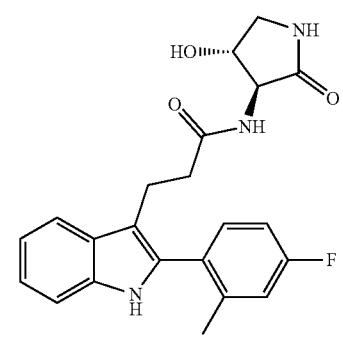 [SMILES: Cc1cc(F)ccc1-c1[nH]c2ccccc2c1CCC(=O)N[C@@H]1C(=O)NC[C@H]1O] | 119 |
| 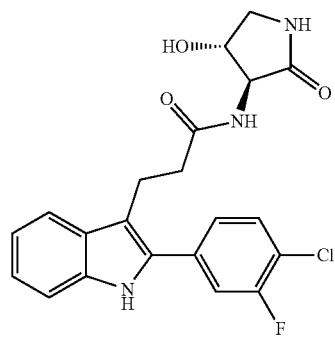 [SMILES: O=C(CCc1c(-c2ccc(Cl)c(F)c2)[nH]c2ccccc12)N[C@@H]1C(=O)NC[C@H]1O] | 120 |
| 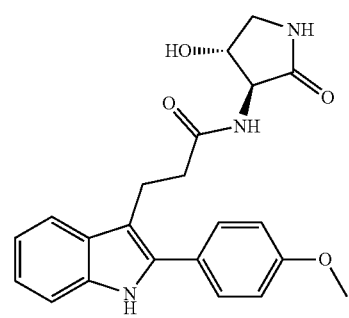 [SMILES: COc1ccc(-c2[nH]c3ccccc3c2CCC(=O)N[C@@H]2C(=O)NC[C@H]2O)cc1] | 121 |

TABLE 1-continued

Compounds 1 to 135

| | |
|---|---|
| (structure) | 122 |
| (structure) | 123 |
| (structure) | 124 |
| (structure) | 125 |
| (structure) | 126 |

TABLE 1-continued

Compounds 1 to 135

| | |
|---|---|
| [Structure of compound 127] | 127 |
| [Structure of compound 128] | 128 |
| [Structure of compound 129] | 129 |
| [Structure of compound 130] | 130 |
| [Structure of compound 131] | 131 |

TABLE 1-continued
Compounds 1 to 135
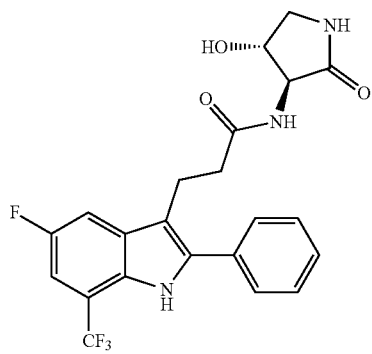 [SMILES: O=C(CCc1c(-c2ccccc2)[nH]c2c(C(F)(F)F)cc(F)cc12)N[C@@H]1C(=O)NC[C@H]1O] 132
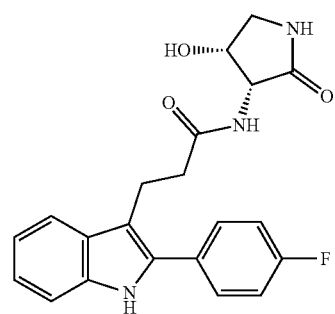 [SMILES: O=C(CCc1c(-c2ccc(F)cc2)[nH]c2ccccc12)N[C@H]1C(=O)NC[C@H]1O] 133
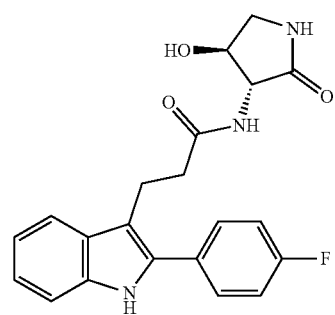 134
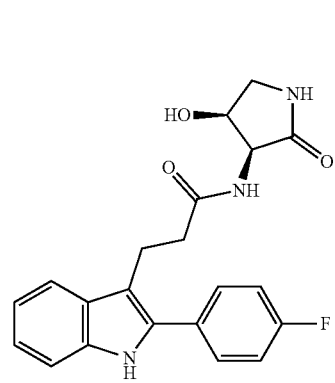 [SMILES: O=C(CCc1c(-c2ccc(F)cc2)[nH]c2ccccc12)N[C@@H]1C(=O)NC[C@@H]1O] 135

Some embodiments of the disclosure include derivatives of Compounds 1 to 135 or compounds of Formulae (I), (II), (IIIa), (IIIb), and (IIIc). In some embodiments, the derivatives are silicon derivatives in which at least one carbon atom in a compound chosen from Compounds 1 to 135 or compounds of Formulae (I), (II), (IIIa), (IIIb), and (IIIc), has been replaced by silicon. In some embodiments, the derivatives are boron derivatives, in which at least one carbon atom in a compound chosen from Compounds 1 to 135 or compounds of Formulae (I), (II), (IIIa), (IIIb), and (IIIc), has been replaced by boron. In other embodiments, the derivatives are phosphorus derivatives, in which at least one carbon atom in a compound chosen from Compounds 1 to 135 or compounds of Formulae (I), (II), (IIIa), (IIIb), and (IIIc) has been replaced by phosphorus. Because the general properties of silicon, boron, and phosphorus are similar to those of carbon, replacement of carbon by silicon, boron, or phosphorus can result in compounds with similar biological activity to a carbon containing original compound.

In some embodiments, the derivative is a silicon derivative in which one carbon atom in a compound chosen from Compounds 1 to 135 or compounds of Formulae (I), (II), (IIIa), (IIIb), and (IIIc) has been replaced by silicon or a silicon derivative (e.g. —Si(CH$_3$)$_2$— or —Si(OH)$_2$—). The carbon replaced by silicon may be a non-aromatic carbon. In other embodiments, a fluorine has been replaced by silicon derivative (e.g. —Si(CH$_3$)$_3$). In some embodiments, the silicon derivatives of the disclosure may include one or more hydrogen atoms replaced by deuterium. In some embodiments, a silicon derivative of compound chosen from Compounds 1 to 135 or compounds of Formulae (I), (II), (IIIa), (IIIb), and (IIIc) may have silicon incorporated into a heterocycle ring.

In some embodiments, examples of silicon derivatives of Compounds 1 to 135 or compounds of Formulae (I), (II), (IIIa), (IIIb), and (IIIc) include the following compounds:

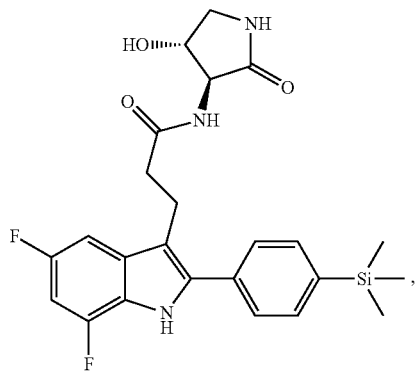

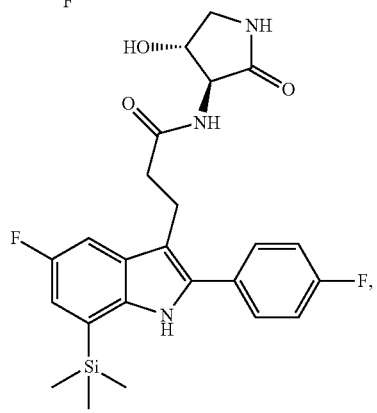

-continued

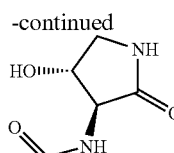

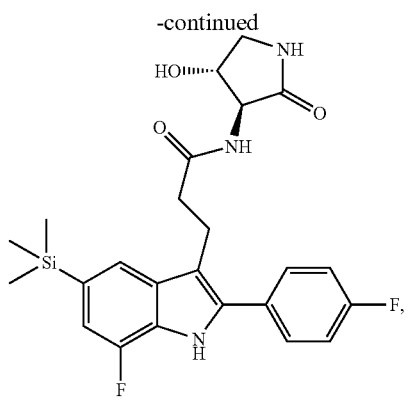

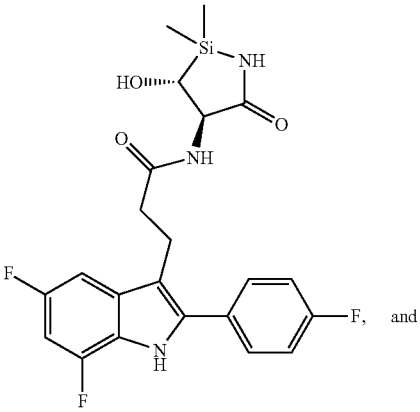

and

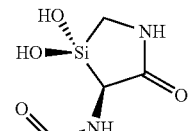

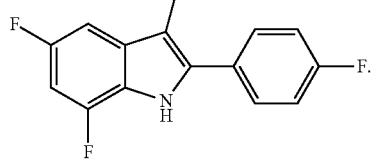

In some embodiments, examples of boron derivatives of Compounds 1 to 135 or compounds of Formulae (I), (II), (IIIa), (IIIb), and (IIIc) include the following compound:

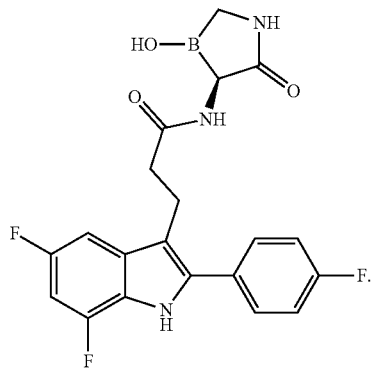 [SMILES: O=C(CCc1c(-c2ccc(F)cc2)[nH]c2c(F)cc(F)cc12)N[C@H]1B(O)CNC1=O]

In some embodiments, examples of phosphorus derivatives of Compounds 1 to 135 or compounds of Formulae (I), (II), (IIIa), (IIIb), and (IIIc) include the following compounds:

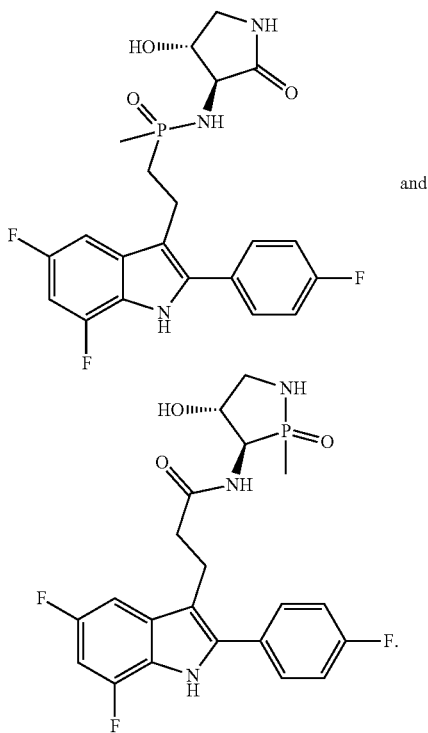

Another aspect of the disclosure provides pharmaceutical compositions comprising at least one compound according to any one formula chosen from Formulae (I), (II), (IIIa), (IIIb), and (IIIc) and Compounds 1 to 135, pharmaceutically acceptable salts of any of those compounds, solvates of any of the foregoing, and deuterated derivatives of any of the foregoing. In some embodiments, the pharmaceutical composition comprising at least one compound chosen from Formulae (I), (II), (IIIa), (IIIb), and (IIIc) and Compounds 1 to 135, pharmaceutically acceptable salts of any of those compounds, solvates of any of the foregoing, and deuterated derivatives of any of the foregoing is administered to a patient in need thereof.

A pharmaceutical composition may further comprise at least one pharmaceutically acceptable carrier. In some embodiments, the at least one pharmaceutically acceptable carrier is chosen from pharmaceutically acceptable vehicles and pharmaceutically acceptable adjuvants. In some embodiments, the at least one pharmaceutically acceptable is chosen from pharmaceutically acceptable fillers, disintegrants, surfactants, binders, lubricants.

It will also be appreciated that a pharmaceutical composition of this disclosure can be employed in combination therapies; that is, the pharmaceutical compositions described herein can further include at least one additional active therapeutic agent. Alternatively, a pharmaceutical composition comprising at least one compound chosen from compounds of Formulae (I), (II), (IIIa), (IIIb), and (IIIc), pharmaceutically acceptable salts of any of those compounds, solvates of any of the foregoing, and deuterated derivatives of any of the foregoing can be administered as a separate composition concurrently with, prior to, or subsequent to, a composition comprising at least one other active therapeutic agent. In some embodiments, a pharmaceutical composition comprising at least one compound chosen from Compounds 1 to 135, pharmaceutically acceptable salts of any of those compounds, solvates of any of the foregoing, and deuterated derivatives of any of the foregoing can be administered as a separate composition concurrently with, prior to, or subsequent to, a composition comprising at least one other active therapeutic agent.

As described above, pharmaceutical compositions disclosed herein may optionally further comprise at least one pharmaceutically acceptable carrier. The at least one pharmaceutically acceptable carrier may be chosen from adjuvants and vehicles. The at least one pharmaceutically acceptable carrier, as used herein, includes any and all solvents, diluents, other liquid vehicles, dispersion aids, suspension aids, surface active agents, isotonic agents, thickening agents, emulsifying agents, preservatives, solid binders, and lubricants, as suited to the particular dosage form desired. Remington: *The Science and Practice of Pharmacy*, 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988 to 1999, Marcel Dekker, New York discloses various carriers used in formulating pharmaceutical compositions and known techniques for the preparation thereof. Except insofar as any conventional carrier is incompatible with the compounds of this disclosure, such as by producing any undesirable biological effect or otherwise interacting in a deleterious manner with any other component(s) of the pharmaceutical composition, its use is contemplated to be within the scope of this disclosure. Non-limiting examples of suitable pharmaceutically acceptable carriers include, but are not limited to, ion exchangers, alumina, aluminum stearate, lecithin, serum proteins (such as human serum albumin), buffer substances (such as phosphates, glycine, sorbic acid, and potassium sorbate), partial glyceride mixtures of saturated vegetable fatty acids, water, salts, and electrolytes (such as protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, wool fat, sugars (such as lactose, glucose and sucrose), starches (such as corn starch and potato starch), cellulose and its derivatives (such as sodium carboxymethyl cellulose, ethyl cellulose and cellulose acetate), powdered tragacanth, malt, gelatin, talc, excipients (such as cocoa butter and suppository waxes), oils (such as peanut oil, cottonseed oil, safflower oil, sesame oil, olive oil, corn oil and soybean oil), glycols (such as propylene glycol and polyethylene glycol), esters (such as ethyl oleate and ethyl laurate), agar, buffering agents (such as magnesium hydroxide and aluminum hydroxide), alginic acid, pyrogen-free water, isotonic saline, Ringer's solution, ethyl alcohol, phosphate buffer solutions, non-toxic compatible lubricants (such as sodium lauryl sulfate and magnesium stearate), coloring agents, releasing agents, coating agents, sweetening agents, flavoring agents, perfuming agents, preservatives, and antioxidants.

In some embodiments of the disclosure, the compounds and the pharmaceutical compositions described herein are used to treat FSGS and/or NDKD. In some embodiments, FSGS is mediated by APOL1. In some embodiments, NDKD is mediated by APOL1.

In some embodiments, the methods of the disclosure comprise administering to a patient in need thereof at least one entity chosen from compounds of Formulae (I), (II), (IIIa), (IIIb), and (IIIc), pharmaceutically acceptable salts of any of those compounds, solvates of any of the foregoing, and deuterated derivatives of any of the foregoing. In some embodiments, the compound of Formula I is chosen from Compounds 1 to 135, pharmaceutically acceptable salts of any of those compounds, solvates of any of the foregoing, and deuterated derivatives of any of the foregoing. In some embodiments, said patient in need thereof possesses APOL1 genetic variants, i.e., G1: S342G:I384 M and G2: N388del: Y389del.

Another aspect of the disclosure provides methods of inhibiting APOL1 activity comprising contacting said APOL1 with at least one entity chosen from compounds of Formulae (I), (II), (IIIa), (IIIb), and (IIIc), pharmaceutically acceptable salts of any of those compounds, solvates of any of the foregoing, and deuterated derivatives of any of the foregoing. In some embodiments, the methods of inhibiting APOL1 activity comprise contacting said APOL1 with at least one entity chosen from Compounds 1 to 135, pharmaceutically acceptable salts of any of those compounds, solvates of any of the foregoing, and deuterated derivatives of any of the foregoing.

Solid Forms of Compound 2

In some embodiments, the at least one entity chosen from compounds of Formula (I) is Compound 2. Compound 2 can be depicted as follows:

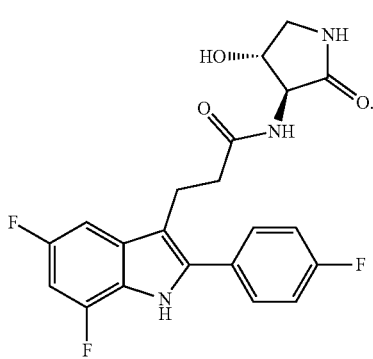

(2)

In some embodiments, Compound 2 is an amorphous solid. In some embodiments, Compound 2 is a crystalline solid. In some embodiments, Compound 2 is in the form of Form A, Hydrate Form A, Hydrate Form B, Hydrate Form C, Hydrate Form C, Hydrate Form D, Hydrate Form E, Compound 2 MTBE solvate, Compound 2 DMF solvate, or a mixture of any two or more of the foregoing.

Form A of Compound 2

In some embodiments, Compound 2 is in the form of Form A. In some embodiments, Compound 2 is in the form of substantially pure Form A. In some embodiments, Form A is characterized by an X-ray powder diffractogram substantially similar to that in FIG. 1. In some embodiments, Form A is characterized by an X-ray powder diffractogram having a signal at at least two two-theta values chosen from 9.5±0.2, 13.2±0.2, 14.4±0.2, 19.2±0.2, 19.5±0.2, 19.8±0.2, 26.3±0.2, 26.7±0.2, and 28.6±0.2. In some embodiments, Form A is characterized by an X-ray powder diffractogram having a signal at at least three two-theta values chosen from 9.5±0.2, 13.2±0.2, 14.4±0.2, 19.2±0.2, 19.5±0.2, 19.8±0.2, 26.3±0.2, 26.7±0.2, and 28.6±0.2. In some embodiments, Form A is characterized by an X-ray powder diffractogram having a signal at at least four two-theta values chosen from 9.5±0.2, 13.2±0.2, 14.4±0.2, 19.2±0.2, 19.5±0.2, 19.8±0.2, 26.3±0.2, 26.7±0.2, and 28.6±0.2. In some embodiments, Form A is characterized by an X-ray powder diffractogram having a signal at at least five two-theta values chosen from 9.5±0.2, 13.2±0.2, 14.4±0.2, 19.2±0.2, 19.5±0.2, 19.8±0.2, 26.3±0.2, 26.7±0.2, and 28.6±0.2. In some embodiments, Form A is characterized by an X-ray powder diffractogram having a signal at at least six two-theta values chosen from 9.5±0.2, 13.2±0.2, 14.4±0.2, 19.2±0.2, 19.5±0.2, 19.8±0.2, 26.3±0.2, 26.7±0.2, and 28.6±0.2. In some embodiments, Form A is characterized by an X-ray powder diffractogram having a signal at at least seven two-theta values chosen from 9.5±0.2, 13.2±0.2, 14.4±0.2, 19.2±0.2, 19.5±0.2, 19.8±0.2, 26.3±0.2, 26.7±0.2, and 28.6±0.2. In some embodiments, Form A is characterized by an X-ray powder diffractogram having a signal at at least eight two-theta values chosen from 9.5±0.2, 13.2±0.2, 14.4±0.2, 19.2±0.2, 19.5±0.2, 19.8±0.2, 26.3±0.2, 26.7±0.2, and 28.6±0.2. In some embodiments, Form A is characterized by an X-ray powder diffractogram having a signal at the following two-theta values 9.5±0.2, 13.2±0.2, 14.4±0.2, 19.2±0.2, 19.5±0.2, 19.8±0.2, 26.3±0.2, 26.7±0.2, and 28.6±0.2.

In some embodiments, Form A is characterized by an X-ray powder diffractogram having a signal at at least one two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, 28.6±0.2, 29.1±0.2, and 29.5±0.2. In some embodiments, Form A is characterized by an X-ray powder diffractogram having a signal at at least two two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, 28.6±0.2, 29.1±0.2, and 29.5±0.2. In some embodiments, Form A is characterized by an X-ray powder diffractogram having a signal at at least three two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, 28.6±0.2, 29.1±0.2, and 29.5±0.2. In some embodiments, Form A is characterized by an X-ray powder diffractogram having a signal at at least four two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, 28.6±0.2, 29.1±0.2, and 29.5±0.2. In some embodiments, Form A is characterized by an X-ray powder diffractogram having a signal at at least five two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, and 28.6±0.2. In some embodiments, Form A is characterized by an X-ray powder diffractogram having a signal at at least six two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, and 28.6±0.2. In some embodiments, Form A is characterized by an X-ray powder diffractogram having a signal at at least seven two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, and 28.6±0.2. In some embodiments, Form A is characterized by an X-ray powder diffractogram having a signal at at least eight two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, and 28.6±0.2. In some embodiments, Form A is characterized by an X-ray powder diffractogram having a signal at at least nine two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, and 28.6±0.2. In some embodiments, Form A is characterized by an X-ray powder diffractogram having a signal at at least ten two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, and 28.6±0.2. In some embodiments, Form A is characterized by an X-ray powder diffractogram having a signal at at least eleven two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, and 28.6±0.2. In some embodiments, Form A is characterized by an X-ray powder diffractogram having a signal at at least twelve two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, and 28.6±0.2. In some embodiments, Form A is characterized by an X-ray powder diffractogram having a signal at at least thirteen two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, and 28.6±0.2. In some embodiments, Form A is characterized by an X-ray powder diffractogram having a signal at at least fourteen two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, and 28.6±0.2. In some embodiments, Form A is characterized by an X-ray powder diffractogram having a signal at at least fifteen two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, and 28.6±0.2. In some embodiments, Form A is characterized by an X-ray powder diffractogram having a signal at at least sixteen two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, and 28.6±0.2. In some embodiments, Form A is characterized by an X-ray powder diffractogram having a signal at at least seventeen two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, and 28.6±0.2. In some embodiments, Form A is characterized by an X-ray powder diffractogram having a signal at at least eighteen two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, and 28.6±0.2. In some embodiments, Form A is characterized by an X-ray powder diffractogram having a signal at at least nineteen two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, and 28.6±0.2. In some embodiments, Form A is characterized by an X-ray powder diffractogram having a signal at at least twenty two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, and 28.6±0.2. In some embodiments, Form A is characterized by an X-ray powder diffractogram having a signal at 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, and 28.6±0.2, two-theta.

In some embodiments, disclosed herein is a composition comprising Form A of Compound 2. In some embodiments, disclosed herein is a composition comprising Compound 2 in substantially pure Form A. In some embodiments, disclosed herein is a composition comprising at least one active compound consisting essentially of Compound 2 in Form A.

Figure 5:
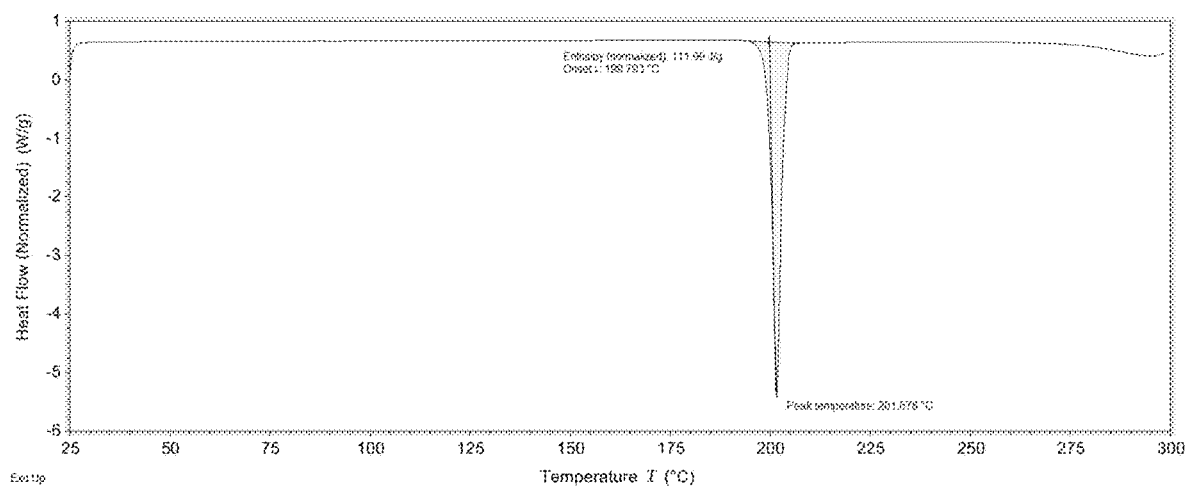
FIG. 5 depicts a DSC curve of Form A of Compound 2.

In some embodiments, Form A is characterized by a DSC curve substantially similar to that in FIG. 5. In some embodiments, Form A is characterized by a DSC curve having a peak at 202° C.

In some embodiments, Form A is characterized by a $^{13}C$ NMR spectrum having a signal at at least one ppm value chosen from 178.7±0.2 ppm, 154.4±0.2 ppm, 127.8±0.2 ppm, 125.2±0.2 ppm, 102.0±0.2 ppm, 59.3±0.2 ppm, 38.9±0.2 ppm, and 24.4±0.2 ppm. In some embodiments, Form A is characterized by a $^{13}C$ NMR spectrum having a signal at at least two ppm values chosen from 178.7±0.2 ppm, 154.4±0.2 ppm, 127.8±0.2 ppm, 125.2±0.2 ppm, 102.0±0.2 ppm, 59.3±0.2 ppm, 38.9±0.2 ppm, and 24.4±0.2 ppm. In some embodiments, Form A is characterized by a $^{13}C$ NMR spectrum having a signal at at least three ppm values chosen from 178.7±0.2 ppm, 154.4±0.2 ppm, 127.8±0.2 ppm, 125.2±0.2 ppm, 102.0±0.2 ppm, 59.3±0.2 ppm, 38.9±0.2 ppm, and 24.4±0.2 ppm. In some embodiments, Form A is characterized by a $^{13}C$ NMR spectrum having a signal at at least four ppm values chosen from 178.7±0.2 ppm, 154.4±0.2 ppm, 127.8±0.2 ppm, 125.2±0.2 ppm, 102.0±0.2 ppm, 59.3±0.2 ppm, 38.9±0.2 ppm, and 24.4±0.2 ppm. In some embodiments, Form A is characterized by a $^{13}C$ NMR spectrum having a signal at 178.7±0.2 ppm, 154.4±0.2 ppm, 127.8±0.2 ppm, 125.2±0.2 ppm, 102.0±0.2 ppm, 59.3±0.2 ppm, 38.9±0.2 ppm, and 24.4±0.2 ppm.

In some embodiments, Form A is characterized by a $^{19}F$ NMR spectrum having a signal at least at one ppm value chosen from −116.0±0.2 ppm, −119.7±0.2 ppm, and −138.1±0.2 ppm. In some embodiments, Form A is characterized by a $^{19}F$ NMR spectrum having a signal at least at two ppm value chosen from −116.0±0.2 ppm, −119.7±0.2 ppm, and −138.1±0.2 ppm. In some embodiments, Form A is characterized by a $^{19}F$ NMR spectrum having a signal at −116.0±0.2 ppm, −119.7±0.2 ppm, and −138.1±0.2 ppm.

In some embodiments, Compound 2 is a crystalline solid. In some embodiments, Compound 2 is a crystalline solid. In some embodiments, the crystalline solid consists of 1% to 99% Form A relative to the total weight of the crystalline solid Compound 2. In some embodiments, the crystalline solid consists of 2% to 99% Form A relative to the total weight of the crystalline solid Compound 2. In some embodiments, the crystalline solid consists of 5% to 99% Form A relative to the total weight of the crystalline solid Compound 2. In some embodiments, the crystalline solid consists of 10% to 99% Form A relative to the total weight of the crystalline solid Compound 2. In some embodiments, the crystalline solid consists of 15% to 99% Form A relative to the total weight of the crystalline solid Compound 2. In some embodiments, the crystalline solid consists of 20% to 99% Form A relative to the total weight of the crystalline solid Compound 2. In some embodiments, the crystalline solid consists of 25% to 99% Form A relative to the total weight of the crystalline solid Compound 2. In some embodiments, the crystalline solid consists of 30% to 99% Form A relative to the total weight of the crystalline solid Compound 2. In some embodiments, the crystalline solid consists of 35% to 99% Form A relative to the total weight of the crystalline solid Compound 2. In some embodiments, the crystalline solid consists of 45% to 99% Form A relative to the total weight of the crystalline solid Compound 2. In some embodiments, the crystalline solid consists of 50% to 99% Form A relative to the total weight of the crystalline solid Compound 2. In some embodiments, the crystalline solid consists of 55% to 99% Form A relative to the total weight of the crystalline solid Compound 2. In some embodiments, the crystalline solid consists of 60% to 99% Form A relative to the total weight of the crystalline solid Compound 2. In some embodiments, the crystalline solid consists of 65% to 99% Form A relative to the total weight of the crystalline solid Compound 2. In some embodiments, the crystalline solid consists of 70% to 99% Form A relative to the total weight of the crystalline solid Compound 2. In some embodiments, the crystalline solid consists of 75% to 99% Form A relative to the total weight of the crystalline solid Compound 2. In some embodiments, the crystalline solid consists of 80% to 99% Form A relative to the total weight of the crystalline solid Compound 2. In some embodiments, the crystalline solid consists of 85% to 99% Form A relative to the total weight of the crystalline solid Compound 2. In some embodiments, the crystalline solid consists of 90% to 99% Form A relative to the total weight of the crystalline solid Compound 2. In some embodiments, the crystalline solid consists of 95% to 99% Form A relative to the total weight of the crystalline solid Compound 2.

Hydrate Form A of Compound 2

Figure 7:
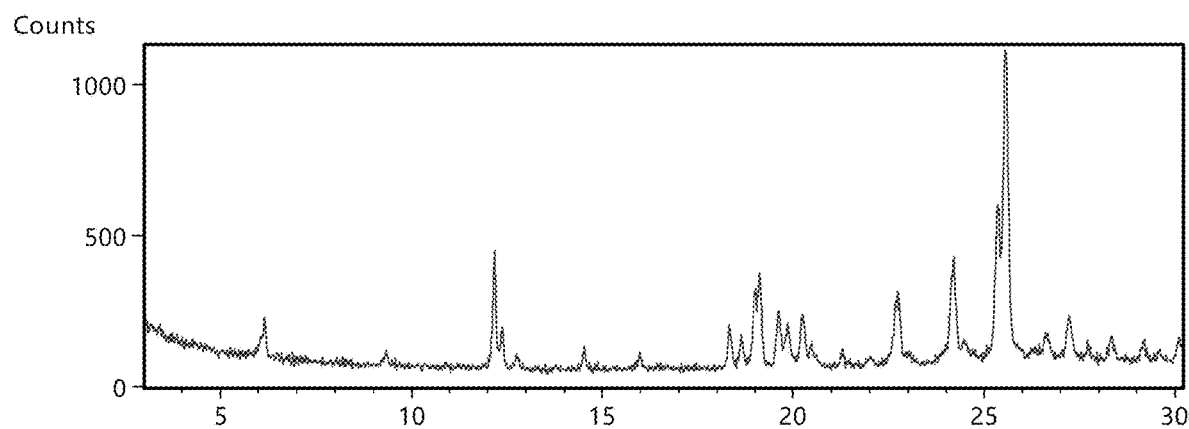
FIG. 7 depicts an XRPD diffractogram of Hydrate Form A of Compound 2.

In some embodiments, Compound 2 is in the form of Hydrate Form A. In some embodiments, Compound 2 is in the form of substantially pure Hydrate Form A. In some embodiments, Hydrate Form A is characterized by an X-ray powder diffractogram substantially similar to that in FIG. 7. In some embodiments, Hydrate Form A is characterized by an X-ray powder diffractogram having a signal at at least two two-theta values chosen from 12.2±0.2, 19.0±0.2, 19.1±0.2, 19.6±0.2, 20.2±0.2, 22.7±0.2, 24.2±0.2, 25.4±0.2, and 25.5±0.2. In some embodiments, Hydrate Form A is characterized by an X-ray powder diffractogram having a signal at at least three two-theta values chosen from 12.2 0.2, 19.0±0.2, 19.1±0.2, 19.6±0.2, 20.2±0.2, 22.7±0.2, 24.2±0.2, 25.4±0.2, and 25.5±0.2. In some embodiments, Hydrate Form A is characterized by an X-ray powder diffractogram having a signal at at least four two-theta values chosen from 12.2±0.2, 19.0±0.2, 19.1±0.2, 19.6±0.2, 20.2±0.2, 22.7±0.2, 24.2±0.2, 25.4±0.2, and 25.5±0.2. In some embodiments, Hydrate Form A is characterized by an X-ray powder diffractogram having a signal at at least five two-theta values chosen from 12.2±0.2, 19.0±0.2, 19.1±0.2, 19.6±0.2, 20.2±0.2, 22.7±0.2, 24.2±0.2, 25.4±0.2, and 25.5±0.2. In some embodiments, Hydrate Form A is characterized by an X-ray powder diffractogram having a signal at at least six two-theta values chosen from 12.2±0.2, 19.0±0.2, 19.1±0.2, 19.6±0.2, 20.2±0.2, 22.7±0.2, 24.2±0.2, 25.4±0.2, and 25.5±0.2.

In some embodiments, Hydrate Form A is characterized by an X-ray powder diffractogram having a signal at at least two two-theta values chosen from 6.2±0.2, 12.2±0.2, 12.4±0.2, 18.3±0.2, 19.0±0.2, 19.1±0.2, 19.6±0.2, 19.9±0.2 and 25.5±0.2. In some embodiments, Hydrate Form A is characterized by an X-ray powder diffractogram having a signal at at least three two-theta values chosen from 6.2±0.2, 12.2±0.2, 12.4±0.2, 18.3±0.2, 19.0±0.2, 19.1±0.2, 19.6±0.2, 19.9±0.2 and 25.5±0.2. In some embodiments, Hydrate Form A is characterized by an X-ray powder diffractogram having a signal at at least four two-theta values chosen from 6.2±0.2, 12.2±0.2, 12.4±0.2, 18.3±0.2, 19.0±0.2, 19.1±0.2, 19.6±0.2, 19.9±0.2 and 25.5±0.2. In some embodiments, Hydrate Form A is characterized by an X-ray powder diffractogram having a signal at at least five two-theta values chosen from 6.2±0.2, 12.2±0.2, 12.4±0.2, 18.3±0.2, 19.0±0.2, 19.1±0.2, 19.6±0.2, 19.9±0.2 and 25.5±0.2. In some embodiments, Hydrate Form A is characterized by an X-ray powder diffractogram having a signal at at least six two-theta values chosen from 6.2±0.2, 12.2±0.2, 12.4±0.2, 18.3±0.2, 19.0±0.2, 19.1±0.2, 19.6±0.2, 19.9±0.2 and 25.5±0.2. In some embodiments, Hydrate Form A is characterized by an X-ray powder diffractogram having a signal at at least seven two-theta values chosen from 6.2±0.2, 12.2±0.2, 12.4±0.2, 18.3±0.2, 19.0±0.2, 19.1±0.2, 19.6±0.2, 19.9±0.2 and 25.5±0.2. In some embodiments, Hydrate Form A is characterized by an X-ray powder diffractogram having a signal at at least eight two-theta values chosen from 6.2±0.2, 12.2±0.2, 12.4±0.2, 18.3±0.2, 19.0±0.2, 19.1±0.2, 19.6±0.2, 19.9±0.2 and 25.5±0.2. In some embodiments, Hydrate Form A is characterized by an X-ray powder diffractogram having a signal at at least nine two-theta values chosen from 6.2±0.2, 12.2±0.2, 12.4±0.2, 18.3±0.2, 19.0±0.2, 19.1±0.2, 19.6±0.2, 19.9±0.2 and 25.5±0.2.

In some embodiments, Hydrate Form A is characterized by an X-ray powder diffractogram having a signal at at least three two-theta values chosen from 6.2±0.2, 12.2±0.2, 12.4±0.2, 18.3±0.2, 19.0±0.2, 19.1±0.2, 19.6±0.2, 19.9±0.2, 20.2±0.2, 22.7±0.2, 24.2±0.2, 25.4±0.2, 25.5±0.2, and 27.2±0.2. In some embodiments, Hydrate Form A is characterized by an X-ray powder diffractogram having a signal at at least four two-theta values chosen from 6.2±0.2, 12.2±0.2, 12.4±0.2, 18.3±0.2, 19.0±0.2, 19.1±0.2, 19.6±0.2, 19.9±0.2, 20.2±0.2, 22.7±0.2, 24.2±0.2, 25.4±0.2, 25.5±0.2, and 27.2±0.2. In some embodiments, Hydrate Form A is characterized by an X-ray powder diffractogram having a signal at at least five two-theta values chosen from 6.2±0.2, 12.2±0.2, 12.4±0.2, 18.3±0.2, 19.0±0.2, 19.1±0.2, 19.6±0.2, 19.9±0.2, 20.2±0.2, 22.7±0.2, 24.2±0.2, 25.4±0.2, 25.5±0.2, and 27.2±0.2. In some embodiments, Hydrate Form A is characterized by an X-ray powder diffractogram having a signal at at least six two-theta values chosen from 6.2±0.2, 12.2±0.2, 12.4±0.2, 18.3±0.2, 19.0±0.2, 19.1±0.2, 19.6±0.2, 19.9±0.2, 20.2±0.2, 22.7±0.2, 24.2±0.2, 25.4±0.2, 25.5±0.2, and 27.2±0.2. In some embodiments, Hydrate Form A is characterized by an X-ray powder diffractogram having a signal at at least seven two-theta values chosen from 6.2±0.2, 12.2±0.2, 12.4±0.2, 18.3±0.2, 19.0±0.2, 19.1±0.2, 19.6±0.2, 19.9±0.2, 20.2±0.2, 22.7±0.2, 24.2±0.2, 25.4±0.2, 25.5±0.2, and 27.2±0.2. In some embodiments, Hydrate Form A is characterized by an X-ray powder diffractogram having a signal at at least eight two-theta values chosen from 6.2±0.2, 12.2±0.2, 12.4±0.2, 18.3±0.2, 19.0±0.2, 19.1±0.2, 19.6±0.2, 19.9±0.2, 20.2±0.2, 22.7±0.2, 24.2±0.2, 25.4±0.2, 25.5±0.2, and 27.2±0.2. In some embodiments, Hydrate Form A is characterized by an X-ray powder diffractogram having a signal at at least nine two-theta values chosen from 6.2±0.2, 12.2±0.2, 12.4±0.2, 18.3±0.2, 19.0±0.2, 19.1±0.2, 19.6±0.2, 19.9±0.2, 20.2±0.2, 22.7±0.2, 24.2±0.2, 25.4±0.2, 25.5±0.2, and 27.2±0.2. In some embodiments, Hydrate Form A is characterized by an X-ray powder diffractogram having a signal at at least ten two-theta values chosen from 6.2±0.2, 12.2±0.2, 12.4±0.2, 18.3±0.2, 19.0±0.2, 19.1±0.2, 19.6±0.2, 19.9±0.2, 20.2±0.2, 22.7±0.2, 24.2±0.2, 25.4±0.2, 25.5±0.2, and 27.2±0.2. In some embodiments, Hydrate Form A is characterized by an X-ray powder diffractogram having a signal at at least eleven two-theta values chosen from 6.2±0.2, 12.2±0.2, 12.4±0.2, 18.3±0.2, 19.0±0.2, 19.1±0.2, 19.6±0.2, 19.9±0.2, 20.2±0.2, 22.7±0.2, 24.2±0.2, 25.4±0.2, 25.5±0.2, and 27.2±0.2. In some embodiments, Hydrate Form A is characterized by an X-ray powder diffractogram having a signal at at least twelve two-theta values chosen from 6.2±0.2, 12.2±0.2, 12.4±0.2, 18.3±0.2, 19.0±0.2, 19.1±0.2, 19.6±0.2, 19.9±0.2, 20.2±0.2, 22.7±0.2, 24.2±0.2, 25.4±0.2, 25.5±0.2, and 27.2±0.2. In some embodiments, Hydrate Form A is characterized by an X-ray powder diffractogram having a signal at at least thirteen two-theta values chosen from 6.2±0.2, 12.2±0.2, 12.4±0.2, 18.3±0.2, 19.0±0.2, 19.1±0.2, 19.6±0.2, 19.9±0.2, 20.2±0.2, 22.7±0.2, 24.2±0.2, 25.4±0.2, 25.5±0.2, and 27.2±0.2. In some embodiments, Hydrate Form A is characterized by an X-ray powder diffractogram having a signal at at least fourteen two-theta values chosen from 6.2±0.2, 12.2±0.2, 12.4±0.2, 18.3±0.2, 19.0±0.2, 19.1±0.2, 19.6±0.2, 19.9±0.2, 20.2±0.2, 22.7±0.2, 24.2±0.2, 25.4±0.2, 25.5±0.2, and 27.2±0.2. In some embodiments, Hydrate Form A is characterized by an X-ray powder diffractogram having a signal at at least fifteen two-theta values chosen from 6.2±0.2, 12.2±0.2, 12.4±0.2, 18.3±0.2, 19.0±0.2, 19.1±0.2, 19.6±0.2, 19.9±0.2, 20.2±0.2, 22.7±0.2, 24.2±0.2, 25.4±0.2, 25.5±0.2, and 27.2±0.2. In some embodiments, Hydrate Form A is characterized by an X-ray powder diffractogram having a signal at at least sixteen two-theta values chosen from 6.2±0.2, 12.2 0.2, 12.4 0.2, 18.3±0.2, 19.0±0.2, 19.1±0.2, 19.6±0.2, 19.9±0.2, 20.2±0.2, 22.7±0.2, 24.2±0.2, 25.4±0.2, 25.5±0.2, and 27.2±0.2. In some embodiments, Hydrate Form A is characterized by an X-ray powder diffractogram having a signal at at least seventeen two-theta values chosen from 6.2±0.2, 12.2±0.2, 12.4±0.2, 18.3±0.2, 19.0±0.2, 19.1±0.2, 19.6±0.2, 19.9±0.2, 20.2±0.2, 22.7±0.2, 24.2±0.2, 25.4±0.2, 25.5±0.2, and 27.2±0.2. In some embodiments, Hydrate Form A is characterized by an X-ray powder diffractogram having a signal at at least eighteen two-theta values chosen from 6.2±0.2, 12.2±0.2, 12.4±0.2, 18.3±0.2, 19.0±0.2, 19.1±0.2, 19.6±0.2, 19.9±0.2, 20.2±0.2, 22.7±0.2, 24.2±0.2, 25.4±0.2, 25.5±0.2, and 27.2±0.2. In some embodiments, Hydrate Form A is characterized by an X-ray powder diffractogram having a signal at at least nineteen two-theta values chosen from 6.2±0.2, 12.2±0.2, 12.4±0.2, 18.3±0.2, 19.0±0.2, 19.1±0.2, 19.6±0.2, 19.9±0.2, 20.2±0.2, 22.7±0.2, 24.2±0.2, 25.4±0.2, 25.5±0.2, and 27.2±0.2. In some embodiments, Hydrate Form A is characterized by an X-ray powder diffractogram having a signal at 6.2±0.2, 12.2±0.2, 12.4±0.2, 18.3±0.2, 19.0±0.2, 19.1±0.2, 19.6±0.2, 19.9±0.2, 20.2±0.2, 22.7±0.2, 24.2±0.2, 25.4±0.2, 25.5±0.2, and 27.2±0.2 two-theta.

In some embodiments, disclosed herein is a composition comprising Hydrate Form A of Compound 2. In some embodiments, disclosed herein is a composition comprising Compound 2 in substantially pure Hydrate Form A. In some embodiments, disclosed herein is a composition comprising at least one active compound consisting essentially of Compound 2 in Hydrate Form A.

Figure 11:
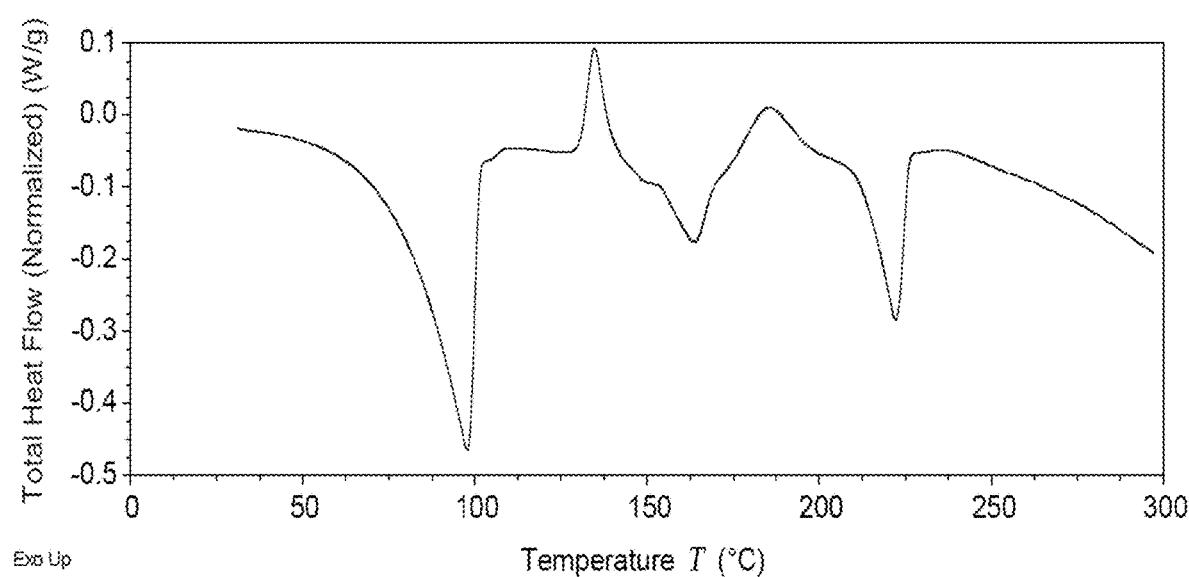
FIG. 11 depicts a DSC curve of Hydrate Form A of Compound 2.

In some embodiments, Hydrate Form A is characterized by a DSC curve substantially similar to that in FIG. 11. In some embodiments, Hydrate Form A is characterized by a DSC curve having a peak at at least one temperature chosen from 97° C., 137° C., 164° C., 185° C., and 222° C.

In some embodiments, Hydrate Form A is characterized by a $^{13}$C NMR spectrum having a signal at at least one ppm value chosen from 177.5±0.2 ppm, 157.7±0.2 ppm, 128.9±0.2 ppm, 95.4±0.2 ppm, 36.9±0.2 ppm, 23.0±0.2 ppm, and 22.3±0.2 ppm. In some embodiments, Hydrate Form A is characterized by a $^{13}$C NMR spectrum having a signal at at least two ppm values chosen from 177.5±0.2 ppm, 157.7±0.2 ppm, 128.9±0.2 ppm, 95.4±0.2 ppm, 36.9±0.2 ppm, 23.0±0.2 ppm, and 22.3±0.2 ppm. In some embodiments, Hydrate Form A is characterized by a $^{13}$C NMR spectrum having a signal at at least three ppm values chosen from 177.5±0.2 ppm, 157.7±0.2 ppm, 128.9±0.2 ppm, 95.4±0.2 ppm, 36.9±0.2 ppm, 23.0±0.2 ppm, and 22.3±0.2 ppm. In some embodiments, Hydrate Form A is characterized by a $^{13}$C NMR spectrum having a signal at at least four ppm values chosen from 177.5±0.2 ppm, 157.7±0.2 ppm, 128.9±0.2 ppm, 95.4±0.2 ppm, 36.9±0.2 ppm, 23.0±0.2 ppm, and 22.3±0.2 ppm. In some embodiments, Hydrate Form A is characterized by a $^{13}$C NMR spectrum having a signal at at least five ppm values chosen from 177.5±0.2 ppm, 157.7±0.2 ppm, 128.9±0.2 ppm, 95.4±0.2 ppm, 36.9±0.2 ppm, 23.0±0.2 ppm, and 22.3±0.2 ppm. In some embodiments, Hydrate Form A is characterized by a $^{13}$C NMR spectrum having a signal at at least six ppm values chosen from 177.5±0.2 ppm, 157.7±0.2 ppm, 128.9±0.2 ppm, 95.4±0.2 ppm, 36.9±0.2 ppm, 23.0±0.2 ppm, and 22.3±0.2 ppm. In some embodiments, Hydrate Form A is characterized by a $^{13}$C NMR spectrum having a signal at 177.5±0.2 ppm, 157.7±0.2 ppm, 128.9±0.2 ppm, 95.4±0.2 ppm, 36.9±0.2 ppm, 23.0±0.2 ppm, and 22.3±0.2 ppm.

In some embodiments, Hydrate Form A is characterized by a $^{19}$F NMR spectrum having a signal at at least one ppm value chosen from −113.8±0.2 ppm, −125.8±0.2 ppm, and −132.8±0.2 ppm. In some embodiments, Hydrate Form A is characterized by a $^{19}$F NMR spectrum having a signal at at least two ppm values chosen from −113.8±0.2 ppm, −125.8±0.2 ppm, and −132.8±0.2 ppm. In some embodiments, Hydrate Form A is characterized by a 9F NMR spectrum having signals at at −113.8±0.2 ppm, −125.8±0.2 ppm, and −132.8±0.2 ppm.

In some embodiments, Compound 2 is a crystalline solid. In some embodiments, the crystalline solid consists of 1% to 99% Hydrate Form A relative to the total weight of the crystalline solid Compound 2. In some embodiments, the crystalline solid consists of 2% to 99% Hydrate Form A relative to the total weight of the crystalline solid Compound 2. In some embodiments, the crystalline solid consists of 5% to 99% Hydrate Form A relative to the total weight of the crystalline solid Compound 2. In some embodiments, the crystalline solid consists of 10% to 99% Hydrate Form A relative to the total weight of the crystalline solid Compound 2. In some embodiments, the crystalline solid consists of 15% to 99% Hydrate Form A relative to the total weight of the crystalline solid Compound 2. In some embodiments, the crystalline solid consists of 20% to 99% Hydrate Form A relative to the total weight of the crystalline solid Compound 2. In some embodiments, the crystalline solid consists of 25% to 99% Hydrate Form A relative to the total weight of the crystalline solid Compound 2. In some embodiments, the crystalline solid consists of 30% to 99% Hydrate Form A relative to the total weight of the crystalline solid Compound 2. In some embodiments, the crystalline solid consists of 35% to 99% Hydrate Form A relative to the total weight of the crystalline solid Compound 2. In some embodiments, the crystalline solid consists of 45% to 99% Hydrate Form A relative to the total weight of the crystalline solid Compound 2. In some embodiments, the crystalline solid consists of 50% to 99% Hydrate Form A relative to the total weight of the crystalline solid Compound 2. In some embodiments, the crystalline solid consists of 55% to 99% Hydrate Form A relative to the total weight of the crystalline solid Compound 2. In some embodiments, the crystalline solid consists of 60% to 99% Hydrate Form A relative to the total weight of the crystalline solid Compound 2. In some embodiments, the crystalline solid consists of 65% to 99% Hydrate Form A relative to the total weight of the crystalline solid Compound 2. In some embodiments, the crystalline solid consists of 70% to 99% Hydrate Form A relative to the total weight of the crystalline solid Compound 2. In some embodiments, the crystalline solid consists of 75% to 99% Hydrate Form A relative to the total weight of the crystalline solid Compound 2. In some embodiments, the crystalline solid consists of 80% to 99% Hydrate Form A relative to the total weight of the crystalline solid Compound 2. In some embodiments, the crystalline solid consists of 85% to 99% Hydrate Form A relative to the total weight of the crystalline solid Compound 2. In some embodiments, the crystalline solid consists of 90% to 99% Hydrate Form A relative to the total weight of the crystalline solid Compound 2. In some embodiments, the crystalline solid consists of 95% to 99% Hydrate Form A relative to the total weight of the crystalline solid Compound 2.

Hydrate Form B of Compound 2

Figure 12:
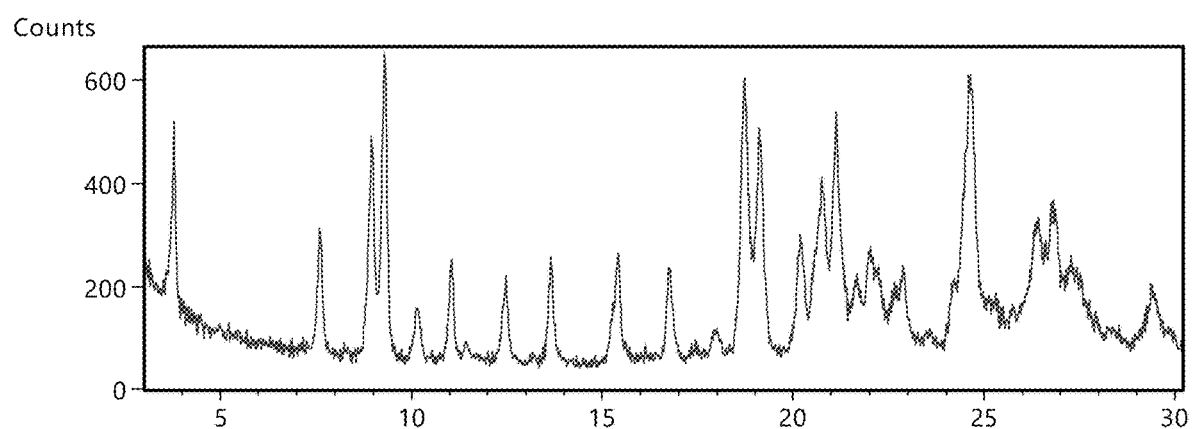
FIG. 12 depicts an XRPD spectrum of Hydrate Form B of Compound 2.

In some embodiments, Compound 2 is in the form of Hydrate Form B. In some embodiments, Compound 2 is in the form of substantially pure Hydrate Form B. In some embodiments, Hydrate Form B is characterized by an X-ray powder diffractogram substantially similar to that in FIG. 12. In some embodiments, Hydrate Form B is characterized by an X-ray powder diffractogram having a signal at at least two two-theta values chosen from 3.8±0.2, 9.0±0.2, 9.3±0.2, 18.7±0.2, 19.1±0.2, 20.8±0.2, 21.1±0.2, 24.6±0.2, and 26.8±0.2. In some embodiments, Hydrate Form B is characterized by an X-ray powder diffractogram having a signal at at least three two-theta values chosen from 3.8±0.2, 9.0±0.2, 9.3±0.2, 18.7±0.2, 19.1±0.2, 20.8±0.2, 21.1±0.2, 24.6±0.2, and 26.8±0.2. In some embodiments, Hydrate Form B is characterized by an X-ray powder diffractogram having a signal at at least four two-theta values chosen from 3.8±0.2, 9.0±0.2, 9.3±0.2, 18.7±0.2, 19.1±0.2, 20.8±0.2, 21.1±0.2, 24.6±0.2, and 26.8±0.2. In some embodiments, Hydrate Form B is characterized by an X-ray powder diffractogram having a signal at at least five two-theta values chosen from 3.8±0.2, 9.0±0.2, 9.3±0.2, 18.7±0.2, 19.1±0.2, 20.8±0.2, 21.1±0.2, 24.6±0.2, and 26.8±0.2. In some embodiments, Hydrate Form B is characterized by an X-ray powder diffractogram having a signal at at least six two-theta values chosen from 3.8±0.2, 9.0±0.2, 9.3±0.2, 18.7±0.2, 19.1±0.2, 20.8±0.2, 21.1±0.2, 24.6±0.2, and 26.8±0.2. In some embodiments, Hydrate Form B is characterized by an X-ray powder diffractogram having a signal at at least seven two-theta values chosen from 3.8±0.2, 9.0±0.2, 9.3±0.2, 18.7±0.2, 19.1±0.2, 20.8±0.2, 21.1±0.2, 24.6±0.2, and 26.8±0.2. In some embodiments, Hydrate Form B is characterized by an X-ray powder diffractogram having a signal at at least eight two-theta values chosen from 3.8±0.2, 9.0±0.2, 9.3±0.2, 18.7±0.2, 19.1±0.2, 20.8±0.2, 21.1±0.2, 24.6±0.2, and 26.8±0.2. In some embodiments, Hydrate Form B is characterized by an X-ray powder diffractogram having a signal at 3.8±0.2, 9.0±0.2, 9.3±0.2, 18.7±0.2, 19.1±0.2, 20.8±0.2, 21.1±0.2, 24.6±0.2, and 26.8±0.2 two-theta.

In some embodiments, Hydrate Form B is characterized by an X-ray powder diffractogram having a signal at at least two two-theta values chosen from 3.8±0.2, 7.6±0.2, 9.0±0.2, 9.3±0.2, 18.7±0.2, and 19.1±0.2. In some embodiments, Hydrate Form B is characterized by an X-ray powder diffractogram having a signal at at least three two-theta values chosen from 3.8±0.2, 7.6±0.2, 9.0±0.2, 9.3±0.2, 18.7±0.2, and 19.1±0.2. In some embodiments, Hydrate Form B is characterized by an X-ray powder diffractogram having a signal at at least four two-theta values chosen from 3.8±0.2, 7.6±0.2, 9.0±0.2, 9.3±0.2, 18.7±0.2, and 19.1±0.2. In some embodiments, Hydrate Form B is characterized by an X-ray powder diffractogram having a signal at at least five two-theta values chosen from 3.8±0.2, 7.6±0.2, 9.0±0.2, 9.3±0.2, 18.7±0.2, and 19.1±0.2. In some embodiments, Hydrate Form B is characterized by an X-ray powder diffractogram having a signal at 3.8±0.2, 7.6±0.2, 9.0±0.2, 9.3±0.2, 18.7±0.2, and 19.1±0.2 two-theta.

In some embodiments, Hydrate Form B is characterized by an X-ray powder diffractogram having a signal at at least three two-theta values chosen from 3.8±0.2, 7.6±0.2, 9.0±0.2, 9.3±0.2, 10.2±0.2, 11.0±0.2, 12.5±0.2, 13.7±0.2, 15.4±0.2, 16.7±0.2, 18.7±0.2, 19.1±0.2, 20.2±0.2, 20.8±0.2, 21.1±0.2, 21.7±0.2, 22.0±0.2, 22.9±0.2, 24.6±0.2, 26.4±0.2, 26.8±0.2, and 29.4±0.2. In some embodiments, Hydrate Form B is characterized by an X-ray powder diffractogram having a signal at at least four two-theta values chosen from 3.8±0.2, 7.6±0.2, 9.0±0.2, 9.3±0.2, 10.2±0.2, 11.0±0.2, 12.5±0.2, 13.7±0.2, 15.4±0.2, 16.7±0.2, 18.7±0.2, 19.1±0.2, 20.2±0.2, 20.8±0.2, 21.1±0.2, 21.7±0.2, 22.0±0.2, 22.9±0.2, 24.6±0.2, 26.4±0.2, 26.8±0.2, and 29.4±0.2. In some embodiments, Hydrate Form B is characterized by an X-ray powder diffractogram having a signal at at least five two-theta values chosen from 3.8±0.2, 7.6±0.2, 9.0±0.2, 9.3±0.2, 10.2±0.2, 11.0±0.2, 12.5±0.2, 13.7±0.2, 15.4±0.2, 16.7±0.2, 18.7±0.2, 19.1±0.2, 20.2±0.2, 20.8±0.2, 21.1±0.2, 21.7±0.2, 22.0±0.2, 22.9±0.2, 24.6±0.2, 26.4±0.2, 26.8±0.2, and 29.4±0.2. In some embodiments, Hydrate Form B is characterized by an X-ray powder diffractogram having a signal at at least six two-theta values chosen from 3.8±0.2, 7.6±0.2, 9.0±0.2, 9.3±0.2, 10.2±0.2, 11.0±0.2, 12.5±0.2, 13.7±0.2, 15.4±0.2, 16.7±0.2, 18.7±0.2, 19.1±0.2, 20.2±0.2, 20.8±0.2, 21.1±0.2, 21.7±0.2, 22.0±0.2, 22.9±0.2, 24.6±0.2, 26.4±0.2, 26.8±0.2, and 29.4±0.2. In some embodiments, Hydrate Form B is characterized by an X-ray powder diffractogram having a signal at at least seven two-theta values chosen from 3.8±0.2, 7.6±0.2, 9.0±0.2, 9.3±0.2, 10.2±0.2, 11.0±0.2, 12.5±0.2, 13.7±0.2, 15.4±0.2, 16.7±0.2, 18.7±0.2, 19.1±0.2, 20.2±0.2, 20.8±0.2, 21.1±0.2, 21.7±0.2, 22.0±0.2, 22.9±0.2, 24.6±0.2, 26.4±0.2, 26.8±0.2, and 29.4±0.2. In some embodiments, Hydrate Form B is characterized by an X-ray powder diffractogram having a signal at at least eight two-theta values chosen from 3.8±0.2, 7.6±0.2, 9.0±0.2, 9.3±0.2, 10.2±0.2, 11.0±0.2, 12.5±0.2, 13.7±0.2, 15.4±0.2, 16.7±0.2, 18.7±0.2, 19.1±0.2, 20.2±0.2, 20.8±0.2, 21.1±0.2, 21.7±0.2, 22.0±0.2, 22.9±0.2, 24.6±0.2, 26.4±0.2, 26.8±0.2, and 29.4±0.2. In some embodiments, Hydrate Form B is characterized by an X-ray powder diffractogram having a signal at at least nine two-theta values chosen from 3.8±0.2, 7.6±0.2, 9.0±0.2, 9.3±0.2, 10.2±0.2, 11.0±0.2, 12.5±0.2, 13.7±0.2, 15.4±0.2, 16.7±0.2, 18.7±0.2, 19.1±0.2, 20.2±0.2, 20.8±0.2, 21.1±0.2, 21.7±0.2, 22.0±0.2, 22.9±0.2, 24.6±0.2, 26.4±0.2, 26.8±0.2, and 29.4±0.2. In some embodiments, Hydrate Form B is characterized by an X-ray powder diffractogram having a signal at at least ten two-theta values chosen from 3.8±0.2, 7.6±0.2, 9.0±0.2, 9.3±0.2, 10.2±0.2, 11.0±0.2, 12.5±0.2, 13.7±0.2, 15.4±0.2, 16.7±0.2, 18.7±0.2, 19.1±0.2, 20.2±0.2, 20.8±0.2, 21.1±0.2, 21.7±0.2, 22.0±0.2, 22.9±0.2, 24.6±0.2, 26.4±0.2, 26.8±0.2, and 29.4±0.2. In some embodiments, Hydrate Form B is characterized by an X-ray powder diffractogram having a signal at at least eleven two-theta values chosen from 3.8±0.2, 7.6±0.2, 9.0±0.2, 9.3±0.2, 10.2±0.2, 11.0±0.2, 12.5±0.2, 13.7±0.2, 15.4±0.2, 16.7±0.2, 18.7±0.2, 19.1±0.2, 20.2±0.2, 20.8±0.2, 21.1±0.2, 21.7±0.2, 22.0±0.2, 22.9±0.2, 24.6±0.2, 26.4±0.2, 26.8±0.2, and 29.4±0.2. In some embodiments, Hydrate Form B is characterized by an X-ray powder diffractogram having a signal at at least twelve two-theta values chosen from 3.8±0.2, 7.6±0.2, 9.0±0.2, 9.3±0.2, 10.2±0.2, 11.0±0.2, 12.5±0.2, 13.7±0.2, 15.4±0.2, 16.7±0.2, 18.7±0.2, 19.1±0.2, 20.2±0.2, 20.8±0.2, 21.1±0.2, 21.7±0.2, 22.0±0.2, 22.9±0.2, 24.6±0.2, 26.4±0.2, 26.8±0.2, and 29.4±0.2. In some embodiments, Hydrate Form B is characterized by an X-ray powder diffractogram having a signal at at least thirteen two-theta values chosen from 3.8±0.2, 7.6±0.2, 9.0±0.2, 9.3±0.2, 10.2±0.2, 11.0±0.2, 12.5±0.2, 13.7±0.2, 15.4±0.2, 16.7±0.2, 18.7±0.2, 19.1±0.2, 20.2±0.2, 20.8±0.2, 21.1±0.2, 21.7±0.2, 22.0±0.2, 22.9±0.2, 24.6±0.2, 26.4±0.2, 26.8±0.2, and 29.4±0.2. In some embodiments, Hydrate Form B is characterized by an X-ray powder diffractogram having a signal at at least fourteen two-theta values chosen from 3.8±0.2, 7.6±0.2, 9.0±0.2, 9.3±0.2, 10.2±0.2, 11.0±0.2, 12.5±0.2, 13.7±0.2, 15.4±0.2, 16.7±0.2, 18.7±0.2, 19.1±0.2, 20.2±0.2, 20.8±0.2, 21.1±0.2, 21.7±0.2, 22.0±0.2, 22.9±0.2, 24.6±0.2, 26.4±0.2, 26.8±0.2, and 29.4±0.2. In some embodiments, Hydrate Form B is characterized by an X-ray powder diffractogram having a signal at at least fifteen two-theta values chosen from 3.8±0.2, 7.6±0.2, 9.0±0.2, 9.3±0.2, 10.2±0.2, 11.0±0.2, 12.5±0.2, 13.7±0.2, 15.4±0.2, 16.7±0.2, 18.7±0.2, 19.1±0.2, 20.2±0.2, 20.8±0.2, 21.1±0.2, 21.7±0.2, 22.0±0.2, 22.9±0.2, 24.6±0.2, 26.4±0.2, 26.8±0.2, and 29.4±0.2.

In some embodiments, disclosed herein is a composition comprising Hydrate Form B of Compound 2. In some embodiments, disclosed herein is a composition comprising Compound 2 in substantially pure Hydrate Form B. In some embodiments, disclosed herein is a composition comprising at least one active compound consisting essentially of Compound 2 in Hydrate Form B.

In some embodiments, Hydrate Form B is characterized by a $^{19}$F NMR spectrum having a signal at at least one ppm value chosen from −117.0±0.2 ppm, −119.1±0.2 ppm, and −137.7±0.2 ppm. In some embodiments, Hydrate Form B is characterized by a $^{19}$F NMR spectrum having a signal at at least two ppm values chosen from −117.0±0.2 ppm, −119.1±0.2 ppm, and −137.7±0.2 ppm. In some embodiments, Hydrate Form B is characterized by a $^{19}$F NMR spectrum having signals at at −117.0±0.2 ppm, −119.1±0.2 ppm, and −137.7±0.2 ppm.

In some embodiments, Compound 2 is a crystalline solid. In some embodiments, the crystalline solid consists of 1% to 99% Hydrate Form B relative to the total weight of the crystalline solid Compound 2. In some embodiments, the crystalline solid consists of 2% to 99% Hydrate Form B relative to the total weight of the crystalline solid Compound 2. In some embodiments, the crystalline solid consists of 5% to 99% Hydrate Form B relative to the total weight of the crystalline solid Compound 2. In some embodiments, the crystalline solid consists of 10% to 99% Hydrate Form B relative to the total weight of the crystalline solid Compound 2. In some embodiments, the crystalline solid consists of 15% to 99% Hydrate Form B relative to the total weight of the crystalline solid Compound 2. In some embodiments, the crystalline solid consists of 20% to 99% Hydrate Form B relative to the total weight of the crystalline solid Compound 2. In some embodiments, the crystalline solid consists of 25% to 99% Hydrate Form B relative to the total weight of the crystalline solid Compound 2. In some embodiments, the crystalline solid consists of 30% to 99% Hydrate Form B relative to the total weight of the crystalline solid Compound 2. In some embodiments, the crystalline solid consists of 35% to 99% Hydrate Form B relative to the total weight of the crystalline solid Compound 2. In some embodiments, the crystalline solid consists of 45% to 99% Hydrate Form B relative to the total weight of the crystalline solid Compound 2. In some embodiments, the crystalline solid consists of 50% to 99% Hydrate Form B relative to the total weight of the crystalline solid Compound 2. In some embodiments, the crystalline solid consists of 55% to 99% Hydrate Form B relative to the total weight of the crystalline solid Compound 2. In some embodiments, the crystalline solid consists of 60% to 99% Hydrate Form B relative to the total weight of the crystalline solid Compound 2. In some embodiments, the crystalline solid consists of 65% to 99% Hydrate Form B relative to the total weight of the crystalline solid Compound 2. In some embodiments, the crystalline solid consists of 70% to 99% Hydrate Form B relative to the total weight of the crystalline solid Compound 2. In some embodiments, the crystalline solid consists of 75% to 99% Hydrate Form B relative to the total weight of the crystalline solid Compound 2. In some embodiments, the crystalline solid consists of 80% to 99% Hydrate Form B relative to the total weight of the crystalline solid Compound 2. In some embodiments, the crystalline solid consists of 85% to 99% Hydrate Form B relative to the total weight of the crystalline solid Compound 2. In some embodiments, the crystalline solid consists of 90% to 99% Hydrate Form B relative to the total weight of the crystalline solid Compound 2. In some embodiments, the crystalline solid consists of 95% to 99% Hydrate Form B relative to the total weight of the crystalline solid Compound 2.

In some embodiments, Compound 2 is a crystalline solid. In some embodiments, Compound 2 is a crystalline solid comprising 60% to 99.9% Hydrate Form A relative to the total weight of the crystalline solid Compound 2 and 0.1% to 40% Hydrate Form B relative to the total weight of the crystalline solid Compound 2. In some embodiments, the crystalline solid comprises 70% to 95% Hydrate Form A relative to the total weight of the crystalline solid Compound 2 and 5% to 30% Hydrate Form B relative to the total weight of the crystalline solid Compound 2. In some embodiments, the crystalline solid comprises 80% to 90% Hydrate Form A relative to the total weight of the crystalline solid Compound 2 and 10% to 20% Hydrate Form B relative to the total weight of the crystalline solid Compound 2.

Hydrate Form C of Compound 2

Figure 14:
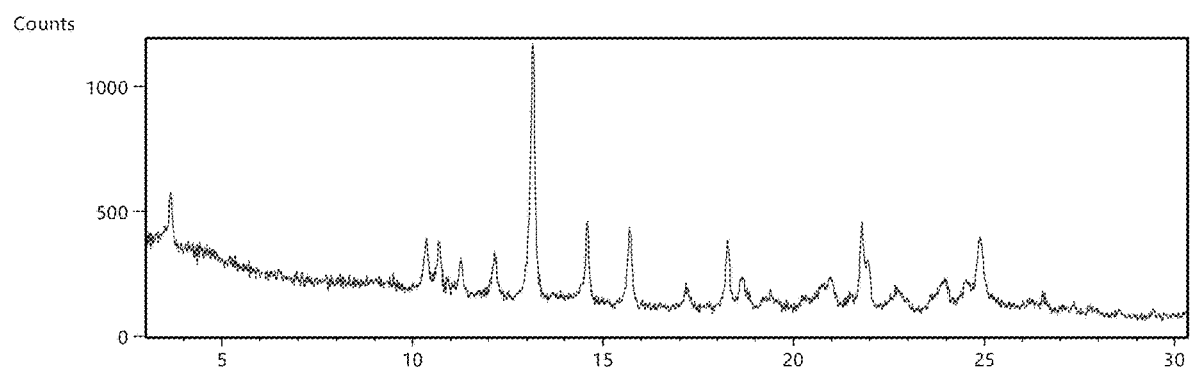
FIG. 14 depicts an XRPD diffractogram of Hydrate Form C of Compound 2.

In some embodiments, Compound 2 is in the form of Hydrate Form C. In some embodiments, Compound 2 is in the form of substantially pure Hydrate Form C. In some embodiments, Hydrate Form C is characterized by an X-ray powder diffractogram substantially similar to that in FIG. 14. In some embodiments, Hydrate Form C is characterized by an X-ray powder diffractogram having a signal at at least two two-theta values chosen from 3.7±0.2, 10.4±0.2, 10.7±0.2, 13.2±0.2, 14.6±0.2, 15.7±0.2, 18.3±0.2, 21.8±0.2, and 24.9±0.2. In some embodiments, Hydrate Form C is characterized by an X-ray powder diffractogram having a signal at at least three two-theta values chosen from 3.7±0.2, 10.4±0.2, 10.7±0.2, 13.2±0.2, 14.6±0.2, 15.7±0.2, 18.3±0.2, 21.8±0.2, and 24.9±0.2. In some embodiments, Hydrate Form C is characterized by an X-ray powder diffractogram having a signal at at least four two-theta values chosen from 3.7±0.2, 10.4±0.2, 10.7±0.2, 13.2±0.2, 14.6±0.2, 15.7±0.2, 18.3±0.2, 21.8±0.2, and 24.9±0.2. In some embodiments, Hydrate Form C is characterized by an X-ray powder diffractogram having a signal at at least five two-theta values chosen from 3.7±0.2, 10.4±0.2, 10.7±0.2, 13.2±0.2, 14.6±0.2, 15.7±0.2, 18.3±0.2, 21.8±0.2, and 24.9±0.2. In some embodiments, Hydrate Form C is characterized by an X-ray powder diffractogram having a signal at at least six two-theta values chosen from 3.7±0.2, 10.4±0.2, 10.7±0.2, 13.2±0.2, 14.6±0.2, 15.7±0.2, 18.3±0.2, 21.8±0.2, and 24.9±0.2. In some embodiments, Hydrate Form C is characterized by an X-ray powder diffractogram having a signal at at least seven two-theta values chosen from 3.7±0.2, 10.4±0.2, 10.7±0.2, 13.2±0.2, 14.6±0.2, 15.7±0.2, 18.3±0.2, 21.8±0.2, and 24.9±0.2. In some embodiments, Hydrate Form C is characterized by an X-ray powder diffractogram having a signal at at least eight two-theta values chosen from 3.7±0.2, 10.4±0.2, 10.7±0.2, 13.2±0.2, 14.6±0.2, 15.7±0.2, 18.3±0.2, 21.8±0.2, and 24.9±0.2. In some embodiments, Hydrate Form C is characterized by an X-ray powder diffractogram having a signal at 3.7±0.2, 10.4±0.2, 10.7±0.2, 13.2±0.2, 14.6±0.2, 15.7±0.2, 18.3±0.2, 21.8±0.2, and 24.9±0.2 two-theta.

In some embodiments, Hydrate Form C is characterized by an X-ray powder diffractogram having a signal at at least three two-theta values chosen from 3.7±0.2, 10.4±0.2, 10.7±0.2, 11.3±0.2, 12.2±0.2, 13.2±0.2, 14.6±0.2, 15.7±0.2, 18.3±0.2, 18.6±0.2, 21.0±0.2, 21.8±0.2, 22.0±0.2, 24.0±0.2, 24.6±0.2, and 24.9±0.2. In some embodiments, Hydrate Form C is characterized by an X-ray powder diffractogram having a signal at at least four two-theta values chosen from 3.7±0.2, 10.4±0.2, 10.7±0.2, 11.3±0.2, 12.2±0.2, 13.2±0.2, 14.6±0.2, 15.7±0.2, 18.3±0.2, 18.6±0.2, 21.0±0.2, 21.8±0.2, 22.0±0.2, 24.0±0.2, 24.6±0.2, and 24.9±0.2. In some embodiments, Hydrate Form C is characterized by an X-ray powder diffractogram having a signal at at least five two-theta values chosen from 3.7±0.2, 10.4±0.2, 10.7±0.2, 11.3±0.2, 12.2±0.2, 13.2±0.2, 14.6±0.2, 15.7±0.2, 18.3±0.2, 18.6±0.2, 21.0±0.2, 21.8±0.2, 22.0±0.2, 24.0±0.2, 24.6±0.2, and 24.9±0.2. In some embodiments, Hydrate Form C is characterized by an X-ray powder diffractogram having a signal at at least six two-theta values chosen 3.7±0.2, 10.4±0.2, 10.7±0.2, 11.3±0.2, 12.2±0.2, 13.2±0.2, 14.6±0.2, 15.7±0.2, 18.3±0.2, 18.6±0.2, 21.0±0.2, 21.8±0.2, 22.0±0.2, 24.0±0.2, 24.6±0.2, and 24.9±0.2. In some embodiments, Hydrate Form C is characterized by an X-ray powder diffractogram having a signal at at least seven two-theta values chosen 3.7±0.2, 10.4±0.2, 10.7±0.2, 11.3±0.2, 12.2±0.2, 13.2±0.2, 14.6±0.2, 15.7±0.2, 18.3±0.2, 18.6±0.2, 21.0±0.2, 21.8±0.2, 22.0±0.2, 24.0±0.2, 24.6±0.2, and 24.9±0.2. In some embodiments, Hydrate Form C is characterized by an X-ray powder diffractogram having a signal at at least eight two-theta values chosen 3.7±0.2, 10.4±0.2, 10.7±0.2, 11.3±0.2, 12.2±0.2, 13.2±0.2, 14.6±0.2, 15.7±0.2, 18.3±0.2, 18.6±0.2, 21.0±0.2, 21.8±0.2, 22.0±0.2, 24.0±0.2, 24.6±0.2, and 24.9±0.2. In some embodiments, Hydrate Form C is characterized by an X-ray powder diffractogram having a signal at at least nine two-theta values chosen 3.7±0.2, 10.4±0.2, 10.7±0.2, 11.3±0.2, 12.2±0.2, 13.2±0.2, 14.6±0.2, 15.7±0.2, 18.3±0.2, 18.6±0.2, 21.0±0.2, 21.8±0.2, 22.0±0.2, 24.0±0.2, 24.6±0.2, and 24.9±0.2. In some embodiments, Hydrate Form C is characterized by an X-ray powder diffractogram having a signal at at least ten two-theta values chosen 3.7±0.2, 10.4±0.2, 10.7±0.2, 11.3±0.2, 12.2±0.2, 13.2±0.2, 14.6±0.2, 15.7±0.2, 18.3±0.2, 18.6±0.2, 21.0±0.2, 21.8±0.2, 22.0±0.2, 24.0±0.2, 24.6±0.2, and 24.9±0.2. In some embodiments, Hydrate Form C is characterized by an X-ray powder diffractogram having a signal at at least eleven two-theta values chosen 3.7±0.2, 10.4±0.2, 10.7±0.2, 11.3±0.2, 12.2±0.2, 13.2±0.2, 14.6±0.2, 15.7±0.2, 18.3±0.2, 18.6±0.2, 21.0±0.2, 21.8±0.2, 22.0±0.2, 24.0±0.2, 24.6±0.2, and 24.9±0.2. In some embodiments, Hydrate Form C is characterized by an X-ray powder diffractogram having a signal at at least twelve two-theta values chosen 3.7±0.2, 10.4±0.2, 10.7±0.2, 11.3±0.2, 12.2±0.2, 13.2±0.2, 14.6±0.2, 15.7±0.2, 18.3±0.2, 18.6±0.2, 21.0±0.2, 21.8±0.2, 22.0±0.2, 24.0±0.2, 24.6±0.2, and 24.9±0.2. In some embodiments, Hydrate Form C is characterized by an X-ray powder diffractogram having a signal at at least thirteen two-theta values chosen 3.7±0.2, 10.4±0.2, 10.7±0.2, 11.3±0.2, 12.2±0.2, 13.2±0.2, 14.6±0.2, 15.7±0.2, 18.3±0.2, 18.6±0.2, 21.0±0.2, 21.8±0.2, 22.0±0.2, 24.0±0.2, 24.6±0.2, and 24.9±0.2. In some embodiments, Hydrate Form C is characterized by an X-ray powder diffractogram having a signal at at least fourteen two-theta values chosen 3.7±0.2, 10.4±0.2, 10.7±0.2, 11.3±0.2, 12.2±0.2, 13.2±0.2, 14.6±0.2, 15.7±0.2, 18.3±0.2, 18.6±0.2, 21.0±0.2, 21.8±0.2, 22.0±0.2, 24.0±0.2, 24.6±0.2, and 24.9±0.2. In some embodiments, Hydrate Form C is characterized by an X-ray powder diffractogram having a signal at at least fifteen two-theta values chosen 3.7±0.2, 10.4±0.2, 10.7±0.2, 11.3±0.2, 12.2±0.2, 13.2±0.2, 14.6±0.2, 15.7±0.2, 18.3±0.2, 18.6±0.2, 21.0±0.2, 21.8±0.2, 22.0±0.2, 24.0±0.2, 24.6±0.2, and 24.9±0.2. In some embodiments, Hydrate Form C is characterized by an X-ray powder diffractogram having a signal at 6.2±0.2, 12.2±0.2, 12.4±0.2, 18.3±0.2, 19.0±0.2, 19.1±0.2, 19.6±0.2, 19.9±0.2, 20.2±0.2, 22.7±0.2, 24.2±0.2, 25.4±0.2, 25.5±0.2, and 27.2±0.2 two-theta.

In some embodiments, disclosed herein is a composition comprising Hydrate Form C of Compound 2. In some embodiments, the composition further comprises Hydrate Form A of Compound 2. In some embodiments, disclosed herein is a composition comprising Compound 2 in substantially pure Hydrate Form C. In some embodiments, disclosed herein is a composition comprising at least one active compound consisting essentially of Compound 2 in Hydrate Form C.

Figure 18:
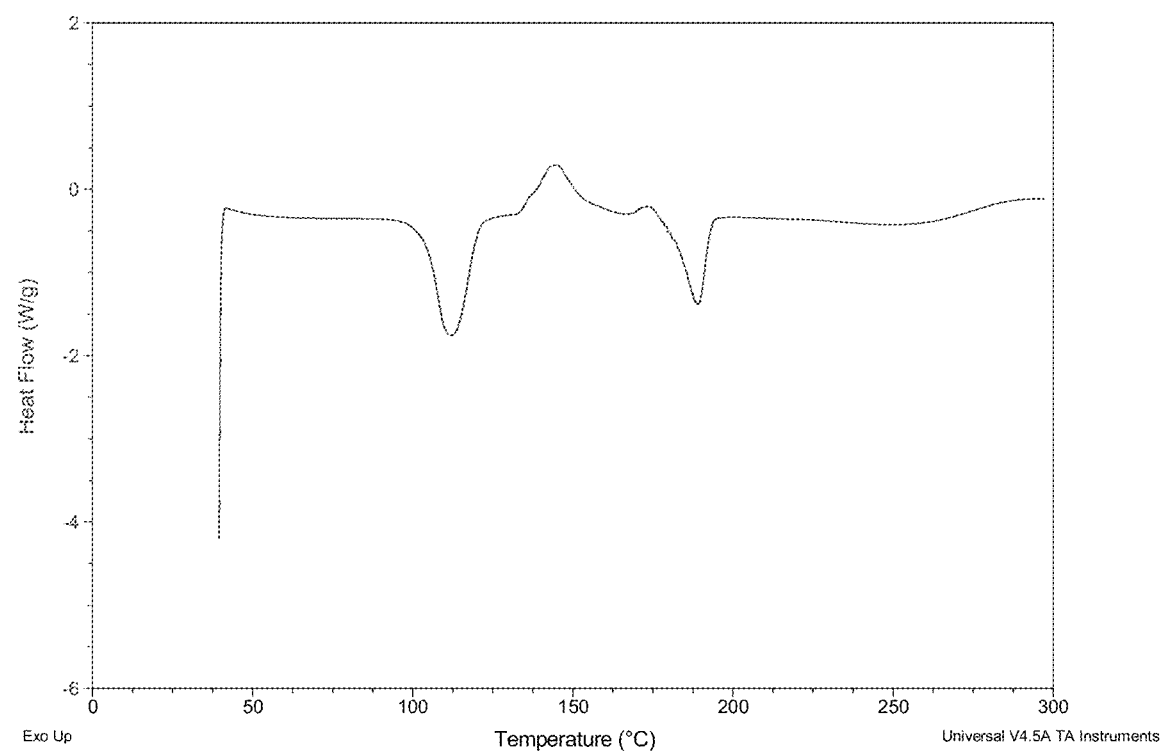
FIG. 18 depicts a DSC curve of Hydrate Form C of Compound 2.

In some embodiments, Hydrate Form C is characterized by a DSC curve substantially similar to that in FIG. 18. In some embodiments, Hydrate Form C is characterized by a DSC curve having a peak at at least one temperature chosen from 112° C., 145° C., and 189° C.

In some embodiments, Hydrate Form C is characterized by a $^{13}$C NMR spectrum having a signal at at least one ppm value chosen from 178.2±0.2 ppm, 127.2±0.2 ppm, 116.9±0.2 ppm, 71.6±0.2 ppm, 57.6±0.2 ppm, 49.6±0.2 ppm, 35.5±0.2 ppm, and 20.0±0.2 ppm. In some embodiments, Hydrate Form C is characterized by a $^{13}$C NMR spectrum having a signal at at least two ppm values chosen from 178.2±0.2 ppm, 127.2±0.2 ppm, 116.9±0.2 ppm, 71.6±0.2 ppm, 57.6±0.2 ppm, 49.6±0.2 ppm, 35.5±0.2 ppm, and 20.0±0.2 ppm. In some embodiments, Hydrate Form C is characterized by a $^{13}$C NMR spectrum having a signal at at least three ppm values chosen from 178.2±0.2 ppm, 127.2±0.2 ppm, 116.9±0.2 ppm, 71.6±0.2 ppm, 57.6±0.2 ppm, 49.6±0.2 ppm, 35.5±0.2 ppm, and 20.0±0.2 ppm. In some embodiments, Hydrate Form C is characterized by a $^{13}$C NMR spectrum having a signal at at least four ppm values chosen from 178.2±0.2 ppm, 127.2±0.2 ppm, 116.9±0.2 ppm, 71.6±0.2 ppm, 57.6±0.2 ppm, 49.6±0.2 ppm, 35.5±0.2 ppm, and 20.0±0.2 ppm. In some embodiments, Hydrate Form C is characterized by a $^{13}$C NMR spectrum having a signal at 178.2±0.2 ppm, 127.2±0.2 ppm, 116.9±0.2 ppm, 71.6±0.2 ppm, 57.6±0.2 ppm, 49.6±0.2 ppm, 35.5±0.2 ppm, and 20.0±0.2 ppm.

In some embodiments, Hydrate Form C is characterized by a $^{19}$F NMR spectrum having a signal at at least one ppm value chosen −109.9±0.2 ppm, −111.5±0.2 ppm, −113.0±0.2, −120.9±0.2, −121.8±0.2 and −123.4±0.2 ppm. In some embodiments, Hydrate Form C is characterized by a $^{19}$F NMR spectrum having a signal at at least two ppm values chosen from −109.9±0.2 ppm, −111.5±0.2 ppm, −113.0±0.2, −120.9±0.2, −121.8±0.2 and −123.4±0.2 ppm. In some embodiments, Hydrate Form C is characterized by a $^{19}$F NMR spectrum having a signal at at least three ppm values chosen from −109.9±0.2 ppm, −111.5±0.2 ppm, −113.0±0.2, −120.9±0.2, −121.8±0.2 and −123.4±0.2 ppm. In some embodiments, Hydrate Form C is characterized by a $^{19}$F NMR spectrum having a signal at at least four ppm values chosen from −109.9±0.2 ppm, −111.5±0.2 ppm, −113.0±0.2, −120.9±0.2, −121.8±0.2 and −123.4±0.2 ppm. In some embodiments, Hydrate Form C is characterized by a $^{19}$F NMR spectrum having a signal at at least five ppm values chosen from −109.9±0.2 ppm, −111.5±0.2 ppm, −113.0±0.2, −120.9±0.2, −121.8±0.2 and −123.4±0.2 ppm. In some embodiments, Hydrate Form C is characterized by a $^{19}$F NMR spectrum having signals at −109.9±0.2 ppm, −111.5±0.2 ppm, −113.0±0.2, −120.9±0.2, −121.8±0.2 and −123.4±0.2 ppm.

In some embodiments, Compound 2 is a crystalline solid. In some embodiments, the crystalline solid consists of 1% to 99% Hydrate Form C relative to the total weight of the crystalline solid Compound 2. In some embodiments, the crystalline solid consists of 2% to 99% Hydrate Form C relative to the total weight of the crystalline solid Compound 2. In some embodiments, the crystalline solid consists of 5% to 99% Hydrate Form C relative to the total weight of the crystalline solid Compound 2. In some embodiments, the crystalline solid consists of 10% to 99% Hydrate Form C relative to the total weight of the crystalline solid Compound 2. In some embodiments, the crystalline solid consists of 15% to 99% Hydrate Form C relative to the total weight of the crystalline solid Compound 2. In some embodiments, the crystalline solid consists of 20% to 99% Hydrate Form C relative to the total weight of the crystalline solid Compound 2. In some embodiments, the crystalline solid consists of 25% to 99% Hydrate Form C relative to the total weight of the crystalline solid Compound 2. In some embodiments, the crystalline solid consists of 30% to 99% Hydrate Form C relative to the total weight of the crystalline solid Compound 2. In some embodiments, the crystalline solid consists of 35% to 99% Hydrate Form C relative to the total weight of the crystalline solid Compound 2. In some embodiments, the crystalline solid consists of 45% to 99% Hydrate Form C relative to the total weight of the crystalline solid Compound 2. In some embodiments, the crystalline solid consists of 50% to 99% Hydrate Form C relative to the total weight of the crystalline solid Compound 2. In some embodiments, the crystalline solid consists of 55% to 99% Hydrate Form C relative to the total weight of the crystalline solid Compound 2. In some embodiments, the crystalline solid consists of 60% to 99% Hydrate Form C relative to the total weight of the crystalline solid Compound 2. In some embodiments, the crystalline solid consists of 65% to 99% Hydrate Form C relative to the total weight of the crystalline solid Compound 2. In some embodiments, the crystalline solid consists of 70% to 99% Hydrate Form C relative to the total weight of the crystalline solid Compound 2. In some embodiments, the crystalline solid consists of 75% to 99% Hydrate Form C relative to the total weight of the crystalline solid Compound 2. In some embodiments, the crystalline solid consists of 80% to 99% Hydrate Form C relative to the total weight of the crystalline solid Compound 2. In some embodiments, the crystalline solid consists of 85% to 99% Hydrate Form C relative to the total weight of the crystalline solid Compound 2. In some embodiments, the crystalline solid consists of 90% to 99% Hydrate Form C relative to the total weight of the crystalline solid Compound 2. In some embodiments, the crystalline solid consists of 95% to 99% Hydrate Form C relative to the total weight of the crystalline solid Compound 2.

Hydrate Form D of Compound 2

Figure 19:
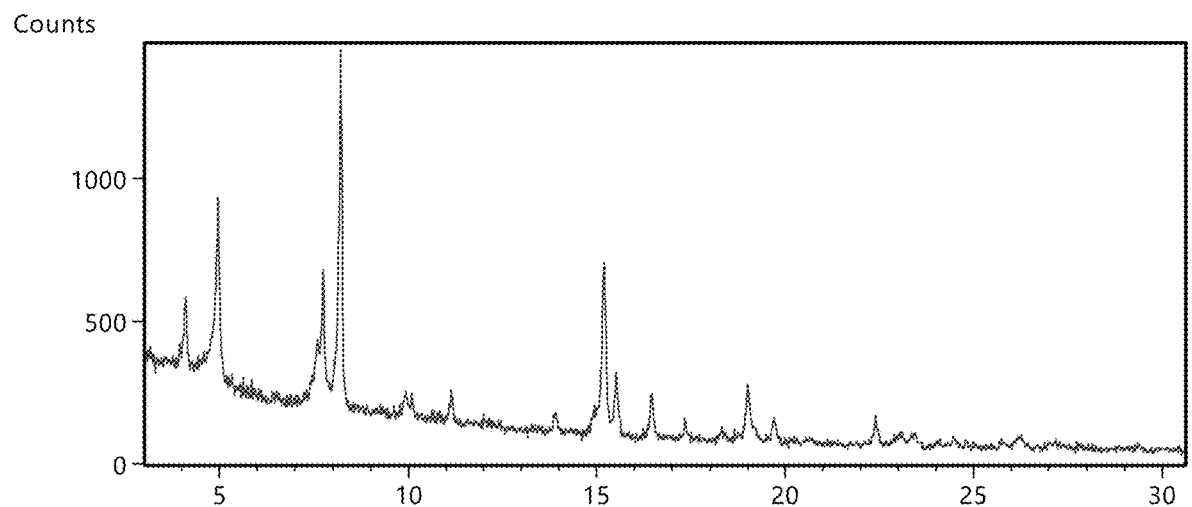
FIG. 19 depicts an XRPD diffractogram of Hydrate Form D of Compound 2.

In some embodiments, Compound 2 is in the form of Hydrate Form D. In some embodiments, Compound 2 is in the form of substantially pure Hydrate Form D. In some embodiments, Hydrate Form D is characterized by an X-ray powder diffractogram substantially similar to that in FIG. 19. In some embodiments, Hydrate Form D is characterized by an X-ray powder diffractogram having a signal at at least two two-theta values chosen from 4.1±0.2, 5.0±0.2, 7.7±0.2, 8.2±0.2, and 15.2±0.2. In some embodiments, Hydrate Form D is characterized by an X-ray powder diffractogram having a signal at at least three two-theta values chosen from 4.1±0.2, 5.0±0.2, 7.7±0.2, 8.2±0.2, and 15.2±0.2. In some embodiments, Hydrate Form D is characterized by an X-ray powder diffractogram having a signal at at least four two-theta values chosen from 4.1±0.2, 5.0±0.2, 7.7±0.2, 8.2±0.2, and 15.2±0.2. In some embodiments, Hydrate Form D is characterized by an X-ray powder diffractogram having a signal at 4.1±0.2, 5.0±0.2, 7.7±0.2, 8.2±0.2, and 15.2±0.2 two-theta.

In some embodiments, Hydrate Form D is characterized by an X-ray powder diffractogram having a signal at at least three two-theta values chosen from 4.1±0.2, 5.0±0.2, 7.6±0.2, 7.7±0.2, 8.2±0.2, 15.2±0.2, 15.5±0.2, 16.5±0.2, and 19.0±0.2. In some embodiments, Hydrate Form D is characterized by an X-ray powder diffractogram having a signal at at least four two-theta values chosen from 4.1±0.2, 5.0±0.2, 7.6±0.2, 7.7±0.2, 8.2±0.2, 15.2±0.2, 15.5±0.2, 16.5±0.2, and 19.0±0.2. In some embodiments, Hydrate Form D is characterized by an X-ray powder diffractogram having a signal at at least five two-theta values chosen from 4.1±0.2, 5.0±0.2, 7.6±0.2, 7.7±0.2, 8.2±0.2, 15.2±0.2, 15.5±0.2, 16.5±0.2, and 19.0±0.2. In some embodiments, Hydrate Form D is characterized by an X-ray powder diffractogram having a signal at at least six two-theta values chosen from 4.1±0.2, 5.0±0.2, 7.6±0.2, 7.7±0.2, 8.2±0.2, 15.2±0.2, 15.5±0.2, 16.5±0.2, and 19.0±0.2. In some embodiments, Hydrate Form D is characterized by an X-ray powder diffractogram having a signal at at least seven two-theta values chosen from 4.1±0.2, 5.0±0.2, 7.6±0.2, 7.7±0.2, 8.2±0.2, 15.2±0.2, 15.5±0.2, 16.5±0.2, and 19.0±0.2. In some embodiments, Hydrate Form D is characterized by an X-ray powder diffractogram having a signal at at least eight two-theta values chosen from 4.1±0.2, 5.0±0.2, 7.6±0.2, 7.7±0.2, 8.2±0.2, 15.2±0.2, 15.5±0.2, 16.5±0.2, and 19.0±0.2. In some embodiments, Hydrate Form D is characterized by an X-ray powder diffractogram having a signal at 4.1±0.2, 5.0±0.2, 7.6±0.2, 7.7±0.2, 8.2±0.2, 15.2±0.2, 15.5±0.2, 16.5±0.2, and 19.0±0.2 two-theta.

In some embodiments, disclosed herein is a composition comprising Hydrate Form D of Compound 2. In some embodiments, disclosed herein is a composition comprising Compound 2 in substantially pure Hydrate Form D. In some embodiments, disclosed herein is a composition comprising at least one active compound consisting essentially of Compound 2 in Hydrate Form D.

Figure 21:
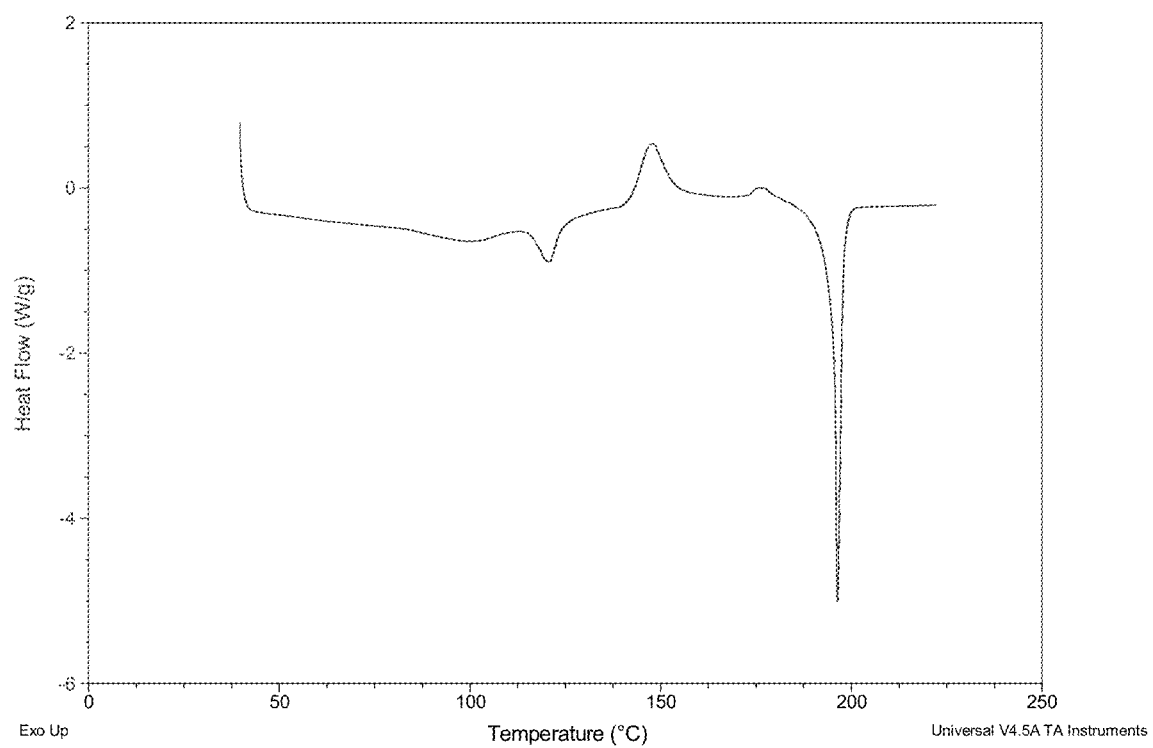
FIG. 21 depicts a DSC curve of Hydrate Form D of Compound 2.

In some embodiments, Hydrate Form D is characterized by a DSC curve substantially similar to that in FIG. 21. In some embodiments, Hydrate Form D is characterized by a DSC curve having a peak at at least one temperature chosen from 121° C., 148° C., 176° C., and 196° C.

In some embodiments, Compound 2 is a crystalline solid. In some embodiments, the crystalline solid consists of 1% to 99% Hydrate Form D relative to the total weight of the crystalline solid Compound 2. In some embodiments, the crystalline solid consists of 2% to 99% Hydrate Form D relative to the total weight of the crystalline solid Compound 2. In some embodiments, the crystalline solid consists of 5% to 99% Hydrate Form D relative to the total weight of the crystalline solid Compound 2. In some embodiments, the crystalline solid consists of 10% to 99% Hydrate Form D relative to the total weight of the crystalline solid Compound 2. In some embodiments, the crystalline solid consists of 15% to 99% Hydrate Form D relative to the total weight of the crystalline solid Compound 2. In some embodiments, the crystalline solid consists of 20% to 99% Hydrate Form D relative to the total weight of the crystalline solid Compound 2. In some embodiments, the crystalline solid consists of 25% to 99% Hydrate Form D relative to the total weight of the crystalline solid Compound 2. In some embodiments, the crystalline solid consists of 30% to 99% Hydrate Form D relative to the total weight of the crystalline solid Compound 2. In some embodiments, the crystalline solid consists of 35% to 99% Hydrate Form D relative to the total weight of the crystalline solid Compound 2. In some embodiments, the crystalline solid consists of 45% to 99% Hydrate Form D relative to the total weight of the crystalline solid Compound 2. In some embodiments, the crystalline solid consists of 50% to 99% Hydrate Form D relative to the total weight of the crystalline solid Compound 2. In some embodiments, the crystalline solid consists of 55% to 99% Hydrate Form D relative to the total weight of the crystalline solid Compound 2. In some embodiments, the crystalline solid consists of 60% to 99% Hydrate Form D relative to the total weight of the crystalline solid Compound 2. In some embodiments, the crystalline solid consists of 65% to 99% Hydrate Form D relative to the total weight of the crystalline solid Compound 2. In some embodiments, the crystalline solid consists of 70% to 99% Hydrate Form D relative to the total weight of the crystalline solid Compound 2. In some embodiments, the crystalline solid consists of 75% to 99% Hydrate Form D relative to the total weight of the crystalline solid Compound 2. In some embodiments, the crystalline solid consists of 80% to 99% Hydrate Form D relative to the total weight of the crystalline solid Compound 2. In some embodiments, the crystalline solid consists of 85% to 99% Hydrate Form D relative to the total weight of the crystalline solid Compound 2. In some embodiments, the crystalline solid consists of 90% to 99% Hydrate Form D relative to the total weight of the crystalline solid Compound 2. In some embodiments, the crystalline solid consists of 95% to 99% Hydrate Form D relative to the total weight of the crystalline solid Compound 2.

Hydrate Form E of Compound 2

Figure 22:
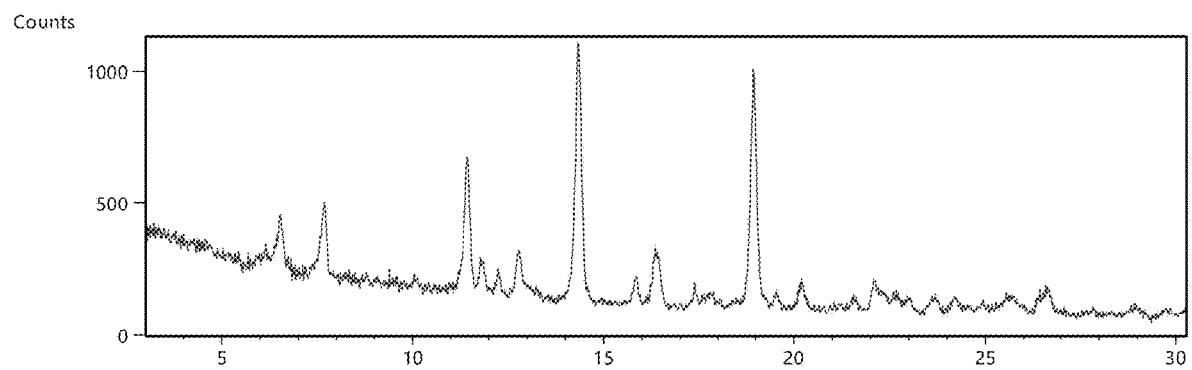
FIG. 22 depicts an XRPD diffractogram of Hydrate Form E of Compound 2.

In some embodiments, Compound 2 is in the form of Hydrate Form E. In some embodiments, Compound 2 is in the form of substantially pure Hydrate Form E. In some embodiments, Hydrate Form E is characterized by an X-ray powder diffractogram substantially similar to that in FIG. 22. In some embodiments, Hydrate Form E is characterized by an X-ray powder diffractogram having a signal at at least two two-theta values chosen from 6.5±0.2, 7.7±0.2, 11.4±0.2, 14.3±0.2, and 18.9±0.2. In some embodiments, Hydrate Form E is characterized by an X-ray powder diffractogram having a signal at at least three two-theta values chosen from 6.5±0.2, 7.7±0.2, 11.4±0.2, 14.3±0.2, and 18.9±0.2. In some embodiments, Hydrate Form E is characterized by an X-ray powder diffractogram having a signal at at least four two-theta values chosen from 6.5±0.2, 7.7±0.2, 11.4±0.2, 14.3±0.2, and 18.9±0.2. In some embodiments, Hydrate Form E is characterized by an X-ray powder diffractogram having a signal at 6.5±0.2, 7.7±0.2, 11.4±0.2, 14.3±0.2, and 18.9±0.2 two-theta.

In some embodiments, Hydrate Form E is characterized by an X-ray powder diffractogram having a signal at at least three two-theta values chosen from 6.5±0.2, 7.7±0.2, 11.4±0.2, 11.8±0.2, 12.8±0.2, 14.3±0.2, 15.8±0.2, 16.4±0.2, 18.9±0.2, and 22.1±0.2. In some embodiments, Hydrate Form E is characterized by an X-ray powder diffractogram having a signal at at least four two-theta values chosen from 6.5±0.2, 7.7±0.2, 11.4±0.2, 11.8±0.2, 12.8±0.2, 14.3±0.2, 15.8±0.2, 16.4±0.2, 18.9±0.2, and 22.1±0.2. In some embodiments, Hydrate Form E is characterized by an X-ray powder diffractogram having a signal at at least five two-theta values chosen from 6.5±0.2, 7.7±0.2, 11.4±0.2, 11.8±0.2, 12.8±0.2, 14.3±0.2, 15.8±0.2, 16.4±0.2, 18.9±0.2, and 22.1±0.2. In some embodiments, Hydrate Form E is characterized by an X-ray powder diffractogram having a signal at at least six two-theta values chosen from 6.5±0.2, 7.7±0.2, 11.4±0.2, 11.8±0.2, 12.8±0.2, 14.3±0.2, 15.8±0.2, 16.4±0.2, 18.9±0.2, and 22.1±0.2. In some embodiments, Hydrate Form E is characterized by an X-ray powder diffractogram having a signal at at least seven two-theta values chosen from 6.5±0.2, 7.7±0.2, 11.4±0.2, 11.8±0.2, 12.8±0.2, 14.3±0.2, 15.8±0.2, 16.4±0.2, 18.9±0.2, and 22.1±0.2. In some embodiments, Hydrate Form E is characterized by an X-ray powder diffractogram having a signal at at least eight two-theta values chosen from 6.5±0.2, 7.7±0.2, 11.4±0.2, 11.8±0.2, 12.8±0.2, 14.3±0.2, 15.8±0.2, 16.4±0.2, 18.9±0.2, and 22.1±0.2. In some embodiments, Hydrate Form E is characterized by an X-ray powder diffractogram having a signal at at least nine two-theta values chosen from 6.5±0.2, 7.7±0.2, 11.4±0.2, 11.8±0.2, 12.8±0.2, 14.3±0.2, 15.8±0.2, 16.4±0.2, 18.9±0.2, and 22.1±0.2. In some embodiments, Hydrate Form E is characterized by an X-ray powder diffractogram having a signal at 6.5±0.2, 7.7±0.2, 11.4±0.2, 11.8±0.2, 12.8±0.2, 14.3±0.2, 15.8±0.2, 16.4±0.2, 18.9±0.2, and 22.1±0.2 two-theta.

In some embodiments, disclosed herein is a composition comprising Hydrate Form E of Compound 2. In some embodiments, disclosed herein is a composition comprising Compound 2 in substantially pure Hydrate Form E. In some embodiments, disclosed herein is a composition comprising at least one active compound consisting essentially of Compound 2 in Hydrate Form E.

Figure 24:
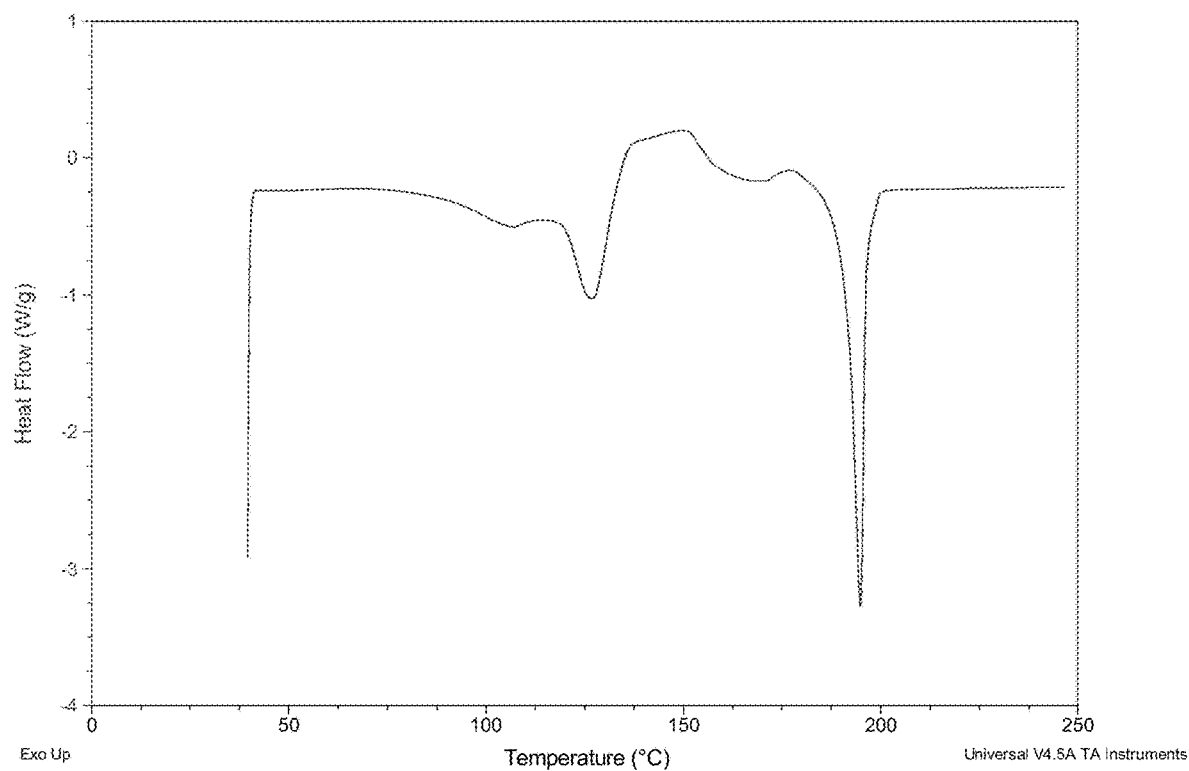
FIG. 24 depicts a DSC curve of Hydrate Form E of Compound 2.

In some embodiments, Hydrate Form E is characterized by a DSC curve substantially similar to that in FIG. 24. In some embodiments, Hydrate Form E is characterized by a DSC curve having a peak at at least one temperature chosen from 107° C., 127° C., 150° C., 177° C., and 195° C.

In some embodiments, Compound 2 is a crystalline solid. In some embodiments, the crystalline solid consists of 1% to 99% Hydrate Form E relative to the total weight of the crystalline solid Compound 2. In some embodiments, the crystalline solid consists of 2% to 99% Hydrate Form E relative to the total weight of the crystalline solid Compound 2. In some embodiments, the crystalline solid consists of 5% to 99% Hydrate Form E relative to the total weight of the crystalline solid Compound 2. In some embodiments, the crystalline solid consists of 10% to 99% Hydrate Form E relative to the total weight of the crystalline solid Compound 2. In some embodiments, the crystalline solid consists of 15% to 99% Hydrate Form E relative to the total weight of the crystalline solid Compound 2. In some embodiments, the crystalline solid consists of 20% to 99% Hydrate Form E relative to the total weight of the crystalline solid Compound 2. In some embodiments, the crystalline solid consists of 25% to 99% Hydrate Form E relative to the total weight of the crystalline solid Compound 2. In some embodiments, the crystalline solid consists of 30% to 99% Hydrate Form E relative to the total weight of the crystalline solid Compound 2. In some embodiments, the crystalline solid consists of 35% to 99% Hydrate Form E relative to the total weight of the crystalline solid Compound 2. In some embodiments, the crystalline solid consists of 45% to 99% Hydrate Form E relative to the total weight of the crystalline solid Compound 2. In some embodiments, the crystalline solid consists of 50% to 99% Hydrate Form E relative to the total weight of the crystalline solid Compound 2. In some embodiments, the crystalline solid consists of 55% to 99% Hydrate Form E relative to the total weight of the crystalline solid Compound 2. In some embodiments, the crystalline solid consists of 60% to 99% Hydrate Form E relative to the total weight of the crystalline solid Compound 2. In some embodiments, the crystalline solid consists of 65% to 99% Hydrate Form E relative to the total weight of the crystalline solid Compound 2. In some embodiments, the crystalline solid consists of 70% to 99% Hydrate Form E relative to the total weight of the crystalline solid Compound 2. In some embodiments, the crystalline solid consists of 75% to 99% Hydrate Form E relative to the total weight of the crystalline solid Compound 2. In some embodiments, the crystalline solid consists of 80% to 99% Hydrate Form E relative to the total weight of the crystalline solid Compound 2. In some embodiments, the crystalline solid consists of 85% to 99% Hydrate Form E relative to the total weight of the crystalline solid Compound 2. In some embodiments, the crystalline solid consists of 90% to 99% Hydrate Form E relative to the total weight of the crystalline solid Compound 2. In some embodiments, the crystalline solid consists of 95% to 99% Hydrate Form E relative to the total weight of the crystalline solid Compound 2.

Hydrate Form F of Compound 2

Figure 25:
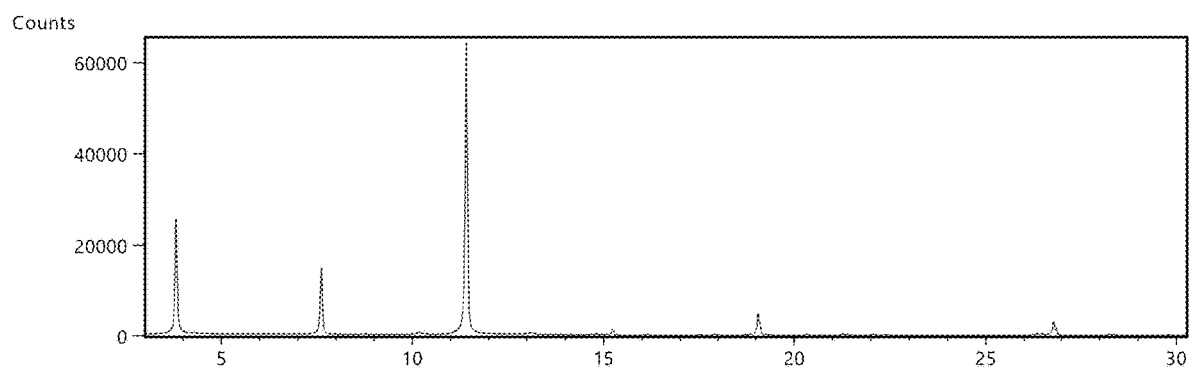
FIG. 25 depicts an XRPD diffractogram of Hydrate Form F of Compound 2.

In some embodiments, Compound 2 is in the form of Hydrate Form F. In some embodiments, Compound 2 is in the form of substantially pure Hydrate Form F. In some embodiments, Hydrate Form F is characterized by an X-ray powder diffractogram substantially similar to that in FIG. 25. In some embodiments, Hydrate Form F is characterized by an X-ray powder diffractogram having a signal at at least two two-theta values chosen from 3.8±0.2, 7.6±0.2, and 11.4±0.2. In some embodiments, Hydrate Form F is characterized by an X-ray powder diffractogram having a signal at 3.8±0.2, 7.6±0.2, and 11.4±0.2 two-theta.

In some embodiments, disclosed herein is a composition comprising Hydrate Form F of Compound 2. In some embodiments, disclosed herein is a composition comprising Compound 2 in substantially pure Hydrate Form F. In some embodiments, disclosed herein is a composition comprising at least one active compound consisting essentially of Compound 2 in Hydrate Form F.

Figure 27:
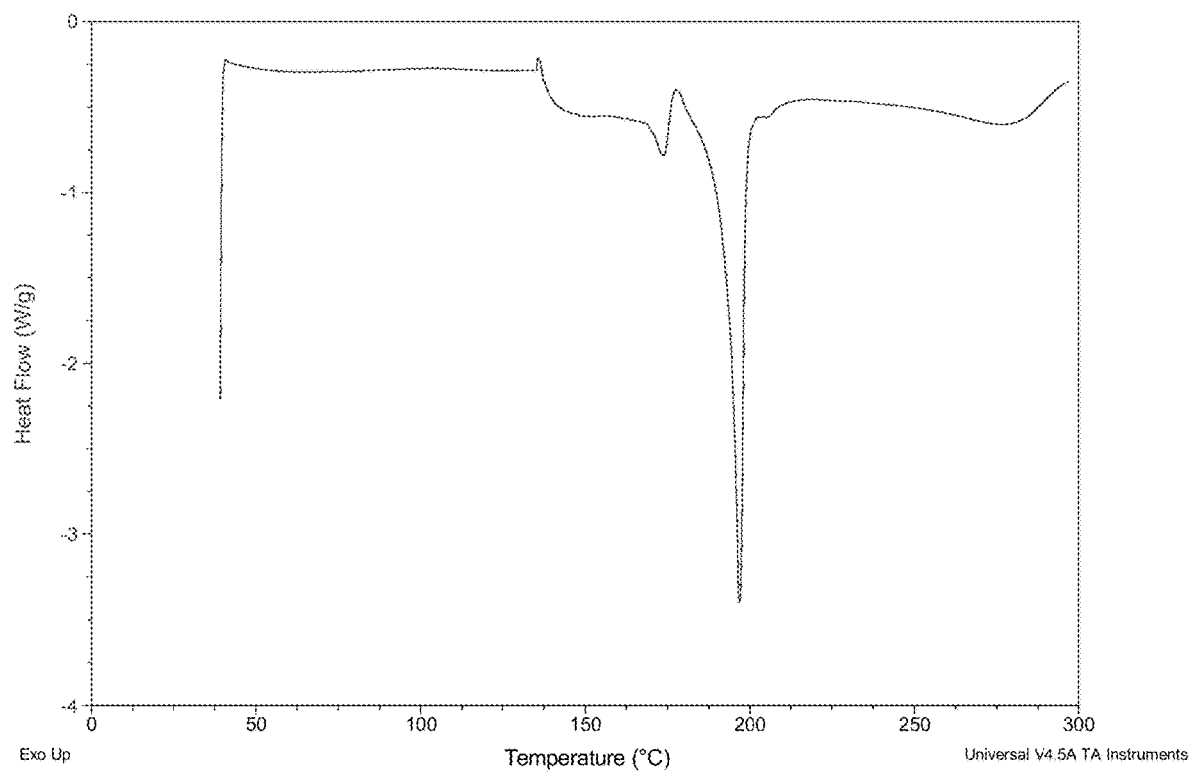
FIG. 27 depicts a DSC curve of Hydrate Form F of Compound 2.

In some embodiments, Hydrate Form F is characterized by a DSC curve substantially similar to that in FIG. 27. In some embodiments, Hydrate Form F is characterized by a DSC curve having a peak at at least one temperature chosen from 174° C., 177° C., and 197° C.

In some embodiments, Compound 2 is a crystalline solid. In some embodiments, the crystalline solid consists of 1% to 99% Hydrate Form F relative to the total weight of the crystalline solid Compound 2. In some embodiments, the crystalline solid consists of 2% to 99% Hydrate Form F relative to the total weight of the crystalline solid Compound 2. In some embodiments, the crystalline solid consists of 5% to 99% Hydrate Form F relative to the total weight of the crystalline solid Compound 2. In some embodiments, the crystalline solid consists of 10% to 99% Hydrate Form F relative to the total weight of the crystalline solid Compound 2. In some embodiments, the crystalline solid consists of 15% to 99% Hydrate Form F relative to the total weight of the crystalline solid Compound 2. In some embodiments, the crystalline solid consists of 20% to 99% Hydrate Form F relative to the total weight of the crystalline solid Compound 2. In some embodiments, the crystalline solid consists of 25% to 99% Hydrate Form F relative to the total weight of the crystalline solid Compound 2. In some embodiments, the crystalline solid consists of 30% to 99% Hydrate Form F relative to the total weight of the crystalline solid Compound 2. In some embodiments, the crystalline solid consists of 35% to 99% Hydrate Form F relative to the total weight of the crystalline solid Compound 2. In some embodiments, the crystalline solid consists of 45% to 99% Hydrate Form F relative to the total weight of the crystalline solid Compound 2. In some embodiments, the crystalline solid consists of 50% to 99% Hydrate Form F relative to the total weight of the crystalline solid Compound 2. In some embodiments, the crystalline solid consists of 55% to 99% Hydrate Form F relative to the total weight of the crystalline solid Compound 2. In some embodiments, the crystalline solid consists of 60% to 99% Hydrate Form F relative to the total weight of the crystalline solid Compound 2. In some embodiments, the crystalline solid consists of 65% to 99% Hydrate Form F relative to the total weight of the crystalline solid Compound 2. In some embodiments, the crystalline solid consists of 70% to 99% Hydrate Form F relative to the total weight of the crystalline solid Compound 2. In some embodiments, the crystalline solid consists of 75% to 99% Hydrate Form F relative to the total weight of the crystalline solid Compound 2. In some embodiments, the crystalline solid consists of 80% to 99% Hydrate Form F relative to the total weight of the crystalline solid Compound 2. In some embodiments, the crystalline solid consists of 85% to 99% Hydrate Form F relative to the total weight of the crystalline solid Compound 2. In some embodiments, the crystalline solid consists of 90% to 99% Hydrate Form F relative to the total weight of the crystalline solid Compound 2. In some embodiments, the crystalline solid consists of 95% to 99% Hydrate Form F relative to the total weight of the crystalline solid Compound 2.

MTBE Solvate Form of Compound 2

Figure 28:
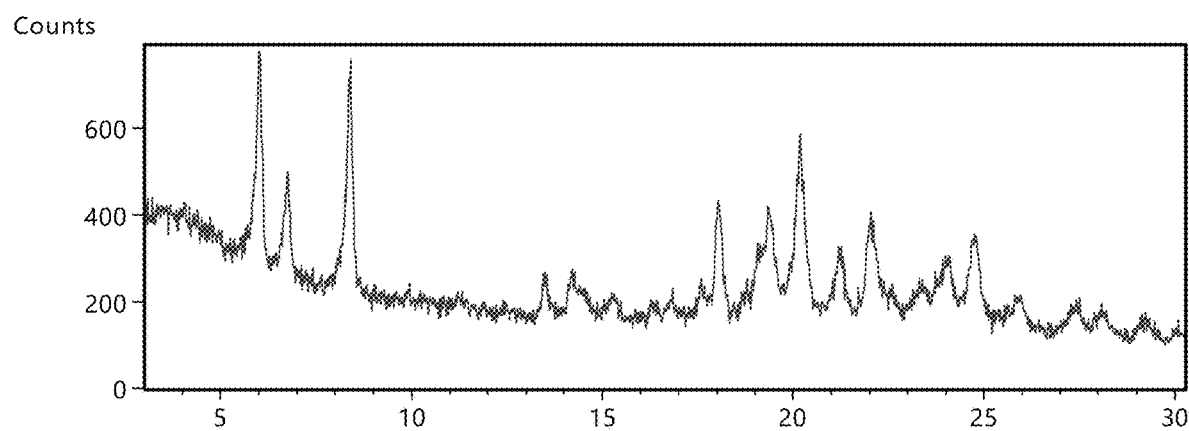
FIG. 28 depicts an XRPD diffractogram of MTBE solvate of Compound 2.

In some embodiments, Compound 2 is in the form of an MTBE Solvate Form. In some embodiments, Compound 2 is in the form of substantially pure MTBE Solvate Form. In some embodiments, MTBE Solvate Form is characterized by an X-ray powder diffractogram substantially similar to that in FIG. 28.

In some embodiments, MTBE Solvate Form is characterized by an X-ray powder diffractogram having a signal at at least two two-theta values chosen from 6.0±0.2, 6.8±0.2, 8.4±0.2, 18.0±0.2, 19.4±0.2, and 20.2±0.2. In some embodiments, MTBE Solvate Form is characterized by an X-ray powder diffractogram having a signal at at least three two-theta values chosen from 6.0±0.2, 6.8±0.2, 8.4±0.2, 18.0±0.2, 19.4±0.2, and 20.2±0.2. In some embodiments, MTBE Solvate Form is characterized by an X-ray powder diffractogram having a signal at at least four two-theta values chosen from 6.0±0.2, 6.8±0.2, 8.4±0.2, 18.0±0.2, 19.4±0.2, and 20.2±0.2. In some embodiments, MTBE Solvate Form is characterized by an X-ray powder diffractogram having a signal at at least five two-theta values chosen from 6.0±0.2, 6.8±0.2, 8.4±0.2, 18.0±0.2, 19.4±0.2, and 20.2±0.2. In some embodiments, MTBE Solvate Form is characterized by an X-ray powder diffractogram having a signal at at least 6.0±0.2, 6.8±0.2, 8.4±0.2, 18.0±0.2, 19.4±0.2, and 20.2±0.2 two-theta.

In some embodiments, disclosed herein is a composition comprising MTBE Solvate Form of Compound 2. In some embodiments, disclosed herein is a composition comprising Compound 2 in substantially pure MTBE Solvate Form. In some embodiments, disclosed herein is a composition comprising at least one active compound consisting essentially of Compound 2 in MTBE Solvate Form.

Figure 30:
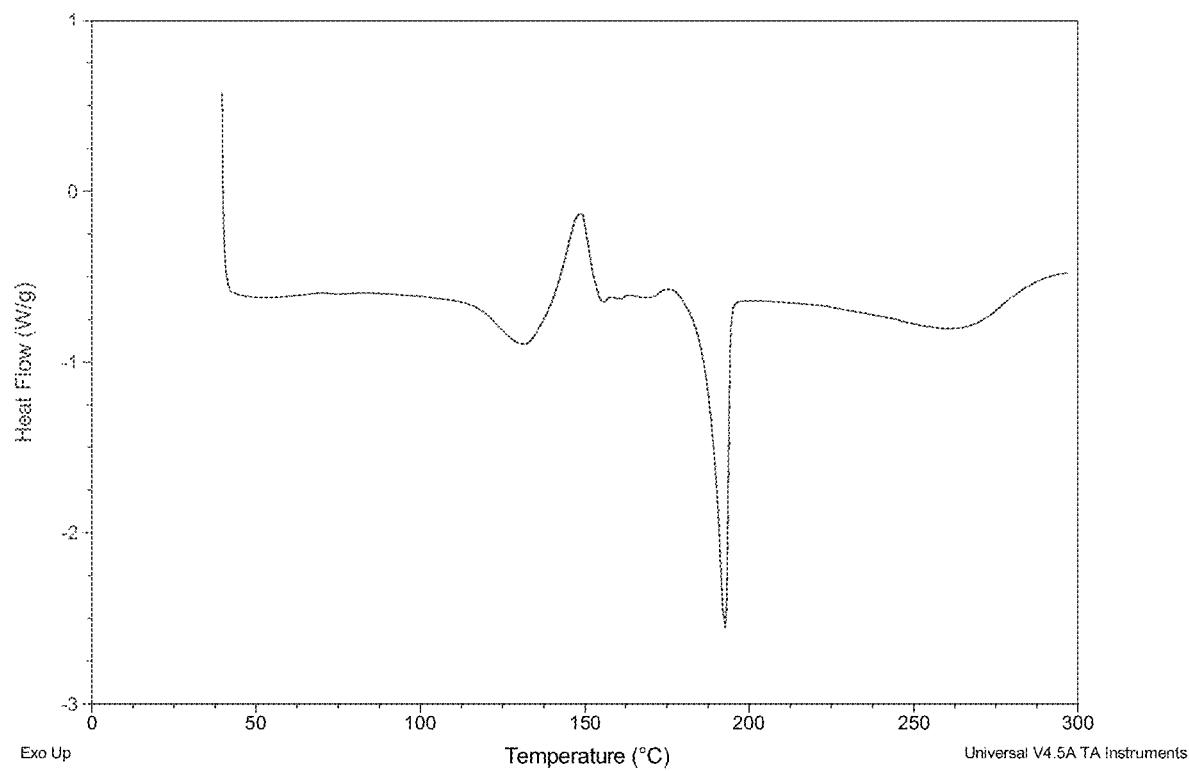
FIG. 30 depicts a DSC curve of MTBE solvate of Compound 2.

In some embodiments, MTBE Solvate Form is characterized by a DSC curve substantially similar to that in FIG. 30. In some embodiments, MTBE Solvate Form is characterized by a DSC curve having a peak at at least one temperature chosen from 131° C., 148° C., and 193° C.

DMF Solvate Form of Compound 2

Figure 31:
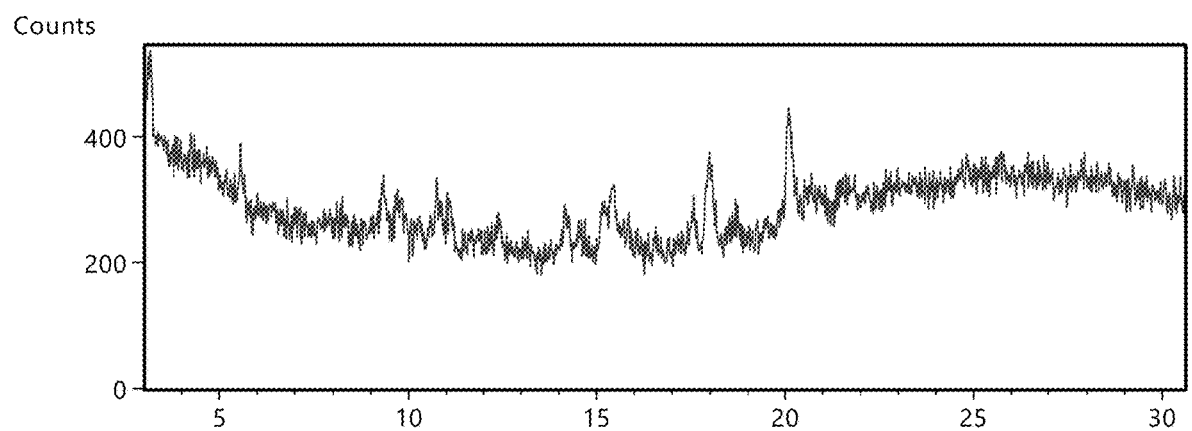
FIG. 31 depicts an XRPD diffractogram of DMF solvate of Compound 2.

In some embodiments, Compound 2 is in the form of a DMF Solvate Form. In some embodiments, Compound 2 is in the form of substantially pure DMF Solvate Form. In some embodiments, DMF Solvate Form is characterized by an X-ray powder diffractogram substantially similar to that in FIG. 31.

In some embodiments, DMF Solvate Form is characterized by an X-ray powder diffractogram having a signal at at least two two-theta values chosen from 15.3±0.2, 18.0±0.2, and 20.1±0.2. In some embodiments, DMF Solvate Form is characterized by an X-ray powder diffractogram having a signal at at least three two-theta values chosen from 15.3±0.2, 18.0±0.2, and 20.1±0.2. In some embodiments, DMF Solvate Form is characterized by an X-ray powder diffractogram having a signal at at least two two-theta values chosen from 5.6±0.2, 9.3±0.2, 15.3±0.2, 18.0±0.2, and 20.1±0.2. In some embodiments, DMF Solvate Form is characterized by an X-ray powder diffractogram having a signal at at least three two-theta values chosen from 5.6±0.2, 9.3±0.2, 15.3±0.2, 18.0±0.2, and 20.1±0.2. In some embodiments, DMF Solvate Form is characterized by an X-ray powder diffractogram having a signal at at least four two-theta values chosen from 5.6±0.2, 9.3±0.2, 15.3±0.2, 18.0±0.2, and 20.1±0.2. In some embodiments, DMF Solvate Form is characterized by an X-ray powder diffractogram having a signal at at least 5.6±0.2, 9.3±0.2, 15.3±0.2, 18.0±0.2, and 20.1±0.2 two-theta.

In some embodiments, disclosed herein is a composition comprising DMF Solvate Form of Compound 2. In some embodiments, disclosed herein is a composition comprising Compound 2 in substantially pure DMF Solvate Form. In some embodiments, disclosed herein is a composition comprising at least one active compound consisting essentially of Compound 2 in DMF Solvate Form.

Figure 33:
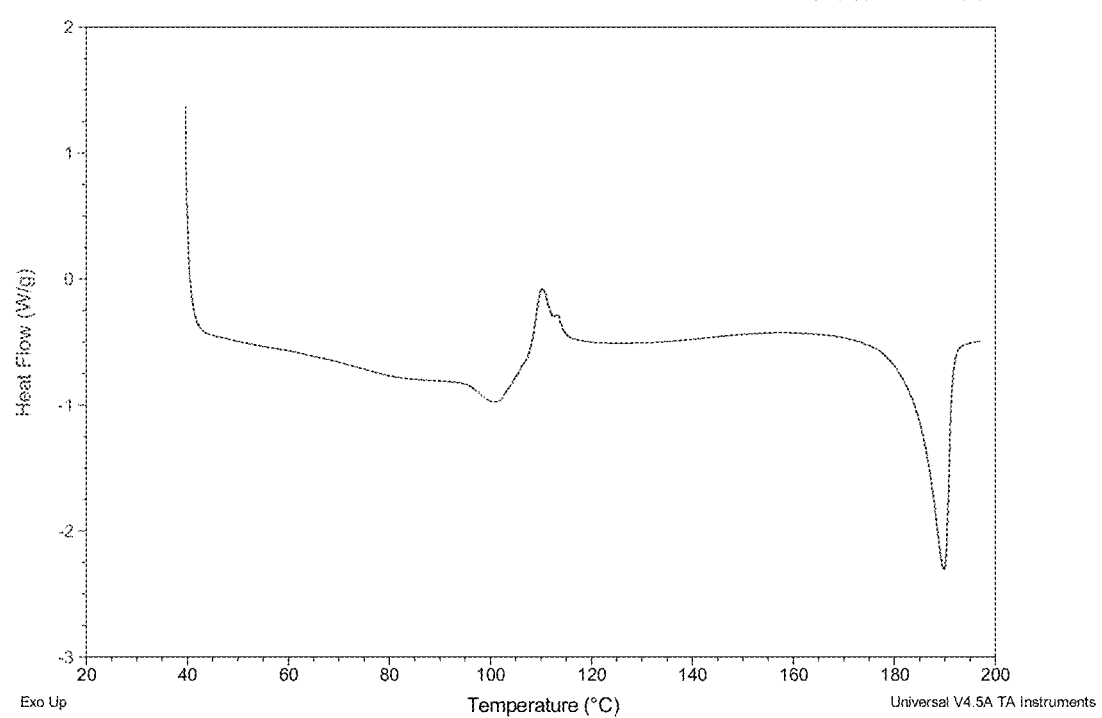
FIG. 33 depicts a DSC curve of DMF solvate of Compound 2.

In some embodiments, DMF Solvate Form is characterized by a DSC curve substantially similar to that in FIG. 33. In some embodiments, DMF Solvate Form is characterized by a DSC curve having a peak at at least one temperature chosen from 101° C., 110° C., and 190° C.

Amorphous Form of Compound 2

Figure 34:
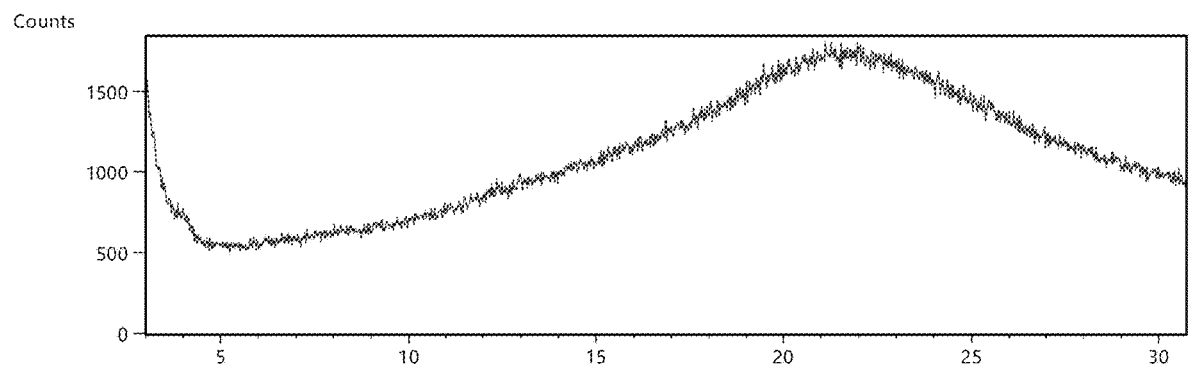
FIG. 34 depicts an XRPD diffractogram of amorphous form of Compound 2.

In some embodiments, Compound 2 is in an amorphous Form. In some embodiments, Compound 2 is in the form of substantially pure amorphous Form. In some embodiments, amorphous Form of Compound 2 is characterized by an X-ray powder diffractogram substantially similar to that in FIG. 34.

In some embodiments, disclosed herein is a composition comprising amorphous Form of Compound 2. In some embodiments, disclosed herein is a composition comprising Compound 2 in substantially pure amorphous Form. In some embodiments, disclosed herein is a composition comprising at least one active compound consisting essentially of Compound 2 in amorphous Form.

Figure 37:
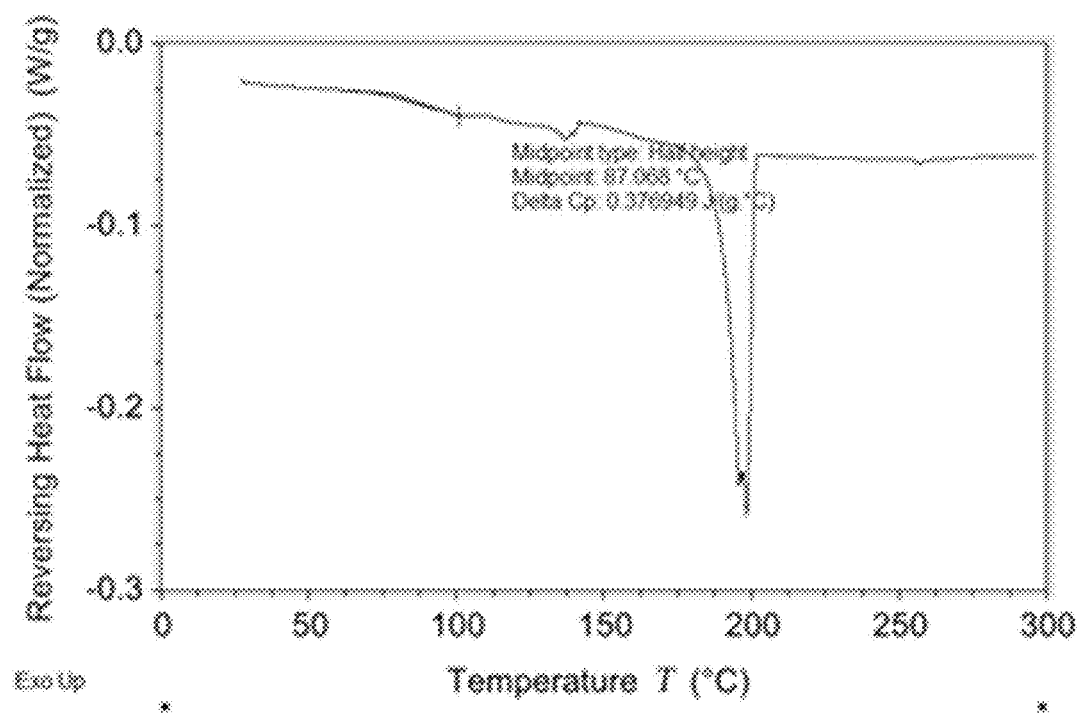
FIG. 37 depicts a DSC curve of amorphous form of Compound 2.

In some embodiments, amorphous Form is characterized by a DSC curve substantially similar to that in FIG. 37. In some embodiments, amorphous Form is characterized by a DSC curve having a glass transition of 87° C.

In some embodiments, amorphous Form is characterized by a $^{13}$C NMR spectrum having a signal at at least one ppm value chosen from 174.7±0.2 ppm, 161.3±0.2 ppm, 130.2±0.2 ppm, 120.9±0.2 ppm, 74.7±0.2 ppm, and 20.5±0.2 ppm. In some embodiments, amorphous Form is characterized by a $^{13}$C NMR spectrum having a signal at at least two ppm values chosen from 174.7±0.2 ppm, 161.3±0.2 ppm, 130.2±0.2 ppm, 120.9±0.2 ppm, 74.7±0.2 ppm, and 20.5±0.2 ppm. In some embodiments, amorphous Form is characterized by a $^{13}$C NMR spectrum having a signal at at least three ppm values chosen from 174.7±0.2 ppm, 161.3±0.2 ppm, 130.2±0.2 ppm, 120.9±0.2 ppm, 74.7±0.2 ppm, and 20.5±0.2 ppm. In some embodiments, amorphous Form is characterized by a $^{13}$C NMR spectrum having a signal at at least four ppm values chosen from 174.7±0.2 ppm, 161.3±0.2 ppm, 130.2±0.2 ppm, 120.9±0.2 ppm, 74.7±0.2 ppm, and 20.5±0.2 ppm. In some embodiments, amorphous Form is characterized by a $^{13}$C NMR spectrum having a signal at at least five ppm values chosen from 174.7±0.2 ppm, 161.3±0.2 ppm, 130.2±0.2 ppm, 120.9±0.2 ppm, 74.7±0.2 ppm, and 20.5±0.2 ppm. In some embodiments, amorphous Form is characterized by a $^{13}$C NMR spectrum having a signal at 174.7±0.2 ppm, 161.3±0.2 ppm, 130.2±0.2 ppm, 120.9±0.2 ppm, 74.7±0.2 ppm, and 20.5±0.2 ppm.

In some embodiments, amorphous Form is characterized by a $^{19}$F NMR spectrum having a signal at at least one ppm value chosen from −122.4±0.2 ppm and −131.1±0.2 ppm. In some embodiments, amorphous Form is characterized by a $^{19}$F NMR spectrum having a signal at −122.4±0.2 ppm and −131.1±0.2 ppm.

Solid forms of Compound 87

In some embodiments, the at least one entity chosen from compounds of Formula (I) is Compound 87. Compound 87 can be depicted as follows:

(87)

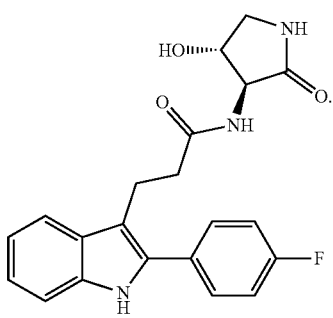

In some embodiments, Compound 87 is an amorphous solid. In some embodiments, Compound 87 is a crystalline solid. In some embodiments, Compound 87 is in the form of Form A, Hydrate Form, IPAc solvate, or a mixture of any two or more of the foregoing.

Form A of Compound 87

Figure 38:
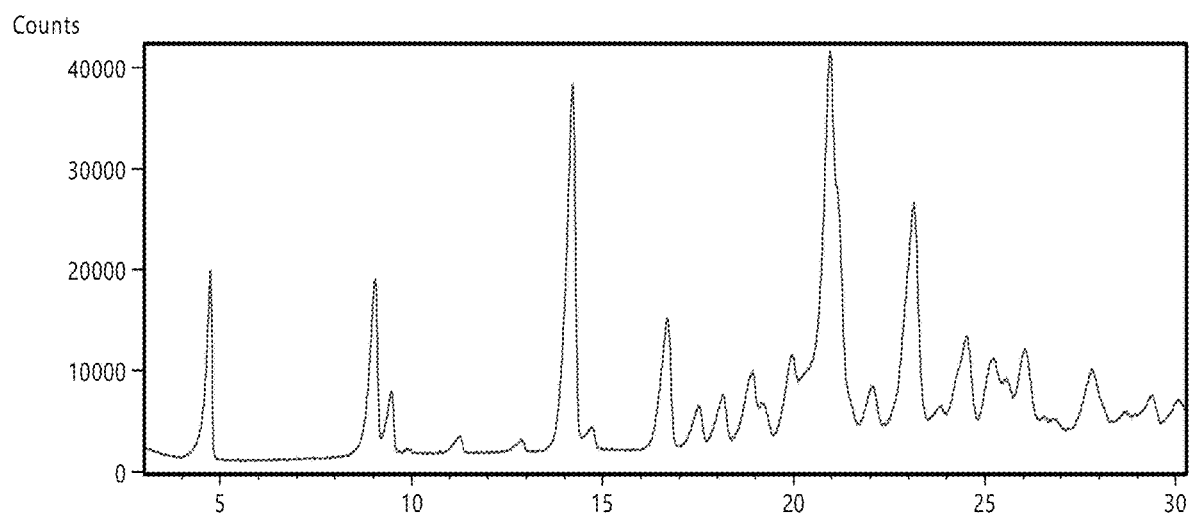
FIG. 38 depicts an XRPD diffractogram of Form A of Compound 87.

In some embodiments, Compound 87 is in the form of Form A. In some embodiments, Compound 87 is in the form of substantially pure Form A. In some embodiments, Form A is characterized by an X-ray powder diffractogram substantially similar to that in FIG. 38. In some embodiments, Form A is characterized by an X-ray powder diffractogram having a signal at at least two two-theta values chosen from 4.7±0.2, 9.0±0.2, 14.2±0.2, 16.7±0.2, 21.0±0.2, 21.2±0.2, 22.9±0.2, 23.1±0.2 and 24.5±0.2. In some embodiments, Form A is characterized by an X-ray powder diffractogram having a signal at at least three two-theta values chosen from 4.7±0.2, 9.0±0.2, 14.2±0.2, 16.7±0.2, 21.0±0.2, 21.2±0.2, 22.9±0.2, 23.1±0.2 and 24.5±0.2. In some embodiments, Form A is characterized by an X-ray powder diffractogram having a signal at at least four two-theta values chosen from 4.7±0.2, 9.0±0.2, 14.2±0.2, 16.7±0.2, 21.0±0.2, 21.2±0.2, 22.9±0.2, 23.1±0.2 and 24.5±0.2. In some embodiments, Form A is characterized by an X-ray powder diffractogram having a signal at at least five two-theta values chosen from 4.7±0.2, 9.0±0.2, 14.2±0.2, 16.7±0.2, 21.0±0.2, 21.2±0.2, 22.9±0.2, 23.1±0.2 and 24.5±0.2. In some embodiments, Form A is characterized by an X-ray powder diffractogram having a signal at at least six two-theta values chosen 4.7±0.2, 9.0±0.2, 14.2±0.2, 16.7±0.2, 21.0±0.2, 21.2±0.2, 22.9±0.2, 23.1±0.2 and 24.5±0.2. In some embodiments, Form A is characterized by an X-ray powder diffractogram having a signal at at least seven two-theta values chosen from 4.7±0.2, 9.0±0.2, 14.2±0.2, 16.7±0.2, 21.0±0.2, 21.2±0.2, 22.9±0.2, 23.1±0.2 and 24.5±0.2. In some embodiments, Form A is characterized by an X-ray powder diffractogram having a signal at at least eight two-theta values chosen from 4.7±0.2, 9.0±0.2, 14.2±0.2, 16.7±0.2, 21.0±0.2, 21.2±0.2, 22.9±0.2, 23.1±0.2 and 24.5±0.2. In some embodiments, Form A is characterized by an X-ray powder diffractogram having a signal at the following two-theta values 4.7±0.2, 9.0±0.2, 14.2±0.2, 16.7±0.2, 21.0±0.2, 21.2±0.2, 22.9±0.2, 23.1±0.2 and 24.5±0.2.

In some embodiments, Form A is characterized by an X-ray powder diffractogram having a signal at at least one two-theta values chosen from 4.7±0.2, 9.0±0.2, 9.5±0.2, 14.2±0.2, 16.7±0.2, 18.1±0.2, 18.9±0.2, 20.0±0.2, 21.0±0.2, 21.9±0.2, 22.1±0.2, 22.9±0.2, 23.1±0.2, 24.3±0.2, 24.5±0.2, 25.2±0.2, 25.6±0.2, 26.0±0.2, 26.1±0.2, and 27.8±0.2. In some embodiments, Form A is characterized by an X-ray powder diffractogram having a signal at at least two two-theta values chosen from 4.7±0.2, 9.0±0.2, 9.5±0.2, 14.2±0.2, 16.7±0.2, 18.1±0.2, 18.9±0.2, 20.0±0.2, 21.0±0.2, 21.9±0.2, 22.1±0.2, 22.9±0.2, 23.1±0.2, 24.3±0.2, 24.5±0.2, 25.2±0.2, 25.6±0.2, 26.0±0.2, 26.1±0.2, and 27.8±0.2. In some embodiments, Form A is characterized by an X-ray powder diffractogram having a signal at at least three two-theta values chosen from 4.7±0.2, 9.0±0.2, 9.5±0.2, 14.2±0.2, 16.7±0.2, 18.1±0.2, 18.9±0.2, 20.0±0.2, 21.0±0.2, 21.9±0.2, 22.1±0.2, 22.9±0.2, 23.1±0.2, 24.3±0.2, 24.5±0.2, 25.2±0.2, 25.6±0.2, 26.0±0.2, 26.1±0.2, and 27.8±0.2. In some embodiments, Form A is characterized by an X-ray powder diffractogram having a signal at at least four two-theta values chosen from 4.7±0.2, 9.0±0.2, 9.5±0.2, 14.2±0.2, 16.7±0.2, 18.1±0.2, 18.9±0.2, 20.0±0.2, 21.0±0.2, 21.9±0.2, 22.1±0.2, 22.9±0.2, 23.1±0.2, 24.3±0.2, 24.5±0.2, 25.2±0.2, 25.6±0.2, 26.0±0.2, 26.1±0.2, and 27.8±0.2. In some embodiments, Form A is characterized by an X-ray powder diffractogram having a signal at at least five two-theta values chosen from 4.7±0.2, 9.0±0.2, 9.5±0.2, 14.2±0.2, 16.7±0.2, 18.1±0.2, 18.9±0.2, 20.0±0.2, 21.0±0.2, 21.9±0.2, 22.1±0.2, 22.9±0.2, 23.1±0.2, 24.3±0.2, 24.5±0.2, 25.2±0.2, 25.6±0.2, 26.0±0.2, 26.1±0.2, and 27.8±0.2. In some embodiments, Form A is characterized by an X-ray powder diffractogram having a signal at at least six two-theta values chosen from 4.7±0.2, 9.0±0.2, 9.5±0.2, 14.2±0.2, 16.7±0.2, 18.1±0.2, 18.9±0.2, 20.0±0.2, 21.0±0.2, 21.9±0.2, 22.1±0.2, 22.9±0.2, 23.1±0.2, 24.3±0.2, 24.5±0.2, 25.2±0.2, 25.6±0.2, 26.0±0.2, 26.1±0.2, and 27.8±0.2. In some embodiments, Form A is characterized by an X-ray powder diffractogram having a signal at at least seven two-theta values chosen from 4.7±0.2, 9.0±0.2, 9.5±0.2, 14.2±0.2, 16.7±0.2, 18.1±0.2, 18.9±0.2, 20.0±0.2, 21.0±0.2, 21.9±0.2, 22.1±0.2, 22.9±0.2, 23.1±0.2, 24.3±0.2, 24.5±0.2, 25.2±0.2, 25.6±0.2, 26.0±0.2, 26.1±0.2, and 27.8±0.2, and 27.8±0.2. In some embodiments, Form A is characterized by an X-ray powder diffractogram having a signal at at least eight two-theta values chosen from 4.7±0.2, 9.0±0.2, 9.5±0.2, 14.2±0.2, 16.7±0.2, 18.1±0.2, 18.9±0.2, 20.0±0.2, 21.0±0.2, 21.9±0.2, 22.1±0.2, 22.9±0.2, 23.1±0.2, 24.3±0.2, 24.5±0.2, 25.2±0.2, 25.6±0.2, 26.0±0.2, 26.1±0.2, and 27.8±0.2. In some embodiments, Form A is characterized by an X-ray powder diffractogram having a signal at at least nine two-theta values chosen from 4.7±0.2, 9.0±0.2, 9.5±0.2, 14.2±0.2, 16.7±0.2, 18.1±0.2, 18.9±0.2, 20.0±0.2, 21.0±0.2, 21.9±0.2, 22.1±0.2, 22.9±0.2, 23.1±0.2, 24.3±0.2, 24.5±0.2, 25.2±0.2, 25.6±0.2, 26.0±0.2, 26.1±0.2, and 27.8±0.2. In some embodiments, Form A is characterized by an X-ray powder diffractogram having a signal at at least ten two-theta values chosen from 4.7±0.2, 9.0±0.2, 9.5±0.2, 14.2±0.2, 16.7±0.2, 18.1±0.2, 18.9±0.2, 20.0±0.2, 21.0±0.2, 21.9±0.2, 22.1±0.2, 22.9±0.2, 23.1±0.2, 24.3±0.2, 24.5±0.2, 25.2±0.2, 25.6±0.2, 26.0±0.2, 26.1±0.2, and 27.8±0.2. In some embodiments, Form A is characterized by an X-ray powder diffractogram having a signal at at least eleven two-theta values chosen from 4.7±0.2, 9.0±0.2, 9.5±0.2, 14.2±0.2, 16.7±0.2, 18.1±0.2, 18.9±0.2, 20.0±0.2, 21.0±0.2, 21.9±0.2, 22.1±0.2, 22.9±0.2, 23.1±0.2, 24.3±0.2, 24.5±0.2, 25.2±0.2, 25.6±0.2, 26.0±0.2, 26.1±0.2, and 27.8±0.2. In some embodiments, Form A is characterized by an X-ray powder diffractogram having a signal at at least twelve two-theta values chosen from 4.7±0.2, 9.0±0.2, 9.5±0.2, 14.2±0.2, 16.7±0.2, 18.1±0.2, 18.9±0.2, 20.0±0.2, 21.0±0.2, 21.9±0.2, 22.1±0.2, 22.9±0.2, 23.1±0.2, 24.3±0.2, 24.5±0.2, 25.2±0.2, 25.6±0.2, 26.0±0.2, 26.1±0.2, and 27.8±0.2. In some embodiments, Form A is characterized by an X-ray powder diffractogram having a signal at at least thirteen two-theta values chosen from 4.7±0.2, 9.0±0.2, 9.5±0.2, 14.2±0.2, 16.7±0.2, 18.1±0.2, 18.9±0.2, 20.0±0.2, 21.0±0.2, 21.9±0.2, 22.1±0.2, 22.9±0.2, 23.1±0.2, 24.3±0.2, 24.5±0.2, 25.2±0.2, 25.6±0.2, 26.0±0.2, 26.1±0.2, and 27.8±0.2. In some embodiments, Form A is characterized by an X-ray powder diffractogram having a signal at at least fourteen two-theta values chosen from 4.7±0.2, 9.0±0.2, 9.5±0.2, 14.2±0.2, 16.7±0.2, 18.1±0.2, 18.9±0.2, 20.0±0.2, 21.0±0.2, 21.9±0.2, 22.1±0.2, 22.9±0.2, 23.1±0.2, 24.3±0.2, 24.5±0.2, 25.2±0.2, 25.6±0.2, 26.0±0.2, 26.1±0.2, and 27.8±0.2. In some embodiments, Form A is characterized by an X-ray powder diffractogram having a signal at at least fifteen two-theta values chosen from 4.7±0.2, 9.0±0.2, 9.5±0.2, 14.2±0.2, 16.7±0.2, 18.1±0.2, 18.9±0.2, 20.0±0.2, 21.0±0.2, 21.9±0.2, 22.1±0.2, 22.9±0.2, 23.1±0.2, 24.3±0.2, 24.5±0.2, 25.2±0.2, 25.6±0.2, 26.0±0.2, 26.1±0.2, and 27.8±0.2. In some embodiments, Form A is characterized by an X-ray powder diffractogram having a signal at at least sixteen two-theta values chosen from 4.7±0.2, 9.0±0.2, 9.5±0.2, 14.2±0.2, 16.7±0.2, 18.1±0.2, 18.9±0.2, 20.0±0.2, 21.0±0.2, 21.9±0.2, 22.1±0.2, 22.9±0.2, 23.1±0.2, 24.3±0.2, 24.5±0.2, 25.2±0.2, 25.6±0.2, 26.0±0.2, 26.1±0.2, and 27.8±0.2. In some embodiments, Form A is characterized by an X-ray powder diffractogram having a signal at at least seventeen two-theta values chosen from 4.7±0.2, 9.0±0.2, 9.5±0.2, 14.2±0.2, 16.7±0.2, 18.1±0.2, 18.9±0.2, 20.0±0.2, 21.0±0.2, 21.9±0.2, 22.1±0.2, 22.9±0.2, 23.1±0.2, 24.3±0.2, 24.5±0.2, 25.2±0.2, 25.6±0.2, 26.0±0.2, 26.1±0.2, and 27.8±0.2. In some embodiments, Form A is characterized by an X-ray powder diffractogram having a signal at at least eighteen two-theta values chosen from 4.7±0.2, 9.0±0.2, 9.5±0.2, 14.2±0.2, 16.7±0.2, 18.1±0.2, 18.9±0.2, 20.0±0.2, 21.0±0.2, 21.9±0.2, 22.1±0.2, 22.9±0.2, 23.1±0.2, 24.3±0.2, 24.5±0.2, 25.2±0.2, 25.6±0.2, 26.0±0.2, 26.1±0.2, and 27.8±0.2. In some embodiments, Form A is characterized by an X-ray powder diffractogram having a signal at at least nineteen two-theta values chosen from 4.7±0.2, 9.0±0.2, 9.5±0.2, 14.2±0.2, 16.7±0.2, 18.1±0.2, 18.9±0.2, 20.0±0.2, 21.0±0.2, 21.9±0.2, 22.1±0.2, 22.9±0.2, 23.1±0.2, 24.3±0.2, 24.5±0.2, 25.2±0.2, 25.6±0.2, 26.0±0.2, 26.1±0.2, and 27.8±0.2. In some embodiments, Form A is characterized by an X-ray powder diffractogram having a signal at 4.7±0.2, 9.0±0.2, 9.5±0.2, 14.2±0.2, 16.7±0.2, 18.1±0.2, 18.9±0.2, 20.0±0.2, 21.0±0.2, 21.9±0.2, 22.1±0.2, 22.9±0.2, 23.1±0.2, 24.3±0.2, 24.5±0.2, 25.2±0.2, 25.6±0.2, 26.0±0.2, 26.1±0.2, and 27.8±0.2 two-theta.

In some embodiments, disclosed herein is a composition comprising Form A of Compound 87. In some embodiments, disclosed herein is a composition comprising Compound 87 in substantially pure Form A. In some embodiments, disclosed herein is a composition comprising at least one active compound consisting essentially of Compound 87 in Form A.

Figure 42:
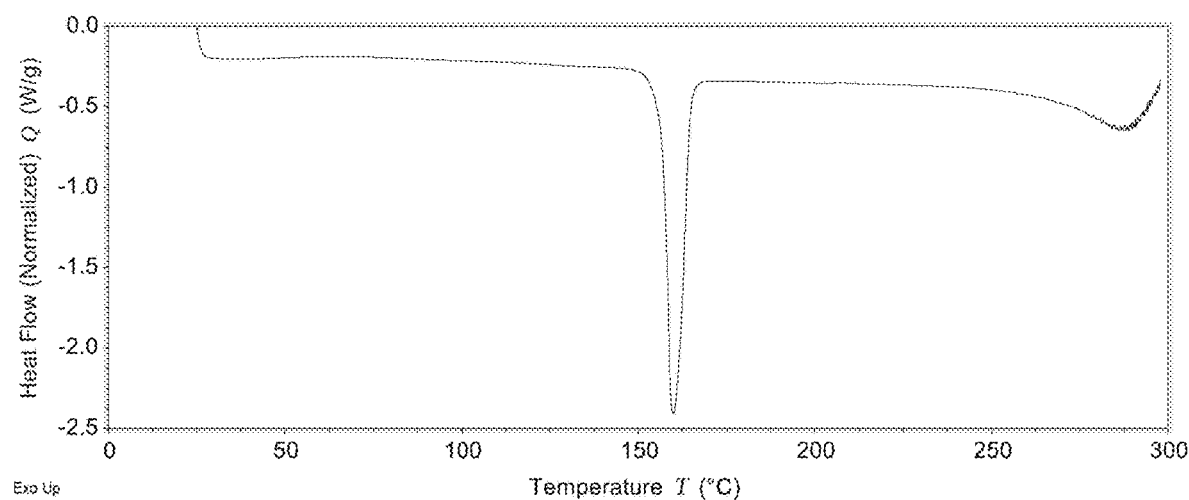
FIG. 42 depicts a DSC curve of Form A of Compound 87.

In some embodiments, Form A is characterized by a DSC curve substantially similar to that in FIG. 42. In some embodiments, Form A is characterized by a DSC curve having a melting onset of 157° C. with a peak at 160° C.

In some embodiments, Form A is characterized by a $^{13}$C NMR spectrum having a signal at at least one ppm value chosen from 128.3±0.2 ppm, 122.0±0.2 ppm, 58.4±0.2 ppm, and 38.4±0.2 ppm. In some embodiments, Form A is characterized by a $^{13}$C NMR spectrum having a signal at at least two ppm values chosen from 128.3±0.2 ppm, 122.0±0.2 ppm, 58.4±0.2 ppm, and 38.4±0.2 ppm. In some embodiments, Form A is characterized by a $^{13}$C NMR spectrum having a signal at at least three ppm values chosen from 128.3±0.2 ppm, 122.0±0.2 ppm, 58.4±0.2 ppm, and 38.4±0.2 ppm. In some embodiments, Form A is characterized by a $^{13}$C NMR spectrum having a signal at 128.3±0.2 ppm, 122.0±0.2 ppm, 58.4±0.2 ppm, and 38.4±0.2 ppm.

In some embodiments, Form A is characterized by a $^{19}$F NMR spectrum having a signal at −110.9±0.2 ppm.

In some embodiments, Compound 87 is a crystalline solid. In some embodiments, Compound 87 is a crystalline solid. In some embodiments, the crystalline solid consists of 1% to 99% Form A relative to the total weight of the crystalline solid Compound 87. In some embodiments, the crystalline solid consists of 2% to 99% Form A relative to the total weight of the crystalline solid Compound 87. In some embodiments, the crystalline solid consists of 5% to 99% Form A relative to the total weight of the crystalline solid Compound 87. In some embodiments, the crystalline solid consists of 10% to 99% Form A relative to the total weight of the crystalline solid Compound 87. In some embodiments, the crystalline solid consists of 15% to 99% Form A relative to the total weight of the crystalline solid Compound 87. In some embodiments, the crystalline solid consists of 20% to 99% Form A relative to the total weight of the crystalline solid Compound 87. In some embodiments, the crystalline solid consists of 25% to 99% Form A relative to the total weight of the crystalline solid Compound 87. In some embodiments, the crystalline solid consists of 30% to 99% Form A relative to the total weight of the crystalline solid Compound 87. In some embodiments, the crystalline solid consists of 35% to 99% Form A relative to the total weight of the crystalline solid Compound 87. In some embodiments, the crystalline solid consists of 45% to 99% Form A relative to the total weight of the crystalline solid Compound 87. In some embodiments, the crystalline solid consists of 50% to 99% Form A relative to the total weight of the crystalline solid Compound 87. In some embodiments, the crystalline solid consists of 55% to 99% Form A relative to the total weight of the crystalline solid Compound 87. In some embodiments, the crystalline solid consists of 60% to 99% Form A relative to the total weight of the crystalline solid Compound 87. In some embodiments, the crystalline solid consists of 65% to 99% Form A relative to the total weight of the crystalline solid Compound 87. In some embodiments, the crystalline solid consists of 70% to 99% Form A relative to the total weight of the crystalline solid Compound 87. In some embodiments, the crystalline solid consists of 75% to 99% Form A relative to the total weight of the crystalline solid Compound 87. In some embodiments, the crystalline solid consists of 80% to 99% Form A relative to the total weight of the crystalline solid Compound 87. In some embodiments, the crystalline solid consists of 85% to 99% Form A relative to the total weight of the crystalline solid Compound 87. In some embodiments, the crystalline solid consists of 90% to 99% Form A relative to the total weight of the crystalline solid Compound 87. In some embodiments, the crystalline solid consists of 95% to 99% Form A relative to the total weight of the crystalline solid Compound 87.

Hydrate Form of Compound 87

Figure 43:
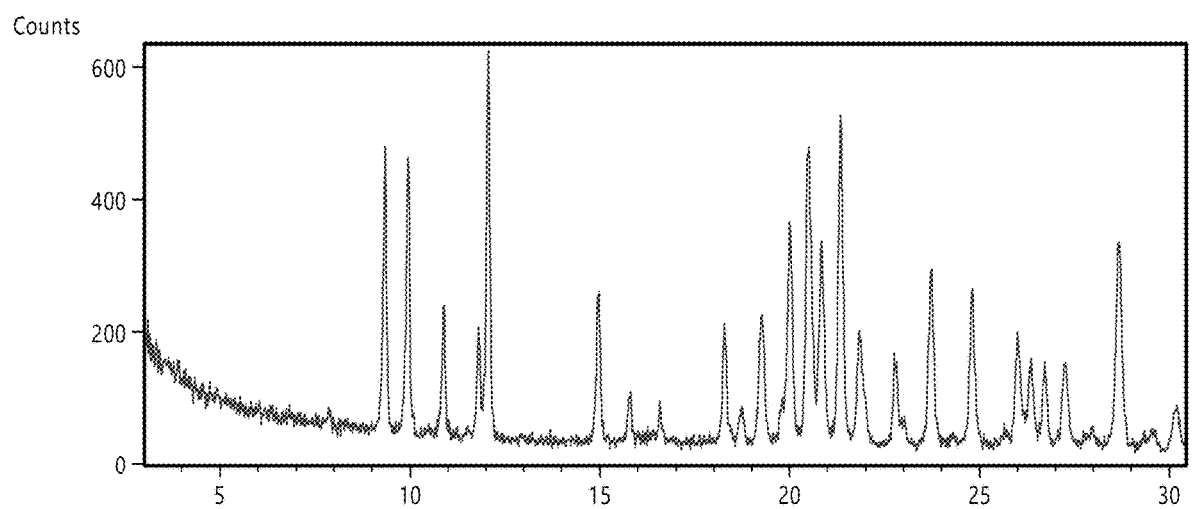
FIG. 43 depicts an XRPD diffractogram of Hydrate Form A of Compound 87.

In some embodiments, Compound 87 is in the form of Hydrate Form. In some embodiments, Compound 87 is in the form of substantially pure Hydrate Form. In some embodiments, Hydrate Form is characterized by an X-ray powder diffractogram substantially similar to that in FIG. 43. In some embodiments, Hydrate Form is characterized by an X-ray powder diffractogram having a signal at at least two two-theta values chosen from 9.3±0.2, 10.0±0.2, 10.9±0.2, 12.1±0.2, 20.0±0.2, 20.5±0.2, 20.8±0.2, 21.3±0.2, and 24.8±0.2. In some embodiments, Hydrate Form is characterized by an X-ray powder diffractogram having a signal at at least three two-theta values chosen from 9.3±0.2, 10.0±0.2, 10.9±0.2, 12.1±0.2, 20.0±0.2, 20.5±0.2, 20.8±0.2, 21.3±0.2, and 24.8±0.2. In some embodiments, Hydrate Form is characterized by an X-ray powder diffractogram having a signal at at least four two-theta values chosen from 9.3±0.2, 10.0±0.2, 10.9±0.2, 12.1±0.2, 20.0±0.2, 20.5±0.2, 20.8±0.2, 21.3±0.2, and 24.8±0.2. In some embodiments, Hydrate Form is characterized by an X-ray powder diffractogram having a signal at at least five two-theta values chosen from 9.3±0.2, 10.0±0.2, 10.9±0.2, 12.1±0.2, 20.0±0.2, 20.5±0.2, 20.8±0.2, 21.3±0.2, and 24.8±0.2. In some embodiments, Hydrate Form is characterized by an X-ray powder diffractogram having a signal at at least six two-theta values chosen from 9.3±0.2, 10.0±0.2, 10.9±0.2, 12.1±0.2, 20.0±0.2, 20.5±0.2, 20.8±0.2, 21.3±0.2, and 24.8±0.2.

In some embodiments, Hydrate Form is characterized by an X-ray powder diffractogram having a signal at at least three two-theta values chosen from 9.3±0.2, 10.0±0.2, 10.9±0.2, 11.8±0.2, 12.1±0.2, 15.0±0.2, 15.8±0.2, 18.3±0.2, 19.3±0.2, 20.0±0.2, 20.1±0.2, 20.5±0.2, 20.8±0.2, 20.9±0.2, 21.3±0.2, 21.8±0.2, 22.0±0.2, 22.7±0.2, 22.8±0.2, 23.7±0.2, 24.8±0.2, 26.0±0.2, 26.1±0.2, 26.3±0.2, 26.4±0.2, 26.7±0.2, 26.8±0.2, 27.3±0.2, 28.6±0.2, and 28.7±0.2. In some embodiments, Hydrate Form is characterized by an X-ray powder diffractogram having a signal at at least four two-theta values chosen from 9.3±0.2, 10.0±0.2, 10.9±0.2, 11.8±0.2, 12.1±0.2, 15.0±0.2, 15.8±0.2, 18.3±0.2, 19.3±0.2, 20.0±0.2, 20.1±0.2, 20.5±0.2, 20.8±0.2, 20.9±0.2, 21.3±0.2, 21.8±0.2, 22.0±0.2, 22.7±0.2, 22.8±0.2, 23.7±0.2, 24.8±0.2, 26.0±0.2, 26.1±0.2, 26.3±0.2, 26.4±0.2, 26.7±0.2, 26.8±0.2, 27.3±0.2, 28.6±0.2, and 28.7±0.2. In some embodiments, Hydrate Form is characterized by an X-ray powder diffractogram having a signal at at least five two-theta values chosen from 9.3±0.2, 10.0±0.2, 10.9±0.2, 11.8±0.2, 12.1±0.2, 15.0±0.2, 15.8±0.2, 18.3±0.2, 19.3±0.2, 20.0±0.2, 20.1±0.2, 20.5±0.2, 20.8±0.2, 20.9±0.2, 21.3±0.2, 21.8±0.2, 22.0±0.2, 22.7±0.2, 22.8±0.2, 23.7±0.2, 24.8±0.2, 26.0±0.2, 26.1±0.2, 26.3±0.2, 26.4±0.2, 26.7±0.2, 26.8±0.2, 27.3±0.2, 28.6±0.2, and 28.7±0.2. In some embodiments, Hydrate Form is characterized by an X-ray powder diffractogram having a signal at at least six two-theta values chosen from 9.3±0.2, 10.0±0.2, 10.9±0.2, 11.8±0.2, 12.1±0.2, 15.0±0.2, 15.8±0.2, 18.3±0.2, 19.3±0.2, 20.0±0.2, 20.1±0.2, 20.5±0.2, 20.8±0.2, 20.9±0.2, 21.3±0.2, 21.8±0.2, 22.0±0.2, 22.7±0.2, 22.8±0.2, 23.7±0.2, 24.8±0.2, 26.0±0.2, 26.1±0.2, 26.3±0.2, 26.4±0.2, 26.7±0.2, 26.8±0.2, 27.3±0.2, 28.6±0.2, and 28.7±0.2. In some embodiments, Hydrate Form is characterized by an X-ray powder diffractogram having a signal at at least seven two-theta values chosen from 9.3±0.2, 10.0±0.2, 10.9±0.2, 11.8±0.2, 12.1±0.2, 15.0±0.2, 15.8±0.2, 18.3±0.2, 19.3±0.2, 20.0±0.2, 20.1±0.2, 20.5±0.2, 20.8±0.2, 20.9±0.2, 21.3±0.2, 21.8±0.2, 22.0±0.2, 22.7±0.2, 22.8±0.2, 23.7±0.2, 24.8±0.2, 26.0±0.2, 26.1±0.2, 26.3±0.2, 26.4±0.2, 26.7±0.2, 26.8±0.2, 27.3±0.2, 28.6±0.2, and 28.7±0.2. In some embodiments, Hydrate Form is characterized by an X-ray powder diffractogram having a signal at at least eight two-theta values chosen from 9.3±0.2, 10.0±0.2, 10.9±0.2, 11.8±0.2, 12.1±0.2, 15.0±0.2, 15.8±0.2, 18.3±0.2, 19.3±0.2, 20.0±0.2, 20.1±0.2, 20.5±0.2, 20.8±0.2, 20.9±0.2, 21.3±0.2, 21.8±0.2, 22.0±0.2, 22.7±0.2, 22.8±0.2, 23.7±0.2, 24.8±0.2, 26.0±0.2, 26.1±0.2, 26.3±0.2, 26.4±0.2, 26.7±0.2, 26.8±0.2, 27.3±0.2, 28.6±0.2, and 28.7±0.2. In some embodiments, Hydrate Form is characterized by an X-ray powder diffractogram having a signal at at least nine two-theta values chosen from 9.3±0.2, 10.0±0.2, 10.9±0.2, 11.8±0.2, 12.1±0.2, 15.0±0.2, 15.8±0.2, 18.3±0.2, 19.3±0.2, 20.0±0.2, 20.1±0.2, 20.5±0.2, 20.8±0.2, 20.9±0.2, 21.3±0.2, 21.8±0.2, 22.0±0.2, 22.7±0.2, 22.8±0.2, 23.7±0.2, 24.8±0.2, 26.0±0.2, 26.1±0.2, 26.3±0.2, 26.4±0.2, 26.7±0.2, 26.8±0.2, 27.3±0.2, 28.6±0.2, and 28.7±0.2. In some embodiments, Hydrate Form is characterized by an X-ray powder diffractogram having a signal at at least ten two-theta values chosen from 9.3±0.2, 10.0±0.2, 10.9±0.2, 11.8±0.2, 12.1±0.2, 15.0±0.2, 15.8±0.2, 18.3±0.2, 19.3±0.2, 20.0±0.2, 20.1±0.2, 20.5±0.2, 20.8±0.2, 20.9±0.2, 21.3±0.2, 21.8±0.2, 22.0±0.2, 22.7±0.2, 22.8±0.2, 23.7±0.2, 24.8±0.2, 26.0±0.2, 26.1±0.2, 26.3±0.2, 26.4±0.2, 26.7±0.2, 26.8±0.2, 27.3±0.2, 28.6±0.2, and 28.7±0.2. In some embodiments, Hydrate Form is characterized by an X-ray powder diffractogram having a signal at at least eleven two-theta values chosen from 9.3±0.2, 10.0±0.2, 10.9±0.2, 11.8±0.2, 12.1±0.2, 15.0±0.2, 15.8±0.2, 18.3±0.2, 19.3±0.2, 20.0±0.2, 20.1±0.2, 20.5±0.2, 20.8±0.2, 20.9±0.2, 21.3±0.2, 21.8±0.2, 22.0±0.2, 22.7±0.2, 22.8±0.2, 23.7±0.2, 24.8±0.2, 26.0±0.2, 26.1±0.2, 26.3±0.2, 26.4±0.2, 26.7±0.2, 26.8±0.2, 27.3±0.2, 28.6±0.2, and 28.7±0.2. In some embodiments, Hydrate Form is characterized by an X-ray powder diffractogram having a signal at at least twelve two-theta values chosen from 9.3±0.2, 10.0±0.2, 10.9±0.2, 11.8±0.2, 12.1±0.2, 15.0±0.2, 15.8±0.2, 18.3±0.2, 19.3±0.2, 20.0±0.2, 20.1±0.2, 20.5±0.2, 20.8±0.2, 20.9±0.2, 21.3±0.2, 21.8±0.2, 22.0±0.2, 22.7±0.2, 22.8±0.2, 23.7±0.2, 24.8±0.2, 26.0±0.2, 26.1±0.2, 26.3±0.2, 26.4±0.2, 26.7±0.2, 26.8±0.2, 27.3±0.2, 28.6±0.2, and 28.7±0.2. In some embodiments, Hydrate Form is characterized by an X-ray powder diffractogram having a signal at at least thirteen two-theta values chosen from 9.3±0.2, 10.0±0.2, 10.9±0.2, 11.8±0.2, 12.1±0.2, 15.0±0.2, 15.8±0.2, 18.3±0.2, 19.3±0.2, 20.0±0.2, 20.1±0.2, 20.5±0.2, 20.8±0.2, 20.9±0.2, 21.3±0.2, 21.8±0.2, 22.0±0.2, 22.7±0.2, 22.8±0.2, 23.7±0.2, 24.8±0.2, 26.0±0.2, 26.1±0.2, 26.3±0.2, 26.4±0.2, 26.7±0.2, 26.8±0.2, 27.3±0.2, 28.6±0.2, and 28.7±0.2. In some embodiments, Hydrate Form is characterized by an X-ray powder diffractogram having a signal at at least fourteen two-theta values chosen from 9.3±0.2, 10.0±0.2, 10.9±0.2, 11.8±0.2, 12.1±0.2, 15.0±0.2, 15.8±0.2, 18.3±0.2, 19.3±0.2, 20.0±0.2, 20.1±0.2, 20.5±0.2, 20.8±0.2, 20.9±0.2, 21.3±0.2, 21.8±0.2, 22.0±0.2, 22.7±0.2, 22.8±0.2, 23.7±0.2, 24.8±0.2, 26.0±0.2, 26.1±0.2, 26.3±0.2, 26.4±0.2, 26.7±0.2, 26.8±0.2, 27.3±0.2, 28.6±0.2, and 28.7±0.2. In some embodiments, Hydrate Form is characterized by an X-ray powder diffractogram having a signal at at least fifteen two-theta values chosen from 9.3±0.2, 10.0±0.2, 10.9±0.2, 11.8±0.2, 12.1±0.2, 15.0±0.2, 15.8±0.2, 18.3±0.2, 19.3±0.2, 20.0±0.2, 20.1±0.2, 20.5±0.2, 20.8±0.2, 20.9±0.2, 21.3±0.2, 21.8±0.2, 22.0±0.2, 22.7±0.2, 22.8±0.2, 23.7±0.2, 24.8±0.2, 26.0±0.2, 26.1±0.2, 26.3±0.2, 26.4±0.2, 26.7±0.2, 26.8±0.2, 27.3±0.2, 28.6±0.2, and 28.7±0.2. In some embodiments, Hydrate Form is characterized by an X-ray powder diffractogram having a signal at at least sixteen two-theta values chosen from 9.3±0.2, 10.0±0.2, 10.9±0.2, 11.8±0.2, 12.1±0.2, 15.0±0.2, 15.8±0.2, 18.3±0.2, 19.3±0.2, 20.0±0.2, 20.1±0.2, 20.5±0.2, 20.8±0.2, 20.9±0.2, 21.3±0.2, 21.8±0.2, 22.0±0.2, 22.7±0.2, 22.8±0.2, 23.7±0.2, 24.8±0.2, 26.0±0.2, 26.1±0.2, 26.3±0.2, 26.4±0.2, 26.7±0.2, 26.8±0.2, 27.3±0.2, 28.6±0.2, and 28.7±0.2. In some embodiments, Hydrate Form is characterized by an X-ray powder diffractogram having a signal at at least seventeen two-theta values chosen from 9.3±0.2, 10.0±0.2, 10.9±0.2, 11.8±0.2, 12.1±0.2, 15.0±0.2, 15.8±0.2, 18.3±0.2, 19.3±0.2, 20.0±0.2, 20.1±0.2, 20.5±0.2, 20.8±0.2, 20.9±0.2, 21.3±0.2, 21.8±0.2, 22.0±0.2, 22.7±0.2, 23.7±0.2, 24.8±0.2, 26.0±0.2, 26.1±0.2, 26.3±0.2, 26.4±0.2, 26.7±0.2, 26.8±0.2, 27.3±0.2, 28.6±0.2, and 28.7±0.2. In some embodiments, Hydrate Form is characterized by an X-ray powder diffractogram having a signal at at least eighteen two-theta values chosen from 9.3±0.2, 10.0±0.2, 10.9±0.2, 11.8±0.2, 12.1±0.2, 15.0±0.2, 15.8±0.2, 18.3±0.2, 19.3±0.2, 20.0±0.2, 20.1±0.2, 20.5±0.2, 20.8±0.2, 20.9±0.2, 21.3±0.2, 21.8±0.2, 22.0±0.2, 22.7±0.2, 22.8±0.2, 23.7±0.2, 24.8±0.2, 26.0±0.2, 26.1±0.2, 26.3±0.2, 26.4±0.2, 26.7±0.2, 26.8±0.2, 27.3±0.2, 28.6±0.2, and 28.7±0.2. In some embodiments, Hydrate Form is characterized by an X-ray powder diffractogram having a signal at at least nineteen two-theta values chosen from 9.3±0.2, 10.0±0.2, 10.9±0.2, 11.8±0.2, 12.1±0.2, 15.0±0.2, 15.8±0.2, 18.3±0.2, 19.3±0.2, 20.0±0.2, 20.1±0.2, 20.5±0.2, 20.8±0.2, 20.9±0.2, 21.3±0.2, 21.8±0.2, 22.0±0.2, 22.7±0.2, 22.8±0.2, 23.7±0.2, 24.8±0.2, 26.0±0.2, 26.1±0.2, 26.3±0.2, 26.4±0.2, 26.7±0.2, 26.8±0.2, 27.3±0.2, 28.6±0.2, and 28.7±0.2. In some embodiments, Hydrate Form is characterized by an X-ray powder diffractogram having a signal at at least twenty two-theta values chosen from 9.3±0.2, 10.0±0.2, 10.9±0.2, 11.8±0.2, 12.1±0.2, 15.0±0.2, 15.8±0.2, 18.3±0.2, 19.3±0.2, 20.0±0.2, 20.1±0.2, 20.5±0.2, 20.8±0.2, 20.9±0.2, 21.3±0.2, 21.8±0.2, 22.0±0.2, 22.7±0.2, 22.8±0.2, 23.7±0.2, 24.8±0.2, 26.0±0.2, 26.1±0.2, 26.3±0.2, 26.4±0.2, 26.7±0.2, 26.8±0.2, 27.3±0.2, 28.6±0.2, and 28.7±0.2. In some embodiments, Hydrate Form is characterized by an X-ray powder diffractogram having a signal at at least twenty one two-theta values chosen from 9.3±0.2, 10.0±0.2, 10.9±0.2, 11.8±0.2, 12.1±0.2, 15.0±0.2, 15.8±0.2, 18.3±0.2, 19.3±0.2, 20.0±0.2, 20.1±0.2, 20.5±0.2, 20.8±0.2, 20.9±0.2, 21.3±0.2, 21.8±0.2, 22.0±0.2, 22.7±0.2, 22.8±0.2, 23.7±0.2, 24.8±0.2, 26.0±0.2, 26.1±0.2, 26.3±0.2, 26.4±0.2, 26.7±0.2, 26.8±0.2, 27.3±0.2, 28.6±0.2, and 28.7±0.2. In some embodiments, Hydrate Form is characterized by an X-ray powder diffractogram having a signal at at least twenty two two-theta values chosen from 9.3±0.2, 10.0±0.2, 10.9±0.2, 11.8±0.2, 12.1±0.2, 15.0±0.2, 15.8±0.2, 18.3±0.2, 19.3±0.2, 20.0±0.2, 20.1±0.2, 20.5±0.2, 20.8±0.2, 20.9±0.2, 21.3±0.2, 21.8±0.2, 22.0±0.2, 22.7±0.2, 22.8±0.2, 23.7±0.2, 24.8±0.2, 26.0±0.2, 26.1±0.2, 26.3±0.2, 26.4±0.2, 26.7±0.2, 26.8±0.2, 27.3±0.2, 28.6±0.2, and 28.7±0.2. In some embodiments, Hydrate Form is characterized by an X-ray powder diffractogram having a signal at at least twenty three two-theta values chosen from 9.3±0.2, 10.0±0.2, 10.9±0.2, 11.8±0.2, 12.1±0.2, 15.0±0.2, 15.8±0.2, 18.3±0.2, 19.3±0.2, 20.0±0.2, 20.1±0.2, 20.5±0.2, 20.8±0.2, 20.9±0.2, 21.3±0.2, 21.8±0.2, 22.0±0.2, 22.7±0.2, 22.8±0.2, 23.7±0.2, 24.8±0.2, 26.0±0.2, 26.1±0.2, 26.3±0.2, 26.4±0.2, 26.7±0.2, 26.8±0.2, 27.3±0.2, 28.6±0.2, and 28.7±0.2. In some embodiments, Hydrate Form is characterized by an X-ray powder diffractogram having a signal at at least twenty four two-theta values chosen from 9.3±0.2, 10.0±0.2, 10.9±0.2, 11.8±0.2, 12.1±0.2, 15.0±0.2, 15.8±0.2, 18.3±0.2, 19.3±0.2, 20.0±0.2, 20.1±0.2, 20.5±0.2, 20.8±0.2, 20.9±0.2, 21.3±0.2, 21.8±0.2, 22.0±0.2, 22.7±0.2, 22.8±0.2, 23.7±0.2, 24.8±0.2, 26.0±0.2, 26.1±0.2, 26.3±0.2, 26.4±0.2, 26.7±0.2, 26.8±0.2, 27.3±0.2, 28.6±0.2, and 28.7±0.2. In some embodiments, Hydrate Form is characterized by an X-ray powder diffractogram having a signal at at least twenty five two-theta values chosen from 9.3±0.2, 10.0±0.2, 10.9±0.2, 11.8±0.2, 12.1±0.2, 15.0±0.2, 15.8±0.2, 18.3±0.2, 19.3±0.2, 20.0±0.2, 20.1±0.2, 20.5±0.2, 20.8±0.2, 20.9±0.2, 21.3±0.2, 21.8±0.2, 22.0±0.2, 22.7±0.2, 22.8±0.2, 23.7±0.2, 24.8±0.2, 26.0±0.2, 26.1±0.2, 26.3±0.2, 26.4±0.2, 26.7±0.2, 26.8±0.2, 27.3±0.2, 28.6±0.2, and 28.7±0.2. In some embodiments, Hydrate Form is characterized by an X-ray powder diffractogram having a signal at at least twenty six two-theta values chosen from 9.3±0.2, 10.0±0.2, 10.9±0.2, 11.8±0.2, 12.1±0.2, 15.0±0.2, 15.8±0.2, 18.3±0.2, 19.3±0.2, 20.0±0.2, 20.1±0.2, 20.5±0.2, 20.8±0.2, 20.9±0.2, 21.3±0.2, 21.8±0.2, 22.0±0.2, 22.7±0.2, 22.8±0.2, 23.7±0.2, 24.8±0.2, 26.0±0.2, 26.1±0.2, 26.3±0.2, 26.4±0.2, 26.7±0.2, 26.8±0.2, 27.3±0.2, 28.6±0.2, and 28.7±0.2. In some embodiments, Hydrate Form is characterized by an X-ray powder diffractogram having a signal at at least twenty seven two-theta values chosen from 9.3±0.2, 10.0±0.2, 10.9±0.2, 11.8±0.2, 12.1±0.2, 15.0±0.2, 15.8±0.2, 18.3±0.2, 19.3±0.2, 20.0±0.2, 20.1±0.2, 20.5±0.2, 20.8±0.2, 20.9±0.2, 21.3±0.2, 21.8±0.2, 22.0±0.2, 22.7±0.2, 22.8±0.2, 23.7±0.2, 24.8±0.2, 26.0±0.2, 26.1±0.2, 26.3±0.2, 26.4±0.2, 26.7±0.2, 26.8±0.2, 27.3±0.2, 28.6±0.2, and 28.7±0.2. In some embodiments, Hydrate Form is characterized by an X-ray powder diffractogram having a signal at at least twenty eight two-theta values chosen from 9.3±0.2, 10.0±0.2, 10.9±0.2, 11.8±0.2, 12.1±0.2, 15.0±0.2, 15.8±0.2, 18.3±0.2, 19.3±0.2, 20.0±0.2, 20.1±0.2, 20.5±0.2, 20.8±0.2, 20.9±0.2, 21.3±0.2, 21.8±0.2, 22.0±0.2, 22.7±0.2, 22.8±0.2, 23.7±0.2, 24.8±0.2, 26.0±0.2, 26.1±0.2, 26.3±0.2, 26.4±0.2, 26.7±0.2, 26.8±0.2, 27.3±0.2, 28.6±0.2, and 28.7±0.2. In some embodiments, Hydrate Form is characterized by an X-ray powder diffractogram having a signal at at least twenty nine two-theta values chosen from 9.3±0.2, 10.0±0.2, 10.9±0.2, 11.8±0.2, 12.1±0.2, 15.0±0.2, 15.8±0.2, 18.3±0.2, 19.3±0.2, 20.0±0.2, 20.1±0.2, 20.5±0.2, 20.8±0.2, 20.9±0.2, 21.3±0.2, 21.8±0.2, 22.0±0.2, 22.7±0.2, 22.8±0.2, 23.7±0.2, 24.8±0.2, 26.0±0.2, 26.1±0.2, 26.3±0.2, 26.4±0.2, 26.7±0.2, 26.8±0.2, 27.3±0.2, 28.6±0.2, and 28.7±0.2. In some embodiments, Hydrate Form is characterized by an X-ray powder diffractogram having a signal at 9.3±0.2, 10.0±0.2, 10.9 0.2, 11.8±0.2, 12.1±0.2, 15.0±0.2, 15.8±0.2, 18.3±0.2, 19.3±0.2, 20.0±0.2, 20.1±0.2, 20.5±0.2, 20.8±0.2, 20.9±0.2, 21.3±0.2, 21.8±0.2, 22.0±0.2, 22.7±0.2, 22.8±0.2, 23.7±0.2, 24.8±0.2, 26.0±0.2, 26.1±0.2, 26.3±0.2, 26.4±0.2, 26.7±0.2, 26.8±0.2, 27.3±0.2, 28.6±0.2, and 28.7±0.2 two-theta.

In some embodiments, Hydrate Form of Compound 87 has a single crystal unit cell characterized as follows:

| Crystal System | Orthorhombic |
|---|---|
| Space Group | $P2_12_12_1$ |
| a (Å) | 4.9 ± 0.1 |
| b (Å) | 9.5 ± 0.1 |
| c (Å) | 44.6 ± 0.1 |
| α (°) | 90 |
| β (°) | 90 |
| γ (°) | 90 |
| V (Å$^3$) | 2064.3 ± 0.2 |
| Z/Z' | 4/1 |

In some embodiments, disclosed herein is a composition comprising Hydrate Form of Compound 87. In some embodiments, disclosed herein is a composition comprising Compound 87 in substantially pure Hydrate Form. In some embodiments, disclosed herein is a composition comprising at least one active compound consisting essentially of Compound 87 in Hydrate Form.

Figure 47:
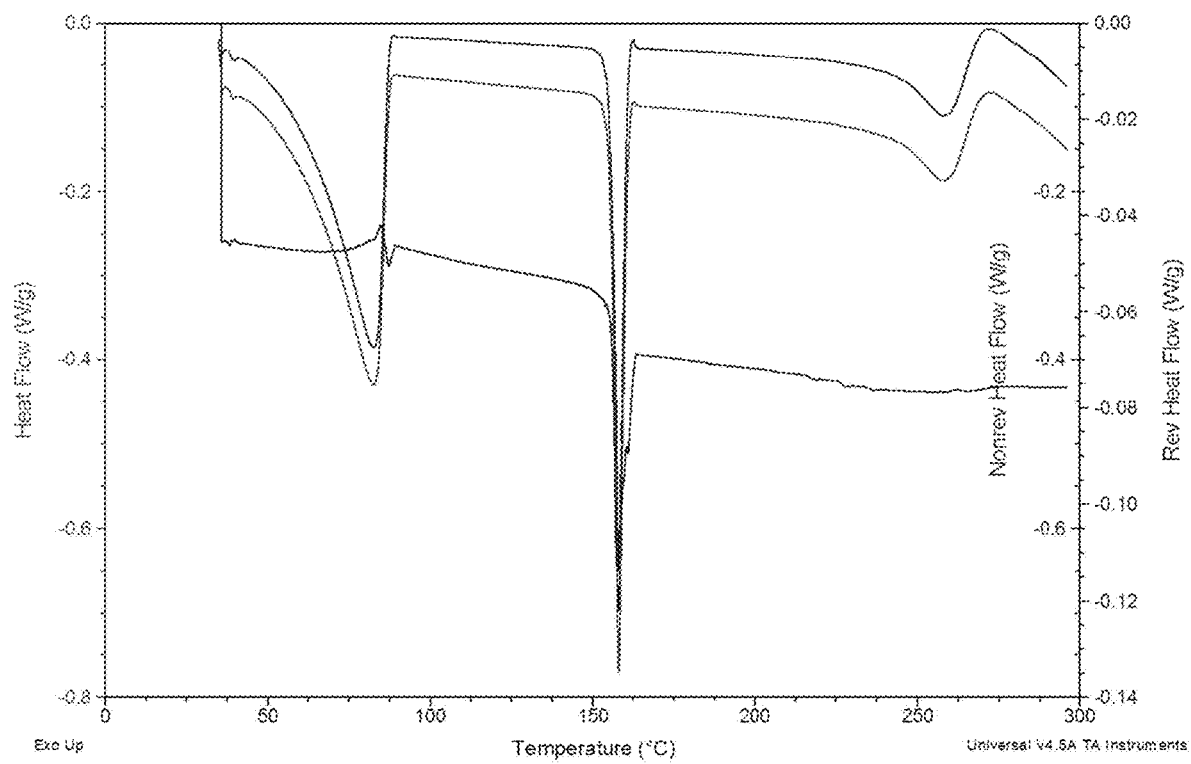
FIG. 47 depicts a DSC curve of Hydrate Form A of Compound 87.

In some embodiments, Hydrate Form is characterized by a DSC curve substantially similar to that in FIG. 47. In some embodiments, Hydrate Form is characterized by a DSC curve having a peak at at least one temperature chosen from 86° C. and 158° C.

In some embodiments, Hydrate Form is characterized by a $^{13}$C NMR spectrum having a signal at at least one ppm value chosen from 133.5±0.2 ppm, 119.8±0.2 ppm, 74.2±0.2 ppm, 56.4±0.2 ppm, and 18.7±0.2 ppm. In some embodiments, Hydrate Form is characterized by a $^{13}$C NMR spectrum having a signal at at least two ppm values chosen from 133.5±0.2 ppm, 119.8±0.2 ppm, 74.2±0.2 ppm, 56.4±0.2 ppm, and 18.7±0.2 ppm. In some embodiments, Hydrate Form is characterized by a $^{13}$C NMR spectrum having a signal at at least three ppm values chosen from 133.5±0.2 ppm, 119.8±0.2 ppm, 74.2±0.2 ppm, 56.4±0.2 ppm, and 18.7±0.2 ppm. In some embodiments, Hydrate Form is characterized by a $^{13}$C NMR spectrum having a signal at at least four ppm values chosen from 133.5±0.2 ppm, 119.8±0.2 ppm, 74.2±0.2 ppm, 56.4±0.2 ppm, and 18.7±0.2 ppm. In some embodiments, Hydrate Form is characterized by a $^{13}$C NMR spectrum having a signal at 133.5±0.2 ppm, 119.8±0.2 ppm, 74.2±0.2 ppm, 56.4±0.2 ppm, and 18.7±0.2 ppm.

In some embodiments, Hydrate Form is characterized by a $^{19}$F NMR spectrum having a signal at −113.6±0.2 ppm.

In some embodiments, Compound 87 is a crystalline solid. In some embodiments, the crystalline solid consists of 1% to 99% Hydrate Form relative to the total weight of the crystalline solid Compound 87. In some embodiments, the crystalline solid consists of 2% to 99% Hydrate Form relative to the total weight of the crystalline solid Compound 87. In some embodiments, the crystalline solid consists of 5% to 99% Hydrate Form relative to the total weight of the crystalline solid Compound 87. In some embodiments, the crystalline solid consists of 10% to 99% Hydrate Form relative to the total weight of the crystalline solid Compound 87. In some embodiments, the crystalline solid consists of 15% to 99% Hydrate Form relative to the total weight of the crystalline solid Compound 87. In some embodiments, the crystalline solid consists of 20% to 99% Hydrate Form relative to the total weight of the crystalline solid Compound 87. In some embodiments, the crystalline solid consists of 25% to 99% Hydrate Form relative to the total weight of the crystalline solid Compound 87. In some embodiments, the crystalline solid consists of 30% to 99% Hydrate Form relative to the total weight of the crystalline solid Compound 87. In some embodiments, the crystalline solid consists of 35% to 99% Hydrate Form relative to the total weight of the crystalline solid Compound 87. In some embodiments, the crystalline solid consists of 45% to 99% Hydrate Form relative to the total weight of the crystalline solid Compound 87. In some embodiments, the crystalline solid consists of 50% to 99% Hydrate Form relative to the total weight of the crystalline solid Compound 87. In some embodiments, the crystalline solid consists of 55% to 99% Hydrate Form relative to the total weight of the crystalline solid Compound 87. In some embodiments, the crystalline solid consists of 60% to 99% Hydrate Form relative to the total weight of the crystalline solid Compound 87. In some embodiments, the crystalline solid consists of 65% to 99% Hydrate Form relative to the total weight of the crystalline solid Compound 87. In some embodiments, the crystalline solid consists of 70% to 99% Hydrate Form relative to the total weight of the crystalline solid Compound 87. In some embodiments, the crystalline solid consists of 75% to 99% Hydrate Form relative to the total weight of the crystalline solid Compound 87. In some embodiments, the crystalline solid consists of 80% to 99% Hydrate Form relative to the total weight of the crystalline solid Compound 87. In some embodiments, the crystalline solid consists of 85% to 99% Hydrate Form relative to the total weight of the crystalline solid Compound 87. In some embodiments, the crystalline solid consists of 90% to 99% Hydrate Form relative to the total weight of the crystalline solid Compound 87. In some embodiments, the crystalline solid consists of 95% to 99% Hydrate Form relative to the total weight of the crystalline solid Compound 87.

IPAc Solvate of Compound 87

Figure 49:
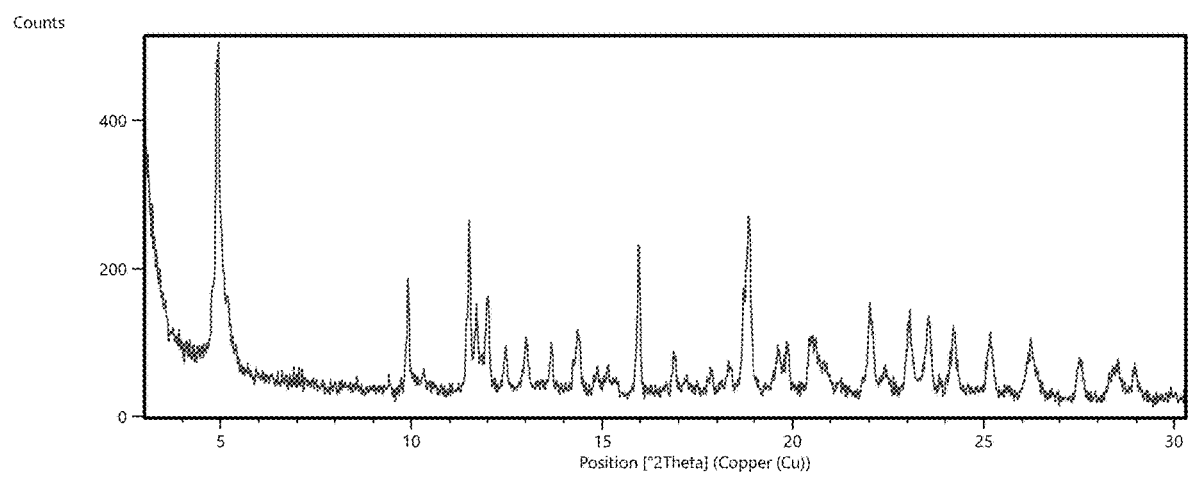
FIG. 49 depicts an XRPD diffractogram of vacuum dried sample of IPAc Solvate of Compound 87.

In some embodiments, Compound 87 is in the form of an IPAc Solvate Form. In some embodiments, Compound 87 is in the form of substantially pure IPAc Solvate Form. In some embodiments, IPAc Solvate Form is characterized by an X-ray powder diffractogram substantially similar to that in FIG. 49. In some embodiments, IPAc Solvate Form is characterized by an X-ray powder diffractogram having a signal at at least two two-theta values chosen from 5.0±0.2, 9.9±0.2, 11.5±0.2, 11.7±0.2, 12.0±0.2, 16.0±0.2, 18.8±0.2, 22.0±0.2, and 23.1±0.2. In some embodiments, IPAc Solvate Form is characterized by an X-ray powder diffractogram having a signal at at least three two-theta values chosen from 5.0±0.2, 9.9±0.2, 11.5±0.2, 11.7±0.2, 12.0±0.2, 16.0±0.2, 18.8±0.2, 22.0±0.2, and 23.1±0.2. In some embodiments, IPAc Solvate Form is characterized by an X-ray powder diffractogram having a signal at at least four two-theta values chosen from 5.0±0.2, 9.9±0.2, 11.5±0.2, 11.7±0.2, 12.0±0.2, 16.0±0.2, 18.8±0.2, 22.0±0.2, and 23.1±0.2. In some embodiments, IPAc Solvate Form is characterized by an X-ray powder diffractogram having a signal at at least five two-theta values chosen from 5.0±0.2, 9.9±0.2, 11.5±0.2, 11.7±0.2, 12.0±0.2, 16.0±0.2, 18.8±0.2, 22.0±0.2, and 23.1±0.2. In some embodiments, IPAc Solvate Form is characterized by an X-ray powder diffractogram having a signal at at least six two-theta values chosen from 5.0±0.2, 9.9±0.2, 11.5±0.2, 11.7±0.2, 12.0±0.2, 16.0±0.2, 18.8±0.2, 22.0±0.2, and 23.1±0.2.

In some embodiments, IPAc Solvate Form is characterized by an X-ray powder diffractogram having a signal at at least three two-theta values chosen from 5.0±0.2, 9.9±0.2, 11.5±0.2, 11.7±0.2, 12.0±0.2, 12.5±0.2, 13.0±0.2, 13.7±0.2, 14.4±0.2, 16.0±0.2, 16.9±0.2, 18.8±0.2, 19.9±0.2, 20.4±0.2, 22.0±0.2, 23.1±0.2, 23.6±0.2, 24.2±0.2, 25.2±0.2, 26.2±0.2, and 27.5±0.2. In some embodiments, IPAc Solvate Form is characterized by an X-ray powder diffractogram having a signal at at least four two-theta values chosen from 5.0±0.2, 9.9±0.2, 11.5±0.2, 11.7±0.2, 12.0±0.2, 12.5±0.2, 13.0±0.2, 13.7±0.2, 14.4±0.2, 16.0±0.2, 16.9±0.2, 18.8±0.2, 19.9±0.2, 20.4±0.2, 22.0±0.2, 23.1±0.2, 23.6±0.2, 24.2±0.2, 25.2±0.2, 26.2±0.2, and 27.5±0.2. In some embodiments, IPAc Solvate Form is characterized by an X-ray powder diffractogram having a signal at at least five two-theta values chosen from 5.0±0.2, 9.9±0.2, 11.5±0.2, 11.7±0.2, 12.0±0.2, 12.5±0.2, 13.0±0.2, 13.7±0.2, 14.4±0.2, 16.0±0.2, 16.9±0.2, 18.8±0.2, 19.9±0.2, 20.4±0.2, 22.0±0.2, 23.1±0.2, 23.6±0.2, 24.2±0.2, 25.2±0.2, 26.2±0.2, and 27.5±0.2. In some embodiments, IPAc Solvate Form is characterized by an X-ray powder diffractogram having a signal at at least six two-theta values chosen from 5.0±0.2, 9.9±0.2, 11.5±0.2, 11.7±0.2, 12.0±0.2, 12.5±0.2, 13.0±0.2, 13.7±0.2, 14.4±0.2, 16.0±0.2, 16.9±0.2, 18.8±0.2, 19.9±0.2, 20.4±0.2, 22.0±0.2, 23.1±0.2, 23.6±0.2, 24.2±0.2, 25.2±0.2, 26.2±0.2, and 27.5±0.2. In some embodiments, IPAc Solvate Form is characterized by an X-ray powder diffractogram having a signal at at least seven two-theta values chosen from 5.0±0.2, 9.9±0.2, 11.5±0.2, 11.7±0.2, 12.0±0.2, 12.5±0.2, 13.0±0.2, 13.7±0.2, 14.4±0.2, 16.0±0.2, 16.9±0.2, 18.8±0.2, 19.9±0.2, 20.4±0.2, 22.0±0.2, 23.1±0.2, 23.6±0.2, 24.2±0.2, 25.2±0.2, 26.2±0.2, and 27.5±0.2. In some embodiments, IPAc Solvate Form is characterized by an X-ray powder diffractogram having a signal at at least eight two-theta values chosen from 5.0±0.2, 9.9±0.2, 11.5±0.2, 11.7±0.2, 12.0±0.2, 12.5±0.2, 13.0±0.2, 13.7±0.2, 14.4±0.2, 16.0±0.2, 16.9±0.2, 18.8±0.2, 19.9±0.2, 20.4±0.2, 22.0±0.2, 23.1±0.2, 23.6±0.2, 24.2±0.2, 25.2±0.2, 26.2±0.2, and 27.5±0.2. In some embodiments, IPAc Solvate Form is characterized by an X-ray powder diffractogram having a signal at at least nine two-theta values chosen from 5.0±0.2, 9.9±0.2, 11.5±0.2, 11.7±0.2, 12.0±0.2, 12.5±0.2, 13.0±0.2, 13.7±0.2, 14.4±0.2, 16.0±0.2, 16.9±0.2, 18.8±0.2, 19.9±0.2, 20.4±0.2, 22.0±0.2, 23.1±0.2, 23.6±0.2, 24.2±0.2, 25.2±0.2, 26.2±0.2, and 27.5±0.2. In some embodiments, IPAc Solvate Form is characterized by an X-ray powder diffractogram having a signal at at least ten two-theta values chosen from 5.0±0.2, 9.9±0.2, 11.5±0.2, 11.7±0.2, 12.0±0.2, 12.5±0.2, 13.0±0.2, 13.7±0.2, 14.4±0.2, 16.0±0.2, 16.9±0.2, 18.8±0.2, 19.9±0.2, 20.4±0.2, 22.0±0.2, 23.1±0.2, 23.6±0.2, 24.2±0.2, 25.2±0.2, 26.2±0.2, and 27.5±0.2. In some embodiments, IPAc Solvate Form is characterized by an X-ray powder diffractogram having a signal at at least eleven two-theta values chosen from 5.0±0.2, 9.9±0.2, 11.5±0.2, 11.7±0.2, 12.0±0.2, 12.5±0.2, 13.0±0.2, 13.7±0.2, 14.4±0.2, 16.0±0.2, 16.9±0.2, 18.8±0.2, 19.9±0.2, 20.4±0.2, 22.0±0.2, 23.1±0.2, 23.6±0.2, 24.2±0.2, 25.2±0.2, 26.2±0.2, and 27.5±0.2. In some embodiments, IPAc Solvate Form is characterized by an X-ray powder diffractogram having a signal at at least twelve two-theta values chosen from 5.0±0.2, 9.9±0.2, 11.5±0.2, 11.7±0.2, 12.0±0.2, 12.5±0.2, 13.0±0.2, 13.7±0.2, 14.4±0.2, 16.0±0.2, 16.9±0.2, 18.8±0.2, 19.9±0.2, 20.4±0.2, 22.0±0.2, 23.1±0.2, 23.6±0.2, 24.2±0.2, 25.2±0.2, 26.2±0.2, and 27.5±0.2. In some embodiments, IPAc Solvate Form is characterized by an X-ray powder diffractogram having a signal at at least thirteen two-theta values chosen from 5.0±0.2, 9.9±0.2, 11.5±0.2, 11.7±0.2, 12.0±0.2, 12.5±0.2, 13.0±0.2, 13.7±0.2, 14.4±0.2, 16.0±0.2, 16.9±0.2, 18.8±0.2, 19.9±0.2, 20.4±0.2, 22.0±0.2, 23.1±0.2, 23.6±0.2, 24.2±0.2, 25.2±0.2, 26.2±0.2, and 27.5±0.2. In some embodiments, IPAc Solvate Form is characterized by an X-ray powder diffractogram having a signal at at least fourteen two-theta values chosen from 5.0±0.2, 9.9±0.2, 11.5±0.2, 11.7±0.2, 12.0±0.2, 12.5±0.2, 13.0±0.2, 13.7±0.2, 14.4±0.2, 16.0±0.2, 16.9±0.2, 18.8±0.2, 19.9±0.2, 20.4±0.2, 22.0±0.2, 23.1±0.2, 23.6±0.2, 24.2±0.2, 25.2±0.2, 26.2±0.2, and 27.5±0.2. In some embodiments, IPAc Solvate Form is characterized by an X-ray powder diffractogram having a signal at at least fifteen two-theta values chosen from 5.0±0.2, 9.9±0.2, 11.5±0.2, 11.7±0.2, 12.0±0.2, 12.5±0.2, 13.0±0.2, 13.7±0.2, 14.4±0.2, 16.0±0.2, 16.9±0.2, 18.8±0.2, 19.9±0.2, 20.4±0.2, 22.0±0.2, 23.1±0.2, 23.6±0.2, 24.2±0.2, 25.2±0.2, 26.2±0.2, and 27.5±0.2. In some embodiments, IPAc Solvate Form is characterized by an X-ray powder diffractogram having a signal at at least sixteen two-theta values chosen from 5.0±0.2, 9.9±0.2, 11.5±0.2, 11.7±0.2, 12.0±0.2, 12.5±0.2, 13.0±0.2, 13.7±0.2, 14.4±0.2, 16.0±0.2, 16.9±0.2, 18.8±0.2, 19.9±0.2, 20.4±0.2, 22.0±0.2, 23.1±0.2, 23.6±0.2, 24.2±0.2, 25.2±0.2, 26.2±0.2, and 27.5±0.2. In some embodiments, IPAc Solvate Form is characterized by an X-ray powder diffractogram having a signal at at least seventeen two-theta values chosen from 5.0±0.2, 9.9±0.2, 11.5±0.2, 11.7±0.2, 12.0±0.2, 12.5±0.2, 13.0±0.2, 13.7±0.2, 14.4±0.2, 16.0±0.2, 16.9±0.2, 18.8±0.2, 19.9±0.2, 20.4±0.2, 22.0±0.2, 23.1±0.2, 23.6±0.2, 24.2±0.2, 25.2±0.2, 26.2±0.2, and 27.5±0.2. In some embodiments, IPAc Solvate Form is characterized by an X-ray powder diffractogram having a signal at at least eighteen two-theta values chosen from 5.0±0.2, 9.9±0.2, 11.5±0.2, 11.7±0.2, 12.0±0.2, 12.5±0.2, 13.0±0.2, 13.7±0.2, 14.4±0.2, 16.0±0.2, 16.9±0.2, 18.8±0.2, 19.9±0.2, 20.4±0.2, 22.0±0.2, 23.1±0.2, 23.6±0.2, 24.2±0.2, 25.2±0.2, 26.2±0.2, and 27.5±0.2. In some embodiments, IPAc Solvate Form is characterized by an X-ray powder diffractogram having a signal at at least nineteen two-theta values chosen from 5.0±0.2, 9.9±0.2, 11.5±0.2, 11.7±0.2, 12.0±0.2, 12.5±0.2, 13.0±0.2, 13.7±0.2, 14.4±0.2, 16.0±0.2, 16.9±0.2, 18.8±0.2, 19.9±0.2, 20.4±0.2, 22.0±0.2, 23.1±0.2, 23.6±0.2, 24.2±0.2, 25.2±0.2, 26.2±0.2, and 27.5±0.2. In some embodiments, IPAc Solvate Form is characterized by an X-ray powder diffractogram having a signal at at least twenty two-theta values chosen from 5.0±0.2, 9.9±0.2, 11.5±0.2, 11.7±0.2, 12.0±0.2, 12.5±0.2, 13.0±0.2, 13.7±0.2, 14.4±0.2, 16.0±0.2, 16.9±0.2, 18.8±0.2, 19.9±0.2, 20.4±0.2, 22.0±0.2, 23.1±0.2, 23.6±0.2, 24.2±0.2, 25.2±0.2, 26.2±0.2, and 27.5±0.2. In some embodiments, IPAc Solvate Form is characterized by an X-ray powder diffractogram having a signal at 5.0±0.2, 9.9±0.2, 11.5±0.2, 11.7±0.2, 12.0±0.2, 12.5±0.2, 13.0±0.2, 13.7±0.2, 14.4±0.2, 16.0±0.2, 16.9±0.2, 18.8±0.2, 19.9±0.2, 20.4±0.2, 22.0±0.2, 23.1±0.2, 23.6±0.2, 24.2±0.2, 25.2±0.2, 26.2±0.2, and 27.5±0.2 degrees two-theta.

In some embodiments, disclosed herein is a composition comprising IPAc Solvate Form of Compound 87. In some embodiments, disclosed herein is a composition comprising Compound 87 in substantially pure IPAc Solvate Form. In some embodiments, disclosed herein is a composition comprising at least one active compound consisting essentially of Compound 87 in IPAc Solvate Form.

Figure 54:
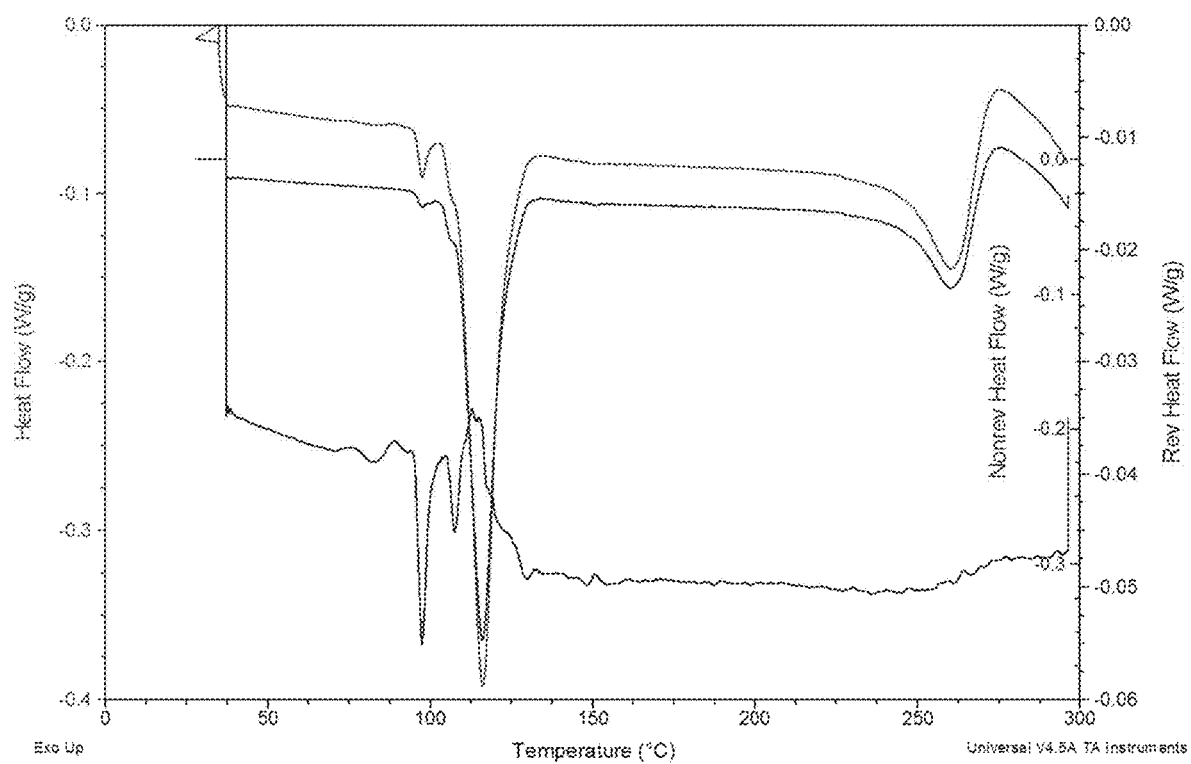
FIG. 54 depicts a DSC curve of shortly vacuum dried sample of IPAc Solvate of Compound 87.

In some embodiments, IPAc Solvate Form is characterized by a DSC curve substantially similar to that in FIG. 54. In some embodiments, IPAc Solvate Form is characterized by a DSC curve having at least one peak at 116° C.

In some embodiments, IPAc Solvate Form is characterized by a $^{13}$C NMR spectrum having a signal at at least one ppm value chosen from 178.3±0.2 ppm, 178.0±0.2 ppm, 177.5±0.2 ppm, 173.2±0.2 ppm, 171.5±0.2 ppm, 138.1±0.2 ppm, 137.9±0.2 ppm, 135.9±0.2 ppm, 132.2±0.2 ppm, 131.4±0.2 ppm, 119.1±0.2 ppm, 118.7±0.2 ppm, 109.8±0.2 ppm, 108.9±0.2 ppm, 107.4±0.2 ppm, 77.1±0.2 ppm, 76.8±0.2 ppm, 76.0±0.2 ppm, 68.5±0.2 ppm, 33.9±0.2 ppm, and 20.8±0.2 ppm. In some embodiments, IPAc Solvate Form is characterized by a $^{13}$C NMR spectrum having a signal at at least two ppm values chosen from 178.3±0.2 ppm, 178.0±0.2 ppm, 177.5±0.2 ppm, 173.2±0.2 ppm, 171.5±0.2 ppm, 138.1±0.2 ppm, 137.9±0.2 ppm, 135.9±0.2 ppm, 132.2±0.2 ppm, 131.4±0.2 ppm, 119.1±0.2 ppm, 118.7±0.2 ppm, 109.8±0.2 ppm, 108.9±0.2 ppm, 107.4±0.2 ppm, 77.1±0.2 ppm, 76.8±0.2 ppm, 76.0±0.2 ppm, 68.5±0.2 ppm, 33.9±0.2 ppm, and 20.8±0.2 ppm. In some embodiments, IPAc Solvate Form is characterized by a $^{13}$C NMR spectrum having a signal at at least three ppm values chosen from 178.3±0.2 ppm, 178.0±0.2 ppm, 177.5±0.2 ppm, 173.2±0.2 ppm, 171.5±0.2 ppm, 138.1±0.2 ppm, 137.9±0.2 ppm, 135.9±0.2 ppm, 132.2±0.2 ppm, 131.4±0.2 ppm, 119.1±0.2 ppm, 118.7±0.2 ppm, 109.8±0.2 ppm, 108.9±0.2 ppm, 107.4±0.2 ppm, 77.1±0.2 ppm, 76.8±0.2 ppm, 76.0±0.2 ppm, 68.5±0.2 ppm, 33.9±0.2 ppm, and 20.8±0.2 ppm. In some embodiments, IPAc Solvate Form is characterized by a $^{13}$C NMR spectrum having a signal at at least four ppm values chosen from 178.3±0.2 ppm, 178.0±0.2 ppm, 177.5±0.2 ppm, 173.2±0.2 ppm, 171.5±0.2 ppm, 138.1±0.2 ppm, 137.9±0.2 ppm, 135.9±0.2 ppm, 132.2±0.2 ppm, 131.4±0.2 ppm, 119.1±0.2 ppm, 118.7±0.2 ppm, 109.8±0.2 ppm, 108.9±0.2 ppm, 107.4±0.2 ppm, 77.1±0.2 ppm, 76.8±0.2 ppm, 76.0±0.2 ppm, 68.5±0.2 ppm, 33.9±0.2 ppm, and 20.8±0.2 ppm. In some embodiments, IPAc Solvate Form is characterized by a $^{13}$C NMR spectrum having a signal at at least five ppm values chosen from 178.3±0.2 ppm, 178.0±0.2 ppm, 177.5±0.2 ppm, 173.2±0.2 ppm, 171.5±0.2 ppm, 138.1±0.2 ppm, 137.9±0.2 ppm, 135.9±0.2 ppm, 132.2±0.2 ppm, 131.4±0.2 ppm, 119.1±0.2 ppm, 118.7±0.2 ppm, 109.8±0.2 ppm, 108.9±0.2 ppm, 107.4±0.2 ppm, 77.1±0.2 ppm, 76.8±0.2 ppm, 76.0±0.2 ppm, 68.5±0.2 ppm, 33.9±0.2 ppm, and 20.8±0.2 ppm. In some embodiments, IPAc Solvate Form is characterized by a $^{13}$C NMR spectrum having a signal at at least six ppm values chosen from 178.3±0.2 ppm, 178.0±0.2 ppm, 177.5±0.2 ppm, 173.2±0.2 ppm, 171.5±0.2 ppm, 138.1±0.2 ppm, 137.9±0.2 ppm, 135.9±0.2 ppm, 132.2±0.2 ppm, 131.4±0.2 ppm, 119.1±0.2 ppm, 118.7±0.2 ppm, 109.8±0.2 ppm, 108.9±0.2 ppm, 107.4±0.2 ppm, 77.1±0.2 ppm, 76.8±0.2 ppm, 76.0±0.2 ppm, 68.5±0.2 ppm, 33.9±0.2 ppm, and 20.8±0.2 ppm. In some embodiments, IPAc Solvate Form is characterized by a $^{13}$C NMR spectrum having a signal at at least seven ppm values chosen from 178.3±0.2 ppm, 178.0±0.2 ppm, 177.5±0.2 ppm, 173.2±0.2 ppm, 171.5±0.2 ppm, 138.1±0.2 ppm, 137.9±0.2 ppm, 135.9±0.2 ppm, 132.2±0.2 ppm, 131.4±0.2 ppm, 119.1±0.2 ppm, 118.7±0.2 ppm, 109.8±0.2 ppm, 108.9±0.2 ppm, 107.4±0.2 ppm, 77.1±0.2 ppm, 76.8±0.2 ppm, 76.0±0.2 ppm, 68.5±0.2 ppm, 33.9±0.2 ppm, and 20.8±0.2 ppm. In some embodiments, IPAc Solvate Form is characterized by a $^{13}$C NMR spectrum having a signal at at least eight ppm values chosen from 178.3±0.2 ppm, 178.0±0.2 ppm, 177.5±0.2 ppm, 173.2±0.2 ppm, 171.5±0.2 ppm, 138.1±0.2 ppm, 137.9±0.2 ppm, 135.9±0.2 ppm, 132.2±0.2 ppm, 131.4±0.2 ppm, 119.1±0.2 ppm, 118.7±0.2 ppm, 109.8±0.2 ppm, 108.9±0.2 ppm, 107.4±0.2 ppm, 77.1±0.2 ppm, 76.8±0.2 ppm, 76.0±0.2 ppm, 68.5±0.2 ppm, 33.9±0.2 ppm, and 20.8±0.2 ppm. In some embodiments, IPAc Solvate Form is characterized by a $^{13}$C NMR spectrum having a signal at at least nine ppm values chosen from 178.3±0.2 ppm, 178.0±0.2 ppm, 177.5±0.2 ppm, 173.2±0.2 ppm, 171.5±0.2 ppm, 138.1±0.2 ppm, 137.9±0.2 ppm, 135.9±0.2 ppm, 132.2±0.2 ppm, 131.4±0.2 ppm, 119.1±0.2 ppm, 118.7±0.2 ppm, 109.8±0.2 ppm, 108.9±0.2 ppm, 107.4±0.2 ppm, 77.1±0.2 ppm, 76.8±0.2 ppm, 76.0±0.2 ppm, 68.5±0.2 ppm, 33.9±0.2 ppm, and 20.8±0.2 ppm. In some embodiments, IPAc Solvate Form is characterized by a $^{13}$C NMR spectrum having a signal at at least ten ppm values chosen from 178.3±0.2 ppm, 178.0±0.2 ppm, 177.5±0.2 ppm, 173.2±0.2 ppm, 171.5±0.2 ppm, 138.1±0.2 ppm, 137.9±0.2 ppm, 135.9±0.2 ppm, 132.2±0.2 ppm, 131.4±0.2 ppm, 119.1±0.2 ppm, 118.7±0.2 ppm, 109.8±0.2 ppm, 108.9±0.2 ppm, 107.4±0.2 ppm, 77.1±0.2 ppm, 76.8±0.2 ppm, 76.0±0.2 ppm, 68.5±0.2 ppm, 33.9±0.2 ppm, and 20.8±0.2 ppm. In some embodiments, IPAc Solvate Form is characterized by a $^{13}$C NMR spectrum having a signal at at least eleven ppm values chosen from 178.3±0.2 ppm, 178.0±0.2 ppm, 177.5±0.2 ppm, 173.2±0.2 ppm, 171.5±0.2 ppm, 138.1±0.2 ppm, 137.9±0.2 ppm, 135.9±0.2 ppm, 132.2±0.2 ppm, 131.4±0.2 ppm, 119.1±0.2 ppm, 118.7±0.2 ppm, 109.8±0.2 ppm, 108.9±0.2 ppm, 107.4±0.2 ppm, 77.1±0.2 ppm, 76.8±0.2 ppm, 76.0±0.2 ppm, 68.5±0.2 ppm, 33.9±0.2 ppm, and 20.8±0.2 ppm. In some embodiments, IPAc Solvate Form is characterized by a $^{13}$C NMR spectrum having a signal at at least twelve ppm values chosen from 178.3±0.2 ppm, 178.0±0.2 ppm, 177.5±0.2 ppm, 173.2±0.2 ppm, 171.5±0.2 ppm, 138.1±0.2 ppm, 137.9±0.2 ppm, 135.9±0.2 ppm, 132.2±0.2 ppm, 131.4±0.2 ppm, 119.1±0.2 ppm, 118.7±0.2 ppm, 109.8±0.2 ppm, 108.9±0.2 ppm, 107.4±0.2 ppm, 77.1±0.2 ppm, 76.8±0.2 ppm, 76.0±0.2 ppm, 68.5±0.2 ppm, 33.9±0.2 ppm, and 20.8±0.2 ppm. In some embodiments, IPAc Solvate Form is characterized by a $^{13}$C NMR spectrum having a signal at at least thirteen ppm values chosen from 178.3±0.2 ppm, 178.0±0.2 ppm, 177.5±0.2 ppm, 173.2±0.2 ppm, 171.5±0.2 ppm, 138.1±0.2 ppm, 137.9±0.2 ppm, 135.9±0.2 ppm, 132.2±0.2 ppm, 131.4±0.2 ppm, 119.1±0.2 ppm, 118.7±0.2 ppm, 109.8±0.2 ppm, 108.9±0.2 ppm, 107.4±0.2 ppm, 77.1±0.2 ppm, 76.8±0.2 ppm, 76.0±0.2 ppm, 68.5±0.2 ppm, 33.9±0.2 ppm, and 20.8±0.2 ppm. In some embodiments, IPAc Solvate Form is characterized by a $^{13}$C NMR spectrum having a signal at at least fourteen ppm values chosen from 178.3±0.2 ppm, 178.0±0.2 ppm, 177.5±0.2 ppm, 173.2±0.2 ppm, 171.5±0.2 ppm, 138.1±0.2 ppm, 137.9±0.2 ppm, 135.9±0.2 ppm, 132.2±0.2 ppm, 131.4±0.2 ppm, 119.1±0.2 ppm, 118.7±0.2 ppm, 109.8±0.2 ppm, 108.9±0.2 ppm, 107.4±0.2 ppm, 77.1±0.2 ppm, 76.8±0.2 ppm, 76.0±0.2 ppm, 68.5±0.2 ppm, 33.9±0.2 ppm, and 20.8±0.2 ppm. In some embodiments, IPAc Solvate Form is characterized by a $^{13}$C NMR spectrum having a signal at at least fifteen ppm values chosen from 178.3±0.2 ppm, 178.0±0.2 ppm, 177.5±0.2 ppm, 173.2±0.2 ppm, 171.5±0.2 ppm, 138.1±0.2 ppm, 137.9±0.2 ppm, 135.9±0.2 ppm, 132.2±0.2 ppm, 131.4±0.2 ppm, 119.1±0.2 ppm, 118.7±0.2 ppm, 109.8±0.2 ppm, 108.9±0.2 ppm, 107.4±0.2 ppm, 77.1±0.2 ppm, 76.8±0.2 ppm, 76.0±0.2 ppm, 68.5±0.2 ppm, 33.9±0.2 ppm, and 20.8±0.2 ppm. In some embodiments, IPAc Solvate Form is characterized by a $^{13}$C NMR spectrum having a signal at at least sixteen ppm values chosen from 178.3±0.2 ppm, 178.0±0.2 ppm, 177.5±0.2 ppm, 173.2±0.2 ppm, 171.5±0.2 ppm, 138.1±0.2 ppm, 137.9±0.2 ppm, 135.9±0.2 ppm, 132.2±0.2 ppm, 131.4±0.2 ppm, 119.1±0.2 ppm, 118.7±0.2 ppm, 109.8±0.2 ppm, 108.9±0.2 ppm, 107.4±0.2 ppm, 77.1±0.2 ppm, 76.8±0.2 ppm, 76.0±0.2 ppm, 68.5±0.2 ppm, 33.9±0.2 ppm, and 20.8±0.2 ppm. In some embodiments, IPAc Solvate Form is characterized by a $^{13}$C NMR spectrum having a signal at at least seventeen ppm values chosen from 178.3±0.2 ppm, 178.0±0.2 ppm, 177.5±0.2 ppm, 173.2±0.2 ppm, 171.5±0.2 ppm, 138.1±0.2 ppm, 137.9±0.2 ppm, 135.9±0.2 ppm, 132.2±0.2 ppm, 131.4±0.2 ppm, 119.1±0.2 ppm, 118.7±0.2 ppm, 109.8±0.2 ppm, 108.9±0.2 ppm, 107.4±0.2 ppm, 77.1±0.2 ppm, 76.8±0.2 ppm, 76.0±0.2 ppm, 68.5±0.2 ppm, 33.9±0.2 ppm, and 20.8±0.2 ppm. In some embodiments, IPAc Solvate Form is characterized by a $^{13}$C NMR spectrum having a signal at at least eighteen ppm values chosen from 178.3±0.2 ppm, 178.0±0.2 ppm, 177.5±0.2 ppm, 173.2±0.2 ppm, 171.5±0.2 ppm, 138.1±0.2 ppm, 137.9±0.2 ppm, 135.9±0.2 ppm, 132.2±0.2 ppm, 131.4±0.2 ppm, 119.1±0.2 ppm, 118.7±0.2 ppm, 109.8±0.2 ppm, 108.9±0.2 ppm, 107.4±0.2 ppm, 77.1±0.2 ppm, 76.8±0.2 ppm, 76.0±0.2 ppm, 68.5±0.2 ppm, 33.9±0.2 ppm, and 20.8±0.2 ppm. In some embodiments, IPAc Solvate Form is characterized by a $^{13}$C NMR spectrum having a signal at at least nineteen ppm values chosen from 178.3±0.2 ppm, 178.0±0.2 ppm, 177.5±0.2 ppm, 173.2±0.2 ppm, 171.5±0.2 ppm, 138.1±0.2 ppm, 137.9±0.2 ppm, 135.9±0.2 ppm, 132.2±0.2 ppm, 131.4±0.2 ppm, 119.1±0.2 ppm, 118.7±0.2 ppm, 109.8±0.2 ppm, 108.9±0.2 ppm, 107.4±0.2 ppm, 77.1±0.2 ppm, 76.8±0.2 ppm, 76.0±0.2 ppm, 68.5±0.2 ppm, 33.9±0.2 ppm, and 20.8±0.2 ppm. In some embodiments, IPAc Solvate Form is characterized by a $^{13}$C NMR spectrum having a signal at at least twenty ppm values chosen from 178.3±0.2 ppm, 178.0±0.2 ppm, 177.5±0.2 ppm, 173.2±0.2 ppm, 171.5±0.2 ppm, 138.1±0.2 ppm, 137.9±0.2 ppm, 135.9±0.2 ppm, 132.2±0.2 ppm, 131.4±0.2 ppm, 119.1±0.2 ppm, 118.7±0.2 ppm, 109.8±0.2 ppm, 108.9±0.2 ppm, 107.4±0.2 ppm, 77.1±0.2 ppm, 76.8±0.2 ppm, 76.0±0.2 ppm, 68.5±0.2 ppm, 33.9±0.2 ppm, and 20.8±0.2 ppm. In some embodiments, IPAc Solvate Form is characterized by a $^{13}$C NMR spectrum having a signal at 178.3±0.2 ppm, 178.0±0.2 ppm, 177.5±0.2 ppm, 173.2±0.2 ppm, 171.5±0.2 ppm, 138.1±0.2 ppm, 137.9±0.2 ppm, 135.9±0.2 ppm, 132.2±0.2 ppm, 131.4±0.2 ppm, 119.1±0.2 ppm, 118.7±0.2 ppm, 109.8±0.2 ppm, 108.9±0.2 ppm, 107.4±0.2 ppm, 77.1±0.2 ppm, 76.8±0.2 ppm, 76.0±0.2 ppm, 68.5±0.2 ppm, 33.9±0.2 ppm, and 20.8±0.2 ppm.

In some embodiments, IPAc Solvate Form is characterized by a $^{19}$F NMR spectrum having a signal at least at one ppm value chosen from −107.1±0.2 ppm, −107.4±0.2 ppm, −108.0±0.2 ppm, −114.5±0.2 ppm, −115.0±0.2 ppm, and −116.2±0.2 ppm. In some embodiments, Form A is characterized by a $^{19}$F NMR spectrum having a signal at least at two ppm value chosen from −107.1±0.2 ppm, −107.4±0.2 ppm, −108.0±0.2 ppm, −114.5±0.2 ppm, −115.0±0.2 ppm, and −116.2±0.2 ppm. In some embodiments, Form A is characterized by a $^{19}$F NMR spectrum having a signal at least at three ppm value chosen from −107.1±0.2 ppm, −107.4±0.2 ppm, −108.0±0.2 ppm, −114.5±0.2 ppm, −115.0±0.2 ppm, and −116.2±0.2 ppm. In some embodiments, Form A is characterized by a $^{19}$F NMR spectrum having a signal at least at four ppm value chosen from −107.1±0.2 ppm, −107.4±0.2 ppm, −108.0±0.2 ppm, −114.5±0.2 ppm, −115.0±0.2 ppm, and −116.2±0.2 ppm. In some embodiments, Form A is characterized by a $^{19}$F NMR spectrum having a signal at least at five ppm value chosen from −107.1±0.2 ppm, −107.4±0.2 ppm, −108.0±0.2 ppm, −114.5±0.2 ppm, −115.0±0.2 ppm, and −116.2±0.2 ppm. In some embodiments, Form A is characterized by a $^{19}$F NMR spectrum having a signal at −107.1±0.2 ppm, −107.4±0.2 ppm, −108.0±0.2 ppm, −114.5±0.2 ppm, −115.0±0.2 ppm, and −116.2±0.2 ppm.

In some embodiments, Compound 87 is a crystalline solid. In some embodiments, the crystalline solid consists of 1% to 99% IPAc Solvate Form relative to the total weight of the crystalline solid Compound 87. In some embodiments, the crystalline solid consists of 2% to 99% IPAc Solvate Form relative to the total weight of the crystalline solid Compound 87. In some embodiments, the crystalline solid consists of 5% to 99% IPAc Solvate Form relative to the total weight of the crystalline solid Compound 87. In some embodiments, the crystalline solid consists of 10% to 99% IPAc Solvate Form relative to the total weight of the crystalline solid Compound 87. In some embodiments, the crystalline solid consists of 15% to 99% IPAc Solvate Form relative to the total weight of the crystalline solid Compound 87. In some embodiments, the crystalline solid consists of 20% to 99% IPAc Solvate Form relative to the total weight of the crystalline solid Compound 87. In some embodiments, the crystalline solid consists of 25% to 99% IPAc Solvate Form relative to the total weight of the crystalline solid Compound 87. In some embodiments, the crystalline solid consists of 30% to 99% IPAc Solvate Form relative to the total weight of the crystalline solid Compound 87. In some embodiments, the crystalline solid consists of 35% to 99% IPAc Solvate Form relative to the total weight of the crystalline solid Compound 87. In some embodiments, the crystalline solid consists of 45% to 99% IPAc Solvate Form relative to the total weight of the crystalline solid Compound 87. In some embodiments, the crystalline solid consists of 50% to 99% IPAc Solvate Form relative to the total weight of the crystalline solid Compound 87. In some embodiments, the crystalline solid consists of 55% to 99% IPAc Solvate Form relative to the total weight of the crystalline solid Compound 87. In some embodiments, the crystalline solid consists of 60% to 99% IPAc Solvate Form relative to the total weight of the crystalline solid Compound 87. In some embodiments, the crystalline solid consists of 65% to 99% IPAc Solvate Form relative to the total weight of the crystalline solid Compound 87. In some embodiments, the crystalline solid consists of 70% to 99% IPAc Solvate Form relative to the total weight of the crystalline solid Compound 87. In some embodiments, the crystalline solid consists of 75% to 99% IPAc Solvate Form relative to the total weight of the crystalline solid Compound 87. In some embodiments, the crystalline solid consists of 80% to 99% IPAc Solvate Form relative to the total weight of the crystalline solid Compound 87. In some embodiments, the crystalline solid consists of 85% to 99% IPAc Solvate Form relative to the total weight of the crystalline solid Compound 87. In some embodiments, the crystalline solid consists of 90% to 99% IPAc Solvate Form relative to the total weight of the crystalline solid Compound 87. In some embodiments, the crystalline solid consists of 95% to 99% IPAc Solvate Form relative to the total weight of the crystalline solid Compound 87.

Amorphous Form of Compound 87

Figure 56:
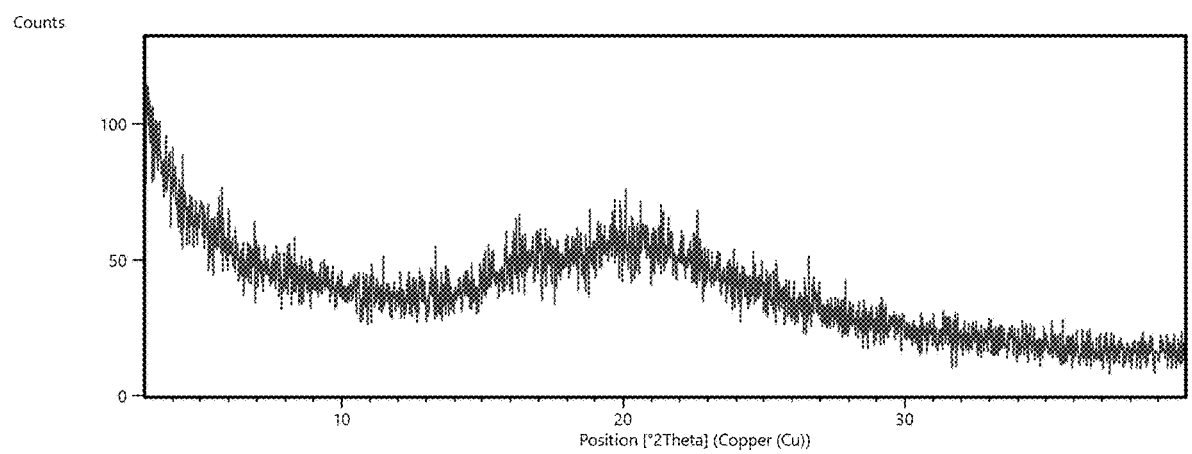
FIG. 56 depicts an XRPD diffractogram of amorphous form of Compound 87.

In some embodiments, Compound 87 is in an amorphous form. In some embodiments, Compound 87 is in the form of substantially pure amorphous form. In some embodiments, amorphous form of Compound 87 is characterized by an X-ray powder diffractogram substantially similar to that in FIG. 56.

In some embodiments, disclosed herein is a composition comprising amorphous form of Compound 87. In some embodiments, disclosed herein is a composition comprising Compound 87 in substantially pure amorphous form. In some embodiments, disclosed herein is a composition comprising at least one active compound consisting essentially of Compound 87 in amorphous form.

In some embodiments, amorphous form is characterized by a $^{13}$C NMR spectrum having a signal at at least one ppm value chosen from 119.5±0.2 ppm, 37.2±0.2 ppm, and 21.2±0.2 ppm. In some embodiments, amorphous form is characterized by a $^{13}$C NMR spectrum having a signal at at least two ppm values chosen from 119.5±0.2 ppm, 37.2±0.2 ppm, and 21.2±0.2 ppm. In some embodiments, amorphous form is characterized by a $^{13}$C NMR spectrum having a signal at 119.5±0.2 ppm, 37.2±0.2 ppm, and 21.2±0.2 ppm.

In some embodiments, amorphous form is characterized by a $^{19}$F NMR spectrum having a signal at −114.1 ppm.

Non-Limiting Exemplary Embodiments

1. At least one entity chosen from compounds of Formula (I):

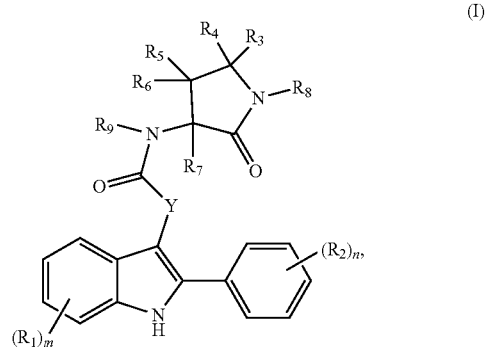

pharmaceutically acceptable salts thereof, solvates of any of the foregoing, and deuterated derivatives of any of the foregoing, wherein:
(i) each $R_1$ is independently chosen from
halogen groups,
hydroxy,
thiol,
amino, cyano,
—OC(O)$C_1$-$C_6$ linear, branched, and cyclic alkyl groups,
—C(O)O$C_1$-$C_6$ linear, branched, and cyclic alkyl groups,
—NHC(O)$C_1$-$C_6$ linear, branched, and cyclic alkyl groups,
—C(O)NH$C_1$-$C_6$ linear, branched, and cyclic alkyl groups,
—NHC(O)aryl groups,
—C(O)NHaryl groups,
—NHC(O)heteroaryl groups,
—C(O)NHheteroaryl groups,
—NHS(O)$_2$$C_1$-$C_6$ linear, branched, and cyclic alkyl groups,
—S(O)$_2$NH$C_1$-$C_6$ linear, branched, and cyclic alkyl groups,
—NHS(O)$_2$aryl groups,
—S(O)$_2$NHaryl groups,
—NHS(O)$_2$heteroaryl groups,
—S(O)$_2$NHheteroaryl groups,
—NHC(O)NH$C_1$-$C_6$ linear, branched, and cyclic alkyl groups,
—NHC(O)NHaryl groups,
—NHC(O)NHheteroaryl groups,
$C_1$-$C_6$ linear, branched, and cyclic alkyl groups,
$C_2$-$C_6$ linear, branched, and cyclic alkenyl groups,
$C_1$-$C_6$ linear, branched, and cyclic hydroxyalkyl groups,
$C_1$-$C_6$ linear, branched, and cyclic alkoxy groups,
$C_1$-$C_6$ linear, branched, and cyclic thioalkyl groups,
$C_1$-$C_6$ linear, branched, and cyclic haloalkyl groups,
$C_1$-$C_6$ linear, branched, and cyclic haloaminoalkyl groups,
$C_1$-$C_6$ linear, branched, and cyclic halothioalkyl groups,
$C_1$-$C_6$ linear, branched, and cyclic haloalkoxy groups,
benzyloxy, benzylamino, or benzylthio groups,
3 to 6-membered heterocycloalkenyl groups,
3 to 6-membered heterocycloalkyl groups, and
5 and 6-membered heteroaryl groups; or
two $R_1$ groups, together with the carbon atoms to which they are attached, form a $C_4$-$C_8$ cycloalkyl group, an aryl group, or a heteroaryl group;
(ii) each $R_2$ is independently chosen from
halogen groups,
hydroxy,
thiol,
amino,
cyano,
—NHC(O)$C_1$-$C_6$ linear, branched, and cyclic alkyl groups,
—C(O)NH$C_1$-$C_6$ linear, branched, and cyclic alkyl groups,
—NHC(O)aryl groups,
—C(O)NHaryl groups,
—NHC(O)heteroaryl groups,
—C(O)NHheteroaryl groups,
—NHS(O)$_2$$C_1$-$C_6$ linear, branched, and cyclic alkyl groups,
—S(O)$_2$NH$C_1$-$C_6$ linear, branched, and cyclic alkyl groups,
—NHS(O)$_2$aryl groups,
—S(O)$_2$NHaryl groups,
—NHS(O)$_2$heteroaryl groups,
—S(O)$_2$NHheteroaryl groups,
—NHC(O)NH$C_1$-$C_4$ linear, branched, and cyclic alkyl groups,
—NHC(O)NH aryl groups,
—NHC(O)NH heteroaryl groups,
$C_1$-$C_4$ linear, branched, and cyclic alkyl groups,
$C_2$-$C_4$ linear, branched, and cyclic alkenyl groups,
$C_1$-$C_4$ linear, branched, and cyclic hydroxyalkyl groups,
$C_1$-$C_4$ linear, branched, and cyclic alkoxy groups,
$C_1$-$C_4$ linear, branched, and cyclic thioalkyl groups,
$C_1$-$C_4$ linear, branched, and cyclic haloalkyl groups,
$C_1$-$C_4$ linear, branched, and cyclic haloaminoalkyl groups,
$C_1$-$C_4$ linear, branched, and cyclic halothioalkyl groups, and
$C_1$-$C_4$ linear, branched, and cyclic haloalkoxy groups;
(iii) m is chosen from 0, 1, 2, 3, and 4;
(iv) n is chosen from 0, 1, 2, 3, 4, and 5;
(v) Y is chosen from divalent $C_1$-$C_8$ linear and branched alkyl groups, divalent $C_1$-$C_8$ linear and branched alkoxy groups, divalent $C_1$-$C_8$ linear and branched aminoalkyl groups, and divalent $C_1$-$C_8$ linear and branched thioalkyl groups, wherein the divalent alkyl groups, divalent alkoxy groups, divalent aminoalkyl groups, and divalent thioalkyl groups are optionally substituted with at least one group chosen from
$C_1$-$C_6$ alkyl groups,
aryl groups,
heteroaryl groups,
halogen groups,
hydroxy, and
amino;
(vi) each of $R_3$ and $R_4$ is independently chosen from
hydrogen,
hydroxy,
thiol,
amino,
halogen groups,
$C_1$-$C_6$ linear, branched, and cyclic hydroxyalkyl groups,
$C_1$-$C_6$ linear, branched, and cyclic alkoxy groups,
$C_1$-$C_6$ linear, branched, and cyclic thioalkyl groups,
$C_1$-$C_6$ linear, branched, and cyclic haloalkyl groups,
$C_1$-$C_6$ linear, branched, and cyclic haloaminoalkyl groups,
$C_1$-$C_6$ linear, branched, and cyclic halothioalkyl groups,
$C_1$-$C_6$ linear, branched, and cyclic haloalkoxy groups, or
$R_3$ and $R_4$, together with the carbon atom to which they are attached, form a $C_3$-$C_6$ cycloalkyl group or carbonyl group;
(vii) each of $R_5$ and $R_6$ is independently chosen from
hydrogen,
thiol,
amino,
halogen groups,
hydroxy,
$C_1$-$C_6$ linear, branched, and cyclic hydroxyalkyl groups,
$C_1$-$C_6$ linear, branched, and cyclic alkoxy groups,
$C_1$-$C_6$ linear, branched, and cyclic thioalkyl groups,
$C_1$-$C_6$ linear, branched, and cyclic haloalkyl groups,
$C_1$-$C_6$ linear, branched, and cyclic haloaminoalkyl groups,
$C_1$-$C_6$ linear, branched, and cyclic halothioalkyl groups, $C_1$-$C_6$ linear, branched, and cyclic haloalkoxy groups,
—OC(O)$C_1$-$C_6$ linear, branched, and cyclic alkyl groups,
—C(O)O$C_1$-$C_6$ linear, branched, and cyclic alkyl groups,
—NHC(O)$C_1$-$C_6$ linear, branched, and cyclic alkyl groups,
—C(O)NH$C_1$-$C_6$ linear, branched, and cyclic alkyl groups,
—NHC(O)aryl groups,
—C(O)NHaryl groups,
—NHC(O)heteroaryl groups,
—C(O)NHheteroaryl groups,
—NHS(O)$_2$$C_1$-$C_6$ linear, branched, and cyclic alkyl groups,
—S(O)$_2$NH$C_1$-$C_6$ linear, branched, and cyclic alkyl groups,
—NHS(O)$_2$aryl groups,
—S(O)$_2$NHaryl groups,
—NHS(O)$_2$heteroaryl groups,
—S(O)$_2$NHheteroaryl groups,
—NHC(O)NH$C_1$-$C_6$ linear, branched, and cyclic alkyl groups,
—NHC(O)NH aryl groups, and
—NHC(O)NH heteroaryl groups; and (viii) each of $R_7$, $R_8$, and $R_9$ is independently chosen from
hydrogen,
$C_1$-$C_6$ linear, branched, and cyclic alkyl groups,
$C_1$-$C_6$ linear, branched, and cyclic hydroxyalkyl groups,
$C_1$-$C_6$ linear, branched, and cyclic alkoxy groups,
$C_1$-$C_6$ linear, branched, and cyclic thioalkyl groups,
$C_1$-$C_6$ linear, branched, and cyclic haloalkyl groups,
$C_1$-$C_6$ linear, branched, and cyclic haloaminoalkyl groups,
$C_1$-$C_6$ linear, branched, and cyclic halothioalkyl groups, and
$C_1$-$C_6$ linear, branched, and cyclic haloalkoxy groups.

2. At least one entity chosen from compounds of Formula (I):

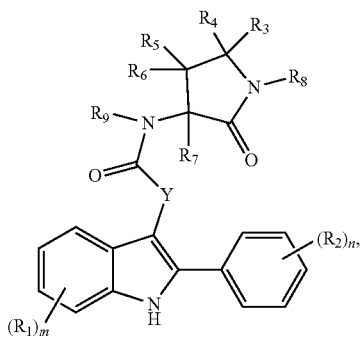

pharmaceutically acceptable salts thereof, solvates of any of the foregoing, and deuterated derivatives of any of the foregoing, wherein:

(i) each $R_1$ is independently chosen from
halogen groups,
hydroxy,
cyano,
$C_1$-$C_4$ linear, branched, and cyclic alkyl groups,
$C_2$-$C_4$ linear, branched, and cyclic alkenyl groups,
$C_1$-$C_4$ linear, branched, and cyclic hydroxyalkyl groups,
$C_1$-$C_4$ linear, branched, and cyclic alkoxy groups,
$C_1$-$C_4$ linear, branched, and cyclic haloalkyl groups,
$C_1$-$C_4$ linear, branched, and cyclic haloalkoxy groups,
benzyloxy groups,
3 to 6-membered heterocycloalkenyl groups,
3 to 6-membered heterocycloalkyl groups, and
5 and 6-membered heteroaryl groups;

(ii) each $R_2$ is independently chosen from
halogen groups,
cyano,
$C_1$-$C_4$ linear, branched, and cyclic alkoxy groups,
$C_1$-$C_4$ linear, branched, and cyclic haloalkoxy groups,
$C_1$-$C_4$ linear, branched, and cyclic alkyl groups, and
$C_1$-$C_4$ linear, branched, and cyclic haloalkyl groups;

(iii) m is chosen from 0, 1, 2, 3, and 4;
(iv) n is chosen from 0, 1, 2, 3, 4, and 5;
(v) Y is chosen from divalent $C_1$-$C_8$ linear and branched alkyl groups and divalent $C_1$-$C_8$ linear and branched cyclic thioalkyl groups, wherein the divalent alkyl groups and divalent thioalkyl groups are optionally substituted with at least one group chosen from
$C_1$-$C_4$ alkyl groups,
halogen groups, and
hydroxy;

(vi) each of $R_3$ and $R_4$ is independently chosen from
hydrogen,
$C_1$-$C_3$ linear, branched, and cyclic alkyl groups,
$C_1$-$C_3$ linear, branched, and cyclic hydroxyalkyl groups, and
$C_1$-$C_3$ linear, branched, and cyclic haloalkyl groups, or
$R_3$ and $R_4$, together with the carbon atom to which they are attached, form a $C_3$-$C_6$ cycloalkyl group or carbonyl group;

(vii) each of $R_5$ and $R_6$ is independently chosen from
hydrogen,
hydroxy,
$C_1$-$C_4$ linear, branched, and cyclic alkyl groups,
$C_1$-$C_4$ linear, branched, and cyclic haloalkyl groups, and
—OC(O)$C_1$-$C_4$ linear, branched, and cyclic alkyl groups; and (viii) each of $R_7$, $R_8$, and $R_9$ is independently chosen from
hydrogen,
$C_1$-$C_4$ linear, branched, and cyclic alkyl groups, and
$C_1$-$C_4$ linear, branched, and cyclic haloalkyl groups.

3. The at least one entity of embodiment 2, wherein $R_3$ is hydrogen and $R_4$ is hydrogen.

4. The at least one entity of any one of embodiments 1 to 3, wherein each $R_5$ and $R_6$ is independently chosen from hydrogen and hydroxy.

5. The at least one entity of any one of embodiments 1 to 4, wherein each $R_1$ is independently chosen from halogen groups.

6. The at least one entity of any one of embodiments 1 to 5, wherein each $R_1$ is fluoro.

7. The at least one entity of any one of embodiments 1 to 6, wherein each $R_2$ is independently chosen from fluoro and methyl.

8. The at least one entity of any one of embodiments 1 to 7, wherein m is 1 or 2.

9. The at least one entity of any one of embodiments 1 to 8, wherein m is 2.

10. The at least one entity of any one of embodiments 1 to 9, wherein n is 1 or 2.

11. The at least one entity of any one of embodiments 1 to 10, wherein n is 1.
12. The at least one entity of any one of embodiments 1 to 11, wherein Y is divalent ethyl optionally substituted with at least one group chosen from $C_1$-$C_4$ alkyl groups, halogen groups, and hydroxy.
13. The at least one entity of any one of embodiments 1 to 12, wherein Y is divalent ethyl.
14. The at least one entity of any one of embodiments 1 to 13, wherein Y is —$CH_2CH(CH_3)$—.
15. The at least one entity of any one of embodiments 1 to 14, wherein Y is divalent ethyl substituted with one or two groups chosen from halogen groups and hydroxy.
16. The at least one entity of any one of embodiments 1 to 12 and 15, wherein Y is divalent ethyl substituted with one halogen.
17. The at least one entity of any one of embodiments 15 and 16, wherein the halogen is fluoro.
18. The at least one entity of any one of embodiments 15 and 16, wherein the halogen is chloro.
19. The at least one entity of any one of embodiments 1 to 12 and 15, wherein Y is divalent ethyl substituted with two halogen groups.
20. The at least one entity of embodiment 19, wherein the halogen groups are fluoro.
21. The at least one entity of embodiment 19, wherein the halogen groups are chloro.
22. The at least one entity of embodiment 19, wherein the halogen groups are fluoro and chloro.
23. The at least one entity of any one of embodiments 1 to 12 and 15, wherein Y is divalent ethyl substituted with one hydroxy.
24. The at least one entity of any one of embodiments 1 to 11, wherein Y is divalent thiomethyl optionally substituted with at least one group chosen from $C_1$-$C_4$ alkyl groups, halogen groups, and hydroxy.
25. The at least one entity of any one of embodiments 1 to 11 and 24, wherein Y is divalent thiomethyl.
26. At least one entity chosen from compounds of Formula II:

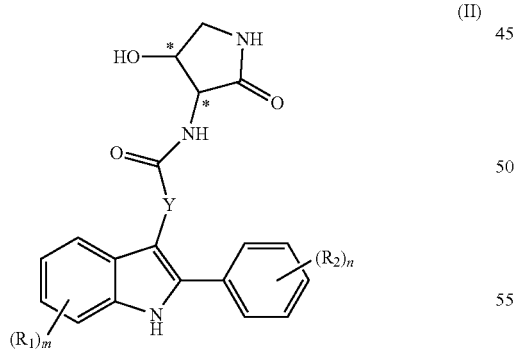

(II)

pharmaceutically acceptable salts thereof, solvates of any of the foregoing, and deuterated derivatives of any of the foregoing, wherein:
(i) each $R_1$ is independently chosen from
halogen groups,
cyano,
methyl,
cyclopropyl,
isopropyl,
$C_2$-$C_3$ linear and branched alkenyl groups,
hydroxypropyl groups,
methoxy,
dihydrofuran groups, and
furan groups;
(ii) each $R_2$ is independently chosen from
fluoro,
cyano, and
methyl;
(iii) m is chosen from 0, 1, 2, and 3;
(iv) n is chosen from 0, 1, and 2; and
(v) Y is divalent ethyl or divalent thiomethyl optionally substituted with at least one group chosen from
fluoro,
methyl, and
hydroxy.
27. The at least one entity of embodiment 1 or 26 chosen from compounds of Formula IIIa:

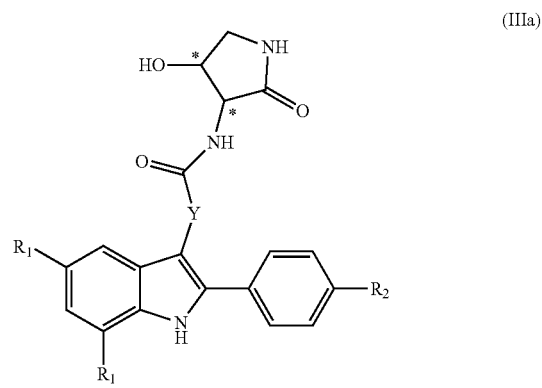

(IIIa)

pharmaceutically acceptable salts thereof, solvates of any of the foregoing, and deuterated derivatives of any of the foregoing, wherein:
(i) each $R_1$ is independently chosen from
fluoro,
chloro,
bromo,
cyano,
methyl,
cyclopropyl,
ethyl,
hydroxypropyl,
isopropyl,
propen-2-yl,
dihydrofuran,
furan, and
methoxy;
(ii) each $R_2$ is independently chosen from
fluoro,
bromo,
cyano, and
methyl; and
(iii) Y is divalent ethyl or divalent thiomethyl optionally substituted with at least one group
chosen from
fluoro,
methyl, and
hydroxy.

28. The at least one entity of embodiment 1 or 26 chosen from compounds of Formula IIIb:

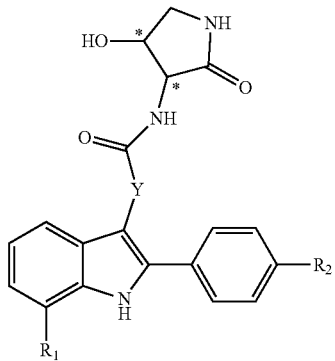

(IIIb)

pharmaceutically acceptable salts thereof, solvates of any of the foregoing, and deuterated derivatives of any of the foregoing, wherein:
(i) each $R_1$ is independently chosen from
fluoro,
chloro,
bromo,
cyano,
methyl,
cyclopropyl,
ethyl,
hydroxypropyl,
isopropyl,
propen-2-yl,
dihydrofuran,
furan, and
methoxy;
(ii) each $R_2$ is independently chosen from
fluoro,
bromo,
cyano, and
methyl; and
(iii) Y is divalent ethyl or divalent thiomethyl optionally substituted with at least one group chosen from
fluoro,
methyl, and
hydroxy.
29. The at least one entity of embodiment 1 or 26 chosen from compounds of Formula IIIc:

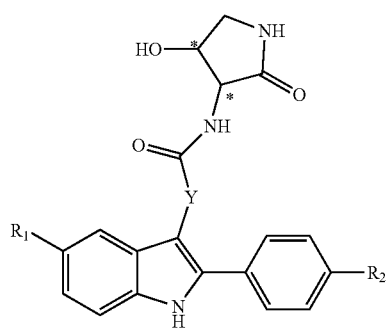

(IIIc)

pharmaceutically acceptable salts thereof, solvates of any of the foregoing, and deuterated derivatives of any of the foregoing, wherein:
(i) each $R_1$ is independently chosen from
fluoro,
chloro,
bromo,
cyano,
methyl,
cyclopropyl,
ethyl,
hydroxypropyl,
isopropyl,
propen-2-yl,
dihydrofuran,
furan, and
methoxy;
(ii) each $R_2$ is independently chosen from
fluoro,
bromo,
cyano, and
methyl; and
(iii) Y is divalent ethyl or divalent thiomethyl optionally substituted with at least one group
chosen from
fluoro,
methyl, and
hydroxy.
30. At least one entity chosen from

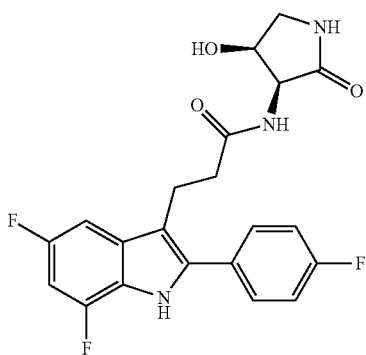

1

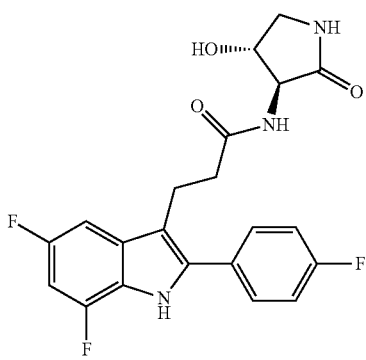

2

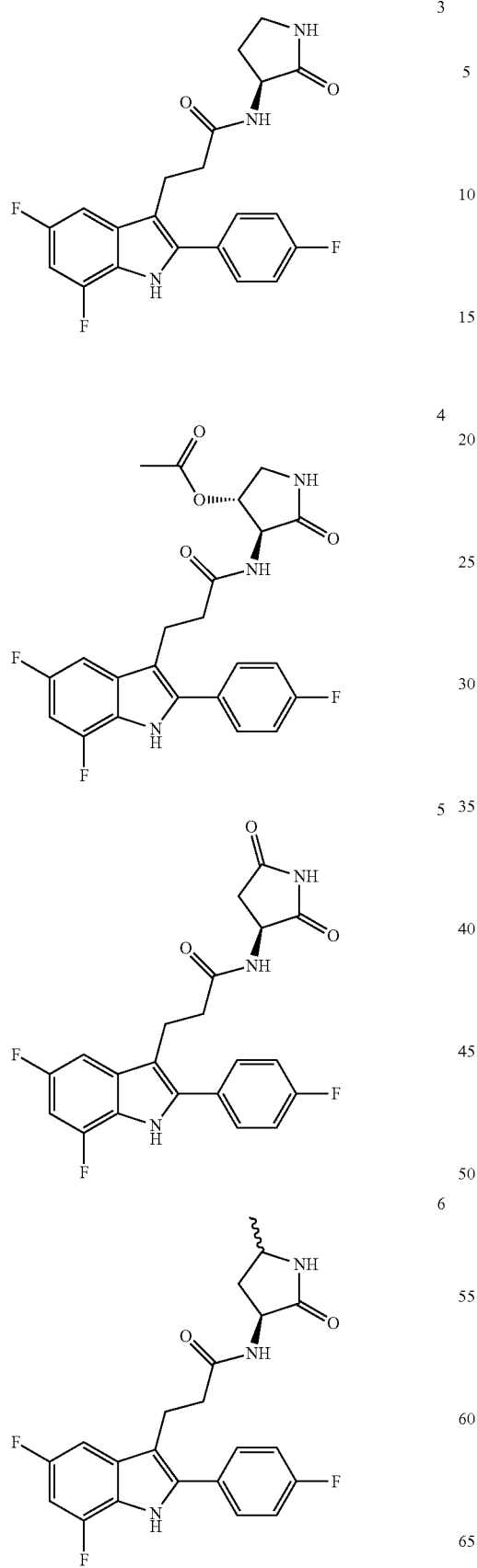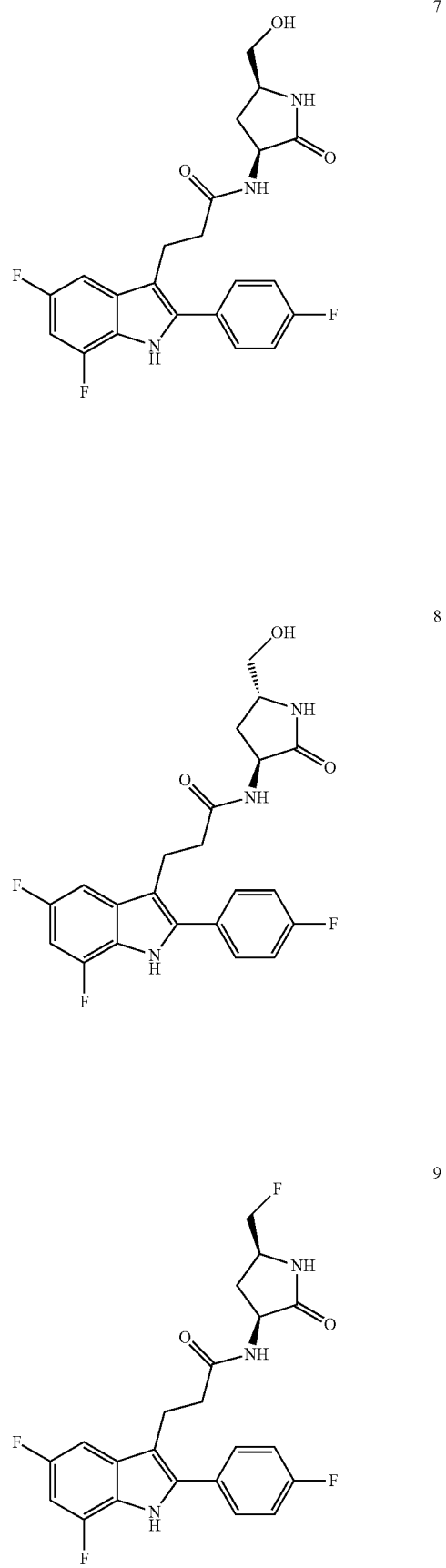

-continued
10 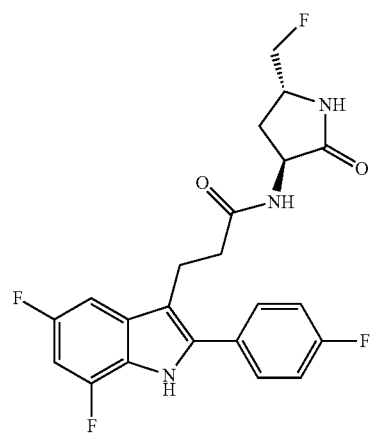
11 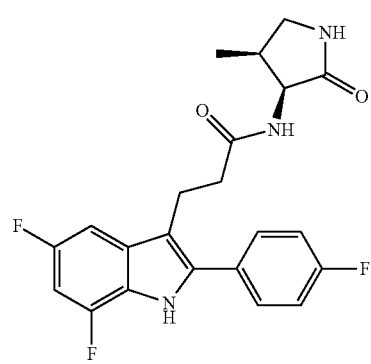
12 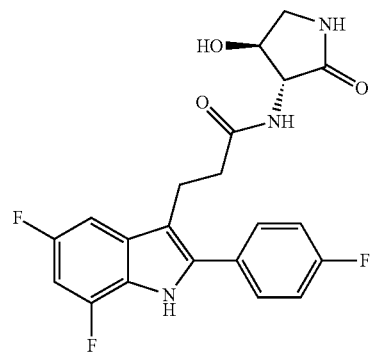
13 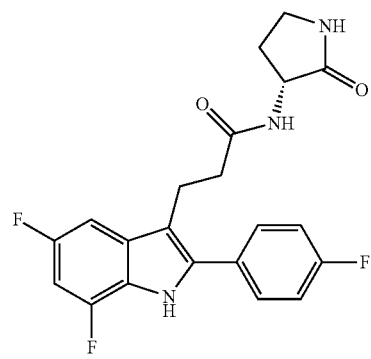
14 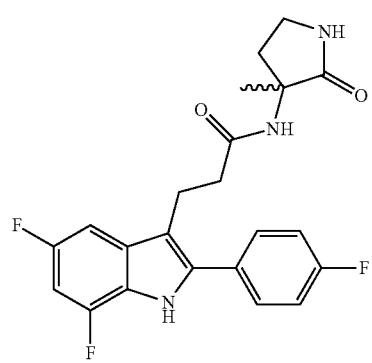
15 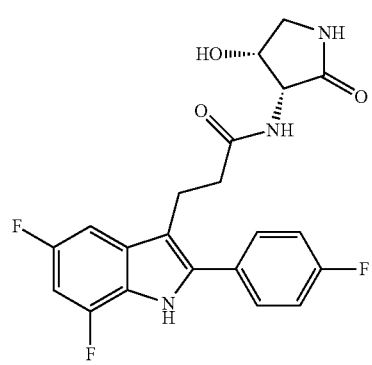
16 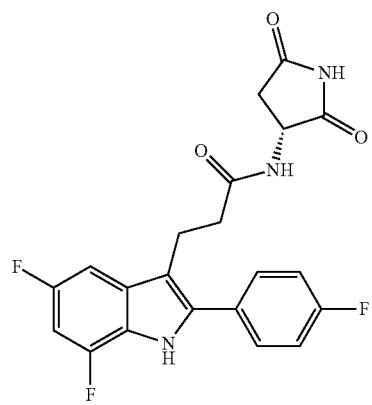
17 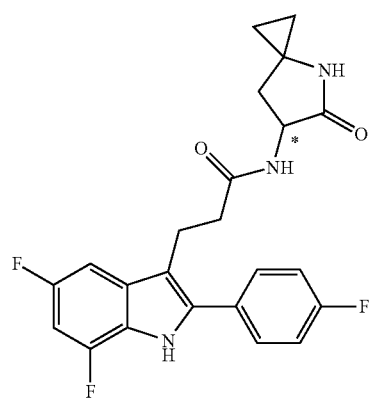

18
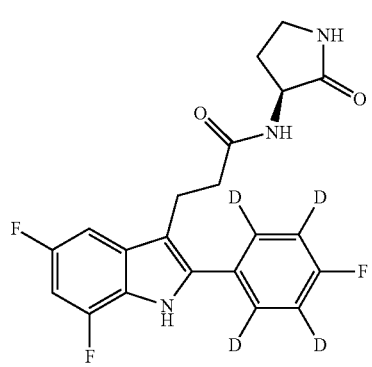
19
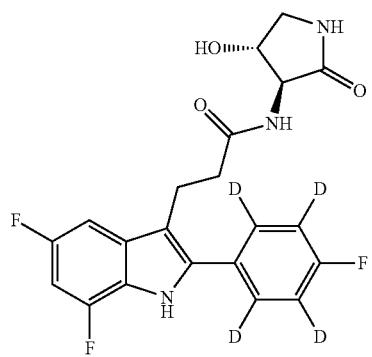
20
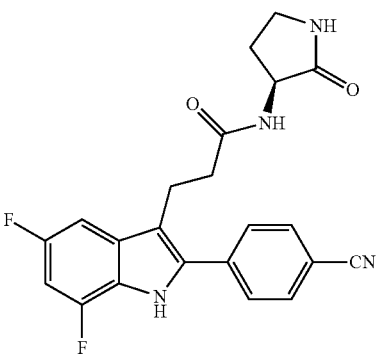
21
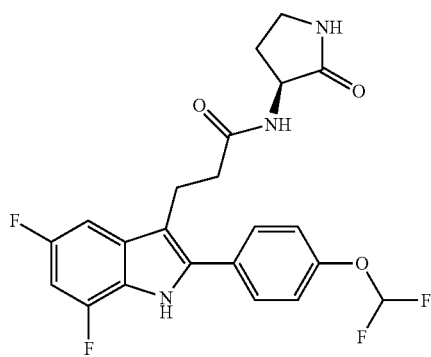
22
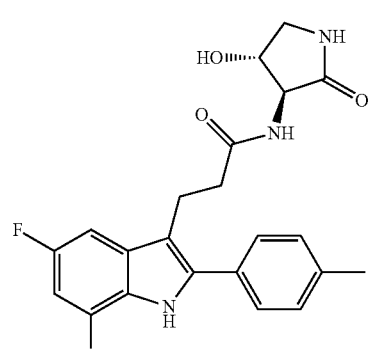
23
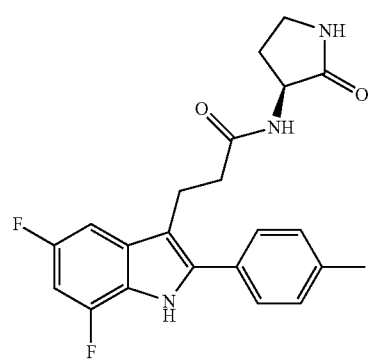
24
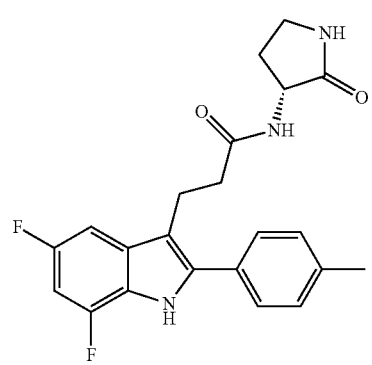
25
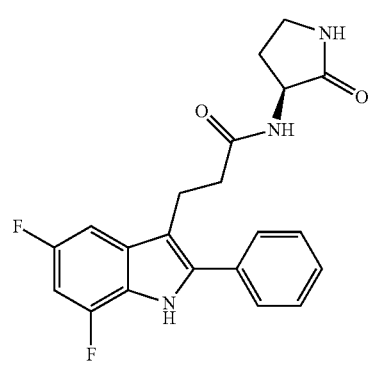

-continued
26
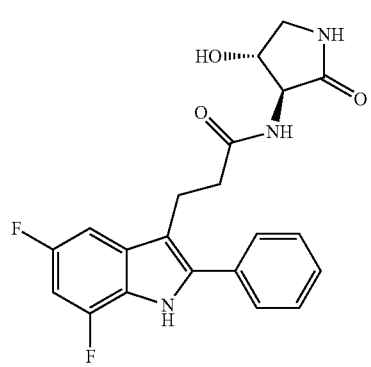
27
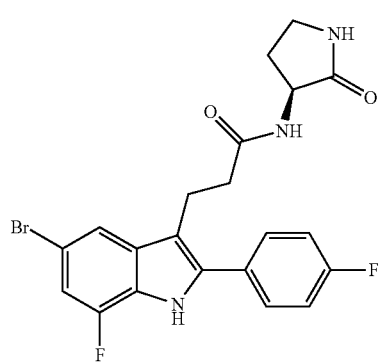
28
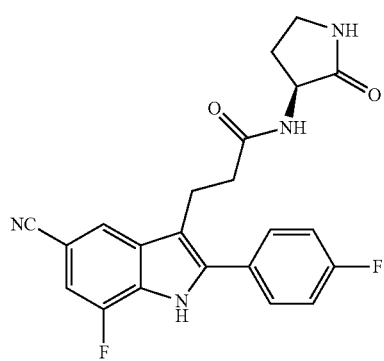
29
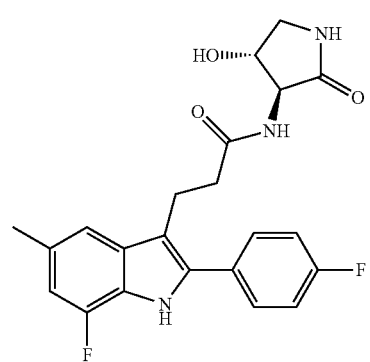
-continued
30
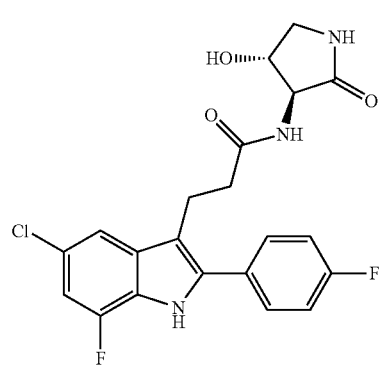
31
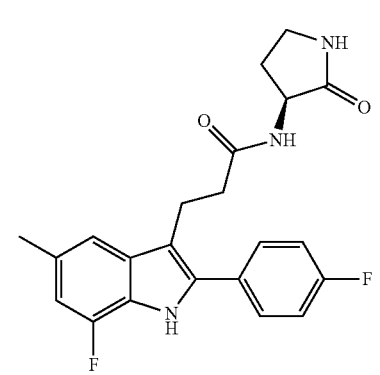
32
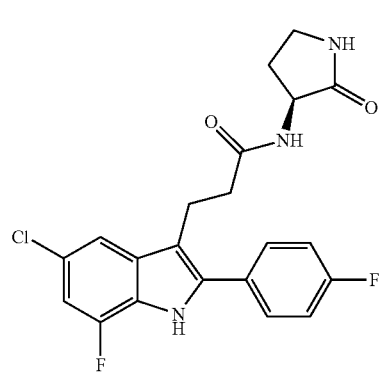
33
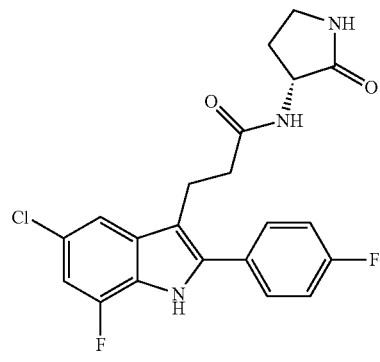

34
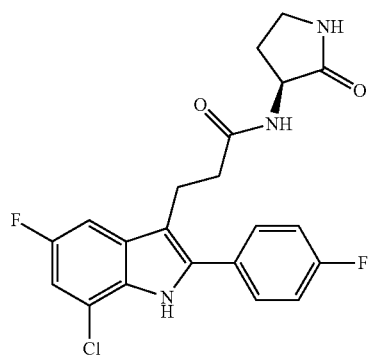
35
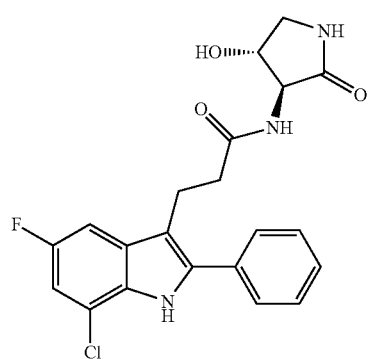
36
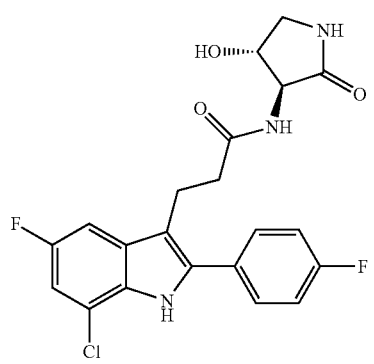
37
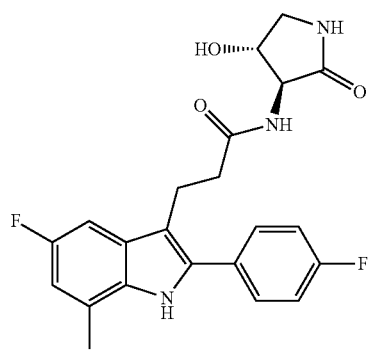
38
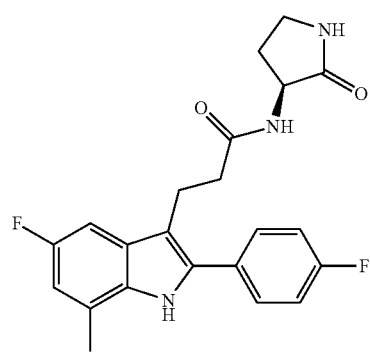
39
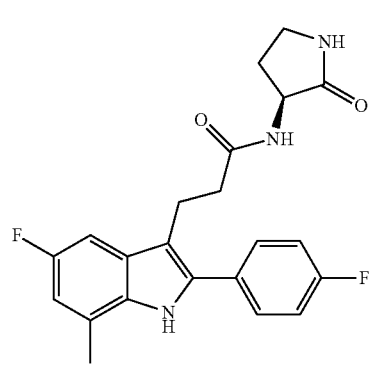
40
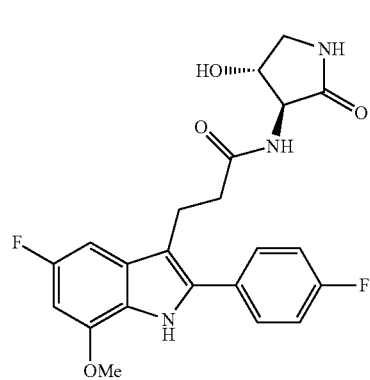
41
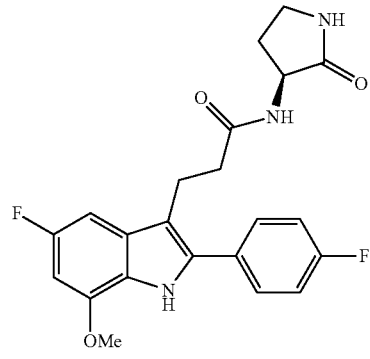

42
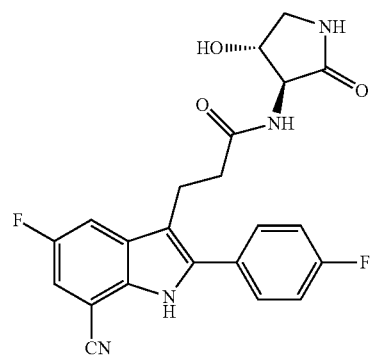
43
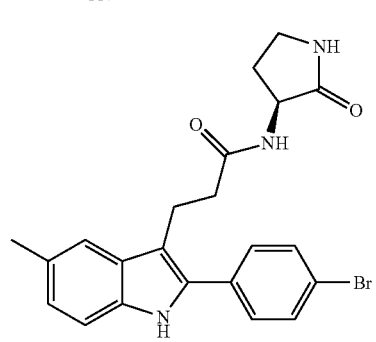
44
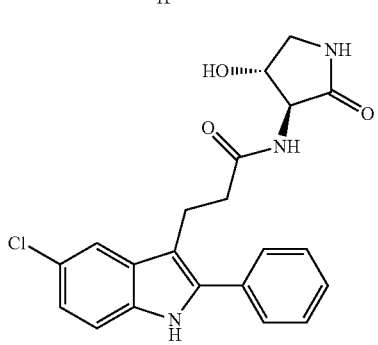
45
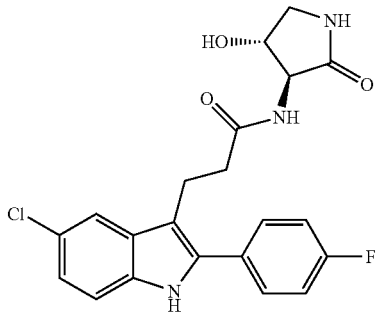
46
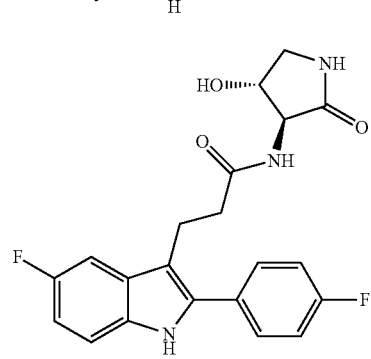
47
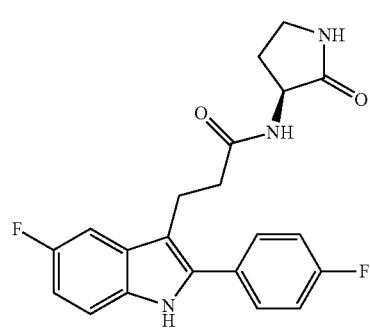
48
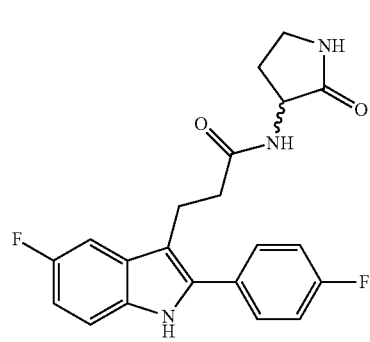
49
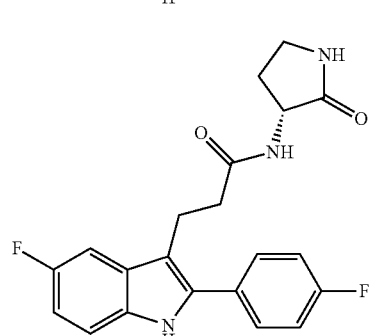
50
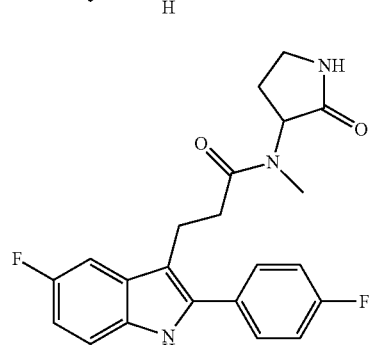
51
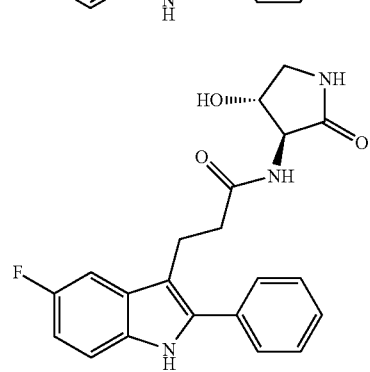

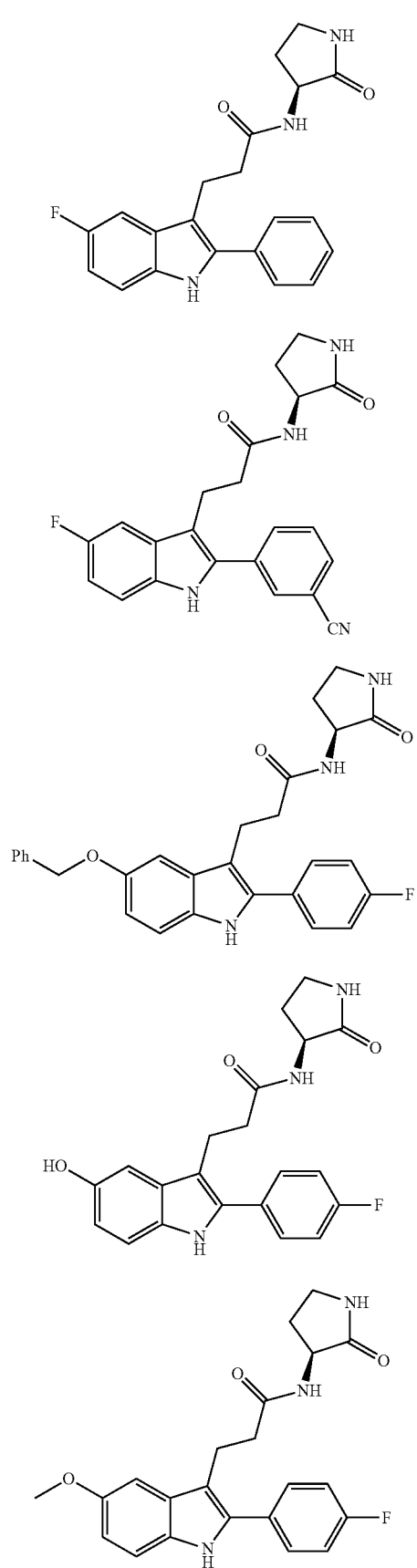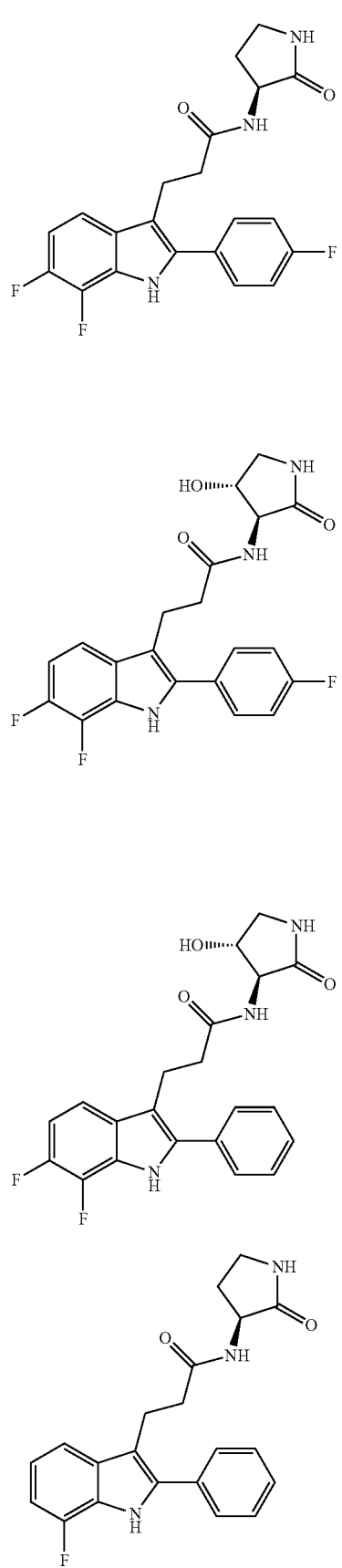

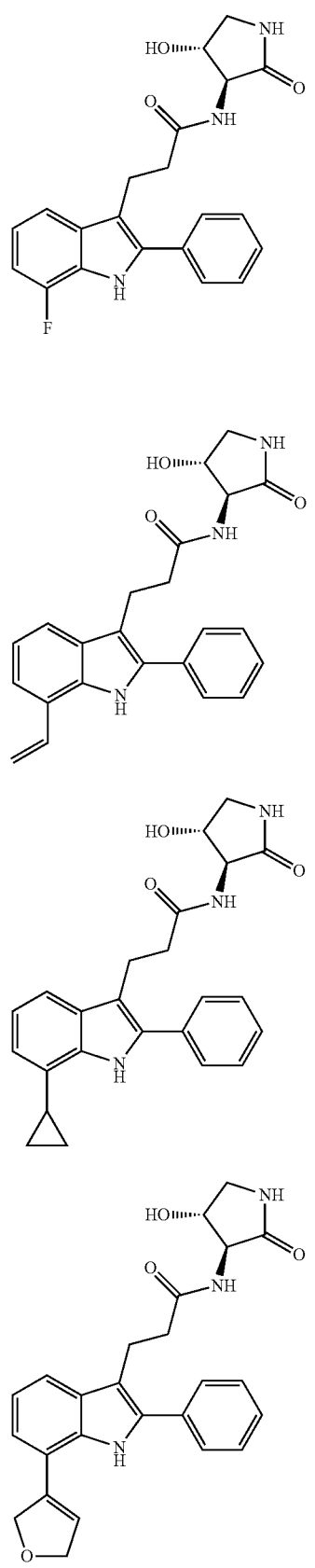
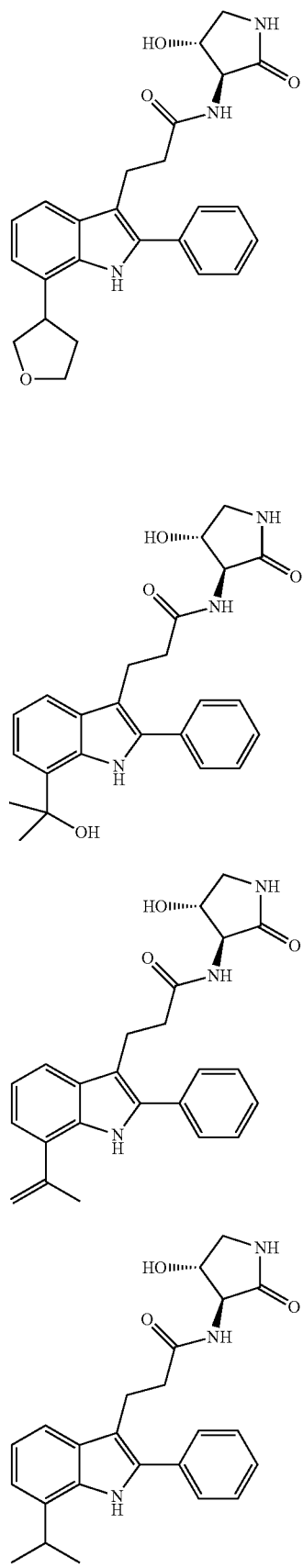

| 69 | 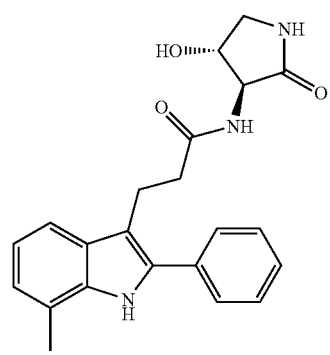 | 73 | 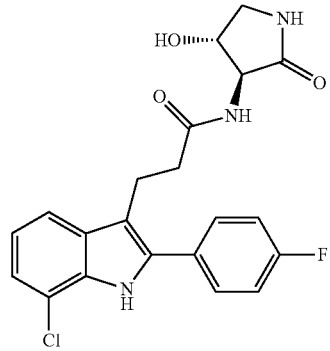 |
| 70 | 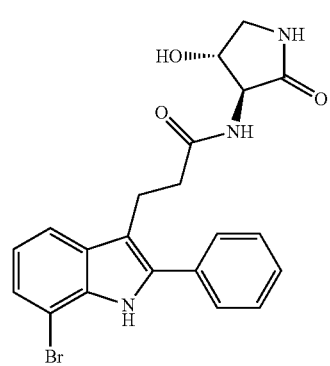 | 74 | 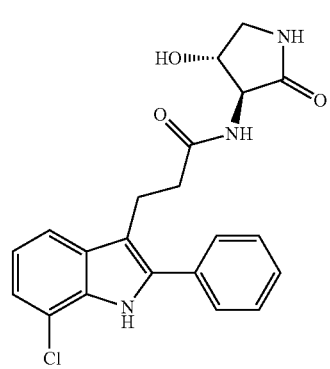 |
| 71 | 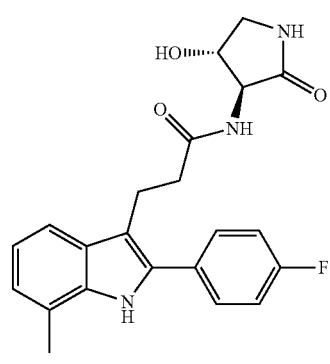 | 75 | 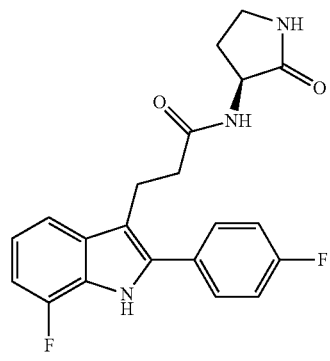 |
| 72 | 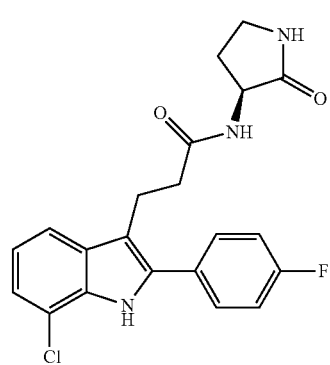 | 76 | 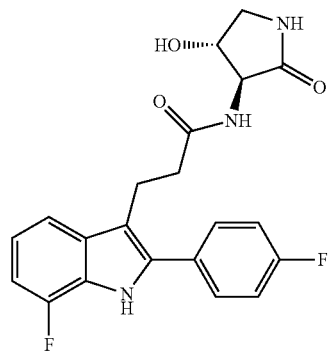 |

-continued
77
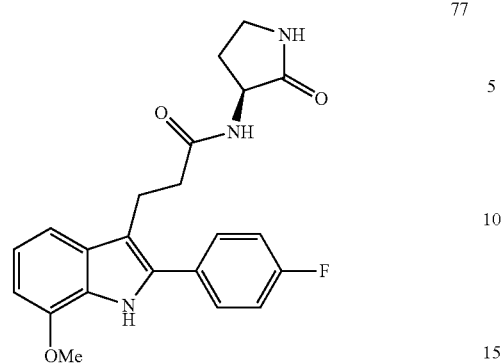
78
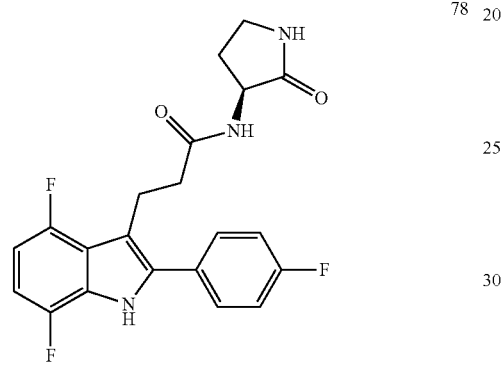
79
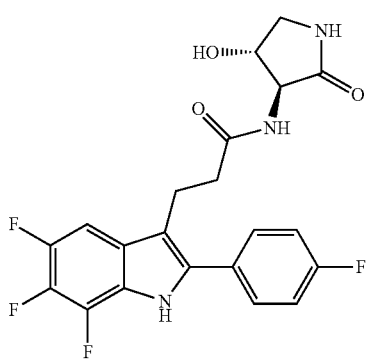
80
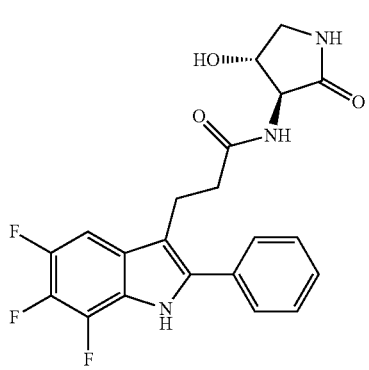
-continued
81
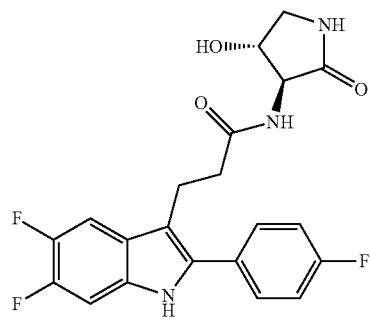
82
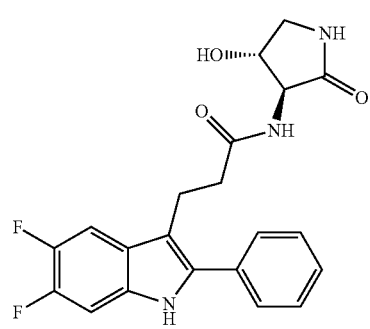
83
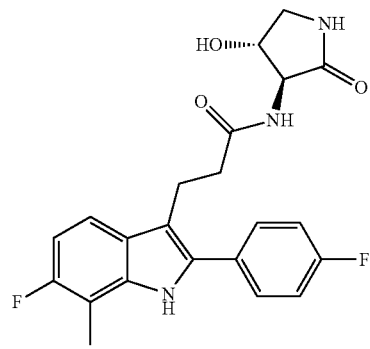
84
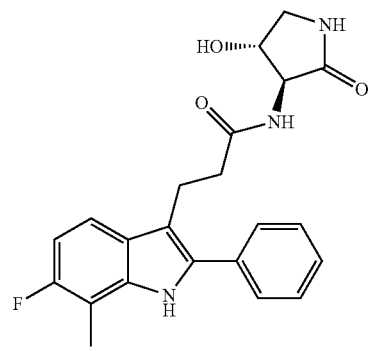

85
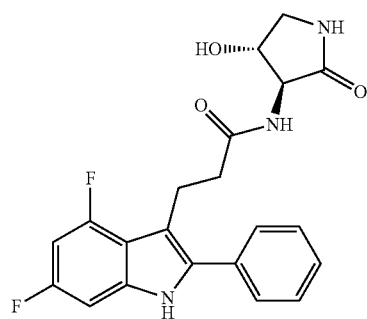
86
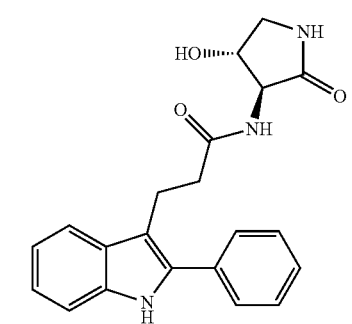
87
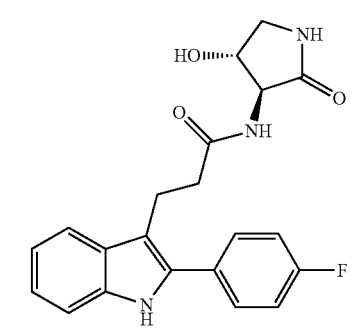
88
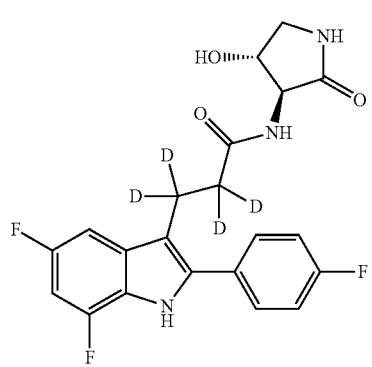
89
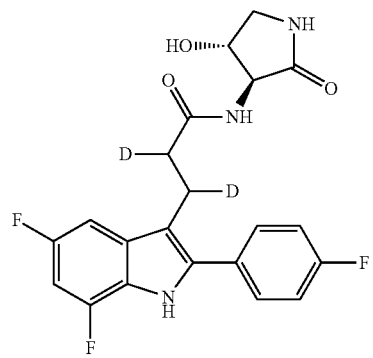
90
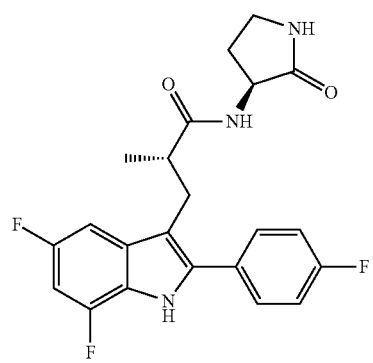
91
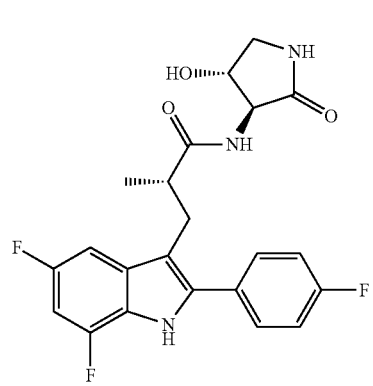
92
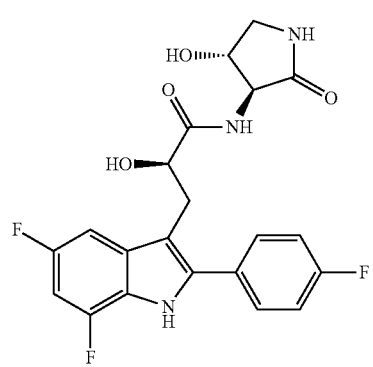

93
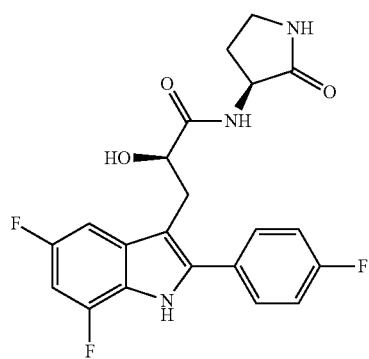
94
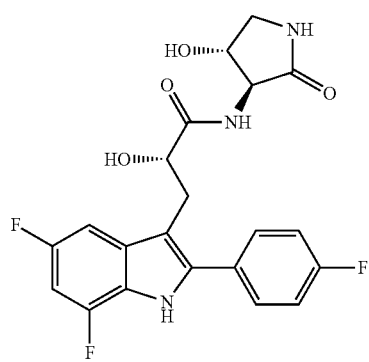
95
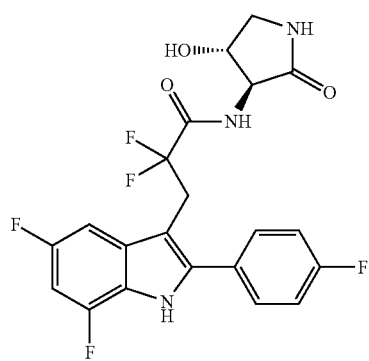
96
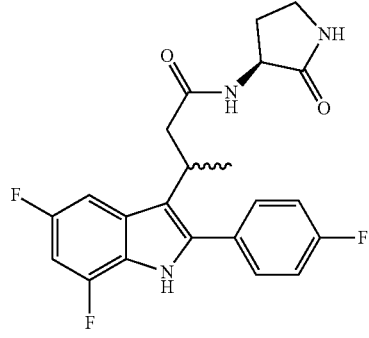
97
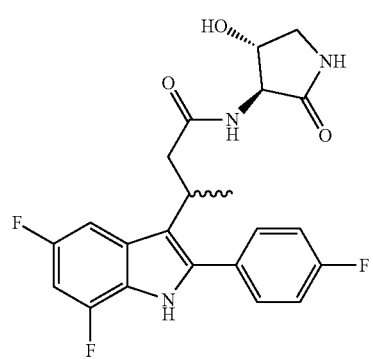
98
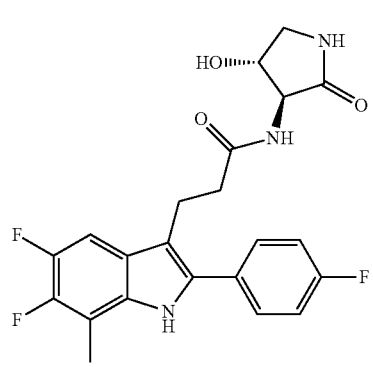
99
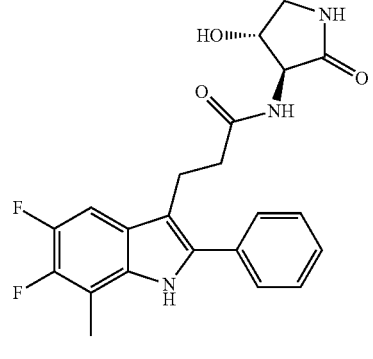
100
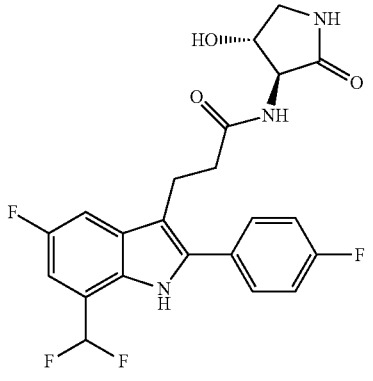

101
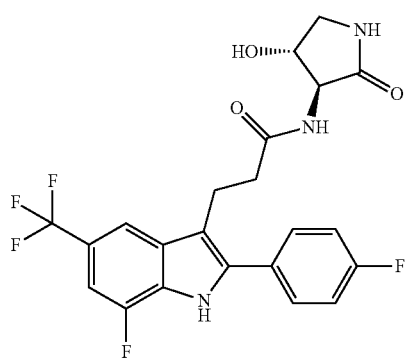
102
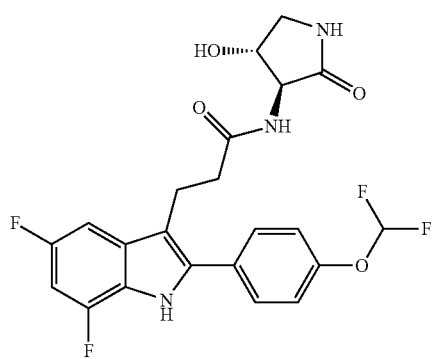
103
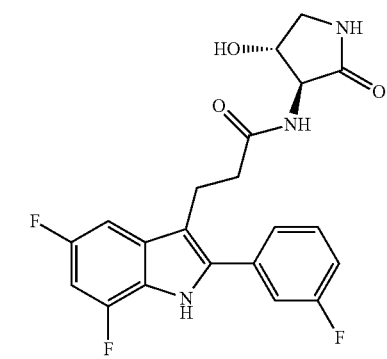
104
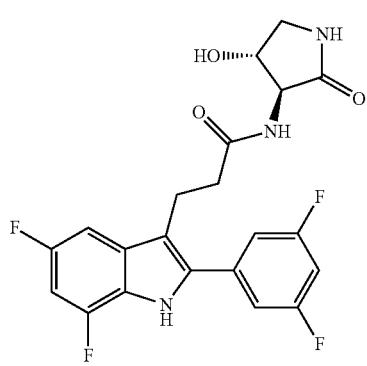
105
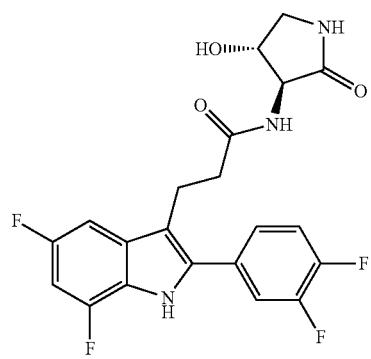
106
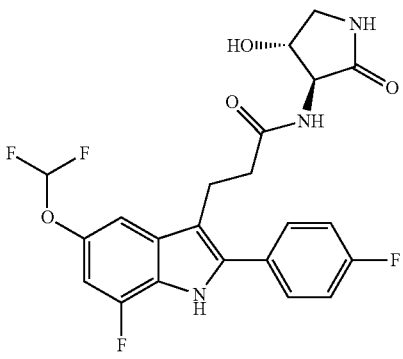
107
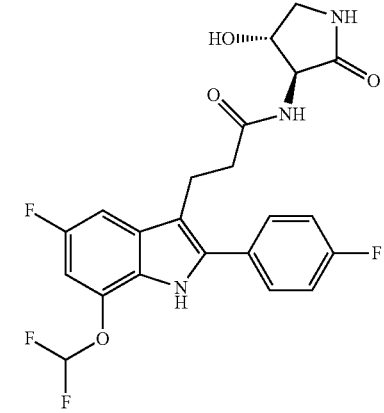
108
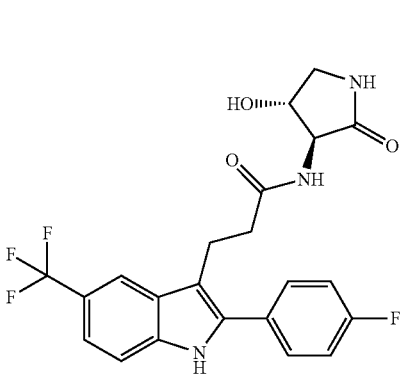

| 109 | 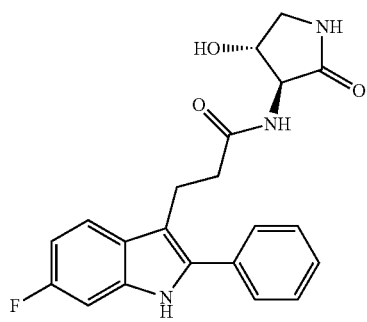 | 113 | 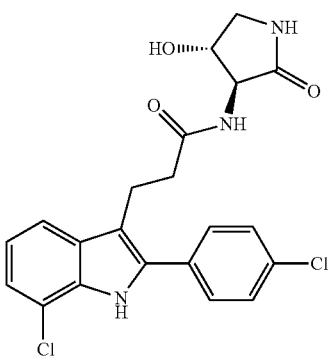 |
| 110 | 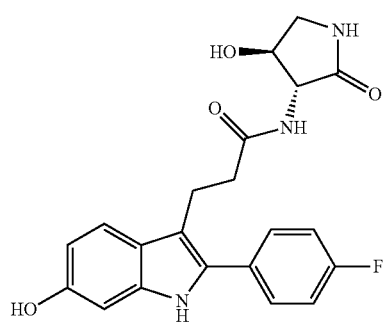 | 114 | 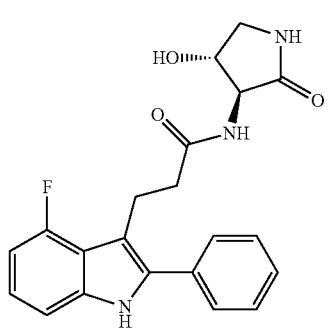 |
| 111 | 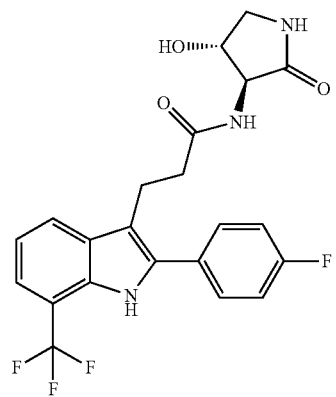 | 115 | 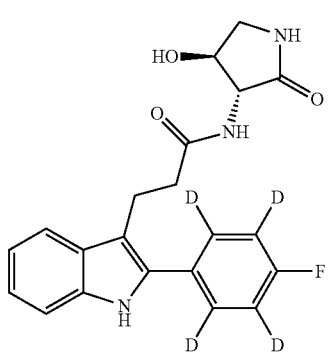 |
| 112 | 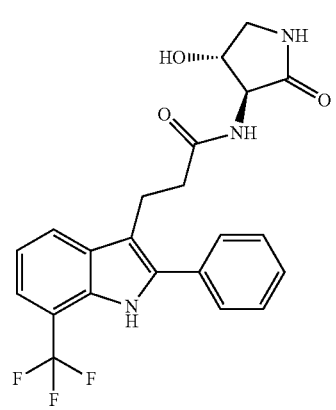 | 116 | 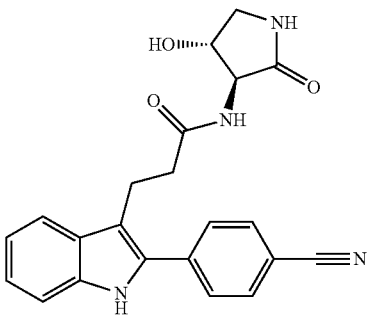 |

117 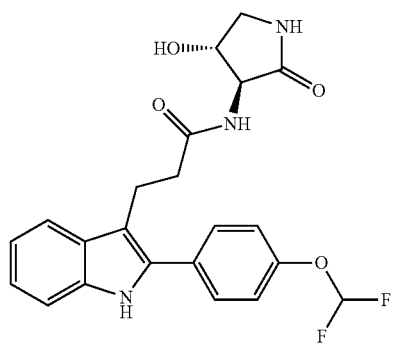
118 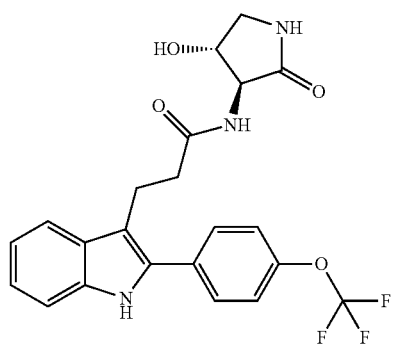
119 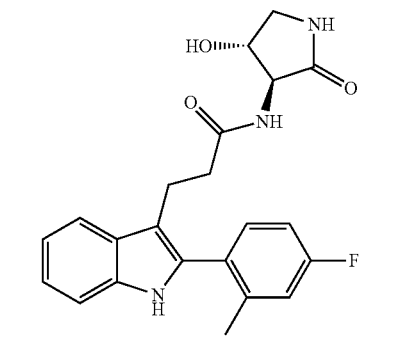
120 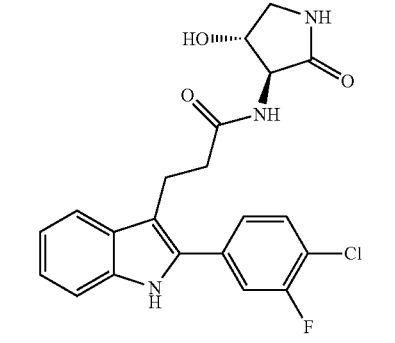
121 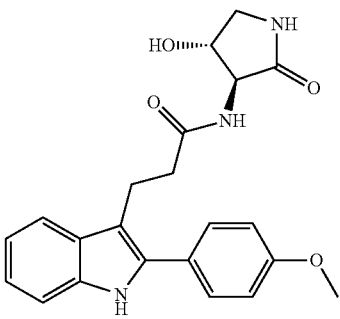
122 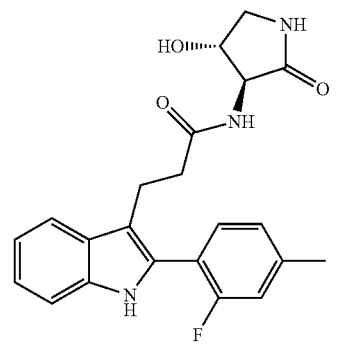
123 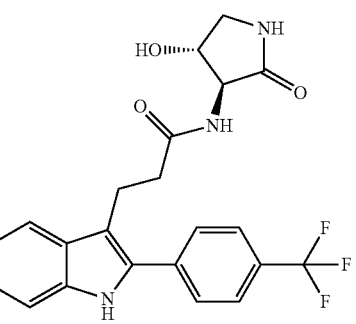
124 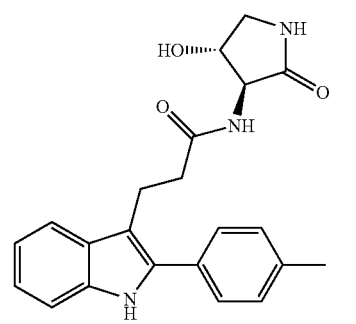
125 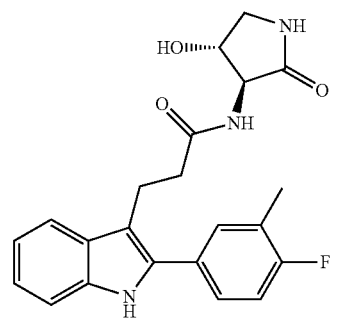

-continued
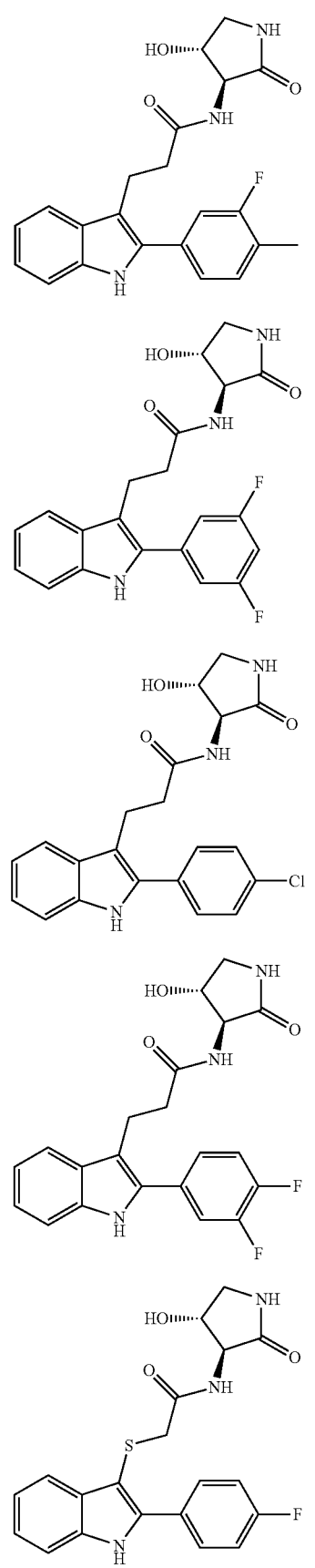
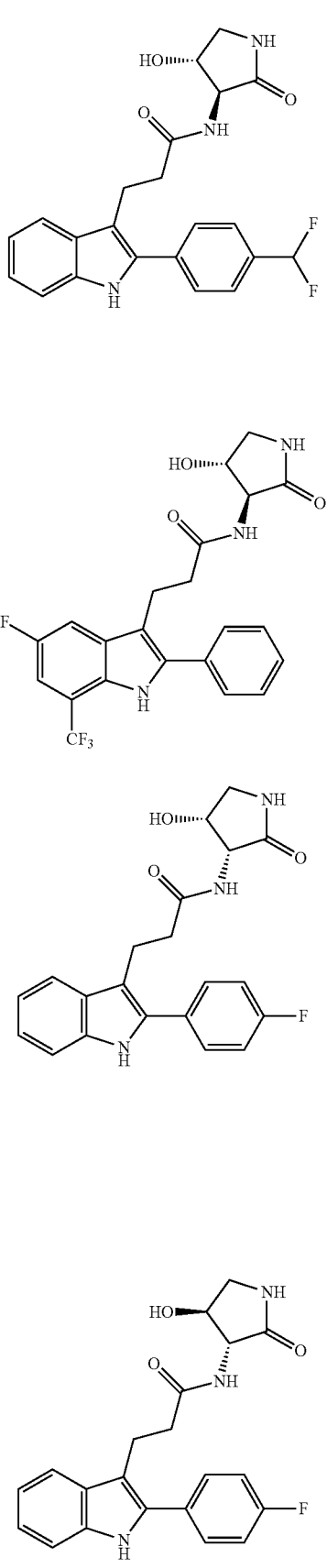

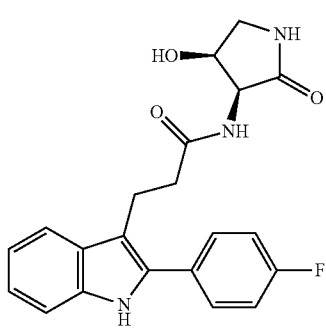

pharmaceutically acceptable salts thereof, solvates of any of the foregoing, and deuterated derivatives of any of the foregoing.

31. A pharmaceutical composition comprising at least one entity according to any one of embodiments 1 to 30 and a pharmaceutically acceptable carrier.
32. A method of treating focal segmental glomerulosclerosis and/or non-diabetic kidney disease comprising administering to a patient in need thereof at least one entity according to any one of embodiments 1 to 30 or a pharmaceutical composition according to embodiment 31.
33. The method according to embodiment 32, wherein the focal segmental glomerulosclerosis and/or non-diabetic kidney disease is associated with APOL1.
34. The method according to embodiment 33, wherein the APOL1 is associated with at least one APOL1 genetic variant chosen from G1: S342G:I384 M and G2: N388del:Y389del.
35. The method according to embodiment 33, wherein the APOL1 is associated with G1: S342G:I384 M and G2: N388del:Y389del.
36. A method of inhibiting APOL1 activity comprising contacting said APOL1 with at least one entity according to any one of embodiments 1 to 30 or a pharmaceutical composition according to embodiment 31.
37. The method according to embodiment 36, wherein the APOL1 is associated with at least one APOL1 genetic variant chosen from G1: S342G:I384 M and G2: N388del:Y389del.
38. The method according to embodiment 36, wherein the APOL1 is associated with G1: S342G:I384 M. The method according to embodiment 36, wherein the APOL1 is associated with G1: S342G:I384 M and G2: N388del:Y389del.
39. A silicon derivative of the at least one entity according to any one of embodiments 1 to 30.
40. A pharmaceutical composition comprising a silicon derivative of embodiment 41.
41. A method of treating focal segmental glomerulosclerosis and/or non-diabetic kidney disease comprising administering to a patient in need thereof a silicon derivative according to embodiment 41 or a pharmaceutical composition according to embodiment 42.
42. A boron derivative of the at least one entity according to any one of embodiments 1 to 30.
43. A pharmaceutical composition comprising a boron derivative of embodiment 44.
44. A method of treating focal segmental glomerulosclerosis and/or non-diabetic kidney disease comprising administering to a patient in need thereof a boron derivative according to embodiment 44 or a pharmaceutical composition according to embodiment 45.
45. A phosphorus derivative of at least one entity according to any one of embodiments 1 to 30.
46. A pharmaceutical composition comprising a phosphorus derivative of embodiment 47.
47. A method of treating focal segmental glomerulosclerosis and/or non-diabetic kidney disease comprising administering to a patient in need thereof a phosphorus derivative according to embodiment 47 or a pharmaceutical composition according to embodiment 48.
48. Form A of Compound 2:

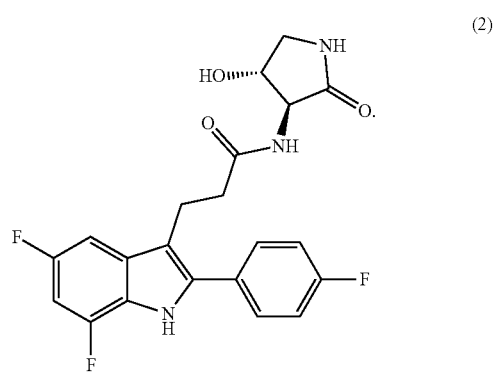 [SMILES: O=C(CCc1c(-c2ccc(F)cc2)[nH]c2c(F)cc(F)cc12)N[C@@H]1C(=O)NC[C@H]1O]

49. Form A according to embodiment 50, characterized by an X-ray powder diffractogram having a signal at at least two two-theta values chosen from 9.5±0.2, 13.2±0.2, 14.4±0.2, 19.2±0.2, 19.5±0.2, 19.8±0.2, 26.3±0.2, 26.7±0.2, and 28.6±0.2.
50. Form A according to embodiment 50, characterized by an X-ray powder diffractogram having a signal at at least two two-theta values chosen from 9.5±0.2, 13.2±0.2, 14.4±0.2, 19.2±0.2, 19.5±0.2, 19.8±0.2, 26.3±0.2, 26.7±0.2, and 28.6±0.2.
51. Form A according to embodiment 50, characterized by an X-ray powder diffractogram having a signal at three two-theta values of 9.5±0.2, 13.2±0.2, and 26.3±0.2.
52. Form A according to embodiment 50, characterized by an X-ray powder diffractogram having a signal at five two-theta values of 9.5±0.2, 13.2±0.2, 19.8±0.2, 26.3±0.2, and 26.7±0.2.
53. Form A of embodiment 50, characterized by an X-ray powder diffractogram substantially similar to that in FIG. 1.
54. Form A of embodiment 50, characterized by a $^{13}$C NMR spectrum having a signal at at least three ppm values chosen from 178.7±0.2 ppm, 154.4±0.2 ppm, 127.8±0.2 ppm, 125.2±0.2 ppm, 102.0±0.2 ppm, 59.3±0.2 ppm, 38.9±0.2 ppm, and 24.4±0.2 ppm.
55. Form A of embodiment 50, characterized by a $^{19}$F NMR spectrum having a signal at at least one ppm value chosen from −116.0±0.2 ppm, −119.7±0.2 ppm, and −138.1±0.2 ppm.
56. Form A of Compound 2 prepared by a process comprising reacting Compound 2 with a 3:1 mixture of 2-propanol/water.

57. Hydrate Form A of Compound 2:

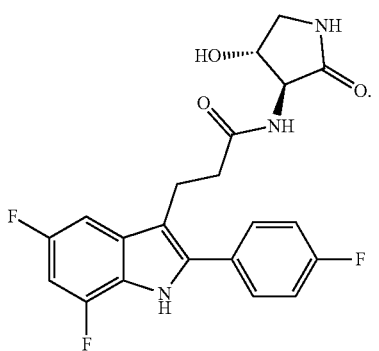

(2)

58. Hydrate Form A according to embodiment 59, characterized by an X-ray powder diffractogram having a signal at at least two two-theta values chosen from 12.2±0.2, 19.0±0.2, 19.1±0.2, 19.6±0.2, 20.2±0.2, 22.7±0.2, 24.2±0.2, 25.4±0.2, and 25.5±0.2.
59. Hydrate Form A according to embodiment 59, characterized by an X-ray powder diffractogram having a signal at at least three two-theta values chosen from 12.2±0.2, 19.0 0.2, 19.1±0.2, 19.6±0.2, 20.2±0.2, 22.7±0.2, 24.2±0.2, 25.4±0.2, and 25.5±0.2.
60. Hydrate Form A according to embodiment 59, characterized by an X-ray powder diffractogram having a signal at three two-theta values of 19.6±0.2, 24.2±0.2, and 25.5±0.2.
61. Hydrate Form A according to embodiment 59, characterized by an X-ray powder diffractogram having a signal at five two-theta values of 12.2±0.2, 19.6±0.2, 24.2±0.2, 25.4±0.2, and 25.5±0.2.
62. Hydrate Form A of embodiment 59, characterized by an X-ray powder diffractogram substantially similar to that in FIG. 7.
63. Hydrate Form A of embodiment 59, characterized by a $^{13}$C NMR spectrum having a signal at at least three ppm values chosen from 177.5±0.2 ppm, 157.7±0.2 ppm, 128.9±0.2 ppm, 95.4±0.2 ppm, 36.9±0.2 ppm, 23.0±0.2 ppm, and 22.3±0.2 ppm.
64. Hydrate Form A of embodiment 59, characterized by a $^{19}$F NMR spectrum having a signal at at least one ppm value chosen from −113.8±0.2 ppm, −125.8±0.2 ppm, and −132.8±0.2 ppm.
65. Hydrate Form A of Compound 2 prepared by a process comprising reacting Compound 2 with water.
66. Hydrate Form B of Compound 2:

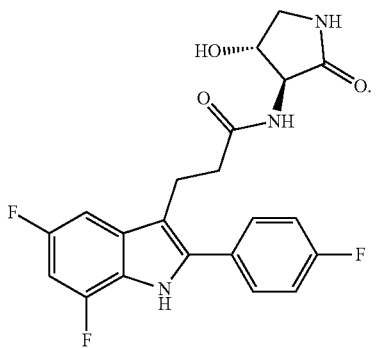

(2)

67. Hydrate Form B according to embodiment 68, characterized by an X-ray powder diffractogram having a signal at at least two two-theta values chosen from 3.8±0.2, 9.0±0.2, 9.3±0.2, 18.7±0.2, 19.1±0.2, 20.8±0.2, 21.1±0.2, 24.6±0.2, and 26.8±0.2.
68. Hydrate Form B according to embodiment 68, characterized by an X-ray powder diffractogram having a signal at at least three two-theta values chosen from 3.8±0.2, 9.0±0.2, 9.3±0.2, 18.7±0.2, 19.1±0.2, 20.8±0.2, 21.1±0.2, 24.6±0.2, and 26.8±0.2.
69. Hydrate Form B according to embodiment 68, characterized by an X-ray powder diffractogram having a signal at three two-theta values of 9.0±0.2, 20.8±0.2, and 21.1±0.2.
70. Hydrate Form B according to embodiment 68, characterized by an X-ray powder diffractogram having a signal at five two-theta values of 9.0±0.2, 9.3±0.2, 18.7±0.2, 20.8±0.2, and 21.1±0.2.
71. Hydrate Form B according to embodiment 68, characterized by an X-ray powder diffractogram substantially similar to that in FIG. 12.
72. Hydrate Form B according to embodiment 68, characterized by a $^{19}$F NMR spectrum having a signal at at least one ppm value chosen from −117.0±0.2 ppm, −119.1±0.2 ppm, and −137.7±0.2 ppm.
73. Hydrate Form B of Compound 2 prepared by a process comprising reacting Compound 2 with water.
74. Hydrate Form C of Compound 2:

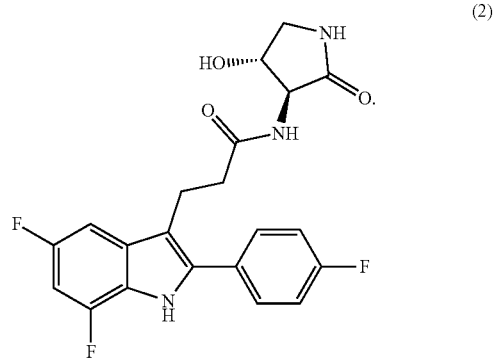 [SMILES: O=C(CCc1c(-c2ccc(F)cc2)[nH]c2c(F)cc(F)cc12)N[C@@H]1C(=O)NC[C@H]1O]

(2)

75. Hydrate Form C according to embodiment 76, characterized by an X-ray powder diffractogram having a signal at at least two two-theta values chosen from 3.7±0.2, 10.4±0.2, 10.7±0.2, 13.2±0.2, 14.6±0.2, 15.7±0.2, 18.3±0.2, 21.8±0.2, and 24.9±0.2.
76. Hydrate Form C according to embodiment 76, characterized by an X-ray powder diffractogram having a signal at at least three two-theta values chosen from 3.7±0.2, 10.4±0.2, 10.7±0.2, 13.2±0.2, 14.6±0.2, 15.7±0.2, 18.3±0.2, 21.8±0.2, and 24.9±0.2.
77. Hydrate Form C according to embodiment 76, characterized by an X-ray powder diffractogram having a signal at three two-theta values of 10.7±0.2, 13.2±0.2, and 24.9±0.2.
78. Hydrate Form C according to embodiment 76, characterized by an X-ray powder diffractogram having a signal at five two-theta values of 10.7±0.2, 13.2±0.2, 14.6±0.2, 21.8±0.2, and 24.9±0.2.
79. Hydrate Form C according to embodiment 76, characterized by an X-ray powder diffractogram substantially similar to that in FIG. 14.

80. Hydrate Form C according to embodiment 76, characterized by a $^{13}C$ NMR spectrum having a signal at at least three ppm values chosen from 178.2±0.2 ppm, 127.2±0.2 ppm, 116.9±0.2 ppm, 71.6±0.2 ppm, 57.6±0.2 ppm, 49.6±0.2 ppm, 35.5±0.2 ppm, and 20.0±0.2 ppm.

81. Hydrate Form C according to embodiment 76, characterized by a $^{19}F$ NMR spectrum having a signal at at least one ppm value chosen from −109.9±0.2 ppm, −111.5±0.2 ppm, −113.0±0.2, −120.9±0.2, −121.8±0.2 and −123.4±0.2 ppm.

82. Hydrate Form C of compound 2 prepared by a process comprising reacting Compound 2 with methanol and water.

83. Hydrate Form D of Compound 2:

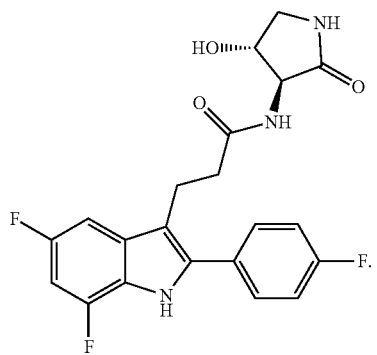

(2)

84. Hydrate Form D according to embodiment 85, characterized by an X-ray powder diffractogram having a signal at at least two two-theta values chosen from 4.1±0.2, 5.0±0.2, 7.6±0.2, 7.7±0.2, 8.2±0.2, 15.2±0.2, 15.5±0.2, 16.5±0.2, and 19.0±0.2.

85. Hydrate Form D according to embodiment 85, characterized by an X-ray powder diffractogram having a signal at at least three two-theta values chosen from 4.1±0.2, 5.0±0.2, 7.6±0.2, 7.7±0.2, 8.2±0.2, 15.2±0.2, 15.5±0.2, 16.5±0.2, and 19.0±0.2.

86. Hydrate Form D according to embodiment 85, characterized by an X-ray powder diffractogram having a signal at three two-theta values of 4.1±0.2, 5.0±0.2, and 8.2±0.2.

87. Hydrate Form D according to embodiment 85, characterized by an X-ray powder diffractogram having a signal at five two-theta values of 4.1±0.2, 5.0±0.2, 7.7±0.2, 8.2±0.2, and 15.2±0.2.

88. Hydrate Form D according to embodiment 85, characterized by an X-ray powder diffractogram substantially similar to that in FIG. 19.

89. Hydrate Form D of Compound 2 prepared by a process comprising suspending Compound 2 in ethanol for 2-5 days at 50° C.

90. Hydrate Form E of Compound 2:

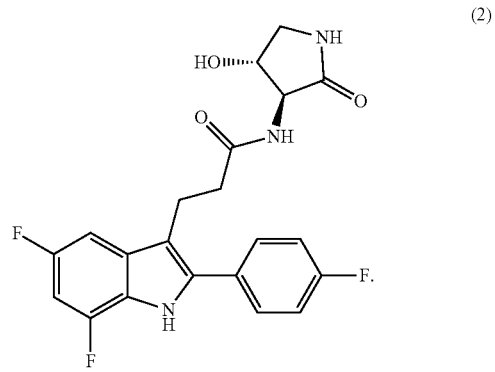 [SMILES: O=C(CCc1c(-c2ccc(F)cc2)[nH]c2c(F)cc(F)cc12)N[C@@H]1C(=O)NC[C@H]1O]

(2)

91. Hydrate Form E according to embodiment 92, characterized by an X-ray powder diffractogram having a signal at at least two two-theta values chosen from 6.5±0.2, 7.7±0.2, 11.4±0.2, 14.3±0.2, and 18.9±0.2.

92. Hydrate Form E according to embodiment 92, characterized by an X-ray powder diffractogram having a signal at at least three two-theta values chosen from 6.5±0.2, 7.7±0.2, 11.4±0.2, 11.8±0.2, 12.8±0.2, 14.3±0.2, 15.8±0.2, 16.4±0.2, 18.9±0.2, and 22.1±0.2.

93. Hydrate Form E according to embodiment 92, characterized by an X-ray powder diffractogram having a signal at three two-theta values chosen from 6.5±0.2, 7.7±0.2, 11.4±0.2, 11.8±0.2, 12.8±0.2, 14.3±0.2, 15.8±0.2, 16.4±0.2, 18.9±0.2, and 22.1±0.2.

94. Hydrate Form E according to embodiment 92, characterized by an X-ray powder diffractogram having a signal at five two-theta values chosen from 6.5±0.2, 7.7±0.2, 11.4±0.2, 11.8±0.2, 12.8±0.2, 14.3±0.2, 15.8±0.2, 16.4±0.2, 18.9±0.2, and 22.1±0.2.

95. Hydrate Form E according to embodiment 92, characterized by an X-ray powder diffractogram substantially similar to that in FIG. 22.

96. Hydrate Form E of Compound 2 prepared by a process comprising evaporating a solution of Compound 2 in methanol.

97. Hydrate Form F of Compound 2:

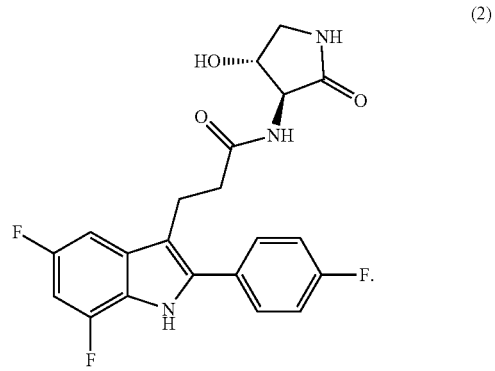 [SMILES: O=C(CCc1c(-c2ccc(F)cc2)[nH]c2c(F)cc(F)cc12)N[C@@H]1C(=O)NC[C@H]1O]

(2)

98. Hydrate Form F according to embodiment 99, characterized by an X-ray powder diffractogram having a signal at at least two two-theta values chosen from 3.8±0.2, 7.6±0.2, and 11.4±0.2.

99. Hydrate Form F according to embodiment 99, characterized by an X-ray powder diffractogram having a signal at at least three two-theta values chosen from 3.8±0.2, 7.6±0.2, and 11.4±0.2.

100. Hydrate Form F of Compound 2 prepared by a process comprising precipitating Compound 2 from acetonitrile.

101. MTBE solvate of Compound 2:

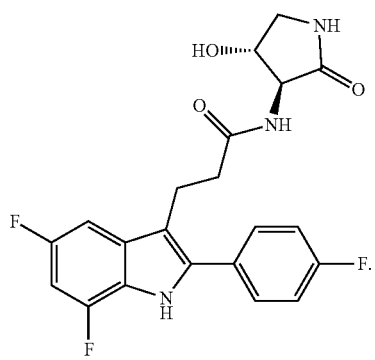
(2)

102. DMF solvate of Compound 2:

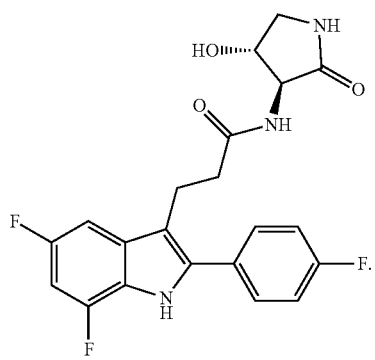
(2)

103. Amorphous form of Compound 2:

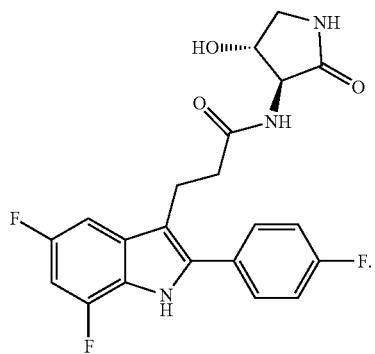
(2)

104. Amorphous form according to embodiment 105, characterized by a $^{13}$C NMR spectrum having a signal at at least three ppm values chosen from 174.7±0.2 ppm, 161.3±0.2 ppm, 130.2±0.2 ppm, 120.9±0.2 ppm, 74.7±0.2 ppm, and 20.5±0.2 ppm.

105. Amorphous form according to embodiment 105, characterized by a $^{19}$F NMR spectrum having a signal at at least one ppm value chosen from −122.4±0.2 ppm and −131.1±0.2 ppm.

106. Form A of Compound 87:

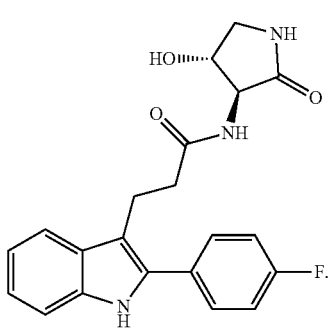
(87)

107. Form A of Compound 87 according to embodiment 108, characterized by an X-ray powder diffractogram substantially similar to that in FIG. 38.

108. Form A of Compound 87 according to embodiment 108, characterized by an X-ray powder diffractogram having a signal at at least two two-theta values chosen from 4.7±0.2, 9.0±0.2, 14.2±0.2, 16.7±0.2, 21.0±0.2, 21.2±0.2, 22.9±0.2, 23.1±0.2, and 24.5±0.2.

109. Form A of Compound 87 according to embodiment 108, characterized by an X-ray powder diffractogram having a signal at at least three two-theta values chosen from 4.7±0.2, 9.0±0.2, 14.2±0.2, 16.7±0.2, 21.0±0.2, 21.2±0.2, 22.9±0.2, 23.1±0.2, and 24.5±0.2.

110. Form A of Compound 87 according to embodiment 108, characterized by an X-ray powder diffractogram having a signal at three two-theta 4.7±0.2, 9.0±0.2, 14.2±0.2, 16.7±0.2, 17.5±0.2, 21.0±0.2, 21.2±0.2, 22.1±0.2, and 23.1±0.2.

111. Form A of Compound 87 according to embodiment 108, characterized by an X-ray powder diffractogram having a signal at five two-theta values of 9.0±0.2, 14.2±0.2, 17.5±0.2, 21.0±0.2, and 21.2±0.2.

112. Form A of Compound 87 according to embodiment 108, characterized by a $^{13}$C NMR spectrum having a signal at at least three ppm values chosen from 128.3±0.2 ppm, 122.0±0.2 ppm, 58.4±0.2 ppm, and 38.4±0.2 ppm.

113. Form A of Compound 87 according to embodiment 108, characterized by a $^{19}$F NMR spectrum having a signal at a ppm value of −110.9±0.2 ppm.

114. Form A of Compound 87 prepared by a process comprising reacting Compound 87 with a mixture of 2-propanol/water.

115. A composition comprising Form A of Compound 87 according to embodiment 108.

116. Hydrate Form of Compound 87:

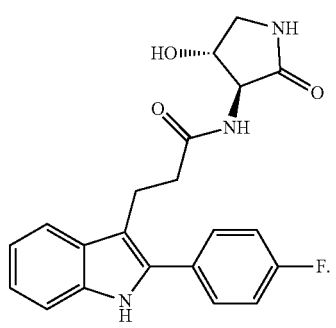
(87)

117. Hydrate Form of Compound 87 according to embodiment 118, characterized by an X-ray powder diffractogram substantially similar to that in FIG. 43.
118. Hydrate Form of Compound 87 according to embodiment 118, characterized by an X-ray powder diffractogram having a signal at at least two two-theta values chosen from 9.3±0.2, 10.0±0.2, 10.9±0.2, 12.1±0.2, 20.0±0.2, 20.5±0.2, 20.8±0.2, 21.3±0.2, and 24.8±0.2.
119. Hydrate Form of Compound 87 according to embodiment 118, characterized by an X-ray powder diffractogram having a signal at at least three two-theta values chosen from 9.3±0.2, 10.0±0.2, 10.9±0.2, 12.1±0.2, 20.0±0.2, 20.5±0.2, 20.8±0.2, 21.3±0.2, and 24.8±0.2.
120. Hydrate Form of Compound 87 according to embodiment 101, characterized by an X-ray powder diffractogram having a signal at three two-theta 9.3±0.2, 10.0±0.2, 10.9±0.2, 12.1±0.2, 20.0±0.2, 20.5±0.2, 20.8±0.2, 21.3±0.2, and 24.8±0.2.
121. Hydrate Form of Compound 87 according to embodiment 118, characterized by an X-ray powder diffractogram having a signal at five two-theta values 9.3±0.2, 10.9±0.2, 12.1±0.2, 21.3±0.2, and 24.8±0.2.
122. Hydrate Form of Compound 87 according to embodiment 118, characterized by a 3C NMR spectrum having a signal at at least three ppm values chosen from 133.5±0.2 ppm, 119.8±0.2 ppm, 74.2±0.2 ppm, 56.4±0.2 ppm, and 18.7±0.2 ppm.
123. Hydrate Form of Compound 87 according to embodiment 118, characterized by a 9F NMR spectrum having a signal at a ppm value of −113.6±0.2 ppm.
124. A composition comprising Hydrate Form according to claim 118.
125. IPAc Solvate Form of Compound 87:

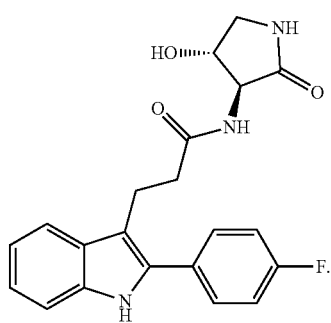
(87)

126. IPAc Solvate Form of Compound 87 according to embodiment 127, characterized by an X-ray powder diffractogram substantially similar to that in FIG. 49.
127. IPAc Solvate Form of Compound 87 according to embodiment 127, characterized by an X-ray powder diffractogram having a signal at at least two two-theta values chosen from 5.0±0.2, 9.9±0.2, 11.5±0.2, 11.7±0.2, 12.0±0.2, 16.0±0.2, 18.8±0.2, 22.0±0.2, and 23.1±0.2.
128. IPAc Solvate Form of Compound 87 according to embodiment 127, characterized by an X-ray powder diffractogram having a signal at at least three two-theta values chosen from 5.0±0.2, 9.9±0.2, 11.5±0.2, 11.7±0.2, 12.0±0.2, 16.0±0.2, 18.8±0.2, 22.0±0.2, and 23.1±0.2.
129. IPAc Solvate Form of Compound 87 according to embodiment 127, characterized by an X-ray powder diffractogram having a signal at three two-theta values 5.0±0.2, 11.5±0.2, and 18.8±0.2.
130. IPAc Solvate Form of Compound 87 according to embodiment 127, characterized by an X-ray powder diffractogram having a signal at five two-theta values 5.0±0.2, 11.5±0.2, 12.5 0.2, 13.1±0.2, and 18.8±0.2.
131. IPAc Solvate Form of Compound 87 according to embodiment 127, characterized by a $^{13}C$ NMR spectrum having a signal at at least three ppm values chosen from 178.3±0.2 ppm, 178.0±0.2 ppm, 177.5±0.2 ppm, 173.2±0.2 ppm, 171.5±0.2 ppm, 138.1±0.2 ppm, 137.9±0.2 ppm, 135.9±0.2 ppm, 132.2±0.2 ppm, 131.4±0.2 ppm, 119.1±0.2 ppm, 118.7±0.2 ppm, 109.8±0.2 ppm, 108.9±0.2 ppm, 107.4±0.2 ppm, 77.1±0.2 ppm, 76.8±0.2 ppm, 76.0±0.2 ppm, 68.5±0.2 ppm, 33.9±0.2 ppm, and 20.8±0.2 ppm.
132. IPAc Solvate Form of Compound 87 according to embodiment 127, characterized by a $^{19}F$ NMR spectrum having a signal at at least three ppm values chosen from −107.1±0.2 ppm, −107.4±0.2 ppm, −108.0±0.2 ppm, −114.5±0.2 ppm, −115.0±0.2 ppm, −116.2±0.2 ppm.
133. IPAc Solvate of Compound 87 prepared by a process comprising reacting Compound 87 with IPAc.
134. A composition comprising IPAc Solvate Form of Compound 87 according to embodiment 127.
135. Amorphous Form of Compound 87:

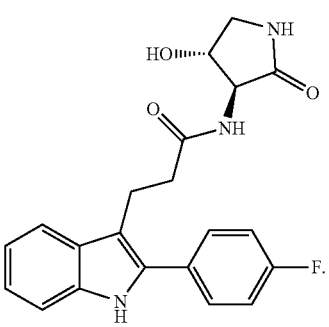
(87)

136. Amorphous Form of Compound 87 according to embodiment 137, characterized by an X-ray powder diffractogram substantially similar to that in FIG. 56.

137. A method of preparing a compound of formula C51

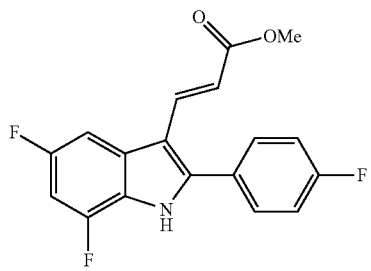

a pharmaceutically acceptable salt thereof, or a deuterated derivative of any of the foregoing, comprising reacting a compound of formula C50

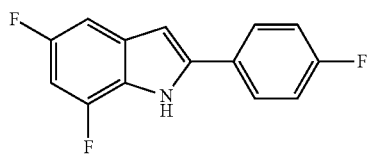

with methyl 3,3-dimethoxypropionate and at least one acid.

138. The method according to embodiment 139, wherein the at least one acid is chosen from organic acids, and mineral acids.

139. The method according to embodiment 139, wherein the organic acid is trifluoroacetic acid or a sulfonic acid.

140. The method according to embodiment 139, wherein the sulfonic acid is methane sulfonic acid, p-toluenesulfonic acid, or benzenesulfonic acid.

141. The method according to embodiment 139, wherein the mineral acid is $H_3PO_4$, HCl, or $H_2SO_4$.

142. A method of preparing a compound of formula C52

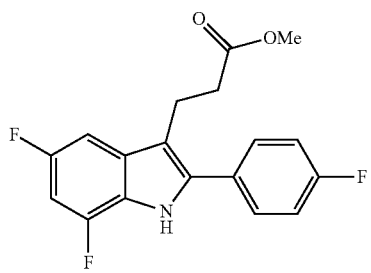

a pharmaceutically acceptable salt thereof, or a deuterated derivative of any of the foregoing, comprising:

reacting a compound of formula 51

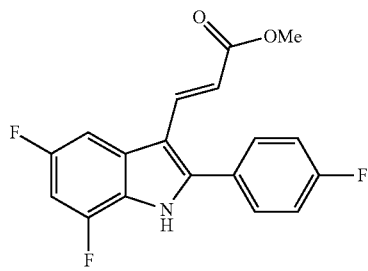

with at least one catalytic reducing agent.

143. The method according to embodiment 144, wherein the at least one catalytic reducing agent is chosen from heterogeneous catalytic reducing agents and homogeneous catalytic reducing agents.

144. A method of preparing a compound of formula S12

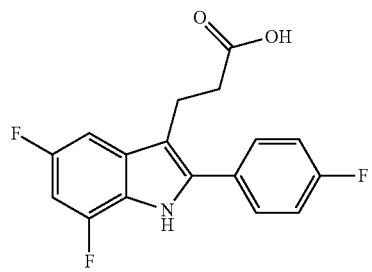

a salt thereof, or a deuterated derivative of any of the foregoing, comprising reacting a compound of formula C52

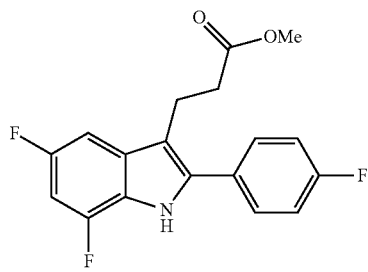

with at least one base or at least one acid.

145. The method according to embodiment 146, wherein the compound of formula S12 is reacted with at least one metal hydroxide.

146. The method according to embodiment 147, wherein the at least one metal hydroxide is NaOH, KOH, CsOH, LiOH, or RbOH.

147. A method of preparing Compound 2

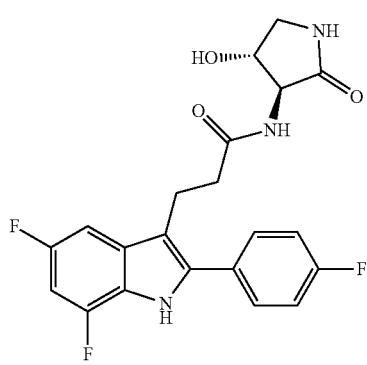

(2)

a salt thereof, or a deuterated derivative of any of the foregoing, comprising heating a solution comprising a compound of formula S12

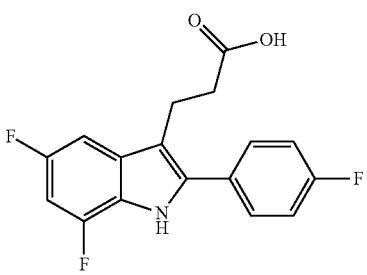

S12 with at least one compound of formula S2

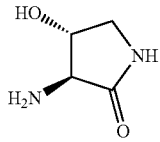

S2 and at least one peptide bond forming reagent.

148. The method according to embodiment 149, wherein the at least one peptide bond forming reagent is chosen from 2-chloro-4,6-dimethoxy-1,3,5-triazine (CDMT), carbonyldiimidazole (CDI), 1-ethyl-3-(3-dimethylaminopropyl)carbodiimide (EDC), hydroxybenzotriazole (HOBt), propylphosphonic anhydride (T3P), thionyl chloride, $SOCl_2$, oxalyl chloride, isobutyl chloroformate (IBCF), 1-[bis(dimethylamino)methylene]-1H-1,2,3-triazolo[4,5-b]pyridinium 3-oxide hexafluorophosphate (HATU), 2-(1H-benzotriazol-1-yl)-1,1,3,3-tetramethyluronium hexafluorophosphate (HBTU), and pivaloyl chloride.

149. A method of preparing a compound of formula C99

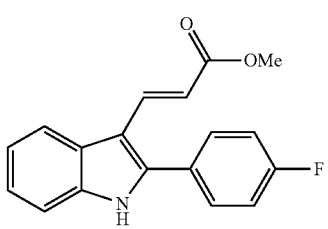

C99 a pharmaceutically acceptable salt thereof, or a deuterated derivative of any of the foregoing, comprising reacting a compound of formula C98

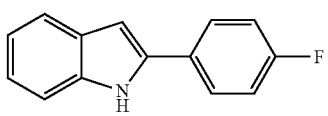

C98 with methyl 3,3-dimethoxypropionate and at least one acid.

150. The method according to embodiment 151, wherein the at least one acid is chosen from trifluoroacetic acid, sulfonic acids, and mineral acids.

151. The method according to embodiment 151, wherein the sulfonic acid is chosen from methane sulfonic acid, camphorsulfonic acid, p-toluenesulfonic acid, and benzenesulfonic acid.

152. The method according to embodiment 151, wherein the mineral acid is chosen from $H_3PO_4$, HCl, and $H_2SO_4$.

153. A method of preparing a compound of formula C100

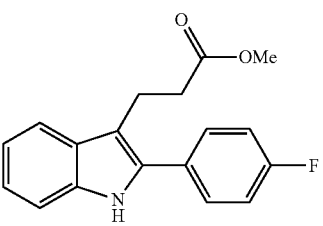

C100 a pharmaceutically acceptable salt thereof, or a deuterated derivative of any of the foregoing, comprising:

reacting a compound of formula C99

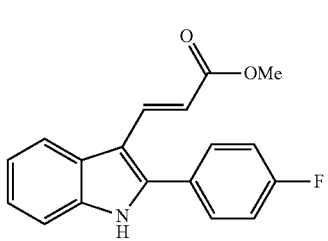

C99 with at least one catalytic reducing agent.

154. The method according to embodiment 147, wherein the catalytic reducing agent is chosen from heterogeneous catalytic reducing agents and homogeneous catalytic reducing agents.

155. A method of preparing a compound of formula C101

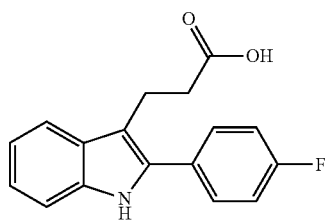

C101 a salt thereof, or a deuterated derivative of any of the foregoing, comprising reacting a compound of formula C100

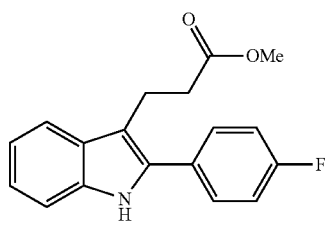

C100 with at least one base or at least one acid.

156. The method according to embodiment 157, wherein the compound of formula C101 is reacted with a metal hydroxide.

157. The method according to embodiment 158, wherein the metal hydroxide is chosen from NaOH, KOH, CsOH, and LiOH, and RbOH.

158. A method of preparing Compound 87

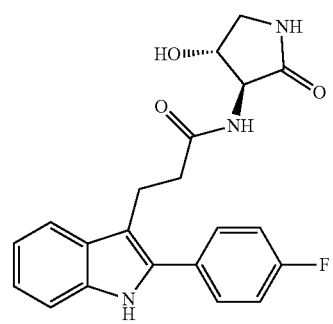

87 a salt thereof, or a deuterated derivative of any of the foregoing, comprising heating a solution comprising a compound of formula C101

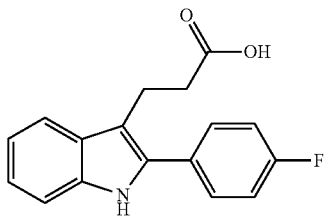

C101 with at least one compound of formula S2

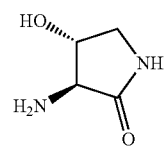

S2 and at least one peptide bond forming reagent.

159. The method according to embodiment 160, wherein the at least one peptide bond forming reagent is chosen from 2-chloro-4,6-dimethoxy-1,3,5-triazine (CDMT), carbonyldiimidazole (CDI), 1-ethyl-3-(3-dimethylaminopropyl)carbodiimide (EDC), hydroxybenzotriazole (HOBt), propylphosphonic anhydride (T3P), thionyl chloride, SOCl$_2$, oxalyl chloride, isobutyl chloroformate (IBCF), 1-[bis(dimethylamino)methylene]-1H-1,2,3-triazolo[4,5-b]pyridinium 3-oxide hexafluorophosphate (HATU), 2-(1H-benzotriazol-1-yl)-1,1,3,3-tetramethyluronium hexafluorophosphate (HBTU), and pivaloyl chloride.

160. A method of preparing a compound of formula C104

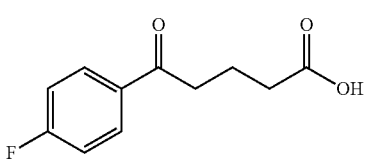

C104 a pharmaceutically acceptable salt thereof, or a deuterated derivative of any of the foregoing, comprising reacting fluorobenzene with glutaric anhydride and at least one acid.

161. A method of preparing a compound of formula C101

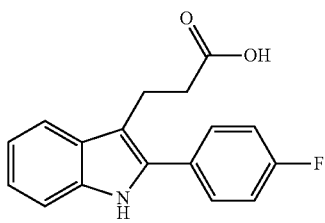

C101 a salt thereof, or a deuterated derivative of any of the foregoing, comprising reacting a compound of formula C104

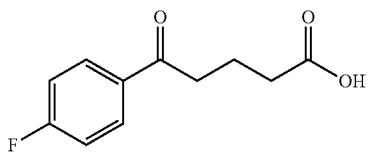

C104 with phenyl hydrazine and at least one acid.
162. The method according to embodiment 163, wherein the at least one acid is chosen from mineral acids, organic acids, and Lewis acids.
163. The method according to embodiment 164, wherein the mineral acid is chosen from $H_3PO_4$, HCl, and $H_2SO_4$.
164. The method according to embodiment 164, wherein the organic acid is a sulfonic acid.
165. The method according to embodiment 166, wherein the sulfonic acid is chosen from methane sulfonic acid, camphorsulfonic acid, p-toluenesulfonic acid, and benzenesulfonic acid.
166. The method according to embodiment 164, wherein the Lewis acid is chosen from $ZnCl_2$ and $ZnBr_2$.

EXAMPLES

In order that the disclosure described herein may be more fully understood, the following examples are set forth. It should be understood that these examples are for illustrative purposes only and are not to be construed as limiting this disclosure in any manner.

The compounds of the disclosure may be made according to standard chemical practices or as described herein. Throughout the following synthetic schemes and in the descriptions for preparing compounds of Formulae (I), (II), (IIIa), (IIIb), and (IIIc), Compounds 1 to 135, pharmaceutically acceptable salts of any of those compounds, solvates of any of the foregoing, and deuterated derivatives of any of the foregoing, the following abbreviations are used:

ABBREVIATIONS

AIBN=Azobisisobutyronitrile
ARP=assay ready plate
BBBPY=4,4'-Di-tert-butyl-2,2'-dipyridyl
CBzCl=Benzyl chloroformate
CDMT=2-Chloro-4,6-dimethoxy-1,3,5-triazine
DIPEA=N,N-Diisopropylethylamine or N-ethyl-N-isopropyl-propan-2-amine
DMAP=dimethylamino pyridine
DMA=dimethyl acetamide
DME=dimethoxyethane
DMEM=Dulbecco's modified Eagle's medium
DMF=dimethylformamide
DMSO=dimethyl sulfoxide
DPPA=diphenylphosphoryl azide
EtOAc=Ethyl Acetate
EtOH=ethanol
FBS=fetal bovine serum
FLU=fluorescent values
HATU=[dimethylamino(triazolo[4,5-b]pyridin-3-yloxy)methylene]-dimethyl-ammonium (Phosphorus Hexafluoride Ion)
HDMC=N-[(5-Chloro-3-oxido-1H-benzotriazol-1-yl)-4-morpholinylmethylene]-N-methylmethanaminium hexafluorophosphate
HEPES=4-(2-hydroxyethyl)-1-piperazineethanesulfonic acid
HBSS=Hank's balanced salt solution
IPA=isopropyl alcohol
LDA=lithium diisopropyl amide
LED=light emitting diode
MeOH=methanol
MTBE=Methyl tert-butyl ether
NMM=N-methyl morpholine
NMP=N-methyl pyrrolidine
PBS=phosphate-buffered saline
$Pd(dppf)_2Cl_2$=[1,1'-Bis(diphenylphosphino)ferrocene]dichloropalladium(II)
$PdCl_2(PPh_3)_2$=Bis(triphenylphosphine)palladium(II) dichloride
PP=polypropylene
PTSA=p-Toluenesulfonic acid monohydrate
T3P=2,4,6-Tripropyl-1,3,5,2,4,6-trioxatriphosphorinane-2,4,6-trioxide
TEA=triethylamine
Tet=tetracycline
TFA=trifluoroacetic acid
THF=tetrahydrofuran
THP=tetrahydropyran
TMSS=Tris(trimethylsilyl)silane Example 1. Synthesis of Compounds All the specific and generic compounds, and the intermediates disclosed for making those compounds, are considered to be part of the disclosure disclosed herein.

Synthesis of Starting Materials

Preparations of describe synthetic routes to intermediates used in the synthesis of compounds 1 to 135.

General Schemes

In some embodiments, processes for preparing compounds of formula I comprise reacting a compound of formula 1-1 with an amine of formula 1-2 in the presence of an amide coupling agent (e.g. HATU, CDMT, HDMC, or T3P) and a suitable base (e.g. DIPEA or TEA), as depicted in Scheme 1. Any suitable conditions for amide bond formation may be used.

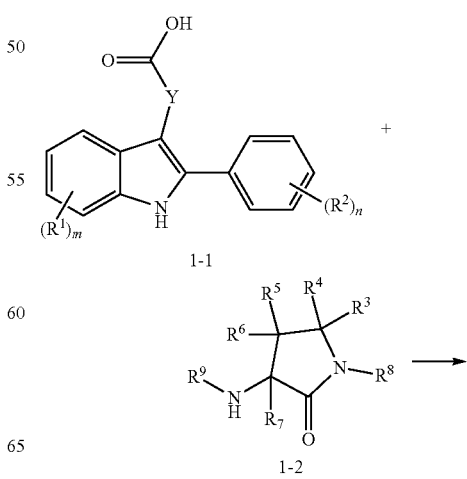

Scheme 1

-continued

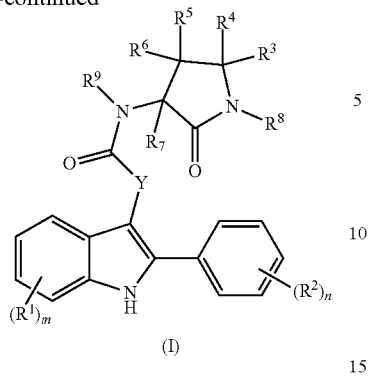

(I)

Scheme 2 provides processes for preparing compounds of formula 2-3, 2-4, 2-5 and 2-6; wherein variables $R^1$, $R^2$, $R^3$, $R^4$, $R^5$, $R^6$, $R^7$, $R^8$, $R^9$, m, and n are as defined in formula I above; $Z^1$ is an acetal protecting group (e.g. Me or Et); $R^{10}$ is any suitable group such that a compound of Formula 2-6 may also be a compound of Formula I (e.g. alkyl, halogen, alkoxy). $R^{11}$ is selected from C1-C6 linear, branched and cyclic alkyl groups;

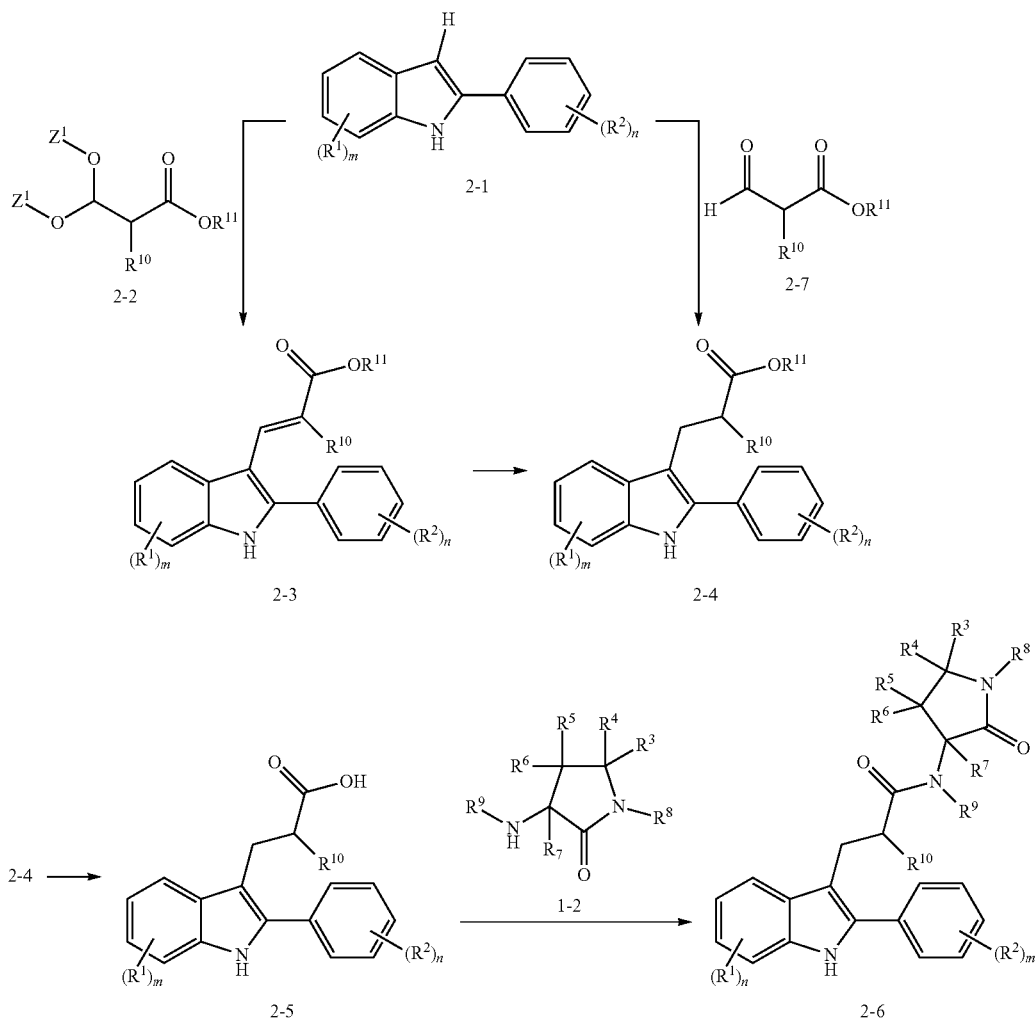

Scheme 2

In some embodiments, a compound of formula 2-3 may be prepared by reacting indoles 2-1 with acetals of formula 2-2 in the presence of an acid such as TFA or methanesulfonic acid in a suitable solvent (e.g. dichloromethane or toluene). Compounds of formula 2-4 may be prepared from compounds of formula 2-3 using reduction methods such as those for hydrogenation of an olefin. For example, in some embodiments the reaction is performed in the presence of hydrogenation reagents such as $H_2$ and palladium on carbon catalyst. In other embodiments, transfer hydrogenation conditions may be used (e.g. $Pd(OH)_2$ catalyst and $NH_4HCO_2$). Alternatively, a compound of formula 2-4 may be prepared directly from a compound of formula 2-1 by reaction with an aldehyde of formula 2-7. The reaction may be performed in the presence of an acid such as methanesulfonic acid, and a reducing agent such as $Et_3SiH$. Any suitable conditions, such as those for the hydrolysis of an ester, may be used for converting a compound of formula 2-4 to formula 2-5. For example, the reaction may be performed in the presence of a base (e.g. LiOH or NaOH) in an aqueous solvent mixture (e.g. THF and water). Compounds of formula 2-5 may be used as a compound of formula 1-1 in Scheme 1. Any suitable conditions, such as those for formation of an amide from a carboxylic acid can be used for reacting a compound of formula 2-5 with an amine of Formula 1-2 to provide compounds of formula 2-6.

Scheme 3 depicts processes for preparation of compounds of Formula 3-5 (wherein variables $R^1$, $R^2$, m and n are defined as in Formula I above; $X^1$ is a halogen e.g. I, Br or Cl; $R^{14}$ is any suitable alkyl e.g. Me or Et. Compounds of Formula 3-2 may be prepared from compounds of formula 3-1 using a suitable halogenating reagent (e.g. N-iodosuccinimide). Any suitable alkyne coupling reactions can be used for converting compounds of formula 3-2 to such as those 3-4. For example, the reaction is performed in the presence of catalysts such as $Pd(PPh_3)_2Cl_2$ and CuI, and a base (e.g. DIPEA or TEA). In some embodiments, hydrogenation conditions can be used to convert 3-4 to compounds of formula 3-5 (e.g. hydrogen and palladium on carbon catalyst) in a suitable solvent, such as MeOH or EtOH.

Scheme 3

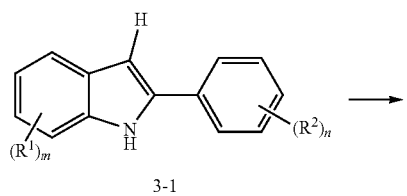

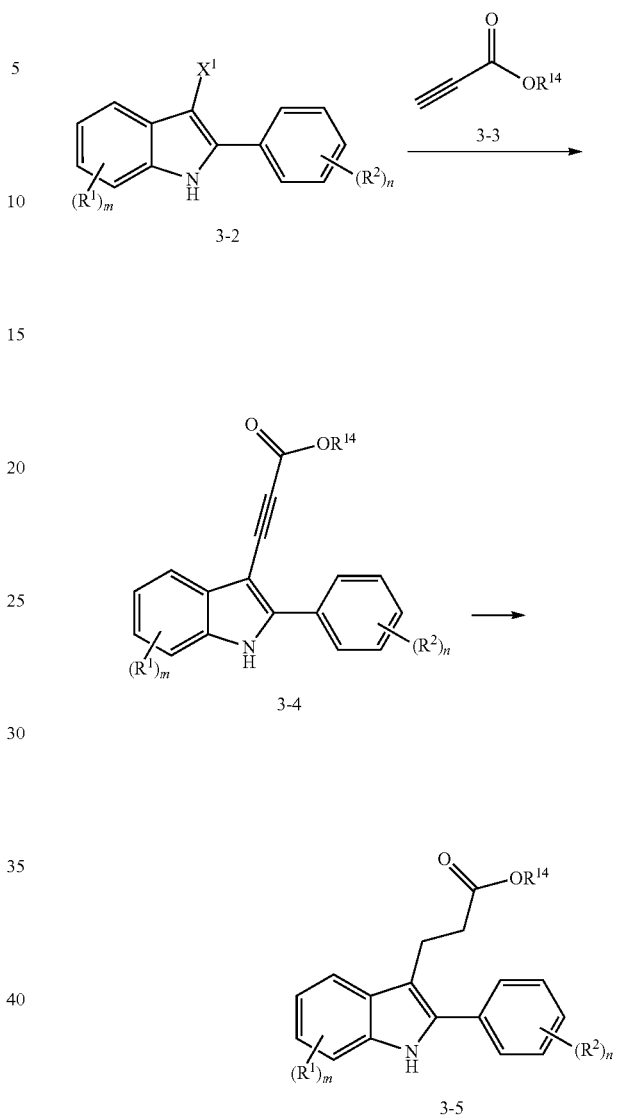

Scheme 4 refers to a process for the preparation of compounds of Formula 4-4 which may be used as a compound of Formula 1-1 in Scheme 1 above. $R^1$, $R^2$, m and n are defined as in scheme 1. $R^{15}$ and $R^{16}$ may be alkyls, halogens, or alkoxy. $R^{11}$ is any suitable alkyl forming an ester group (e.g. Me or Et). Any suitable conditions for a performing a Fischer indole synthesis may be used in the reaction of a diketone of formula 4-1 with a hydrazine of Formula 4-2. For example, $ZnCl_2$ in a solvent such as AcOH and toluene at elevated temperature (110° C.). In an alternative embodiment, $BF_3 \cdot OEt_2$ in xylene solvent in the presence of added heat may be used. Any suitable conditions for the hydrolysis of an ester may be used in the preparation of 4-4 from 4-3. A compound of formula 4-4 may be prepared from a compound of formula 4-5 and a hydrazine of formula 4-3 using any suitable Fischer indole synthesis conditions. In some embodiments, $ZnCl_2$ and AcOH may be used. The reaction may be performed in the presence of added heat. Hydrazines of formula 4-2 may be used as free bases or as salts, such as the hydrochloride salt.

Scheme 4

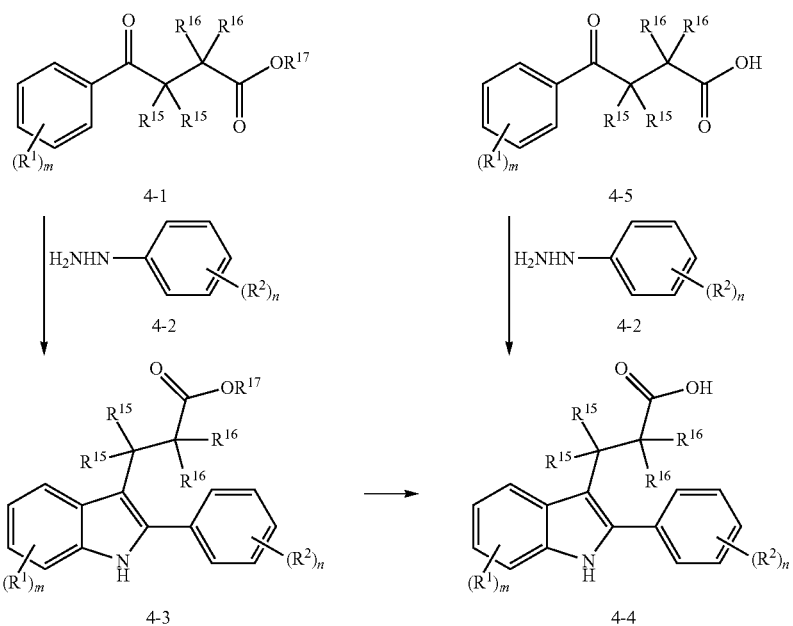

Scheme 5 provides processes for preparation of compounds of formula 5-3. $X^2$ is a halogen (e.g. Br). A compound of Formula 5-3 may be prepared by reaction of compound of formula 5-1 with an alkyl halide of Formula 5-2 under suitable photochemical coupling conditions. For example, in some embodiments a catalyst system containing $NiCl_2 \cdot (OMeCH_2)_2$, Iridium photocatalyst and TMSS, in the presence of a ligand such as BBBPY and under irradiation with blue LED light may be used.

Scheme 5

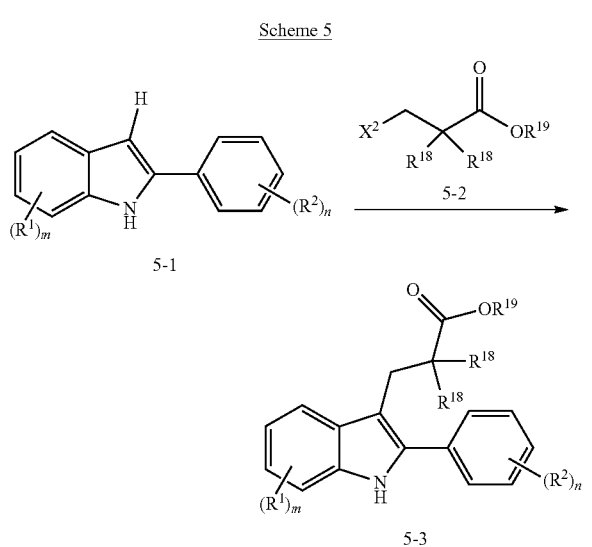

Scheme 6 provides a process for preparation of compounds of Formula 6-3 from compounds of Formula 6-1 and 6-2. Any suitable conditions for ring opening of an epoxide may be used. In some embodiments, the reaction is performed in the presence of a reagent such as $SnCl_4$.

Scheme 6

Scheme 7 refers to processes for preparation of compounds of Formula 7-4 from compounds of formula 7-1 or 7-5. $X^3$ and $X^4$ are halogens such are Cl, I, or Br. Any suitable conditions for coupling an alkyne can be used to convert aryl halides of Formula 7-1 and alkynes of formula 7-2 to an alkyne of Formula 7-3. For example, the coupling may be performed in the presence of a CuI and $Pd(PPh_3)_2Cl_2$ catalyst system. The reaction may be performed in the presence of a base (e.g. $NEt_3$). Conversion of compounds of formula 7-3 to indoles of Formula 7-4 may be accomplished by treatment with CuI or $PdCl_2$ in a polar solvent (e.g. DMF or MeCN) in the presence of added heat (>100° C.). A compound of formula 7-3 may also be prepared from a compound of formula 7-5 and an aryl halide of formula 7-6. Any suitable Sonogashira coupling condition may be used. For example, Pd(PPh$_3$)$_2$Cl$_2$ and CuI in the presence of a base such as DIPEA or NEt$_3$.

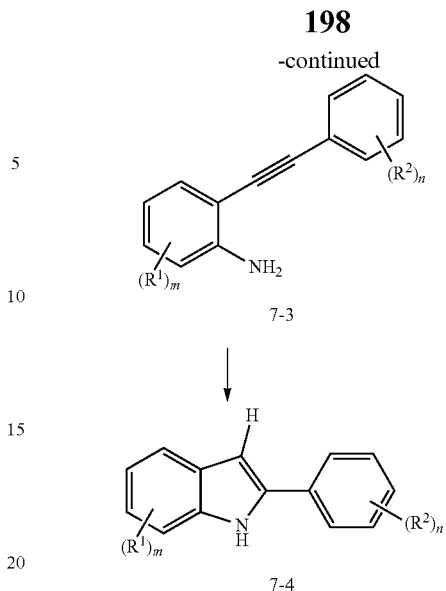

7-3

7-4

Scheme 8 refers to a process for preparation of compounds of Formula 8-3 from an indole such as that represented by Formula 8-1, and an alkyl halide of formula 8-2, where X$^4$ is a halogen (e.g. I or Br). R$^{20}$ is an alkyl group such as Me or Et. The two R$^{20}$ groups may be linked by a carbon carbon bond to form a cyclic boronate ester. In some embodiments, the reaction is performed in the presence of a catalyst such as PdCl$_2$CN$_2$, a ligand such as norbornylene, and a base (e.g. K$_2$CO$_3$). The reaction may be performed in a solvent such as dimethylacetamide at elevated temperature (e.g. 90° C.). Compounds of formula 8-3 may also be prepared from indoles of formula 8-1 and aryl boronic acids or esters of formula 8-5. In some embodiments, the reaction is performed in the presence of a palladium catalyst (e.g. Pd(OAc)$_2$.trimer in a solvent such as AcOH. The reaction is performed in the presence of oxygen.

Scheme 7

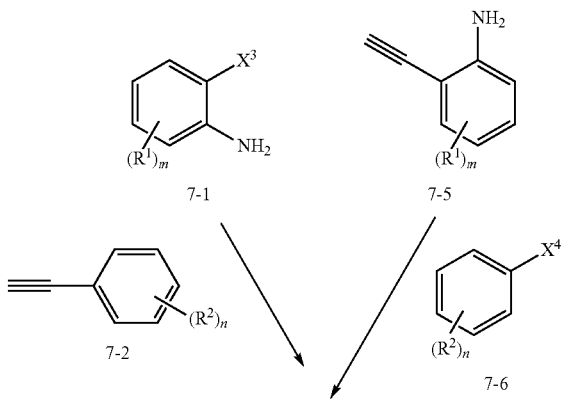

7-1

7-2

7-5

7-6

Scheme 8

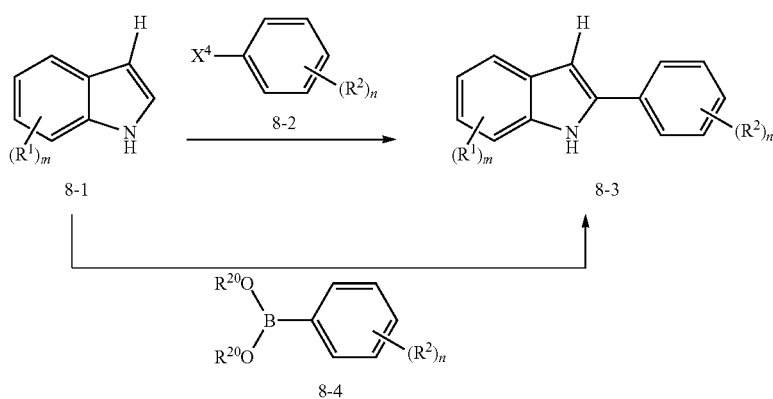

8-1

8-2

8-3

8-4

Scheme 9 provides processes for preparing compounds of Formula 9-5 wherein variables depicted in scheme 9 are as defined in Formula I. $X^5$ is a halogen (e.g. I, Br or Cl) and $R^{21}$ is an alkyl group (e.g. Me, Et or tBu). In some embodiments, the conversion of 9-1 to an epoxide of Formula 9-2 may be performed in the presence of a base (e.g. $K_2CO_3$ or $Cs_2CO_3$). Any suitable conditions for displacement of a halide with an azide group may be employed to obtain compounds of Formula 9-3 from 9-2 (e.g. $NaN_3$). In some embodiments, the reaction generating a compound of Formula 9-4 from 9-3 is performed in the presence of a reducing system (e.g. AIBN, nBuSnH). In some embodiments, a reaction generating a compound of Formula 9-5 from 9-4 may be performed in the presence of an amine source (e.g. liquid $NH_3$). In an alternative embodiment, compounds of Formula 9-5 may be obtained from 9-2 by treatment with an amine source (e.g. $NH_3$ gas) under conditions of elevated pressure and temperature (e.g. autoclave conditions).

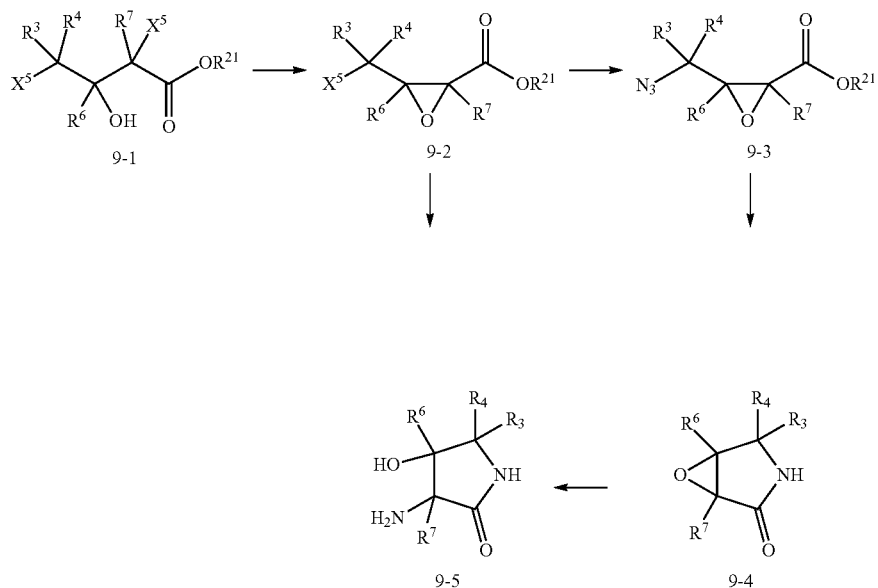

Scheme 10 describes processes for the preparation of compounds of Formula 10-5, wherein variables $R^3$, $R^4$, $R^6$, $R^7$, are as defined in Formula I. $R^{22}$ is any alkyl group that forms a suitable ester (e.g. Me or Et). $PG^1$ is a suitable amine protecting group such as t-butyl carbamate (Boc), Benzyl carbamate (CBz) or 9-fluorenylmethyl carbamate (Fmoc). In some embodiments, as shown in scheme 10, epoxides of Formula 10-2 may be prepared from compounds of Formula 10-1 in the presence of a reagent such as mCPBA. Compounds of formula 10-3 may be prepared from compounds of formula 10-2 by treatment with an azide source (e.g. $NaN_3$) in a polar solvent (e.g. DMF) in the presence of additional heat. As depicted in scheme 10, a compound of Formula 10-4 may be prepared from 10-3 in the presence of a suitable reducing agent (e.g. $PPh_3$). Any suitable conditions for the removal of a nitrogen atom protecting group may be used in the conversion of compounds of Formula 10-4 to compounds of Formula 10-5. For example, in some embodiments where $PG^1$ is CBz, hydrogenation conditions (e.g. $H_2$ and a palladium on carbon catalyst) may be used.

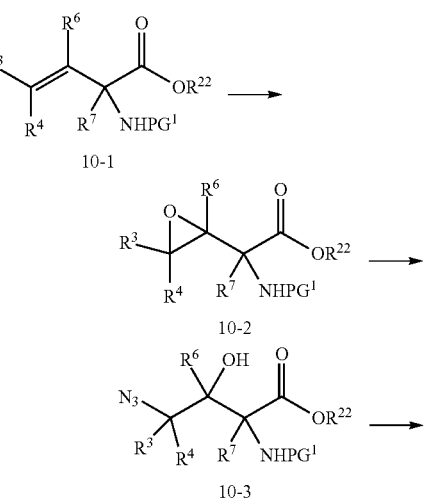

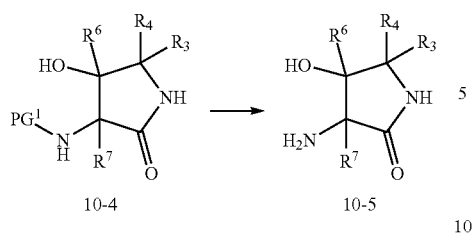

10-4    10-5

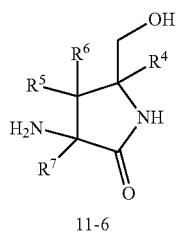

11-6

Scheme 11 shows processes for preparation of compounds of Formula 11-6. $R^4$, $R^5$, $R^6$ and $R^7$ are defined as in formula I. $R^{23}$ is a suitable alkyl group which forms an appropriate ester (e.g. Me or Et). $PG^2$ is an alcohol protecting group (e.g. TBDMS) Compounds of Formula 11-1 may be converted to compounds of Formula 11-2 by heating in the presence of a suitable solvent (e.g. toluene at 110° C.). Any suitable conditions for the reduction of ester groups to alcohols may be used to prepare compounds 11-3 from compounds of Formula 11-2. For example, in some embodiments, sodium borohydride in protic solvent (e.g. IPA) may be used. In some embodiments, compounds of Formula 11-4 may be prepared from Formula 11-3 by the treatment with a silylating reagent (e.g. tButyldimethyl silyl chloride) in the presence of imidazole or other suitable base. Amination of compounds of Formula 11-4 to give compounds of Formula 11-5 may be achieved by any suitable aminating reagents known to those in the art. For example, deprotonation using a base such as LDA and treatment with diphenylphosphoryl azide, followed by Boc protecting of the resulting amine with $Boc_2O$ affords compounds of Formula 11-5 where $PG^3$ is a Boc group. In some embodiments, where $PG^2$ is an acid labile group such as TBDMS, and $PG^3$ is a group such as Boc, compounds of Formula 11-6 may be prepared by treatment of 11-5 with suitable deprotection reagents (e.g. HCl).

A process for preparation of compounds of formula 12-4 from amino alkynes of formula 7-3 is shown in scheme 12. $R^{24}$ may be any suitable alkyl group that forms an ester (e.g. Et, Me, tBu). Formula 7-3 compounds may react with compounds of formula 12-1 to afford compounds of formula 12-2. In some embodiments, the reaction is performed in the presence of $PdCl_2$ and KI under an air atmosphere. A polar solvent such as DMF may be used. The reaction may be performed in the presence of added heat (e.g. 100° C.). A compound of formula 12-4 may be prepared from compounds of formula 12-2 by reduction of the alkene, and then ester hydrolysis. In one embodiment, hydrogenation with a palladium on carbon catalyst under an atmosphere of hydrogen gas, then ester hydrolysis with sodium hydroxide in a solvent such as THF and water.

Scheme 11

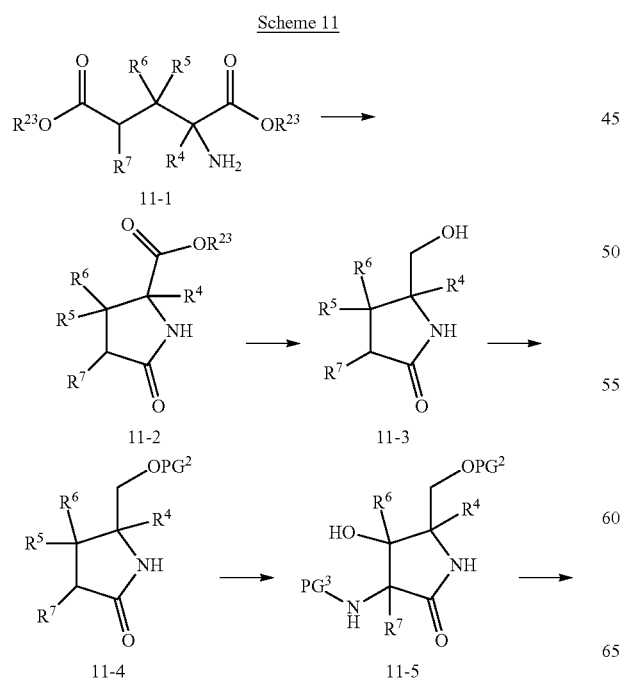

Scheme 12

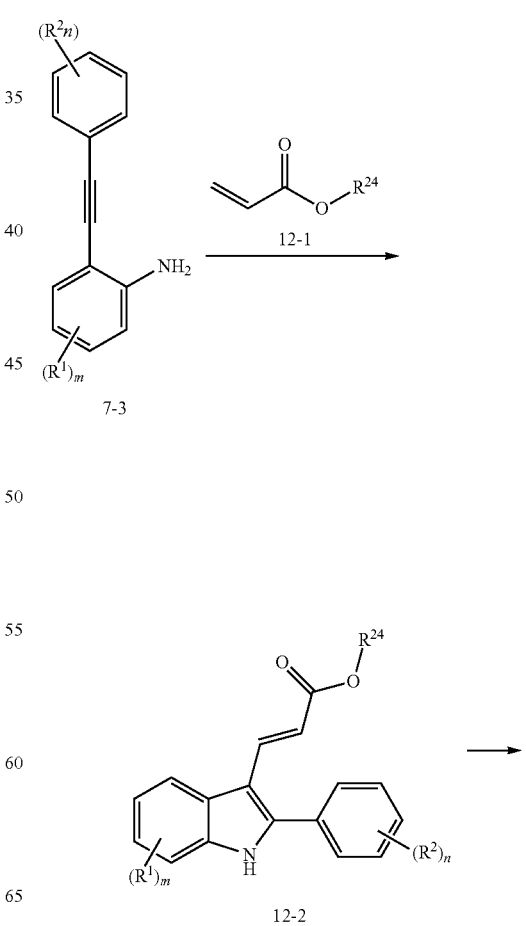

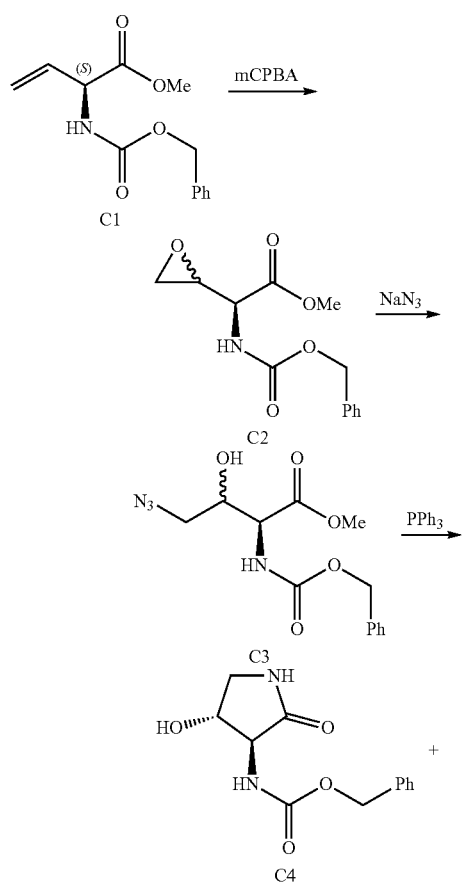

12-3

12-4

Preparation S1

3-[5,7-difluoro-2-(4-fluorophenyl)-1H-indol-3-yl]-N-[(3S,4S)-4-hydroxy-2-oxo-pyrrolidin-3-yl]propanamide (S1

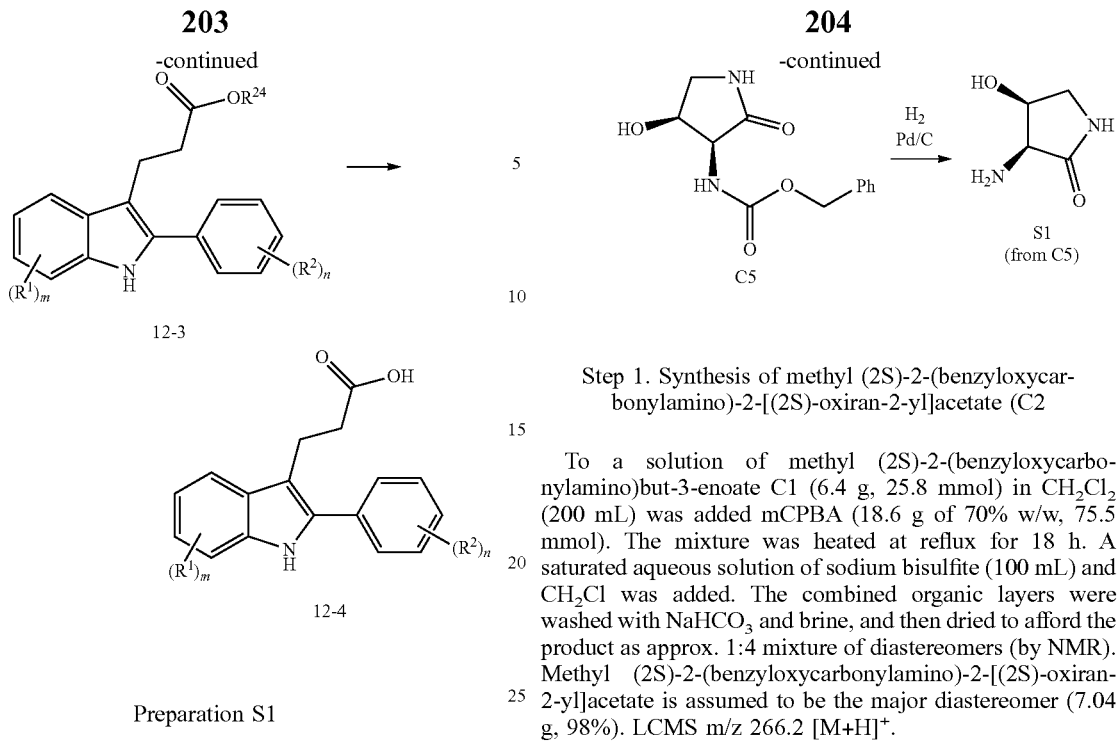

Step 1. Synthesis of methyl (2S)-2-(benzyloxycarbonylamino)-2-[(2S)-oxiran-2-yl]acetate (C2

To a solution of methyl (2S)-2-(benzyloxycarbonylamino)but-3-enoate C1 (6.4 g, 25.8 mmol) in $CH_2Cl_2$ (200 mL) was added mCPBA (18.6 g of 70% w/w, 75.5 mmol). The mixture was heated at reflux for 18 h. A saturated aqueous solution of sodium bisulfite (100 mL) and $CH_2Cl$ was added. The combined organic layers were washed with $NaHCO_3$ and brine, and then dried to afford the product as approx. 1:4 mixture of diastereomers (by NMR). Methyl (2S)-2-(benzyloxycarbonylamino)-2-[(2S)-oxiran-2-yl]acetate is assumed to be the major diastereomer (7.04 g, 98%). LCMS m/z 266.2 $[M+H]^+$.

Step 2. Synthesis of methyl (2S,3R)-4-azido-2-(benzyloxycarbonylamino)-3-hydroxy-butanoate (C3

A mixture of methyl (2S)-2-(benzyloxycarbonylamino)-2-[(2S)-oxiran-2-yl]acetate C2 (1.0 g, 3.7 mmol), sodium azide (2.4 g, 36.9 mmol) and $NH_4Cl$ (206 mg, 3.9 mmol) in DMF (10 mL) was heated at 60° C. overnight. Water (60 mL) was added and the mixture extracted with EtOAc. The organic phase was dried and concentrated to afford the product which was used in the subsequent step without purification. (1.1 g, 91%). LCMS m/z 309.2 $[M+H]^+$.

Step 3. Synthesis of benzyl N-[(3S,4R)-4-hydroxy-2-oxo-pyrrolidin-3-yl]carbamate (C4) and benzyl N-[(3S,4S)-4-hydroxy-2-oxo-pyrrolidin-3-yl]carbamate (C5

A solution of methyl (2S,3R)-4-azido-2-(benzyloxycarbonylamino)-3-hydroxy-butanoate C3 (221 mg, 0.22 mmol) and $PPh_3$ (200 mg, 0.8 mmol) in MeOH (5 mL), water (1 mL) and THF (4 mL) was heated at 100° C. for 18 h. Purification by reverse phase chromatography (column: C18 column; Gradient: MeCN in water with 0.2% formic acid) afforded two diastereomeric products in an 8:1 ratio.

C4 is the major diastereomer and is presumed to have 3S,4R stereochemistry. benzyl N-[(3S,4R)-4-hydroxy-2-oxo-pyrrolidin-3-yl]carbamate (55 mg, 28%). $^1H$ NMR (300 MHz, $CD_3OD$) δ 7.51-7.27 (m, 5H), 5.12 (s, 2H), 4.42 (q, J=7.8 Hz, 1H), 4.06 (d, J=8.3 Hz, 1H), 3.56 (dd, J=9.8, 7.7 Hz, 1H), 3.10 (dd, J=9.9, 7.4 Hz, 1H). LCMS m/z 251.2 $[M+H]^+$.

C5 is the minor diastereomer and is presumed to have 3S,4S stereochemistry. benzyl N-[(3S,4S)-4-hydroxy-2-oxo-pyrrolidin-3-yl]carbamate (8.8 mg, 8%). $^1H$ NMR (300 MHz, $CD_3OD$) δ 7.37 (dddd, J=16.2, 8.6, 6.7, 3.5 Hz, 5H), 5.15 (s, 2H), 4.52-4.34 (m, 2H), 3.69-3.53 (m, 1H), 3.25 (d, J=11.3 Hz, 1H). LCMS m/z 251.1 $[M+H]^+$.

Step 4. Synthesis of 3-[5,7-difluoro-2-(4-fluorophenyl)-1H-indol-3-yl]-N-[(3S,4S)-4-hydroxy-2-oxopyrrolidin-3-yl]propanamide (S1

To a solution of benzyl N-[(3S,4S)-4-hydroxy-2-oxopyrrolidin-3-yl]carbamate C5 (8.8 mg, 0.03 mmol) in MeOH (8 mL) was added 5% Palladium on carbon (10 mg). The mixture was subjected to hydrogenation conditions (50 psi $H_2$) for 4 h. The mixture was filtered through Celite®, washing with MeOH, then concentrated in vacuo to afford the product which was used directly in the synthesis of compound 1. $^1$H NMR (300 MHz, $CD_3OD$) δ 4.34 (dd, J=5.1, 3.8 Hz, 1H), 3.57-3.49 (m, 1H), 3.45 (d, J=5.1 Hz, 1H), 3.23 (d, J=11.2 Hz, 1H).

Preparation S2

(3S,4R)-3-amino-4-hydroxy-pyrrolidin-2-one (S2

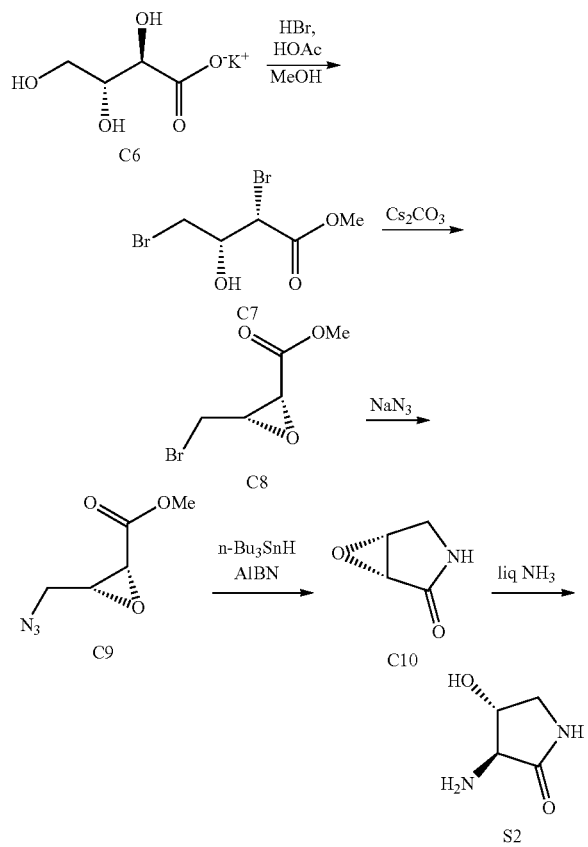

Step 1. Synthesis of methyl (2S,3R)-2,4-dibromo-3-hydroxy-butanoate (C7

Potassium (2R,3R)-2,3,4-trihydroxybutanoate C6 (10 g, 57.1 mmol) was stirred with HBr in Acetic acid (154 g, 103 mL of 30% w/w, 570.8 mmol) for 16 h. Anhydrous MeOH (250 mL) was added and the mixture heated at reflux for 4 h. The mixture was concentrated dryness and the residue dissolved in EtOAc (100 mL). The solution was washed with water (50 mL) and brine (50 mL), then dried over $Na_2SO_4$, and concentrated in vacuo. Purification by silica gel chromatography (Gradient: 15-20% EtOAc in hexane) afforded the product as a colorless liquid (13 g, 83%). $^1$H NMR (400 MHz, $CDCl_3$) δ 4.71 (d, J=3.4 Hz, 1H), 4.17-4.14 (m, 1H), 3.82 (s, 3H), 3.53-3.44 (m, 2H).

Step 1. Alternative procedure for synthesis of methyl (2S,3R)-2,4-dibromo-3-hydroxy-butanoate (C7

Potassium (2R,3R)-2,3,4-trihydroxybutanoate C6 (280 g) was stirred with a 33% solution of HBr in acetic acid (1 L) at room temperature for 24 h. The reaction mixture was then poured into MeOH (5 L). The mixture was stirred at room temperature for 8 h, then at 65° C. for 4 h. The mixture was concentrated, the residue was dissolved in MeOH (1.2 L) and then concentrated sulfuric acid (30 mL) was slowly added. The mixture was heated under reflux for 6 h, then concentrated. The residue was taken up with EtOAc (400 mL). The resulting solution was washed with water (250 mL), dried over $Na_2SO_4$, filtered and concentrated in vacuo to give the product as an oil which solidified upon storage at 4° C. (375 g, 74%).

Step 2. Synthesis of methyl (2R,3S)-3-(bromomethyl)oxirane-2-carboxylate (C8

Methyl (2R,3R)-2,4-dibromo-3-hydroxy-butanoate C7 (524.8 g, 1.9 mol) was dissolved in acetone (4.5 L) in a 12 L round-bottomed flask equipped with an overhead stirrer. The reaction was cooled to 0° C. in an ice-bath and $Cs_2CO_3$ (994 g, 3.1 mol) was added. The reaction was stirred for 30 minutes at 0° C. and then for 2 h at room temperature. The mixture was filtered, washing with acetone, and then concentrated in vacuo to afford a dark grey oil residue. The product was dissolved in $CH_2Cl_2$ and filtered over a short plug of silica gel, eluting with $CH_2Cl_2$ (approx. 1 L). The filtrate was concentrated in vacuo to afford the product as a clear yellow oil (377.3 g, quantitative). $^1$H NMR (300 MHz, $CDCl_3$) δ 3.83 (s, 3H), 3.71-3.61 (m, 2H), 3.61-3.53 (m, 1H), 3.46 (dd, J=9.9, 6.6 Hz, 1H) ppm. $^{13}$C NMR (75 MHz, $CDCl_3$) δ 167.58, 55.89, 53.52, 52.77, 26.83 ppm.

Step 2. Alternative Procedure for Synthesis of Methyl (2R,3S)-3-(bromomethyl)oxirane-2-carboxylate (C8)

To a solution of methyl (2R,3R)-2,4-dibromo-3-hydroxy-butanoate C7 (200 g, 0.73 mol) in acetone (2.0 L) was added anhydrous $K_2CO_3$ (151.1 g, 1.1 mol), while the reaction temperature was maintained at 0-5° C. The reaction was stirred at 0-5° C. for 2 h, then gradually warmed to room temperature over 4 h The reaction mixture was filtered and the filtrate was concentrated under reduced pressure. The residue was distilled under vacuum 75-80° C./200-300 Pa to give the product as a colorless liquid (105 g, 74%).

Step 3. Synthesis of Methyl (2R,3R)-3-(azidomethyl)oxirane-2-carboxylate (C9

Methyl (2R,3S)-3-(bromomethyl)oxirane-2-carboxylate C8 (52.6 g, 269.7 mmol) was dissolved in DMF (500 mL) in a 3 L round-bottomed flask equipped with a magnetic stir bar. $NaN_3$ (25.3 g, 388.4 mmol) was added and the mixture was stirred at room temperature for 1 h. The reaction was poured into water, and extracted with EtOAc. The extract was washed with water, dried over $MgSO_4$, and concentrated in vacuo to afford a dark red oil. The oil residue was dissolved in CH₂Cl₂, and filtered over a plug of silica gel eluting with CH₂Cl₂. The filtrate was concentrated in vacuo to afford the product as a clear, light red oil (40.8 g, 96%). $^1$H NMR (300 MHz, CDCl₃) δ 3.87-3.74 (m, 3H), 3.67-3.55 (m, 2H), 3.47 (dd, J=13.3, 5.1 Hz, 1H), 3.38 (ddd, J=6.3, 5.0, 4.4 Hz, 1H). $^{13}$C NMR (75 MHz, CDCl₃) δ 167.76, 54.81, 52.67, 51.32, 48.74.

Step 4. Synthesis of (1R,5R)-6-oxa-3-azabicyclo [3.1.0]hexan-2-one (C10

A 2 L 3-neck flask with overhead stirrer was charged with methyl (2R,3R)-3-(azidomethyl)oxirane-2-carboxylate C9 (67 g, 402.5 mmol) in toluene (500 mL), stirred for 10 minutes, and then warmed to 80° C. Bu₃SnH (220 mL, 817.8 mmol) and AIBN (2 g, 12.2 mmol) were dissolved in toluene (500 mL) and then added to the reaction over 3 h using an additional funnel. The resulting reaction mixture was stirred at 80-87° C. for 1 h, then cooled to ambient temperature, and concentrated under reduced pressure. The residue was partitioned between acetonitrile (2 L) and pentane (1 L), stirred for 10 minutes and then the acetonitrile phase (bottom) was separated. The acetonitrile phase was washed with pentane (2×500 mL) and concentrated in vacuo to afford a light yellow solid. The solid residue was triturated with pentane (~200 mL) to afford the product as a yellow solid which was used without further purification (52 g, 98%). $^1$H NMR (300 MHz, CDCl₃) δ 5.89 (s, 1H), 4.00 (q, J=2.5 Hz, 1H), 3.74-3.50 (m, 2H), 3.44 (dd, J=12.4, 2.4 Hz, 1H). $^{13}$C NMR (75 MHz, CDCl₃) δ 173.24, 53.28, 52.18, 44.00.

Step 5. Synthesis of (3S,4R)-3-amino-4-hydroxy-pyrrolidin-2-one (S2

A parr vessel containing (1R,5R)-6-oxa-3-azabicyclo [3.1.0]hexan-2-one C10 (60 g, 605.5 mmol) and NH₃ (1.5 L, 58.6 mol) was pressurized to 200 psi and allowed to stir at 18° C. for 2 days. NH₃ was released from the vessel to provide a grey solid. Heptane was added and the mixture stirred for 30 min. The solid was filtered, and then the filter cake was isolated, and then EtOAc and heptane to the solid. The mixture was concentrated in vacuo to afford the product (55 g, 78%). $^1$H NMR (300 MHz, D₂O) δ 4.13 (q, J=7.2 Hz, 1H), 3.53 (dd, J=10.4, 7.4 Hz, 1H), 3.36 (d, J=7.5 Hz, 1H), 3.05 (dd, J=10.4, 6.8 Hz, 1H).

Alternative Preparation S2

(3S,4R)-3-amino-4-hydroxypyrrolidin-2-one hydrochloride (S2

Step 1 & 2. Synthesis of N-Boc-(3S,4R)-3-amino-4-hydroxypyrrolidin-2-one (C12

At −60° C., ammonia gas was condensed into an autoclave containing a frozen solution of methyl (2R,3S)-3-(bromomethyl)oxirane-2-carboxylate C8 (81 g, 0.42 mol) in 1,4-dioxane (160 mL) until approx. 400 mL of liquid was collected. The autoclave was closed, allowed to warm gradually to room temperature and then heated at 50-60° C. for 2 h. The autoclave was then cooled back to −60° C. and depressurized. The reaction mixture was warmed gradually to allow the liquid ammonia to evaporate, leaving a viscous residue. The residue was taken up with MeOH (500 mL) and the suspension was treated with a 28% solution of sodium methoxide in MeOH (86 g, 0.42 mol). The mixture was stirred at room temperature for 30 min then concentrated. The residue was dissolved in water (500 mL), then Na₂CO₃ (89 g, 0.84 mol) and a solution of Boc₂O (110 g, 0.5 mol) in THF (200 mL) was added. The mixture was stirred at room temperature for 10 h. The aqueous phase was then saturated with NaCl, and extracted THF (3×200 mL). The combined organic phases were dried over Na₂SO₄ and concentrated in vacuo. The residue was triturated with warm MTBE (200 mL) and the precipitated solid was collected by filtration, washed with MTBE and dried under vacuum to afford the product as a white solid (28 g, 31% yield).

Step 3. Synthesis of (3S,4R)-3-amino-4-hydroxypyrrolidin-2-one hydrochloride (S2

To solution of N-Boc-(3S,4R)-3-amino-4-hydroxypyrrolidin-2-one C12 (28 g, 129 mmol) in EtOH (300 mL) heated at 50-60° C. was added a solution of HCl in EtOH (5.0 M, 75 mL). The reaction mixture was kept at 50-60° C. for 2 h. The suspension was cooled to room temperature and the solid was collected by filtration, washed with EtOH and dried in vacuo to afford the product as an off-white solid (18 g, 90%). $^1$H NMR (500 MHz, DMSO-d₆) δ 8.73 (brs, 3H), 8.28 (s, 1H), 6.03 (s, 1H), 4.42-4.37 (m, 1H), 3.74 (d, J=6.8 Hz, 1H), 3.48-3.39 (m, 1H), 3.03-3.00 (m, 1H).

Preparation S3

(3S)-3-amino-5-methyl-pyrrolidin-2-one (S3

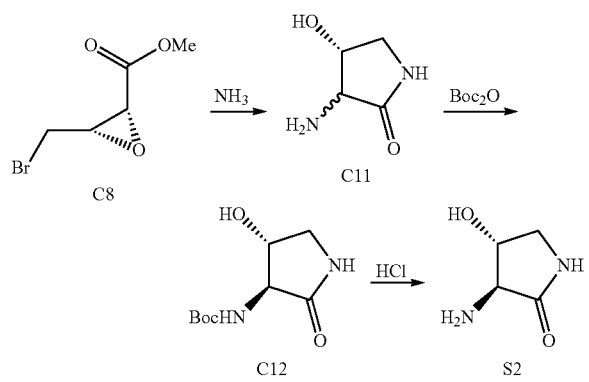

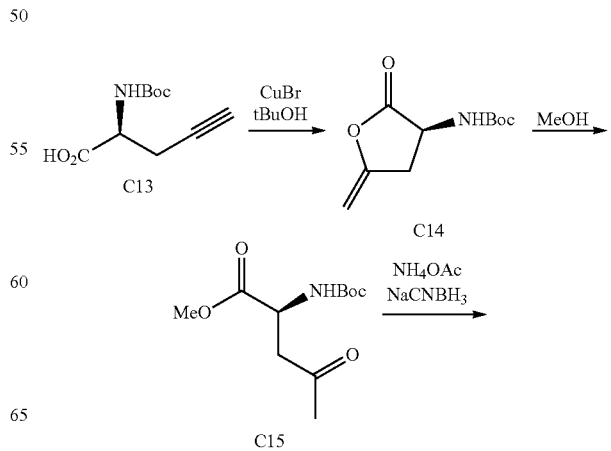

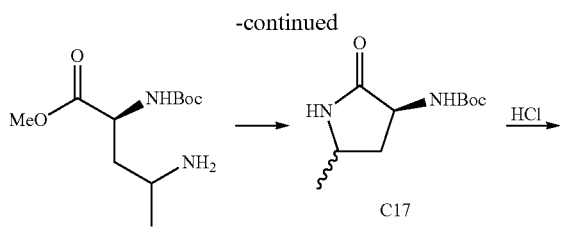

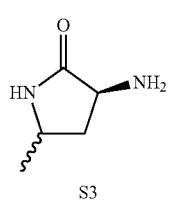

Step 1. Synthesis of tert-butyl (S)-(5-methylene-2-oxotetrahydrofuran-3-yl)carbamate (C14

CuBr (6723 mg, 4.7 mmol) was added to a solution of (2S)-2-(tert-butoxycarbonylamino)pent-4-ynoic acid C13 (5 g, 23.5 mmol) in tBuOH (50 mL) and water (50 mL) and stirred at room temperature for 24 h. The mixture was concentrated in vacuo to afford the product as an off-white solid (4.5 g, 80%). $^1$H NMR (400 MHz, DMSO-$d_6$): δ 7.56 (d, 1H, J=7.88), 4.64 (s, 1H), 4.49-4.43 (m, 1H), 4.34 (s, 1H), 3.12-3.05 (m, 1H), 2.78-2.72 (m, 1H), 1.38 (s, 9H). LCMS m/z 214.3 $[M+H]^+$.

Step 2. Synthesis of Methyl (2S)-2-(tert-butoxycarbonylamino)-4-oxo-pentanoate (C15

A solution of tert-butyl (S)-(5-methylene-2-oxotetrahydrofuran-3-yl)carbamate C14 (500 mg, 2.4 mmol) in MeOH (100 mL) was stirred at room temperature for 24 h. The solvent was evaporated under reduced pressure and the residue purified by silica gel chromatography (Gradient: 10% EtOAc in hexane) to afford the product as a colorless oil (300 mg, 51%). $^1$H NMR (400 MHz, DMSO-$d_6$) δ 7.16 (d, 1H J=7.64 Hz), 4.37-4.31 (m, 1H), 3.60 (s, 3H), 2.89-2.73 (m, 2H), 2.09 (s, 3H), 1.38 (s, 9H). LCMS m/z 246.0 $[M+H]^+$.

Step 3. Synthesis of methyl (2S)-4-amino-2-(tert-butoxycarbonylamino)pentanoate (C16

To a solution of methyl (2S)-2-(tert-butoxycarbonylamino)-4-oxo-pentanoate C15 (2.5 g, 10.2 mmol) in MeOH (30 mL) was added ammonium acetate (6.3 g, 81.5 mmol) and NaCNBH$_3$ (6.4 g, 101.9 mmol) at 0° C. The mixture was stirred at room temperature for 24 h. The mixture was concentrated in vacuo and the residue was quenched with sat. solution of NH$_4$Cl (25 mL). The aqueous layer was extracted with 10% MeOH in CH$_2$Cl$_2$ (4×25 mL). The combined organic layers were washed sequentially with water (10 mL) and brine (10 mL), then dried over magnesium sulfate, and concentrated in vacuo to afford the product which was used without further purification (2.5 g, 100%). LCMS m/z 247.3 $[M+H]^+$.

Step 4. Synthesis of tert-butyl N-[(3S)-5-methyl-2-oxo-pyrrolidin-3-yl]carbamate (C17

A solution of methyl (2S)-4-amino-2-(tert-butoxycarbonylamino)pentanoate C16 (2.5 g, 10.2 mmol) in 1,4-dioxane (100 mL) was heated at 90° C. for 24 h. The solvent was evaporated under reduced pressure. Purification by silica gel column chromatography (Gradient: 5% MeOH/DCM) afforded the product. (2 g, 92%) $^1$H NMR (400 MHz, DMSO-$d_6$): δ 7.82 (d, J=11.68 Hz, 1H), 7.00 (q, 1H), 4.09-4.01 (m, 1H), 3.56-3.45 (m, 2H), 1.90-1.87 (m, 1H), 1.37 (s, 9H), 1.08 (s, 3H). LCMS m/z 214.9 $[M+H]^+$.

Step 5. Synthesis of (3S)-3-amino-5-methyl-pyrrolidin-2-one Hydrochloride (S3

To a solution of tert-butyl N-[(3S)-5-methyl-2-oxo-pyrrolidin-3-yl]carbamate C17 (2 g, 9.3 mmol) in 1,4-dioxane (10 mL) was added HCl in 1,4-dioxane (23.3 mL of 4 M, 93.3 mmol). The mixture was stirred at room temperature for 6 h. The reaction mixture was concentrated under reduced pressure and the residue was triturated with diethylether and n-pentane. Lyophilization afforded the product mixture of two diastereomers as an off white solid (927 mg, 65%). $^1$H NMR (300 MHz, DMSO-$d_6$) δ 8.61 (brs), 8.42 (d, J=9.9 Hz, 1H), 4.02-3.82 (m, 1H), 3.70-3.57 (m, 1H), 2.60-2.51 (m, 1H of one diastereomer), 2.29-2.16 (m, 1H of one diastereomer), 2.02 (ddd, J=13.0, 8.8, 2.2 Hz, 1H of one diastereomer), 1.57 (ddd, J=12.2, 11.0, 9.0 Hz, 1H of one diastereomer), 1.14 (dd, J=6.3, 3.5 Hz, 3H). LCMS m/z 115.0 $[M+H]^+$.

Preparation S4

(3S,5S)-3-amino-5-(hydroxymethyl)pyrrolidin-2-one (S4

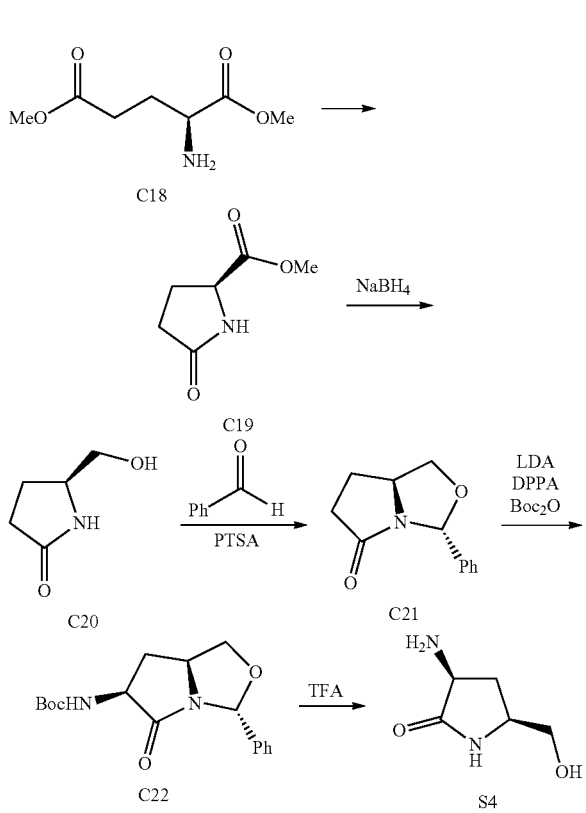

Step 1. Synthesis of methyl (2S)-5-oxopyrrolidine-2-carboxylate (C19

A solution of dimethyl (2S)-2-aminopentanedioate C18 (16 g, 91.3 mmol) in toluene (150 mL) was refluxed at 110° C. for 6 h. The reaction mixture was concentrated in vacuo. Silica gel chromatography (Gradient: 5% MeOH in $CH_2Cl_2$). afforded the product as a colorless liquid (4.2 g, 32%). $^1H$ NMR (400 MHz, $CDCl_3$) δ 6.14 (s, 1H), 4.32 (s, 1H), 3.78 (s, 3H), 2.52 (s, 1H), 2.40 (s, 2H), 2.29 (s, 1H).

Step 2. Synthesis of (5S)-5-(hydroxymethyl)pyrrolidin-2-one (C20

To a solution of methyl (2S)-5-oxopyrrolidine-2-carboxylate C19 (4.2 g, 29.3 mmol) in IPA (40 mL) was added $NaBH_4$ (6.7 g, 7.0 mL, 176 mmol), the reaction was allowed to stirred at room temperature for 20 h. The mixture was then quenched with MeOH and concentrated in vacuo. Purification by column chromatography (Gradient: 5% MeOH in $CH_2Cl_2$) afforded the product as a colorless liquid (3.3 g, 98%). $^1H$ NMR (400 MHz, $CDCl_3$) δ 7.29 (s, 1H), 4.25 (s, 1H), 3.79-3.74 (m, 1H), 3.64 (d, J=11.8 Hz, 1H), 3.43 (t, J=10.2 Hz, 1H), 2.35-2.30 (m, 2H), 2.27-2.20 (m, 1H), 1.81-1.73 (m, 1H).

Step 3. Synthesis of (3R,7αS)-3-phenyl-3,6,7,7α-tetrahydro-1H-pyrrolo[1,2-c]oxazol-5-one (C21

To a solution of (5S)-5-(hydroxymethyl)pyrrolidin-2-one C20 (4.7 g, 40.8 mmol) in toluene (75 mL) was added benzaldehyde (6.9 g, 6.7 mL, 65.3 mmol) and PTSA (388 mg, 2.0 mmol) and the reaction mixture was allowed to stirred at same temperature for 17 h. The mixture was then refluxed for 6 h with a Dean-Stark apparatus to remove water. The mixture was concentrated in vacuo and purified by silica gel chromatography (Eluent: 30% Ethyl acetate in hexane) to afford the product as a light yellow liquid (4.8 g, 48%). $^1H$ NMR (400 MHz, $CDCl_3$) δ 7.43 (d, J=7 Hz, 2H), 7.37-7.29 (m, 3H), 6.32 (s, 1H), 4.24-4.17 (m, 1H), 4.15-4.11 (m, 1H), 3.48 (t, J=8.04 Hz, 1H), 2.85-2.76 (m, 1H), 2.59-2.51 (m, 1H), 2.42-2.33 (m, 1H), 1.98-1.91 (m, 1H). LCMS m/z 204.0 $[M+H]^+$.

Step 4. Synthesis of tert-butyl N-[(3R,6S,7αS)-5-oxo-3-phenyl-3,6,7,7α-tetrahydro-1H-pyrrolo[1,2-c]oxazol-6-yl]carbamate (C22

LDA (5.1 mL of 2 M, 10.3 mmol) was cooled to −78° C. then a solution of (3R,7αS)-3-phenyl-3,6,7,7α-tetrahydro-1H-pyrrolo[1,2-c]oxazol-5-one C21 (1.75 g, 8.6 mmol) in THF (20 mL) was added and the reaction mixture was stirred at −78° C. for 30 minutes. DPPA (4.7 g, 3.7 mL, 17.2 mmol) was then added, and reaction mixture was stirred for a further 10 minutes. Boc-anhydride (3.8 g, 3.9 mL, 17.2 mmol) was added to the mixture and the reaction allowed to stir for 17 h. Ethyl acetate (125 mL) was added and the mixture was washed with brine solution (2×200 mL). The organic layer was dried over anhydrous magnesium sulfate and concentrated in vacuo. Purification by silica gel chromatography (Eluent: 22% Ethyl acetate in hexanes) afforded the product (750 mg, 25%) $^1H$ NMR (400 MHz, $CDCl_3$) δ 7.46-7.28 (m, 5H), 6.34 (s, 1H), 5.18 (s, 1H), 4.62 (s, 1H), 4.30-4.21 (m, 1H), 4.06 (p, J=6.8 Hz, 1H), 3.62 (t, J=7.6 Hz, 1H), 3.00 (s, 1H), 1.75 (q, J=11.8, 11.3 Hz, 1H), 1.45 (s, 9H). LCMS m/z 319.0 $[M+H]^+$.

Step 5. Synthesis of (3S,5S)-3-amino-5-(hydroxymethyl)pyrrolidin-2-one hydrochloride (S4

TFA (11.1 g, 7.5 mL, 97.3 mmol) was added to a solution of tert-butyl N-[(3R,6S,7αS)-5-oxo-3-phenyl-3,6,7,7α-tetrahydro-1H-pyrrolo[1,2-c]oxazol-6-yl]carbamate C22 (1.5 g, 4.7 mmol) in $CH_2Cl_2$ (15 mL) cooled to 0° C. The mixture was allowed to stir at room temperature for 2 h, and then concentrated in vacuo. 4 M HCl in 1,4-dioxane was added and the mixture was washed with pentane to afford the product as the hydrochloride salt (750 mg, 96%). $^1H$ NMR (400 MHz, DMSO-$d_6$ and $D_2O$) δ 3.89 (t, 9.3 Hz, 3H), 3.63-3.56 (m, 1H), 3.43-3.32 (dd, J=10.9, 4.5 Hz, 2H), 2.45-2.38 (m, 1H), 1.67-1.59 (m, 1H). LCMS m/z 131.0 $[M+H]^+$.

Preparation S5

(3S,5R)-3-amino-5-(hydroxymethyl)pyrrolidin-2-one (S5

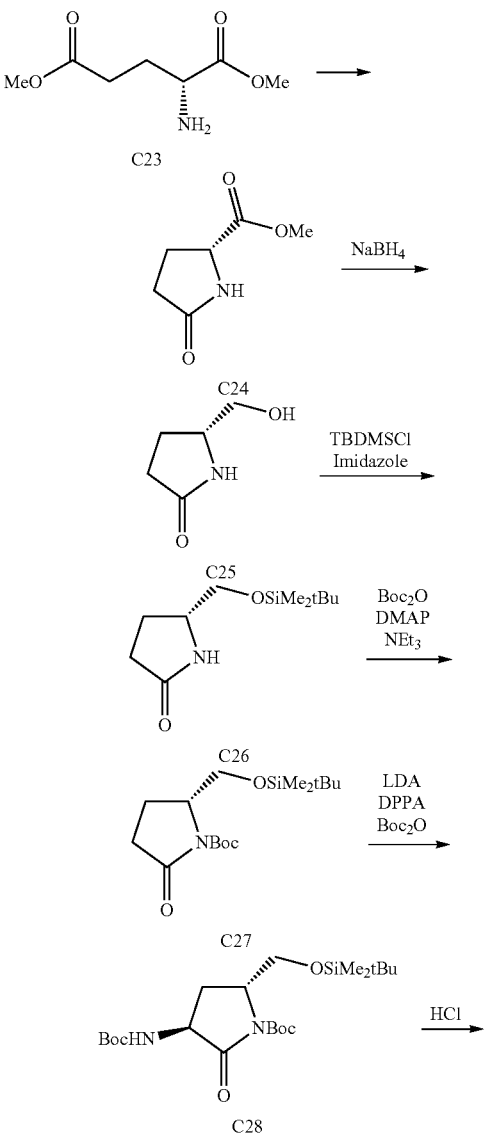

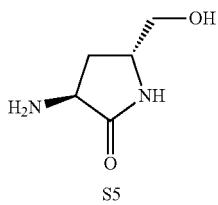

Step 1. Synthesis of methyl (2R)-5-oxopyrrolidine-2-carboxylate (C24

A solution of dimethyl (2R)-2-aminopentanedioate hydrochloride salt C23 (25 g, 118.2 mmol) in Toluene (300 mL) was heated under reflux for 4 h. The solvent was removed and purification by silica gel column chromatography (Eluent: 5-6% MeOH in $CH_2Cl_2$) afforded the product as a light brown oil (12 g, 71%). $^1H$ NMR (400 MHz, $CDCl_3$) δ: 6.39 (s, 1H), 4.26 (s, 1H), 3.76 (s, 3H), 2.46 (m, 1H), 2.36 (m, 2H), 2.02 (m, 1H).

Step 2. Synthesis of (5R)-5-(hydroxymethyl)pyrrolidin-2-one (C25

$NaBH_4$ (5.3 g, 5.6 mL, 140.8 mmol) was added to a solution of methyl (2R)-5-oxopyrrolidine-2-carboxylate C24 (5 g, 34.9 mmol) in IPA (50 mL). The mixture was allowed to stir at room temperature for 20 h. Methanol (5 mL) was added drop-wise to the reaction mixture, which was then concentrated in vacuo. Purification by silica gel chromatography (2-4% MeOH in $CH_2Cl_2$) afforded the product which was used in the subsequent step without further purification (3 g, 75%).

Step 3. Synthesis of (5R)-5-[[tert-butyl(dimethyl)silyl]oxymethyl]pyrrolidin-2-one (C26

To a solution of (5R)-5-(hydroxymethyl)pyrrolidin-2-one C25 (10 g, 86.9 mmol) in $CH_2Cl_2$ (100 mL) was added imidazole (14.8 g, 217.2 mmol) and TBDMSCl (15.7 g, 104.2 mmol). The reaction mixture was stirred at room temperature for 6 h. Water (50 mL) was added and the reaction mixture extracted with $CH_2Cl_2$ (100 mL). The organic layer was dried over $Na_2SO_4$ and concentrated in vacuo afford the product (18 g, 90%) $^1H$ NMR (400 MHz, $CDCl_3$) δ 6.02 (s, 1H), 3.73-3.71 (m, 1H), 3.60 (dd, J=10.08, 10.08 Hz, 1H), 3.44-3.40 (m, 1H), 2.34-2.29 (m, 2H), 2.17-2.12 (m, 1H), 1.73-1.71 (m, 1H), 0.88 (s, 9H), 0.04 (s, 6H). LCMS m/z 230.2 $[M+H]^+$.

Step 4. Synthesis of tert-butyl (2R)-2-[[tert-butyl(dimethyl)silyl]oxymethyl]-5-oxo-pyrrolidine-1-carboxylate (C27

To a solution of (5R)-5-[[tert-butyl(dimethyl)silyl]oxymethyl]pyrrolidin-2-one C26 (12.5 g, 54.5 mmol) in $CH_2Cl_2$ (50 mL) at 0° C. was added Boc anhydride (23.8 g, 109 mmol), DMAP (6.7 g, 54.5 mmol) and triethyl amine (5.5 g, 7.6 mL, 54.5 mmol) and the mixture allowed to stir at room temperature for 16 h. Water (50 mL) was added to the reaction mixture and extracted with $CH_2Cl_2$ (50 mL×3). Combined organic layers were dried over $Na_2SO_4$ and concentrated in vacuo. Purification by silica gel chromatography (Gradient: 10% EtOAc in hexane) provided the product as a light yellow oil (15 g, 82%). $^1H$ NMR (400 MHz, $CDCl_3$) δ 4.16-4.14 (m, 1H), 3.90 (dd, J=10.4, 4.0 Hz, 1H), 3.68 (dd, J=10.5, 2.3 Hz, 1H), 2.69 (dt, J=17.5, 10.4 Hz, 1H), 2.36 (ddd, J=17.6, 9.7, 2.3 Hz, 1H), 2.04 (dq, J=22.6, 11.9, 11.4 Hz, 2H), 1.52 (s, 9H), 0.87 (s, 9H), 0.03 (s, 6H). LCMS m/z 330.0 $[M+H]^+$.

Step 5. Synthesis of tert-butyl (3S,5R)-3-(tert-butoxycarbonylamino)-5-[[tert-butyl(dimethyl)silyl]oxymethyl]-2-oxo-pyrrolidine-1-carboxylate (C28

A solution of LDA (13.6 mL of 2 M in THF, 27.0 mmol) was cooled to −78° C., and a solution of tert-butyl (2R)-2-[[tert-butyl(dimethyl)silyl]oxymethyl]-5-oxo-pyrrolidine-1-carboxylate C27 (6 g, 18.2 mmol) in THF (80 mL) was added. After 30 minutes, DPPA (12.5 g, 9.8 mL, 45.5 mmol) was added and the mixture was stirred for 5 minutes. Boc anhydride (9.9 g, 10.5 mL, 45.5 mmol) was then added and the mixture stirred for 16 h. Water (100 mL) was added and the mixture extracted with EtOAc (100 mL×3). The combined organic layers were dried over $Na_2SO_4$, and concentrated in vacuo. Purification by silica gel chromatography (Eluent: 5-6% EtOAc in hexane) afforded the product as a light yellow oil (2.7 g, 24%). $^1H$ NMR (400 MHz, DMSO-$d_6$) δ 7.08 (d, J=8.76 Hz, 1H), 4.41 (d, J=11.12 Hz, 1H), 4.06 (d, J=8.48 Hz, 1H), 3.89 (dd, J=10.56, 10.6 Hz, 1H), 3.66 (d, J=9.96 Hz, 1H), 2.15-2.02 (m, 2H), 1.45-1.34 (m, 18H), 0.85 (s, 9H), 0.03 (d, J=6.8, 6H). LCMS m/z 445.3 $[M+H]^+$.

Step 6. Synthesis of (3S,5R)-3-amino-5-(hydroxymethyl)pyrrolidin-2-one hydrochloride (S5

To a solution of tert-butyl (3S,5R)-3-(tert-butoxycarbonylamino)-5-[[tert-butyl(dimethyl)silyl]oxymethyl]-2-oxo-pyrrolidine-1-carboxylate C28 (1.5 g, 3.4 mmol) at 0° C. was added in HCl in 1,4-dioxane (20 mL of 4 M, 80 mmol). The mixture was allowed to stir at room temperature for 1.5 h. The mixture was concentrated in vacuo, and the residue washed with diethyl ether to afford the product as the hydrochloride salt (500 mg, 80%). $^1H$ NMR (400 MHz, DMSO-$d_6$) δ 8.42-8.35 (m, 4H), 3.88 (d, J=4.88 Hz, 1H), 3.57 (d, J=8.0 Hz, 1H), 3.40-3.36 (m, 2H), 2.28-2.23 (m, 1H), 2.11-1.98 (m, 1H). LCMS m/z 131.0 $[M+H]^+$.

Preparation S6

(3S,5S)-3-amino-5-(fluoromethyl)pyrrolidin-2-one (S6

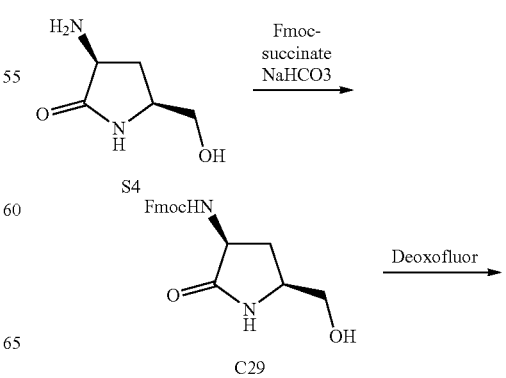

-continued

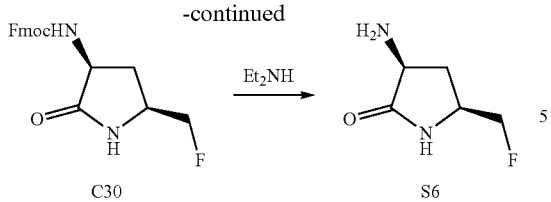

Step 1. Synthesis of 9H-fluoren-9-ylmethyl N-[(3S,5S)-5-(hydroxymethyl)-2-oxo-pyrrolidin-3-yl]carbamate (C29

A solution of Fmoc-oSu (746 mg, 2.2 mmol) in MeCN (4 mL) was added to a solution of (3S,5S)-3-amino-5-(hydroxymethyl)pyrrolidin-2-one S4 (320 mg, 2.5 mmol) in aqueous $NaHCO_3$ (6 mL). Then reaction was stirred at room temperature for 2 h. The reaction mixture was then filtered, washed with water and hexane, then dried under vacuum to afford the product as an off-white solid (410 mg, 32%). $^1H$ NMR (400 MHz, DMSO-$d_6$) δ 7.95-7.86 (m, 2H), 7.80 (s, 1H), 7.70 (t, J=8.6 Hz, 2H), 7.54 (t, J=10.4 Hz, 1H), 7.39 (ddt, J=35.4, 14.4, 7.4 Hz, 4H), 4.85-4.76 (m, 1H), 4.25 (dd, J=17.6, 6.4 Hz, 2H), 3.46 (s, 1H), 2.75 (s, 1H). LCMS m/z 353.0 $[M+H]^+$.

Step 2. Synthesis of 9H-fluoren-9-ylmethyl N-[(3S,5S)-5-(fluoromethyl)-2-oxo-pyrrolidin-3-yl]carbamate (C30

To a solution of 9H-fluoren-9-ylmethyl N-[(3S,5S)-5-(hydroxymethyl)-2-oxo-pyrrolidin-3-yl]carbamate C29 (100 mg, 0.28 mmol) in $CH_2Cl_2$ (2.8 mL) was cooled to 0° C., then Deoxo-Fluor® (0.14 mL of 50% w/w, 0.31 mmol) was added. The mixture was stirred at room temperature for 4 h. The reaction mixture was diluted with water and extracted with $CH_2Cl_2$. The organic layer was dried over anhydrous magnesium sulfate, then concentrated in vacuo. Purification by silica gel chromatography (Eluent: 2% MeOH in $CH_2Cl_2$) afforded the product as an off-white solid which was used directly in the subsequent step (50 mg, 48%). LCMS m/z 355.0 $[M+H]^+$.

Step 3. Synthesis of (3S,5S)-3-amino-5-(fluoromethyl)pyrrolidin-2-one (S6

To a solution of 9H-fluoren-9-ylmethyl N-[(3S,5S)-5-(fluoromethyl)-2-oxo-pyrrolidin-3-yl]carbamate C30 (70 mg, 0.20 mmol) in THF (3 mL) was added diethyl amine (0.01 mL of 4 M, 0.04 mmol) and the reaction mixture was allowed to stir at room temperature for 2 h. The mixture was evaporated under reduced pressure, then diethyl ether-HCl was added and the mixture stirred for an additional 30 minutes. The mixture was concentrated in vacuo with pentane to afford the product as an off-white solid (20 mg, 60%). $^1H$ NMR (400 MHz, DMSO-$d_6$) 8.68 (s, 1H), 8.36 (brs, 2H), 4.57-4.43 (m, 1H), 4.38-4.24 (m, 1H), 4.00-3.98 (m, 1H), 3.87 (s, 1H), 2.43-2.32 (m, 1H), 1.69-1.66 (m, 1H).

Preparation S7

(3S,5R)-3-amino-5-(fluoromethyl)pyrrolidin-2-one (S7

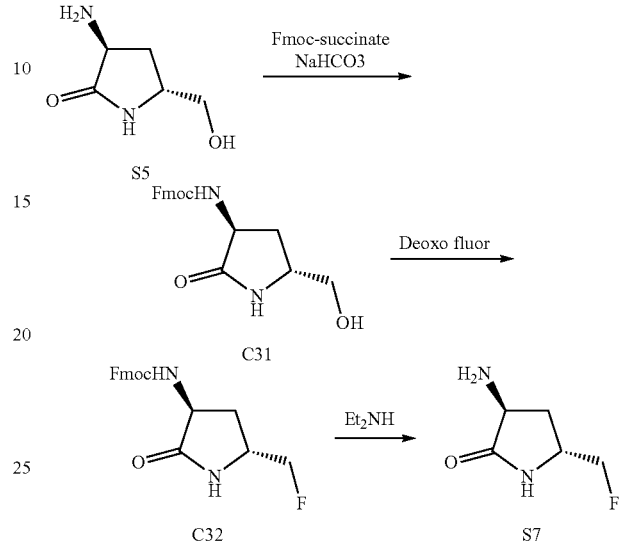

Step 1. Synthesis of 9H-fluoren-9-ylmethyl N-[(3S,5R)-5-(hydroxymethyl)-2-oxo-pyrrolidin-3-yl]carbamate (C31

9H-fluoren-9-ylmethyl N-[(3S,5R)-5-(hydroxymethyl)-2-oxo-pyrrolidin-3-yl]carbamate C31 was prepared from (3S,5R)-3-amino-5-(hydroxymethyl)pyrrolidin-2-one S5 (100 mg, 0.7684 mmol) as described in preparation S6 (130 mg, 47%). $^1H$ NMR (400 MHz, DMSO-$d_6$) δ7.89 (d, J=7.52 Hz, 2H), 7.80 (s, 1H), 7.71 (d, J=7.32 Hz, 2H), 7.52 (d, J=9.0 Hz, 2H), 7.41 (t, J=7.2 Hz, 2H), 7.33 (t, J=7.32 Hz, 2H), 4.88-4.86 (m, 1H), 4.29-4.28 (m, 2H), 4.23-4.12 (m, 2H), 3.44 (s, 1H), 3.32 (s, 1H), 2.16-2.11 (m, 1H), 1.95-1.92 (m, 1H). LCMS m/z 353.1 $[M+H]^+$.

Step 2. Synthesis of 9H-fluoren-9-ylmethyl N-[(3S,5R)-5-(fluoromethyl)-2-oxo-pyrrolidin-3-yl]carbamate (C32

9H-fluoren-9-ylmethyl N-[(3S,5R)-5-(fluoromethyl)-2-oxo-pyrrolidin-3-yl]carbamate C32 was prepared from 9H-fluoren-9-ylmethyl N-[(3S,5R)-5-(hydroxymethyl)-2-oxo-pyrrolidin-3-yl]carbamate C31 (600 mg, 1.7 mmol) as described in preparation S6 (170 mg, 27%). $^1H$ NMR (400 MHz, DMSO-$d_6$) δ 8.08 (s, 1H), 7.98 (d, J=7.44 Hz, 2H), 7.70 (d, J=7.36 Hz, 2H), 7.58 (d, J=8.68 Hz, 1H), 7.41 (t, J=7.28 Hz, 2H), 7.33 (t, J=7.4 Hz, 2H), 4.43 (d, J=3.88 Hz, 1H), 4.31-4.20 (m, 4H), 4.11 (d, J=9.24 Hz, 1H), 3.76-3.69 (m, 2H), 2.17-1.98 (m, 2H). LCMS m/z 355.2 $[M+H]^+$.

Step 3. Synthesis of (3S,5R)-3-amino-5-(fluoromethyl)pyrrolidin-2-one Hydrochloride (S7

(3S,5R)-3-amino-5-(fluoromethyl)pyrrolidin-2-one hydrochloride salt S7 was prepared from 9H-fluoren-9-ylmethyl N-[(3S,5R)-5-(fluoromethyl)-2-oxo-pyrrolidin-3-yl]carbamate C32 (170 mg, 0.5 mmol) as described in preparation S6. (49 mg, 61%) ¹H NMR (400 MHz, DMSO-d₆) δ 8.58 (s, 1H), 8.10-7.85 (m, 2H), 4.46 (d, J=3.8 Hz, 1H), 4.34 (d, J=3.76 Hz, 1H), 3.83 (t, J=9.4 Hz, 2H), 2.32-2.11 (m, 2H). LCMS m/z 133.0 [M+H]⁺.

Preparation S8

(3S,4S)-3-amino-4-methyl-pyrrolidin-2-one (S8

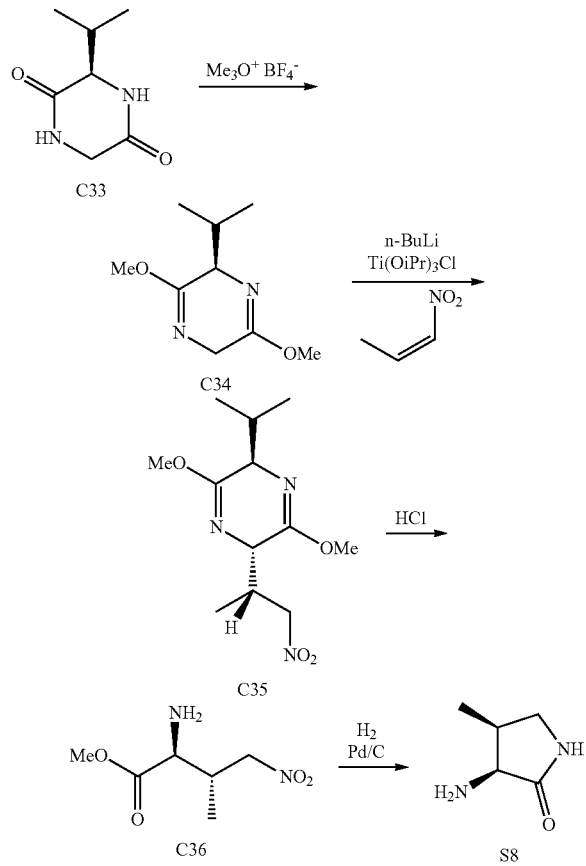

Step 1. Synthesis of (2R)-2-isopropyl-3,6-dimethoxy-2,5-dihydropyrazine (C34

To a mixture of (3R)-3-isopropylpiperazine-2,5-dione C33 (2 g, 12.8 mmol) and trimethyloxonium tetrafluoroborate (6.6 g, 44.8 mmol) was added CH₂Cl (50 mL). The mixture was stirred at room temperature for 24 h. The resulting solid was collected by filtration under a nitrogen atmosphere, and washed with CH₂Cl (300 mL). The solid was added in portions to a vigorously stirred mixture of saturated aqueous NaHCO₃ and CH₂Cl at 4° C., while maintaining the pH between 8-9 with simultaneous addition of 3 M aqueous NaOH as required. The mixture was separated, and the aqueous phase was extracted with CH₂Cl₂. The combined organic phases were washed with brine, dried, and concentrated under in vacuo. Purification by silica gel chromatography afforded the product (1.5 g, 64%). ¹H NMR (400 MHz, DMSO-d₆) 3.99-3.89 (m, 3H), 3.63 (s, 3H), 3.60 (s, 3H, 2.15 (dtt, J=10.3, 6.9, 3.5 Hz, 1H), 0.98 (d, J=6.9 Hz, 3H), 0.67 (d, J=6.8 Hz, 3H). LCMS m/z 185.0 [M+H]⁺.

Step 2. Synthesis of (2R,5S)-2-isopropyl-3,6-dimethoxy-5-[(1S)-1-methyl-2-nitro-ethyl]-2,5-dihydropyrazine (C35 n-Butyllithium (5.2 mL of 2.5 M, 13.0 mmol) was added to a solution of (2R)-2-isopropyl-3,6-dimethoxy-2,5-dihydropyrazine C34 (2 g, 10.9 mmol) in THF (25 mL) at −78° C. Upon stirring for 15 minutes, TiCl(OiPr)₃ (11.9 mL of 1 M, 11.9 mmol) was added and stirring continued for 1 h. This solution was then added to a pre-cooled solution (−78° C.) of (Z)-1-nitroprop-1-ene (1.1 g, 13.0 mmol) in THF and stirring continued for 12 h. Phosphate buffer (25 mL, pH 7) was added and the reaction mixture was allowed to warm up to −40° C. Water (25 mL) was added, the aqueous layer was extracted with diethyl ether (4×50 mL) and the combined organic layers were dried over Na₂SO₄. Silica gel chromatography afforded the product (1.6 g, 54%). ¹H NMR (400 MHz, CDCl₃) δ 4.72 (ddd, J=12.6, 6.8, 3.2 Hz, 1H), 4.47-4.27 (m, 1H), 4.22-4.03 (m, 1H), 4.01-3.84 (m, 2H), 3.73-3.61 (m, 6H), 2.23 (dtq, J=9.8, 6.8, 3.0 Hz, 1H), 1.17-1.07 (m, 2H), 1.11-0.99 (m, 3H), 0.79-0.66 (m, 3H), 0.69-0.62 (m, 2H).

Step 3. Synthesis of methyl (2S,3S)-2-amino-3-methyl-4-nitro-butanoate (C36

A suspension of (2R,5S)-2-isopropyl-3,6-dimethoxy-5-[(1S)-1-methyl-2-nitro-ethyl]-2,5-dihydropyrazine C35 (630 mg, 2.3 mmol) in HCl (18.6 mL of 0.25 M, 4.6 mmol) and THF (2 mL) was allowed to stir at room temperature for 24 h. The mixture was concentrated in vacuo and the aqueous solution was washed with diethyl ether (25 mL). Diethyl ether (25 mL) was then added to the aqueous layer and the mixture was adjusted to pH 8-10 with aqueous ammonia. The layers were separated and the aqueous layer was extracted with diethyl ether (2×25 mL). The combined diethyl ether layers were dried with Na₂SO₄ and concentrated in vacuo. Purification by silica gel chromatography afforded the product (300 mg, 73%). ¹H NMR (400 MHz, CDCl₃) δ 4.62-4.66 (m, 1H), 4.32-4.38 (m, 1H), 3.76 (s, 3H), 3.49 (d, J=6 Hz, 1H), 2.70 (brs, 1H), 1.06 (d, J=6.8 Hz, 3H).

Step 4. Synthesis of (3S,4S)-3-amino-4-methyl-pyrrolidin-2-one (S8

To a suspension of methyl (2S,3S)-2-amino-3-methyl-4-nitro-butanoate C36 (310 mg, 1.76 mmol) in MeOH was added 10% Pd on carbon (132.9 mg, 0.62 mmol). The mixture was stirred under an atmosphere of hydrogen at room temperature for 3 h. Then the reaction mixture was filtered through Celite®, washed with MeOH and concentrated in vacuo. Purification by chromatography on neutral alumina (Eluent: 1-2% MeOH in CH₂Cl₂) afforded the product as a hydrochloride salt (80 mg, 30%) ¹H NMR (400 MHz, CD₃OD) δ 3.64 (d, J=10.6 Hz, 1H), 3.51 (t, J=8.44 Hz, 1H), 3.02 (t, J=9.6 Hz, 1H), 2.48-2.45 (m, 1H), 1.28 (d, J=2.84 Hz, 3H).

Preparation S9 and S10

3-[5,7-difluoro-2-(4-fluorophenyl)-1H-indol-3-yl]-N-[(3R,4S)-4-hydroxy-2-oxo-pyrrolidin-3-yl]propanamide (S9) and of 3-[5,7-difluoro-2-(4-fluorophenyl)-1H-indol-3-yl]-N-[(3R,4R)-4-hydroxy-2-oxo-pyrrolidin-3-yl]propanamide (S10

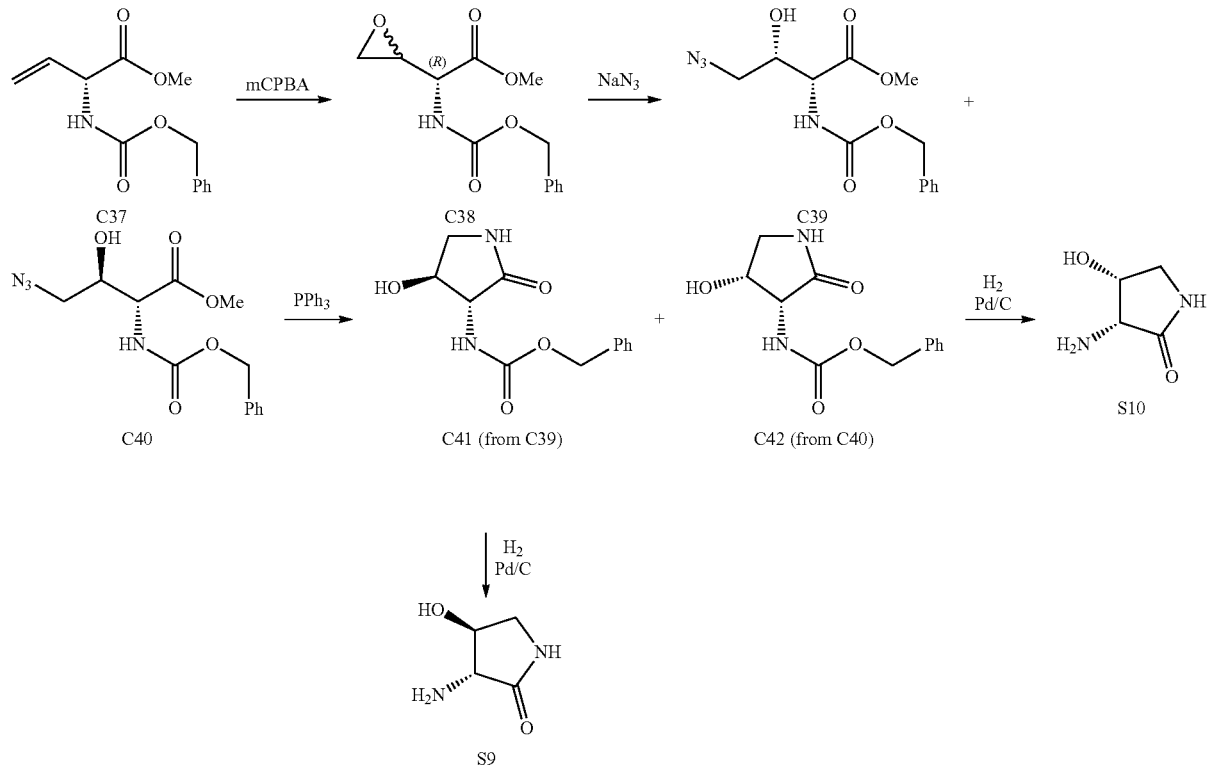

Step 1. Synthesis of methyl (2R)-2-(((benzyloxy)carbonyl)amino)-2-(oxiran-2-yl)acetate (C38

To methyl (2R)-2-(benzyloxycarbonylamino)but-3-enoate C37 (2.4 g, 9.7 mmol) in CH$_2$Cl$_2$ (40 mL) was added mCPBA (4.8 g of 70% w/w, 19.5 mmol). The mixture was heated at reflux for 5 h. Additional mCPBA (2.4 g of 70% w/w, 9.7 mmol) was added and the mixture allowed to stir for a further 30 minutes. A saturated solution of Na$_2$HSO$_3$ (sodium bisulfite) and then 100 mL CH$_2$Cl$_2$ were added. The CH$_2$Cl$_2$ layer was washed with NaHCO$_3$ and brine. Purification by chromatography on silica gel (Gradient: 0 to 100% Ethyl acetate in heptane) afforded methyl (2R)-2-(((benzyloxy)carbonyl)amino)-2-(oxiran-2-yl)acetate as a mixture of diastereomers which were used in the subsequent step without separation (1.6 g, 60%). $^1$H NMR (300 MHz, CDCl$_3$) δ 7.48-7.30 (m, 5H), 5.27 (d, J=8.9 Hz, 1H), 5.14 (d, J=1.2 Hz, 2H), 4.82-4.68 (m, 1H), 3.83 (d, J=4.4 Hz, 3H), 3.49 (d, J=3.7 Hz, 1H), 2.90-2.75 (m, 1H), 2.70 (dd, J=4.7, 2.6 Hz, 1H). LCMS m/z 266.2 [M+H]$^+$.

Step 2. Synthesis of methyl (2R,3S)-4-azido-2-(benzyloxycarbonylamino)-3-hydroxy-butanoate (C39) and methyl (2R,3R)-4-azido-2-(((benzyloxy)carbonyl)amino)-3-hydroxybutanoate (C40

A mixture of methyl (2R)-2-(benzyloxycarbonylamino)-2-(oxiran-2-yl)acetate C38 (476 mg, 1.7 mmol), sodium azide (1.1 g, 17.1 mmol) and NH$_4$Cl (100 mg, 1.9 mmol) in DMF (4 mL) was heated at 60° C. overnight. Water (60 mL) was added and the mixture extracted with EtOAc (120 mL). The organic phase was dried and concentrated in vacuo to afford the product as a mixture of major and minor diastereomers, methyl (2R,3S)-4-azido-2-(((benzyloxy)carbonyl)amino)-3-hydroxybutanoate C39 and methyl (2R,3R)-4-azido-2-(((benzyloxy)carbonyl)amino)-3-hydroxybutanoate C40 which were progressed, without separation, to the subsequent step. The 2R,3S diastereomer C39 is presumed to be the major component. LCMS m/z 308.9 [M+H]$^+$.

Step 3. Synthesis of benzyl N-[(3R,4S)-4-hydroxy-2-oxo-pyrrolidin-3-yl]carbamate (C41) and Benzyl N-[(3R,4R)-4-hydroxy-2-oxo-pyrrolidin-3-yl]carbamate (C42

To a solution of methyl (2R,3S)-4-azido-2-(benzyloxycarbonylamino)-3-hydroxy-butanoate C39 and (2R,3R)-4-azido-2-(((benzyloxy)carbonyl)amino)-3-hydroxybutanoate C40 (543 mg, 1.708 mmol) in a mixture of MeOH (8 mL), THF (6 mL), and water (4 mL), was added PPh$_3$ (1.56 g, 5.9 mmol). The mixture was heated at 90° C. for 5 days. Purification by reverse phase HPLC (C18 Column; Gradient: Acetonitrile in water with 0.1% TFA) to provide the two diastereomers C41 and C42.

C41 is the major peak and is presumed to be benzyl N-[(3R,4S)-4-hydroxy-2-oxo-pyrrolidin-3-yl]carbamate (86 mg, 20%). $^1$H NMR (300 MHz, CD$_3$OD) δ 7.51-7.23 (m, 5H), 5.12 (s, 2H), 4.41 (q, J=7.8 Hz, 1H), 4.06 (d, J=8.3 Hz, 1H), 3.56 (dd, J=9.8, 7.7 Hz, 1H), 3.10 (dd, J=9.9, 7.3 Hz, 1H). LCMS m/z 251.07 [M+H]$^+$.

C42 is the minor peak and is presumed to be benzyl N-[(3R,4R)-4-hydroxy-2-oxo-pyrrolidin-3-yl]carbamate (15 mg, 3%). $^1$H NMR (300 MHz, CD$_3$OD) δ 7.51-7.15 (m, 5H), 5.15 (s, 2H), 4.53-4.32 (m, 2H), 3.60 (dd, J=11.2, 3.7 Hz, 1H), 3.25 (d, J=11.3 Hz, 1H). LCMS m/z 251.1 [M+H]$^+$.

Step 4. Synthesis of 3-[5,7-difluoro-2-(4-fluorophenyl)-1H-indol-3-yl]-N-[(3R,4S)-4-hydroxy-2-oxo-pyrrolidin-3-yl]propanamide (S9

To a suspension of benzyl N-[(3R,4S)-4-hydroxy-2-oxo-pyrrolidin-3-yl]carbamate C41 (86 mg, 0.34 mmol) in 20 mL MeOH was added 5% Palladium on carbon catalyst (20 mg). The mixture was subjected to hydrogenation conditions of 50 psi H$_2$ for 4 h. Filtration through a pad of Celite®, washing with MeOH and CH$_2$Cl$_2$, then concentration of the filtrate in vacuo afforded hydroxy lactam S9 which was used in subsequent step without further purification. $^1$H NMR (300 MHz, CD$_3$OD) δ 4.26-4.18 (m, 1H), 3.42 (dd, J=11.2, 3.9 Hz, 1H), 3.33 (d, J=5.1 Hz, 1H), 3.11 (d, J=11.2 Hz, 1H).

Step 5. Synthesis of 3-[5,7-difluoro-2-(4-fluorophenyl)-1H-indol-3-yl]-N-[(3R,4R)-4-hydroxy-2-oxo-pyrrolidin-3-yl]propanamide (S10

To a suspension of benzyl N-[(3R,4R)-4-hydroxy-2-oxo-pyrrolidin-3-yl]carbamate C42 (15 mg, 0.06 mmol) in MeOH (10 mL) was added 5% Palladium on carbon catalyst (10 mg). The mixture was subjected to hydrogenation conditions of 50 psi H$_2$ for 4 h. Filtration through a pad of Celite®, washing with MeOH and CH$_2$Cl$_2$, then concentration of the filtrate in vacuo afforded hydroxy lactam S10 which was used in subsequent steps without further purification.

Preparation S11

6-amino-4-azaspiro[2.4]heptan-5-one (S11

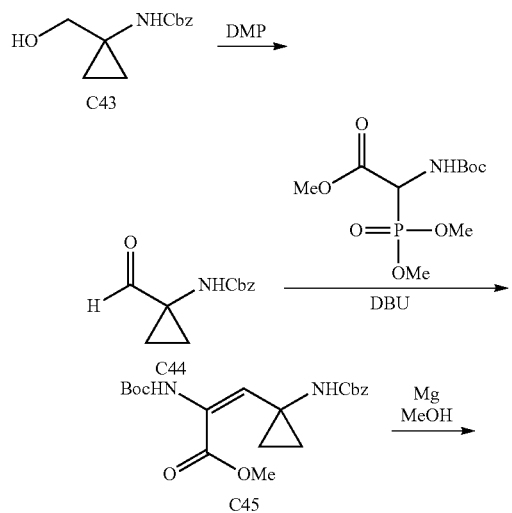

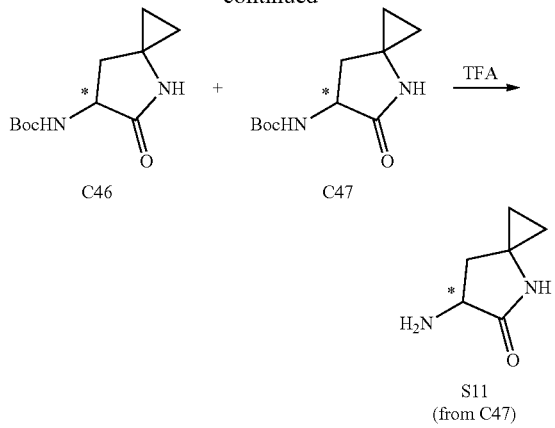

Step 1. Synthesis of Benzyl N-(1-formylcyclopropyl)carbamate (C44

To a solution of benzyl N-[1-(hydroxymethyl)cyclopropyl]carbamate C43 (7.8 g, 35.3 mmol) in CH$_2$Cl$_2$ (160 mL) was added Dess Martin Periodinane (22.4 g, 52.9 mmol) at 0° C. and the reaction mixture stirred at room temperature for 3 h. Upon completion, the reaction was quenched with mixture of saturated NaHCO$_3$ (100 mL) and sodium thiosulfate solution (100 mL). The mixture was extracted with CH$_2$Cl$_2$ and combined organic layers were dried over anhydrous sodium sulfate. Purification by silica gel chromatography (Eluent: 15% EtOAc in hexane) afforded the product as a light yellow solid (7.5 g, 78%). $^1$H NMR (400 MHz, CDCl$_3$) δ 9.12 (s, 1H), 7.35 (m, 5H), 5.35 (s, 1H), 5.13 (s, 2H), 1.53 (m, 2H), 1.38 (s, 2H). LCMS m/z 220.0 [M+H]$^+$.

Step 2. Synthesis of methyl (Z)-3-[1-(benzyloxycarbonylamino)cyclopropyl]-2-(tert-butoxycarbonylamino)prop-2-enoate (C45

To a solution of benzyl N-(1-formylcyclopropyl)carbamate C44 (7.5 g, 34.2 mmol) in CH$_2$Cl$_2$ (350 mL) was added N-Boc-2-Phosphonoglycine trimethyl ester (20.3 g, 68.4 mmol) and DBU (10.4 g, 10.2 mL, 68.4 mmol) and the mixture was stirred at room temperature overnight. The reaction mixture was quenched with saturated aqueous NH$_4$Cl and extracted into CH$_2$Cl$_2$ (2×100 mL). The organic layer was dried over anhydrous sodium sulfate and evaporated. Purification by silica gel chromatography (Eluent: 20% EtOAc in hexane) afforded the product as white solid. (10 g, 75%). $^1$H NMR (400 MHz, DMSO-d$_6$) δ 8.21 (s, 1H), 7.73 (s, 1H), 7.38-7.31 (m, 5H), 5.98 (s, 1H), 4.99 (s, 2H), 3.71-3.68 (m, 3H), 1.38 (d, J=11.1 Hz, 9H), 1.02 (d, J=4.6 Hz, 4H). LCMS m/z 391.0 [M+H]$^+$.

Step 3. tert-butyl N-(5-oxo-4-azaspiro[2.4]heptan-6-yl)carbamate (C46) and tert-butyl N-(5-oxo-4-azaspiro[2.4]heptan-6-yl)carbamate (C47

Mg (8.7 g, 358.6 mmol) was added to a solution of methyl (Z)-3-[1-(benzyloxycarbonylamino)cyclopropyl]-2-(tert-butoxycarbonylamino)prop-2-enoate C45 (14 g, 35.9 mmol) in MeOH (140 mL) and the mixture allowed to stir at 0° C. for 4 h, then at 25° C. for 8 h. Upon completion, the reaction mixture was neutralized with NH$_4$Cl solution, and extracted with EtOAc (3×100 mL). The organic phase was washed with brine (50 mL), dried over anhydrous sodium sulfate and concentrated in vacuo. The crude product mixture was purified by silica gel chromatography (Eluent: 50% EtOAc in hexane) to afford the racemic product. Purification by chiral HPLC [Chiralpak IA column (21.0×250 mm), 5μ Mobile phase: n-Hexane/EtOH/Dichloromethane: 50/25/25 Flow rate: 21.0 mL/min] afforded single enantiomers C46 and C47, both as white solids.

C46 was the first eluting enantiomer. (Yield 2 g, 24%) $^1$H NMR (400 MHz, DMSO-d$_6$) δ 7.78 (s, 1H), 7.11 (d, J=8.9 Hz, 1H), 4.23 (q, J=9.3 Hz, 1H), 2.15 (t, J=11.4 Hz, 1H), 2.06-1.97 (m, 1H), 1.39 (s, 9H), 0.74 (m, 1H), 0.64 (m, 1H), 0.53 (m, 2H). LCMS m/z 227.0 [M+H]$^+$.

C47 was the second eluting enantiomer. (2 g, 24%) $^1$H NMR (400 MHz, DMSO-d$_6$) δ 7.78 (s, 1H), 7.11 (d, J=8.9 Hz, 1H), 4.23 (q, J=9.4 Hz, 1H), 2.15 (t, J=11.4 Hz, 1H), 2.02 (m, 1H), 1.39 (s, 9H), 0.81-0.59 (m, 2H), 0.53 (m, 2H). LCMS m/z 227.0 [M+H]$^+$.

Step 4. Synthesis of
6-amino-4-azaspiro[2.4]heptan-5-one Hydrochloride
(S11

To a stirred solution of tert-butyl N-(5-oxo-4-azaspiro [2.4]heptan-6-yl)carbamate C47 (850 mg, 3.8 mmol) in CH$_2$Cl$_2$ (8 mL) at 0° C. was added TFA (12.8 g, 8.9 mL, 112.7 mmol). The reaction mixture was stirred at room temperature for 2 h. The mixture was then concentrated in vacuo. 4 M HCl in 1,4-dioxane (8 mL) was added and upon stirring for 30 min at room temperature, reaction mixture was concentrated in vacuo. The resulting solid was washed with ether to afford the product as a hydrochloride salt (180 mg, 18%). $^1$H NMR (400 MHz, DMSO-d$_6$) δ 8.51 (s, 3H), 8.39 (s, 1H), 4.15-4.10 (m, 1H), 2.31 (dd, J=12.6, 10.2 Hz, 1H), 2.20 (dd, J=12.7, 8.8 Hz, 1H), 0.86-0.84 (m, 1H), 0.77-0.74 (m, 1H), 0.72-0.66 (m, 2H). LCMS m/z 127.0 [M+H]$^+$.

Preparation S12

(3-[5,7-difluoro-2-(4-fluorophenyl)-1H-indol-3-yl] propanoic Acid) (S12

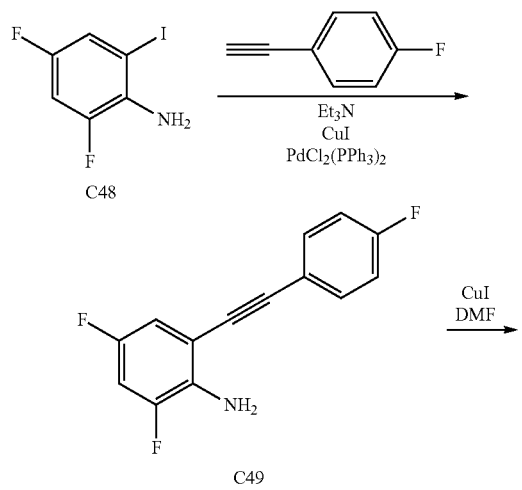

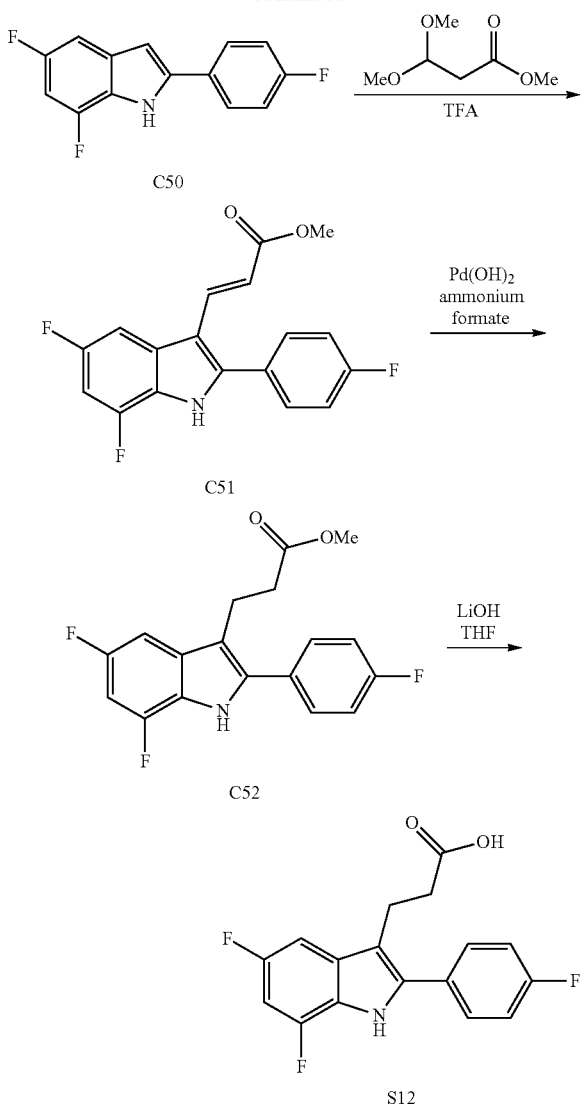

Step 1. Synthesis of 2,4-difluoro-6-[2-(4-fluorophenyl)ethynyl]aniline (C49

Method A: Sonagashira Coupling Method. To a flask containing 2,4-difluoro-6-iodo-aniline C48 (134 g, 525.5 mmol) was added NEt$_3$ (1.3 L), followed by DMF (250 mL), 1-ethynyl-4-fluoro-benzene (83.5 g, 695.1 mmol), CuI (20.5 g, 107.6 mmol), and PdCl$_2$(PPh$_3$)$_2$ (25 g, 35.6 mmol). The mixture was allowed to stir at room temperature for 2 h. Solvent was removed under reduced pressure and water (500 mL) was added. The mixture was extracted with Ethyl acetate, filtered and concentrated in vacuo. The product mixture was filtered through a silica gel plug (Eluent: CH$_2$Cl$_2$), followed by a second silica plug filtration (Eluent: 30-40% EtOAc in Heptane). Silica gel chromatography (Gradient: 0-20% EtOAc in heptane) afforded the product as a pale yellow solid. (87 g, 60%). $^1$H NMR (300 MHz, CDCl$_3$) δ 7.58-7.45 (m, 2H), 7.14-7.02 (m, 2H), 6.92 (ddd, J=8.8, 2.8, 1.7 Hz, 1H), 6.87-6.71 (m, 1H), 4.15 (s, 2H). LCMS m/z 248.0 [M+H]$^+$.

Step 2. Synthesis of 5,7-difluoro-2-(4-fluorophenyl)-1H-indole (C50

Method B: Amine-Alkyne cyclization Method (CuI promoted). To a solution of 2,4-difluoro-6-[2-(4-fluorophenyl)ethynyl]aniline C49 (46 g, 167.5 mmol) in DMF (600 mL) was added CuI (1.9 g, 10.0 mmol) and the reaction was heated at reflux. Water (800 mL) was added and the mixture extracted with MTBE. The mixture was then washed with sat. NaCl solution, dried over $Na_2SO_4$ and then concentrated in vacuo to afford the product, which was used in subsequent steps without further purification (41 g, 87%). $^1H$ NMR (300 MHz, $CDCl_3$) δ 8.43 (s, 1H), 7.72-7.58 (m, 2H), 7.27-7.15 (m, 2H), 7.09 (dd, J=9.0, 2.1 Hz, 1H), 6.85-6.63 (m, 2H). LCMS m/z 248.0 $[M+H]^+$.

Step 3. Synthesis of Methyl (E)-3-[5,7-difluoro-2-(4-fluorophenyl)-1H-indol-3-yl]prop-2-enoate (C51)

Method C: Reductive Alkylation Method (TFA promoted). A 12 L flask with overhead stirrer was charged with 5,7-difluoro-2-(4-fluorophenyl)-1H-indole C50 (300 g, 1.2 mol), $CH_2Cl_2$ (3 L), methyl 3,3-dimethoxypropanoate (195 mL, 1.4 mol) and TFA (300 mL, 3.9 mol). The reaction was heated to reflux for 4 h. Additional $CH_2Cl_2$ was added to facilitate stirring. Upon cooling to room temperature, the solid product was filtered, washed with minimal $CH_2Cl_2$ and dried to afford the product (388 g, 96%). $^1H$ NMR (400 MHz, DMSO-$d_6$) δ 12.66 (s, 1H), 7.77-7.57 (m, 4H), 7.56-7.37 (m, 2H), 7.19 (ddd, J=11.0, 9.7, 2.1 Hz, 1H), 6.47 (d, J=16.1 Hz, 1H), 3.69 (s, 3H). LCMS m/z 332.4 $[M+H]^+$.

Step 4. Synthesis of methyl 3-[5,7-difluoro-2-(4-fluorophenyl)-1H-indol-3-yl]propanoate (C52

Method D: $Pd(OH)_2$ Catalyzed Transfer Hydrogenation. To a suspension of methyl (E)-3-[5,7-difluoro-2-(4-fluorophenyl)-1H-indol-3-yl]prop-2-enoate C51 (80 g, 236.5 mmol) in EtOH (1.5 L) under a nitrogen atmosphere was added $Pd(OH)_2$ (6 g of 20% w/w 8.5 mmol) and ammonium formate (160 g, 2.5 mol). The mixture was heated at reflux for ~3 h, then filtered to remove catalyst. The filtrate was concentrated in vacuo to afford the product as an off-white solid which was used without further purification (82 g, 100%). $^1H$ NMR (300 MHz, $CDCl_3$) δ 8.18 (s, 1H), 7.65-7.47 (m, 2H), 7.27-7.14 (m, 2H), 7.14-7.00 (m, 1H), 6.76 (ddd, J=10.8, 9.4, 2.2 Hz, 1H), 3.65 (s, 3H), 3.27-3.04 (m, 2H), 2.75-2.49 (m, 2H). LCMS m/z 334.3 $[M+H]^+$.

Step 5. Synthesis of 3-[5,7-difluoro-2-(4-fluorophenyl)-1H-indol-3-yl]propanoic Acid (S12

Method E: Ester hydrolysis with LiOH. LiOH (67 g, 2.8 mol) was added to a solution of methyl 3-[5,7-difluoro-2-(4-fluorophenyl)-1H-indol-3-yl]propanoate C52 (217 g, 651.1 mmol) in THF (1 L) and water (100 mL). The mixture was heated at reflux for 2 h, and then allowed to cool overnight. THF was removed by concentration under reduced pressure, and water was added (approx. 1 L). The mixture was cooled on an ice bath and HCl (250 mL of 11.7 M, 2.9 mol) was added to adjust pH to ~4. EtOAc (300 mL) was added, and the aqueous layer extracted with further EtOAc (100 mL). Combined organic extracts were dried over sodium sulfate ($Na_2SO_4$), filtered through a plug of silica gel rinsing with EtOAc. The filtrate was concentrated in vacuo to afford an orange oil (50-75 mL). Heptanes (~50 mL) were added and the mixture chilled on dry ice. Upon agitation, a crystalline solid formed. The mixture was allowed to stir on an ice-bath until to allow completion of the crystallization process. The solid was filtered, washed with heptane and air dried to afford the product (208 g, 96%). $^1H$ NMR (300 MHz, $CDCl_3$) δ 8.15 (s, 1H), 7.60-7.46 (m, 2H), 7.27-7.15 (m, 2H), 7.09 (dd, J=9.1, 2.2 Hz, 1H), 6.77 (ddd, J=10.8, 9.4, 2.2 Hz, 1H), 3.26-3.05 (m, 2H), 2.78-2.57 (m, 2H). LCMS m/z 320.0 $[M+H]^+$.

Alternative Preparation S12

Step 3. Synthesis of methyl (E)-3-[5,7-difluoro-2-(4-fluorophenyl)-1H-indol-3-yl]prop-2-enoate (C51

A reactor was charged with 5,7-difluoro-2-(4-fluorophenyl)-1H-indole C50 (4.0 kg, 16.5 mol), $CH_2Cl_2$ (37 L) and methyl 3,3-dimethoxypropanoate (2.6 L, 18.1 mol) followed by TFA (3.9 L, 51.0 mol) at ambient temperature. The resulting mixture was heated to reflux for 6 h. The batch was then cooled to 20° C., charged with n-heptane (2 vol) and filtered. The filter cake was dried under vacuum at 45° C. to afford the product in ~90% yield. $^1H$ NMR (300 MHz, DMSO-$d_6$) δ 12.63 (s, 1H), 7.76-7.54 (m, 4H), 7.55-7.39 (m, 2H), 7.18 (ddd, J=11.1, 9.7, 2.2 Hz, 1H), 6.46 (d, J=16.1 Hz, 1H), 3.69 (s, 3H). LCMS m/z 332.1 $[M+H]^+$.

Step 4. Synthesis of Methyl 3-[5,7-difluoro-2-(4-fluorophenyl)-1H-indol-3-yl]propanoate (C52

Methyl (E)-3-[5,7-difluoro-2-(4-fluorophenyl)-1H-indol-3-yl]prop-2-enoate C51 (1.5 kg, 9.06 mol) was slurried with THF (7 L) in a vessel. $Pd(OH)_2$ (10 g of 20% w/w, ~50% water, 0.014 mol) was charged. The mixture was purged with N2 three times, then once with $H_2$ and the vessel pressurized to 50 psi with $H_2$. The mixture was agitated at 20° C. until $H_2$ uptake ceased. After 1.5 h, the mixture was purged with N2 (×3) and filtered through Solka-Floc using a THF (2 vol) rinse. The resulting filtrate was concentrated in vacuo at 45° C. (to 1.5 vol), charged with cyclohexane (1 vol), and concentrated again (to 1.5 vol) at 45° C. The slurry was cooled to 15-20° C. and filtered. The filter cake was then washed with cold cyclohexane (1 vol), and dried under vacuum at 45° C. to afford the product in 95% yield.

Step 5. Synthesis of 3-[5,7-difluoro-2-(4-fluorophenyl)-1H-indol-3-yl]propanoic Acid (S12

A mixture of methyl 3-[5,7-difluoro-2-(4-fluorophenyl)-1H-indol-3-yl]propanoate C52 (9 kg, 27 mmol) in 2-MeTHF (54 L, 6 vol) and MeOH (8.1 L, 0.9 vol) was charged with 20% KOH (2 equiv, 54 mol). The mixture was stirred at 35° C. for 6 h. The mixture was then distilled under vacuum to 27 L (3 vol) and cooled to 10-15° C. Water (7.5 L) and 2-MeTHF (16 L) were charged and the resulting biphasic mixture was pH adjusted with 6 M HCl to a pH~2. The temperature was adjusted to 20° C. and the phases separated. The organic phase was washed with water (15 L), filtered through Celite® with 2-MeTHF rinse (18 L, 2 vol), and concentrated under vacuum to 18 L (2 vol). 18 L (2 vol) of n-heptane was charged and the batch again concentrated under vacuum to 18 L (3 vol). This cycle was repeated once more and the batch was seeded. 16 L (1.8 vol) n-heptane was charged and the temperature adjusted to 20° C. The slurry was stirred for 2 h, filtered and the cake washed with 2×18 L (2×2 vol) n-heptane. The filter cake was dried under vacuum at 45° C. to afford the desired product in 90% yield. $^1H$ NMR (300 MHz, $CDCl_3$) δ 8.28 (s, 1H), 7.53 (ddd, J=8.7, 5.4, 2.8 Hz, 2H), 7.27-7.13 (m, 2H), 7.08 (dd, J=9.1, 2.1 Hz, 1H), 6.76 (ddd, J=11.3, 9.4, 2.2 Hz, 1H), 3.91-3.69 (m, 4H), 3.28-3.07 (m, 2H), 2.79-2.53 (m, 2H), 2.00-1.74 (m, 3H). LCMS m/z 320.4 [M+H]+.

Compound 1

3-[5,7-difluoro-2-(4-fluorophenyl)-1H-indol-3-yl]-N-[(3S,4S)-4-hydroxy-2-oxo-pyrrolidin-3-yl]propanamide (1

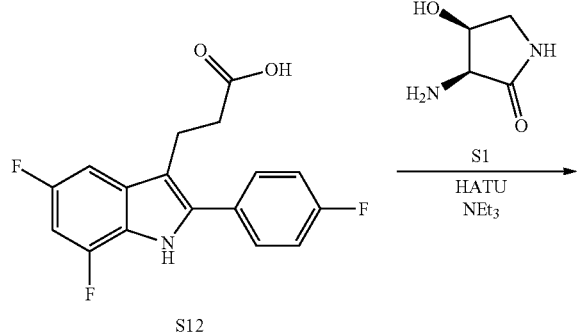

Method F: Amide Coupling with HATU. To a solution of 3-[5,7-difluoro-2-(4-fluorophenyl)-1H-indol-3-yl]-N-[(3S,4S)-4-hydroxy-2-oxo-pyrrolidin-3-yl]propanamide S1 in DMSO (1 mL) was added 3-[5,7-difluoro-2-(4-fluorophenyl)-1H-indol-3-yl]propanoic acid S12 (25 mg, 0.08 mmol), HATU (33 mg, 0.09 mmol) and NEt₃ (30 μL, 0.22 mmol). The mixture was allowed to stir at room temperature for 2 h. The mixture was then purified by reversed phase chromatography (C18 column; Gradient: MeCN in H₂O with 0.2% formic acid) to afford the product (6 mg, 40%). ¹H NMR (300 MHz, CD₃OD) δ 7.68 (ddd, J=9.2, 5.1, 2.3 Hz, 2H), 7.37-7.19 (m, 3H), 6.75 (ddt, J=11.4, 9.6, 1.9 Hz, 1H), 4.68 (d, J=5.1 Hz, 1H), 4.40 (dd, J=5.1, 3.9 Hz, 1H), 3.65-3.57 (m, 1H), 3.26 (d, J=11.3 Hz, 1H), 3.20-3.08 (m, 2H), 2.75-2.64 (m, 2H). LCMS m/z 418.1 [M+H]+.

Compound 2

3-[5,7-difluoro-2-(4-fluorophenyl)-1H-indol-3-yl]-N-[(3S,4R)-4-hydroxy-2-oxo-pyrrolidin-3-yl]propanamide (2

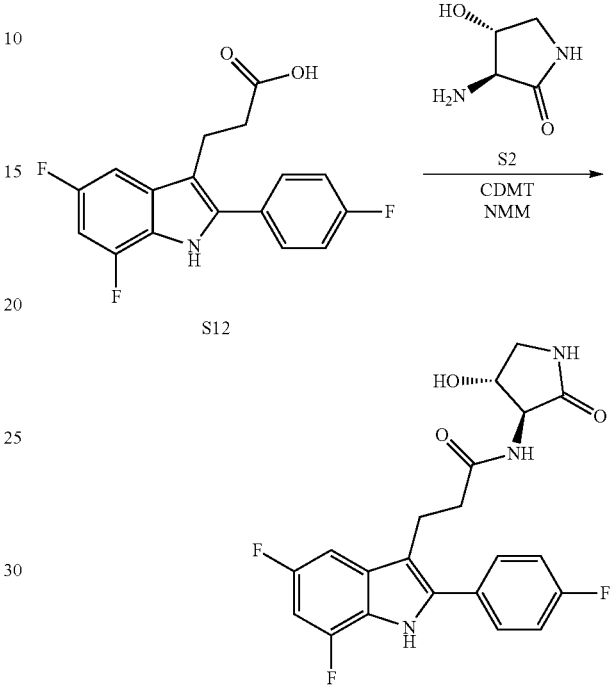

Synthesis of 3-[5,7-difluoro-2-(4-fluorophenyl)-1H-indol-3-yl]-N-[(3S,4R)-4-hydroxy-2-oxo-pyrrolidin-3-yl]propanamide (2

Method G: Amide Coupling with CDMT. A 2 L 3-neck RB flask with magnetic stirrer, temperature probe and nitrogen inlet was charged with 3-[5,7-difluoro-2-(4-fluorophenyl)-1H-indol-3-yl]propanoic acid S12 (90.5 g, 283.5 mmol) and (3S,4R)-3-amino-4-hydroxy-pyrrolidin-2-one S2 (39.9 g, 343.6 mmol) in DMF (1.65 L), and stirred for 15 minutes. CDMT (61.1 g, 348 mmol) was added. The mixture was then cooled to ~2° C. on an ice bath. N-methylmorpholine was added (131 mL, 1.2 mol) dropwise over 20 minutes and the mixture was heated at 30° C. overnight. The reaction mixture was added into approx. 4.5 L of ice water, and extracted with EtOAc (1.2 L×4). The combined organic layers, were washed with 1.2 L of 1 M HCl (×3) and then water (1.2 L) and brine (1.2 L). The combined organic layers were dried over Na₂SO₄, filtered and concentrated. The mixture was washed through a silica gel plug (1.8 L of silica gel), first eluting with 25% EtOAc in dichloromethane (8 L) to remove impurities, followed by hot EtOAc (8 L), to elute the product. The EtOAc filtrate was concentrated in vacuo. TBME was then added (400 mL), and the mixture allowed to stirred for overnight. Filtration of the resulting solid afforded the product as a white solid. 62 g, 52%) ¹H NMR (300 MHz, CD₃OD) δ 7.70-7.58 (m, 2H), 7.29-7.13 (m, 3H), 6.73 (ddd, J=11.1, 9.6, 2.2 Hz, 1H), 4.34 (td, J=7.6, 6.8 Hz, 1H), 4.21 (d, J=7.8 Hz, 1H), 3.56 (dd, J=9.9, 7.6 Hz, 1H), 3.20-3.04 (m, 3H), 2.65-2.53 (m, 2H). LCMS m/z 418.2 [M+H]$^+$. Optical rotation: $[\alpha]_D^{20.7}$=−14.01 (c=1.0, 10 mg in 1 mL of MeOH).

Alternative Procedure for Synthesis of Compound (2)

Step 1. Synthesis of Methyl (E)-3-[5,7-difluoro-2-(4-fluorophenyl)-1H-indol-3-yl]prop-2-enoate (C51

A solution of 5,7-difluoro-2-(4-fluorophenyl)-1H-indole C50 (100 g, 1.0 equiv) in dichloromethane (850 mL, 8.5 vol) was agitated at 22° C. Methyl 3,3-dimethoxypropionate (63 mL, 1.1 equiv) was charged followed by trifluoroacetic acid (96 mL, 3.1 equiv), which was rinsed forward with dichloromethane (25 mL, 0.25 vol). The batch was heated to 38° C. and stirred at that temperature. After 4 h, the batch was cooled to 22° C. and charged with n-heptane (200 mL, 2 vol). The mixture was stirred for no less than 1 h at 22° C. The slurry was filtered, and the reactor and the filter cake were washed with n-heptane (1×2 vol (200 mL) and 1×3 vol (300 mL)). The resulting solid was dried under vacuum with nitrogen bleed at 45° C. to afford the product C51 (127.7 g, 95% yield).

Step 2. Synthesis of Methyl 3-[5,7-difluoro-2-(4-fluorophenyl)-1H-indol-3-yl]propanoate (C52

To a hydrogenator was charged methyl (E)-3-[5,7-difluoro-2-(4-fluorophenyl)-1H-indol-3-yl]prop-2-enoate C51 (100.4 g, 1.0 equiv) followed by Pd(OH)$_2$/C (0.014 equiv). The vessel was sealed and three vacuum/purge cycles with N2 were performed. 2-MeTHF (2000 mL, 20 vol) was charged using residual vacuum and the resulting mixture was stirred at 22° C. The vessel was sealed and three vacuum/purge cycles with N2 were performed followed by one vacuum purge cycle with hydrogen (H$_2$). The temperature was adjusted to 22° C., and the vessel pressurized with 20 psi H$_2$. The mixture was agitated at 22° C. for 4 h. Three vacuum/purge cycles with nitrogen N2 were performed. The batch was filtered through a pad of Hyflo® and the filter cake was rinsed with 2-MeTHF (2×300 mL, 2×3 vol). The combined filtrates were placed under vacuum and distilled at ≤45.0° C. to 2.0 to 3.0 total volumes. The batch temperature was adjusted to 22° C. and the vessel was charge with n-heptane (1000 mL, 10 vol) over at least 1 h. A vacuum was applied and the filtrate distilled at 45.0° C. to 3.5 to 4.5 total volumes. The slurry was cooled to 22° C. and allowed to stir for no less than 1 h. The slurry was filtered and the filter cake was washed with n-heptane (1×1 vol (100 mL) and 1×0.5 vol (50 mL)). The solids were dried under vacuum with nitrogen bleed at 45° C. to afford the product C52 (91.9 g, 91% yield).

Step 3. Synthesis of 3-[5,7-difluoro-2-(4-fluorophenyl)-1H-indol-3-yl]propanoic Acid (S12

A mixture of methyl 3-[5,7-difluoro-2-(4-fluorophenyl)-1H-indol-3-yl]propanoate C52 (80.0 g, 1.0 equiv) and 2-MeTHF (480 mL, 6 vol) was agitated at 22° C. and treated with methanol (72 mL, 0.9 vol). A solution of KOH (27.1 g, 2.0 equiv) in water (107 mL, 1.3 vol) was charged over approximately 20 min. The resulting mixture was heated to an internal temperature of 35° C. and stirred for 3 h. The temperature was adjusted to 22° C. A vacuum was applied and the mixture was distilled at ≤45° C. to 3.0 total volumes. The internal temperature was adjusted to 12° C. The mixture was then charged with water (64 mL, 0.8 vol) and 2-MeTHF (304 mL, 3.8 vol). 6N HCl (75 mL, 0.9 vol) was slowly charged into the mixture with vigorous agitation until the batch attained a pH<3. The internal temperature was adjusted to 22° C., and the biphasic mixture was stirred for no less than 0.5 h. The stirring was stopped and the phases were allowed to separate for no less than 0.5 h. The lower aqueous phase was removed. Water (160 mL, 2 vol) was charged to the reactor at 22° C., and the biphasic mixture stirred for no less than 0.5 h. The stirring was stopped, and the phases allowed separated over no less than 0.5 h. The lower aqueous phase was removed and the batch was filtered through a pad of Hyflo®. The reactor and filter cake were rinsed with 2-MeTHF (160 mL, 2 vol). A vacuum was applied and the combined filtrates distilled at ≤40.0° C. to 2-3 total volumes. The vessel was charged with n-heptane (160 mL, 2 vol), a vacuum was applied and the filtrate distilled at 40.0° C. to 2 total volumes (this step was repeated one additional time). The mixture was then charged with additional n-heptane (144 mL, 1.8 vol). The internal temperature was adjusted to 40° C. and stirred for no less than 2 h. The internal temperature was adjusted to 22° C. over a minimum of 5 h and stirred for no less than 16 hours. The slurry was filtered. The filter cake was washed with n-heptane (3×40 mL, 3×0.5 vol). The solids were dried under vacuum with nitrogen bleed at 45° C. to afford product S12 (72.6 g, 95% yield).

Step 4. Synthesis of 3-[5,7-difluoro-2-(4-fluorophenyl)-1H-indol-3-yl]-N-[(3S,4R)-4-hydroxy-2-oxo-pyrrolidin-3-yl]propanamide (2

A mixture of S12 (50.0 g, 1.0 equiv), (3S,4R)-3-amino-4-hydroxypyrrolidin-2-one hydrochloride S2 (25.1 g, 1.05 equiv), and CDMT (30.3 g, 1.1 equiv) in DMF (250 mL, 5 vol) was agitated and cooled to 0° C. The reactor was charged with NMM (60 mL, 3.5 equiv) over no less than 1 h, while maintaining the internal temperature at ≤5° C. The batch was stirred at −5° C. for no less than 1 h. The batch was warmed to 22° C. over at least 1 h and stirred at 22° C. for 16 h. The batch was cooled to 0° C. Water (250 mL, 5 vol) was charged, while keeping the internal temperature <20° C. The mixture was charged with a 90/10 mixture of EtOAc/IPA (1000 mL, 20 vol). 6N HCl (40 mL, 0.8 vol) was then charged, while maintaining an internal temperature <10° C., until a pH~1-3 was achieved. The internal temperature was adjusted to 22° C. and the biphasic mixture stirred for no less than 0.5 h. Stirring was stopped and the phases allowed to separate for no less than 0.5 h. The lower aqueous phase was removed. The aqueous layer was back extracted with a 90/10 mixture of EtOAc/IPA (2×250 mL, 2×5 vol) at 22° C. The combined organic phases from extractions were washed with water (5×500 mL, 5×10 vol) at 22° C., by mixing for no less than 0.5 h and settling for no less than 0.5 h for each wash. The batch was polish filtered. A vacuum was applied and the organic phase distilled at <50° C. to 9.5-10.5 total volumes. The mixture was charged with EtOAc (500 mL, 10 vol), vacuum was applied and the organic phase distilled at <50° C. to 9.5-10.5 total volumes (this step was repeated one more time). The mixture was charged with EtOAc (300 mL, 6 vol) and n-heptane (200 mL, 4 vol). The resulting slurry was heated to 50° C. and stirred for no less than 17 h. The mixture was then cooled to 22° C. over 2 h, and stirred for no less than 1 h. The slurry was filtered. The filter cake was washed with 1:1 EtOAc/n-heptane (2×150 mL, 2×3 vol). The solids were dried under vacuum with nitrogen bleed at ≤45° C. to afford Compound 2 (52.6 g, 80% yield).

Re-Crystallization of Compound 2

Compound 2 (37.6 g, 1.0 equiv) was charged to a reactor followed by a 3:1 mixture of IPA/water (240 mL, 6.4 vol). The slurry was heated to an internal temperature of 75° C. The batch was cooled to an internal temperature of 55° C. and stirred at that temperature for at least 0.5 h. The batch was seeded with 0.5 wt % of a previously generated batch of Compound 2, as a suspension in a mixture of 3:1 IPA/water (4 mL, 0.1 vol). The mixture was stirred at 55° C. for no less than 1.5 h. Water (218 mL, 5.8 vol) was added over minimum period of 5 h while maintaining the temperature at 55° C. The slurry was cooled to 22° C. over no less than 5 h and stirred for no less than 2 h. The slurry was filtered. The filter cake was washed with 2:3 IPA/water (2×114 mL, 2×3 vol). The solids were dried under vacuum with nitrogen bleed at ≤45° C. to afford Compound 2 (34.5 g, 92% yield).

Form A of Compound 2

12.3 kg of Compound 2 was charged to the reactor follow by a 3:1 mixture of 2-propanol/water. Agitation was initiated and the mixture was heated to 75° C. to achieve complete dissolution. The mixture was cooled to 55° C. over 1 hour and agitated at that temperature for 30 minutes. Agitation was continued for 1.5 hours. Water (5.8 vol) was charged over 5 h at 55° C., after which the mixture was cooled to 22° C. over 6 hours. The mixture was agitated at 22° C. for 2 hours then filtered under vacuum. The resulting wet cake was washed with a 3:1 mixture of 2-propanol/water (2.74 vol×2) and pulled dry under vacuum. The wet cake was further dried under vacuum with nitrogen bleed at 45° C. to yield 11.2 kg of Form A.

Hydrate Form A of Compound 2

200 mg of Compound 2 was charged with 10 mL of water. The slurry was cooled to 5° C. and allowed to stir. Hydrate A was observed after 3 days of stirring.

Hydrate Form B of Compound 2 Form A 1 g of Compound 2 was charged with 50 mL of water. The slurry was cooled to 5° C. and allowed to stir. Hydrate B was observed after 18 hours of stirring.

Hydrate Form C of Compound 2 Form A

A solution of Compound 2 in MeOH was sealed into a system with water vapor, allowing the vapor to interact with the solution. The precipitate was isolated and analyzed to be Hydrate Form C.

Hydrate Form D of Compound 2 Form A

A suspension of Form A was magnetically stirred at 50° C. for 2~5 days in EtOH before the solid was isolated and analyzed. The resulted solid was Hydrate Form D.

Hydrate Form E of Compound 2 Form A

A clear solution of Compound 2 in MeOH was covered using parafilm with 3-4 pinholes, and kept at room temperature allowing the solvent to evaporate slowly. The resulted form was Hydrate Form E.

Hydrate Form F of Compound 2 Form A

A saturated solution of Compound 2 in ACN was cooled from 50° C. to 5° C. at a rate of 0.1° C./min. The precipitate was equilibrated at 5° C. before isolation and analysis. The resulted solid was Hydrate Form F.

MTBE Solvate of Compound 2 Form A

MTBE was added into a clear solution of Compound 2 in MeOH. The precipitate was stirred at RT/5° C. before isolated and analyzed. The resulted solid was the MTBE solvate.

DMF Solvate of Compound 2 Form A

Water was added into a clear solution of Compound 2 in DMF. The precipitate was stirred at RT/5° C. before isolated and analyzed. The resulted solid was the DMF solvate.

Amorphous Form of Compound 2 Form A

The amorphous form was made by spray drying a solution of Compound 2 at ~7% solid load in 95:5 w/w acetone:water.

Compound 3

3-[5,7-difluoro-2-(4-fluorophenyl)-1H-indol-3-yl]-N-[(3S)-2-oxopyrrolidin-3-yl]propanamide (3

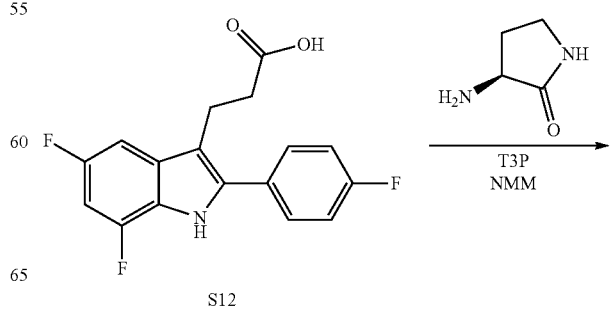

S12

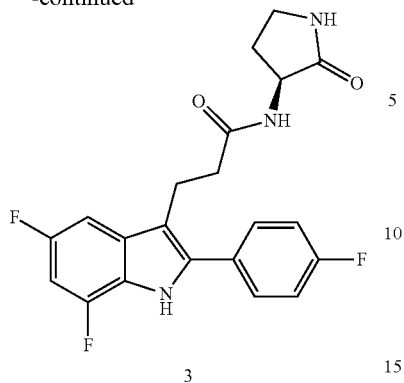

3

Synthesis of 3-[5,7-difluoro-2-(4-fluorophenyl)-1H-indol-3-yl]-N-[(3S)-2-oxopyrrolidin-3-yl]propanamide (3

Method H: Amide coupling with T3P. A 3 L flask was charged with 3-[5,7-difluoro-2-(4-fluorophenyl)-1H-indol-3-yl]propanoic acid S12 (41 g, 128.4 mmol), (3S)-3-aminopyrrolidin-2-one (16.5 g, 164.8 mmol), 4-methylmorpholine (48 mL, 436.6 mmol) and DMF (450 mL). 2,4,6-Tripropyl-1,3,5,2,4,6-trioxatriphosphorinane-2,4,6-trioxide solution (92 mL of 50% w/w, 154.5 mmol) was added and the reaction allowed to stir for 24 h at room temperature. The reaction was diluted with water (2 L) and the resultant precipitate filtered off, and dried under vacuum to afford a tan solid which was then recrystallized from hot EtOH (2 L) to afford the product (43.9 g, 84%). $^1$H NMR (300 MHz, DMSO-$d_6$) δ 11.68 (s, 1H), 8.19 (d, J=8.0 Hz, 1H), 7.83 (s, 1H), 7.76-7.63 (m, 2H), 7.44-7.32 (m, 2H), 7.27 (dd, J=9.6, 2.2 Hz, 1H), 6.97 (ddd, J=11.7, 9.8, 2.2 Hz, 1H), 4.28 (dt, J=10.3, 8.3 Hz, 1H), 3.16 (dd, J=9.2, 4.3 Hz, 2H), 3.04-2.92 (m, 2H), 2.50-2.39 (m, 2H), 2.27 (ddt, J=12.6, 8.5, 4.2 Hz, 1H), 1.78-1.58 (m, 1H). LCMS m/z 402.4 [M+H]$^+$.

Compound 4

[(3R,4S)-4-[3-[5,7-difluoro-2-(4-fluorophenyl)-1H-indol-3-yl]propanoylamino]-5-oxo-pyrrolidin-3-yl]acetate (4

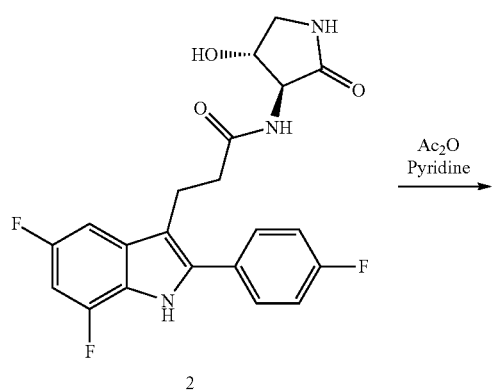

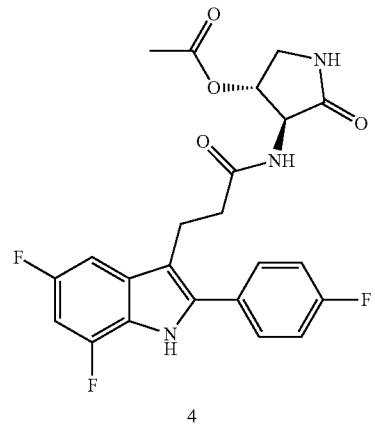

4

Synthesis of [(3R,4S)-4-[3-[5,7-difluoro-2-(4-fluorophenyl)-1H-indol-3-yl]propanoylamino]-5-oxo-pyrrolidin-3-yl]acetate (4

To 3-[5,7-difluoro-2-(4-fluorophenyl)-1H-indol-3-yl]-N-[(3S,4R)-4-hydroxy-2-oxo-pyrrolidin-3-yl]propanamide 2 (25 mg, 0.06 mmol) in CH$_2$Cl$_2$ (1 mL) was added pyridine (1 mL, 12.36 mmol) and Ac$_2$O (100 μL, 1.1 mmol). The mixture was allowed to stir overnight at room temperature. The reaction was concentrated in vacuo and purified by reversed phase chromatography to afford the product (21 mg, 76%). $^1$H NMR (300 MHz, CD$_3$OD) δ 7.64-7.41 (m, 2H), 7.23-7.01 (m, 3H), 6.63 (ddd, J=11.1, 9.6, 2.2 Hz, 1H), 5.13 (ddd, J=7.9, 6.9, 5.9 Hz, 1H), 4.22 (d, J=6.9 Hz, 1H), 3.67 (dd, J=10.5, 7.9 Hz, 1H), 3.19-3.10 (m, 1H), 3.08-2.94 (m, 2H), 2.55-2.35 (m, 2H), 1.94 (s, 3H). LCMS m/z 460.0 [M+H]$^+$.

Compounds 5-17

Compounds 5-17 (see Table 2) were prepared in a single step from intermediate S12 using the appropriate reagent, and using the amide formation methods as described for compounds 1-3 (using coupling reagents such as HATU, CDMT, or T3P). Amines were prepared by methods described above or obtained from commercial sources. Any modifications to methods are noted in Table 2 and accompanying footnotes.

TABLE 2

Method of preparation, structure and physicochemical data for compounds 5-17

| Compound | Product | Amine Reagent | Amine Coupling Method | $^1$H NMR; LCMS m/z [M + H]$^+$ |
|---|---|---|---|---|
| 5 | 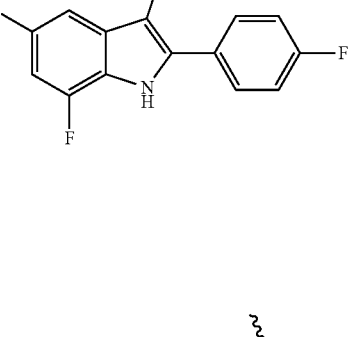 |  | Method F.[1] | $^1$H NMR (400 MHz, DMSO-d$_6$) δ 11.71 (s, 1H), 11.23 (s, 1H), 8.53 (d, J = 7.6 Hz, 1H), 7.71-7.63 (m, 2H), 7.37 (t, J = 8.9 Hz, 2H), 7.24 (dd, J = 9.6, 2.2 Hz, 1H), 6.98 (ddd, J = 11.6, 9.7, 2.2 Hz, 1H), 4.42-4.32 (m, 1H), 3.02-2.93 (m, 2H), 2.79 (dd, J = 17.6, 9.3 Hz, 1H), 2.46-2.32 (m, 3H). LCMS m/z 416.1 [M + H]$^+$. |
| 6 | 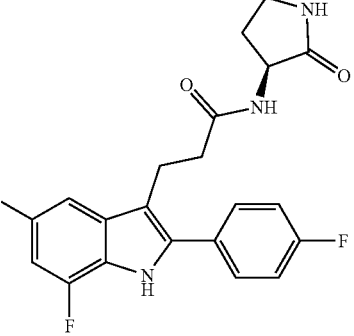 |  | Method F.[1] | $^1$H NMR (400 MHz, DMSO-d$_6$) δ 11.69 (s, 1H), 8.20 (dd, J = 10.2, 8.1 Hz, 1H), 7.96 (d, J = 10.2 Hz, 1H), 7.73-7.64 (m, 2H), 7.37 (t, J = 8.9 Hz, 2H), 7.27 (dt, J = 9.7, 2.2 Hz, 1H), 6.98 (ddd, J = 11.7, 9.8, 2.2 Hz, 1H), 4.40-4.28 (m, 1H), 3.07-2.84 (m, 3H), 2.47-2.37 (m, 2H), 1.95-1.80 (m, 1H), 1.21 (q, J = 11.0 Hz, 1H), 1.10 (d, J = 6.0 Hz, 3H). LCMS m/z 446.3 [M + H]$^+$. |
| 7 | 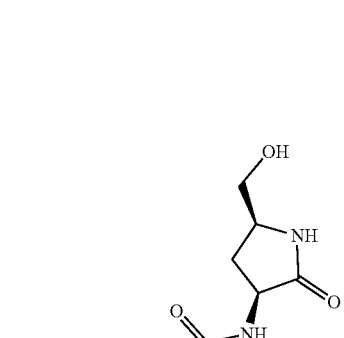 | 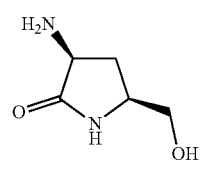 S4 | Method F.[1] | $^1$H NMR (400 MHz, DMSO-d$_6$) δ 11.69 (s, 1H), 8.20 (d, J = 8.1 Hz, 1H), 7.87 (s, 1H), 7.73-7.65 (m, 2H), 7.37 (t, J = 8.8 Hz, 2H), 7.28 (dd, J = 9.6, 2.2 Hz, 1H), 6.98 (ddd, J = 11.6, 9.7, 2.2 Hz, 1H), 4.82 (t, J = 5.4 Hz, 1H), 4.35 (q, J = 9.2 Hz, 1H), 3.02-2.92 (m, 3H), 2.48-2.39 (m, 2H), 2.36-2.25 (m, 1H), 1.44-1.32 (m, 1H). LCMS m/z 416.3 [M + H]$^+$. |

TABLE 2-continued

Method of preparation, structure and physicochemical data for compounds 5-17

| Compound | Product | Amine Reagent | Amine Coupling Method | $^1$H NMR; LCMS m/z [M + H]$^+$ |
|---|---|---|---|---|
| 8 | (structure) | S5 | Method F.$^1$ | $^1$H NMR (400 MHz, DMSO-d$_6$) δ 11.69 (s, 1H), 8.16 (d, J = 8.1 Hz, 1H), 7.88 (s, 1H), 7.73-7.65 (m, 2H), 7.37 (t, J = 8.9 Hz, 2H), 7.27 (dd, J = 9.6, 2.2 Hz, 1H), 6.98 (ddd, J = 11.7, 9.9, 2.3 Hz, 1H), 4.92 (t, J = 5.3 Hz, 1H), 4.38 (q, J = 9.0 Hz, 1H), 3.34 (s, 1H), 3.02-2.93 (m, 3H), 2.55 (s, 14H), 2.43 (dd, J = 9.4, 6.6 Hz, 2H), 2.16 (dd, J = 12.7, 9.0 Hz, 1H), 1.77 (dt, J = 12.5, 9.0 Hz, 1H). LCMS m/z 432.0 [M + H]$^+$. |
| 9 | (structure) | S6 | Method F.$^1$ | $^1$H NMR (400 MHz, DMSO-d$_6$) δ 11.69 (s, 1H), 8.28-8.18 (m, 2H), 7.73-7.65 (m, 2H), 7.37 (t, J = 8.9 Hz, 2H), 7.27 (dd, J = 9.5, 2.2 Hz, 1H), 6.98 (ddd, J = 11.6, 9.8, 2.2 Hz, 1H), 4.54-4.13 (m, 4H), 3.75 (d, J = 20.9 Hz, 1H), 3.02-2.93 (m, 2H), 2.44 (t, J = 8.1 Hz, 2H), 2.37-2.28 (m, 1H), 1.47-1.35 (m, 1H). LCMS m/z 434.0 [M + H]$^+$. |
| 10 | (structure) | S7 | Method F.$^1$ | $^1$H NMR (400 MHz, DMSO-d$_6$) δ 11.71 (s, 1H), 8.23 (d, J = 8.3 Hz, 1H), 8.16 (s, 1H), 7.73-7.65 (m, 2H), 7.42-7.32 (m, 2H), 7.27 (dd, J = 9.7, 2.2 Hz, 1H), 6.98 (ddd, J = 11.6, 9.7, 2.2 Hz, 1H), 4.43 (d, J = 4.2 Hz, 1H), 4.38-4.27 (m, 2H), 3.77 (d, J = 8.7 Hz, 1H), 3.71 (s, 1H), 3.02-2.93 (m, 2H), 2.44 (dd, J = 9.5, 6.5 Hz, 2H), 2.23-2.02 (m, 1H), 1.94-1.81 (m, 1H). LCMS m/z, 434.0 [M + H]$^+$. |

TABLE 2-continued

Method of preparation, structure and physicochemical data for compounds 5-17

| Compound | Product | Amine Reagent | Amine Coupling Method | $^1$H NMR; LCMS m/z [M + H]$^+$ |
|---|---|---|---|---|
| 11 | | S8 | Method F.[1] | $^1$H NMR (300 MHz. CD$_3$OD) δ 8.18 (d, J = 8.7 Hz, 1H), 7.81-7.53 (m, 2H), 7.38-7.11 (m, 3H), 6.74 (ddd, J = 11.1, 9.6, 2.2 Hz, 1H), 4.22-4.07 (m, 1H), 3.40 (dd, J = 9.8, 8.0 Hz, 1H), 3.17 (ddd, J = 8.9, 6.2, 1.4 Hz, 2H), 2.93 (t, J = 9.5 Hz, 1H), 2.68-2.57 (m, 2H), 2.39-2.19 (m, 1H), 1.02 (d, J = 6.7 Hz, 3H). LCMS m/z 416.3 [M + H]$^+$. |
| 12 | | S9 | Method F.[1] | $^1$H NMR (300 MHz, CD$_3$OD) δ 7.73-7.57 (m, 2H), 7.30-7.15 (m, 3H), 6.75 (ddd, J = 11.1, 9.6, 2.2 Hz, 1H), 4.36 (td, J = 7.6, 6.9 Hz, 1H), 4.23 (d, J = 7.8 Hz, 1H), 3.58 (dd, J = 9.9, 7.6 Hz, 1H), 3.21-2.98 (m, 3H), 2.68-2.46 (m, 2H). LCMS m/z 418.0[M + H]$^+$. |
| 13 | | | Method F.[1] | $^1$H NMR (300 MHz, CDCl$_3$) δ 8.16 (s, 1H), 7.56 (dd, J = 8.7, 5.3 Hz, 2H), 7.22 (t, J = 8.6 Hz, 2H), 7.11 (dd, J = 9.1, 2.1 Hz, 1H), 6.84-6.67 (m, 1H), 5.93 (d, J = 15.8 Hz, 2H), 4.38-4.21 (m, 1H), 3.39 (dd, J = 9.6, 3.8 Hz, 2H), 3.19 (dd, J = 8.5, 6.9 Hz, 2H), 2.78 (tt, J = 8.5, 3.9 Hz, 1H), 2.56 (td, J = 7.6, 3.9 Hz, 2H). LCMS m/z 402.2 [M + H]$^+$. |
| 14 | | | Method F[1] | $^1$H NMR (300 MHz, CD$_3$OD) δ 7.71-7.48 (m, 2H), 7.31-7.07 (m, 3H), 6.79-6.60 (m, 1H), 3.38 (td, J = 9.8, 2.4 Hz, 1H), 3.28-3.22 (m, 1H), 3.15-3.01 (m, 2H), 2,61-2.38 (m, 3H), 1.95 (ddd, J = 12.7, 7.6, 2.4 Hz, 1H), 1.30 (s, 3H). LCMS m/z 416.1 [M + H]$^+$. |

TABLE 2-continued

Method of preparation, structure and physicochemical data for compounds 5-17

| Compound | Product | Amine Reagent | Amine Coupling Method | $^1$H NMR; LCMS m/z [M + H]$^+$ |
|---|---|---|---|---|
| 15 | 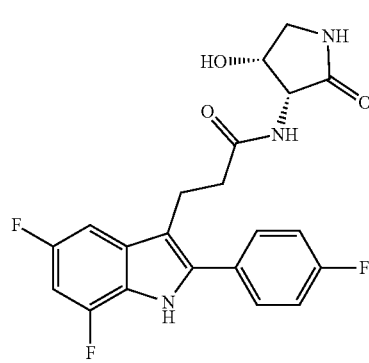 [SMILES: O=C(CCc1c(-c2ccc(F)cc2)[nH]c2c(F)cc(F)cc12)N[C@H]1C(=O)NC[C@H]1O] | 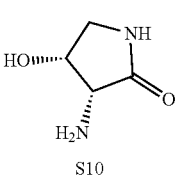 S10 | Method .[1] | $^1$H NMR (300 MHz, CD$_3$OD) δ 7.73-7.58 (m, 2H), 7.25 (td, J = 9.0, 2.3 Hz, 3H), 6.74 (ddd, J = 11.1, 9.6, 2.2 Hz, 1H), 4.68 (d, J = 5.0 Hz, 1H), 4.44-4.33 (m, 1H), 3.61 (dd, J = 11.3, 4.0 Hz, 1H), 3.26 (d, J = 11.3 Hz, 1H), 3.23-3.05 (m, 2H), 2.77-2.59 (m, 2H). LCMS m/z 418.1 [M + H]$^+$ |
| 16 | 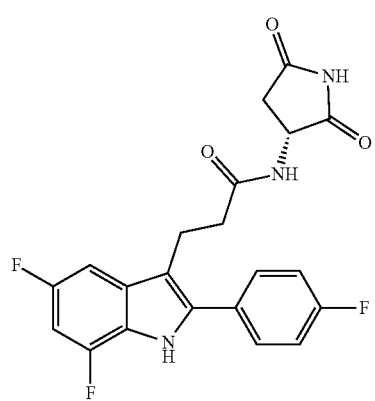 [SMILES: O=C1C[C@@H](NC(=O)CCc2c(-c3ccc(F)cc3)[nH]c3c(F)cc(F)cc23)C(=O)N1] | 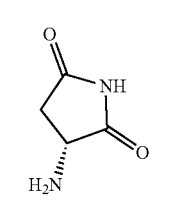 | Method F[1] | $^1$H NMR (400 MHz, DMSO-d6) δ 11.71 (s, 1H), 11.23 (s, 1H), 8.53 (d, J = 7.6 Hz, 1H), 7.71-7.63 (m, 2H), 7.37 (t, J = 8.9 Hz, 2H), 7.24 (dd, J = 9.6, 2.2 Hz, 1H), 6.98 (ddd, J = 11.6, 9.6, 2.1 Hz, 1H), 4.37 (ddd, J = 9.1, 7.5, 5.5 Hz, 1H), 3.02-2.92 (m, 2H), 2.79 (dd, J = 17.6, 9.3 Hz, 1H), 2.42 (s, 1H), 2.47-2.32 (m, 2H). LCMS m/z 416.2 [M + H]+. |
| 17 | 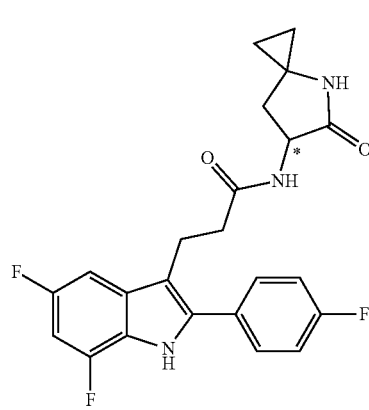 [SMILES: O=C(CCc1c(-c2ccc(F)cc2)[nH]c2c(F)cc(F)cc12)NC1CC2(CC2)NC1=O] | 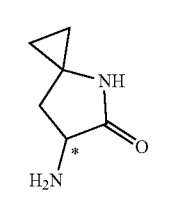 | Method F[1] | $^1$H NMR (400 MHz, DMSO-d$_6$) δ 11.69 (s, 1H), 8.31 (d, J = 8.0 Hz, 1H), 7.93 (s, 1H), 7.74-7.64 (m, 2H), 7.37 (t, J = 8.9 Hz, 2H), 7.27 (dd, J = 9.6, 2.2 Hz, 1H), 6.98 (ddd, J = 11.6, 9.7, 2.2 Hz, 1H), 4.49 (q, J = 8.9 Hz, 1H), 2.99-2.94 (m, 2H), 2.45 (dd, J = 9.3, 6.7 Hz, 2H), 2.09 (dd, J = 12.4, 8.8 Hz, 1H), 1.99 (dd, J = 12.4, 10.1 Hz, 1H), 0.77 (dt, J = 10.8, 5.4 Hz, 1H), 0.67 (dt, J = 10.5, 5.1 Hz, 1H), 0.55 (ddt, J = 21.1, 9.9, 6.0 Hz, 2H). LCMS m/z 428.0 [M + H]$^+$. |

[1]Purification by reversed-phase HPLC. Method: C18 Waters Sunfire column (30 × 150 mm, 5 micron). Gradient: 10-100% MeCN in H$_2$O with 0.2% formic acid.

Compound 18
(S)-3-(5,7-Difluoro-2-(4-fluorophenyl-2,3,5,6-$d_4$)-1H-indol-3-yl)-N-(2-oxopyrrolidin-3-yl)propanamide (18
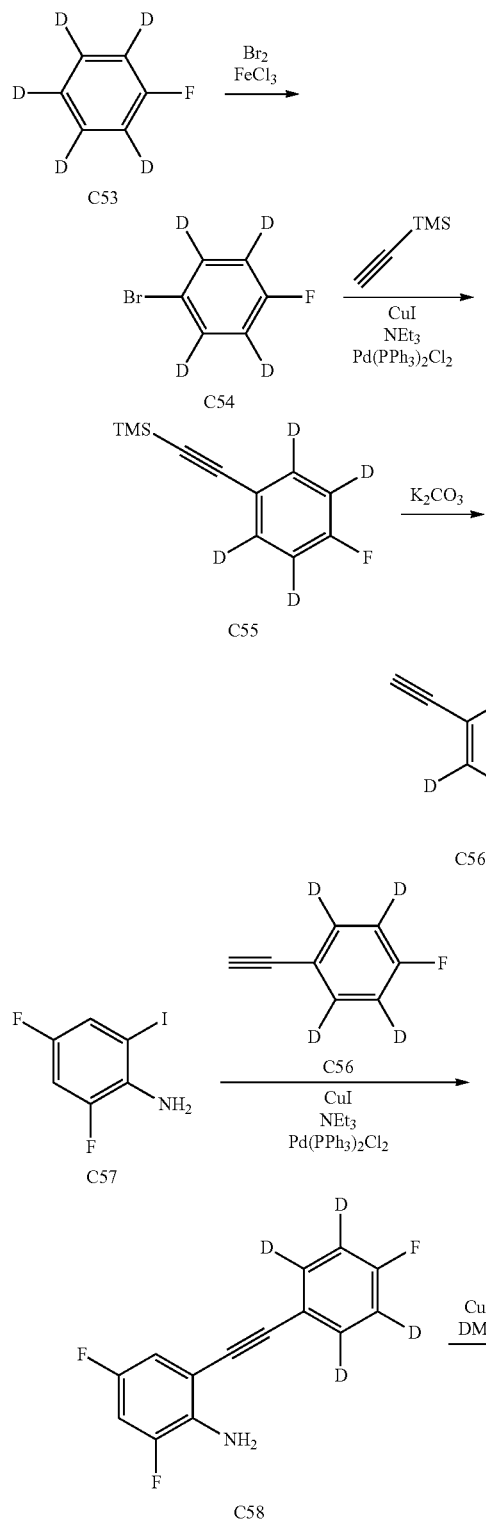
Step 1. Synthesis of 1-Bromo-4-fluorobenzene-2,3,5,6-$d_4$ (C54
A solution of bromine (34.8 g, 218 mmol, 1.1 equiv) in $CH_2Cl_2$ (40 mL) was added dropwise to a solution of 1-fluorobenzene-2,3,4,5,6-$d_5$ C53 (20 g, 200 mol, 1 equiv) and $FeCl_3$ (0.6 g, 3.7 mmol, 0.02 equiv) in $CH_2Cl_2$ (40 mL) at 18-20° C. After stirring at room temperature for 1.5 h, the mixture was washed with water (3×50 mL), sodium thiosulfate solution (0.72 M, 50 mL) and additional water (50 mL). The organic layer was dried over sodium sulfate and filtered. A small scale run of this reaction (5 g of 1-fluorobenzene-2,3,4,5,6-$d_5$) which was processed in same manner was combined for distillation to remove solvent. The combined organic layers were evaporated under atmospheric distillation to remove dichloromethane and then distilled to afford the product (33.3 g, 75% yield, b.p. 150-152° C.) as a colorless oil.

Step 2. ((4-Fluorophenyl-2,3,5,6-$d_4$)ethynyl)trimethylsilane (C55

(Trimethylsilyl) acetylene (32.9 mL, 232.5 mmol, 1.3 equiv), copper(I) iodide (3.5 g, 18.6 mmol, 0.1 equiv) and $PdCl_2(PPh_3)_2$ (6.5 g, 9.3 mmol, 0.05 equiv) were added to a mixture of 1-Bromo-4-fluorobenzene-2,3,5,6-$d_4$ C54 (33.3 g, 186.0 mmol, 1 equiv) in $NEt_3$ (310 mL) at room temperature. The mixture was purged with nitrogen for 10 minutes, then stirred at 70-80° C. for 18 h. After cooling to room temperature, the mixture was diluted with EtOAc (300 mL), filtered through Celite®, which was washed with EtOAc (2×100 mL). The filtrate was concentrated under reduced pressure at 30° C. to afford the product (45.3 g) as a dark-brown oil, which was used subsequently.

Step 3. 1-Ethynyl-4-fluorobenzene-2,3,5,6-$d_4$ (C56

Potassium carbonate (128.5 g, 930 mmol, 5 equiv) was added to a mixture of ((4-Fluorophenyl-2,3,5,6-$d_4$)ethynyl)trimethylsilane C55 (45.3 g, 186 mmol, 1 equiv) in MeOH (620 mL) at room temperature. The mixture was stirred at room temperature for 2 h. The mixture was filtered through Celite®, washing with MeOH (50 mL) and hexanes (3×50 mL). The filtrate was diluted with water (2000 mL) and separated. The aqueous layer was extracted with hexanes (3×500 mL). The combined organic layers were washed with water (200 mL), dried over sodium sulfate, filtered and concentrated under reduced pressure (50 mbar, 5° C.) to give the product (30 g, theoretical yield 23.09 g) as a dark oil. (Note: 1-Ethynyl-4-fluorobenzene-2,3,5,6-$d_4$ is volatile, and it was co-distilled with other solvents (MeOH, hexanes) under reduced pressure or under atmospheric distillation. The crude 1-Ethynyl-4-fluorobenzene-2,3,5,6-$d_4$ C56 was used in next step without column purification in order to minimize the loss during evaporation of solvents.)

Step 4. 2,4-Difluoro-6-((4-fluorophenyl-2,3,5,6-$d_4$) ethynyl)aniline (C58

A mixture of crude 2,4-difluoro-6-iodoaniline C57 (59.7 g, 58% purity, 135.8 mmol, 1 equiv) and crude 1-Ethynyl-4-fluorobenzene-2,3,5,6-$d_4$ C56 (28.1 g, 60% purity, 135.80 mmol, 1 equiv) in $NEt_3$ (550 mL) was purged with nitrogen for 10 minutes. CuI (5.2 g, 27.2 mmol, 0.2 equiv) and $Pd(PPh_3)Cl_2$ (9.5 g, 13.6 mmol, 0.1 equiv) were added. The mixture was stirred at room temperature for 20 h, and then the mixture was concentrated under reduced pressure at 40° C. The residue was purified twice over silica gel (800 g silica gel, dry-loading, eluting each time with a gradient of 0 to 10% dichloromethane in heptanes) to give the product C58 (40.5 g) as a brown solid which was used in subsequent steps without further purification. (This material still contained some unreacted 2,4-difluoro-6-iodoaniline (40% based on LCMS)).

Step 5. 5,7-Difluoro-2-(4-fluorophenyl-2,3,5,6-$d_4$)-1H-indole (C59

A solution of 2,4-Difluoro-6-((4-fluorophenyl-2,3,5,6-$d_4$) ethynyl)aniline C58 (39.5 g, 60% purity, 157.2 mmol, 1 equiv) in DMF (400 mL) was purged with nitrogen for 10 minutes. CuI (3.0 g, 15.7 mmol, 0.1 equiv) was added, and the mixture was purged with nitrogen for an additional 10 minutes. The mixture was heated at 145° C. for 20 h and cooled to room temperature. The mixture was concentrated under reduced pressure at 60° C. to remove most of DMF. The residue was diluted with water (500 mL) and t-butyl methyl ether (300 mL). The mixture was filtered through Celite®, which was washed with t-butyl methyl ether (100 mL). The layers of the filtrate were separated and the aqueous layer was extracted with t-butyl methyl ether (2×200 mL). The combined organic layers were washed with saturated brine (500 mL), dried over sodium sulfate, filtered and concentrated under reduced pressure at 40° C. Purification by silica gel chromatography (Gradient: 0-10% EtOAc in heptanes) afforded 5,7-Difluoro-2-(4-fluorophenyl-2,3,5,6-$d_4$)-1H-indole as an orange-brown solid (19 g, 80% yield).

Step 6. Methyl (E)-3-(5,7-difluoro-2-(4-fluorophenyl-2,3,5,6-$d_4$)-1H-indol-3-yl)acrylate (C60

Methyl 3,3-dimethoxypropanoate (11.8 mL, 83.2 mmol, 1.1 equiv) and TFA (31.9 mL, 415.9 mmol, 5.5 equiv) were added to a solution of 5,7-Difluoro-2-(4-fluorophenyl-2,3,5,6-$d_4$)-1H-indole C59 (19.0 g, 75.6 mmol, 1 equiv) in $CH_2Cl_2$ (300 mL) at room temperature. After refluxing for 2.5 h, the reaction was cooled to room temperature, the solid was filtered and washed with $CH_2Cl_2$ (2×20 mL) to give methyl (E)-3-(5,7-difluoro-2-(4-fluorophenyl-2,3,5,6-$d_4$)-1H-indol-3-yl)acrylate as a grey solid (21.2 g, 84% yield).

Step 7 & 8. 3-(5,7-Difluoro-2-(4-fluorophenyl-2,3,5,6-$d_4$)-1H-indol-3-yl)propanoic Acid (C62

A mixture of methyl (E)-3-(5,7-difluoro-2-(4-fluorophenyl-2,3,5,6-$d_4$)-1H-indol-3-yl)acrylate C60 (21.2 g, 63.2 mmol, 1 equiv) in EtOH (200 proof, 400 mL) was purged with nitrogen for 15 minutes. 20% Palladium hydroxide on carbon (2.12 g, 10% by weight) and ammonium formate (42.4 g, 672.4 mmol, 10.6 equiv) were added. The mixture was purged with nitrogen for an additional 20 minutes, then heated at reflux for 5 hours. A smaller scale batch of (1.28 g of methyl (E)-3-(5,7-difluoro-2-(4-fluorophenyl-2,3,5,6-$d_4$)-1H-indol-3-yl)acrylate) was processed in same manner and both batches were combined for work-up. The mixture was filtered through Celite® at 60° C. and the filter cake was washed with EtOH (2×100 mL). The filtrate was concentrated under reduced pressure at 40° C. to afford the product C61 (21 g, 93% yield). LiOH (2.85 g, 118.6 mmol, 2 equiv) was added to a mixture of methyl 3-(5,7-difluoro-2-(4-fluorophenyl-2,3,5,6-$d_4$)-1H-indol-3-yl)propanoate C61 (20 g, 59.3 mmol, 1 equiv) in THF (300 mL) and water (60 mL). After stirring at room temperature for 20 h, the reaction was adjusted to pH 3 with 1 M HCl solution (125 mL) and concentrated under reduced pressure to remove the THF. The residue was extracted with $CH_2Cl_2$ (3×300 mL) and the combined organic layers were washed with saturated brine (200 mL), dried over sodium sulfate, filtered and concentrated under reduced pressure at 40° C. to afford the product as a light-yellow solid (19.8 g, 97% yield).

Step 9. (S)-3-(5,7-Difluoro-2-(4-fluorophenyl-2,3,5,6-d₄)-1H-indol-3-yl)-N-(2-oxopyrrolidin-3-yl)propanamide (18

HATU (35.4 g, 93.1 mmol, 1.6 equiv) and NEt₃ (20.3 mL) were added to a solution of 3-(5,7-Difluoro-2-(4-fluorophenyl-2,3,5,6-d₄)-1H-indol-3-yl)propanoic acid C62 (18.8 g, 58.2 mmol, 1 equiv) in DMF (300 mL) and the mixture was stirred at room temperature for 10 minutes. (S)-3-aminopyrrolidin-2-one (7.0 g, 69.8 mmol, 1.2 equiv) was added and the resulting mixture was stirred at room temperature for 4 h. Water (600 mL) was added and the mixture was extracted with EtOAc (3×500 mL). The combined organic layers were washed with saturated brine (400 mL), filtered, and concentrated under reduced pressure at 40° C. Purification by silica gel chromatography (Eluent: 0 to 10% MeOH in CH₂Cl₂) afforded the product as an off-white solid (26.0 g). This material was recrystallized with 2-propanol (250 mL) to afford the product as an off white solid (20 g, 95% purity, 85% yield).

Additional Purification of (S)-3-(5,7-Difluoro-2-(4-fluorophenyl-2,3,5,6-d₄)-1H-indol-3-yl)-N-(2-oxopyrrolidin-3-yl)propanamide (18

(S)-3-(5,7-Difluoro-2-(4-fluorophenyl-2,3,5,6-d₄)-1H-indol-3-yl)-N-(2-oxopyrrolidin-3-yl)propanamide (18 g, 95% purity) was further purified by silica gel chromatography (×3) (Gradient: 0 to 10% acetone in EtOAc). Purified fractions were combined and concentrated under reduced pressure. The residue was diluted with EtOH (3×200 mL) and concentrated each time under reduced pressure. The product was dried under vacuum at 50° C. for 20 h to give product (9.2 g, >99% purity) as a white solid which contained a small amount of EtOH. This material was re-dissolved in 50% EtOH in water (500 mL), and concentrated under reduced pressure at 50° C. to dryness. The residue was triturated with a mixture of Et₂O (120 mL) and EtOAc (20 mL) at room temperature for 30 minutes, filtered and dried under vacuum at 50° C. for 20 hours to give solvent-free product as a white solid. (8.3 g, 99.6% purity). ¹H NMR (400 MHz, DMSO-d₆) 11.7 (s, 1H), 8.16 (d, 1H), 7.80 (s, 1H), 7.28-7.26 (m, 1H), 6.97 (m, 1H), 4.29-4.25 (m, 1H), 3.18-3.14 (m, 2H), 2.99 (m, 2H), 2.51-2.43 (m, 2H), 2.25 (m, 1H), 1.71-1.65 (m, 1H). LCMS m/z 406.1 [M+H]⁺.

Compound 19

3-(5,7-Difluoro-2-([D₄]-4-fluorophenyl)-1H-indol-3-yl)-N-(3S,4R)-4-hydroxy-2-oxopyrrolidin-3-yl)propanamide (19

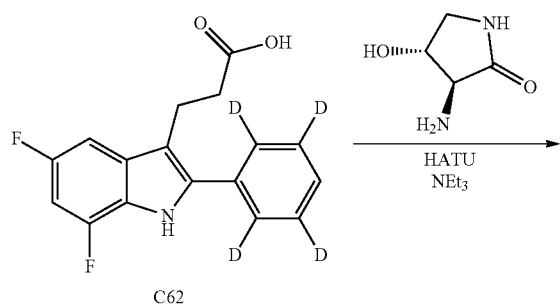

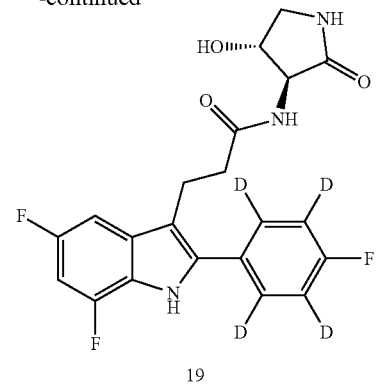

Synthesis of 3-(5,7-Difluoro-2-([D₄]-4-fluorophenyl)-1H-indol-3-yl)-N-(3S,4R)-4-hydroxy-2-oxopyrrolidin-3-yl)propanamide (19

HATU (30.2 g, 79.3 mmol, 1.3 equiv) and NEt₃ (25.5 mL, 183 mmol, 3 equiv) were added to a solution of 3-(5,7-Difluoro-2-(4-fluorophenyl-2,3,5,6-d₄)-1H-indol-3-yl)propanoic acid C62 (19.7 g, 61 mmol, 1 equiv) in dimethyl sulfoxide (200 mL) and the mixture was stirred at room temperature for 10 minutes. (3S,4R)-3-amino-4-hydroxy-pyrrolidin-2-one (7.1 g, 61 mmol, 1.0 equiv) was added and the resulting mixture was stirred at room temperature for 20 h. A smaller batch (0.97 g of 3-(5,7-Difluoro-2-(4-fluorophenyl-2,3,5,6-d₄)-1H-indol-3-yl)propanoic acid) was processed in same manner and both batches were combined for work-up. Water (500 mL) was added and the mixture was extracted with EtOAc (3×400 mL). The combined organic layers were washed with water (400 mL), saturated brine (400 mL), filtered, and concentrated under reduced pressure at 40° C. The residue was triturated with 10% MeOH in CH₂Cl₂ (500 mL) at 40° C. to give the product as an off-white solid (14.0 g, 92.5% purity by LC).

Purification of 3-(5,7-Difluoro-2-([D₄]-4-fluorophenyl)-1H-indol-3-yl)-N-(3S,4R)-4-hydroxy-2-oxopyrrolidin-3-yl)propanamide (19

A portion of this material (3 g) was further purified by reversed phase chromatography (Column: 330 g Interchim Puriflash Bio100-C18-N-15 um-F300 reverse phase column. Gradient: 0-100% acetonitrile in water) to afford the product as an off-white solid (1.0 g, 98% purity with 1-2% single impurity). The additional material was further purified by silica gel chromatography (×5) (Gradient: 0 to 10% acetone in EtOAc). Mixed fractions were further purified by silica gel chromatography (×2) (Gradient: 0 to 10% acetone in EtOAc). All fractions with >99% purity by LC were combined and concentrated under reduced pressure then dried under vacuum dried (50° C. for 24 h, and then at 55° C. for 24 h) to afford the product as a white solid (8.3 g, 99.7% purity, containing 1.7 mol % EtOAc). ¹H NMR (400 MHz, DMSO-d₆) 11.6 (s, 1H), 8.21 (d, J=7.7 Hz, 1H), 7.79-7.68 (m, 1H), 7.27 (dd, J=2.2, 9.5 Hz, 1H), 6.97 (ddd, J=2.2, 9.6, 11.3 Hz, 1H), 5.46 (d, J=5.1 Hz, 1H), 4.15-4.05 (m, 2H), 3.41-3.35 (m, 1H), 3.05-2.95 (m, 2H), 2.92 (dd, J=6.8, 9.5 Hz, 1H), 2.49-2.41 (m, 2H). LCMS m/z 422.2 [M+H]⁺.

Compound 20

3-[2-(4-cyanophenyl)-5,7-difluoro-1H-indol-3-yl]-N-[(3S)-2-oxopyrrolidin-3-yl]propanamide (20

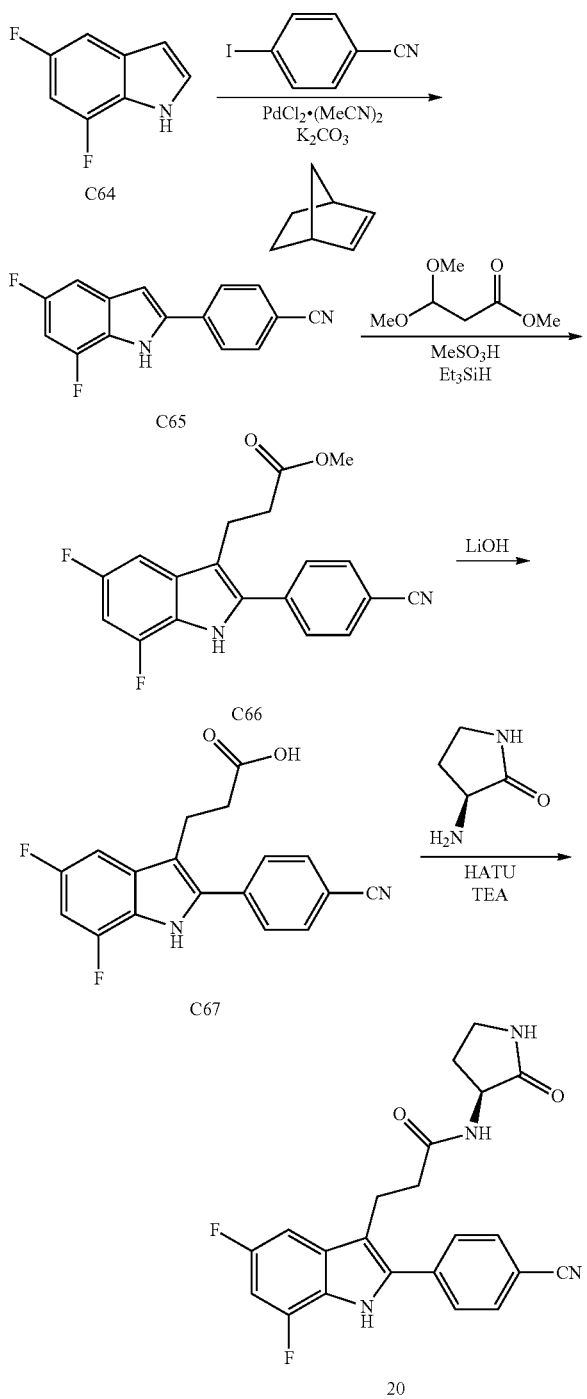

Step 1. Synthesis of 4-(5,7-difluoro-1H-indol-2-yl)benzonitrile (C65

Method I: Pd Catalyzed CH activation and aryl halide coupling. To a solution of 5,7-difluoro-1H-indole C64 (297 mg, 1.9 mmol), 4-iodobenzonitrile (445 mg, 1.9 mmol) in DMA (3.6 mL) was added water (451 µL), $K_2CO_3$ (670 mg, 4.8 mmol), bicyclo[2.2.1]hept-2-ene (365 mg, 3.9 mmol), and $PdCl_2(MeCN)_2$ (50 mg, 0.12 mmol). The reaction was allowed to stir at 90° C. overnight. Water (~75 mL) was added and the mixture was extracted with EtOAc (2×50 mL). The combined organic extracts were washed with brine, dried over ($MgSO_4$), filtered and concentrated in vacuo. Purification via silica gel chromatography (Eluent: 10% EtOAc in heptane) afforded the product (277 mg, 53%). LCMS m/z 255.4 [M+H]$^+$.

Step 2. Synthesis of methyl 3-[2-(4-cyanophenyl)-5,7-difluoro-1H-indol-3-yl]propanoate (C66

Method J: Reductive Alkylation Method 2 ($MeSO_3H$ Promoted). To 4-(5,7-difluoro-1H-indol-2-yl)benzonitrile C65 (621 mg, 2.3 mmol) in dichloroethane (8 mL) at 70° C. was added methanesulfonic acid (240 µL, 3.7 mmol), $Et_3SiH$ (1.2 mL, 7.5 mmol) and methyl 3,3-dimethoxypropanoate (440 mg, 3.0 mmol). The mixture was heated at 70° C. for 2 h. Additional methyl 3,3-dimethoxypropanoate (2×440 mg, 3.0 mmol), methanesulfonic acid (2×240 µL, 3.7 mmol), and $Et_3SiH$ (2×1.2 mL, 7.5 mmol) were added. The mixture was heated at 90° C. overnight. Water (100 mL) was added and the mixture extracted with $CH_2Cl_2$ (3×70 mL). Combined organic layers were purified by silica gel chromatography (Gradient: 0 to 100% EtOAc/heptane) afford the product (66 mg, 8%). Methyl 3-[2-(4-cyanophenyl)-5,7-difluoro-1H-indol-3-yl]propanoate (66 mg, 8%). $^1$H NMR (300 MHz, $CDCl_3$) δ 8.28 (s, 1H), 7.83-7.77 (m, 2H), 7.75-7.65 (m, 2H), 7.16-7.03 (m, 1H), 6.86-6.75 (m, 1H), 3.65 (s, 3H), 3.28-3.10 (m, 2H), 2.80-2.55 (m, 2H). LCMS m/z 341.1 [M+H]$^+$. Recovered starting material was also obtained (353 mg, 61%).

Step 3. Synthesis of 3-[2-(4-cyanophenyl)-5,7-difluoro-1H-indol-3-yl]propanoic Acid (C67

To methyl 3-[2-(4-cyanophenyl)-5,7-difluoro-1H-indol-3-yl]propanoate C66 (16 mg, 0.04 mmol) in MeOH (1 mL) and THF (2 mL) was added LiOH-water (1 mL). The mixture was allowed to stir at 50° C. for 3 h. The mixture was concentrated in vacuo, and water (40 mL) was added. The pH was adjusted to ~1 with conc. HCl. The mixture was then extracted with $CH_2Cl_2$ (3×25 mL), washed with brine, dried and concentrated in vacuo to afford the product (14 mg, 97%) which was used in subsequent steps without further purification. LCMS m/z 327.0 [M+H]$^+$.

Step 4. Synthesis of 3-[2-(4-cyanophenyl)-5,7-difluoro-1H-indol-3-yl]-N-[(3S)-2-oxopyrrolidin-3-yl]propanamide (20

To a mixture of 3-[2-(4-cyanophenyl)-5,7-difluoro-1H-indol-3-yl]propanoic acid C67 (45 mg, 0.14 mmol), HATU (103 mg, 0.3 mmol) and (3S)-3-aminopyrrolidin-2-one (27 mg, 0.3 mmol) in DMSO (2 mL) was added $NEt_3$ (95 µL, 0.7 mmol). The mixture was allowed to stir at room temperature for 12 h. Purification by reverse phase chromatography afforded the product (14.2 mg, 25%). $^1$H NMR (300 MHz, $CD_3OD$) δ 7.93-7.81 (m, 4H), 7.23 (dd, J=9.2, 2.2 Hz, 1H), 6.86-6.73 (m, 1H), 4.45 (dd, J=10.3, 8.8 Hz, 1H), 3.35 (m, 2H, obscured by MeOH solvent), 3.19 (t, J=7.9 Hz, 2H), 2.65-2.52 (m, 2H), 2.48-2.35 (m, 1H), 1.90-1.74 (m, 1H). LCMS m/z 409.2 [M+H]$^+$.

General Routes for Preparation of Indole Propanoic Acids

Routes A-E describe typical procedures used to generate indole propanoic acids which are used as starting materials in the preparation of Compounds 21-133 below. Detailed experimental procedures for each route are described in the examples noted below.

Indole Preparation Route A: Alkyne Coupling and Cyclization (See Preparation S12 and Compound 18

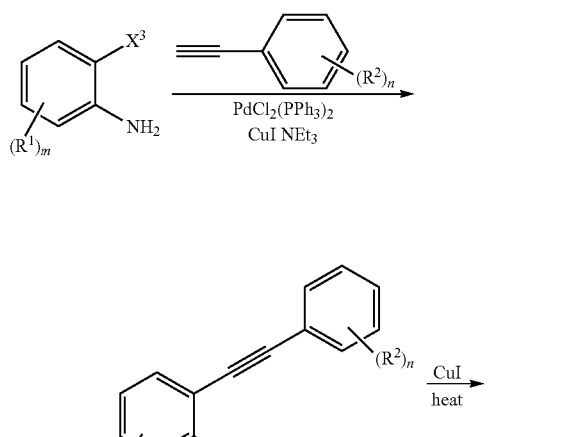

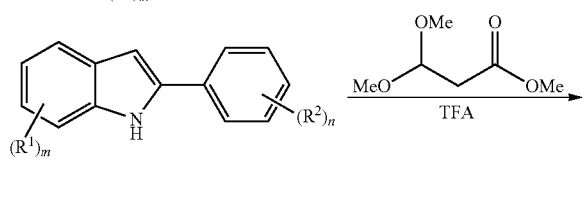

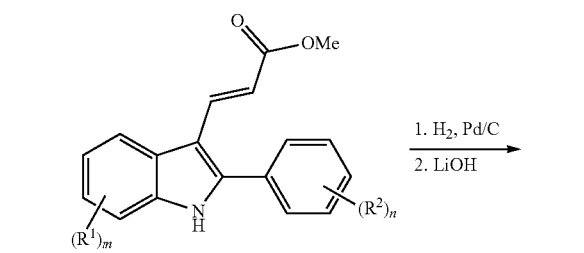

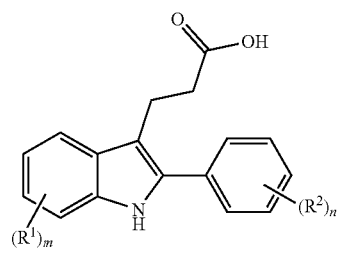

Indole Preparation Route B: Indole Arylation with Aryl Halide (See Compound 20 and 55

Indole Preparation Route C: Indole Arylation with Aryl Boronic Acid (See Compound 87 Alternative Preparation I

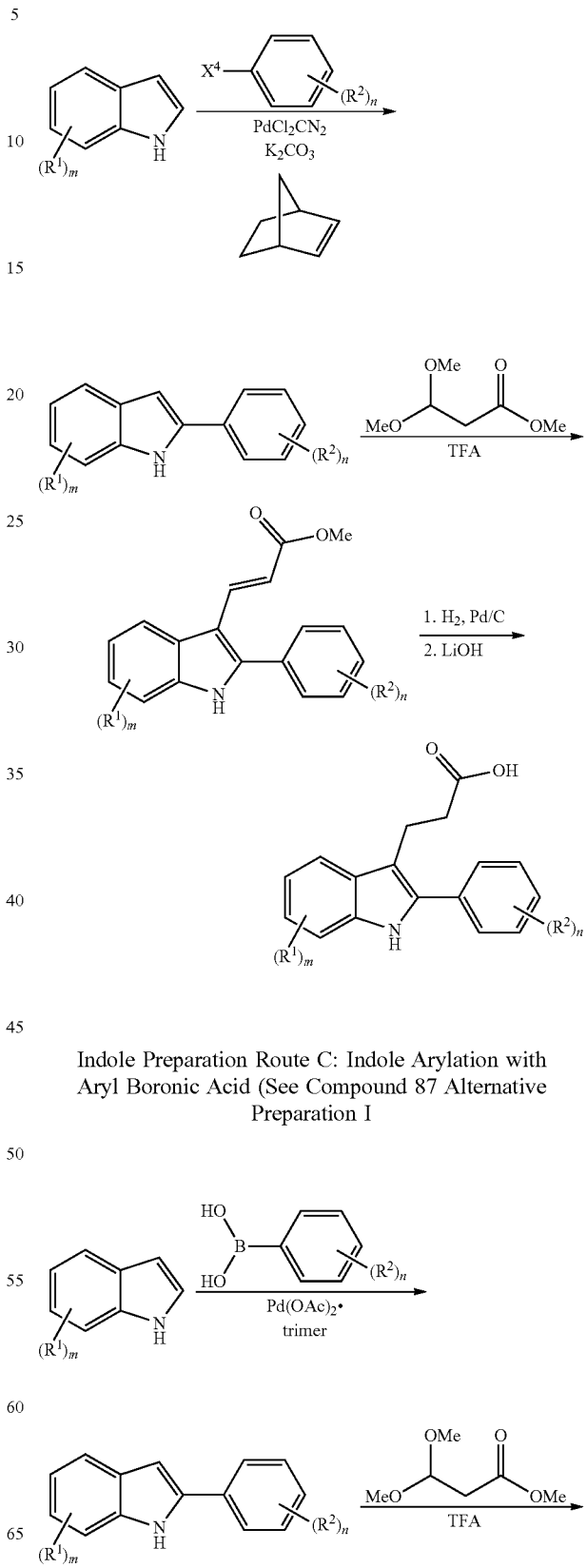

253
-continued
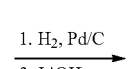
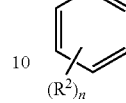
1. H₂, Pd/C
2. LiOH
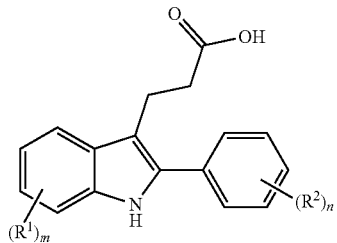
Indole Preparation Route D: Fisher Indole Synthesis (See Compound 87 Alternative Preparation II
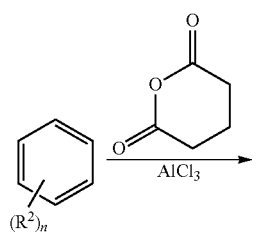
254
-continued
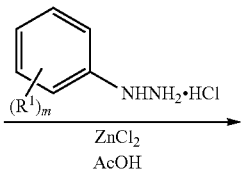
ZnCl₂
AcOH
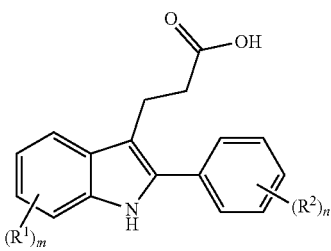
Indole Preparation Route E: 2-Amino Alkyne Cyclization and Oxidative Heck Reaction (See Compound 116
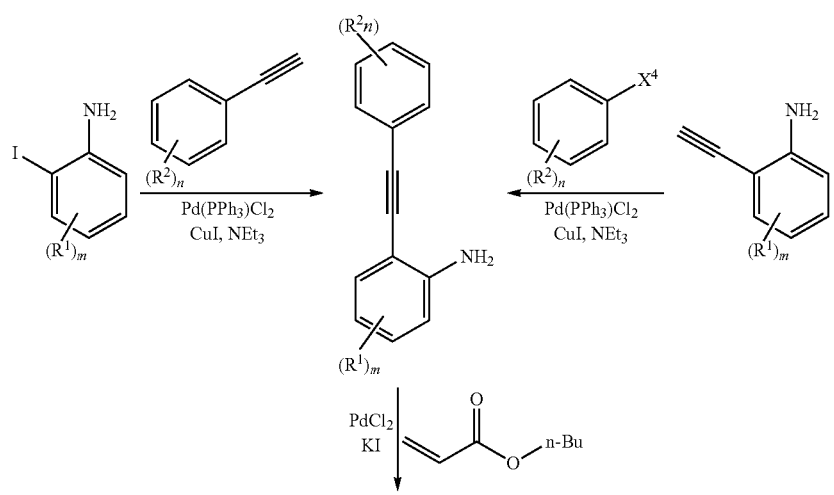

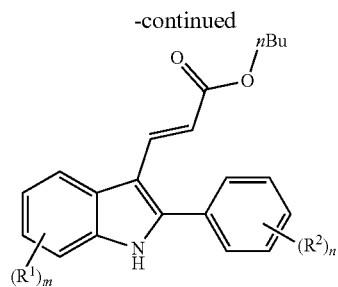

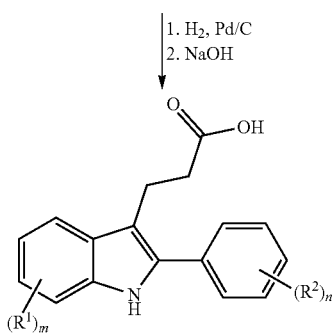

Compounds 21-26

Compounds 21-26 (Table 3) were prepared from the appropriate indole propanoic acid and amine via an amide coupling reaction. An amide coupling reagent such as HATU, and an organic base (NEt$_3$ or DIPEA) as described in the preparation of compound 1 or compound 18 was used. Any modifications to these methods are noted in Table 3 and accompanying footnotes. Indole propanoic acids were prepared according to route B unless otherwise noted.

TABLE 3

Method of preparation, structure and physicochemical data for compounds 21-26

| Compound | Product | Indole Preparation; Amine coupling method; non-commercial amine | $^1$H NMR; LCMS m/z [M + H]$^+$ |
|---|---|---|---|
| 21 | | Route B; Method F[1]. | $^1$H NMR (300 MHz, CD$_3$OD) δ 7.73-7.58 (m, 2H), 7.36-7.22 (m, 2H), 7.19-7.10 (m, 1H), 6.96-6.56 (m, 2H), 4.45 (dd, J = 10.3, 8.8 Hz, 1H), 3.36-3.32 (m, 2H), 3.14 (t, J = 8.0 Hz, 2H), 2.60-2.48 (m, 2H), 2.40-2.30 (m, 1H), 1.84 (ddt, J = 12.5, 10.4, 9.2 Hz, 1H). LCMS m/z 450.0 [M + H]$^+$. |
| 22 | | Route B; Method F[1]; S2 | $^1$H NMR (300 MHz, CD$_3$OD) δ 7.68-7.42 (m, 2H), 7.41-7.29 (m, 2H), 7.19 (dd, J = 9.5, 2.2 Hz, 1H), 6.72 (ddd, J = 11.1 9.6, 2.2 Hz, 1H), 4.36 (td, J = 7.6, 6.8 Hz, 1H), 4.22 (d, J = 7.7 Hz, 1H), 3.58 (dd, J = 9.9, 7.5 Hz, 1H), 3.24-3.04 (m, 3H), 2.68-2.52 (m, 2H), 2.42 (s, 3H). LCMS m/z 414.0 [M + H]$^+$. |

TABLE 3-continued

Method of preparation, structure and physicochemical data for compounds 21-26

| Compound | Product | Indole Preparation; Amine coupling method; non-commercial amine | $^1$H NMR; LCMS m/z [M + H]$^+$ |
|---|---|---|---|
| 23 | 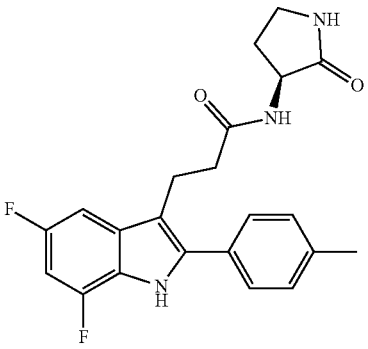 [SMILES: Cc1ccc(-c2[nH]c3c(F)cc(F)cc3c2CCC(=O)N[C@H]2CCNC2=O)cc1] | Route B; Method F[1]. | $^1$H NMR (400 MHz, DMSO-d$_6$) δ 11.62 (s, 1H), 8.20 (d, J = 8.0 Hz, 1H), 7.83 (s, 1H), 7.57-7.51 (m, 2H), 7.33 (d, J = 7.8 Hz, 2H), 7.26 (dd, J = 9.6, 2.2 Hz, 1H), 6.95 (ddd, J = 11.6, 9.7, 2.2 Hz, 1H), 4.29 (dt, J = 10.1, 8.3 Hz, 1H), 3.16 (dd, J = 9.2, 4.3 Hz, 2H), 3.02-2.94 (m, 2H), 2.47-2.39 (m, 2H), 2.38 (s, 3H), 2.29 (ddd, J = 12.5, 8.4, 4.3 Hz, 1H), 1.77-1.62 (m, 1H). LCMS m/z 398.2 [M + H]$^+$. |
| 24 | 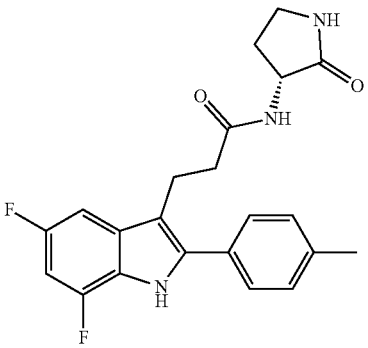 | Route B; Method F[1]. | $^1$H NMR (400 MHz, DMSO-d$_6$) δ 11.62 (s, 1H), 8.20 (d, J = 8.0 Hz, 1H), 7.83 (s, 1H), 7.57-7.51 (m, 2H), 7.33 (d, J = 7.8 Hz, 2H), 7.26 (dd, J = 9.6, 2.2 Hz, 1H), 6.95 (ddd, J = 11.7, 9.8, 2.3 Hz, 1H), 4.29 (q, J = 8.7 Hz, 1H), 3.16 (dd, J = 9.2, 4.3 Hz, 2H), 3.02-2.94 (m, 2H), 2.47-2.39 (m, 2H), 2.38 (s, 3H), 2.29 (tt, J = 8.4, 4.5 Hz, 1H), 1.69 (p, J = 10.4, 10.0 Hz, 1H). LCMS m/z 398.2 [M + H]$^+$. |
| 25 | 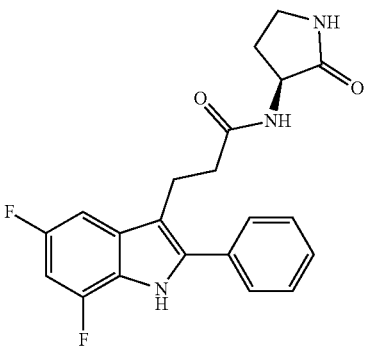 [SMILES: O=C(CCc1c(-c2ccccc2)[nH]c2c(F)cc(F)cc12)N[C@H]1CCNC1=O] | Route B; Method F[1]. | $^1$H NMR (300 MHz, CD$_3$OD) δ 7.73-7.58 (m, 2H), 7.57-7.47 (m, 2H), 7.47-7.34 (m, 1H), 7.25-7.15 (m, 1H), 6.74 (ddd, J = 11.1, 9.6, 2.2 Hz, 1H), 4.48 (dd, J = 10.3, 8.8 Hz, 1H), 3.33-3.24 (m, 2H), 3.18 (t, J = 8.0 Hz, 2H), 2.64-2.52 (m, 2H), 2.44-2.32 (m, 1H), 1.86 (ddt, J = 12.5, 10.4, 9.2 Hz, 1H). LCMS m/z 384.1 [M + H]$^+$. |
| 26 | 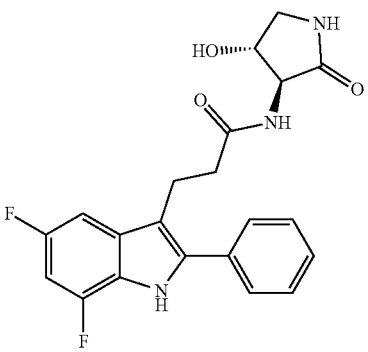 [SMILES: O=C(CCc1c(-c2ccccc2)[nH]c2c(F)cc(F)cc12)N[C@@H]1C(=O)NC[C@H]1O] | Route B; Method F[1]. S2 | $^1$H NMR (300 MHz, CD$_3$OD) δ 7.73-7.60 (m, 2H), 7.57-7.45 (m, 2H), 7.45-7.32 (m, 1H), 7.22 (dd, J = 9.4, 2.2 Hz, 1H), 6.74 (ddd, J = 11.1, 9.6, 2.2 Hz, 1H), 4.37 (td, J = 7.6, 6.8 Hz, 1H), 4.24 (d, J = 7.8 Hz, 1H), 3.58 (dd, J = 9.9, 7.5 Hz, 1H), 3.25-3.08 (m, 3H), 2.71-2.50 (m, 2H), LCMS m/z 400.1 [M + H]$^+$. |

[1]Purification by reversed-phase HPLC. Method: C18 Waters Sunfire column (30 × 150 mm, 5 micron). Gradient: 10-100% MeCN in H$_2$O with 0.2% formic acid.

Compounds 27-42

Compounds 27-42 (Table 4) were prepared from the appropriate indole propanoic acid and the appropriate amine via an amide coupling reaction. An amide coupling reagent such as HATU, and an organic base (NEt$_3$ or DIPEA) as described in the preparation of compound 1 or compound 18 was used. Alternatively, CDMT/NMM conditions were used as described for preparation of compound 2. Any modifications to methods are noted in Table 4 and accompanying footnotes. Indole propanoic acids were prepared according to route A unless otherwise noted.

TABLE 4

Method of preparation, structure and physicochemical data for compounds 27-42

| Compound | Product | Indole Preparation; Amine coupling method; non-commercial amine | $^1$H NMR; LCMS m/z [M + H]$^+$ |
|---|---|---|---|
| 27 | (structure: 5-bromo-7-fluoro-2-(4-fluorophenyl)indole with propanamide linked to 2-oxopyrrolidin-3-yl) | Route A; compound 1; commercial[1,2]. | $^1$H NMR (300 MHz, CD$_3$OD) δ 7.74-7.55 (m, 3H), 7.30-7.15 (m, 2H), 7.02 (dd, J = 10.5, 1.6 Hz, 1H), 4.44 (ddt, J = 10.2, 8.4, 4.0 Hz, 1H), 3.34-3.32 (m, 2H), 3.13 (t, J = 7.9 Hz, 2H), 2.62-2.49 (m, 2H), 2.45-2.32 (m, 1H), 1.93-1.71 (m, 1H). LCMS m/z 458.2 [M + H]$^+$. |
| 28 | (structure: 5-cyano-7-fluoro-2-(4-fluorophenyl)indole with propanamide linked to 2-oxopyrrolidin-3-yl) | From 27[3] (see footnote) | $^1$H NMR (300 MHz, CD$_3$OD) δ 11.82 (s, 1H), 7.97 (d, J = 1.2 Hz, 1H), 7.80-7.56 (m, 2H), 7.39-7.10 (m, 3H), 4.45 (dd, J = 10.3, 8.8 Hz, 1H), 3.42-3.32 (m, 1H), 3.19 (t, J = 7.9 Hz, 2H), 2.57 (td, J = 7.6, 3.4 Hz, 2H), 2.41-2.31 (m, 1H), 1.84 (dd, J = 12.5, 10.2 Hz, 1H). LCMS m/z 409.0 [M + H]$^+$. |
| 29 | (structure: 5-methyl-7-fluoro-2-(4-fluorophenyl)indole with propanamide linked to 4-hydroxy-2-oxopyrrolidin-3-yl) | Route A; Method F[1]. S2 | $^1$H NMR (300 MHz, CD$_3$OD) δ 7.70-7.49 (m, 2H), 7.30-7.12 (m, 3H), 6.69 (dd, J = 12.2, 1.2 Hz, 1H), 4.34 (td, J = 7.6, 6.8 Hz, 1H), 4.21 (d, J = 7.6 Hz, 1H), 3.56 (dd, J = 9.9, 7.5 Hz, 1H), 3.23-3.02 (m, 3H), 2.71-2.49 (m, 2H), 2.47-2.31 (m, 3H). LCMS m/z 414.0 [M + H]$^+$. |

TABLE 4-continued

Method of preparation, structure and physicochemical data for compounds 27-42

| Compound | Product | Indole Preparation; Amine coupling method; non-commercial amine | ¹H NMR; LCMS m/z [M + H]⁺ |
|---|---|---|---|
| 30 | | Route A; Method F¹; S2 | ¹H NMR (300 MHz, CD₃OD) δ 11.22 (s, 1H), 7.76-7.54 (m, 2H), 7.48 (dd, J = 1.7, 0.6 Hz, 1H), 7.36-7.08 (m, 2H), 6.89 (dd, J = 10.7, 1.7 Hz, 1H), 4.34 (tdd, J = 7.8, 6.8, 1.2 Hz, 1H), 4.28-4.06 (m, 1H), 3.57 (dd, J = 9.9, 7.6 Hz, 1H), 3.20-2.90 (m, 3H), 2.74-2.28 (m, 2H). LCMS m/z 433.9 [M + H]⁺. |
| 31 | | Route A; Method F¹. | ¹H NMR (400 MHz, DMSO-d₆) δ 11.42 (s, 1H), 8.19 (d, J = 8.1 Hz, 1H), 7.83 (s, 1H), 7.72-7.64 (m, 2H), 7.35 (t, J = 8.9 Hz, 2H), 7.20 (s, 1H), 6.78 (d, J = 12.2 Hz, 1H), 4.29 (dt, J = 10.2, 8.3 Hz, 1H), 3.17 (dd, J = 9.2, 4.4 Hz, 2H), 3.02-2.94 (m, 2H), 2.50-2.41 (m, 2H), 2.40 (s, 3H), 2.29 (tt, J = 8.4, 4.6 Hz, 1H), 1.79-1.64 (m, 1H). LCMS m/z 398.1 [M + H]⁺. |
| 32 | | Route A; Method F¹. | ¹H NMR (300 MHz, CD₃OD) δ 7.68-7.55 (m, 2H), 7.47 (d, J = 1.7 Hz, 1H), 7.30-7.08 (m, 2H), 6.89 (dd, J = 10.7, 1.7 Hz, 1H), 4.44 (dd, J = 10.3, 8.8 Hz, 1H), 3.3 (2H, peak obscured by solvent) 3.14 (t, J = 7.9 Hz, 2H), 2.63-2.47 (m, 2H), 2.46-2.33 (m, 1H), 1.84 (ddt, J = 12.6, 10.3, 9.2 Hz, 1H). LCMS m/z 418.2 [M + H]⁺. |
| 33 | | Route A; Method F¹. | ¹H NMR (400 MHz, DMSO-d₆) δ 11.83 (s, 1H), 8.21 (d, J = 8.0 Hz, 1H), 7.83 (s, 1H), 7.74-7.65 (m, 2H), 7.52 (d, J = 1.7 Hz, 1H), 7.38 (t, J = 8.9 Hz, 2H), 7.09 (dd, J = 10.8, 1.7 Hz, 1H), 4.27 (dt, J = 10.1, 8.2 Hz, 1H), 3.16 (dd, J = 9.2, 4.3 Hz, 2H), 3.03-2.94 (m, 2H), 2.49-2.38 (m, 2H), 2.27 (td, J = 8.5, 4.5 Hz, 1H), 1.68 (dt, J = 20.5, 9.6 Hz, 1H). LCMS m/z 418.1 [M + H]⁺. |

TABLE 4-continued

Method of preparation, structure and physicochemical data for compounds 27-42

| Compound | Product | Indole Preparation; Amine coupling method; non-commercial amine | $^1$H NMR; LCMS m/z [M + H]$^+$ |
|---|---|---|---|
| 34 | | Route A; Method F$^1$. | $^1$H NMR (400 MHz, DMSO-d$_6$) δ 11.52 (s, 1H), 8.19 (d, J = 8.0 Hz, 1H), 7.83 (s, 1H), 7.72-7.64 (m, 2H), 7.46-7.32 (m, 3H), 7.17 (dd, J = 9.2, 2.3 Hz, 1H), 4.27 (dt, J = 10.2, 8.2 Hz, 1H), 3.16 (dd, J = 9.2, 4.3 Hz, 2H), 2.98-2.92 m, 2H), 2.43 (t, J = 8.0 Hz, 2H), 2.27 (ddt, J = 12.6, 8.5, 4.3 Hz, 1H), 1.74-1.60 (m, 1H). LCMS m/z 418.3 [M + H]$^+$. |
| 35 | | Route A; Method F$^1$; S2 | $^1$H NMR (300 MHz, CD$_3$OD) δ 7.75-7.60 (m, 2H), 7.58-7.48 (m, 2H), 7.47-7.29 (m, 2H), 6.99 (dd, J = 9.2, 2.3 Hz, 1H), 4.36 (td, J = 7.6, 6.8 Hz, 1H), 4.23 (d, J = 7.8 Hz, 1H), 3.58 (dd, J = 9.9, 7.6 Hz, 1H), 3.23-3.02 (m, 3H), 2.65-2.46 (m, 2H). LCMS m/z 416.1 [M + H]$^+$. |
| 36 | | Route A; Method F$^4$; S2 | $^1$H NMR (300 MHz, CD$_3$OD) δ 7.71-7.59 (m, 2H), 7.34 (dd, J = 9.5, 2.3 Hz, 1H), 7.29-7.17 (m, 2H), 6.98 (dd, J = 9.2, 2.3 Hz, 1H), 4.33 (q, J = 7.5 Hz, 1H), 4.21 (d, J = 7.8 Hz, 1H), 3.56 (dd, J = 9.9, 7.5 Hz, 1H), 3.23-3.04 (m, 3H), 2.68-2.47 (m, 2H). LCMS m/z 434.3 [M + H]$^+$. |
| 37 | | Route A; Method G$^5$; S2 | $^1$H NMR (300 MHz, CD$_3$OD) δ 7.69-7.59 (m, 2H), 7.27-7.17 (m, 2H), 7.18-7.11 (m, 1H), 6.70 (ddd, J = 10.1, 2.5, 1.0 Hz, 1H), 4.34 (td, J = 7.6, 6.8 Hz, 1H), 4.22 (d, J = 7.7 Hz, 1H), 3.56 (dd, J = 9.9, 7.5 Hz, 1H), 3.18-3.05 (m, 3H), 2.65-2.54 (m, 2H), 2.50 (d, J = 0.7 Hz, 3H). LCMS m/z 414.3 [M + H]$^+$. |

TABLE 4-continued

Method of preparation, structure and physicochemical data for compounds 27-42

| Compound | Product | Indole Preparation; Amine coupling method; non-commercial amine | $^1$H NMR; LCMS m/z [M + H]$^+$ |
|---|---|---|---|
| 38 | | Route A; Method F$^1$. | $^1$H NMR (300 MHz, CD$_3$OD) δ 7.71-7.59 (m, 2H), 7.34 (dd, J = 9.5, 2.3 Hz, 1H), 7.29-7.17 (m, 2H), 6.98 (dd, J = 9.2, 2.3 Hz, 1H), 4.33 (q, J = 7.5 Hz, 1H), 4.21 (d, J = 7.8 Hz, 1H), 3.56 (dd, J = 9.9, 7.5 Hz, 1H), 3.3 2H, peak obscured by solvent), 3.23-3.04 (m, 3H), 2.68-2.47 (m, 2H). LCMS m/z 434.3 [M + H]$^+$. |
| 39 | | Route A; Method F$^1$. | $^1$H NMR (400 MHz, DMSO-d$_6$) δ 11.42 (s, 1H), 8.19 (d, J = 8.1 Hz, 1H), 7.83 (s, 1H), 7.72-7.64 (m, 2H), 7.35 (t, J = 8.9 Hz, 2H), 7.20 (s, 1H), 6.78 (d, J = 12.2 Hz, 1H), 4.29 (dt, J = 10.1, 8.3 Hz, 1H), 3.17 (dd, J = 9.3, 4.3 Hz, 2H), 3.02-2.94 (m, 2H), 2.50-2.41 (m, 2H), 2.40 (s, 3H), 2.28 (ddt, J = 12.6, 8.7, 4.5 Hz, 1H), 1.79-1.4 (m, 1H). LCMS m/z 398.2 [M + H]$^+$. |
| 40 | | Route A; Method F$^1$; S2 | $^1$H NMR (300 MHz, CD$_3$OD) δ 7.67-7.49 (m, 2H), 7.29-7.13 (m, 2H), 6.93 (dd, J = 9.6, 2.1 Hz, 1H), 6.50 (dd, J = 11.3, 2.1 Hz, 1H), 4.43-4.31 (m, 1H), 4.21 (d, J = 7.7 Hz, 1H), 3.95 (s, 3H), 3.56 (dd, J = 9.9, 7.6 Hz, 1H), 3.20-2.96 (m, 3H), 2.68-2.48 (m, 2H). LCMS m/z 430.2 [M + H]$^+$. |
| 41 | | Route A; Method F$^1$; commercial | $^1$H NMR (400 MHz, DMSO-d$_6$) δ 11.28 (s, 1H), 8.20 (d, J = 8.0 Hz, 1H), 7.83 (s, 1H), 7.69-7.61 (m, 2H), 7.32 (t, J = 8.9 Hz, 2H), 6.96 (dd, J = 9.6, 2.1 Hz, 1H), 6,62 (dd, J = 11.5, 2.2 Hz, 1H), 4.29 (dt, J = 10.1, 8.3 Hz, 1H), 3.93 (s, 3H), 3.16 (dd, J = 9.2, 4.3 Hz, 2H), 2.94 (dd, J = 9.8, 6.5 Hz, 2H), 2.46-2.38 (m, 2H), 2.29 (tt, J = 8.4, 4.5 Hz, 1H), 1.78-1.63 (m, 1H). LCMS m/z 414.2 [M + H]$^+$. |

TABLE 4-continued

Method of preparation, structure and physicochemical data for compounds 27-42

| Compound | Product | Indole Preparation; Amine coupling method; non-commercial amine | ¹H NMR; LCMS m/z [M + H]⁺ |
|---|---|---|---|
| 42 | (structure shown) | Route A; Method F[1]; S2 | ¹H NMR (300 MHz, CD₃OD) δ 11.57 (s, 1H), 7.80-7.63 (m, 3H), 7.29 (dt, J = 17.3, 8.8 Hz, 3H), 4.31 (d, J = 7.2 Hz, 1H), 4.21 (d, J = 7.8 Hz, 1H), 3.67-3.49 (m, 1H), 3.13 (dt, J = 17.8, 8.3 Hz, 3H), 2.58 (t, J = 8.2 Hz, 2H). LCMS m/z, 425.3 [M + H]⁺. |

[1]Purification by reversed-phase HPLC, Method: C18 Waters Sunfire column (30 × 150 mm, 5 micron). Gradient: 10-100% MeCN in H₂O with 0.2% formic acid.
[2]DMF used as solvent for coupling reaction.
[3]Compound 28 was prepared from compound 27 via a cyanation reaction. Compound 27 (33 mg, 0.07 mmol) and CuCN (24 mg, 0.27 mmol) in NMP (12 mL) were heated at 220° C. under microwave conditions for 2 h. Purification of the reaction mixture by reversed-phase chromatography afforded the product.
[4]Purification by reversed-phase HPLC. Method: C18 Waters Sunfire column (30 × 150 mm, 5 micron). Gradient: 10-100% MeCN in H₂O with 0.1% TFA.
[5]Purified by trituration with 2% MeOH in CH₂Cl₂.

Compound 43

3-[2-(4-bromophenyl)-5-methyl-1H-indol-3-yl]-N-[(3S)-2-oxopyrrolidin-3-yl]propanamide (43

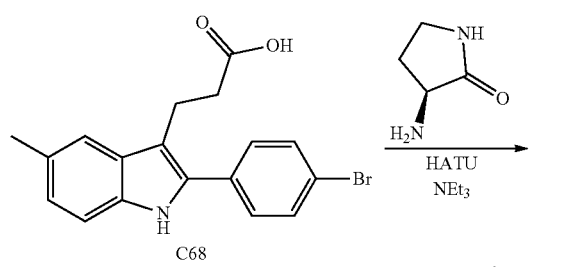

Synthesis of 3-[2-(4-bromophenyl)-5-methyl-1H-indol-3-yl]-N-[(3S)-2-oxopyrrolidin-3-yl]propanamide (43

Compound 43 was prepared from commercially available 3-[2-(4-bromophenyl)-5-methyl-1H-indol-3-yl]propanoic acid C68 and (3S)-3-aminopyrrolidin-2-one using the method described for compound 1. Purification by reversed phase chromatography afforded the product. ¹H NMR (300 MHz, CD₃OD) δ 7.67-7.58 (m, 2H), 7.58-7.49 (m, 2H), 7.44 (dt, J=1.8, 0.8 Hz, 1H), 7.25 (dd, J=8.2, 0.7 Hz, 1H), 7.03-6.93 (m, 1H), 4.47 (dd, J=10.3, 8.8 Hz, 1H), 3.3 (2H, obscured by solvent), 3.20 (dd, J=8.7, 7.4 Hz, 2H), 2.69-2.53 (m, 2H), 2.45 (s, 3H), 2.37 (dddd, J=12.6, 8.8, 5.1, 3.7 Hz, 1H), 1.85 (ddt, J=12.6, 10.3, 9.2 Hz, 1H). LCMS m/z 440.0 [M+H]⁺.

Compound 44

3-(5-chloro-2-phenyl-1H-indol-3-yl)-N-[(3S,4R)-4-hydroxy-2-oxo-pyrrolidin-3-yl]propanamide (44

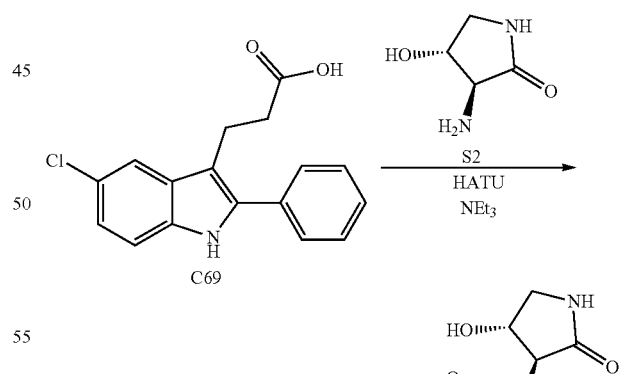

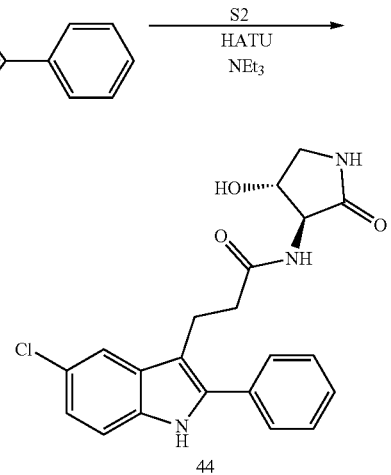

Synthesis of 3-(5-chloro-2-phenyl-1H-indol-3-yl)-N-[(3S,4R)-4-hydroxy-2-oxo-pyrrolidin-3-yl]propanamide (44

Compound 44 was prepared from 3-(5-chloro-2-phenyl-1H-indol-3-yl)propanoic acid C69 and S2 using the method as described for compound 1. Purification by reversed phase chromatography afforded the product. $^1$H NMR (300 MHz, CD$_3$OD) δ 7.72-7.56 (m, 3H), 7.55-7.44 (m, 2H), 7.39-7.25 (m, 2H), 7.07 (dd, J=8.6, 2.0 Hz, 1H), 4.36 (td, J=7.6, 6.8 Hz, 1H), 4.22 (d, J=7.7 Hz, 1H), 3.57 (dd, J=9.9, 7.6 Hz, 1H), 3.28-3.15 (m, 2H), 3.11 (dd, J=9.9, 6.8 Hz, 1H), 2.76-2.52 (m, 2H). LCMS m/z 398.1 [M+H]$^+$.

Compound 45

3-[5-chloro-2-(4-fluorophenyl)-1H-indol-3-yl]-N-[(3S,4R)-4-hydroxy-2-oxo-pyrrolidin-3-yl]propanamide (45

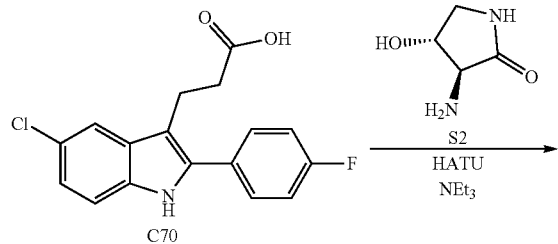

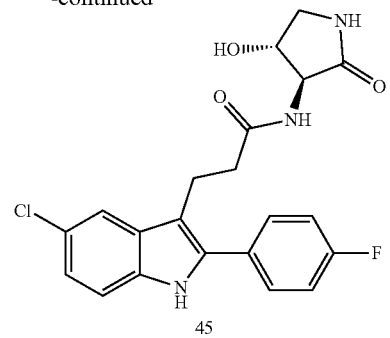

Synthesis of 3-[5-chloro-2-(4-fluorophenyl)-1H-indol-3-yl]-N-[(3S,4R)-4-hydroxy-2-oxo-pyrrolidin-3-yl]propanamide (45

To a mixture of 3-[5-chloro-2-(4-fluorophenyl)-1H-indol-3-yl]propanoic acid C70 (30 mg, 0.09 mmol) (prepared using method A), (3S,4R)-3-amino-4-hydroxy-pyrrolidin-2-one (13 mg, 0.1 mmol), HATU (50 mg, 0.13 mmol) in DMSO (5 mL) was added NEt$_3$ (43 µL, 0.3 mmol). The reaction mixture was allowed to stir at room temperature for 1 h. Purification by reverse phase chromatography (C18 column; Gradient: 10-100% acetonitrile in water with 0.2% formic acid) afforded product. (31.3 mg, 81%) $^1$H NMR (300 MHz, CD$_3$OD) δ 7.72-7.52 (m, 3H), 7.31 (dd, J=8.6, 0.6 Hz, 1H), 7.22 (t, J=8.8 Hz, 2H), 7.07 (dd, J=8.6, 2.0 Hz, 1H), 4.35 (td, J=7.6, 6.8 Hz, 1H), 4.21 (d, J=7.7 Hz, 1H), 3.57 (dd, J=9.9, 7.6 Hz, 1H), 3.23-2.99 (m, 3H), 2.74-2.52 (m, 2H). LCMS m/z 416.1 [M+H]$^+$.

Compound 46-53

Compounds 46-53 (Table 5) were prepared from the appropriate indole propanoic acid and the appropriate amine via an amide coupling reaction. An amide coupling reagent such as HATU, and an organic base (NEt$_3$ or DIPEA) as described in the preparation of compound 1 was used. Any modifications to methods are noted in Table 5 and accompanying footnotes. Indole propanoic acids were either commercially sourced or prepared according to route B.

TABLE 5

Method of preparation, structure and physicochemical data for compounds 46-53

| Compound | Product | Indole Preparation; Amine coupling method; non-commerical amine | $^1$H NMR; LCMS m/z [M + H]$^+$ |
|---|---|---|---|
| 46 | ![structure] | Commerical; Method F$^1$; S2 | $^1$H NMR (300 MHz, DMSO-d$_6$) δ 11.30 (s, 1H), 8.24 (d, J = 7.4 Hz, 1H), 7.77 (s, 1H), 7.67 (ddd, J = 8.8, 5.4, 2.7 Hz, 2H), 7.52-7.22 (m, 4H), 6.95 (td, J = 9.2, 2.5 Hz, 1H), 5.48 (d, J = 4.9 Hz, 1H), 4.16-3.97 (m, 2H), 3.45-3.33 (m, 1H), 3.13-2.78 (m, 3H) 2.5 (2H, obscured by solvent). LCMS m/z 400.2 [M + H]$^+$. |

TABLE 5-continued

Method of preparation, structure and physicochemical data for compounds 46-53

| Compound | Product | Indole Preparation; Amine coupling method; non-commercial amine | ¹H NMR; LCMS m/z [M + H]⁺ |
|---|---|---|---|
| 47 | (structure) | Commercial; Method F¹. | ¹H NMR (300 MHz, CD₃OD) δ 7.73-7.56 (m, 2H), 7.38-7.27 (m, 2H), 7.28-7.15 (m, 2H), 6.87 (ddd, J = 9.5, 8.8, 2.5 Hz, 1H), 4.46 (dd, J = 10.3, 8.8 Hz, 1H), 3.31 (dt, J = 3.3, 1.9 Hz, 2H), 3.15 (t, J = 7.9 Hz, 2H), 2.62-2.44 (m, 2H), 2.36 (dddd, J = 12.6, 8.8, 5.1, 3.6 Hz, 1H), 1.83 (ddt, J = 12.6, 10.5, 9.2 Hz, 1H). LCMS m/z 384.2 [M + H]⁺. |
| 48 | (structure) | Commercial; Method F¹. | ¹H NMR (400 MHz, DMSO-d₆) δ 11.30 (s, 1H), 8.21 (d, J = 8.0 Hz, 1H), 7.83 (s, 1H), 7.71-7.63 (m, 2H), 7.42-7.29 (m, 4H), 6.94 (td, J = 9.2, 2.5 Hz, 1H), 4.29 (dt, J = 10.2, 8.3 Hz, 1H), 3.16 (dd, J = 9.2, 4.3 Hz, 2H), 3.04-2.96 (m, 2H), 2.50-2.41 (m, 2H), 2.28 (ddd, J = 12.6, 8.4, 4.3 Hz, 1H), 1.77-1.62 (m, 1H). LCMS m/z 384.0 [M + H]⁺. |
| 49 | (structure) | Commercial; Method F¹. | ¹H NMR (300 MHz, CD₃OD) δ 7.74-7.52 (m, 2H), 7.36-7.15 (m, 4H), 6.87 (ddd, J = 9.5, 8.8, 2.5 Hz, 1H), 4.46 (dd, J = 10.3, 8.8 Hz, 1H), 3.32 (dd, J = 3.8, 2.2 Hz, 2H), 3.15 (t, J = 8.0 Hz, 2H), 2.61-2.51 (m, 2H), 2.37 (dddd, J = 12.5, 8.8, 5.0, 3.7 Hz, 1H), 1.83 (ddt, J = 12.5, 10.3, 9.2 Hz, 1H). LCMS m/z 384.2 [M + H]⁺. |
| 50 | (structure) | Commercial; Method F¹. | ¹H NMR (300 MHz, CD₃OD) δ 7.78-7.52 (m, 2H), 7.36-7.19 (m, 4H), 6.88 (ddt, J = 9.4, 8.7, 2.1 Hz, 1H), 3.41-3.32 (m, 2H), 3.20-3.08 (m, 2H), 2.81 (s, 3H), 2.77-2.66 (m, 3H), 2.37-2.17 (m, 1H), 2.00-1.85 (m, 1H). LCMS m/z 398.1 [M + H]⁺. |

TABLE 5-continued

Method of preparation, structure and physicochemical data for compounds 46-53

| Compound | Product | Indole Preparation; Amine coupling method; non-commerical amine | $^1$H NMR; LCMS m/z [M + H]$^+$ |
|---|---|---|---|
| 51 | 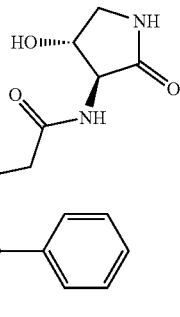 | Commercial; Method F$^1$; S2 | $^1$H NMR (300 MHz, CD$_3$OD) δ 7.74-7.55 (m, 2H), 7.57-7.38 (m, 2H), 7.39-7.19 (m, 3H), 6.87 (ddd, J = 9.5, 8.8, 2.5 Hz, 1H), 4.45-4.31 (m, 1H), 4.21 (d, J = 7.7 Hz, 1H), 3.56 (dd, J = 9.9, 7.5 Hz, 1H), 3.30-3.14 (m, 2H), 3.10 (dd, J = 9.9, 6.8 Hz, 1H), 2.74-2.52 (m, 2H). LCMS m/z 382.1 [M + H]$^+$. |
| 52 | 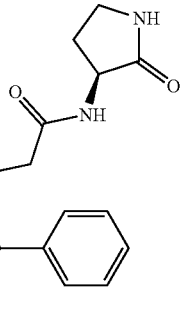 | Commercial; Method F$^1$. | $^1$H NMR (300 MHz, CD$_3$OD) δ 7.70-7.56 (m, 2H), 7.55-7.42 (m, 2H), 7.40-7.34 (m, 1H), 7.35-7.26 (m, 2H), 6.86 (td, J = 9.1, 2.5 Hz, 1H), 4.45 (dd, J = 10.2, 8.8 Hz, 1H), 3.3 (2H, peak obscured by solvent), 3.19 (t, J = 8.0 Hz, 2H), 2.69-2.52 (m, 2H), 2.37 (dddd, J = 12.6, 8.8, 5.0, 3.8 Hz, 1H), 1.84 (ddt, J = 12.5, 10.2, 9.5 Hz, 1H). LCMS m/z 366.2 [M + H]$^+$. |
| 53 | 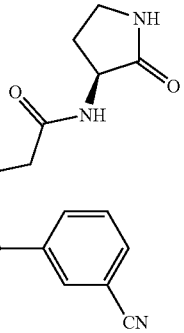 | Route B; Method F$^2$. | $^1$H NMR (400 MHz, DMSO-d$_6$) δ 11.44 (s, 1H), 8.02 (d, J = 8.2 Hz, 1H), 8.08 (s, 1H), 7.98 (d, J = 8.0 Hz, 1H), 7.90-7.80 (m, 2H), 7.74 (t, J = 7.9 Hz, 1H), 7.41 (d, J = 10.2 Hz, 1H), 7.36 (s, 1H), 7.00 (d, J = 9.6 Hz, 1H), 4.27 (d, J = 9.8 Hz, 1H), 3.15 (s, 2H), 3.04 (s, 2H), 2.57-2.52 (m, 2H), 2.26 (s, 1H), 1.66 (t, J = 10.4 Hz, 1H). LCMS m/z 391.3 [M + H]$^+$. |

$^1$Purification by reversed-phase HPLC. Method: C18 Waters Sunfire column (30 × 150 mm, 5 micron). Gradient: 10-100% MeCN in H$_2$O with 0.2% formic acid.

$^2$DIPEA used as base in the HATU coupling reaction. Purification by reversed-phase HPLC. Method: C18 Waters Sunfire column (30 × 150 mm, 5 micron). Gradient: 10-100% MeCN in H$_2$O with 0.1% TFA.

Compound 54 and Compound 55

3-[5-benzyloxy-2-(4-fluorophenyl)-1H-indol-3-yl]-
N-[(3S)-2-oxopyrrolidin-3-yl]propanamide (54) and
3-[2-(4-fluorophenyl)-5-hydroxy-1H-indol-3-yl]-N-
[(3S)-2-oxopyrrolidin-3-yl]propanamide (55

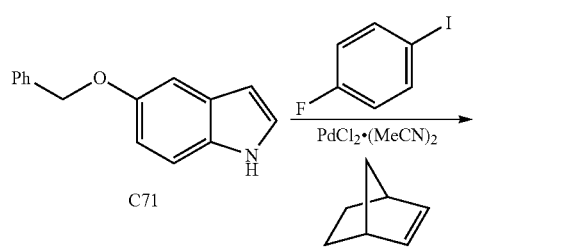

Step 1. Synthesis of 5-benzyloxy-2-(4-fluorophenyl)-1H-indole (C72

A solution of 1-fluoro-4-iodo-benzene (3 mL, 26.0 mmol), 5-benzyloxy-1H-indole C71 (5.2 g, 23.4 mmol), PdCl$_2$(PPh$_3$)$_2$ (600 mg, 2.3 mmol), bicyclo[2.2.1]hept-2-ene (4.5 g, 47.3 mmol) and K$_2$CO$_3$ (6.8 g, 49.4 mmol) in DMA (50 mL) and water (5 mL) was stirred at 90° C. overnight. Water (100 mL) was added and the mixture extracted with EtOAc (3×50 mL). Purification by silica gel chromatography (Gradient: 0-100% EtOAc in heptane) afforded the product (4.9 g, 64%). $^1$H NMR (300 MHz, CDCl$_3$) δ 8.16 (s, 1H), 7.70-7.58 (m, 2H), 7.59-7.47 (m, 2H), 7.46-7.28 (m, 4H), 7.25-7.05 (m, 3H), 6.96 (dd, J=8.8, 2.4 Hz, 1H), 6.70 (dd, J=2.2, 0.9 Hz, 1H), 5.14 (s, 2H). LCMS m/z 318.0 [M+H]$^+$.

Step 2. Synthesis of Methyl 3-[5-benzyloxy-2-(4-fluorophenyl)-1H-indol-3-yl]propanoate (C73

To 5-benzyloxy-2-(4-fluorophenyl)-1H-indole C72 (455 mg, 1.4 mmol) and methyl 3,3-dimethoxypropanoate (260 μL, 1.8 mmol) in dichloroethane (6 mL) was added MeSO$_3$H (200 μL, 3.1 mmol) and Et$_3$SiH (700 μL, 4.4 mmol). The mixture was heated at 90° C. for 12 h. Water (50 mL) was added and the mixture was acidified to pH 2. The mixture was then extracted with dichloromethane (3×30 mL), washed with brine, dried and concentrated in vacuo. Silica gel chromatography (Gradient: 0-100% EtOAc in heptane) afforded the product (314 mg, 51%). $^1$H NMR (300 MHz, CDCl$_3$) δ 7.89 (s, 1H), 7.60-7.49 (m, 4H), 7.47-7.32 (m, 3H), 7.24-7.04 (m, 3H), 6.97 (dd, J=8.7, 2.4 Hz, 1H), 5.15 (s, 2H), 3.66 (s, 3H), 3.24-3.08 (m, 2H), 2.77-2.45 (m, 2H). LCMS m/z 404.2 [M+H]$^+$.

Step 3. Synthesis of 3-[5-benzyloxy-2-(4-fluorophenyl)-1H-indol-3-yl]propanoic Acid (C74)

A mixture of methyl 3-[5-benzyloxy-2-(4-fluorophenyl)-1H-indol-3-yl]propanoate C73 (302 mg, 0.7 mmol), LiOH (166 mg, 6.9 mmol) in MeOH (3 mL), 3 mL THF (3 mL) and water (5 mL) was stirred at 50° C. for 2 h. The mixture was concentrated and water (50 mL) was added. The mixture was adjusted to pH 1 using HCl, then extracted with CH$_2$Cl$_2$ (3×30 mL), washed with brine, dried and concentrated in vacuo to afford the product. (245 mg, 91%). $^1$H NMR (300 MHz, CDCl$_3$) δ 7.81 (s, 1H), 7.47-7.17 (m, 8H), 7.07 (ddd, J=8.7, 6.2, 2.7 Hz, 3H), 5.10 (s, 2H), 6.88 (dd, J=8.8, 2.4 Hz, 1H), 3.19-2.97 (m, 2H), 2.70-2.47 (m, 2H). LCMS m/z 390.1 [M+H]$^+$.

Step 4. Synthesis of 3-[5-benzyloxy-2-(4-fluorophenyl)-1H-indol-3-yl]-N-[(3S)-2-oxopyrrolidin-3-yl]propanamide (54

To a mixture of 3-[5-benzyloxy-2-(4-fluorophenyl)-1H-indol-3-yl]propanoic acid C74 (84 mg, 0.2 mmol), (3S)-3-aminopyrrolidin-2-one (30 mg, 0.3 mmol) and HATU (171 mg, 0.4 mmol) in DMF (4 mL) was added TEA (125 µL, 0.9 mmol). The mixture was allowed to stir at room temperature for 4 h, then evaporated to remove DMF. 5 M HCl (30 mL) was added and the mixture extracted with EtOAc (2×20 mL). Purification by Silica gel column (Gradient: 0 to 20% MeOH in dichloromethane) afforded the product (91.2 mg, 89%). $^1$H NMR (300 MHz, CD$_3$OD) δ 8.53-8.15 (m, 1H), 7.97 (s, 1H), 7.69-7.55 (m, 2H), 7.53-7.44 (m, 2H), 7.42-7.27 (m, 3H), 7.27-7.14 (m, 3H), 6.85 (dd, J=8.7, 2.4 Hz, 1H), 5.12 (s, 2H), 4.56-4.31 (m, 1H), 3.29-3.19 (m, 2H, peak obscured by solvent), 3.17 (t, J=7.8 Hz, 2H), 2.65-2.52 (m, 2H), 2.35 (ddd, J=12.1, 8.8, 4.6 Hz, 1H), 1.81 (dq, J=12.4, 9.3 Hz, 1H). LCMS m/z 472.3 [M+H]$^+$.

Step 5. Synthesis of 3-[2-(4-fluorophenyl)-5-hydroxy-1H-indol-3-yl]-N-[(3S)-2-oxopyrrolidin-3-yl]propanamide (55

Method K: Palladium on Carbon Catalyzed Hydrogenation. A mixture of 3-[5-benzyloxy-2-(4-fluorophenyl)-1H-indol-3-yl]-N-[(3S)-2-oxopyrrolidin-3-yl]propanamide 54 (89 mg, 0.19 mmol), 5% Pd/C (20 mg) in MeOH (10 mL) and EtOAc (10 mL) was subjected to hydrogenation conditions of 50 psi of H$_2$ for 3 h. Filtration through Celite® and concentration in vacuo afforded the product (59 mg, 80%) $^1$H NMR (300 MHz, CD$_3$OD) δ 7.98 (s, 1H), 7.67-7.52 (m, 2H), 7.18 (td, J=8.6, 1.8 Hz, 3H), 7.00 (d, J=2.3 Hz, 1H), 6.71 (dd, J=8.6, 2.3 Hz, 1H), 4.46 (dd, J=10.3, 8.8 Hz, 1H), 3.3 (2H, peak obscured by solvent), 3.15 (t, J=7.8 Hz, 2H), 2.70-2.52 (m, 2H), 2.40 (dddd, J=12.4, 8.8, 5.3, 3.6 Hz, 1H), 2.00-1.69 (m, 1H). LCMS m/z 382.1 [M+H]$^+$.

Compound 56

3-[2-(4-fluorophenyl)-5-methoxy-1H-indol-3-yl]-N-[(3S)-2-oxopyrrolidin-3-yl]propanamide (56

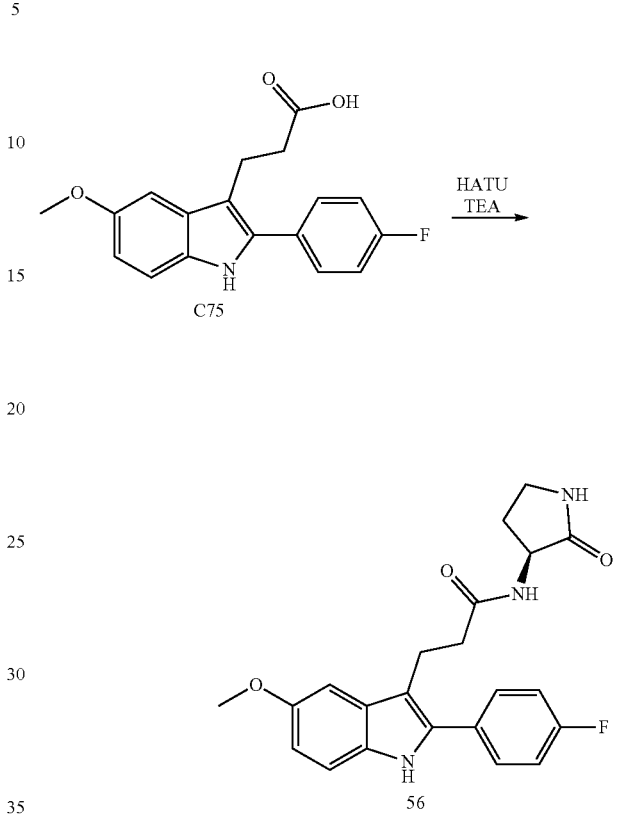

Synthesis of 3-[2-(4-fluorophenyl)-5-methoxy-1H-indol-3-yl]-N-[(3S)-2-oxopyrrolidin-3-yl]propanamide (56

To a mixture of 3-[2-(4-fluorophenyl)-5-methoxy-1H-indol-3-yl]propanoic acid C75 (42 mg, 0.13 mmol), 3-aminopyrrolidin-2-one (19 mg, 0.19 mmol) and HATU (77 mg, 0.2 mmol) in DMSO (1 mL) was added NEt$_3$ (75 µL, 0.5 mmol) and the mixture allowed to stir at room temperature for 13 h. Purification by reversed phase chromatography (C18 column; Gradient: MeCN in H$_2$O with 0.2% formic acid) afforded the product (37 mg, 69%)$^1$H NMR (300 MHz, CD$_3$OD) δ 7.67-7.51 (m, 2H), 7.27-7.05 (m, 4H), 6.77 (dd, J=8.7, 2.4 Hz, 1H), 4.45 (dd, J=10.3, 8.8 Hz, 1H), 3.84 (s, 3H), 3.33-3.27 (m, 2H), 3.21-3.05 (m, 2H), 2.70-2.51 (m, 2H), 2.33 (dddd, J=12.5, 8.8, 5.2, 3.6 Hz, 1H), 1.81 (ddt, J=12.6, 10.4, 9.2 Hz, 1H). LCMS m/z 396.2 [M+H]$^+$.

Compounds 57-61

Compounds 57-61 (Table 6) were prepared from indole propionic acids and the appropriate amine via an amide coupling reaction. 3-[6,7-difluoro-2-(4-fluorophenyl)-1H-indol-3-yl]propanoic acid used in preparation of compounds 57 to 59 was synthesized from 6,7-difluoro-2-(4-fluorophenyl)-1H-indole using the method described for compound 54. An amide coupling reagent such as HATU, and an organic base (NEt$_3$ or DIPEA) as described in the preparation of compound 1 was used. Any modifications to these methods are noted in Table 6 and accompanying footnotes.

TABLE 6

Method of preparation, structure and physicochemical data for compounds 57-61

| Compound | Product | Indole Preparation; Amine coupling method; non-commercial amine | $^1$H NMR; LCMS m/z [M + H]$^+$ |
|---|---|---|---|
| 57 | | From 6,7-difluoro-2-(4-fluorophenyl)-1H-indole; Method F$^1$. | $^1$H NMR (300 MHz, CD$_3$OD) δ 7.77-7.58 (m, 2H), 7.37 (ddd, J = 8.7, 4.1, 1.1 Hz, 1H), 7.31-7.13 (m, 2H), 6.94 (ddd, J = 11.4, 8.7, 7.0 Hz, 1H), 4.47 (dd, J = 10.3, 8.8 Hz, 1H), 3.33 (2H, peak obscured by solvent), 3.17 (t, J = 8.0 Hz, 2H), 2.61-2.51 (m, 2H), 2.39 (dddd, J = 12.5, 8.8, 5.1, 3.6 Hz, 1H), 1.86 (ddt, J = 12.5, 10.4, 9.2 Hz, 1H). LCMS m/z 402.1 [M + H]$^+$. |
| 58 | | From 6,7-difluoro-2-(4-fluorophenyl)-1H-indole; Method F$^1$; S2 | $^1$H NMR (300 MHz, CD$_3$OD) δ 7.75-7.49 (m, 2H), 7.38 (ddd, J = 8.7, 4.1, 1.1 Hz, 1H), 7.31-7.15 (m, 2H), 6.94 (ddd, J = 11.3, 8.7, 7.0 Hz, 1H), 4.36 (td, J = 7.6, 6.8 Hz, 1H), 4.24 (d, J = 7.8 Hz, 1H), 3.58 (dd, J = 9.9, 7.5 Hz, 1H), 3.22-3.04 (m, 3H), 2.67-2.53 (m, 2H). LCMS m/z 418.1 [M + H]$^+$. |
| 59 | | Route B; Method F$^1$; S2 | $^1$H NMR (300 MHz, CD$_3$OD) δ 7.72-7.58 (m, 2H), 7.54-7.43 (m, 2H), 7.37 (ddt, J = 8.8, 5.6, 1.4 Hz, 2H), 6.92 (ddd, J = 11.4, 8.7, 7.0 Hz, 1H), 4.44-4.28 (m, 1H), 4.21 (d, J = 7.7 Hz, 1H), 3.56 (dd, J = 9.9, 7.5 Hz, 1H), 3.27-3.13 (m, 2H), 3.10 (dd, J = 9.9, 6.8 Hz, 1H), 2.69-2.53 (m, 2H). LCMS m/z 400.3 [M + H]$^+$. |
| 60 | | Commercial core; Method F$^1$. | $^1$H NMR (300 MHz, CD$_3$OD) δ 7.74-7.58 (m, 2H), 7.55-7.28 (m, 4H), 6.99 (td, J = 7.9, 4.7 Hz, 1H), 6.85 (ddd, J = 11.3, 7.8, 0.8 Hz, 1H), 4.47 (dd, J = 10.3, 8.8 Hz, 1H), 3.3 (2H, peak obscured by solvent), 3.23 (t, J = 8.0 Hz, 2H), 2.73-2.54 (m, 2H), 2.37 (dddd, J = 12.4, 8.8, 5.3, 3.5 Hz, 1H), 1.92-1.79 (m, 1H). LCMS m/z 366.0 [M + H]$^+$. |

TABLE 6-continued

Method of preparation, structure and physicochemical data for compounds 57-61

| Compound | Product | Indole Preparation; Amine coupling method; non-commercial amine | $^1$H NMR; LCMS m/z [M + H]$^+$ |
|---|---|---|---|
| 61 | 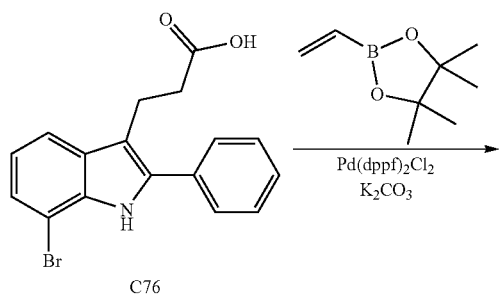 | Commercial core; Method F[2]; S2 | $^1$H NMR (300 MHz, CD$_3$OD) δ 7.69-7.59 (m, 2H), 7.46 (td, J = 7.9, 2.9 Hz, 3H), 7.41-7.26 (m, 1H), 6.97 (td, J = 7.9, 4.7 Hz, 1H), 6.91-6.74 (m, 1H), 4.35 (q, J = 7.4 Hz, 1H), 4.24 (d, J = 7.7 Hz, 1H), 3.55 (dd, J = 9.9, 7.5 Hz, 1H), 3.29-3.16 (m, 2H), 3.10 (dd, J = 9.9, 6.8 Hz, 1H), 2.74-2.50 (m, 2H). LCMS m/z 382.1 [M + H]$^+$. |

[1]Purification by reversed-phase HPLC. Method: C18 Waters Sunfire column (30 × 150 mm, 5 micron). Gradient: MeCN in H$_2$O with 0.2% formic acid.
[2]HATU coupling reaction was performed in DMF using DIPEA as the base. Purification by reversed-phase HPLC. Method: C18 Waters Sunfire column (30 × 150 mm, 5 micron). Gradient: MeCN with H$_2$O in 0.1% TFA.

Compound 62

N-[(3S,4R)-4-hydroxy-2-oxo-pyrrolidin-3-yl]-3-(2-phenyl-7-vinyl-1H-indol-3-yl)propanamide (62

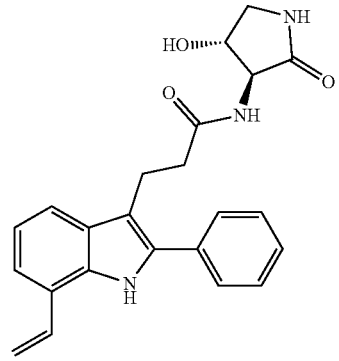

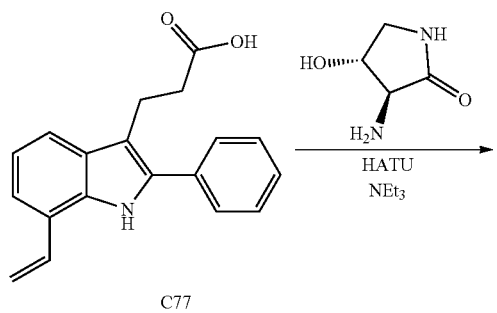

Step 1. Synthesis of 3-(2-phenyl-7-vinyl-1H-indol-3-yl)propanoic acid (C77

A mixture of 3-(7-bromo-2-phenyl-1H-indol-3-yl)propanoic acid C76 (134 mg, 0.4 mmol), Pd(dppf)$_2$Cl$_2$ (33 mg, 0.04 mmol), K$_2$CO$_3$ (165 mg, 1.2 mmol) and 4,4,5,5-tetramethyl-2-vinyl-1,3,2-dioxaborolane (126 mg, 0.8 mmol) in 1,4-dioxane (4 mL) and water (1 mL) was heated under microwave conditions at 140° C. for 1 h. The mixture was concentrated, 1 M HCl (10 mL) was added, and then extracted with (3×CH$_2$Cl$_2$). The mixture was purified by reversed phase chromatography (C18 column; Gradient: 10-100% acetonitrile in water with 0.1% TFA) to afford the product (28.5 mg, 25%). LCMS m/z 292.0 [M+H]$^+$.

Step 2. Synthesis of N-[(3S,4R)-4-hydroxy-2-oxo-pyrrolidin-3-yl]-3-(2-phenyl-7-vinyl-1H-indol-3-yl)propanamide (62

To a mixture of 3-(2-phenyl-7-vinyl-1H-indol-3-yl)propanoic acid C77 (28.5 mg, 0.097 mmol), (3S,4R)-3-amino-4-hydroxy-pyrrolidin-2-one (14 mg, 0.12 mmol), and HATU (53 mg, 0.14 mmol) in DMSO (5 mL) was added NEt$_3$ (45 μL, 0.3 mmol) the mixture was allowed to stir at room temperature. Purification by revered phase chromatography (C18 column; Gradient: 10-100% acetonitrile in water with 0.2% formic acid) afforded the product (15 mg, 39%). $^1$H NMR (300 MHz, CD$_3$OD) δ 8.38 (d, J=7.9 Hz, 1H), 7.72-7.63 (m, 2H), 7.60 (d, J=7.9 Hz, 1H), 7.56-7.45 (m, 2H), 7.43-7.30 (m, 2H), 7.34-7.22 (m, 1H), 7.07 (t, J=7.7 Hz, 1H), 5.88 (dd, J=17.5, 1.4 Hz, 1H), 5.34 (dd, J=11.0, 1.4 Hz, 1H), 4.35 (q, J=7.4 Hz, 1H), 4.29-4.16 (m, 1H), 3.66-3.52 (m, 1H), 3.28-3.19 (m, 2H), 3.12 (dd, J=9.9, 6.8 Hz, 1H), 2.74-2.63 (m, 2H). LCMS m/z 390.3 [M+H]$^+$.

Compounds 63-70

Compounds 63-70 (Table 7) were prepared from commercially available 3-(7-bromo-2-phenyl-1H-indol-3-yl)propanoic acid using the method described for example 62. The appropriate boronic ester and amine was used in each example. All compounds were purified by reversed-phase chromatography (C18 Waters Sunfire column (30×150 mm, 5 micron). Gradient: 10-100% acetonitrile in water with 0.2% formic acid).

TABLE 7

Method of preparation, structure and physicochemical data for compounds 63-70

| Cmpd | Product | Boronic ester; Amine coupling method; non-commercial amine | $^1$H NMR; LCMS m/z [M + H]$^+$ |
|---|---|---|---|
| 63 | 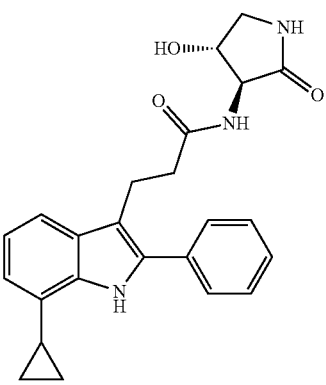 [SMILES: O=C(CCc1c(-c2ccccc2)[nH]c2c(C3CC3)cccc12)N[C@@H]1C(=O)NC[C@H]1O] | 2-cyclopropyl-4,4,5,5-tetramethyl-1,3,2-dioxaborolane; Method F$^1$; S2 | $^1$H NMR (300 MHz, CD$_3$OD) δ 8.09 (d, J = 4.3 Hz, 1H), 7.73-7.61 (m, 2H), 7.57-7.42 (m, 3H), 7.43-7.28 (m, 1H), 6.98 (t, J = 7.6 Hz, 1H), 6.74 (dt, J = 7.3, 0.9 Hz, 1H), 4.35 (td, J = 7.6, 6.8 Hz, 1H), 4.23 (d, J = 7.7 Hz, 1H), 3.57 (dd, J = 9.9, 7.5 Hz, 1H), 3.28-3.17 (m, 2H), 3.11 (dd, J = 9.9, 6.8 Hz, 1H), 2.76-2.51 (m, 2H), 2.36-2.20 (m, 1H), 1.12-0.92 (m, 2H), 0.83-0.62 (m, 2H). LCMS m/z 404.3 [M + H]$^+$. |
| 64 | 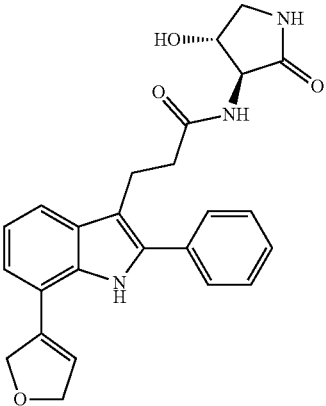 [SMILES: O=C(CCc1c(-c2ccccc2)[nH]c2c(C3=CCOC3)cccc12)N[C@@H]1C(=O)NC[C@H]1O] | 2-(2,5-dihydrofuran-3-yl)-4,4,5,5-tetramethyl-1,3,2-dioxaborolane; Method F$^1$; S2 | $^1$H NMR (300 MHz, CD$_3$OD) δ 7.75-7.57 (m, 3H), 7.59-7.46 (m, 2H), 7.45-7.24 (m, 1H), 7.09 (dd, J = 7.9, 7.3 Hz, 1H), 7.00 (dd, J = 7.3, 1.1 Hz, 1H), 6.52 (p, J = 2.0 Hz, 1H), 5.12 (td, J = 4.7, 2.2 Hz, 2H), 4.94 (dd, J = 4.9, 1.9 Hz, 1H), 4.36 (td, J = 7.6, 6.8 Hz, 1H), 4.23 (d, J = 7.7 Hz, 1H), 3.57 (dd, J = 9.9, 7.5 Hz, 1H), 3.28-3.17 (m, 2H), 3.11 (dd, J = 9.9, 6.8 Hz, 1H), 2.74-2.56 (m, 2H). LCMS m/z 432.0 [M + H]$^+$. |

US 12,060,346 B2

285 286

TABLE 7-continued

Method of preparation, structure and physicochemical data for compounds 63-70

| Cmpd | Product | Boronic ester; Amine coupling method; non-commercial amine | $^1$H NMR; LCMS m/z [M + H]$^+$ |
|---|---|---|---|
| 65 | | From 64[2,1] | $^1$H NMR (300 MHz, CD$_3$OD) δ 9.81 (s, 1H), 7.51-7.33 (m, 1H), 7.04-6.80 (m, 2H), 4.36 (q, J = 7.3 Hz, 1H), 4.29-4.07 (m, 3H), 4.07-3.82 (m, 3H), 3.58 (dd, J = 9.9, 7.5 Hz, 1H), 3.22-2.80 (m, 4H), 2.67-2.42 (m, 3H), 2.23-1.40 (m, 11H). LCMS m/z 440.1 [M + H]$^+$. |
| 66 | | 2-isopropenyl-4,4,5,5-tetramethyl-1,3,2-dioxaborolane[3]; Method F; S2 | $^1$H NMR (300 MHz, CD$_3$OD) δ 7.73-7.60 (m, 3H), 7.60-7.44 (m, 3H), 7.40-7.24 (m, 1H), 7.11-6.95 (m, 2H), 4.35 (td, J = 7.6, 6.7 Hz, 1H), 4.23 (d, J = 7.7 Hz, 1H), 3.62-3.52 (m, 1H), 3.30-3.20 (m, 2H), 3.11 (dd, J = 9.9, 6.8 Hz, 1H), 2.73-2.61 (m, 3H), 1.72 (s, 6H). LCMS m/z 421.2 [M + H]$^+$. |
| 67 | | 2-isopropenyl-4,4,5,5-tetramethyl-1,3,2-dioxaborolane[3]; Method F; S2 | $^1$H NMR (300 MHz, CD$_3$OD) δ 7.68-7.55 (m, 3H), 7.45-7.29 (m, 1H), 7.10-6.84 (m, 2H), 5.36 (q, J = 1.2 Hz, 2H), 4.36 (td, J = 7.6, 6.8 Hz, 1H), 4.23 (d, J = 7.7 Hz, 1H), 3.68-3.49 (m, 1H), 3.19 (s, 2H), 3.12 (dd, J = 9.9, 6.8 Hz, 1H), 2.75-2.53 (m, 2H), 2.25 (t, J = 1.2 Hz, 3H). LCMS m/z 404.2 [M + H]$^+$. |
| 68 | | From 67[4] | $^1$H NMR (400 MHz, DMSO-d$_6$) δ 10.87 (s, 1H), 8.24 (d, J = 7.8 Hz, 1H), 7.77 (s, 1H), 7.64 (d, J = 7.6 Hz, 2H), 7.52 (t, J = 7.7 Hz, 2H), 7.41 (d, J = 7.6 Hz, 2H), 7.00 (d, J = 4.4 Hz, 2H), 5.50 (s, 1H), 4.12 (s, 2H), 3.55 (s, 1H), 3.01 (d, J = 12.1 Hz, 2H), 2.91 (t, J = 8.3 Hz, 1H), 2.57-2.49 (m, 3H), 1.29 (d, J = 6.7 Hz, 6H). LCMS m/z 406.2 [M + H]$^+$. |

TABLE 7-continued

Method of preparation, structure and physicochemical data for compounds 63-70

| Cmpd | Product | Boronic ester;<br>Amine coupling method;<br>non-commercial amine | $^1$H NMR; LCMS m/z [M + H]$^+$ |
|---|---|---|---|
| 69 | | Commercial core; Method F$^1$; S2 | $^1$H NMR (300 MHz, CD$_3$OD) δ 7.71-7.60 (m, 2H), 7.56-7.40 (m, 3H), 7.39-7.26 (m, 1H), 7.02-6.81 (m, 2H), 4.33 (td, J = 7.6, 6.8 Hz, 1H), 4.21 (d, J = 7.7 Hz, 1H), 3.55 (dd, J = 9.9, 7.5 Hz, 1H), 3.27-3.15 (m, 2H), 3.09 (dd, J = 9.9, 6.8 Hz, 1H), 2.72-2.57 (m, 2H), 2.51 (t, J = 0.7 Hz, 3H). LCMS m/z 378.3 [M + H]$^+$. |
| 70 | | Commercial core; Method F$^1$; S2 | $^1$H NMR (300 MHz, CDCl$_3$) δ 8.23 (s, 1H), 7.65-7.51 (m, 5H), 7.45 (t, J = 7.2 Hz, 1H), 7.38 (dd, J = 7.6, 0.9 Hz, 1H), 7.06 (t, J = 7.8 Hz, 1H), 6.21 (s, 1H), 5.55 (s, 1H), 5.52 (s, 1H), 4.22-4.16 (m, 1H), 4.00 (dd, J = 8.1, 2.0 Hz, 1H), 3.67-3.55 (m, 1H), 3.37-3.15 (m, 3H), 2.70-2.57 (m, 2H). LCMS m/z 442.2 [M + H]$^+$. |

$^1$Purification by reversed-phase HPLC. Method: C18 Waters Sunfire column (30 × 150 mm, 5 micron). Gradient: MeCN in H$_2$O with 0.2% formic acid.

$^2$Compound 65 was prepared from hydrogenation of compound 64 by hydrogenation using 5% Pd on carbon catalyst. This hydrogenation reaction also gave the over-reduced product 3-(2-cyclohexyl-7-tetrahydrofuran-3-yl-1H-indol-3-yl)-N-[(3S,4R)-4-hydroxy-2-oxo-pyrrolidin-3-yl]propanamide.

$^3$Coupling of with 2-isopropenyl-4,4,5,5-tetramethyl-1,3,2-dioxaborolane with 3-(7-bromo-2-phenyl-1H-indol-3-yl)propanoic acid afforded two products. 3-(7-isopropenyl-2-phenyl-1H-indol-3-yl)propanoic acid (64.8 mg, 46%) was used in the preparation of compound 67. 3-[7-(1-hydroxy-1-methyl-ethyl)-2-phenyl-1H-indol-3-yl]propanoic acid (19.5 mg, 13%) was used in the preparation of compound 66.

$^4$Compound 68 was prepared from hydrogenation of compound 67 by hydrogenation using 5% Pd on carbon catalyst.

Compounds 71-87

Compounds 71-87 (Table 8) were prepared from indole propionic acids and the appropriate amine via an amide coupling reaction. An amide coupling reagent such as HATU, and an organic base (NEt$_3$ or DIPEA) as described in the preparation of compound 1 was used. Indole cores were made according to routes A or B. In some examples, indoles were prepared via Fischer indole synthesis routes. Any modifications to these methods are noted in Table 8 and accompanying footnotes.

TABLE 8

Method of preparation, structure and physicochemical data for compounds 71-87

| Cmpd | Product | Indole Preparation method; Amine coupling method; non-commercial amine | $^1$H NMR; LCMS m/z [M + H]$^+$ |
|---|---|---|---|
| 71 | 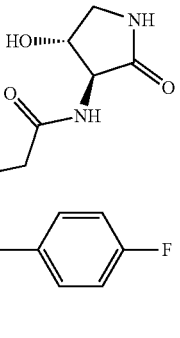 | Fischer indole synthesis[1] (see footnote); Method F[2]; S2 | $^1$H NMR (300 MHz, CD$_3$OD) δ 8.08 (s, 1H), 7.70-7.59 (m, 2H), 7.46 (ddd, J = 7.7, 1.5, 0.7 Hz, 1H), 7.30-7.15 (m, 2H), 7.02-6.86 (m, 2H), 4.33 (td, J = 7.6, 6.8 Hz, 1H), 4.21 (d, J = 7.7 Hz, 1H), 3.55 (dd, J = 9.9, 7.5 Hz, 1H), 3.23-3.02 (m, 3H), 2.68-2.59 (m, 2H), 2.5 (s, 3H). LCMS m/z 396.0 [M + H]$^+$. |
| 72 | 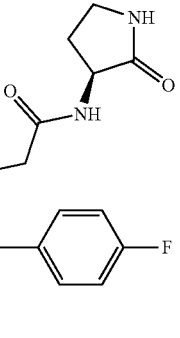 | Commercial core[2]; S2; | $^1$H NMR (300 MHz, CD$_3$OD) δ 7.74-7.61 (m, 2H), 7.58 (dd, J = 7.9, 1.0 Hz, 1H), 7.32-7.17 (m, 2H), 7.14 (dd, J = 7.6, 1.0 Hz, 1H), 7.02 (t, J = 7.7 Hz, 1H), 4.46 (dd, J = 10.3, 8.8 Hz, 1H), 3.33-3.27 (m, 3H), 3.21-3.06 (m, 2H), 2.68-2.50 (m, 2H), 2.36 (dddd, J = 12.4, 8.8, 5.3, 3.4 Hz, 1H), 1.84 (ddt, J = 12.5, 10.4, 9.2 Hz, 1H). LCMS m/z 400.1 [M + H]$^+$. |
| 73 | 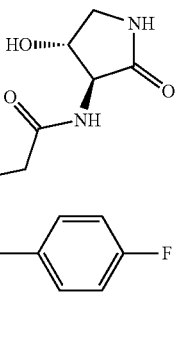 | Commercial core[2]; S2; | $^1$H NMR (300 MHz, CD$_3$OD) δ 7.71-7.62 (m, 2H), 7.59 (dd, J = 7.9, 1.0 Hz, 1H), 7.29-7.17 (m, 2H), 7.13 (dd, J = 7.6, 1.0 Hz, 1H), 7.02 (t, J = 7.7 Hz, 1H), 4.41-4.28 (m, 1H), 4.21 (d, J = 7.7 Hz, 1H), 3.55 (dd, J = 9.9, 7.5 Hz, 1H), 3.23-3.03 (m, 3H), 2.68-2.57 (m, 2H). LCMS m/z 416.0 [M + H]$^+$. |

TABLE 8-continued

Method of preparation, structure and physicochemical data for compounds 71-87

| Cmpd | Product | Indole Preparation method; Amine coupling method; non-commercial amine | $^1$H NMR; LCMS m/z [M + H]$^+$ |
|---|---|---|---|
| 74 | (structure) | Commercial core$^2$; S2; | 1H NMR (300 MHz, CD$_3$OD) δ 7.74-7.54 (m, 3H), 7.56-7.44 (m, 2H), 7.46-7.34 (m, 1H), 7.14 (dd, J = 7.6, 1.0 Hz, 1H), 7.03 (t, J = 7.7 Hz, 1H), 4.36 (td, J = 7.6, 6.8 Hz, 1H), 4.24 (d, J = 7.8 Hz, 1H), 3.57 (dd, J = 9.9, 7.5 Hz, 1H), 3.29-3.18 (m, 2H), 3.11 (dd, J = 9.9, 6.8 Hz, 1H), 2.71-2.57 (m, 2H). LCMS m/z 398.1 [M + H]$^+$ |
| 75 | (structure) | Commercial Method F$^2$; S2 | $^1$H NMR (300 MHz, CD$_3$OD) δ 7.97 (s, 1H), 7.72-7.55 (m, 2H), 7.42 (d, J = 7.9 Hz, 1H), 7.33-7.13 (m, 2H), 6.97 (td, J = 7.9, 4.7 Hz, 1H), 6.84 (ddd, J = 11.3, 7.8, 0.9 Hz, 1H), 4.45 (dd, J = 10.2, 8.8 Hz, 1H), 3.34 (d, J = 5.8 Hz, 1H), 3.18 (t, J = 8.0 Hz, 2H), 2.72-2.51 (m, 2H), 2.36 (dddd, J = 12.3, 8.8, 5.6, 3.2 Hz, 1H), 1.96-1.74 (m, 2H). LCMS m/z 384.1 [M + H]$^+$. |
| 76 | (structure) | Commercial; Method F$^2$; S2 | $^1$H NMR (300 MHz, DMSO-d$_6$) δ 11.58 (s, 1H), 8.22 (d, J = 7.5 Hz, 1H), 7.86-7.62 (m, 3H), 7.52-7.28 (m, 3H), 7.17-6.83 (m, 2H), 5.47 (s, 1H), 4.26-3.99 (m, 2H), 3.38 (ddd, J = 8.7, 6.9, 1.7 Hz, 1H), 3.16-2.99 (m, 2H), 2.96-2.79 (m, 1H) 2.5 (2H, peak obscured by solvent). LCMS m/z 400.3 [M + H]$^+$. |
| 77 | (structure) | Commercial; Method F$^2$. | $^1$H NMR (300 MHz, CD$_3$OD) δ 7.72-7.50 (m, 2H), 7.35-7.12 (m, 3H), 6.96 (t, J = 7.9 Hz, 1H), 6.65 (dd, J = 7.8, 0.8 Hz, 1H), 4.44 (dd, J = 10.3, 8.8 Hz, 1H), 3.94 (s, 3H), 3.31 (dt, J = 3.3, 1.6 Hz, 2H), 3.15 (dd, J = 8.6, 7.5 Hz, 2H), 2.65-2.50 (m, 2H), 2.35 (dddd, J = 12.5, 8.8, 5.2, 3.6 Hz, 1H), 1.83 (ddt, J = 12.6, 10.4, 9.2 Hz, 1H). LCMS m/z 396.2 [M + H]$^+$. |

TABLE 8-continued

Method of preparation, structure and physicochemical data for compounds 71-87

| Cmpd | Product | Indole Preparation method; Amine coupling method; non-commercial amine | ¹H NMR; LCMS m/z [M + H]⁺ |
|---|---|---|---|
| 78 | | Route B; Method F². | ¹H NMR (300 MHz, CD₃OD) δ 7.74-7.46 (m, 2H), 7.38-7.09 (m, 2H), 6.76 (ddd, J = 10.3, 8.5, 3.5 Hz, 1H), 6.62 (ddd, J = 10.5, 8.5, 3.2 Hz, 1H), 4.60-4.34 (m, 1H), 3.31 (td, J = 3.8, 3.3, 2.1 Hz, 2H), 3.25-3.05 (m, 2H), 2.75-2.51 (m, 2H), 2.41 (dddd, J = 12.1, 8.8, 5.7, 3.0 Hz, 1H), 1.91 (dq, J = 12.4, 9.3 Hz, 1H). LCMS m/z 402.2 [M + H]⁺. |
| 79 | | Route A; Method F²; S2. | ¹H NMR (300 MHz, CD₃OD) δ 7.70-7.55 (m, 2H), 7.41-7.32 (m, 1H), 7.27-7.15 (m, 2H), 4.34 (td, J = 7.7, 6.9 Hz, 1H), 4.22 (d, J = 7.8 Hz, 1H), 3.57 (dd, J = 9.9, 7.6 Hz, 1H), 3.23-2.96 (m, 3H), 2.66-2.41 (m, 2H). LCMS m/z 436.1 [M + H]⁺. |
| 80 | | Route A; Method F²; S2. | ¹H NMR (300 MHz, CD₃OD) δ 7.70-7.57 (m, 2H), 7.55-7.46 (m, 2H), 7.45-7.26 (m, 2H), 4.33 (td, J = 7.6, 6.8 Hz, 1H), 4.21 (d, J = 7.7 Hz, 1H), 3.56 (dd, J = 9.9, 7.5 Hz, 1H), 3.24-3.01 (m, 3H), 2.62-2.50 (m, 2H). LCMS m/z 418.0 [M + H]⁺. |
| 81 | | Route A; Method F²; S2. | ¹H NMR (300 MHz, CD₃OD) δ 7.67-7.51 (m, 2H), 7.47 (dd, J = 11.3, 7.9 Hz, 1H), 7.31-7.08 (m, 3H), 4.35 (td, J = 7.6, 6.9 Hz, 1H), 4.23 (d, J = 7.8 Hz, 1H), 3.57 (dd, J = 9.9, 7.5 Hz, 1H), 3.25-3.03 (m, 3H), 2.65-2.40 (m, 2H). LCMS m/z 418.2 [M + H]⁺. |

TABLE 8-continued

Method of preparation, structure and physicochemical data for compounds 71-87

| Cmpd | Product | Indole Preparation method; Amine coupling method; non-commercial amine | ¹H NMR; LCMS m/z [M + H]⁺ |
|---|---|---|---|
| 82 | | Route B; Method F²; S2. | ¹H NMR (300 MHz, CD₃OD) δ 7.67-7.57 (m, 2H), 7.54-7.40 (m, 3H), 7.41-7.27 (m, 1H), 7.18 (dd, J = 11.0, 6.8 Hz, 1H), 4.34 (td, J = 7.6, 6.8 Hz, 1H), 4.22 (d, J = 7.7 Hz, 1H), 3.57 (dd, J = 9.9, 7.5 Hz, 1H), 3.25-3.08 (m, 3H), 2.68-2.52 (m, 2H). LCMS m/z 400.2 [M + H]⁺. |
| 83 | | Fisher indole synthesis³ (see footnote); Method F²; S2. | ¹H NMR (300 MHz, CD₃OD) δ 7.72-7.55 (m, 2H), 7.48-7.32 (m, 1H), 7.29-7.06 (m, 2H), 6.80 (dd, J = 10.4, 8.6 Hz, 1H), 4.34 (td, J = 7.6, 6.8 Hz, 1H), 4.22 (d, J = 7.8 Hz, 1H), 3.56 (dd, J = 9.9, 7.6 Hz, 1H), 3.22-3.00 (m, 3H), 2.68-2.53 (m, 2H), 2.40 (d, J = 1.7 Hz, 3H). LCMS m/z 414.2 [M + H]⁺. |
| 84 | | Fisher indole synthesis⁴ (see footnote); Method F²; S2. | ¹H NMR (300 MHz, CD₃OD) δ 7.65-7.56 (m, 2H), 7.53-7.20 (m, 4H), 6.80 (dd, J = 10.4, 8.6 Hz, 1H), 4.34 (td, J = 7.6, 6.8 Hz, 1H), 4.21 (d, J = 7.7 Hz, 1H), 3.56 (dd, J = 9.9, 7.6 Hz, 1H), 3.24-3.14 (m, 2H), 3.10 (dd, J = 9.9, 6.8 Hz, 1H), 2.66-2.53 (m, 2H), 2.41 (d, J = 1.7 Hz, 3H). LCMS m/z 396.1 [M + H]⁺. |
| 85 | | Route B; Method F²; S2. | ¹H NMR (300 MHz, CD₃OD) δ 7.68-7.52 (m, 2H), 7.52-7.41 (m, 2H), 7.43-7.26 (m, 1H), 6.90 (dd, J = 9.3, 2.1 Hz, 1H), 6.57 (ddd, J = 11.3, 10.1, 2.1 Hz, 1H), 4.35 (td, J = 7.6, 6.8 Hz, 1H), 4.20 (d, J = 7.7 Hz, 1H), 3.56 (dd, J = 9.9, 7.6 Hz, 1H), 3.20 (m, 3H) 3.10 (dd, J = 9.9, 6.8 Hz, 1H), 2.77-2.54 (m, 2H). LCMS m/z 400.1 [M + H]⁺. |

TABLE 8-continued

Method of preparation, structure and physicochemical data for compounds 71-87

| Cmpd | Product | Indole Preparation method; Amine coupling method; non-commercial amine | $^1$H NMR; LCMS m/z [M + H]$^+$ |
|---|---|---|---|
| 86 | (structure) | Commercial Method F$^2$; S2. | $^1$H NMR (300 MHz, CD$_3$OD) δ 7.64 (dq, J = 7.7, 1.3 Hz, 3H), 7.48 (ddd, J = 7.8, 6.9, 1.2 Hz, 2H), 7.42-7.29 (m, 2H), 7.11 (ddd, J = 8.1, 7.0, 1.3 Hz, 1H), 7.03 (ddd, J = 8.1, 7.0, 1.2 Hz, 1H), 4.40-4.27 (m, 1H), 4.27-4.15 (m, 1H), 3.56 (dd, J = 9.9, 7.5 Hz, 1H), 3.27-3.19 (m, 2H), 3.10 (dd, J = 9.9, 6.8 Hz, 1H), 2.74-2.57 (m, 2H). LCMS m/z 364.2 [M + H]$^+$. |
| 87 | (structure) | Commercial; Method F$^2$; S2. | $^1$H NMR (300 MHz, CD$_3$OD) δ 7.75-7.56 (m, 3H), 7.35 (dt, J = 8.1, 1.0 Hz, 1H), 7.31-7.17 (m, 2H), 7.07 (dddd, J = 23.8, 8.1, 7.1, 1.2 Hz, 2H), 4.34 (td, J = 7.6, 6.8 Hz, 1H), 4.22 (d, J = 7.7 Hz, 1H), 3.55 (dd, J = 9.9, 7.5 Hz, 1H), 3.27-3.15 (m, 2H), 3.10 (dd, J = 9.9, 6.8 Hz, 1H), 2.78-2.51 (m, 2H). LCMS m/z 382.3 [M + H]$^+$. |

$^1$Indole core used in preparation of compound 71 was prepared by heating 4-fluoro-N-[(E)-1-(o-tolyl)ethylideneamino]aniline in xylene with BF$_3$•OEt$_2$.
$^2$Purification by reversed-phase HPLC. Method: C18 Waters Sunfire column (30 × 150 mm, 5 micron). Gradient: MeCN in H$_2$O with 0.2% formic acid.
$^3$Indole core was prepared via a Fischer indole synthesis method from (3-fluoro-2-methyl-phenyl)hydrazine and 1-(4-fluorophenyl) ethanone. See procedure described for the preparation of compound 95.
$^4$Indole core was prepared via a Fischer indole synthesis method from (3-fluoro-2-methyl-phenyl)hydrazine and 1-phenylethanone.

Alternative Preparation I of Compound 87 (Indole Preparation Route C

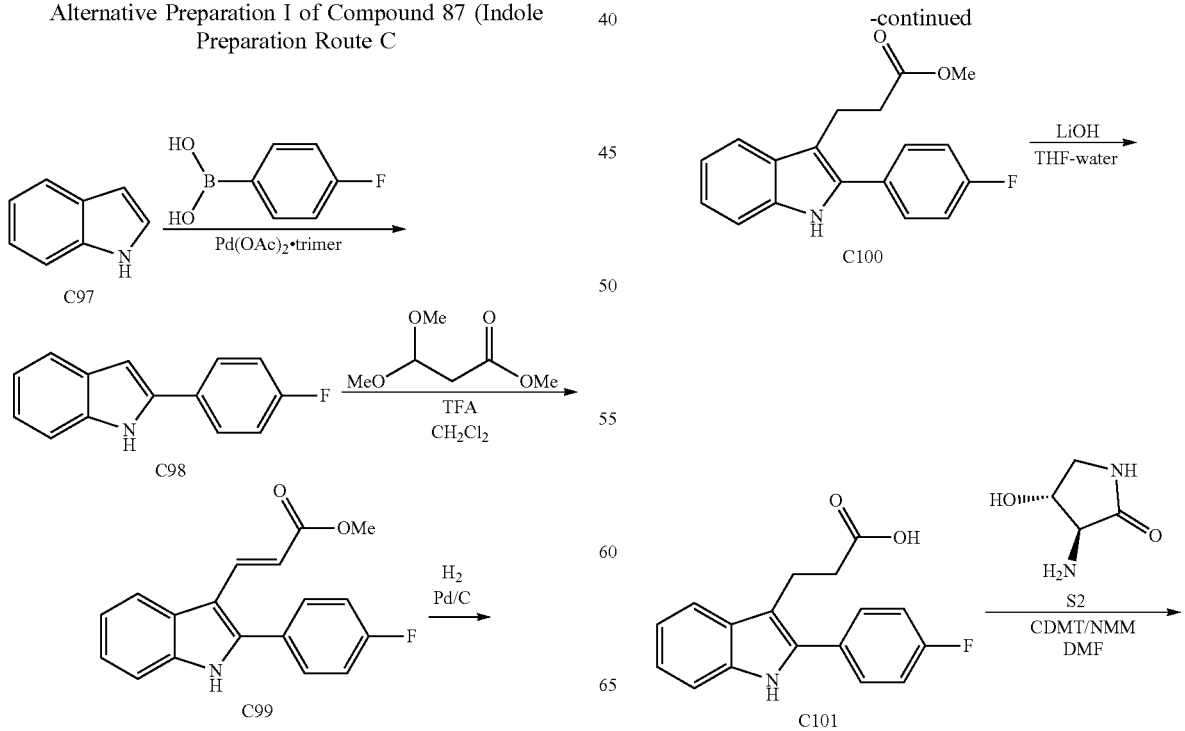

-continued

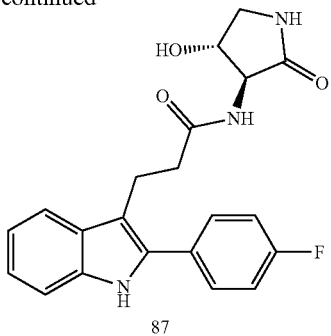

87

Step 1. Synthesis of 2-(4-fluorophenyl)-1H-indole (C98

To a stirred suspension of indole (5 g, 42.7 mmol) and (4-fluorophenyl)boronic acid (8.96 g, 64.0 mmol) in AcOH (200 mL) was added Pd(OAc)$_2$. Trimer (1.44 g, 6.4 mmol) and the mixture stirred at room temperature for 16 h under O$_2$-balloon pressure. Then the reaction mixture was filtered through a Celite® pad, washed with EtOAc (500 mL). The filtrates were washed with water, sat. NaHCO$_3$ solution, brine solution, then dried over Na$_2$SO$_4$ and concentrated under reduced pressure. Purification by silica gel chromatography (Gradient: 0-10% EtOAc in heptane) yielded the product afforded 2-(4-fluorophenyl)-1H-indole (5.5 g, 61%). $^1$H NMR (300 MHz, DMSO-d$_6$) δ 11.51 (s, 1H), 7.9 (t, J=5.4 Hz, 2H), 7.52 (d, J=7.8 Hz, 1H), 7.39 (d, J=8.1 Hz, 1H), 7.30 (t, J=8.7 Hz, 2H), 7.09 (t, J=7.2 Hz, 1H), 6.99 (t, J=7.5 Hz, 1H), 6.86 (s, 1H). LCMS m/z 212.4 [M+H]$^+$.

Step 2. Synthesis of Methyl (E)-3-[2-(4-fluorophenyl)-1H-indol-3-yl]prop-2-enoate (C99

2-(4-fluorophenyl)-1H-indole (1.0 g, 4.76 mmol) and methyl 3,3-dimethoxypropanoate (0.81 mL, 5.7 mmol) were suspended in dichloromethane (15 mL). Trifluoroacetic acid (2.00 mL, 26 mmol) was added rapidly via syringe, resulting in a clear brown solution. The reaction mixture was heated to 40° C. for three hours. The reaction was diluted with dichloromethane (15 mL) to give an amber solution which was washed with saturated aqueous NaHCO$_3$ (25 mL) to yield a bright yellow/light amber biphasic mixture. The phases were separated and the organic layer was washed with saturated NaHCO$_3$ (30 mL), then dried (MgSO$_4$) and filtered. The mixture was concentrated under a nitrogen stream overnight. The crude product was obtained as a yellow powder. The product was dissolved in minimum 2-MeTHF and pentane added until the suspension became lightly cloudy. The suspension was allowed to stand overnight, and the precipitate was filtered off. The filter cake was washed with heptane (2×15 mL), and dried in vacuo at 40° C. to afford the product as a yellow powder. Methyl (E)-3-[2-(4-fluorophenyl)-1H-indol-3-yl]prop-2-enoate (1.30 g, 86%). $^1$H NMR (300 MHz, Chloroform-d) δ 8.41 (s, 1H), 8.01-7.95 (m, 1H), 7.92 (d, J=16.0 Hz, 1H), 7.58-7.50 (m, 2H), 7.46-7.41 (m, 1H), 7.33-7.27 (m, 2H), 7.22 (t, J=8.6 Hz, 2H), 6.59 (d, J=16.0 Hz, 1H), 3.79 (s, 3H). LCMS m/z 295.97 [M+H]$^+$.

Step 3. Synthesis of Methyl 3-[2-(4-fluorophenyl)-1H-indol-3-yl]propanoate (C100

To a solution of methyl (E)-3-[2-(4-fluorophenyl)-1H-indol-3-yl]prop-2-enoate (7 g, 0.02 mol) in EtOAc (350 mL) was added Palladium on carbon (4 g, 10% w/w, 0.004 mol) and stirred at room temperature for 2 h under an atmosphere of H$_2$ (bladder pressure). The reaction mixture was filtered through a pad of Celite® and washed with EtOAc (400 mL). The filtrates was concentrated to afford methyl 3-[2-(4-fluorophenyl)-1H-indol-3-yl]propanoate (7.1 g, 100%). $^1$H NMR (300 MHz, DMSO-d$_6$) δ 11.2 (s, 1H), 7.65 (q, J=5.4 Hz, 2H), 7.54 (d, J=8.1 Hz, 1H), 7.36 (t, J=9.0 Hz, 3H), 7.10 (t, J=8.1 Hz, 1H), 7.02 (t, J=7.8 Hz, 1H), 3.53 (s, 3H), 3.10 (t, J=15.9 Hz, 2H), 2.63 (t, J=15.9 Hz, 2H). LCMS m/z 298.21 [M+H]$^+$. The product was used directly in the subsequent step without further purification.

Step 4. Synthesis of 3-[2-(4-fluorophenyl)-1H-indol-3-yl]propanoic acid (C101

To stirred solution of methyl 3-[2-(4-fluorophenyl)-1H-indol-3-yl]propanoate (14.4 g, 0.05 mol) in THF (300 mL), MeOH (300 mL) and H$_2$O (250 mL) was cooled to −10° C. LiOH·H$_2$O (10.1 g, 0.24 mol) was slowly added in a portion-wise manner. The reaction mixture was allowed to stir at room temperature for 16 h. The mixture was evaporated and ice cold water (200 mL) was added, pH was adjusted to pH~2 with 1 M HCl (400 mL, Cold solution). The mixture was stirred for 10 minutes, filtered and dried to afford 3-[2-(4-fluorophenyl)-1H-indol-3-yl]propanoic acid (12.9 g, 94%). $^1$H NMR (400 MHz, DMSO-d$_6$) δ 12.11 (s, 1H), 11.18 (s, 1H), 7.65 (q, J=5.2 Hz, 2H), 7.56 (d, J=7.6 Hz, 1H), 7.36 (t, J=8.8 Hz, 3H), 7.10 (t, J=8 Hz, 1H), 7.01 (t, J=8 Hz, 1H), 3.06 (t, J=16.4 Hz, 2H), 2.55 (t, J=16 Hz, 2H). LCMS m/z 284.21 [M+H]$^+$.

Step 5. Synthesis of 3-[2-(4-fluorophenyl)-1H-indol-3-yl]-N-[(3S,4R)-4-hydroxy-2-oxo-pyrrolidin-3-yl]propanamide (87

A mixture of 3-[2-(4-fluorophenyl)-1H-indol-3-yl]propanoic acid C101 (40 g, 120.0 mmol) and (3S,4R)-3-amino-4-hydroxy-pyrrolidin-2-one (Hydrochloride salt) S2 (23.8 g, 156.0 mmol) in DMF (270 mL) was stirred at room temperature for 5 minutes. CDMT (27.2 g, 154.9 mmol) and NMM (53 mL, 482.1 mmol) were added and the mixture was stirred at room temperature for 2 h. The mixture was poured into water (140 mL) and then stirred for 1 h at room temperature, then filtered and washing the solids with water (50 mL). The solids were dissolved in 1:1 IPA/water (~400 mL, until all solids dissolved) with heating (reflux) and stirring. The mixture was allowed to cool slowly to room temperature overnight. The mixture was cooled to 0° C. and stirred to break up crystals for filtration. The crystals were then filtered off, rinsed with cold 1:1 IPA/water to afford a tan solid (45 g). The solid was dissolved in IPA (200 mL) and heated to 80° C. to dissolve the solid. Activated charcoal (10 g) was added and the mixture was heated with stirring for 30 minutes. The mixture was filtered through Celite® and solvent removed under reduced pressure. A mixture of 40:60 IPA/water (350 mL) was added to the solid and the mixture was heated until all solids dissolved. The mixture was cooled to room temperature over 5 h. Solids precipitated within the mixture. The mixture was then cooled to 0° C. and stirred for 1 h. The solids were filtered off and air dried on funnel for 1 h, then in a vacuum at 55° C. overnight to afford the product. 3-[2-(4-fluorophenyl)-1H-indol-3-yl]-N-[(3S,4R)-4-hydroxy-2-oxo-pyrrolidin-3-yl]propanamide (36.6 g, 79%). $^1$H NMR (300 MHz, Methanol-d$_4$) δ 7.63 (ddt, J=8.6, 5.1, 2.7 Hz, 3H), 7.35 (dt, J=8.1, 1.0 Hz, 1H), 7.25-7.16 (m, 2H), 7.11 (ddd, J=8.1, 7.0, 1.3 Hz, 1H), 7.03 (ddd, J=8.0, 7.0, 1.2 Hz, 1H), 4.34 (td, J=7.6, 6.8 Hz, 1H), 4.22 (d, J=7.7 Hz, 1H), 3.55 (dd, J=9.9, 7.5 Hz, 1H), 3.26-3.18 (m, 2H), 3.10 (dd, J=9.9, 6.8 Hz, 1H), 2.69-2.59 (m, 2H). LCMS m/z 382.05 [M+H]$^+$. The product contained 0.23% IPA by weight by NMR (1439 ppm IPA by residual solvent analysis). Purity is 99.5% by (qNMR).

Alternative Preparation II of Compound 87 (Indole Preparation Route D

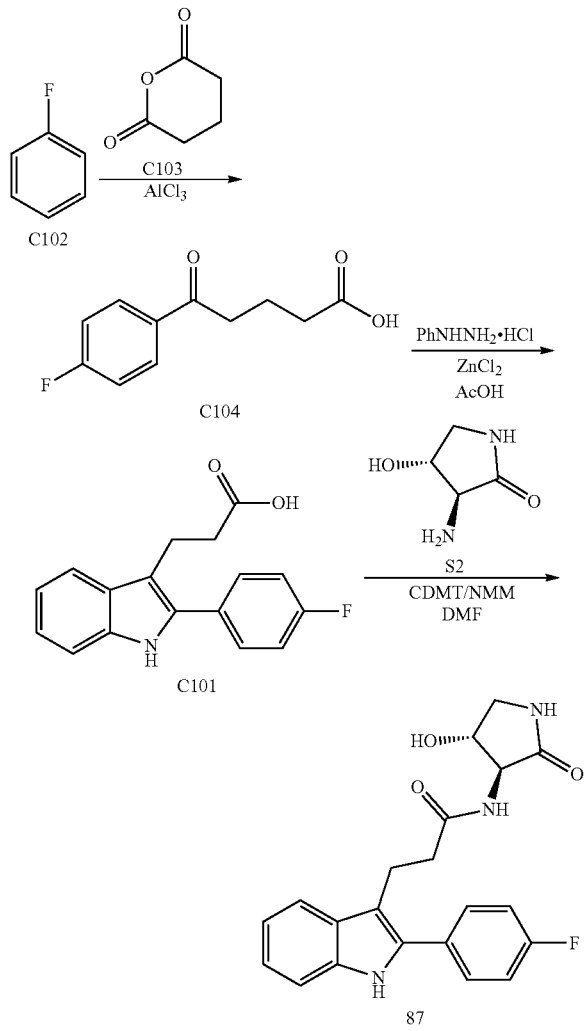

Step 1. Synthesis of 5-(4-fluorophenyl)-5-oxo-pentanoic acid (C104

To a stirred suspension of AlCl$_3$ (13.9 g, 0.10 mol) in dichloromethane (50 mL) was added a solution of tetrahydropyran-2,6-dione (5.93 g, 0.05 mol) in dichloromethane (100 mL) at 0° C. over a period of 15 minutes and stirred for 30 min. Then to the reaction mixture was added fluorobenzene (5 g, 0.05 mol) at 0° C. over a period of 15 min, gradually allowed to room temperature and stirred for 16 h. Then the reaction mixture was added to ice water (50 mL) under stirring. The resulting solid was filtered to afford a light yellow solid. The solid was diluted with 3% NaOH solution (50 mL) and dichloromethane (50 mL). The aqueous layer was separated and acidified with 1N HCl at 0° C. The mixture was then extracted with EtOAc (100 mL), dried over Na$_2$SO$_4$, and concentrated under reduced pressure. The solid was then washed with pentane and dried to afford 5-(4-fluorophenyl)-5-oxo-pentanoic acid as an off white solid. (6 g, 53%). $^1$H NMR (300 MHz, DMSO-d$_6$) δ 12.07 (s, 1H), 8.06 (d, J=6 Hz, 1H), 8.02 (d, J=5.4 Hz, 1H), 7.36 (t, J=8.7 Hz, 2H), 3.06 (t, J=7.2 Hz, 2H), 2.31 (t, J=7.2 Hz, 2H), 1.86-1.78 (m, 2H). LCMS m/z 211.18 [M+H]$^+$.

Step 2. Synthesis of 3-[2-(4-fluorophenyl)-1H-indol-3-yl]propanoic Acid (C101

Phenylhydrazine (Hydrochloride salt) (375.7 g, 2.6 mol) was combined with the 5-(4-fluorophenyl)-5-oxo-pentanoic acid (507.7 g, 2.4 mol) in a 12 L three-necked round-bottomed flask equipped with an overhead stirrer, temperature probe, and reflux condenser. AcOH (5 L) was added. The stirring was initiated and ZnCl$_2$ (605 g, 4.44 mol) was added. The white suspension rapidly thickened after a few minutes (due to formation of the hydrazine intermediate). Approx. 500 mL of extra AcOH was added to aid stirring. The reaction was then heated to 100° C. for three hours. The reaction was cooled to room temperature and poured into water (approx. 6 L). The mixture was extracted with EtOAc (approx 8 L). The extract was washed with water, dried (MgSO$_4$), filtered, and evaporated in vacuo to afford a golden yellow solid. The solid was triturated with approx. 4 L of 10% EtOAc/DCM and filtered. The filter cake was washed with 50% dichloromethane/heptane (approx 1 L). The filter cake was dissolved in 40% EtOAc/dichloromethane (approx. 2 L) and filtered over a plug of silica gel. The plug was eluted with 40% EtOAc/dichloromethane until the product had been eluted (checked by TLC (25% EtOAc/dichloromethane)). The filtrate was evaporated in vacuo to afford 382.6 g of an off-white solid (Crop 1). All filtrates were combined and evaporated in vacuo. The remaining solid was dissolved in 10% EtOAc/dichloromethane (approx. 1 L) and chromatographed on a 3 kg silica gel cartridge on the ISCO Torrent (isocratic gradient of 10% EtOAc/dichloromethane). Product fractions were combined and evaporated in vacuo to afford a yellow solid that was slurried with dichloromethane, cooled under a stream of nitrogen, and filtered. The filter cake was washed with 50% dichloromethane/heptane and dried in vacuo to afford 244.2 g of product (Crop 2). Altogether, both crops afforded 3-[2-(4-fluorophenyl)-1H-indol-3-yl]propanoic acid (626.8 g, 93%). $^1$H NMR (300 MHz, DMSO-d$_6$) δ 12.15 (s, 1H), 11.20 (s, 1H), 7.74-7.62 (m, 2H), 7.57 (d, J=7.8 Hz, 1H), 7.47-7.28 (m, 3H), 7.11 (ddd, J=8.1, 7.0, 1.2 Hz, 1H), 7.02 (ddd, J=7.9, 7.0, 1.1 Hz, 1H), 3.17-2.85 (m, 2H), 2.61-2.52 (m, 2H) ppm. $^{19}$F NMR (282 MHz, DMSO-d$_6$) δ−114.53 ppm. LCMS m/z 284.15 [M+H]$^+$.

Step 3. Synthesis of 3-[2-(4-fluorophenyl)-1H-indol-3-yl]-N-[(3S,4R)-4-hydroxy-2-oxo-pyrrolidin-3-yl]propanamide (87

A 3-L three neck RBF under nitrogen was equipped with a 150 mL addition funnel and thermocouple, then loaded with 3-[2-(4-fluorophenyl)-1H-indol-3-yl]propanoic acid (77.2 g, 228.6 mmol), (3S,4R)-3-amino-4-hydroxy-pyrrolidin-2-one (Hydrochloride salt) (36.6 g, 239.9 mmol) and CDMT (44.2 g, 251.7 mmol). DMF (320 mL) was added and the orange slurry was cooled to −5° C. (acetone/brine/dry ice). NMM (88 mL, 800.4 mmol) was added via a funnel over 75 minutes to keep the internal temp <0° C. The slurry was stirred at between −10 and 0° C. for 1 hour, then allowed to warm to ambient temperature progressively over 2 hours. Additional reagents were added (10% of the initial quantities), and the mixture was stirred overnight at ambient temperature. Water (850 mL) was added over 60 minutes, maintaining the internal temperature at <25° C. (ice bath). This slow water addition allows for complete dissolution of any visible salt before precipitation of the product. The resulting thick slurry was stirred at ambient temperature overnight. The solid was recovered by filtration and washed with water (3×500 mL). The solid was dried under a stream of air at ambient temperature, then purified by crystallization.

Crystallization of 3-[2-(4-fluorophenyl)-1H-indol-3-yl]-N-[(3S,4R)-4-hydroxy-2-oxo-pyrrolidin-3-yl]propanamide (87

Under nitrogen atmosphere, a 2-L, 3-neck flask equipped with addition funnel and thermocouple was charged with a light brown suspension of the crude 3-[2-(4-fluorophenyl)-1H-indol-3-yl]-N-[(3S,4R)-4-hydroxy-2-oxo-pyrrolidin-3-yl]propanamide (89.5 g) in IPA (225 mL, 2.5 vol). The slurry was heated to 50° C. and water (675 mL, 7.5 vol) was added until near-complete dissolution of solid was observed. The temperature was adjusted to 70° C.—to achieve full dissolution, yielding a clear amber solution. After 30 minutes, the heat source was removed and the mixture was cooled to ambient temperature over the weekend, stirring gently while maintaining the nitrogen atmosphere. The solid was recovered by filtration, washed with IPA:H$_2$O=1:2 (2×300 mL, 2×3.3 vol) dried under a stream of air overnight to afford the product. 3-[2-(4-fluorophenyl)-1H-indol-3-yl]-N-[(3S,4R)-4-hydroxy-2-oxo-pyrrolidin-3-yl]propanamide (84.8 g, 92%). $^1$H NMR (300 MHz, DMSO-d$_6$) δ 11.19 (s, 1H), 8.23 (d, J=7.5 Hz, 1H), 7.77 (s, 1H), 7.72-7.63 (m, 2H), 7.60 (d, J=7.8 Hz, 1H), 7.41-7.31 (m, 3H), 7.12 (ddd, J=8.1, 7.0, 1.2 Hz, 1H), 7.03 (ddd, J=8.0, 7.0, 1.1 Hz, 1H), 5.49 (d, J=5.0 Hz, 1H), 4.20-4.06 (m, 2H), 3.38 (s, 1H), 3.11-3.00 (m, 2H), 2.92 (dd, J=9.4, 6.6 Hz, 1H). LCMS m/z 382.15 [M+H]$^+$.

Crystallization of 3-[2-(4-fluorophenyl)-1H-indol-3-yl]-N-[(3S,4R)-4-hydroxy-2-oxo-pyrrolidin-3-yl]propanamide (87

A 2-L, 3-neck flask equipped with addition funnel and thermocouple was charged with a light brown suspension of the crude 3-[2-(4-fluorophenyl)-1H-indol-3-yl]-N-[(3S,4R)-4-hydroxy-2-oxo-pyrrolidin-3-yl]propanamide in IPA (225 mL, 1 vol). The slurry was heated to 50° C. and water (675 mL, 3 vol) was added until near-complete dissolution of solid observed (mL). Temperature was increased to 70° C. under nitrogen (full dissolution, yielding a clear amber solution). After 30 minutes, the heat was removed and the mixture cooled to ambient temperature over the weekend, stirring gently under nitrogen atmosphere. The solid was recovered by filtration and washed with IPA:H$_2$O=1:2 (2×300 mL). The solid was dried under a stream of air overnight to afford the product. 3-[2-(4-fluorophenyl)-1H-indol-3-yl]-N-[(3S,4R)-4-hydroxy-2-oxo-pyrrolidin-3-yl]propanamide (84.8 g, 92%). $^1$H NMR (300 MHz, DMSO-d$_6$) δ 11.19 (s, 1H), 8.23 (d, J=7.5 Hz, 1H), 7.77 (s, 1H), 7.72-7.63 (m, 2H), 7.60 (d, J=7.8 Hz, 1H), 7.41-7.31 (m, 3H), 7.12 (ddd, J=8.1, 7.0, 1.2 Hz, 1H), 7.03 (ddd, J=8.0, 7.0, 1.1 Hz, 1H), 5.49 (d, J=5.0 Hz, 1H), 4.20-4.06 (m, 2H), 3.38 (s, 1H), 3.11-3.00 (m, 2H), 2.92 (dd, J=9.4, 6.6 Hz, 1H). LCMS m/z 382.15 [M+H]$^+$.

Large Scale Preparation of Compound 87

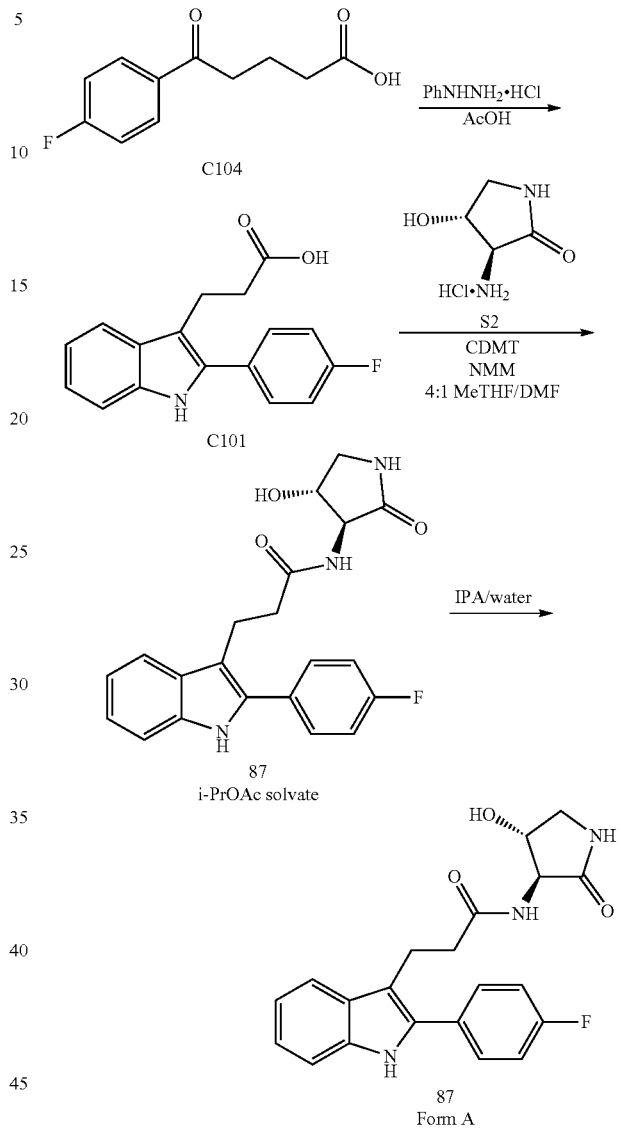

Step 1. Synthesis of 3-[2-(4-fluorophenyl)-1H-indol-3-yl]propanoic Acid (C101

To a mixture of C104 (100.0 g, 1.0 equiv) and phenyl hydrazine hydrochloride (72.2 g, 1.05 eqiv) was charged AcOH (800 mL, 8 vol). The mixture was agitated and heated to 85° C. for 16 hours. The batch was cooled to 22° C. A vacuum was applied and the batch distill at <70° C. to ~3 total volumes. The batch was cooled to 19-25° C. The reactor was charged with iPrOAc (800 mL, 8 vol) and then charged with water (800 mL, 8 vol). The internal temperature was adjusted to 20-25° C. and the biphasic mixture was stirred for no less than 0.5 h. Stirring was stopped and the phases allowed to separate for no less than 0.5 h. The lower aqueous layer was removed. 1N HCl (500 mL, 5 vol) was charged to the reactor. The internal temperature was adjusted to 20-25° C., and the biphasic mixture was stirred for no less than 0.5 h. Stirring was stopped and phases were allowed to separate for no less than 0.5 h. The lower aqueous layer was removed. The reactor was charged with 1N HCl (500 mL, 5 vol). The internal temperature was adjusted to 20-25° C., and the biphasic mixture was stirred for no less than 0.5 h. Stirring was stopped and phases were allowed to separate for no less than 0.5 h. The lower aqueous layer was removed. Water (500 mL, 5 vol) was charged to the reactor. The internal temperature was adjusted to 20-25° C., and the biphasic mixture was stirred for no less than 0.5 h. Stirring was stopped and phases were allowed to separate for no less than 0.5 h. The lower aqueous layer was removed. Water (500 mL, 5 vol) was charged to the reactor. The internal temperature was adjusted to 20-25° C., and the biphasic mixture was stirred for no less than 0.5 h. Stirring was stopped and phases were allowed to separate for no less than 0.5 h. The lower aqueous layer was removed. The organic phase was distilled under vacuum at <75° C. to 3 total volumes. The reactor was charged with toluene (1000 mL, 10 vol). The organic phase was distilled under vacuum at <75° C. to 5 total volumes. The reactor was charged with toluene (1000 mL, 10 vol). The organic phase was distilled under vacuum at <75° C. to 5 total volumes. The resulting slurry was heated to an internal temperature of 85° C. until complete dissolution of solids was achieved. The mixture was allowed to stir for 0.5 h at 85° C. and then cooled to an internal temperature of 19-25° C. over 5 h. The mixture was allowed to stir at 25° C. for no less than 2 h. The slurry was filtered. The filter cake was washed with toluene (1×2 vol (200 mL) and 1×1.5 vol (150 mL)). The solids were dried under vacuum with nitrogen bleed at 60° C. to afford product C101 (95.03 g, 70%).

Purification of Compound 87 by Recrystallization to Form A

Compound 87 as an iPrOAc solvate (17.16 g after correction for iPrOAc content, 1.0 equiv) was charged to a reactor. A mixture of IPA (77 mL, 4.5 vol) and water (137 mL, 8 vol) were charged to the reactor. The slurry was heated to an internal temperature of 75° C. The batch was cooled to an internal temperature of 25° C. over 10 h and then stirred at 25° C. for at least 12 h. The slurry was filtered. The filter cake was washed with 36/64 IPA/water (2×52 mL, 2×3 vol). The solids were dried under vacuum with nitrogen bleed at 60° C. to afford Compound 87 as a neat, crystalline form (Form A, 15.35 g, 89%).

Synthetic Procedure

A mixture of 3-[2-(4-fluorophenyl)-1H-indol-3-yl]propanoic acid C101 (50 g, 1.0 equiv), S2 hydrochloride (28.3 g, 1.05 equiv), and CDMT (34.1 g, 1.1 equiv) was charged with 2-MeTHF (200 mL, 4 vol) and DMF (50 mL, 1 vol) and the mixture was agitated. The internal temperature adjusted to ≤13° C. The reactor was charged with NMM (64.5 g, 3.5 equiv) over 1 h, while maintaining internal temperature ≤20° C. The internal temperature was adjusted to 25° C. and the batch was stirred at that temperature for 14 h. The batch was cooled to 10° C. and charged with water (250 mL, 5 vol) while keeping the internal temperature <20° C. The batch was then warmed to 20-25° C. Stirring was stopped, and the phases allowed to separate for 10 min. The lower aqueous phase was removed. The aqueous layer was back extracted with 2-MeTHF (2×200 mL, 2×4 vol) at 20-25° C. The combined organic phases were washed with 1N HCl (500 mL, 10 vol) at 20-25° C. by mixing for 10 min and settling for 10 min. The lower aqueous phase was removed. The organic phases were washed with 0.25N HCl (2×250 mL, 2×5 vol) at 20-25° C. by mixing for 10 min and settling for 10 min for each wash. Lower aqueous phases were removed after each wash. The organic phase was washed with water (250 mL, 5 vol) at 20-25° C. by mixing for 10 min and settling for 10 min. The reactor was charged with 20 wt % Nuchar RGC® and stirred for 4 h. The reaction mixture was filtered through a pad of Celite®. The reactor and Celite® pad were rinsed with 2-MeTHF. The combined organics were distilled under vacuum at <50° C. to 5 total volumes. The reactor was charged with iPrOAc (500 mL, 10 vol). The organic phase was distilled under vacuum at <50° C. to 5 total volumes. The mixture was charged with additional iPrOAc (400 mL, 8 vol) and distillation under vacuum was repeated. The mixture was charged with additional iPrOAc (250 mL, 5 vol), heated to an internal temperature of 75° C. and stirred for 5 h. The slurry was cooled to 25° C., over 5 h and stirred for no less than 12 h. The slurry was filtered and the filter cake washed with iPrOAc (2×50 mL, 2×1 vol). The solids were dried under vacuum with nitrogen bleed at 55-60° C. to afford Compound 87 as an iPrOAc solvate (60.38 g including 9.9% w/w iPrOAc, 80.8% yield).

Form A of Compound 87

Compound 87 hydrate form was converted to the dehydrated, neat crystalline form (Form A) after drying.

Hydrate Form A of Compound 87

A mixture of IPA (4.5 vol) and water (8 vol) was added to compound 87 (iPrOAc solvate containing ~2.5-11 wt % iPrOAc, 1.0 equiv). The slurry was heated to an internal temperature of 75° C. and filtered hot. The filtrate was cooled to 25° C. for at least 12 h. The slurry was filtered. The filter cake was washed with 36/64 IPA/water (2×3 vol). The solids were dried under vacuum with nitrogen bleed at 55-60° C. The product was isolated as Hydrate form.

IPAC Solvate of Compound 87

The large scale synthesis described above provided an iPrOAc solvate containing ~2.5-11 wt % iPrOAc after drying.

Amorphous Form of Compound 87

~1 g of compound 87 was dissolved in 22 mL of acetone. The solution was evaporated using a Genevac. The resulted solid was dried at 60° C. under vacuum overnight. The dried solid was amorphous form.

Compound 88

2,2,3,3-tetradeuterio-3-[5,7-difluoro-2-(4-fluorophenyl)-1H-indol-3-yl]-N-[(3S,4R)-4-hydroxy-2-oxopyrrolidin-3-yl]propanamide (88

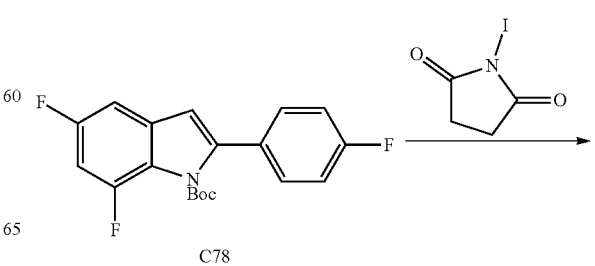

C78

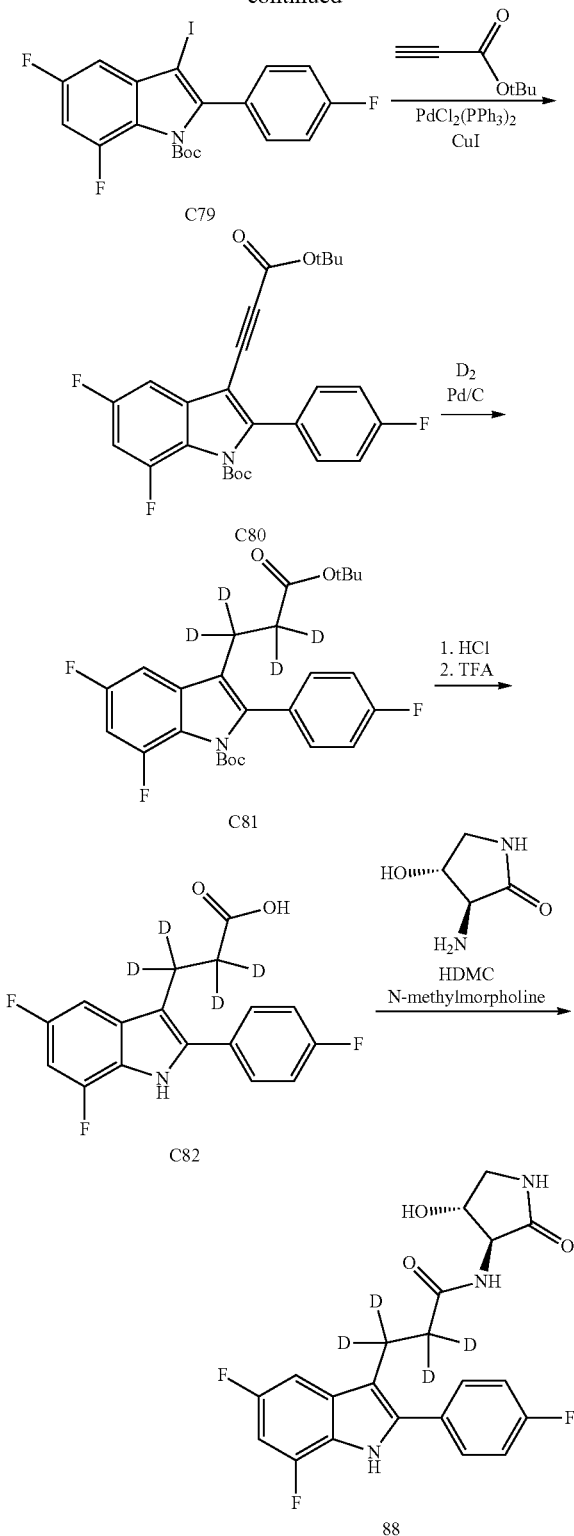

10.2 mmol). The mixture was stirred at 0° C. for 3 h. Additional 1-iodopyrrolidine-2,5-dione was added. The reaction was quenched with sat. $Na_2SO_3$ (20 mL), then diluted with water (30 mL). The organic layer was separated, and the aqueous layer was extracted with $CH_2Cl$ (3×50 mL), dried over $Na_2SO_4$ and concentrated in vacuo. The residual solid was washed with heptane to afford the product as a white solid which was used without further purification (4.1 g, 91%). LCMS m/z 472.9 $[M+H]^+$.

Step 2. tert-butyl 3-(3-tert-butoxy-3-oxo-prop-1-ynyl)-5,7-difluoro-2-(4-fluorophenyl)indole-1-carboxylate (C80

To a solution of tert-butyl 5,7-difluoro-2-(4-fluorophenyl)-3-iodo-indole-1-carboxylate C79 (262 mg, 0.6 mmol), $K_2CO_3$ (153 mg, 1.1 mmol) and DME (4 mL) under argon was added tert-butyl prop-2-ynoate (349 mg, 2.8 mmol), $PdCl_2PPh_3$ (38 mg, 0.05 mmol) and CuI (22 mg, 0.12 mmol). The flask was sealed and the reaction mixture was stirred at 70° C. overnight. The mixture was concentrated in vacuo. Purification by silica gel chromatography (Gradient: 0-15% of EtOAc in hexane), afforded the product (139 mg, 51%). LCMS m/z 472.5 $[M+H]^+$.

Step 3. tert-butyl 3-(3-tert-butoxy-1,1,2,2-tetradeuterio-3-oxo-propyl)-5,7-difluoro-2-(4-fluorophenyl)indole-1-carboxylate (C81

EtOAc (10 mL) was added to a flask containing tert-butyl 3-(3-tert-butoxy-3-oxo-prop-1-ynyl)-5,7-difluoro-2-(4-fluorophenyl)indole-1-carboxylate C80 (111 mg, 0.24 mmol) and Pd on carbon (25 mg, 0.02 mmol). The reaction mixture was subjected to an atmosphere of $D_2$ at balloon pressure. The system was evacuated then refilled with $D_2$ (×3) and the reaction mixture was stirred overnight. Filtration through Celite® and concentration in vacuo afforded the product (86 mg, 51%). LCMS m/z 480.2 $[M+H]^+$.

Step 4. 2,2,3,3-tetradeuterio-3-[5,7-difluoro-2-(4-fluorophenyl)-1H-indol-3-yl]propanoic acid (C82

A solution of HCl (2 mL of 4 M, 8.0 mmol) was added to tert-butyl 3-(3-tert-butoxy-3-oxo-prop-1-ynyl)-5,7-difluoro-2-(4-fluorophenyl)indole-1-carboxylate C81 (86 mg) and the mixture allowed to stir for 2 h. The mixture was concentrated in vacuo to afford 2,2,3,3-tetradeuterio-3-[5,7-difluoro-2-(4-fluorophenyl)-1H-indol-3-yl]propanoic acid which was used without further purification (48 mg, 51%). LCMS m/z 323.3 $[M+H]^+$. A solution of 2,2,3,3-tetradeuterio-3-[5,7-difluoro-2-(4-fluorophenyl)-1H-indol-3-yl]propanoic acid in $CH_2Cl_2$ (2 mL) and TFA (500 µL, 6.5 mmol) was added. The mixture was allowed to stir at room temperature for 1 h. The mixture was concentrated in vacuo. Purification by silica gel chromatography (0-100% EtOAc in Hexanes) afforded the product (55 mg, 48%). LCMS m/z 377.7 $[M+H]^+$.

Step 5. 2,2,3,3-tetradeuterio-3-[5,7-difluoro-2-(4-fluorophenyl)-1H-indol-3-yl]-N-[(3S,4R)-4-hydroxy-2-oxo-pyrrolidin-3-yl]propanamide (88

A solution of 2,2,3,3-tetradeuterio-3-[5,7-difluoro-2-(4-fluorophenyl)-1H-indol-3-yl]propanoic acid C82 (48 mg, 0.15 mmol) and [(5-chloro-3-oxido-benzotriazol-3-ium-1-yl)-morpholino-methylene]-dimethyl-ammonium hexafluorophosphate (68 mg, 0.15 mmol) in DMF (4 mL) was Step 1. tert-butyl 5,7-difluoro-2-(4-fluorophenyl)-3-iodo-indole-1-carboxylate (C79

To a solution of tert-butyl 5,7-difluoro-2-(4-fluorophenyl) indole-1-carboxylate C78 (3.1 g, 8.9 mmol) in $CHCl_3$ (50 mL) at 0° C. was added 1-iodopyrrolidine-2,5-dione (2.3 g, allowed to stir at room temperature for 5 min. A mixture of (3S,4R)-3-amino-4-hydroxy-pyrrolidin-2-one (19 mg, 0.16 mmol) and 4-methylmorpholine (65 µL, 0.6 mmol) in DMF (500p) was added. The mixture was allowed to stir for 1 h. Water was added and the mixture was extracted with EtOAc (2×5 mL). The combined organic layers were washed with $H_2O$ (2 mL), brine (2 mL), dried over sodium sulfate, and concentrated in vacuo. Purification by silica gel chromatography (Gradient: 0-100% EtOAc in Hexanes) afforded the product (32 mg, 48%). $^1H$ NMR (300 MHz, $CD_3OD$) δ 7.77-7.50 (m, 2H), 7.32-7.10 (m, 3H), 6.73 (ddd, J=11.0, 9.6, 2.2 Hz, 1H), 4.34 (q, J=7.4 Hz, 1H), 4.21 (d, J=7.8 Hz, 1H), 3.56 (dd, J=9.9, 7.5 Hz, 1H), 3.10 (dd, J=9.9, 6.8 Hz, 1H). LCMS m/z 422.5 $[M+H]^+$.

Compound 89

Synthesis of 2,3-dideuterio-3-[5,7-difluoro-2-(4-fluorophenyl)-1H-indol-3-yl]-N-[(3S,4R)-4-hydroxy-2-oxo-pyrrolidin-3-yl]propanamide (89

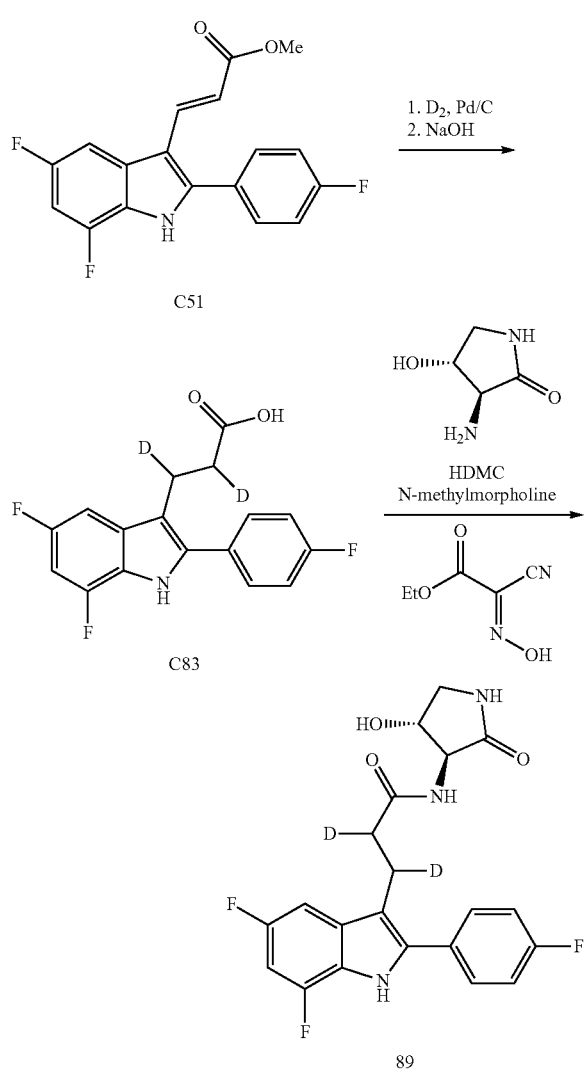

Step 1. Synthesis of Methyl 2,3-dideuterio-3-[5,7-difluoro-2-(4-fluorophenyl)-1H-indol-3-yl]propanoate To a solution of methyl (E)-3-[5,7-difluoro-2-(4-fluorophenyl)-1H-indol-3-yl]prop-2-enoate C51 (28 mg, 0.078 mmol) in EtOAc (4 mL) under a nitrogen atmosphere was added palladium on carbon catalyst (9 mg, 0.008 mmol). The reaction mixture was subjected to an atmosphere of $D_2$ at balloon pressure. The system was evacuated then refilled with $D_2$ (×3) and the reaction mixture was stirred overnight. Filtration through Celite® and concentration in vacuo afforded the product (26 mg, 82%). LCMS m/z 335.4 $[M+H]^+$.

Step 2. Synthesis of 2,3-dideuterio-3-[5,7-difluoro-2-(4-fluorophenyl)-1H-indol-3-yl]propanoic Acid (C83

NaOH (500 µL of 2 M, 1.0 mmol) was added to a solution of methyl 2,3-dideuterio-3-[5,7-difluoro-2-(4-fluorophenyl)-1H-indol-3-yl]propanoate (26 mg) in THF (1 mL) and NaOH (500 µL of 2 M, 1.0 mmol). The mixture was stirred at room temperature overnight. EtOAc and $H_2O$ were added to the reaction mixture, which was then extracted with additional EtOAc (3×2 mL). Combined organic layers were washed with $H_2O$ (1×2 mL), brine (1×2 mL), dried over sodium sulfate, then concentrated to dryness to afford the product (25 mg, 92%). LCMS m/z 321.3 $[M+H]^+$.

Step 4. Synthesis of 2,3-dideuterio-3-[5,7-difluoro-2-(4-fluorophenyl)-1H-indol-3-yl]-N-[(3S,4R)-4-hydroxy-2-oxo-pyrrolidin-3-yl]propanamide (89

A solution of 2,3-dideuterio-3-[5,7-difluoro-2-(4-fluorophenyl)-1H-indol-3-yl]propanoic acid C83 (28 mg, 0.09 mmol) and ethyl (2E)-2-cyano-2-hydroxyimino-acetate (13 mg, 0.09 mmol) in DMF (2 mL), was allowed to stir for 5 min, then [(5-chloro-3-oxido-benzotriazol-3-ium-1-yl)-morpholino-methylene]-dimethyl-ammonium hexafluorophosphate (40 mg, 0.09 mmol) was added. The mixture was allowed to stir at room temperature for 10 min, then a mixture of (3S,4R)-3-amino-4-hydroxy-pyrrolidin-2-one (11 mg, 0.09 mmol) and 4-methylmorpholine (39 µL, 0.4 mmol) in DMF (500 µL) was added. The reaction was allowed to stir for an additional hour. Water was added and the mixture extracted with EtOAc (3×2 mL). Combined organic layers were washed with $H_2O$ (1×2 mL), brine (1×2 mL), dried over sodium sulfate, and concentrated in vacuo. Purification by silica gel chromatography afforded the product. (14 mg, 33%). $^1H$ NMR (300 MHz, $CD_3OD$) δ 7.76-7.55 (m, 2H), 7.33-7.06 (m, 3H), 6.73 (ddd, J=11.1, 9.6, 2.2 Hz, 1H), 4.41-4.28 (m, 1H), 4.22 (d, J=7.8 Hz, 1H), 3.75-3.44 (m, 2H), 3.25-3.04 (m, 3H), 2.84 (s, 1H), 2.68-2.49 (m, 1H). LCMS m/z 419.5 $[M+H]^+$.

Compound 90

(2S)-3-[5,7-difluoro-2-(4-fluorophenyl)-1H-indol-3-yl]-2-methyl-N-[(3S)-2-oxopyrrolidin-3-yl]propanamide (90

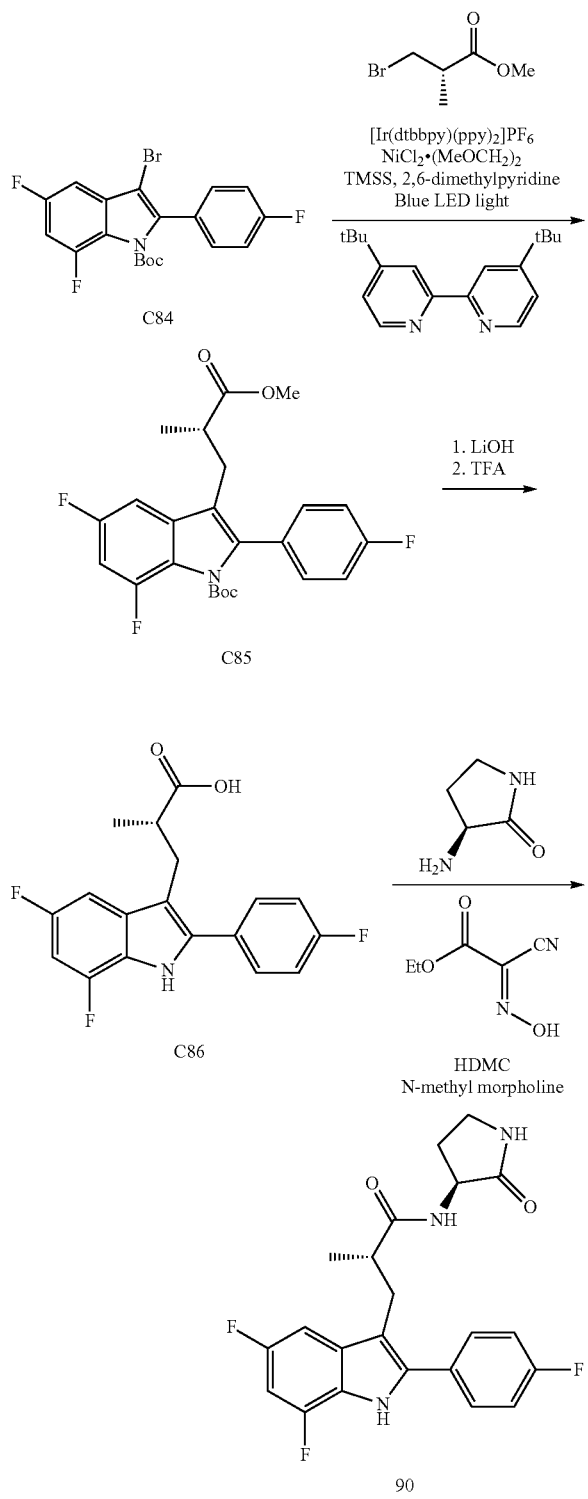

Step 1. tert-butyl 5,7-difluoro-2-(4-fluorophenyl)-3-[(2S)-3-methoxy-2-methyl-3-oxo-propyl]indole-1-carboxylate (C85

A mixture of 3-bromo-N-tert-butyl-5,7-difluoro-2-(4-fluorophenyl)indole-1-carboxamide C84 (600 mg, 1.41 mmol), methyl (2S)-3-bromo-2-methyl-propanoate (200 mg, 1.1 mmol), Tris(trimethylsilyl)silane (265 mg, 1.1 mmol), 2,6-dimethylpyridine (380 mg, 3.5 mmol) and [Ir(dtbbpy)(ppy)$_2$]PF$_6$ (3 mg, 0.003 mmol) in DME (6 mL) was degassed. A mixture of NiCl$_2$·(OMeCH$_2$)$_2$ (10 mg, 0.05 mmol) and 4,4'-Di-tert-butyl-2,2'-dipyridyl (10 mg, 0.04 mmol) in DME (2 mL) was prepared and 100 µL of this mixture was added to the reaction. The mixture was degassed for an additional minute, then subjected to irradiation with a blue LED light overnight. The reaction mixture was diluted with EtOAc and aq. NaHCO$_3$. The organic layer was washed with brine and dried over Na$_2$SO$_4$. Purification by silica gel chromatography (0-100% EtOAc in heptanes) afforded the product (600 mg, 26%). $^1$H NMR (400 MHz, Acetone-d$_6$) δ 7.40-7.24 (m, 2H), 7.21-6.97 (m, 3H), 6.80 (ddd, J=11.9, 9.5, 2.3 Hz, 1H), 3.32 (s, 3H), 2.78 (dd, J=13.9, 6.7 Hz, 1H), 2.60-2.34 (m, 2H), 1.12 (d, J=0.8 Hz, 9H), 0.81 (d, J=6.7 Hz, 3H). LCMS m/z 448.1 [M+H]$^+$.

Step 2. (2S)-3-[I-tert-butoxycarbonyl-5,7-difluoro-2-(4-fluorophenyl)indol-3-yl]-2-methyl-propanoic Acid (C86

To a solution of tert-butyl 5,7-difluoro-2-(4-fluorophenyl)-3-[(2S)-3-methoxy-2-methyl-3-oxo-propyl]indole-1-carboxylate C85 (350 mg, 0.8 mmol) in THF (10 mL) was added LiOH (30 mg, 1.3 mmol) followed by water (3 mL) then stirred at room temperature overnight. The mixture was concentrated and re-dissolved in EtOAc and water. The organic layer was washed with brine, dried over Na$_2$SO$_4$, and concentrated in vacuo. The product was then dissolved in TFA (5 mL) and CH$_2$Cl$_2$ (5 mL) and allowed to stir for 2 h. The mixture was concentrated in vacuo and used in the subsequent step without further purification (150 mg, 32%) LCMS m/z 334.4 [M+H]$^+$.

Step 3. (2S)-3-[5,7-difluoro-2-(4-fluorophenyl)-1H-indol-3-yl]-2-methyl-N-[(3S)-2-oxopyrrolidin-3-yl]propanamide (90

To a solution of (2S)-3-[5,7-difluoro-2-(4-fluorophenyl)-1H-indol-3-yl]-2-methyl-propanoic acid C86 (25 mg, 0.08 mmol) in DMF (2 mL) was added HDMC (33 mg, 0.07 mmol) and ethyl (2E)-2-cyano-2-hydroxyimino-acetate (12 mg, 0.08 mmol). The reaction was stirred at room temperature for 10 min, then (3S)-3-aminopyrrolidin-2-one (10 mg, 0.1 mmol) and N-methyl morpholine (35 mg, 0.4 mmol) were added. The mixture was allowed to stir at room temperature for 30 minutes, then filtered and purified by reversed phase chromatography (C18 column; Gradient: MeCN in H$_2$O with 0.1% TFA) to afford (20 mg, 47%) $^1$H NMR (300 MHz, DMSO-d$_6$) δ 11.66 (s, 1H), 8.08 (d, J=8.2 Hz, 1H), 7.88-7.53 (m, 3H), 7.48-7.17 (m, 3H), 6.95 (ddd, J=11.7, 9.8, 2.2 Hz, 1H), 4.26 (dt, J=10.2, 8.3 Hz, 1H), 3.24-2.88 (m, 3H), 2.81-2.60 (m, 2H), 2.10 (dtd, J=12.4, 6.2, 3.1 Hz, 1H), 1.39 (dq, J=12.1, 9.2 Hz, 1H), 0.91 (d, J=6.0 Hz, 3H). LCMS m/z 416.2 [M+H]$^+$.

Compound 91

(2S)-3-[5,7-difluoro-2-(4-fluorophenyl)-1H-indol-3-yl]-N-[(3S,4R)-4-hydroxy-2-oxo-pyrrolidin-3-yl]-2-methyl-propanamide (91

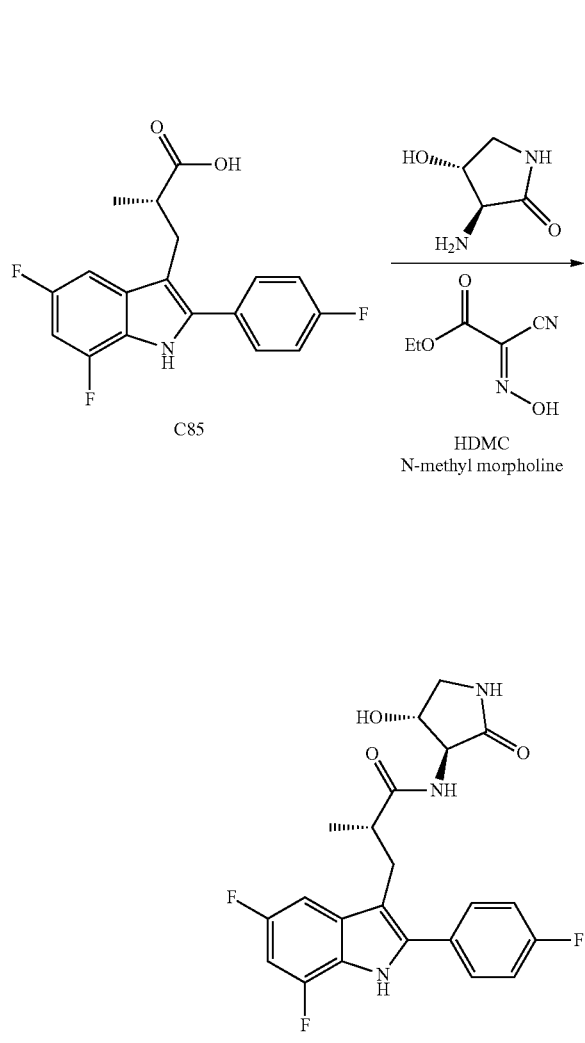

Synthesis of (2S)-3-[5,7-difluoro-2-(4-fluorophenyl)-1H-indol-3-yl]-N-[(3S,4R)-4-hydroxy-2-oxo-pyrrolidin-3-yl]-2-methyl-propanamide (91

Compound 91 was prepared from C85 and S2 as described for compound 90, using S2 as the amine. Purification by reversed phase chromatography (C18 column; Gradient: MeCN in H$_2$O with 0.1% TFA) afforded the product (25 mg, 36%). $^1$H NMR (300 MHz, Acetone-d$_6$) δ 10.73 (s, 1H), 7.86-7.61 (m, 2H), 7.38-7.20 (m, 4H), 7.07 (s, 1H), 6.81 (ddd, J=11.1, 9.6, 2.2 Hz, 1H), 4.12-3.79 (m, 2H), 3.46 (t, J=8.5 Hz, 1H), 3.23 (dd, J=13.8, 7.4 Hz, 1H), 3.14-2.82 (m, 3H), 1.10 (d, J=6.6 Hz, 3H). LCMS m/z 432.1 [M+H]$^+$.

Compound 92

(2R)-3-[5,7-difluoro-2-(4-fluorophenyl)-1H-indol-3-yl]-2-hydroxy-N-[(3S,4R)-4-hydroxy-2-oxo-pyrrolidin-3-yl]propanamide (92

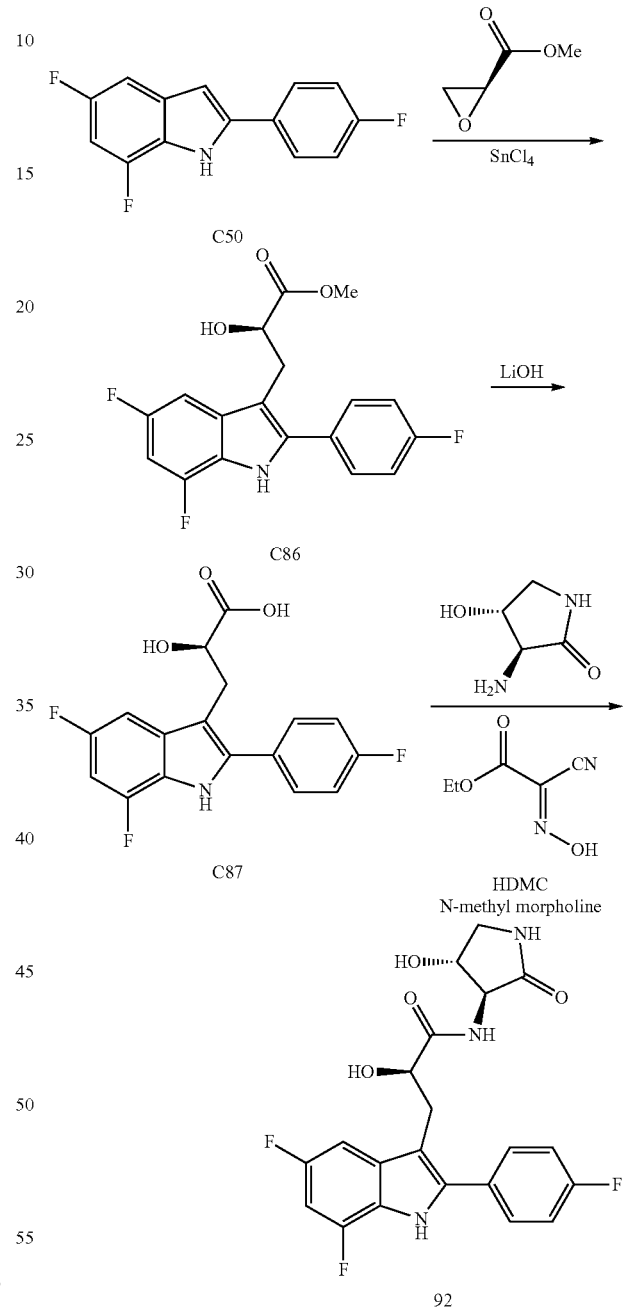

Step 1. Methyl (2R)-3-[5,7-difluoro-2-(4-fluorophenyl)-1H-indol-3-yl]-2-hydroxy-propanoate (C86

To a solution of 5,7-difluoro-2-(4-fluorophenyl)-1H-indole C50 (1000 mg, 4.0 mmol) and methyl (2R)-oxirane-2-carboxylate (500 mg, 4.9 mmol) in CCl$_4$ (20 mL) at 0° C. was added SnCl$_4$ (6 mL of 1 M, 6.0 mmol). The reaction was allowed to stir for 2 h. The reaction was quenched with aq. NaHCO₃ and extracted with CH₂Cl₂. The organic layer was washed with brine, and then dried over Na₂SO₄. Purification by silica gel chromatography (Gradient: 0-50% EtOAc in hexanes) afforded the product (200 mg, 10%). ¹H NMR (400 MHz, Acetone-d₆) δ 10.79 (s, 1H), 7.99-7.84 (m, 2H), 7.40-7.17 (m, 3H), 6.85 (ddd, J=11.1, 9.6, 2.2 Hz, 1H), 4.58-4.50 (m, 2H), 3.63 (s, 3H), 3.38-3.28 (m, 1H), 3.23-3.12 (m, 1H). LCMS m/z 350.4 [M+H]⁺.

Step 2. (2R)-3-[5,7-difluoro-2-(4-fluorophenyl)-1H-indol-3-yl]-2-hydroxy-propanoic Acid (C87

To a solution of methyl (2R)-3-[5,7-difluoro-2-(4-fluorophenyl)-1H-indol-3-yl]-2-hydroxy-propanoate C86 (200 mg, 0.6 mmol) in THF (8 mL) was added LiOH (22 mg, 0.92 mmol) followed by water (2 mL). The reaction was stirred at room temperature overnight then concentrated in vacuo. The residue was dissolved in EtOAc and water. The organic layer was washed with brine and dried over Na₂SO₄ to afford the product which was used without further purification (150 mg, 46%). LCMS m/z 336.3 [M+H]⁺.

Step 3. (2R)-3-[5,7-difluoro-2-(4-fluorophenyl)-1H-indol-3-yl]-2-hydroxy-N-[(3S,4R)-4-hydroxy-2-oxo-pyrrolidin-3-yl]propanamide (92

To a solution of (2R)-3-[5,7-difluoro-2-(4-fluorophenyl)-1H-indol-3-yl]-2-hydroxy-propanoic acid C87 (53 mg, 0.1251 mmol) in DMF (2 mL) and added HDMC (65 mg, 0.14 mmol) and ethyl (2E)-2-cyano-2-hydroxyimino-acetate (20 mg, 0.14 mmol). The reaction mix was stirred at room temperature for 10 min. (3S,4R)-3-amino-4-hydroxy-pyrrolidin-2-one S2 (16 mg, 0.14 mmol) and N-methyl morpholine (50 mg, 0.50 mmol) were then added and the mixture allowed to stir for an additional for 30 min. Purification by reversed phase chromatography (C18 column. Gradient: MeCN in H₂O with 0.1% TFA) afforded the product. (30 mg, 35%). ¹H NMR (400 MHz, Acetone-d₆) δ 10.79 (s, 1H), 8.00-7.88 (m, 2H), 7.33-7.17 (m, 4H), 6.84 (ddd, J=11.1, 9.6, 2.2 Hz, 1H), 4.55 (dd, J=9.5, 3.2 Hz, 1H), 4.41 (q, J=7.8 Hz, 1H), 4.18 (dd, J=8.2, 4.8 Hz, 1H), 3.63 (ddd, J=9.5, 7.7, 1.8 Hz, 1H), 3.44 (dd, J=14.7, 3.2 Hz, 1H), 3.25-2.98 (m, 2H). LCMS m/z 434.1 [M+H]⁺.

Compound 93

(2R)-3-[5,7-difluoro-2-(4-fluorophenyl)-1H-indol-3-yl]-2-hydroxy-N-[(3S)-2-oxopyrrolidin-3-yl]propanamide (93

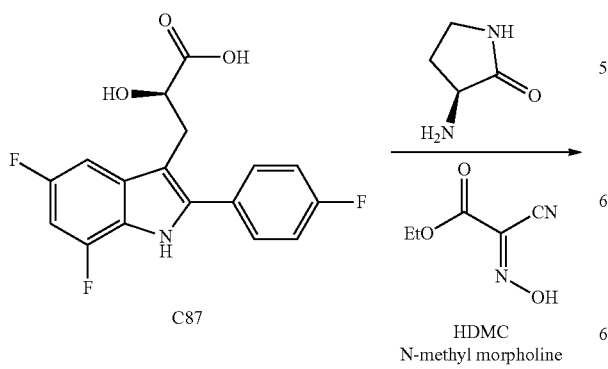

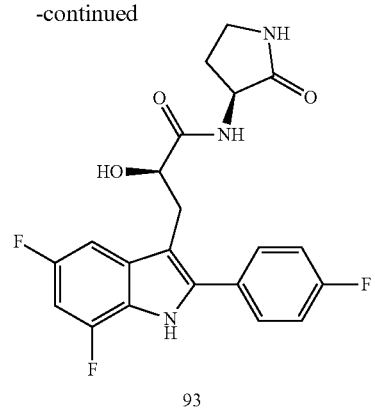

Synthesis of (2R)-3-[5,7-difluoro-2-(4-fluorophenyl)-1H-indol-3-yl]-2-hydroxy-N-[(3S)-2-oxopyrrolidin-3-yl]propanamide (93

Compound 93 was prepared from (2R)-3-[5,7-difluoro-2-(4-fluorophenyl)-1H-indol-3-yl]-2-hydroxy-propanoic acid C87 (25 mg, 0.06 mmol) and (3S)-3-aminopyrrolidin-2-one as described for compound 90. Purification by reversed phase chromatography (C18 column. Gradient: MeCN in H₂O with 0.1% TFA) afforded the product (10 mg, 30%). ¹H NMR (400 MHz, Acetone-d₆) δ 10.75 (s, 1H), 8.05-7.83 (m, 2H), 7.69 (d, J=7.0 Hz, 1H), 7.41-7.19 (m, 4H), 6.82 (ddd, J=11.0, 9.6, 2.2 Hz, 1H), 4.46-4.28 (m, 2H), 3.48-3.34 (m, 3H), 3.03 (dd, J=14.7, 9.4 Hz, 1H), 2.65-2.43 (m, 1H), 2.04-1.89 (m, 1H). LCMS m/z 418.5 [M+H]⁺.

Compound 94

(2S)-3-[5,7-difluoro-2-(4-fluorophenyl)-1H-indol-3-yl]-2-hydroxy-N-[(3S,4R)-4-hydroxy-2-oxo-pyrrolidin-3-yl]propanamide (94

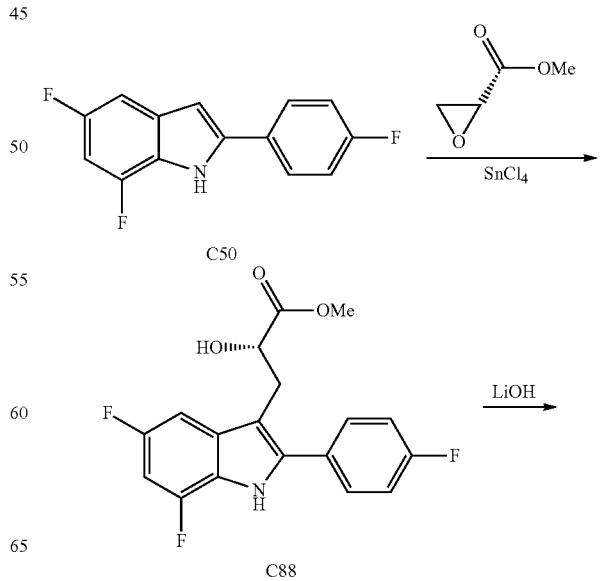

-continued

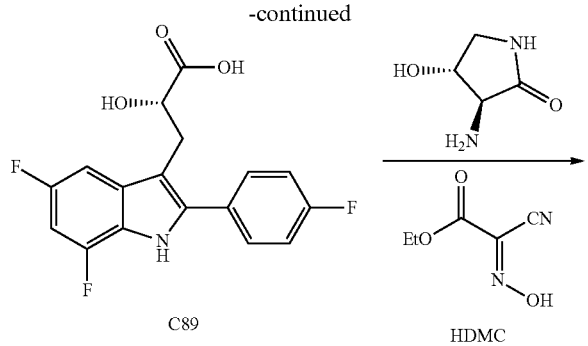

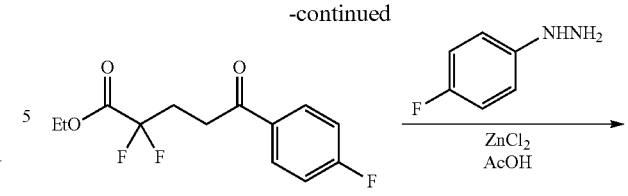

Synthesis of (2S)-3-[5,7-difluoro-2-(4-fluorophenyl)-1H-indol-3-yl]-2-hydroxy-N-[(3S,4R)-4-hydroxy-2-oxo-pyrrolidin-3-yl]propanamide (94

Compound 94 was prepared in three steps from 5,7-difluoro-2-(4-fluorophenyl)-1H-indole C50 in the manner described for the preparation of compound 92. Purification by reversed phase chromatography afforded the product (30 mg, 36%). $^1$H NMR (400 MHz, Acetone-$d_6$) δ 10.78 (s, 1H), 8.04-7.83 (m, 2H), 7.81-7.66 (m, 1H), 7.38-7.24 (m, 3H), 7.21-7.06 (m, 1H), 6.85 (ddd, J=11.1, 9.6, 2.2 Hz, 1H), 4.53 (dd, J=9.3, 3.2 Hz, 1H), 4.28 (q, J=7.9 Hz, 1H), 4.15 (dd, J=8.2, 4.1 Hz, 2H), 3.59 (ddd, J=9.6, 7.7, 2.0 Hz, 1H), 3.43 (dd, J=14.7, 3.2 Hz, 1H), 3.23-2.96 (m, 2H). LCMS m/z 434.0 [M+H]$^+$.

Compound 95

3-[5,7-difluoro-2-(4-fluorophenyl)-1H-indol-3-yl]-2,2-difluoro-N-[(3S,4R)-4-hydroxy-2-oxo-pyrrolidin-3-yl]propanamide (95

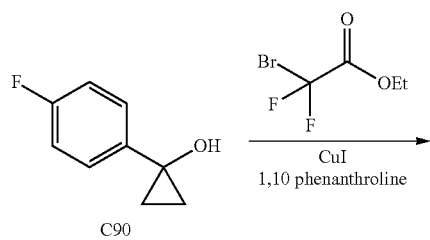

Step 1. Synthesis of ethyl 2,2-difluoro-5-(4-fluorophenyl)-5-oxo-pentanoate (C91

To a solution of 1-(4-fluorophenyl)cyclopropanol C90 (660 mg, 4.3 mmol) in MeCN (45 mL) under an argon atmosphere, was added ethyl 2-bromo-2,2-difluoro-acetate (3.5 g, 17.2 mmol), CuI (84 mg, 0.4 mmol), 1,10-phenanthroline (158 mg, 0.9 mmol), and $K_2CO_3$ (1.2 g, 8.7 mmol). The mixture was allowed to stir at 80° C. The mixture was quenched with water, and then partitioned with EtOAc. The aqueous layer was separated and extracted with EtOAc (3×). The combined organics were washed with saturated NaCl (3×), dried over anhydrous sodium sulfate, filtered and concentrated in vacuo. Purification by chromatography on silica gel (Gradient: 0-20% EtOAc in Heptane)

afforded the product (389 mg, 29%). ¹H NMR (300 MHz, CDCl₃) δ 8.05-7.95 (m, 2H), 7.21-7.07 (m, 2H), 4.33 (q, J=7.1 Hz, 2H), 3.26-3.16 (m, 2H), 2.65-2.46 (m, 2H), 1.35 (t, J=7.2 Hz, 3H). LCMS m/z 275.2 [M+H]⁺.

Step 2. Synthesis of ethyl 3-[5,7-difluoro-2-(4-fluorophenyl)-1H-indol-3-yl]-2,2-difluoro-propanoate (C92

A solution of ethyl 2,2-difluoro-5-(4-fluorophenyl)-5-oxo-pentanoate C91 (389 mg, 1.4 mmol), (2,4-difluorophenyl)hydrazine (Hydrochloride salt) (510 mg, 2.8 mmol), and zinc chloride (915 mg, 6.7 mmol) in acetic acid (4 mL) and toluene (4 mL) was heated at 115° C. overnight. The reaction was concentrated in vacuo, then partitioned between EtOAc and water. The aqueous layer washed with EtOAc (3×) and the combined organic layers were washed with brine, dried over anhydrous sodium sulfate, filtered, and concentrated in vacuo. Purification by silica gel chromatography (Gradient: 0-20% EtOAc in Heptanes) afforded the product (228.4 mg, 40%) ¹H NMR (300 MHz, CDCl₃) δ 8.27 (s, 1H), 7.56 (ddd, J=7.1, 5.3, 2.7 Hz, 2H), 7.25-7.09 (m, 3H), 6.77 (ddd, J=10.7, 9.4, 2.1 Hz, 1H), 4.19 (q, J=7.1 Hz, 2H), 3.53 (t, J=16.9 Hz, 2H), 1.24 (t, J=7.1 Hz, 3H). LCMS m/z 384.2 [M+H]⁺.

Step 3. 3-[5,7-difluoro-2-(4-fluorophenyl)-1H-indol-3-yl]-2,2-difluoro-propanoic Acid (C93

To a solution of ethyl 3-[5,7-difluoro-2-(4-fluorophenyl)-1H-indol-3-yl]-2,2-difluoro-propanoate C92 (210 mg, 0.5 mmol) in THF (2 mL), MeOH (2 mL) and water (1 mL) was added LiOH (28 mg, 1.2 mmol) and the reaction mixture was allowed to stir at ambient temperature for ~2 h. The reaction mixture was concentrated in vacuo, then the aqueous layer was acidified to pH 3 with 1 M HCl, followed by extraction with EtOAc (3×). The combined organic layers were washed with brine, dried over anhydrous sodium sulfate, filtered, and concentrated in vacuo to afford the product (155 mg, 80%). ¹H NMR (300 MHz, CDCl₃) δ 8.28 (s, 1H), 7.54 (ddd, J=8.8, 5.0, 2.3 Hz, 2H), 7.27-7.10 (m, 6H), 6.78 (ddd, J=10.7, 9.4, 2.2 Hz, 1H), 3.53 (t, J=17.1 Hz, 2H). LCMS m/z 356.0 [M+H]⁺.

Step 4. 3-[5,7-difluoro-2-(4-fluorophenyl)-1H-indol-3-yl]-2,2-difluoro-N-[(3S,4R)-4-hydroxy-2-oxo-pyrrolidin-3-yl]propanamide (95

To a solution of 3-[5,7-difluoro-2-(4-fluorophenyl)-1H-indol-3-yl]-2,2-difluoro-propanoic acid C93 (25 mg, 0.07 mmol) in DMF (2 mL) was added ethyl (2E)-2-cyano-2-hydroxyimino-acetate (10 mg, 0.07 mmol) and HDMC (35 mg, 0.08 mmol). The reaction was allowed to stir at room temperature for 30 min. Then (3 S,4R)-3-amino-4-hydroxy-pyrrolidin-2-one S2 (10 mg, 0.09 mmol) and N-methyl morpholine (35 mg, 0.4 mmol) were added and the reaction allowed to stir for an additional 30 minutes. The reaction mixture was diluted with water and EtOAc. The organic layer was washed with brine, dried over Na₂SO₄ then concentrated. Purification by reversed phase HPLC (C18 column. Gradient: MeCN in H₂O with 0.1% TFA) afforded the product (5 mg, 9%). ¹H NMR (300 MHz, Acetone-d₆) δ 10.99 (s, 1H), 8.08 (d, J=7.7 Hz, 1H), 7.88-7.65 (m, 2H), 7.41-7.17 (m, 3H), 7.10-6.74 (m, 2H), 4.44 (q, J=7.7 Hz, 1H), 4.36-4.20 (m, 1H), 3.82-3.45 (m, 3H), 3.24-3.04 (m, 1H). LCMS m/z 454.1 [M+H]⁺.

Compound 96

3-[5,7-difluoro-2-(4-fluorophenyl)-1H-indol-3-yl] butanoic acid (96

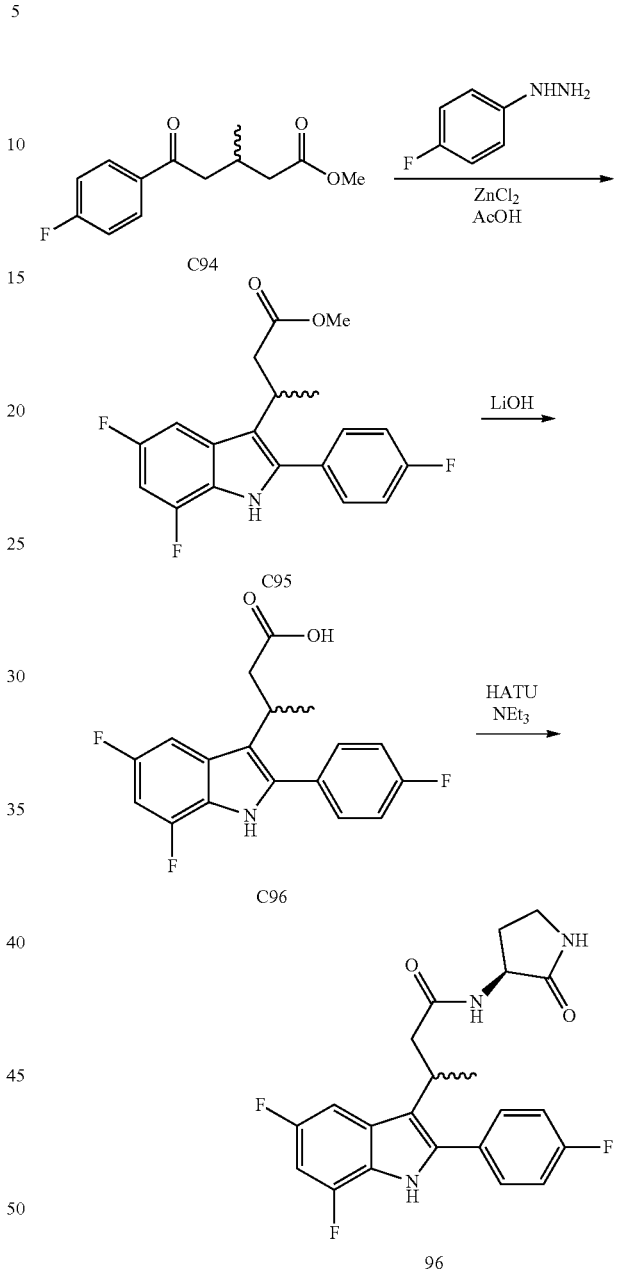

Step 1. Synthesis of Methyl 3-[5,7-difluoro-2-(4-fluorophenyl)-1H-indol-3-yl]butanoate (C95

A solution of methyl 5-(4-fluorophenyl)-3-methyl-5-oxo-pentanoate C94 (91 mg, 0.4 mmol) in acetic acid (1 mL) and toluene (1 mL) was treated with (2,4-difluorophenyl)hydrazine (Hydrochloride salt) (137 mg, 0.8 mmol) followed by zinc chloride (235 mg, 1.7 mmol). The resulting mixture was stirred at 115° C. overnight. The reaction was concentrated in vacuo, then partitioned between EtOAc and water. The aqueous layer was extracted with EtOAc (×3). The combined organic layers were washed with brine, dried over anhydrous sodium sulfate, filtered and concentrated in vacuo. Purification by silica gel chromatography (Gradient: 0-100% EtOAc in heptanes) afforded the product (38.3 mg, 28%) ¹H NMR (300 MHz, CDCl₃) δ 8.05 (s, 1H), 7.57-7.49 (m, 2H), 7.22-7.14 (m, 3H), 6.74 (ddd, J=10.8, 9.4, 2.1 Hz, 1H), 3.65 (dt, J=14.7, 7.3 Hz, 1H), 3.56 (s, 3H), 2.79 (dd, J=7.7, 1.6 Hz, 2H), 1.42 (d, J=7.1 Hz, 3H). LCMS m/z 344.9 [M+H]⁺.

Step 2. 3-[5,7-difluoro-2-(4-fluorophenyl)-1H-indol-3-yl]butanoic Acid (C96

To a solution of methyl 3-[5,7-difluoro-2-(4-fluorophenyl)-1H-indol-3-yl]butanoate C95 (392 mg, 1.1 mmol) in THF (5 mL), MeOH (5 mL) and water (2 mL) was added LiOH (55 mg, 2.3 mmol), and the mixture stirred at room temperature for ~2 h. The reaction was concentrated in vacuo, then the aqueous layer was acidified to pH 3 with 1 M HCl, and extracted with EtOAc (3×). The combined organic layers were washed with brine, dried over anhydrous sodium sulfate, filtered, and concentrated in vacuo to afford the product (350 mg, 93%). ¹H NMR (300 MHz, CDCl₃) δ 8.03 (s, 1H), 7.49-7.40 (m, 2H), 7.20-7.11 (m, 3H), 6.74 (ddd, J=10.7, 9.4, 2.1 Hz, 1H), 3.58 (p, J=7.3 Hz, 1H), 2.88-2.72 (m, 2H), 1.44 (d, J=7.1 Hz, 3H). LCMS m/z 334.1 [M+H]⁺.

Step 3. 3-[5,7-difluoro-2-(4-fluorophenyl)-1H-indol-3-yl]-N-[(3S)-2-oxopyrrolidin-3-yl]butanamide (96

To a solution of 3-[5,7-difluoro-2-(4-fluorophenyl)-1H-indol-3-yl]butanoic acid C96 (30 mg, 0.09 mmol) in DMSO (2 mL) was added HATU (69 mg, 0.2 mmol), TEA (63 µL, 0.5 mmol) and (3S)-3-aminopyrrolidin-2-one (14 mg, 0.14 mmol). The reaction mixture was allowed to stir at room temperature for 12 h. Purification by reverse phase chromatography afforded the product as a mixture of diastereomers (19 mg, 49%). ¹H NMR (300 MHz, CD₃OD) δ 7.73-7.52 (m, 2H), 7.39-7.15 (m, 3H), 6.72 (ddd, J=11.0, 9.6, 2.1 Hz, 1H), 4.37 (ddd, J=14.1, 10.1, 8.8 Hz, 1H), 3.64 (dt, J=8.8, 6.7 Hz, 1H), 3.3 (2H, obscured by solvent peak) 2.90-2.74 (m, 1H), 2.71-2.55 (m, 1H), 2.48-2.28 (m, 1H), 1.86 (ddt, J=12.5, 10.2, 9.1 Hz, 1H), 1.42 (dd, J=7.1, 4.4 Hz, 3H). LCMS m/z 416.1 [M+H]⁺.

Compound 97

3-[5,7-difluoro-2-(4-fluorophenyl)-1H-indol-3-yl]-N-[(3S,4R)-4-hydroxy-2-oxo-pyrrolidin-3-yl]butanamide (97

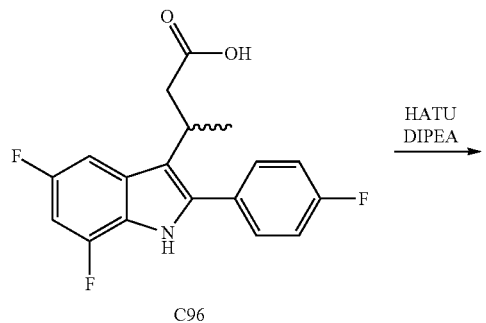

C96

HATU
DIPEA

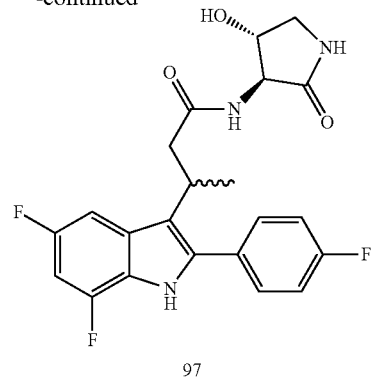

97

Synthesis of 3-[5,7-difluoro-2-(4-fluorophenyl)-1H-indol-3-yl]-N-[(3S,4R)-4-hydroxy-2-oxo-pyrrolidin-3-yl]butanamide (97

To a solution of 3-[5,7-difluoro-2-(4-fluorophenyl)-1H-indol-3-yl]butanoic acid C96 (21 mg, 0.06 mmol) in DMF (1 mL) was added HATU (~36 mg, 0.09 mmol), then (3S,4R)-3-amino-4-hydroxy-pyrrolidin-2-one S2 (~7.3 mg, 0.06 mmol) and DIPEA (approximately 24.4 mg, 32.9 µL, 0.19 mmol). The reaction mixture was allowed to stir overnight at room temperature. Purification by reverse phase chromatography (C18 column. Gradient: MeCN in H₂O with 0.1% TFA) afforded the product as a mixture of diastereomers (17.6 mg, 63%). ¹H NMR (400 MHz, DMSO-d₆) δ 11.65 (s, 1H), 8.30 (dd, J=22.4, 7.9 Hz, 1H), 7.77 (d, J=3.3 Hz, 1H), 7.67-7.59 (m, 2H), 7.39 (q, J=9.5, 8.7 Hz, 3H), 6.98 (td, J=11.1, 10.3, 2.1 Hz, 1H), 5.47 (s, 1H), 4.06 (ddt, J=31.3, 15.8, 7.6 Hz, 2H), 2.95-2.81 (m, 2H), 2.55 (1H, peak obscured by solvent), 2.41-2.33 (m, 1H), 1.33 (dd, J=8.9, 7.0 Hz, 3H). LCMS m/z 432.1 [M+H]⁺.

Compound 98

3-[5,6-difluoro-2-(4-fluorophenyl)-7-methyl-1H-indol-3-yl]-N-[(3S,4R)-4-hydroxy-2-oxo-pyrrolidin-3-yl]propanamide (98

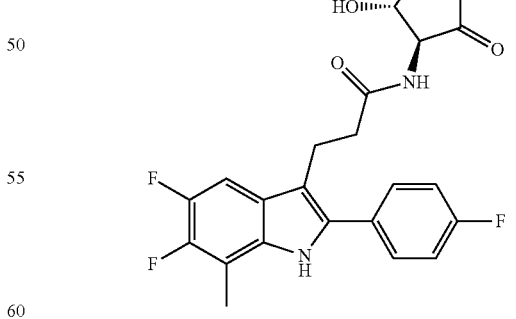

Compound 98 was prepared from 6-bromo-3,4-difluoro-2-methyl-aniline and 1-ethynyl-4-fluoro-benzene by indole preparation route A, then amide bond formation with S2 using standard method F (HATU). p-Toluene sulfonic acid (pTSA) was substituted for TFA in the reductive alkylation step. ¹H NMR (400 MHz, CD₃OD) δ 7.75-7.54 (m, 2H), 7.31 (dd, J=10.9, 7.5 Hz, 1H), 7.27-7.13 (m, 2H), 4.46-4.27 (m, 1H), 4.27-4.14 (m, 1H), 3.57 (dd, J=9.9, 7.6 Hz, 1H), 3.21-3.03 (m, 3H), 2.71-2.53 (m, 2H), 2.46 (d, J=1.9 Hz, 3H). LCMS m/z 432.13 [M+H]$^+$.

Compound 99

3-(5,6-difluoro-7-methyl-2-phenyl-1H-indol-3-yl)-N-[(3S,4R)-4-hydroxy-2-oxo-pyrrolidin-3-yl]propanamide (99

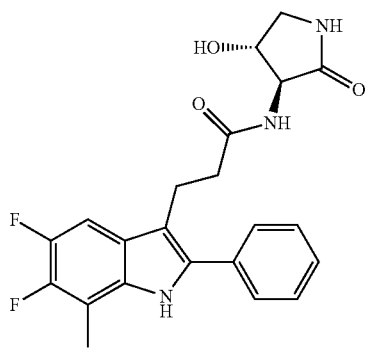 [SMILES: Cc1c(F)c(F)cc2c(CCC(=O)N[C@@H]3C(=O)NC[C@H]3O)c(-c3ccc(F)cc3)[nH]c12]

Compound 99 was prepared from 6-bromo-3,4-difluoro-2-methyl-aniline and ethynylbenzene by indole preparation route A, and then amide bond formation with S2 using standard method F (HATU). p-Toluene sulfonic acid (pTSA) was substituted for TFA in the reductive alkylation step. LCMS m/z 414.15 [M+H]$^+$.

Compound 100

3-[7-(difluoromethyl)-5-fluoro-2-(4-fluorophenyl)-1H-indol-3-yl]-N-[(3S,4R)-4-hydroxy-2-oxo-pyrrolidin-3-yl]propanamide (100

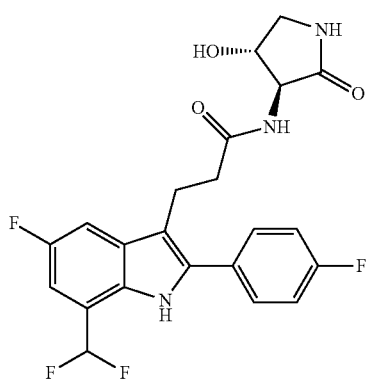

Compound 100 was prepared from 2-bromo-6-(difluoromethyl)-4-fluoro-aniline and 1-ethynyl-4-fluoro-benzene by indole preparation route A, and then amide bond formation with S2 using standard method F (HATU). p-Toluene sulfonic acid (pTSA) was substituted for TFA in the reductive alkylation step. $^1$H NMR (300 MHz, Methanol-d$_4$) δ 7.71-7.59 (m, 2H), 7.52 (d, J=8.3 Hz, 1H), 7.30-7.18 (m, 2H), 7.24 (t, J=54 Hz, 1H) 7.11 (d, J=17.0 Hz, 1H), 4.33 (q, J=7.5 Hz, 1H), 4.21 (d, J=7.8 Hz, 1H), 3.67-3.46 (m, 1H), 3.24-3.01 (m, 3H), 2.70-2.49 (m, 2H). LCMS m/z 450.16 [M+H]$^+$.

Compound 101

3-[7-fluoro-2-(4-fluorophenyl)-5-(trifluoromethyl)-1H-indol-3-yl]-N-[(3S,4R)-4-hydroxy-2-oxo-pyrrolidin-3-yl]propanamide (101

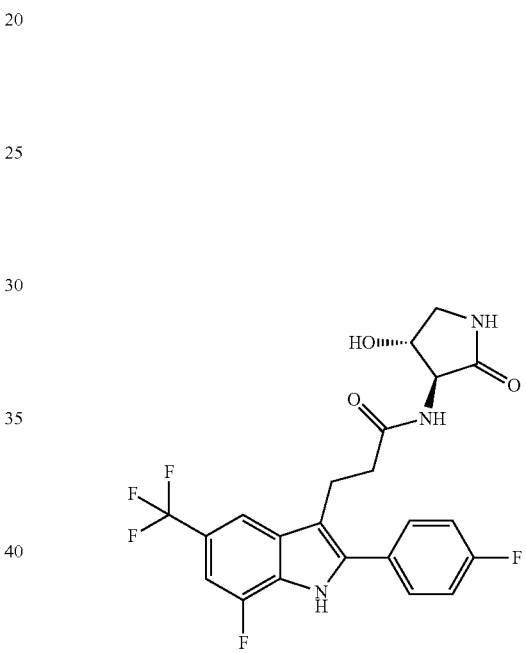

Compound 101 was prepared from 1-ethynyl-4-fluorobenzene and 2-fluoro-6-iodo-4-(trifluoromethyl)aniline by indole preparation route A, and then amide bond formation with S2 using standard method F (HATU). p-Toluene sulfonic acid (pTSA) was substituted for TFA in the reductive alkylation step. $^1$H NMR (300 MHz, Methanol-d$_4$) δ 11.62 (s, 1H), 7.85 (s, 1H), 7.76-7.55 (m, 2H), 7.40-7.20 (m, 2H), 7.20-6.99 (m, 1H), 4.35 (q, J=7.4 Hz, 1H), 4.22 (d, J=7.8 Hz, 1H), 3.58 (dd, J=9.9, 7.6 Hz, 1H), 3.28-3.17 (m, 2H), 3.11 (dd, J=9.9, 6.9 Hz, 1H), 2.73-2.49 (m, 2H). LCMS m/z 468.25 [M+H]$^+$.

Compound 102-107

Compounds 102-107 (Table 9) were prepared by indole preparation route A from the appropriate commercially available alkyne and 2-halo anilines, followed by amide coupling with S2 using standard method F. Purification by reversed-phase chromatography (Column: C18. Gradient: 0-100% MeCN in water with either 0.1% formic acid or 0.2% TFA modifier) afforded the product.

TABLE 9

Method of preparation, structure and physicochemical data for compounds 102-107

| Compound | Structure | Indole preparation method; Amide Formation; non-commercial amine | ¹H NMR; LCMS m/z [M + H]⁺ |
|---|---|---|---|
| 102 | 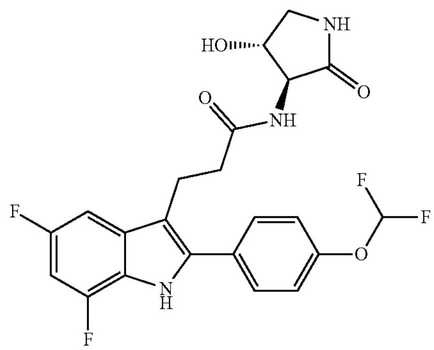 [SMILES: O=C(CCc1c(-c2ccc(OC(F)F)cc2)[nH]c2c(F)cc(F)cc12)N[C@@H]1C(=O)NC[C@H]1O] | Route A; Standard Method F; S2 | ¹H NMR (300 MHz, CD$_3$OD) δ 7.77-7.59 (m, 2H), 7.28 (d, J = 8.7 Hz, 2H), 7.20 (dd, J = 9.4, 2.2 Hz, 1H), 6.90 (s, 1H), 6.83-6.68 (m, 1H), 4.34 (td, J = 7.7, 6.9 Hz, 1H), 4.21 (d, J = 7.8 Hz, 1H), 3.56 (dd, J = 9.9, 7.5 Hz, 1H), 3.23-3.00 (m, 3H), 2.70-2.46 (m, 2H). LCMS m/z 466.1 [M + H]⁺. |
| 103 | 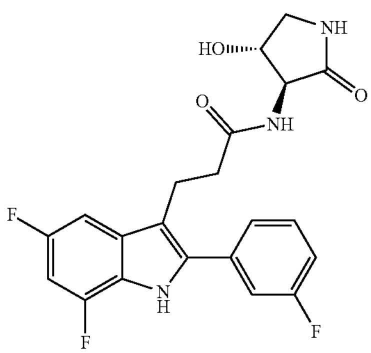 [SMILES: O=C(CCc1c(-c2cccc(F)c2)[nH]c2c(F)cc(F)cc12)N[C@@H]1C(=O)NC[C@H]1O] | Route A; Standard Method F; S2 | ¹H NMR (300 MHz, MeOD) δ 7.60-7.44 (m, 2H), 7.39 (dd, J = 10.2, 2.5 Hz, 1H), 7.22 (dd, J = 9.4, 2.2 Hz, 1H), 7.20-7.07 (m, 1H), 6.84-6.60 (m, 1H), 4.33 (q, J = 7.5 Hz, 1H), 4.21 (d, J = 7.8 Hz, 1H), 3.65-3.46 (m, 1H), 3.24-3.00 (m, 3H), 2.67-2.49 (m, 2H). LCMS m/z 417.96 [M + H]⁺. |
| 104 | 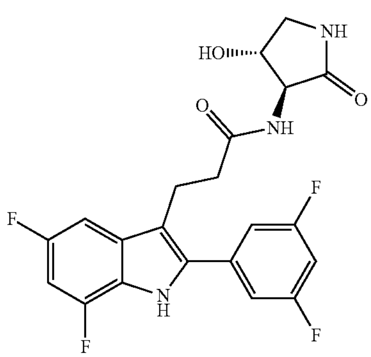 [SMILES: O=C(CCc1c(-c2cc(F)cc(F)c2)[nH]c2c(F)cc(F)cc12)N[C@@H]1C(=O)NC[C@H]1O] | Route A; Standard Method F; S2 | ¹H NMR (400 MHz, CD$_3$OD) δ 7.35-7.15 (m, 3H), 7.00 (tt, J = 9.2, 2.3 Hz, 1H), 6.78 (ddd, J = 11.1, 9.6, 2.2 Hz, 1H), 4.32 (td, J = 7.7, 6.9 Hz, 1H), 4.21 (d, J = 7.8 Hz, 1H), 3.56 (dd, J = 9.9, 7.6 Hz, 1H), 3.23-3.14 (m, 2H), 3.10 (dd, J = 9.9, 6.9 Hz, 1H), 2.68-2.50 (m, 2H). LCMS m/z 436.1 [M + H]⁺ |
| 105 | 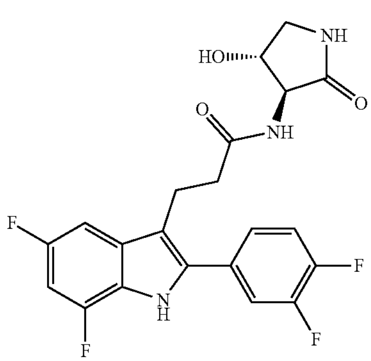 [SMILES: O=C(CCc1c(-c2ccc(F)c(F)c2)[nH]c2c(F)cc(F)cc12)N[C@@H]1C(=O)NC[C@H]1O] | Route A; Standard Method F; S2 | ¹H NMR (400 MHz, CD$_3$OD) δ 7.56 (ddd, J = 11.7, 7.6, 2.1 Hz, 1H), 7.50-7.32 (m, 2H), 7.21 (dd, J = 9.4, 2.2 Hz, 1H), 6.76 (ddd, J = 11.1, 9.6, 2.2 Hz, 1H), 4.32 (td, J = 7.7, 6.9 Hz, 1H), 4.21 (d, J = 7.8 Hz, 1H), 3.56 (dd, J = 9.9, 7.6 Hz, 1H), 3.22-3.01 (m, 3H), 2.69-2.50 (m, 2H). LCMS m/z 435.97 [M + H]⁺. |

TABLE 9-continued

Method of preparation, structure and physicochemical data for compounds 102-107

| Compound | Structure | Indole preparation method; Amide Formation; non-commercial amine | $^1$H NMR; LCMS m/z [M + H]$^+$ |
|---|---|---|---|
| 106 | 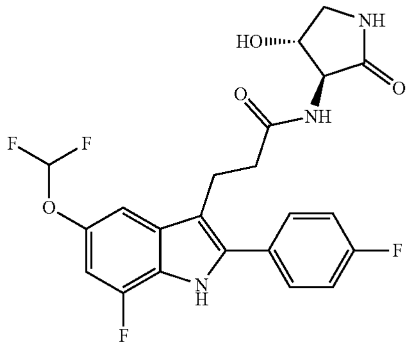 [SMILES: O=C(CCc1c(-c2ccc(F)cc2)[nH]c2c(F)cc(OC(F)F)cc12)N[C@@H]1C(=O)NC[C@H]1O] | Route A; Standard Method F; S2 | $^1$H NMR (300 MHz, MeOD) δ 7.79-7.53 (m, 2H), 7.33-7.14 (m, 3H), 6.99 (t, J = 54 Hz, 1H), 6.87-6.71 (m, 1H), 4.33 (q, J = 7.3 Hz, 1H), 4.27-4.12 (m, 1H), 3.56 (dd, J = 9.9, 7.6 Hz, 1H), 3.21-3.01 (m, 3H), 2.67-2.50 (m, 2H). LCMS m/z 466.19 [M + H]$^+$. |
| 107 | 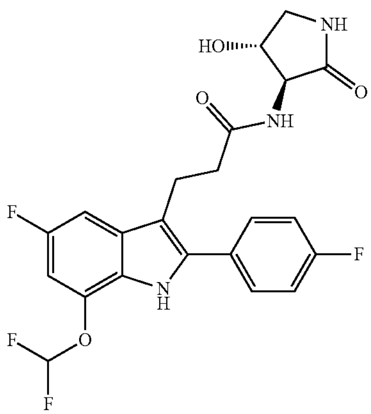 [SMILES: O=C(CCc1c(-c2ccc(F)cc2)[nH]c2c(OC(F)F)cc(F)cc12)N[C@@H]1C(=O)NC[C@H]1O] | Route A; Standard Method F; S2 | $^1$H NMR (300 MHz, Methanol-d$_4$) δ 7.80-7.57 (m, 2H), 7.37-7.16 (m, 3H), 6.80 (t, J = 54 Hz, 1H), 6.75 (m, 1H), 4.34 (td, J = 7.6, 6.9 Hz, 1H), 4.22 (d, J = 7.8 Hz, 1H), 3.57 (dd, J = 9.9, 7.6 Hz, 1H), 3.24-3.02 (m, 3H), 2.71-2.46 (m, 2H). LCMS m/z 466.07 [M + H]$^+$. |

Compound 108

3-[2-(4-fluorophenyl)-5-(trifluoromethyl)-1H-indol-3-yl]-N-[(3S,4R)-4-hydroxy-2-oxo-pyrrolidin-3-yl]propanamide (108

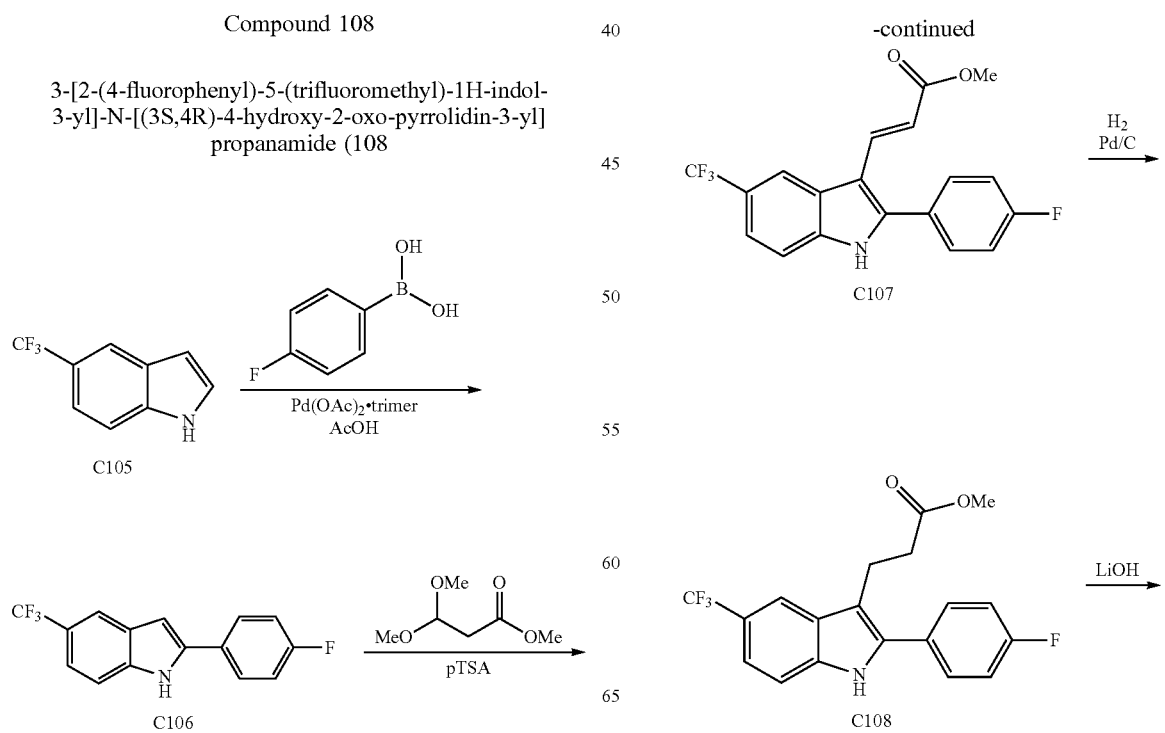

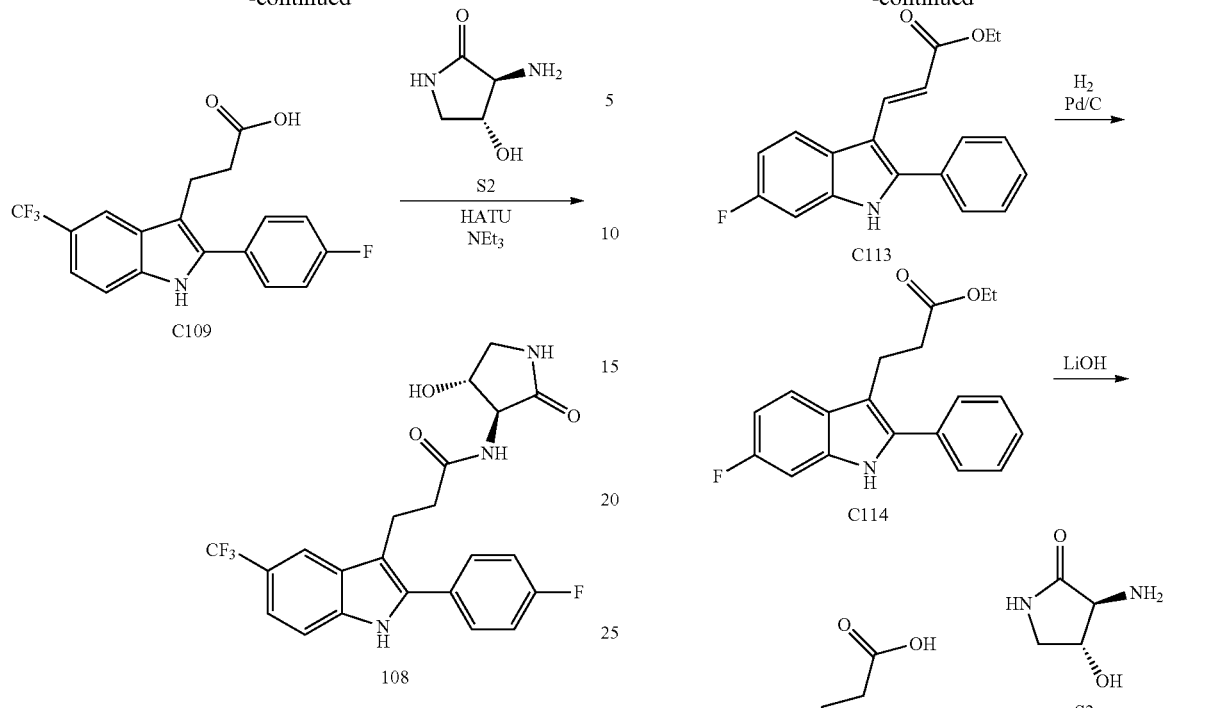

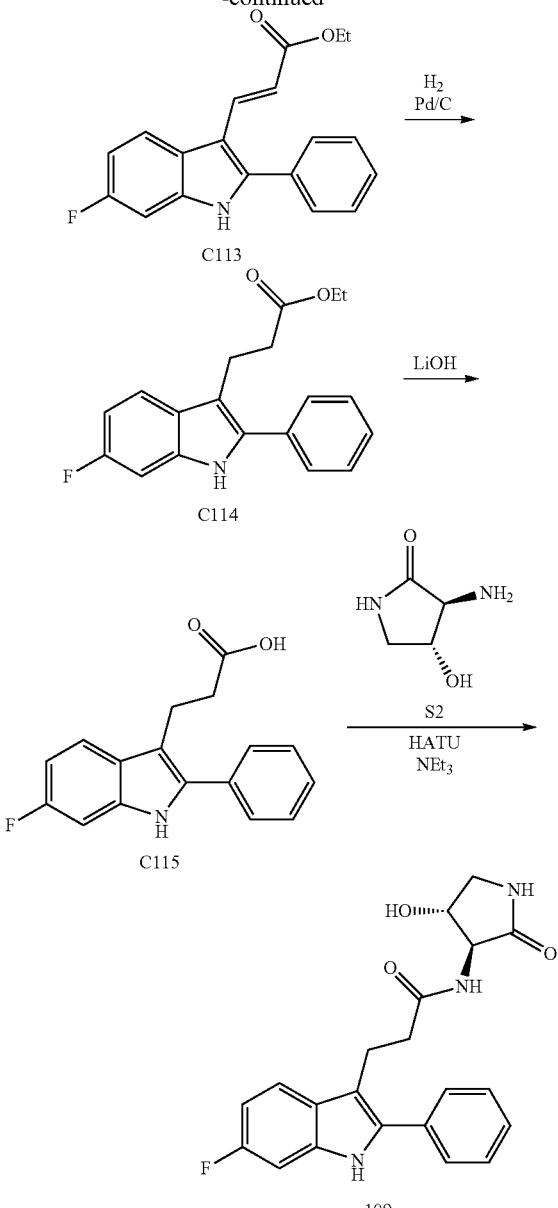

Compound 108 was prepared from indole C105 and 4-fluoro boronic acid using indole preparation route C to form C109, followed by coupling with S2 using standard method. $^1$H NMR (300 MHz, CD$_3$OD) δ 7.99 (dt, J=1.8, 0.9 Hz, 1H), 7.80-7.58 (m, 2H), 7.49 (dt, J=8.5, 0.7 Hz, 1H), 7.37 (dd, J=8.8, 1.6 Hz, 1H), 7.34-7.14 (m, 2H), 4.35 (td, J=7.6, 6.9 Hz, 1H), 4.21 (d, J=7.8 Hz, 1H), 3.57 (dd, J=9.9, 7.6 Hz, 1H), 3.27-3.16 (m, 2H), 3.10 (dd, J=9.9, 6.9 Hz, 1H), 2.75-2.49 (m, 2H). LCMS m/z 450.11 [M+H]$^+$.

Compound 109

3-(6-fluoro-2-phenyl-1H-indol-3-yl)-N-[(3S,4R)-4-hydroxy-2-oxo-pyrrolidin-3-yl]propanamide (109

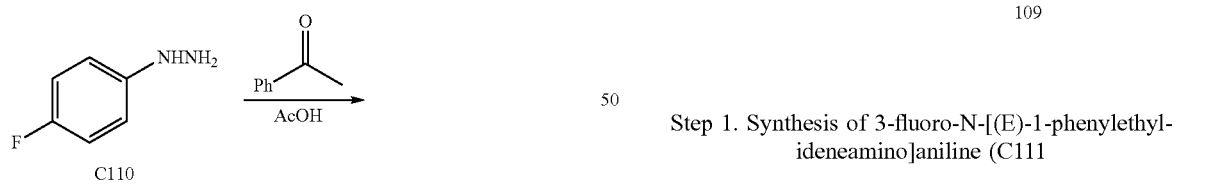

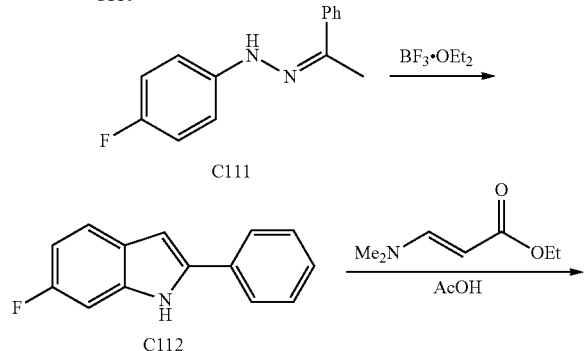

Step 1. Synthesis of 3-fluoro-N-[(E)-1-phenylethyl-ideneamino]aniline (C111

To a stirred solution of 1-phenylethanone (2 g, 1.76 mL, 16.6 mmol) and (3-fluorophenyl)hydrazine (2.99 g, 18.8 mmol) in EtOH (10 mL) and catalytic amount of acetic acid (0.5 mL) was added and the reaction mixture was heated at 80° C. for 4 h. The reaction mixture was washed with EtOAc (15 mL×3) and water (10 mL). The combined organic layer was evaporated under reduced pressure. Purification by flash chromatography on silica gel (Gradient: 0-5% EtOAc in hexane) afforded 3-fluoro-N-[(E)-1-phenylethylide-neamino]aniline (3.5 g, 86%). $^1$H NMR (300 MHz, MeOD) δ 7.73-7.55 (m, 3H), 7.55-7.43 (m, 2H), 7.43-7.28 (m, 1H), 7.05 (ddd, J=9.9, 2.4, 0.5 Hz, 1H), 6.82 (ddd, J=9.8, 8.7, 2.3 Hz, 1H), 4.35 (td, J=7.6, 6.8 Hz, 1H), 4.22 (d, J=7.7 Hz, 1H), 3.57 (dd, J=9.9, 7.5 Hz, 1H), 3.28-3.18 (m, 3H), 3.11 (dd, J=9.9, 6.8 Hz, 1H), 2.72-2.51 (m, 2H). LCMS m/z 229.0 [M+1]⁺.

Step 2. Synthesis of 6-fluoro-2-phenyl-1H-indole (C112) and 4-fluoro-2-phenyl-1H-indole To a stirred solution of 3-fluoro-N-[(E)-1-phenylethylideneamino]aniline (3.5 g, 15.3 mmol) in Xylene (10 mL) was degassed with nitrogen for 10 minutes then boron trifluoride diethyl etherate (10.9 g, 9.5 mL, 76.7 mmol) was added. The reaction mixture was heated to 130° C. for 16 h. After completion, the reaction mixture was quenched with cold water (80 mL) and washed with EtOAc (3×10 mL). The combined organic layer was evaporated under reduced pressure to get the crude material. Purification by flash chromatography on silica gel using (0-2% EtOAc in hexane) afforded separated the product 6-fluoro-2-phenyl-1H-indole and isomer 4-fluoro-2-phenyl-1H-indole.

Compound C112. 6-fluoro-2-phenyl-1H-indole (700 mg, 21%). ¹H NMR (400 MHz, DMSO-d₆) δ 11.64 (s, 1H), 7.87-7.80 (m, 2H), 7.53 (dd, J=8.6, 5.5 Hz, 1H), 7.46 (t, J=7.6 Hz, 2H), 7.31 (t, J=7.4 Hz, 1H), 7.13 (dd, J=10.2, 2.3 Hz, 1H), 6.91 (d, J=2.2 Hz, 1H), 6.86 (ddd, J=10.7, 8.6, 2.4 Hz, 1H). LCMS m/z 212.2 [M+1]+.

4-fluoro-2-phenyl-1H-indole (250 mg, 5%). ¹H NMR (400 MHz, DMSO-d₆) δ 11.84 (s, 1H), 7.93-7.87 (m, 2H), 7.48 (t, J=7.6 Hz, 2H), 7.34 (t, J=7.4 Hz, 1H), 7.25 (d, J=8.1 Hz, 1H), 7.07 (td, J=8.0, 5.3 Hz, 1H), 6.98 (d, J=2.3 Hz, 1H), 6.78 (dd, J=10.7, 7.8 Hz, 1H). LCMS m/z 212.0 [M+1]+.

Step 3. Synthesis of ethyl (E)-3-(6-fluoro-2-phenyl-1H-indol-3-yl)prop-2-enoate (C113

In a seal tube, 6-fluoro-2-phenyl-1H-indole C112 (600 mg, 2.84 mmol) and ethyl (E)-3-(dimethylamino)prop-2-enoate (488 mg, 0.4401 mL, 3.4 mmol) in acetic acid (5 mL) was heated at 95° C. for 2 h. The reaction mixture was neutralized in cold condition with saturated NaHCO₃ solution. The reaction mixture was partitioned between ethyl acetate (20 mL). The organic phase was dried over Na₂SO₄ and concentrated. Purification by column chromatography on silica gel (100-200 mesh) using 10% EtOAc/hexane afforded the product. Ethyl (E)-3-(6-fluoro-2-phenyl-1H-indol-3-yl)prop-2-enoate (400 mg, 38%). LCMS m/z 310.4 [M+H]⁺.

Steps 4-6. Preparation of 3-(6-fluoro-2-phenyl-1H-indol-3-yl)-N-[(3S,4R)-4-hydroxy-2-oxo-pyrrolidin-3-yl]propanamide (109

Compound 109 was prepared from C113 by hydrogenation (according to standard method K), ester hydrolysis (according to standard method E) and coupling of C115 with S2 according to standard method F.

¹H NMR (300 MHz, CD₃OD) δ 7.73-7.55 (m, 3H), 7.55-7.43 (m, 2H), 7.43-7.28 (m, 1H), 7.05 (ddd, J=9.9, 2.4, 0.5 Hz, 1H), 6.82 (ddd, J=9.8, 8.7, 2.3 Hz, 1H), 4.35 (td, J=7.6, 6.8 Hz, 1H), 4.22 (d, J=7.7 Hz, 1H), 3.57 (dd, J=9.9, 7.5 Hz, 1H), 3.28-3.18 (m, 2H), 3.11 (dd, J=9.9, 6.8 Hz, 1H), 2.72-2.51 (m, 2H). LCMS m/z 381.99 [M+H]⁺.

Compound 110

3-[2-(4-fluorophenyl)-6-hydroxy-1H-indol-3-yl]-N-[(3S,4R)-4-hydroxy-2-oxo-pyrrolidin-3-yl]propanamide (110

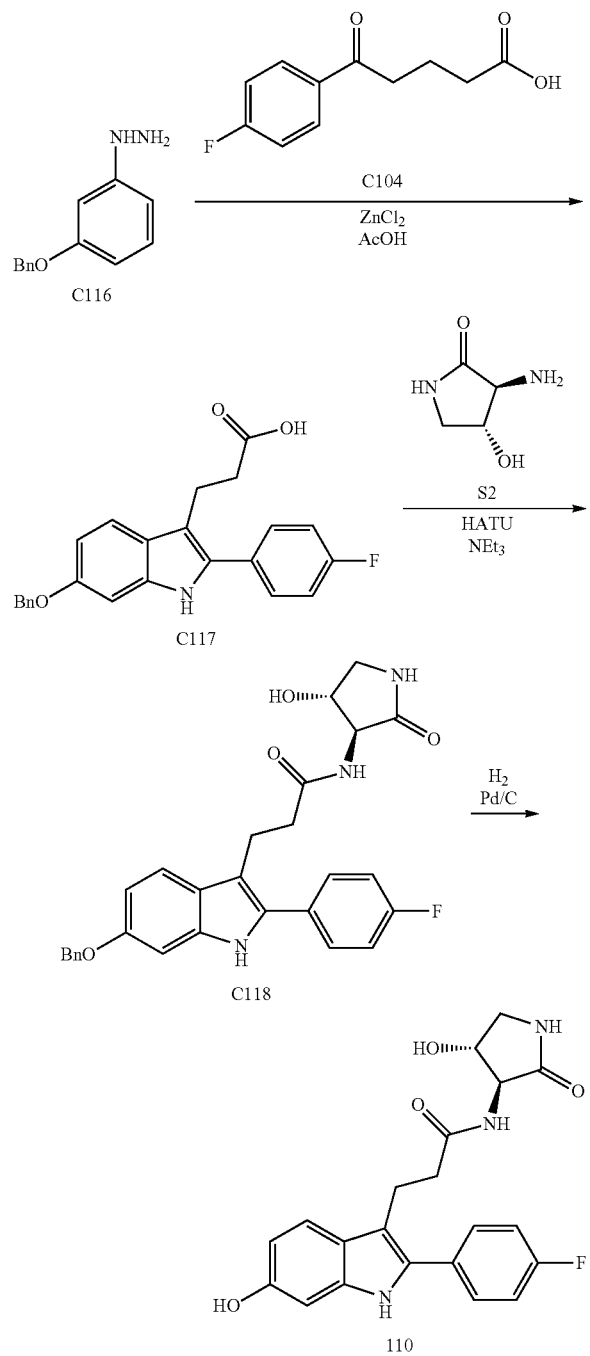

Compound 110 was prepared from (3-benzyloxyphenyl)hydrazine C166 using the indole preparation method D (as described for an alternative preparation of compound 87). Coupling of S2 with propanoic acid C177 according to standard method F, followed by removal of the benzyl protecting group by hydrogenation using standard method K (as described for compound 55) afforded compound 110. LCMS m/z 398.28 [M+H]⁺.

Compound 111

3-[2-(4-fluorophenyl)-7-(trifluoromethyl)-1H-indol-3-yl]-N-[(3S,4R)-4-hydroxy-2-oxo-pyrrolidin-3-yl]propanamide (111

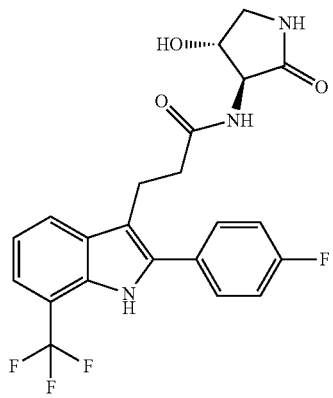 [SMILES: O=C(CCc1c(-c2ccc(F)cc2)[nH]c2c(C(F)(F)F)cccc12)N[C@@H]1C(=O)NC[C@H]1O]

Compound 111 was prepared from 7-(trifluoromethyl)-1H-indole and (4-fluorophenyl)boronic acid using indole preparation route C, then amide bond formation with S2 using standard method F (HATU). ¹H NMR (300 MHz, DMSO) δ 11.39 (s, 1H), 8.20 (d, J=7.4 Hz, 1H), 7.91 (d, J=7.9 Hz, 1H), 7.75 (s, 1H), 7.71-7.57 (m, 2H), 7.45 (d, J=7.5 Hz, 1H), 7.35 (t, J=8.9 Hz, 2H), 7.19 (t, J=7.7 Hz, 1H), 4.24-3.92 (m, 2H), 3.00 (dd, J=10.0, 6.6 Hz, 2H), 2.89 (dd, J=9.3, 6.6 Hz, 1H). LCMS m/z 450.24 [M+H]⁺.

Compound 112

N-[(3S,4R)-4-hydroxy-2-oxo-pyrrolidin-3-yl]-3-[2-phenyl-7-(trifluoromethyl)-1H-indol-3-yl]propanamide (112

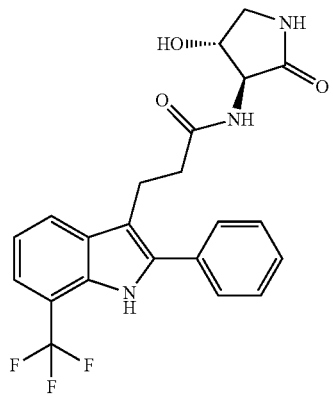 [SMILES: O=C(CCc1c(-c2ccccc2)[nH]c2c(C(F)(F)F)cccc12)N[C@@H]1C(=O)NC[C@H]1O]

Compound 112 was prepared from 7-(trifluoromethyl)-1H-indole and phenyl boronic acid using indole preparation route C, then amide bond formation with S2 using standard method F (HATU). ¹H NMR (300 MHz, Methanol-d₄) δ 10.68 (s, 1H), 8.37 (d, J=7.8 Hz, 1H), 7.91 (d, J=8.0 Hz, 1H), 7.71-7.58 (m, 2H), 7.58-7.31 (m, 4H), 7.18 (t, J=7.7 Hz, 1H), 4.33 (q, J=7.3 Hz, 1H), 4.22 (t, J=7.7 Hz, 1H), 3.55 (dd, J=9.9, 7.5 Hz, 1H), 3.26-3.15 (m, 2H), 3.10 (dd, J=9.9, 6.8 Hz, 1H), 2.75-2.43 (m, 2H). LCMS m/z 431.96 [M+H]⁺.

Compound 113

3-[7-chloro-2-(4-chlorophenyl)-1H-indol-3-yl]-N-[(3S,4R)-4-hydroxy-2-oxo-pyrrolidin-3-yl]propanamide (113

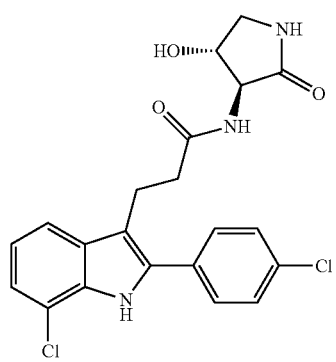 [SMILES: O=C(CCc1c(-c2ccc(Cl)cc2)[nH]c2c(Cl)cccc12)N[C@@H]1C(=O)NC[C@H]1O]

Compound 113 was prepared from 7-(chloro)-1H-indole and (4-chloro phenyl) boronic acid using indole preparation route C, then amide bond formation with S2 using standard method F (HATU). ¹H NMR (300 MHz, CD₃OD) δ 7.73-7.56 (m, 3H), 7.56-7.43 (m, 2H), 7.14 (dd, J=7.6, 1.0 Hz, 1H), 7.03 (t, J=7.8 Hz, 1H), 4.33 (q, J=7.5 Hz, 1H), 4.21 (d, J=7.8 Hz, 1H), 3.55 (dd, J=9.9, 7.5 Hz, 1H), 3.25-3.15 (m, 2H), 3.10 (dd, J=9.9, 6.9 Hz, 1H), 2.76-2.49 (m, 2H). LCMS m/z 432.03 [M+H]⁺.

Compound 114

3-(4-fluoro-2-phenyl-1H-indol-3-yl)-N-[(3S,4R)-4-hydroxy-2-oxo-pyrrolidin-3-yl]propanamide (114

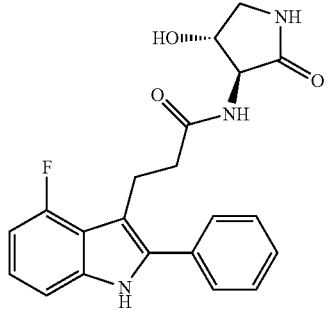 [SMILES: O=C(CCc1c(-c2ccccc2)[nH]c2cccc(F)c12)N[C@@H]1C(=O)NC[C@H]1O]

Compound 114 was prepared from 3-fluorophenyl hydrazine and 1-phenylethanone by fisher indole synthesis as described for the preparation of compound 109. ¹H NMR (300 MHz, CD₃OD) δ 7.61 (dd, J=8.3, 1.5 Hz, 2H), 7.56-7.42 (m, 2H), 7.42-7.27 (m, 1H), 7.15 (dd, J=8.1, 0.9 Hz, 1H), 7.03 (td, J=7.9, 5.0 Hz, 1H), 6.78-6.55 (m, 1H), 4.36 (td, J=7.7, 6.8 Hz, 1H), 4.21 (d, J=7.7 Hz, 1H), 3.68-3.45 (m, 1H), 3.23 (d, J=8.4 Hz, 2H), 3.16-3.01 (m, 1H), 2.81-2.61 (m, 2H). LCMS m/z 381.149 [M+H]⁺.

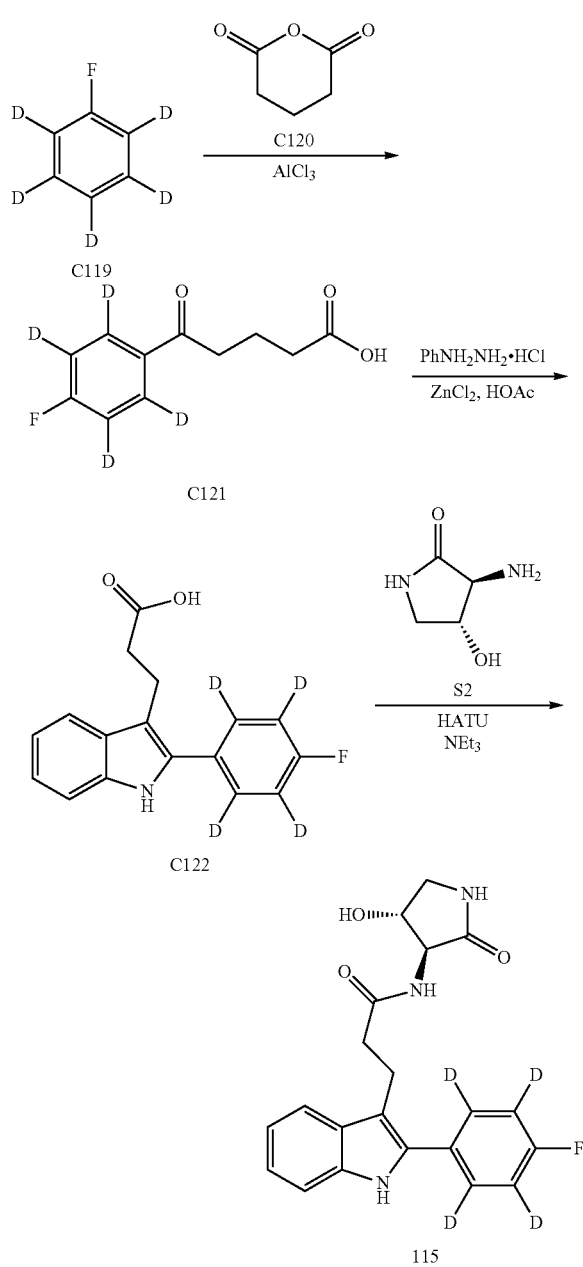

Step 1. Synthesis of 5-(4-Fluorophenyl-2,3,5,6-d$_4$)-5-oxopentanoic Acid (C121

A solution of glutaric acid (22.6 g, 197.8 mmol, 1 equiv) in anhydrous dichloromethane (50 mL) was added to a suspension of aluminum chloride (58.0 g, 435.1 mmol, 2.2 equiv) in anhydrous dichloromethane (500 mL) at 5° C. The resulting mixture was stirred at 0-5° C. for 30 minutes. Fluorobenzene-d$_5$ (20 g, 197.8 mmol, 1 equiv) was added drop wise at 0-5° C., and the mixture was stirred at 0-5° C. for 1 hour. The mixture was stirred at room temperature for 1 The mixture was poured into ice-water (1 L) and the solids were collected by filtration. The wet filter cake was dissolved in saturated sodium bicarbonate solution (300 mL) and 3% aqueous sodium hydroxide solution (300 mL) and washed with dichloromethane (500 mL). The aqueous layer was adjusted to pH 1 with concentrated hydrogen chloride solution (300 mL). The resulting solids were collected by filtration, washed with water (2×20 mL) and dried under vacuum at 50° C. overnight to give the desired product (26.8 g, 63% yield) as a white solid.

Step 2. Synthesis of 3-(2-(4-Fluorophenyl-2,3,5,6-d$_4$)-1H-indol-3-yl)propanoic Acid (C122

Phenylhydrazine hydrochloride (19.1 g, 132.1 mmol, 1.1 equiv) and zinc chloride (27.8 g, 204.1 mmol, 1.7 equiv) were added to a solution of 5-(4-Fluorophenyl-2,3,5,6-d$_4$)-5-oxopentanoic acid (25.72 g, 120.07 mmol, 1.0 equiv) in acetic acid (500 mL) at room temperature and the mixture was heated at 100° C. for 7 hours. A front run of this reaction (1.07 g of 5-(4-Fluorophenyl-2,3,5,6-d$_4$)-5-oxopentanoic acid used) was processed in the same manner and both batches were combined for work-up. After cooling to room temperature, the mixture was concentrated under reduced pressure to remove most of acetic acid, and the residue was diluted with water (200 mL). The mixture was extracted with ethyl acetate (4×300 mL). The combined organic layers were washed with saturated brine (200 mL), dried over sodium sulfate, filtered, and concentrated under reduced pressure. The residue was purified on a Büchi Reveleris X2-UV automated chromatography system (330 g Redisep silica gel column), eluting with a gradient of 0 to 5% ethyl acetate in dichloromethane to give 3-(2-(4-Fluorophenyl-2,3,5,6-d$_4$)-1H-indol-3-yl)propanoic acid (37.0 g) as a yellow solid which still contained a small amount of impurities. This material was triturated with 50% dichloromethane in heptanes (100 mL) to give pure 3-(2-(4-Fluorophenyl-2,3,5,6-d$_4$)-1H-indol-3-yl)propanoic acid (31.32 g, 87% yield) as a white solid.

Step 3. Synthesis of 3-(2-(4-Fluorophenyl-2,3,5,6-d$_4$)-1H-indol-3-yl)-N-((3S,4R)-4-hydroxy-2-oxopyrrolidin-3-yl)propanamide (115

HATU (32.38 g, 85.2 mmol, 1.3 equiv) and triethylamine (36.5 mL, 262.0 mmol, 4 equiv) were added to a mixture of 3-(2-(4-Fluorophenyl-2,3,5,6-d$_4$)-1H-indol-3-yl)propanoic acid (18.8 g, 65.5 mmol, 1 equiv) and (3S,4R)-3-amino-4-hydroxypyrrolidin-2-one (10.0 g, 65.5 mmol, 1 equiv.) in dimethyl sulfoxide (190 mL) at room temperature. The mixture was stirred at room temperature for 16 hours. Water (400 mL) was added and the mixture was extracted with ethyl acetate (3×300 mL). The combined organic layers were washed with saturated brine (400 mL), dried over sodium sulfate, filtered and concentrated under reduced pressure. The residue was purified on a Büchi Reveleris X2-UV automated chromatography system (330 g Redisep silica gel column with dry-loading), eluting with a gradient of 0 to 10% methanol in dichloromethane, to give 3-(2-(4-Fluorophenyl-2,3,5,6-d$_4$)-1H-indol-3-yl)-N-((3S,4R)-4-hydroxy-2-oxopyrrolidin-3-yl)propanamide (24.0 g, 95% yield, 94% purity) as a yellow-brown foamy solid. A front run of this reaction (3.0 g of compound 3-(2-(4-Fluorophenyl-2,3,5,6-d$_4$)-1H-indol-3-yl)propanoic acid used) was processed in same manner to give compound 3-(2-(4-Fluorophenyl-2,3,5,6-d$_4$)-1H-indol-3-yl)-N-((3S,4R)-4-hydroxy-2-oxopyrrolidin-3-yl)propanamide (3.3 g, 82% yield, 96% purity) as a yellow-brown foamy solid. 3-(2-(4-Fluorophenyl-2,3,5,6-d$_4$)-1H-indol-3-yl)-N-((3S,4R)-4-hydroxy-2-oxopyrrolidin-3-yl)propanamide (27 g total) from both batches was further purified on a Büchi Reveleris X2-UV automated chromatography system (330 g Redisep silica gel column with dry-loading), eluting with a gradient of 0 to 10% acetone in ethyl acetate to give compound 3-(2-(4-Fluorophenyl-2,3,5,6-d$_4$)-1H-indol-3-yl)-N-((3S,4R)-4-hydroxy-2-oxopyrrolidin-3-yl)propanamide which contained 1 mol % ethyl acetate. This material was dissolved in acetonitrile (3×300 mL) and concentrated under reduced pressure. The product was dried under vacuum at 45° C. for 3 days to give compound 3-(2-(4-Fluorophenyl-2,3,5,6-d$_4$)-1H-indol-3-yl)-N-((3S,4R)-4-hydroxy-2-oxopyrrolidin-3-yl)propanamide (17.8 g, 99.7% purity) as a white solid. LCMS m/z=386.1 [M+H]$^+$. $^1$H NMR (400 MHz, DMSO-d$_6$) δ=11.17 (s, 1H), 8.21 (d, J=7.8 Hz, 1H), 7.75 (s, 1H), 7.60 (d, J=7.9 Hz, 1H), 7.36 (d, J=7.9 Hz, 1H), 7.11 (ddd, J=1.2, 7.0, 8.1 Hz, 1H), 7.03 (ddd, J=1.0, 7.0, 7.9 Hz, 1H), 5.47 (d, J=5.3 Hz, 1H), 4.18-4.08 (m, 2H), 3.42-3.36 (m, 1H), 3.10-3.02 (m, 2H), 2.92 (dd, J=6.8, 9.5 Hz, 1H), 2.54-2.51 (m, 1H), 2.49-2.46 (m, 1H). $^{19}$F NMR (376 MHz, DMSO-d$_6$) δ=−115.12 (s, 1F). $^{13}$C NMR (100 MHz, DMSO-d$_6$) δ=172.62, 172.61, 163.12, 160.69, 136.44, 133.53, 129.64, 129.60, 128.76, 122.06, 119.20, 119.10, 111.64, 111.35, 72.26, 58.28, 48.56, 37.05, 21.14, 1.60. $^2$H NMR (61 MHz, DMSO-d$_6$) δ=7.70 (br s), 7.39 (br s). Melting Point=108.3-113.7° C.

Compound 116

3-[2-(4-cyanophenyl)-1H-indol-3-yl]-N-[(3S,4R)-4-hydroxy-2-oxo-pyrrolidin-3-yl]propanamide (116

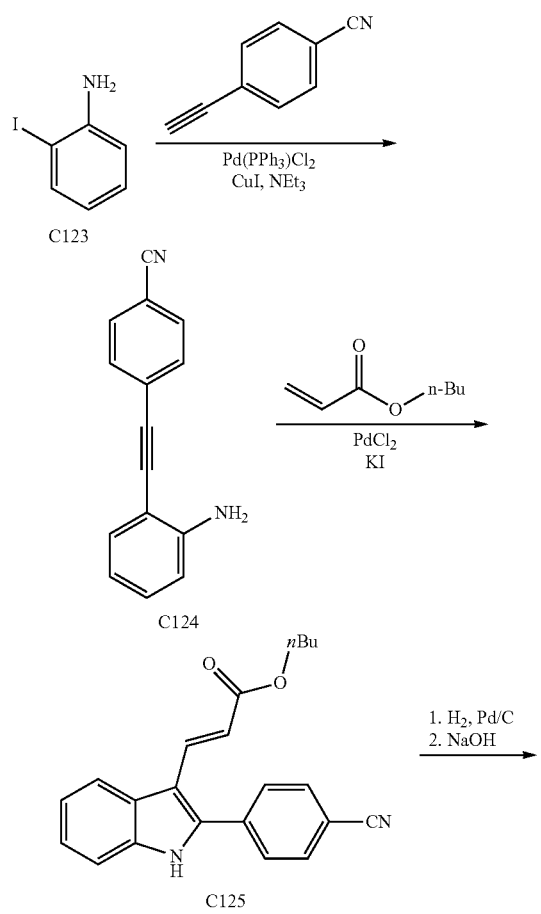

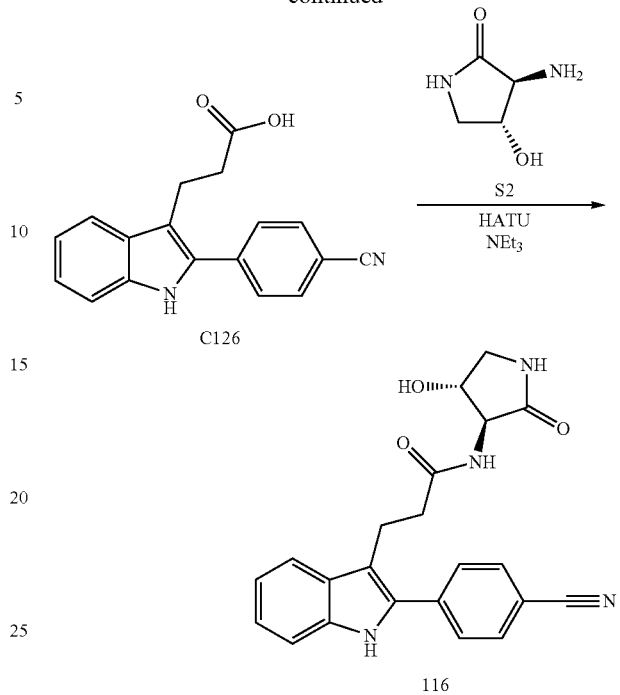

Step 1. Synthesis of 4-[2-(2-aminophenyl)ethynyl]benzonitrile (C124

2-iodoaniline (2 g, 9.13 mmol), PdCl$_2$(PPh$_3$)$_2$ (320 mg, 0.46 mmol), and CuI (45 mg, 0.24 mmol), were dissolved in degassed Et$_3$N (45 mL). 4-ethynylbenzonitrile (1.3 g, 10.2 mmol) was added, and the reaction mixture and stirred at 60° C. for 4 h. The resulting suspension was filtered, washed with Et$_2$O, then concentrated under reduced pressure to yield 4-[2-(2-aminophenyl)ethynyl]benzonitrile (2 g, 94%) as a maroon solid, used directly in the next step without further purification. LCMS m/z 219.3 [M+H]$^+$.

Step 2. Synthesis of Butyl (E)-3-[2-(4-cyanophenyl)-1H-indol-3-yl]prop-2-enoate (C125

A mixture of 4-[2-(2-aminophenyl)ethynyl]benzonitrile (250 mg, 1.15 mmol), butyl prop-2-enoate (894 mg, 1 mL, 6.98 mmol), PdCl$_2$ (10.0 mg, 0.06 mmol), and KI (100 mg, 0.6 mmol) in DMF (10 mL), was stirred at 100° C., overnight. The reaction was performed in the presence of air. The mixture was cooled to room temperature, and filtered through Celite®. The filter cake was washed with EtOAc and the filtrate was evaporated under reduced pressure. The viscous oil was taken into EtOAc (150 mL). H$_2$O (150 mL) was added, and the layers were separated. The organic layer was washed with H$_2$O (3×100 mL), brine (1×100 mL), dried over Na$_2$SO$_4$, filtered, and concentrated under reduced pressure. The residue was dried under high vacuum overnight to afford butyl (E)-3-[2-(4-cyanophenyl)-1H-indol-3-yl]prop-2-enoate (500 mg, 118%) as a brown oil, which was used in the next step without further purification. LCMS m/z 345.0 [M+H]$^+$.

Step 3. Synthesis of 3-[2-(4-cyanophenyl)-1H-indol-3-yl]propanoic Acid (C126

Butyl (E)-3-[2-(4-cyanophenyl)-1H-indol-3-yl]prop-2-enoate (95.6 mg, 0.28 mmol) was dissolved in THF (3 mL) and MeOH (3 mL) then palladium on carbon (44 mg, 10% w/w, 0.042 mmol) was added. The reaction was stirred under hydrogen (balloon pressure) for 3 hours. Upon completion, Celite® was added and the solids were filtered off. The filtrate was concentrated to a yellow oil. The residue was then dissolved in THF (5 mL) Water (1 mL) and MeOH (2.5 mL) to give a homogenous solution. NaOH (110 mg, 2.8 mmol) was added and the reaction stirred for 1 hour. The reaction was quenched by the addition of 1 M HCl (5 mL). The aqueous layer was extracted with EtOAc (3×5 mL), then the organic layers were dried over $Na_2SO_4$ and concentrated to give 3-[2-(4-cyanophenyl)-1H-indol-3-yl]propanoic acid (95 mg, 112%) as a yellow solid. No further was purification was performed. The product was used directly in the subsequent reaction. $^1$H NMR (500 MHz, DMSO-$d_6$) δ 12.15 (s, 1H), 11.39 (s, 1H), 7.98 (d, J=8.4 Hz, 2H), 7.84 (d, J=8.4 Hz, 2H), 7.62 (d, J=8.0 Hz, 1H), 7.39 (d, J=8.1 Hz, 1H), 7.16 (t, J=7.6 Hz, 1H), 7.05 (t, J=7.5 Hz, 1H), 3.19-3.08 (m, 2H), 2.62-2.54 (m, 2H). LCMS m/z 290.7 [M+H]$^+$.

Step 4. Synthesis of 3-[2-(4-cyanophenyl)-1H-indol-3-yl]-N-[(3S,4R)-4-hydroxy-2-oxo-pyrrolidin-3-yl]propanamide (116

A 20 mL vial was charged with 3-[2-(4-cyanophenyl)-1H-indol-3-yl]propanoic acid (125 mg, 0.43 mmol), (3S,4R)-3-amino-4-hydroxy-pyrrolidin-2-one (Hydrochloride salt) (105 mg, 0.69 mmol), DMF (1000 µL), hunig's base (205 mg, 1.59 mmol), and HATU (303 mg, 0.80 mmol). The reaction was allowed to stir overnight at room temperature, and was then diluted with water (20 mL). The resulting mixture was sonicated for 5 minutes, a precipitate formed which was collected by vacuum filtration using a Buchner funnel. The solids were washed with additional water (~20 mL), allowed to air dry. Purification by reversed-phase chromatography (Column: C18. Gradient: 0-100% MeCN in water with 0.1% formic acid) afforded the product. 3-[2-(4-cyanophenyl)-1H-indol-3-yl]-N-[(3S,4R)-4-hydroxy-2-oxo-pyrrolidin-3-yl]propanamide (111 mg, 64%). $^1$H NMR (300 MHz, Methanol-$d_4$) δ 7.83 (s, 4H), 7.68 (dt, J=8.0, 1.0 Hz, 1H), 7.38 (dt, J=8.1, 1.0 Hz, 1H), 7.17 (ddd, J=8.2, 7.0, 1.2 Hz, 1H), 7.06 (ddd, J=8.0, 7.0, 1.1 Hz, 1H), 4.33 (q, J=7.5 Hz, 1H), 4.22 (d, J=7.8 Hz, 1H), 3.56 (dd, J=9.9, 7.5 Hz, 1H), 3.32-3.22 (m, 2H, obscured by solvent peak), 3.10 (dd, J=9.9, 6.8 Hz, 1H), 2.72-2.60 (m, 2H). LCMS m/z 389.23 [M+H]$^+$.

Compound 117-126

Compounds 117-126 (Table 10) were prepared by Sonagashira coupling of Building Block 9-A (either 2-iodoaniline or 2-ethynylaniline) and Building Block 9-B (an appropriate aryl alkyne or an appropriate aryl halide). The route described for the preparation of compound 116 was used in either case. Building Blocks 9-A and 9-B were obtained from commercially available sources. Intermediate 2-amino aryl alkynes (analogous to C124) were prepared by Sonagashira coupling of 2-iodoaniline and the appropriate alkyne, or by Sonagashira coupling of 2-ethynylaniline with the appropriate aryl halide. 2-Amino aryl alkynes (analogous to C124) were subjected to a one-pot intramolecular amine-alkyne cyclization and oxidative Heck coupling with butyl prop-2-enoate as described for the preparation of compound 116. The final amide formation step was performed with HATU according to standard method F.

TABLE 10

Method of Preparation, Structure and Physicochemical Properties

| Compound | Structure | Building Block 9-A; Building Block 9-B; Indole preparation method | $^1$H NMR; LCMS m/z [M + H]$^+$ |
|---|---|---|---|
| 117 | 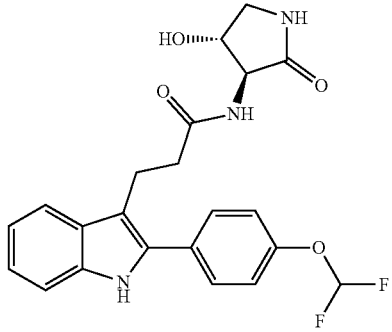 [SMILES: O=C(CCc1c(-c2ccc(OC(F)F)cc2)[nH]c2ccccc12)N[C@@H]1C(=O)NC[C@H]1O] | 2-ethynylaniline; 1-bromo-4-(difluoromethoxy)benzene; Route E | $^1$H NMR (300 MHz, CD$_3$OD) δ 7.77-7.52 (m, 3H), 7.35 (dt, J = 8.1, 1.0 Hz, 1H), 7.32-7.20 (m, 2H), 7.15-6.95 (m, 2H), 6.75 (d, J = 74.1 Hz, 1H), 4.34 (td, J = 7.6, 6.8 Hz, 1H), 4.22 (d, J = 7.7 Hz, 1H), 3.56 (dd, J = 9.9, 7.5 Hz, 1H), 3.29-3.18 (m, 2H), 3.10 (dd, J = 9.9, 6.8 Hz, 1H), 2.76-2.53 (m, 2H). LCMS m/z 430.19 [M + H]$^+$. |

TABLE 10-continued

Method of Preparation, Structure and Physicochemical Properties

| Compound | Structure | Building Block 9-A; Building Block 9-B; Indole preparation method | $^1$H NMR; LCMS m/z [M + H]$^+$ |
|---|---|---|---|
| 118 | 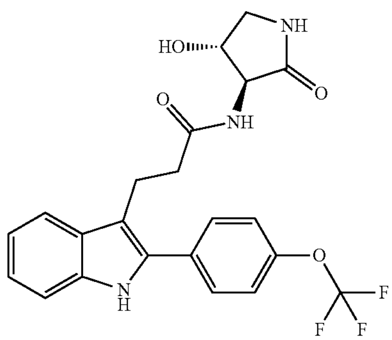 | 2-ethynylaniline; 1-bromo-4-(trifluoro-methoxy)benzene; Route E | $^1$H NMR (300 MHz, CD$_3$OD) δ 7.82-7.70 (m, 2H), 7.65 (dt, J = 7.8, 1.0 Hz, 1H), 7.38 (tt, J = 8.0, 1.0 Hz, 3H), 7.09 (dddd, J = 25.9, 8.0, 7.0, 1.2 Hz, 2H), 4.34 (td, J = 7.6, 6.8 Hz, 1H), 4.22 (d, J = 7.7 Hz, 1H), 3.56 (dd, J = 9.9, 7.6 Hz, 1H), 3.28-3.19 (m, 2H), 3.10 (dd, J = 9.9, 6.8 Hz, 1H), 2.76-2.56 (m, 2H). LCMS m/z 448.23 [M + H]$^+$. |
| 119 | 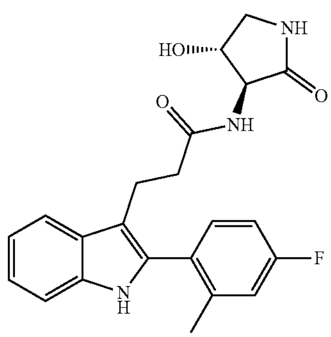 [SMILES: Cc1cc(F)ccc1-c1[nH]c2ccccc2c1CCC(=O)N[C@@H]1C(=O)NC[C@H]1O] | 2-ethynylaniline; 1-bromo-4-fluoro-2-methyl-benzene; Route E | $^1$H NMR (300 MHz, Methanol-d$_4$) δ 7.68-7.58 (m, 1H), 7.41-7.26 (m, 2H), 7.16-6.93 (m, 4H), 4.32 (td, J = 7.6, 6.8 Hz, 1H), 4.18 (d, J = 7.7 Hz, 1H), 3.54 (dd, J = 9.9, 7.6 Hz, 1H), 3.08 (dd, J = 9.9, 6.9 Hz, 1H), 3.01-2.88 (m, 2H), 2.58-2.46 (m, 2H), 2.23 (s, 3H). LCMS m/z 396.16 [M + H]$^+$. |
| 120 | 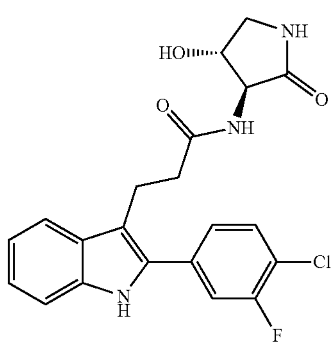 [SMILES: O=C(CCc1c(-c2ccc(Cl)c(F)c2)[nH]c2ccccc12)N[C@@H]1C(=O)NC[C@H]1O] | 2-ethynylaniline; 4-bromo-1-chloro-2-fluoro-benzene; Route E | $^1$H NMR (300 MHz, CD$_3$OD) δ 7.66 (dt, J = 7.7, 1.0 Hz, 1H), 7.62-7.43 (m, 3H), 7.36 (dt, J = 8.0, 0.9 Hz, 1H), 7.14 (ddd, J = 8.2, 7.0, 1.2 Hz, 1H), 7.05 (ddd, J = 8.0, 7.0, 1.1 Hz, 1H), 4.32 (td, J = 7.6, 6.8 Hz, 1H), 4.21 (d, J = 7.7 Hz, 1H), 3.55 (dd, J = 9.9, 7.5 Hz, 1H), 3.29-3.19 (m, 2H), 3.10 (dd, J = 9.9, 6.8 Hz, 1H), 2.76-2.49 (m, 2H). LCMS m/z 416.19 [M + H]$^+$ |
| 121 | 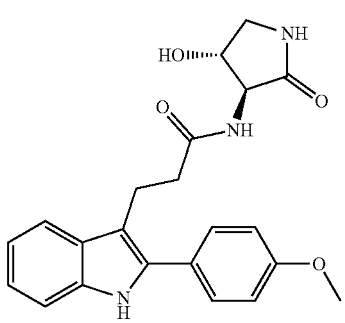 [SMILES: COc1ccc(-c2[nH]c3ccccc3c2CCC(=O)N[C@@H]2C(=O)NC[C@H]2O)cc1] | 2-iodoanilane; 1-ethynyl-4-methoxy-benzene; Route E | $^1$H NMR (300 MHz, CD$_3$OD) δ 7.69-7.46 (m, 3H), 7.41-7.24 (m, 1H), 7.15-6.88 (m, 4H), 4.34 (td, J = 7.6, 6.8 Hz, 1H), 4.21 (d, J = 7.6 Hz, 1H), 3.84 (s, 3H), 3.56 (dd, J = 9.9, 7.5 Hz, 1H), 3.28-3.15 (m, 2H), 3.10 (dd, J = 9.9, 6.8 Hz, 1H), 2.75-2.49 (m, 2H) LCMS m/z 394.18 [M + H]$^+$. |

TABLE 10-continued

Method of Preparation, Structure and Physicochemical Properties

| Compound | Structure | Building Block 9-A; Building Block 9-B; Indole preparation method | $^1$H NMR; LCMS m/z [M + H]$^+$ |
|---|---|---|---|
| 122 | 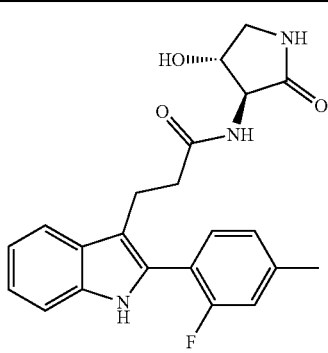 | 2-ethynylaniline; 1-bromo-2-fluoro-4-methyl-benzene; Route E | $^1$H NMR (300 MHz, CD$_3$OD) δ 7.64 (ddd, J = 7.8, 1.3, 0.8 Hz, 1H), 7.42 (t, J = 7.8 Hz, 1H), 7.34 (dt, J = 8.1, 1.0 Hz, 1H), 7.23-6.88 (m, 4H), 4.34 (td, J = 7.6, 6.8 Hz, 1H), 4.19 (d, J = 7.6 Hz, 1H), 3.55 (dd, J = 9.9, 7.6 Hz, 1H), 3.22-2.98 (m, 3H), 2.71-2.52 (m, 2H), 2.41 (d, J = 0.7 Hz, 3H). LCMS m/z 396.16 [M + H]$^+$. |
| 123 | 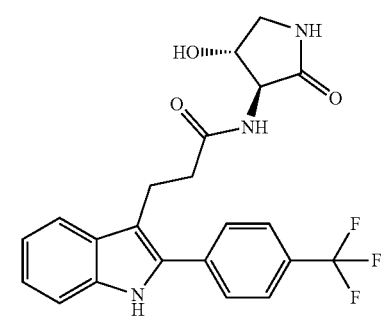 [SMILES: O=C(CCc1c(-c2ccc(C(F)(F)F)cc2)[nH]c2ccccc12)N[C@@H]1C(=O)NC[C@H]1O] | 2-iodoaniline; 1-ethynyl-4-(trifluoromethyl)benzene; Route E | $^1$H NMR (300 MHz, Methanol-d$_4$) δ 7.89-7.72 (m, 4H), 7.68 (dt, J = 7.9, 1.1 Hz, 1H), 7.38 (dt, J = 8.1, 1.0 Hz, 1H), 7.16 (ddd, J = 8.2, 7.0, 1.2 Hz, 1H), 7.06 (ddd, J = 8.0, 7.0, 1.1 Hz, 1H), 4.34 (td, J = 7.6, 6.8 Hz, 1H), 4.22 (d, J = 7.7 Hz, 1H), 3.55 (dd, J = 10.0, 7.5 Hz, 1H), 3.32-3.22 (m, 1H), 3.10 (dd, J = 9.9, 6.8 Hz, 1H), 2.72-2.60 (m, 2H). LCMS m/z 432.21 [M + H]$^+$. |
| 124 | 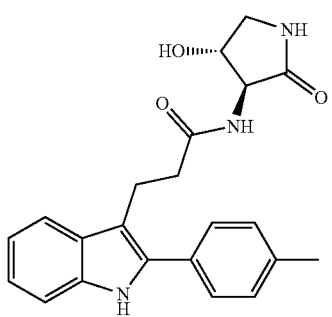 | 2-iodoaniline; 1-ethynyl-4-methyl-benzene; Route E | $^1$H NMR (300 MHz, Methanol-d$_4$) δ 7.64 (ddd, J = 7.8, 1.3, 0.8 Hz, 1H), 7.42 (t, J = 7.8 Hz, 1H), 7.34 (dt, J = 8.0, 1.0 Hz, 1H), 7.17-6.97 (m, 5H), 4.34 (td, J = 7.6, 6.8 Hz, 1H), 4.19 (d, J = 7.6 Hz, 1H), 3.55 (dd, J = 9.9, 7.6 Hz, 1H), 3.15-3.03 (m, 3H), 2.66-2.54 (m, 2H), 2.41 (d, J = 0.8 Hz, 3H). LCMS m/z 378.16 [M + H]$^+$. |
| 125 | 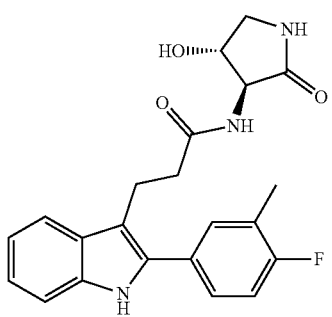 | 4-bromo-1-fluoro-2-methyl-benzene; Route E | $^1$H NMR (300 MHz, CD$_3$OD) δ 7.62 (dd, J = 7.7, 1.2 Hz, 1H), 7.58-7.39 (m, 2H), 7.34 (dt, J = 8.1, 1.1 Hz, 1H), 7.23-6.92 (m, 3H), 4.42-4.26 (m, 1H), 4.26-4.14 (m, 1H), 3.55 (dd, J = 9.9, 7.5 Hz, 1H), 3.27-3.17 (m, 2H), 3.17-3.01 (m, 1H), 2.75-2.50 (m, 2H), 2.35 (d, J = 2.0 Hz, 3H). LCMS m/z 396.11 [M + H]$^+$. |

TABLE 10-continued

Method of Preparation, Structure and Physicochemical Properties

| Compound | Structure | Building Block 9-A; Building Block 9-B; Indole preparation method | ¹H NMR; LCMS m/z [M + H]⁺ |
|---|---|---|---|
| 126 | 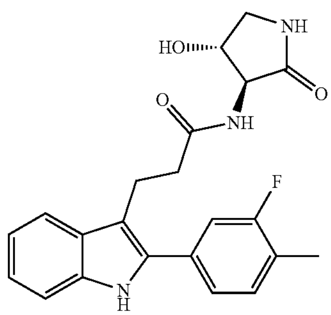 [SMILES: Cc1ccc(-c2[nH]c3ccccc3c2CCC(=O)N[C@@H]2C(=O)NC[C@H]2O)cc1F] | 2-ethynylaniline; 2-fluoro-4-iodo-1-methyl-benzene; Route E | ¹H NMR (300 MHz, CD₃OD) δ 7.63 (dt, J = 7.8, 1.0 Hz, 1H), 7.46-7.24 (m, 4H), 7.07 (dddd, J = 25.0, 8.0, 7.0, 1.2 Hz, 2H), 4.33 (td, J = 7.6, 6.7 Hz, 1H), 4.21 (d, J = 7.7 Hz, 1H), 3.55 (dd, J = 10.0, 7.5 Hz, 1H), 3.28-3.17 (m, 2H), 3.10 (dd, J = 9.9, 6.8 Hz, 1H), 2.72-2.53 (m, 2H), 2.31 (d, J = 1.9 Hz, 3H). LCMS m/z 396.2 [M + H]⁺. |

Compound 127

3-[2-(3,5-difluorophenyl)-1H-indol-3-yl]-N-[(3S,4R)-4-hydroxy-2-oxo-pyrrolidin-3-yl]propanamide (127

Compound 128

3-[2-(4-chlorophenyl)-1H-indol-3-yl]-N-[(3S,4R)-4-hydroxy-2-oxo-pyrrolidin-3-yl]propanamide (128

Compound 127 was prepared from indole and (3,5-difluorophenyl)boronic acid using indole preparation route C, then amide bond formation with S2 using standard method F (HATU). ¹H NMR (400 MHz, CD₃OD) δ 7.67 (dt, J=8.0, 1.0 Hz, 1H), 7.37 (dt, J=8.1, 0.9 Hz, 1H), 7.33-7.21 (m, 2H), 7.16 (ddd, J=8.1, 7.0, 1.1 Hz, 1H), 7.06 (ddd, J=8.1, 7.0, 1.0 Hz, 1H), 6.95 (tt, J=9.1, 2.3 Hz, 1H), 4.33 (td, J=7.6, 6.8 Hz, 1H), 4.22 (d, J=7.7 Hz, 1H), 3.56 (dd, J=9.9, 7.6 Hz, 1H), 3.30-3.21 (m, 2H), 3.10 (dd, J=9.9, 6.8 Hz, 1H), 2.66 (ddd, J=9.7, 6.5, 1.1 Hz, 2H). LCMS m/z 400.14 [M+H]⁺.

Compound 128 was prepared from indole and (4-chlorophenyl)boronic acid using indole preparation route C, then amide bond formation with S2 using standard method F (HATU). ¹H NMR (300 MHz, DMSO) δ 11.23 (s, 1H), 8.22 (d, J=7.5 Hz, 1H), 7.76 (s, 1H), 7.72-7.50 (m, 4H), 7.36 (d, J=8.0 Hz, 1H), 7.23-6.92 (m, 2H), 5.47 (s, 1H), 4.11 (p, J=7.7 Hz, 2H), 3.21-2.98 (m, 2H), 2.91 (dd, J=9.4, 6.7 Hz, 1H). LCMS m/z 398.09 [M+H]⁺.

Compound 129

3-[2-(3,4-difluorophenyl)-1H-indol-3-yl]-N-[(3S,4R)-4-hydroxy-2-oxo-pyrrolidin-3-yl]propanamide (129)

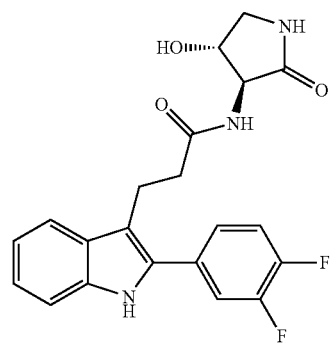 [SMILES: O=C(CCc1c(-c2ccc(F)c(F)c2)[nH]c2ccccc12)N[C@@H]1C(=O)NC[C@H]1O]

Compound 129 was prepared from indole and (3,4-difluorophenyl)boronic acid using indole preparation route C, then amide bond formation with S2 using standard method F (HATU). $^1$H NMR (300 MHz, DMSO) δ 11.25 (s, 1H), 8.23 (d, J=7.5 Hz, 1H), 7.75 (d, J=7.2 Hz, 1H), 7.73-7.66 (m, 1H), 7.66-7.57 (m, 1H), 7.57-7.43 (m, 1H), 7.40-7.32 (m, 1H), 7.14 (ddd, J=8.1, 7.0, 1.2 Hz, 1H), 7.04 (ddd, J=7.9, 7.0, 1.1 Hz, 1H), 5.47 (d, J=5.0 Hz, 1H), 4.33-3.92 (m, 2H), 3.37 (t, J=7.7 Hz, 3H), 3.07 (dd, J=9.8, 6.6 Hz, 2H), 2.91 (dd, J=9.7, 6.4 Hz, 1H). LCMS m/z 400.08 [M+H]$^+$

Compound 130

2-[[2-(4-fluorophenyl)-1H-indol-3-yl]sulfanyl]-N-[(3S,4R)-4-hydroxy-2-oxo-pyrrolidin-3-yl]acetamide (130)

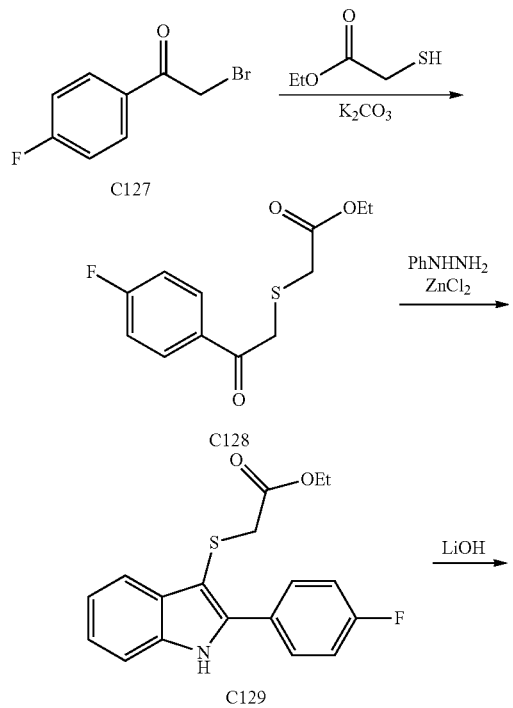

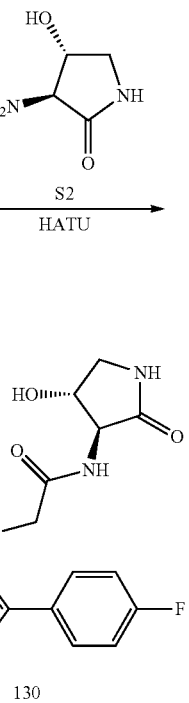

Step 1. Synthesis of Ethyl 2-[2-(4-fluorophenyl)-2-oxo-ethyl]sulfanylacetate (C128)

To a stirred solution of ethyl 2-sulfanylacetate (297.00 mg, 0.27 mL, 0.003 mol) in Acetone (10 mL) was added K$_2$CO$_3$ (511.4 mg, 0.004 mol) at room temperature, then stirred for 30 min. Then 2-bromo-1-(4-fluorophenyl)ethanone (500 mg, 0.002 mol) was added at room temperature. Then the reaction mixture was heated to 65° C., maintaining the temperature for 1 h. The reaction mixture was quenched with ice cold water, extracted with Ethyl acetate. The organic layer was dried over Na$_2$SO$_4$, filtered and concentrated, to afford ethyl 2-[2-(4-fluorophenyl)-2-oxo-ethyl]sulfanylacetate (520 mg, 81%). $^1$H NMR (400 MHz, CDCl$_3$) δ 8.02-7.99 (m, 2H), 7.17-7.13 (m, 2H), 4.19 (q, J=7.2 Hz, 2H), 4.00 (s, 2H), 3.32 (s, 2H), 1.30-1.25 (m, 3H). LCMS m/z 257.21 [M+H]$^+$.

Step 2. Synthesis of Ethyl 2-[[2-(4-fluorophenyl)-1H-indol-3-yl]sulfanyl]acetate (C129)

To a stirred solution of ethyl 2-[2-(4-fluorophenyl)-2-oxo-ethyl]sulfanylacetate (520 mg, 0.002 mol) in AcOH (5.2 mL) were added ZnCl$_2$ (177.17 mg, 0.0013 mol) and phenylhydrazine (227 mg, 0.21 mL, 0.002 mol) at room temperature. Then reaction mixture was heated to 125° C., maintaining the temperature for 16 h. Then the reaction mixture was quenched with saturated NaHCO$_3$ solution at 0° C. The mixture was then extracted with ethyl acetate. The organic layer was isolated and dried over Na$_2$SO$_4$, then filtered and concentrated to afford ethyl 2-[[2-(4-fluorophenyl)-1H-indol-3-yl]sulfanyl]acetate (590 mg, 72%). LCMS m/z 330.25 [M+H]$^+$.

Step 3. Synthesis of 2-[[2-(4-fluorophenyl)-1H-indol-3-yl]sulfanyl]acetic Acid (C130)

To a stirred solution of ethyl 2-[[2-(4-fluorophenyl)-1H-indol-3-yl]sulfanyl]acetate (590 mg, 0.0014 mol) in THF (5.9 mL) and Water (5.9 mL) was added LiOH (hydrate) (587 mg, 0.014 mol) at room temperature. Then reaction mixture was stirred at room temperature for 16 h. The reaction was evaporated, diluted with ice cold water and extracted with ethyl acetate. The aqueous later was washed with ethyl acetate (2×20 mL), acidified with aq. 10% HCl, and then extracted with Ethyl acetate. The organic layer was dried on $Na_2SO_4$, filtered and concentrated to afford 2-[[2-(4-fluorophenyl)-1H-indol-3-yl]sulfanyl]acetic acid (240 mg, 57%). $^1$H NMR (400 MHz, DMSO-$d_6$) δ 12.21 (s, 1H), 11.79 (s, 1H), 8.03-7.99 (m, 2H), 7.66 (d, J=8.0 Hz, 1H), 7.43-7.34 (m, 3H), 7.30-7.16 (m, 1H), 7.14-7.10 (m, 1H), 3.38 (s, 2H). LCMS m/z 302.13 [M+H]$^+$.

Step 4. Synthesis of 2-[[2-(4-fluorophenyl)-1H-indol-3-yl]sulfanyl]-N-[(3S,4R)-4-hydroxy-2-oxo-pyrrolidin-3-yl]acetamide (130

A 20 mL vial was charged with a magnetic stir bar, 2-[[2-(4-fluorophenyl)-1H-indol-3-yl]sulfanyl]acetic acid (150 mg, 0.5 mmol), (3S,4R)-3-amino-4-hydroxy-pyrrolidin-2-one (Hydrochloride salt) (105 mg, 0.69 mmol), DMF (1000 μL), hunig's base (205 mg, 1.59 mmol), and HATU (303 mg, 0.80 mmol). The reaction was allowed to stir overnight at room temperature, and then diluted with water (20 mL). The resulting mixture was sonicated for 5 minutes, a precipitate formed and was collected by vacuum filtration using a Buchner funnel. The solids were washed with additional water (~20 mL), allowed to air dry, and then collected. Purification by reversed-phase chromatography (Column: C18. Gradient: 0-100% MeCN in water with 0.1% formic acid) afforded the product. 2-[[2-(4-fluorophenyl)-1H-indol-3-yl]sulfanyl]-N-[(3S,4R)-4-hydroxy-2-oxo-pyrrolidin-3-yl]acetamide (145 mg, 72%). $^1$H NMR (400 MHz, Methanol-$d_4$) δ 8.05-7.95 (m, 2H), 7.81-7.74 (m, 1H), 7.44-7.37 (m, 1H), 7.29-7.10 (m, 5H), 4.08-3.84 (m, 3H), 3.40 (d, J=1.8 Hz, 3H), 3.01 (dd, J=10.0, 6.3 Hz, 1H). LCMS m/z 400.16 [M+H]$^+$.

Compound 131

3-[2-[4-(difluoromethyl)phenyl]-1H-indol-3-yl]-N-[(3S,4R)-4-hydroxy-2-oxo-pyrrolidin-3-yl]propanamide (131

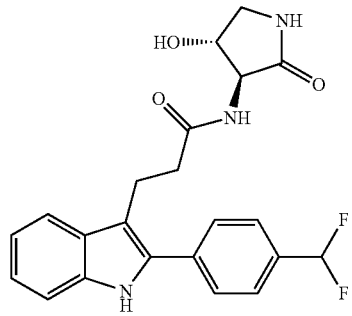 [SMILES: O=C(CCc1c(-c2ccc(C(F)F)cc2)[nH]c2ccccc12)N[C@@H]1C(=O)NC[C@H]1O]

Compound 131 was prepared from 2-ethynylaniline and 1-bromo-4-(difluoromethyl)benzene using indole preparation route E, followed by amide coupling of S2 using standard method F. $^1$H NMR (300 MHz, CD$_3$OD) δ 7.77 (d, J=8.4 Hz, 2H), 7.73-7.60 (m, 3H), 7.37 (dt, J=8.0, 1.0 Hz, 1H), 7.14 (ddd, J=8.1, 7.0, 1.2 Hz, 1H), 7.10-6.98 (m, 1H), 6.72 (d, J=56.2 Hz, 1H), 4.34 (td, J=7.6, 6.8 Hz, 1H), 4.22 (d, J=7.7 Hz, 1H), 3.56 (dd, J=9.9, 7.5 Hz, 1H), 3.30-3.21 (m, 4H), 3.10 (dd, J=9.9, 6.8 Hz, 1H), 2.75-2.54 (m, 2H). LCMS m/z 414.21 [M+H]$^+$.

Compound 132

3-[5-fluoro-2-phenyl-7-(trifluoromethyl)-1H-indol-3-yl]-N-[(3S,4R)-4-hydroxy-2-oxo-pyrrolidin-3-yl]propanamide (132

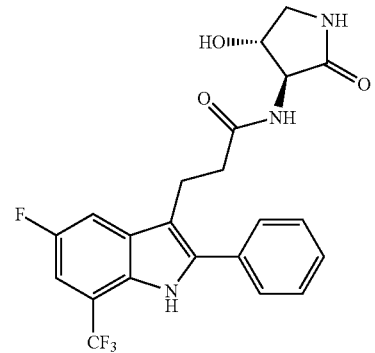 [SMILES: O=C(CCc1c(-c2ccccc2)[nH]c2c(C(F)(F)F)cc(F)cc12)N[C@@H]1C(=O)NC[C@H]1O]

Compound 132 was prepared from 2-bromo-4-fluoro-6-(trifluoromethyl)aniline and ethynylbenzene using indole preparation route A, followed by amide coupling of S2 using standard method F. $^1$H NMR (300 MHz, CD$_3$OD) δ 7.76-7.57 (m, 2H), 7.58-7.46 (m, 2H), 7.49-7.38 (m, 1H), 7.22 (dd, J=9.3, 2.5 Hz, 1H), 4.43-4.26 (m, 1H), 4.22 (d, J=7.8 Hz, 1H), 3.57 (dd, J=9.9, 7.5 Hz, 1H), 3.24-3.03 (m, 3H), 2.69-2.49 (m, 2H). LCMS m/z 450.08 [M+H]$^+$.

Compound 133

3-[2-(4-fluorophenyl)-1H-indol-3-yl]-N-[(3R,4R)-4-hydroxy-2-oxo-pyrrolidin-3-yl]propanamide (133

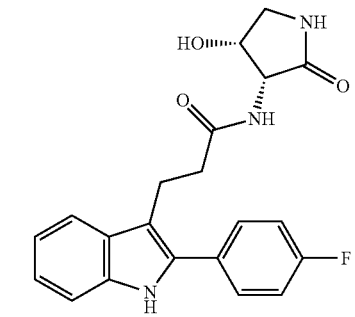 [SMILES: O=C(CCc1c(-c2ccc(F)cc2)[nH]c2ccccc12)N[C@H]1C(=O)NC[C@H]1O]

Compound 133 was prepared from 3-[2-(4-fluorophenyl)-1H-indol-3-yl]propanoic acid C101 and S10 by amide coupling using standard method G (CDMT), as described for the preparation of compound 2. 3-[2-(4-fluorophenyl)-1H-indol-3-yl]-N-[(3R,4R)-4-hydroxy-2-oxo-pyrrolidin-3-yl]propanamide (147 mg, 79%). $^1$H NMR (400 MHz, Methanol-$d_4$) δ 7.69-7.62 (m, 3H), 7.34 (dt, J=8.1, 1.0 Hz, 1H), 7.26-7.17 (m, 2H), 7.11 (ddd, J=8.1, 7.0, 1.2 Hz, 1H), 7.03 (ddd, J=8.0, 7.0, 1.1 Hz, 1H), 4.66 (d, J=5.0 Hz, 1H), 4.37

(dd, J=5.1, 3.9 Hz, 1H), 3.59 (dd, J=11.3, 4.0 Hz, 1H), 3.27-3.19 (m, 3H), 2.78-2.64 (m, 2H). LCMS m/z 382.12 [M+H]⁺.

Compound 134

3-[2-(4-fluorophenyl)-1H-indol-3-yl]-N-[(3R,4S)-4-hydroxy-2-oxo-pyrrolidin-3-yl]propanamide (134

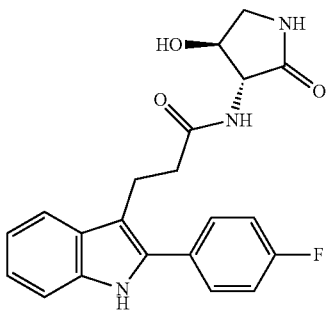 [SMILES: O=C(CCc1c(-c2ccc(F)cc2)[nH]c2ccccc12)N[C@H]1C(=O)NC[C@@H]1O]

Compound 134 was prepared from 3-[2-(4-fluorophenyl)-1H-indol-3-yl]propanoic acid C101 and S9 by amide coupling using standard method G, as described for the preparation of compound 2. 3-[2-(4-fluorophenyl)-1H-indol-3-yl]-N-[(3R,4S)-4-hydroxy-2-oxo-pyrrolidin-3-yl]propanamide (2.506 g, 99%). ¹H NMR (400 MHz, Methanol-d₄) δ 7.69-7.60 (m, 3H), 7.35 (dt, J=8.1, 0.9 Hz, 1H), 7.26-7.17 (m, 2H), 7.12 (ddd, J=8.1, 7.0, 1.2 Hz, 1H), 7.04 (ddd, J=8.0, 7.0, 1.1 Hz, 1H), 4.34 (td, J=7.6, 6.8 Hz, 1H), 4.22 (d, J=7.8 Hz, 1H), 3.56 (dd, J=9.9, 7.6 Hz, 1H), 3.27-3.17 (m, 2H), 3.10 (dd, J=9.9, 6.9 Hz, 1H), 2.70-2.59 (m, 2H). LCMS m/z 382.07 [M+H]⁺.

Compound 135

3-[2-(4-fluorophenyl)-1H-indol-3-yl]-N-[(3S,4S)-4-hydroxy-2-oxo-pyrrolidin-3-yl]propanamide (135

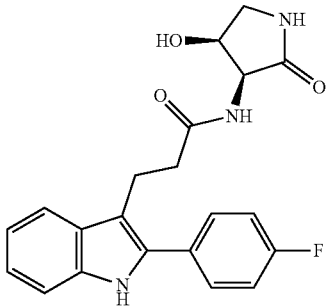 [SMILES: O=C(CCc1c(-c2ccc(F)cc2)[nH]c2ccccc12)N[C@@H]1C(=O)NC[C@@H]1O]

Compound 135 was prepared from 3-[2-(4-fluorophenyl)-1H-indol-3-yl]propanoic acid C101 and S1 by amide coupling using standard method G, as described for the preparation of compound 2. 3-[2-(4-fluorophenyl)-1H-indol-3-yl]-N-[(3S,4S)-4-hydroxy-2-oxo-pyrrolidin-3-yl]propanamide (155 mg, 82%). ¹H NMR (400 MHz, Methanol-d₄) δ 7.70-7.61 (m, 3H), 7.34 (dt, J=8.1, 0.9 Hz, 1H), 7.25-7.18 (m, 2H), 7.11 (ddd, J=8.1, 7.1, 1.2 Hz, 1H), 7.03 (ddd, J=8.0, 7.0, 1.1 Hz, 1H), 4.66 (d, J=5.1 Hz, 1H), 4.37 (dd, J=5.0, 3.9 Hz, 1H), 3.59 (dd, J=11.3, 4.0 Hz, 1H), 3.27-3.18 (m, 3H), 2.79-2.64 (m, 2H). LCMS m/z 382.12 [M+H]⁺.

Example 2. Solid State NMR Experimental

Bruker-Biospin 400 MHz wide-bore spectrometer equipped with Bruker-Biospin 4 mm HFX probe was used. Samples were packed into 4 mm ZrO₂ rotors and spun under Magic Angle Spinning (MAS) condition with spinning speed typically set to 12.5 kHz. The proton relaxation time was measured using ¹H MAS T₁ saturation recovery relaxation experiment in order to set up proper recycle delay of the ¹³C cross-polarization (CP) MAS experiment. The fluorine relaxation time was measured using ¹⁹F MAS T₁ saturation recovery relaxation experiment in order to set up proper recycle delay of the ¹⁹F MAS experiment. The CP contact time of carbon CPMAS experiment was set to 2 ms. A CP proton pulse with linear ramp (from 50% to 100%) was employed. The carbon Hartmann-Hahn match was optimized on external reference sample (glycine). Both carbon and fluorine spectra were recorded with proton decoupling using TPPM15 decoupling sequence with the field strength of approximately 100 kHz.

X-Ray Powder Diffraction for Forms of Compound 2

Form A

X-Ray Powder Diffraction

The powder X-ray powder diffraction diffractogram of Form A (FIG. 1) was acquired at room temperature using the PANalytical Empyrean diffractometer equipped with PIXcel 1D detector. The peaks are listed in table 11 below.

TABLE 11

Peak list from powder X-ray powder diffraction diffractogram of Form A

| Angle (Degrees 2-Theta ± 0.2) | Intensity % |
|---|---|
| 26.3 | 100.0 |
| 13.2 | 76.6 |
| 9.5 | 53.9 |
| 26.7 | 40.9 |
| 19.8 | 38.7 |
| 14.4 | 32.5 |
| 19.2 | 30.5 |
| 28.6 | 25.0 |
| 19.5 | 23.5 |
| 18.8 | 22.3 |
| 20.7 | 21.2 |
| 21.4 | 17.7 |
| 17.7 | 17.6 |
| 24.0 | 16.7 |
| 22.9 | 16.4 |
| 21.7 | 15.7 |
| 27.7 | 12.7 |
| 27.1 | 12.4 |
| 16.1 | 12.0 |
| 29.1 | 11.0 |
| 29.5 | 10.4 |
| 23.3 | 10.3 |
| 22.4 | 10.1 |

Solid State NMR

Figure 2:
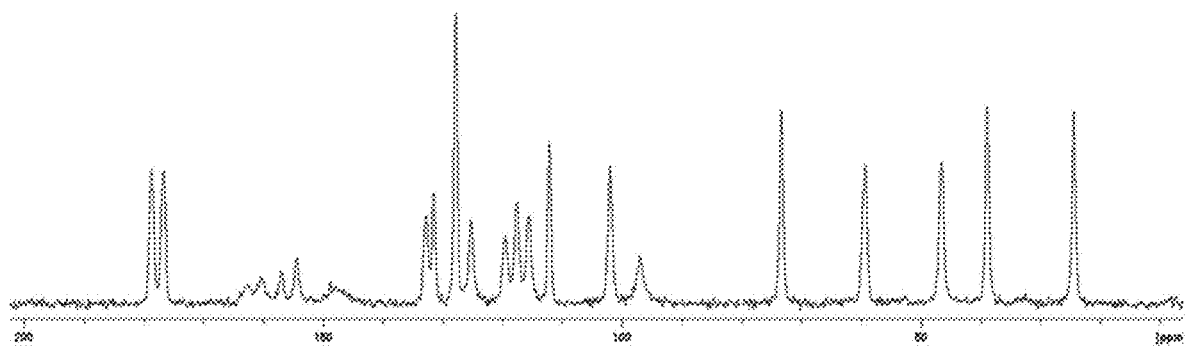
FIG. 2 depicts a solid state $^{13}$C NMR spectrum for Form A of Compound 2.

The ¹³C CPMAS of Form A (FIG. 2) was acquired at 275K with the following parameters: 12.5 kHz spinning; ref. adamantane 29.5 ppm. The peaks are listed in table 12 below. The carbon peaks highlighted in bold are unique for Form A with respect to following forms: Hydrate A, Hydrate C and amorphous form.

TABLE 12

Peak list from $^{13}$C CPMAS of Form A

| Chem Shift [ppm] | Intensity [rel] |
|---|---|
| 178.7 | 46.1 |
| 176.7 | 46 |
| 162.5 | 6.6 |
| 160.3 | 9.6 |
| 157.0 | 11.4 |
| 154.4 | 16.2 |
| 148.8 | 7.6 |
| 132.8 | 30.8 |
| 131.5 | 39.0 |
| 127.8 | 100.0 |
| 125.2 | 28.7 |
| 119.4 | 23.3 |
| 117.5 | 35.0 |
| 115.5 | 30.8 |
| 112.1 | 55.8 |
| 102.0 | 47.5 |
| 97.0 | 16.7 |
| 73.3 | 67.0 |
| 59.3 | 48.0 |
| 46.6 | 49.1 |
| 38.9 | 68.3 |
| 24.4 | 66.5 |

Figure 3:
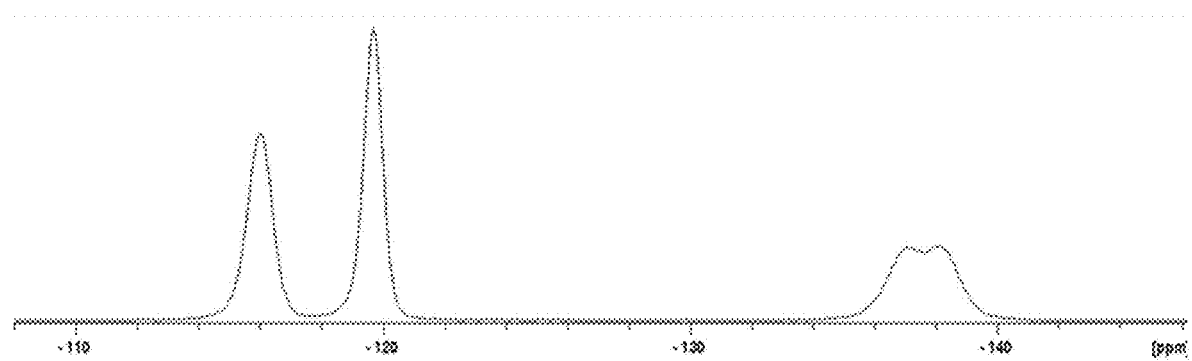
FIG. 3 depicts a $^{19}$F MAS (magnetic angle spinning) spectrum for Form A of Compound 2.

The $^{19}$F MAS of Form A (FIG. 3) was acquired at 275K with the following parameters: 12.5 kHz spinning; ref. adamantane 29.5 ppm. The peaks are listed in table 13 below. The fluorine peaks highlighted in bold are unique for Form A with respect to following forms: Hydrate A, Hydrae B, Hydrate C and amorphous form.

TABLE 13

Peak list from $^{19}$F MAS of Form A

| Chem Shift [ppm] | Intensity [rel] |
|---|---|
| −116.0 | 8 |
| −119.7 | 12.5 |
| −137.1 | 3.2 |
| −138.1 | 3.2 |

Thermogravimetric Analysis

Figure 4:
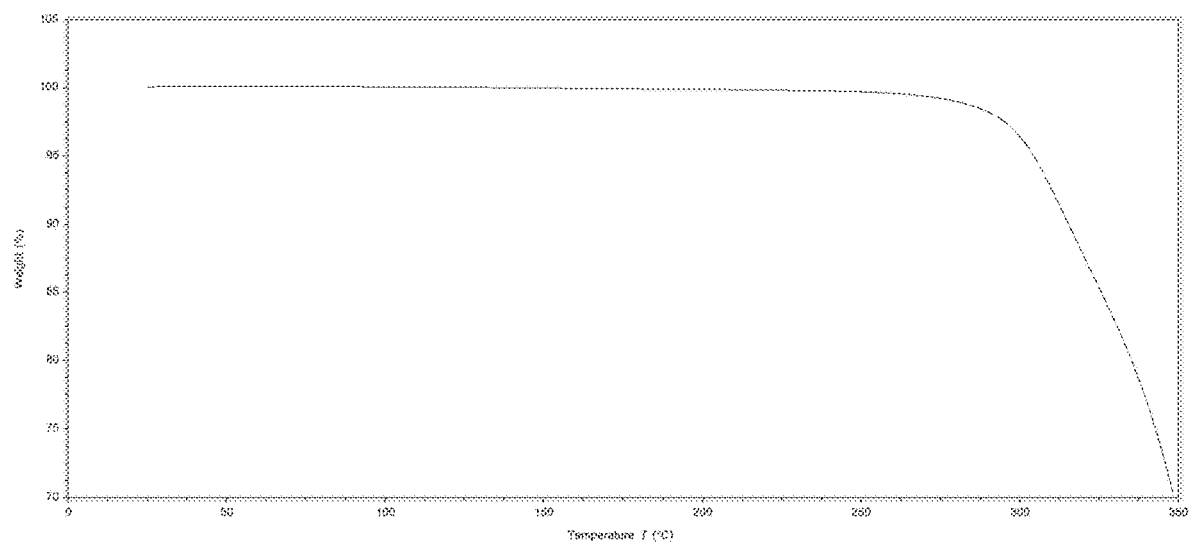
FIG. 4 depicts a TGA thermogram of Form A of Compound 2.

Thermal gravimetric analysis of Form A was measured using the TA Instruments Q5000 TGA. The TGA thermogram (FIG. 4) shows negligible weight loss from ambient temperature up until thermal degradation.

Differential Scanning Calorimetry Analysis

The melting point of Form A was measured using the TA Instruments Discovery DSC. The thermogram (FIG. 5) shows a melting onset of 200° C. with a peak at 202° C.

IR Spectroscopy

Figure 6:
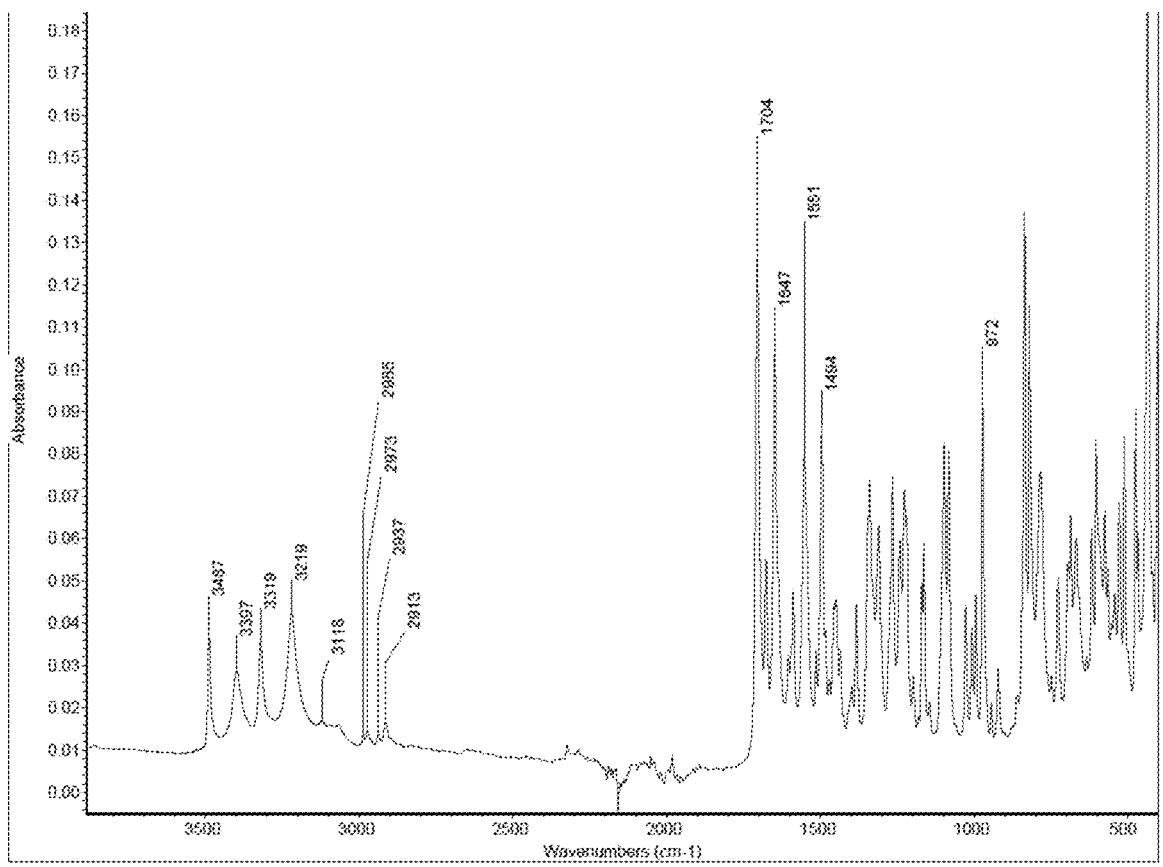
FIG. 6 depicts an IR spectrum of Form A of Compound 2.

The IR spectrum (FIG. 6) of Form A was collected using Thermo Scientific Nicolet iS50 Spectrometer equipped with a diamond ATR sampling accessory. The peaks are listed in table 14 below. The fluorine peaks highlighted in bold are unique for Form A with respect to following forms: Hydrate A, Hydrate B, Hydrate C and amorphous form.

TABLE 14

Frequency list from IR Spectrum of Form A

| Frequency (cm$^{-1}$) | Moiety | Vibration |
|---|---|---|
| 3487 | OH | Stretch |
| 3397, 3319, 3219 | NH | Stretch |
| 2985, 2973, 2937, 2913 | Aliphatic CH | Stretch |
| 3118 | Aromatic CH | Stretch |
| 1704, 1647 | Amide CO | Stretch |
| 1551, 1494 | Aromatic and heteroaromatic ring | Stretch |
| 972 | Aliphatic CO | Stretch |

Hydrate Form A

X-Ray Powder Diffraction

X-ray powder diffraction (XRPD) spectra were recorded at room temperature in transmission mode using a PANalytical Empyrean system equipped with a sealed tube source and a PIXcel 1D Medipix-3 detector (Malvern PANalytical Inc, Westborough, Massachusetts). The X-Ray generator operated at a voltage of 45 kV and a current of 40 mA with copper radiation (1.54060 Å). The powder sample was placed on a 96 well sample holder with mylar film and loaded into the instrument. The sample was scanned over the range of about 3° to about 40° 2θ with a step size of 0.0131303° and 49 s per step.

The powder X-ray powder diffraction diffractogram of Hydrate Form A (FIG. 7) was acquired at room temperature using the PANalytical Empyrean diffractometer equipped with PIXcel 1D detector. The peaks are listed in Table 15 below.

TABLE 15

Peak list from powder X-ray powder diffraction diffractogram of Hydrate Form A

| Angle (Degrees 2-Theta ± 0.2) | Intensity % |
|---|---|
| 25.5 | 100.0 |
| 25.4 | 49.5 |
| 12.2 | 38.5 |
| 24.2 | 30.7 |
| 19.1 | 30.4 |
| 19.0 | 23.5 |
| 22.7 | 22.4 |
| 19.6 | 17.9 |
| 20.2 | 15.9 |
| 18.3 | 14.1 |
| 27.2 | 13.6 |
| 12.4 | 12.6 |
| 19.9 | 12.5 |
| 6.2 | 11.7 |

Solid State NMR

Figure 8:
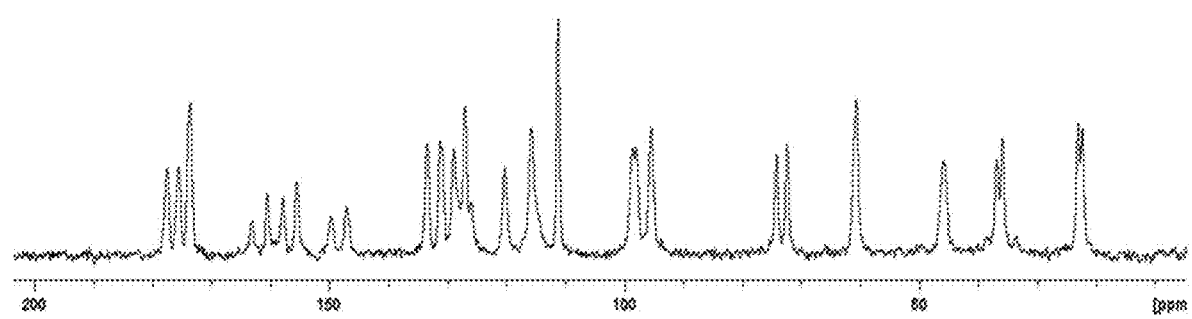
FIG. 8 depicts a solid state $^{13}$C NMR spectrum for Hydrate Form A of Compound 2.

The $^{13}$C CPMAS of Hydrate Form A (FIG. 8) was acquired at 275K with the following parameters: 12.5 kHz spinning; ref. adamantane 29.5 ppm. The peaks are listed in Table 16 below. The carbon peaks highlighted in bold are unique for Hydrate Form A with respect to following forms: Hydrate A, Hydrate C and amorphous form.

TABLE 16

Peak list from $^{13}$C CPMAS of Hydrate Form A

| Chem Shift [ppm] | Intensity [ref] |
|---|---|
| 177.5 | 37.1 |
| 175.4 | 37.7 |
| 173.5 | 64.4 |
| 163.0 | 14.5 |
| 160.4 | 25.8 |
| 157.7 | 24.6 |
| 155.5 | 31.6 |
| 149.7 | 16.0 |
| 146.9 | 20.3 |
| 133.4 | 47.1 |
| 131.2 | 48.9 |
| 128.9 | 45.4 |
| 126.9 | 62.9 |
| 125.8 | 22.7 |
| 120.2 | 37.3 |
| 115.7 | 54.1 |
| 111.1 | 100.0 |
| 98.5 | 45.6 |
| 97.9 | 45.6 |
| 95.4 | 54.3 |
| 74.1 | 42.7 |
| 72.3 | 47.6 |
| 60.6 | 66.2 |
| 45.9 | 40.3 |
| 36.9 | 40.7 |
| 35.9 | 49.2 |
| 33.5 | 8.1 |
| 23.0 | 56.2 |
| 22.3 | 53.9 |

Figure 9:
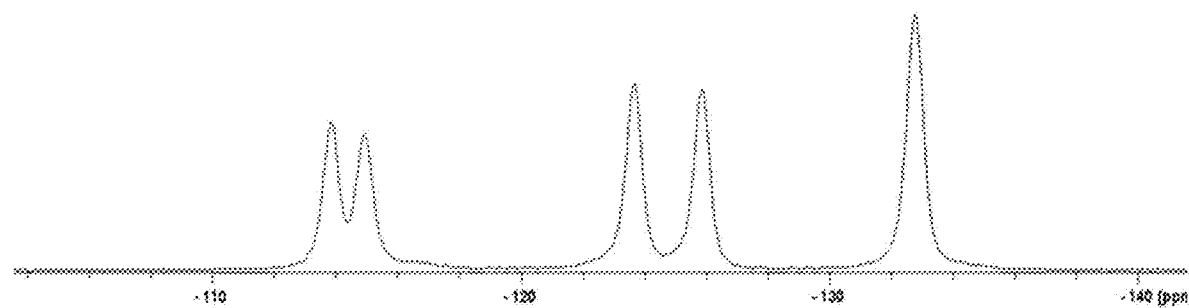
FIG. 9 depicts a $^{19}$F MAS (magnetic angle spinning) spectrum for Hydrate Form A of Compound 2.

The $^{19}$F MAS of Hydrate Form A (FIG. 9) was acquired at 275K with the following parameters: 12.5 kHz spinning; ref. adamantane 29.5 ppm. The peaks are listed in table 17 below. The fluorine peaks highlighted in bold are unique for Hydrate Form A with respect to following forms: Hydrate A, Hydrate B, Hydrate C and amorphous form.

TABLE 17

Peak list from $^{19}$F MAS of Hydrate Form A

| Chem Shift [ppm] | Intensity [rel] |
|---|---|
| −113.8 | 7.2 |
| −114.9 | 6.7 |
| −123.7 | 9.1 |
| −125.8 | 8.8 |
| −132.8 | 12.5 |

Thermogravimetric Analysis

Figure 10:
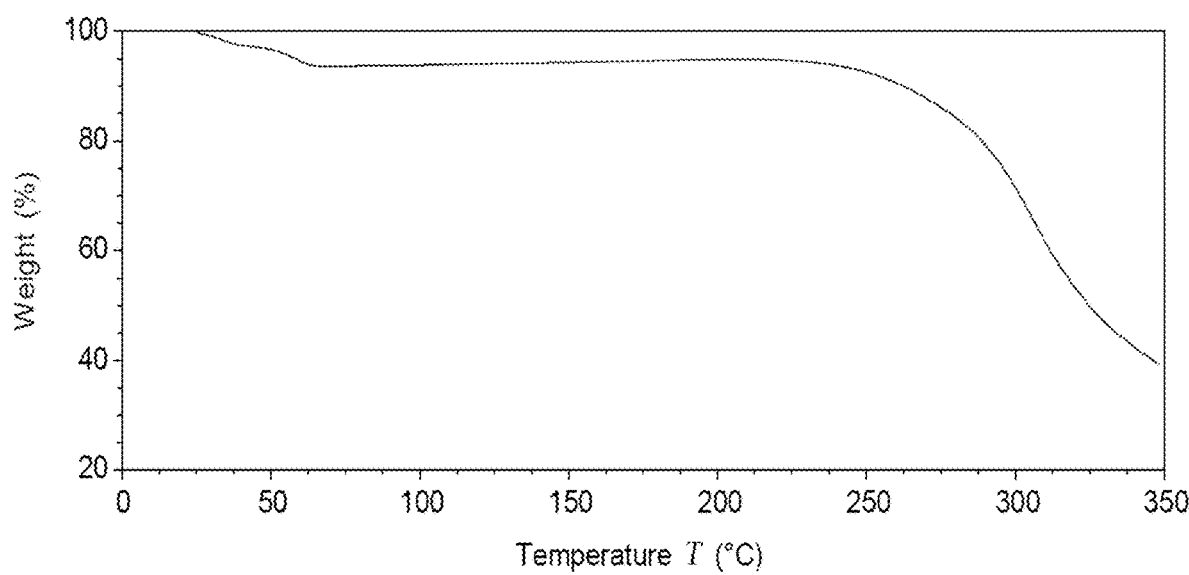
FIG. 10 depicts a TGA thermogram of Hydrate Form A of Compound 2.

TGA data were collected on a TA Discovery Thermogravimetric Analyzer (TA Instruments, New Castle, DE). A sample with weight of approximately 1-10 mg was scanned from 25° C. to 300° C. at a heating rate of 10° C./min. Data were collected and analyzed by Trios Analysis software (TA Instruments, New Castle, DE). The thermogram (FIG. 10) shows 6.2% (w/w) weight loss up to ~75° C.

Differential Scanning Calorimetry Analysis:

DSC was performed using TA Discovery differential scanning calorimeter (TA Instruments, New Castle, DE). The instrument was calibrated with indium. Samples of approximately 1-10 mg were weighed into hermetic pans that were crimped using lids with one hole. The DSC samples were scanned from 25° C. to 300° C. at a heating rate of 10° C./min. Data was collected and analyzed by Trios Analysis software (TA Instruments, New Castle, DE). The thermogram (FIG. 11) of shows multiple endothermic and exothermic peaks at ~97° C., ~137° C., ~164° C., 185° C., 222° C.

Hydrate Form B

X-Ray Powder Diffraction

X-ray powder diffraction (XRPD) spectra were recorded at room temperature in transmission mode using a PANalytical Empyrean system equipped with a sealed tube source and a PIXcel 1D Medipix-3 detector (Malvern PANalytical Inc, Westborough, Massachusetts). The X-Ray generator operated at a voltage of 45 kV and a current of 40 mA with copper radiation (1.54060 Å). The powder sample was placed on a 96 well sample holder with mylar film and loaded into the instrument. The sample was scanned over the range of about 3° to about 40° 2θ with a step size of 0.0131303° and 49 s per step.

The powder X-ray powder diffraction diffractogram of Hydrate Form B (FIG. 12) was acquired at room temperature using the PANalytical Empyrean diffractometer equipped with PIXcel 1D detector. The peaks are listed in Table 18 below.

TABLE 18

Peak list from powder X-ray powder diffraction diffractogram of Hydrate Form B

| Angle (Degrees 2-Theta ± 0.2) | Intensity % |
|---|---|
| 9.3 | 100.0 |
| 18.7 | 89.7 |
| 24.6 | 88.4 |
| 21.1 | 73.6 |
| 19.1 | 72.9 |
| 9.0 | 69.3 |
| 3.8 | 59.5 |
| 20.8 | 56.1 |
| 26.8 | 46.5 |
| 26.4 | 40.7 |
| 7.6 | 40.5 |
| 20.2 | 36.6 |
| 15.4 | 35.4 |
| 13.7 | 34.4 |
| 22.0 | 32.7 |
| 11.0 | 32.0 |
| 16.7 | 28.7 |
| 12.5 | 28.6 |
| 22.9 | 27.2 |
| 21.7 | 23.3 |
| 29.4 | 20.7 |
| 10.2 | 16.5 |

Solid State NMR

Figure 13:
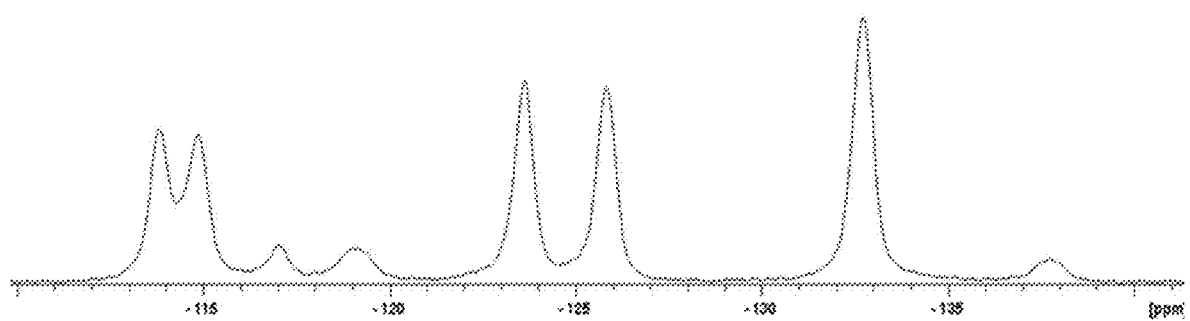
FIG. 13 depicts a $^{19}$F MAS (magnetic angle spinning) spectrum for a mixture of Hydrate Form A and Hydrate Form B of Compound 2.

The $^{19}$F MAS of a mixture of Hydrate Form A and Hydrate Form B (FIG. 13) was acquired at 275K with the following parameters: 12.5 kHz spinning; ref adamantane 29.5 ppm. The peaks are listed in table 19 below. The fluorine peaks highlighted in bold are unique for Hydrate B with respect to following forms: Form A, Hydrate A, Hydrate C and amorphous form.

TABLE 19

Peak list from $^{19}$F MAS of Hydrate Form B

| Chem Shift [ppm] | Intensity [rel] | Phase ID |
|---|---|---|
| −113.8 | 7.2 | Hydrate A |
| −114.8 | 6.9 | Hydrate A |

TABLE 19-continued

Peak list from $^{19}$F MAS of Hydrate Form B

| Chem Shift [ppm] | Intensity [rel] | Phase ID |
|---|---|---|
| −117.0 | 1.8 | Hydrate B |
| −119.1 | 1.5 | Hydrate B |
| −123.6 | 9.5 | Hydrate A |
| −125.8 | 9.2 | Hydrate A |
| −132.7 | 12.5 | Hydrate A |
| −137.7 | 1.1 | Hydrate B |

Hydrate Form C

X-Ray Powder Diffraction

XRPD was performed with a Panalytical X'Pert$^3$ Powder XRPD on a Si zero-background holder. The 2θ position was calibrated against a Panalytical Si reference standard disc.

The powder X-ray powder diffraction diffractogram of Hydrate Form C (FIG. 14) was acquired at room temperature using the PANalytical Empyrean diffractometer equipped with PIXcel 1D detector. The peaks are listed in Table 20 below.

TABLE 20

Peak list from powder X-ray powder diffraction diffractogram of Hydrate Form C

| Angle (Degrees 2-Theta ± 0.2) | Intensity % |
|---|---|
| 13.2 | 100.0 |
| 21.8 | 33.9 |
| 14.6 | 31.6 |
| 15.7 | 28.6 |
| 24.9 | 28.2 |
| 3.7 | 25.6 |
| 18.3 | 25.4 |
| 10.4 | 19.4 |
| 10.7 | 18.4 |
| 22.0 | 18.2 |
| 12.2 | 15.6 |
| 11.3 | 13.3 |
| 24.0 | 11.8 |
| 21.0 | 11.7 |
| 18.6 | 11.1 |
| 24.6 | 11.1 |

Solid State NMR

Figure 15:
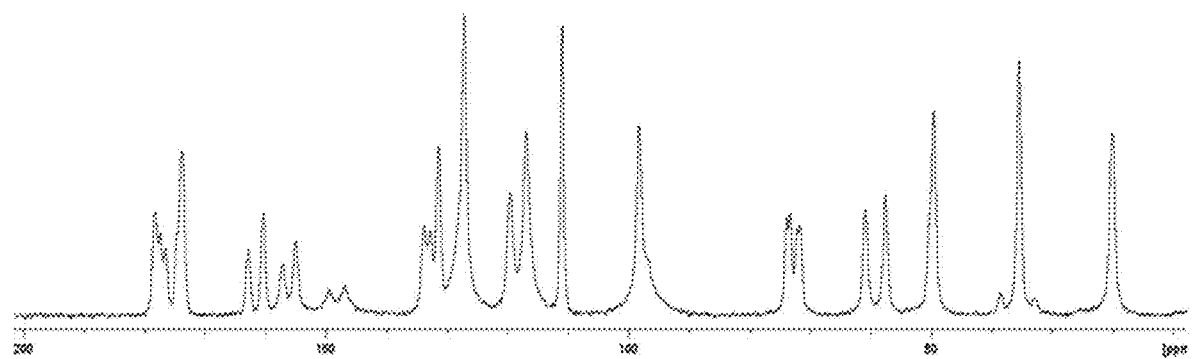
FIG. 15 depicts a solid state $^{13}$C NMR spectrum for Hydrate Form C of Compound 2.

The $^{13}$C CPMAS of Hydrate Form C (FIG. 15) was acquired at 275K with the following parameters: 12.5 kHz spinning; ref. adamantane 29.5 ppm. The peaks are listed in table 21 below. The carbon peaks highlighted in bold are unique for Hydrate C with respect to following forms: Form A, Hydrate A and amorphous form.

TABLE 21

Peak list from $^{13}$C CPMAS of Hydrate Form C

| Chem Shift [ppm] | Intensity [rel] |
|---|---|
| 178.2 | 34.8 |
| 177.4 | 27.5 |
| 176.6 | 22.4 |
| 173.8 | 54.8 |
| 162.8 | 21.7 |
| 160.3 | 34.0 |
| 157.1 | 16.8 |
| 155.0 | 24.7 |
| 149.5 | 8.6 |
| 146.8 | 9.8 |

TABLE 21-continued

Peak list from $^{13}$C CPMAS of Hydrate Form C

| Chem Shift [ppm] | Intensity [rel] |
|---|---|
| 133.8 | 30.0 |
| 132.8 | 27.9 |
| 131.4 | 56.3 |
| 127.2 | 100.0 |
| 119.5 | 40.9 |
| 116.9 | 60.8 |
| 111.0 | 96.4 |
| 98.2 | 63.2 |
| 73.8 | 32.7 |
| 73.3 | 34.0 |
| 72.1 | 28.7 |
| 71.6 | 29.9 |
| 60.8 | 35.6 |
| 57.6 | 40.2 |
| 49.6 | 68.0 |
| 35.5 | 85.1 |
| 20.0 | 60.5 |

Figure 16:
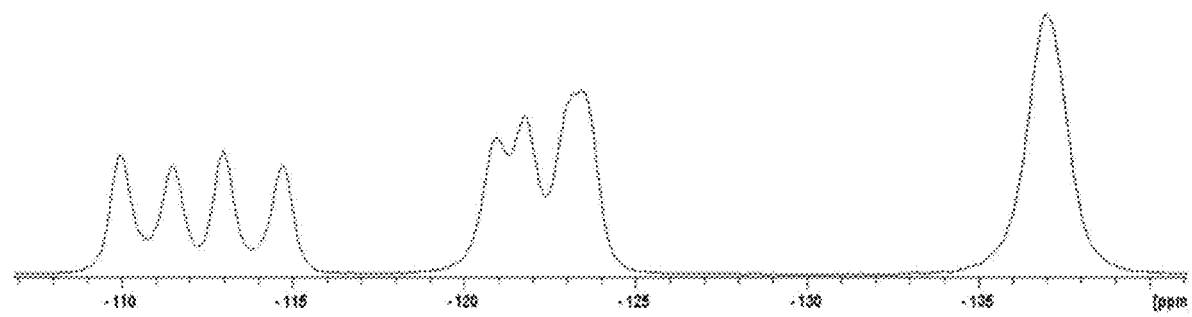
FIG. 16 depicts a $^{19}$F MAS (magnetic angle spinning) spectrum for Hydrate Form C of Compound 2.

The $^{19}$F MAS of Hydrate Form C (FIG. 16) was acquired at 275K with the following parameters: 12.5 kHz spinning; ref. adamantane 29.5 ppm. The peaks are listed in table 22 below. The fluorine peaks highlighted in bold are unique for Hydrate C with respect to following forms: Form A, Hydrate A, Hydrate B and amorphous form.

TABLE 22

Peak list from $^{19}$F MAS of Hydrate Form C

| Chem Shift [ppm] | Intensity [rel] |
|---|---|
| −109.9 | 5.8 |
| −111.5 | 5.2 |
| −113.0 | 6.0 |
| −114.7 | 5.2 |
| −120.9 | 6.6 |
| −121.8 | 7.6 |
| −123.1 | 8.6 |
| −123.4 | 8.8 |
| −137.0 | 12.5 |

Thermogravimetric Analysis

Figure 17:
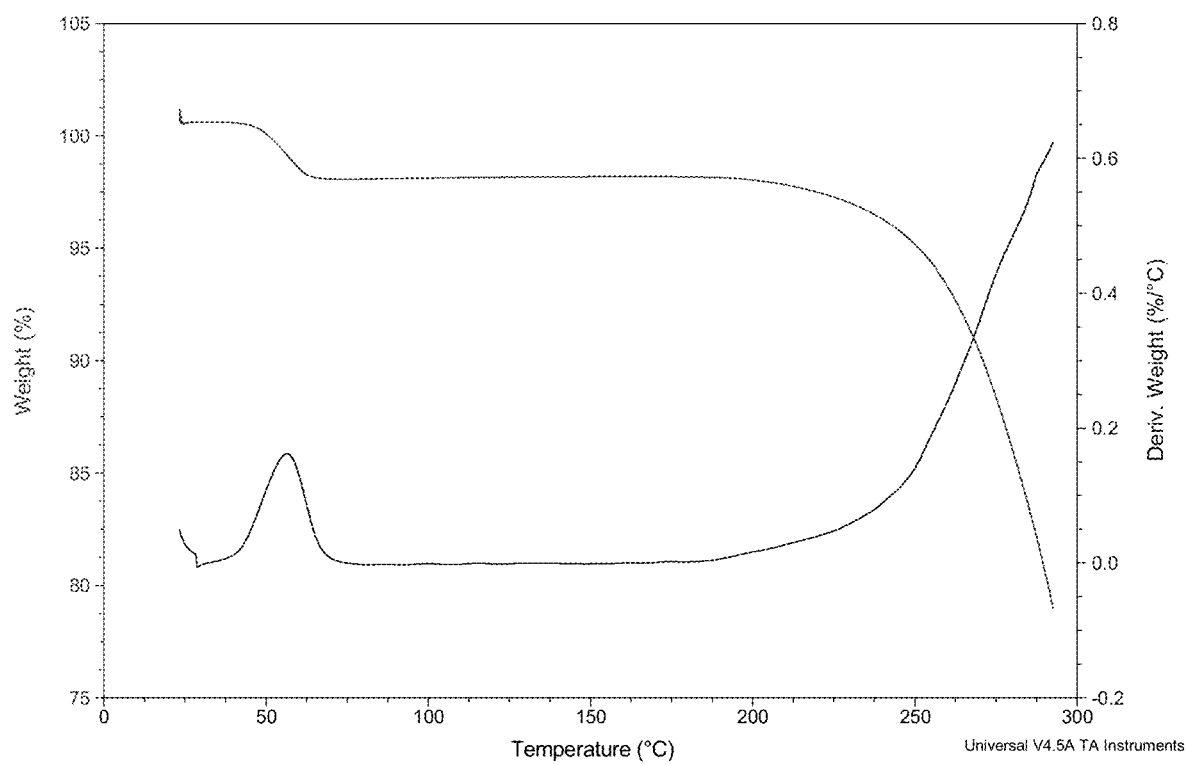
FIG. 17 depicts a TGA thermogram of Hydrate Form C of Compound 2.

TGA data was collected using a Discovery 550 TGA from TA Instrument. The thermogram (FIG. 17) shows ~2.5% (w/w) weight loss up to ~100° C.

Differential Scanning Calorimetry Analysis

DSC was performed using a TA Q2000 DSC from TA Instrument. DSC was calibrated with Indium reference standard and the TGA was calibrated using nickel reference standard. The thermogram (FIG. 18) shows multiple endothermic and exothermic peaks at ~112° C., ~145° C., ~189° C.

Hydrate Form D

X-Ray Powder Diffraction

XRPD was performed with a Panalytical X'Pert$^3$ Powder XRPD on a Si zero-background holder. The 2θ position was calibrated against a Panalytical Si reference standard disc. The powder X-ray powder diffraction diffractogram of Hydrate Form D (FIG. 19) was acquired. The peaks are listed in table 23 below.

TABLE 23

Peak list from powder X-ray powder diffraction diffractogram of Hydrate Form D

| Angle (Degrees 2-Theta ± 0.2) | Intensity % |
|---|---|
| 8.2 | 100.0 |
| 5.0 | 52.1 |
| 15.2 | 48.1 |
| 7.7 | 38.2 |
| 4.1 | 18.5 |
| 15.5 | 17.5 |
| 19.0 | 15.7 |
| 7.6 | 12.7 |
| 16.5 | 12.1 |

Figure 20:
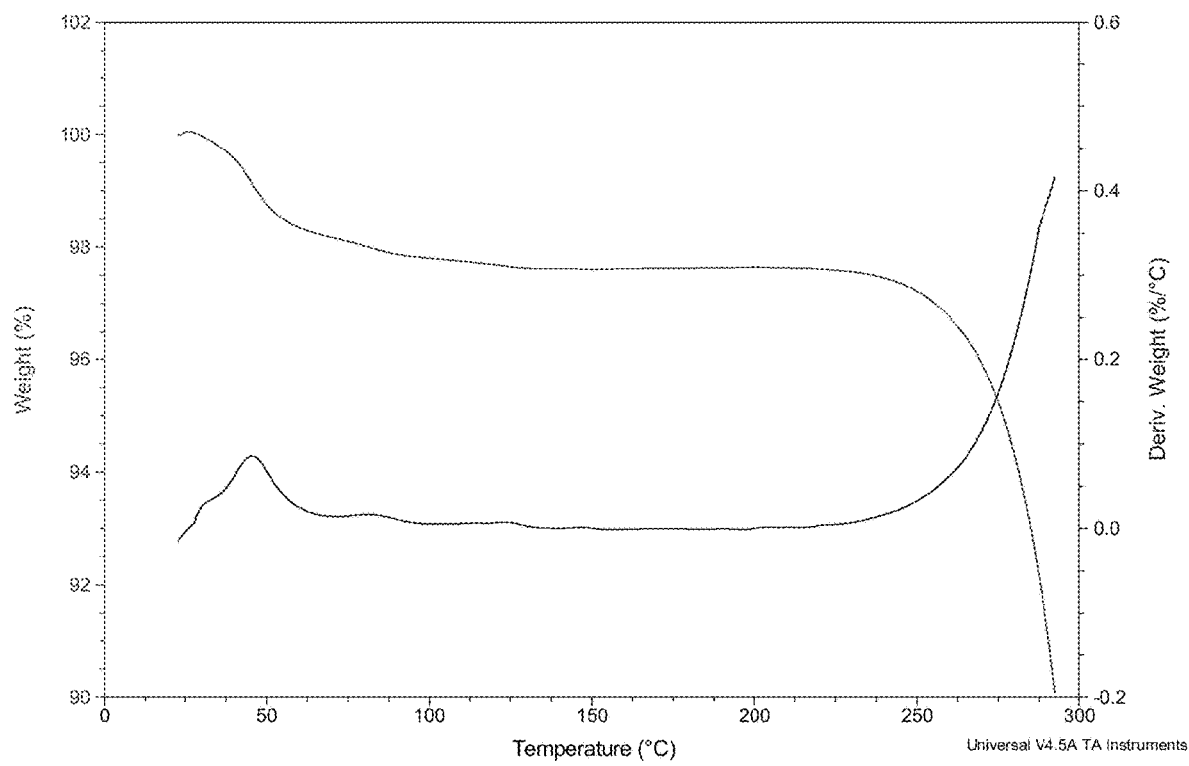
FIG. 20 depicts a TGA thermogram of Hydrate Form D of Compound 2.

Thermogravimetric Analysis:

TGA data was collected using a Discovery 550 TGA from TA Instrument. The thermogram (FIG. 20) shows ~2.4% (w/w) weight loss up to ~175° C.

Differential Scanning Calorimetry Analysis:

DSC was performed using a TA Q2000 DSC from TA Instrument. DSC was calibrated with Indium reference standard and the TGA was calibrated using nickel reference standard. The thermogram (FIG. 21) shows multiple endothermic and exothermic peaks at ~121° C., ~148° C., ~176° C., ~196° C.

Hydrate Form E

X-Ray Powder Diffraction

XRPD was performed with a Panalytical X'Pert³ Powder XRPD on a Si zero-background holder. The 2θ position was calibrated against a Panalytical Si reference standard disc. The powder X-ray powder diffraction diffractogram of Hydrate Form E (FIG. 22) was acquired. The peaks are listed in table 24 below.

TABLE 24

Peak list from powder X-ray powder diffraction diffractogram of Hydrate Form E

| Angle (Degrees 2-Theta ± 0.2) | Intensity % |
|---|---|
| 14.3 | 100.0 |
| 18.9 | 85.7 |
| 11.4 | 51.4 |
| 7.7 | 28.4 |
| 6.5 | 20.7 |
| 16.4 | 20.1 |
| 12.8 | 17.1 |
| 11.8 | 11.4 |
| 22.1 | 10.6 |
| 15.8 | 10.3 |

Figure 23:
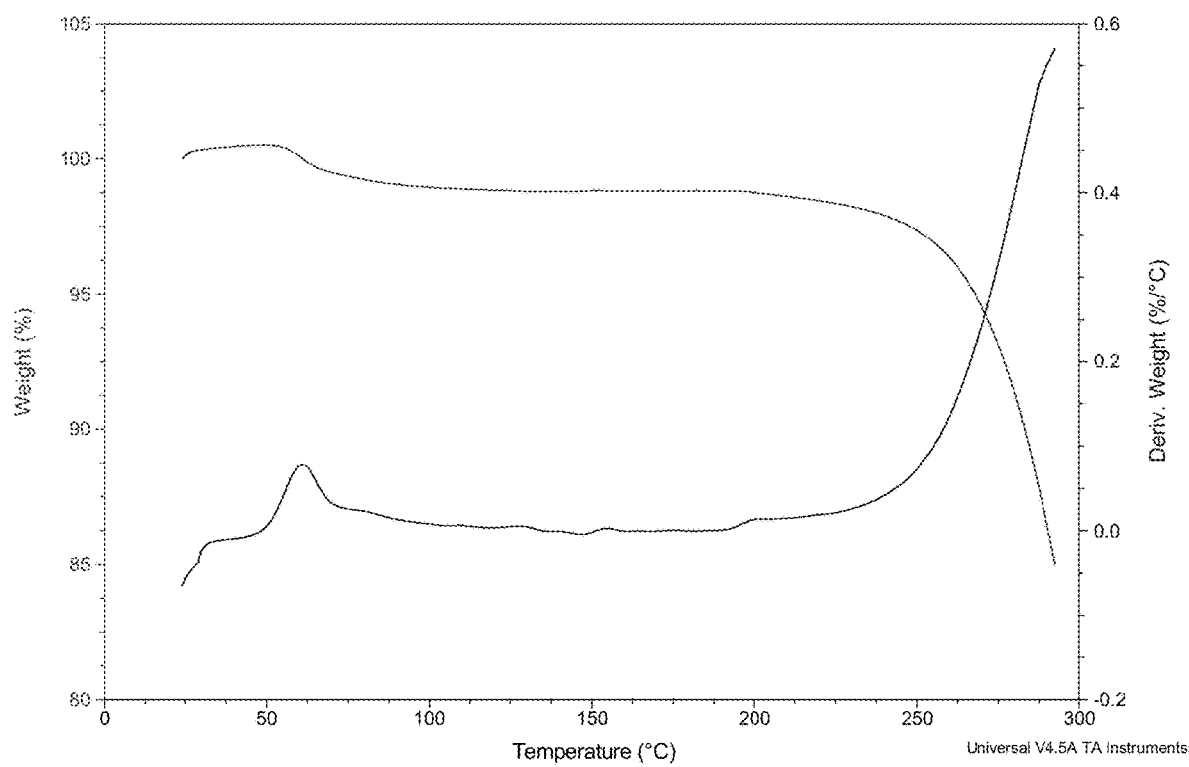
FIG. 23 depicts a TGA thermogram of Hydrate Form E of Compound 2.

Thermogravimetric Analysis:

TGA data was collected using a Discovery 550 TGA from TA Instrument. The thermogram (FIG. 23) shows ~1.6% (w/w) weight loss up to ~150° C.

Differential Scanning Calorimetry Analysis

DSC was performed using a TA Q2000 DSC from TA Instrument. DSC was calibrated with Indium reference standard and the TGA was calibrated using nickel reference standard. The thermogram (FIG. 24) shows multiple endothermic and exothermic peaks at ~107° C., ~127° C., ~150° C., ~177° C., ~195° C.

Hydrate Form F

X-Ray Powder Diffraction:

XRPD was performed with a Panalytical X'Pert³ Powder XRPD on a Si zero-background holder. The 2θ position was calibrated against a Panalytical Si reference standard disc. The powder X-ray powder diffraction diffractogram of Hydrate Form F (FIG. 25) was acquired. The peaks are listed in table 25 below.

TABLE 25

Peak list from powder X-ray powder diffraction diffractogram of Hydrate Form F

| Angle (Degrees 2-Theta ± 0.2) | Intensity % |
|---|---|
| 11.4 | 100.0 |
| 3.8 | 39.8 |
| 7.6 | 23.1 |

Figure 26:
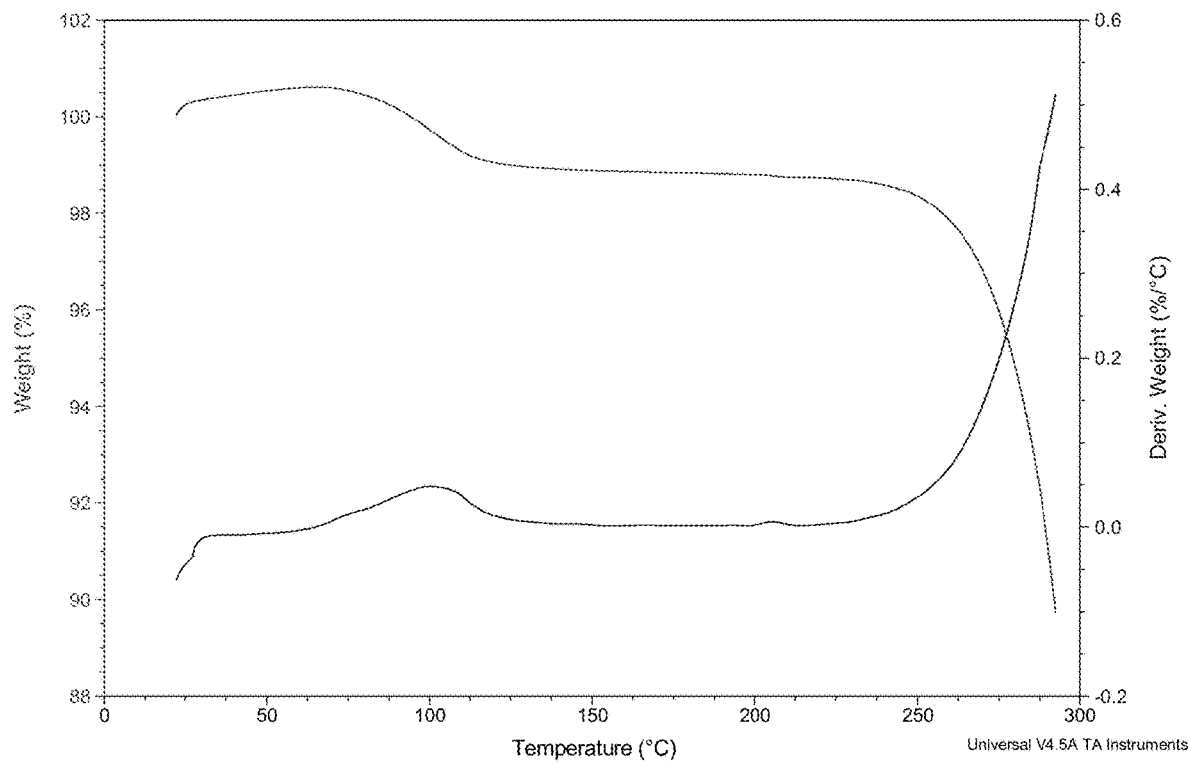
FIG. 26 depicts a TGA thermogram of Hydrate Form F of Compound 2.

Thermogravimetric Analysis:

TGA data was collected using a Discovery 550 TGA from TA Instrument. The thermogram (FIG. 26) shows ~1.8% (w/w) weight loss up to ~175° C.

Differential Scanning Calorimetry Analysis:

DSC was performed using a TA Q2000 DSC from TA Instrument. DSC was calibrated with Indium reference standard and the TGA was calibrated using nickel reference standard. The thermogram (FIG. 27) shows multiple endothermic and exothermic peaks at ~174° C., ~177° C., ~197° C.

MTBE Solvate

X-Ray Powder Diffraction

XRPD was performed with a Panalytical X'Pert³ Powder XRPD on a Si zero-background holder. The 2θ position was calibrated against a Panalytical Si reference standard disc. The powder X-ray powder diffraction diffractogram of the MTBE Solvate (FIG. 28) was acquired. The peaks are listed in table 26 below.

TABLE 26

Peak list from powder X-ray powder diffraction diffractogram of the MTBE Solvate

| Angle (Degrees 2-Theta ± 0.2) | Intensity % |
|---|---|
| 6.0 | 100.0 |
| 8.4 | 96.9 |
| 20.2 | 77.9 |
| 18.0 | 51.8 |
| 19.4 | 45.4 |
| 6.8 | 45.0 |
| 22.0 | 43.5 |
| 24.7 | 36.9 |
| 24.1 | 24.0 |
| 21.2 | 23.4 |
| 14.2 | 21.1 |
| 13.5 | 18.5 |
| 17.6 | 12.3 |
| 27.4 | 11.8 |
| 25.9 | 10.9 |
| 6.0 | 100.0 |

Thermogravimetric Analysis

Figure 29:
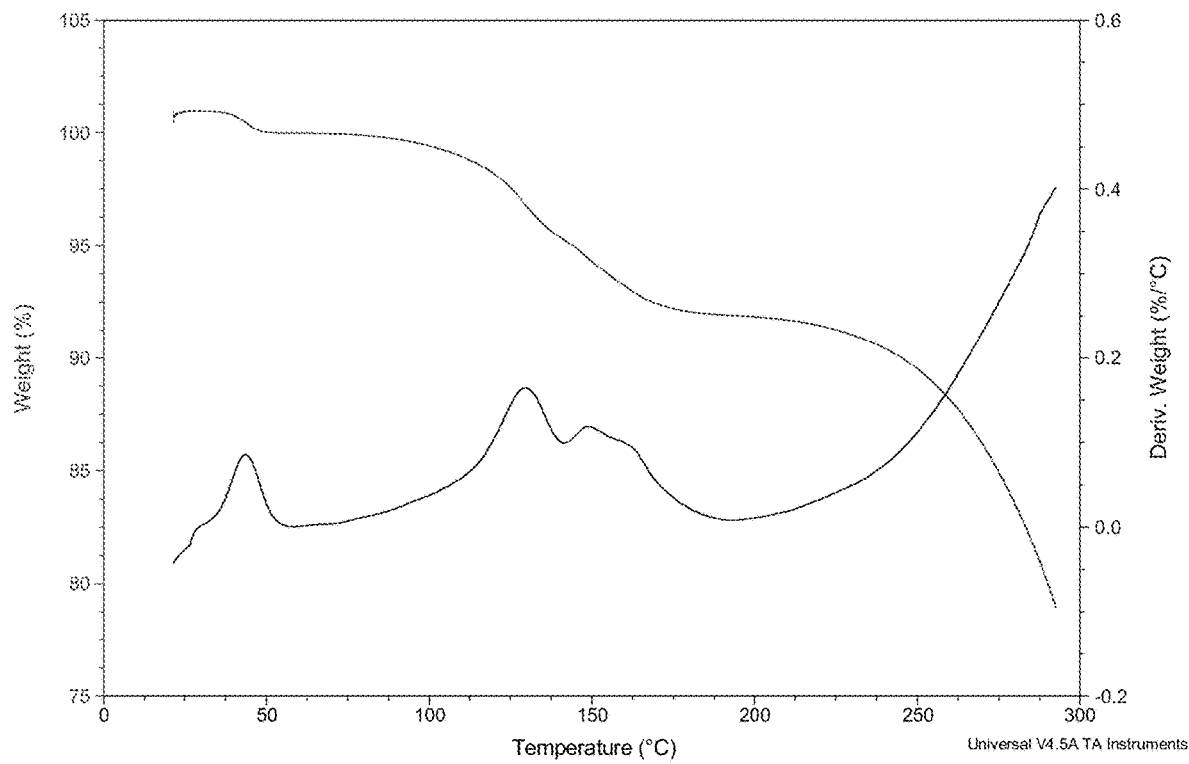
FIG. 29 depicts a TGA thermogram of MTBE solvate of Compound 2.

TGA data was collected using a Discovery 550 TGA from TA Instrument. The thermogram (FIG. 29) shows ~1.0% (w/w) weight loss up to ~58° C., and ~8.0% w/w) weight loss from ~58° C. to ~193° C.

Differential Scanning Calorimetry Analysis:

DSC was performed using a TA Q2000 DSC from TA Instrument. DSC was calibrated with Indium reference standard and the TGA was calibrated using nickel reference standard. The thermogram (FIG. 30) shows multiple endothermic and exothermic peaks at ~131° C., ~148° C., ~193° C.

DMF Solvate

X-Ray Powder Diffraction

XRPD was performed with a Panalytical X'Pert³ Powder XRPD on a Si zero-background holder. The 2θ position was calibrated against a Panalytical Si reference standard disc. The powder X-ray powder diffraction diffractogram of the DMF Solvate (FIG. 31) was acquired. The peaks are listed in table 27 below.

TABLE 27

Peak list from powder X-ray powder diffraction diffractogram of the DMF Solvate

| Angle (Degrees 2-Theta ± 0.2) | Intensity % |
| --- | --- |
| 20.1 | 100.0 |
| 18.0 | 73.6 |
| 15.3 | 48.8 |
| 9.3 | 44.9 |
| 5.6 | 36.8 |
| 14.2 | 32.2 |
| 9.8 | 30.0 |
| 17.5 | 29.5 |
| 10.9 | 22.4 |

Figure 32:
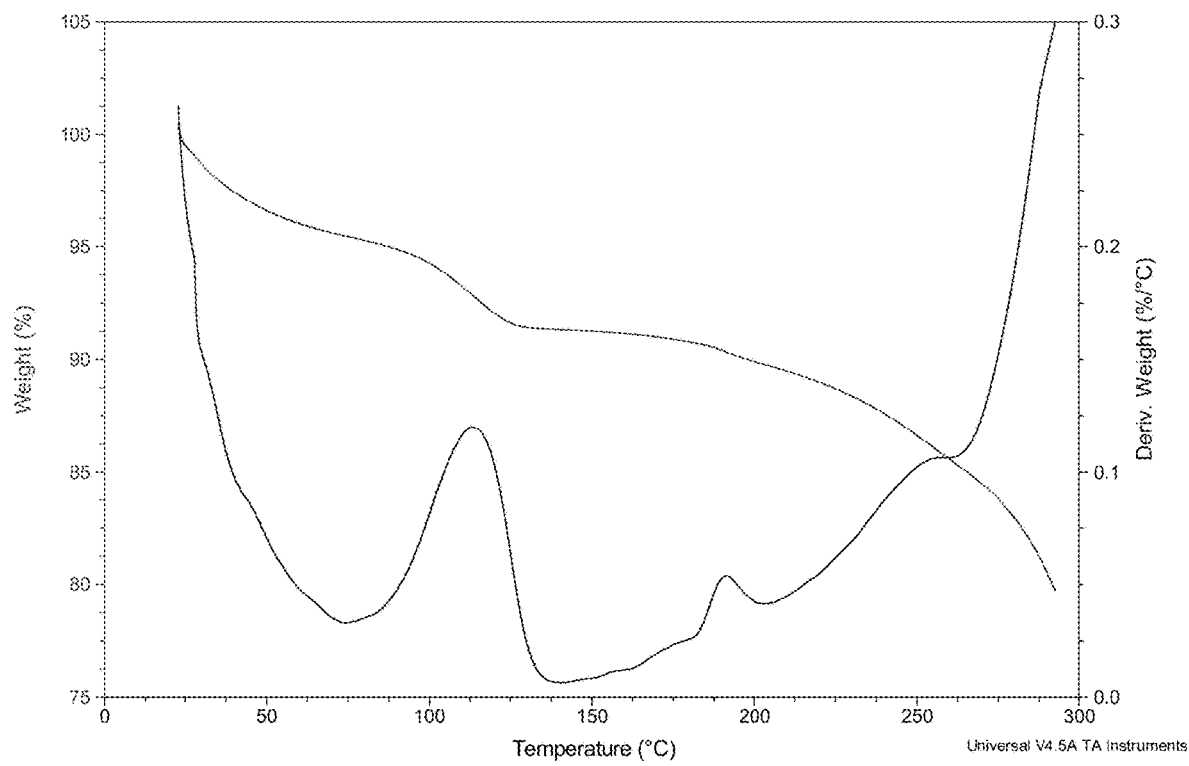
FIG. 32 depicts a TGA thermogram of DMF solvate of Compound 2.

Thermogravimetric Analysis:

TGA data was collected using a Discovery 550 TGA from TA Instrument. The thermogram (FIG. 32) shows ~8.9% (w/w) weight loss up to ~141° C.

Differential Scanning Calorimetry Analysis:

DSC was performed using a TA Q2000 DSC from TA Instrument. DSC was calibrated with Indium reference standard and the TGA was calibrated using nickel reference standard. The thermogram (FIG. 33) shows multiple endothermic and exothermic peaks at ~101° C., ~110° C., ~190° C.

Amorphous Form

X-Ray Powder Diffraction:

The XRPD patterns are acquired at room temperature in reflection mode using a Bruker Advance equipped with Vantec-1 detector. Sample was analyzed on a silicon sample holder from 3-40° 2-theta on continuous mode with step size of 0.0144531° and time per step of 0.25 seconds. Sample was spinning at 15 rpm. The powder X-ray powder diffraction diffractogram of the amorphous form (FIG. 34) was acquired.

Figure 35:
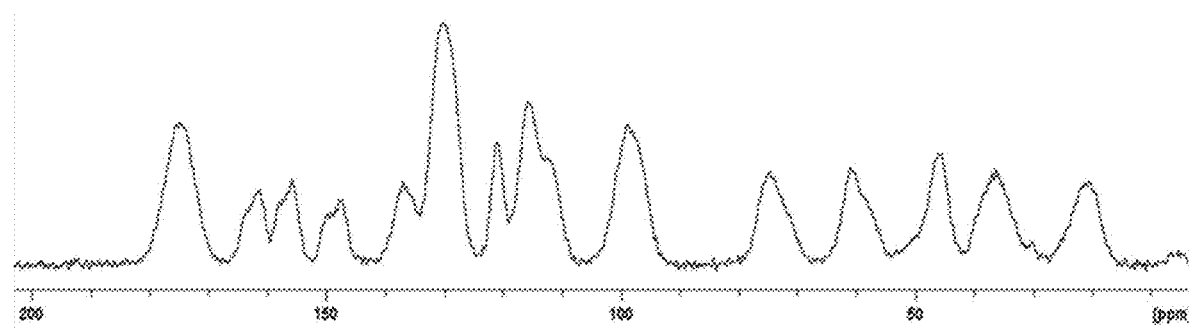
FIG. 35 depicts a solid state $^{13}$C NMR spectrum for amorphous form of Compound 2.

Solid State NMR The ¹³C CPMAS of the Amorphous Form (FIG. 35) was acquired at 275K with the following parameters: 12.5 kHz spinning; ref. adamantane 29.5 ppm. The peaks are listed in table 28 below. The carbon peaks in bold are unique to the amorphous form with respect to following forms: Form A, Hydrate A, Hydrate C.

TABLE 28

Peak list from ¹³C CPMAS of the Amorphous Form

| Chem Shift [ppm] | Intensity [rel] |
| --- | --- |
| 174.7 | 58.9 |
| 161.3 | 31.0 |
| 155.8 | 35.1 |
| 147.4 | 27.0 |
| 137.0 | 34.4 |
| 130.2 | 100.0 |
| 120.9 | 50.5 |
| 115.5 | 67.7 |
| 112.3 | 43.4 |
| 98.8 | 58.3 |
| 74.7 | 38.7 |
| 61.0 | 40.6 |
| 45.7 | 46.2 |
| 36.4 | 39.5 |
| 20.5 | 34.8 |

Figure 36:
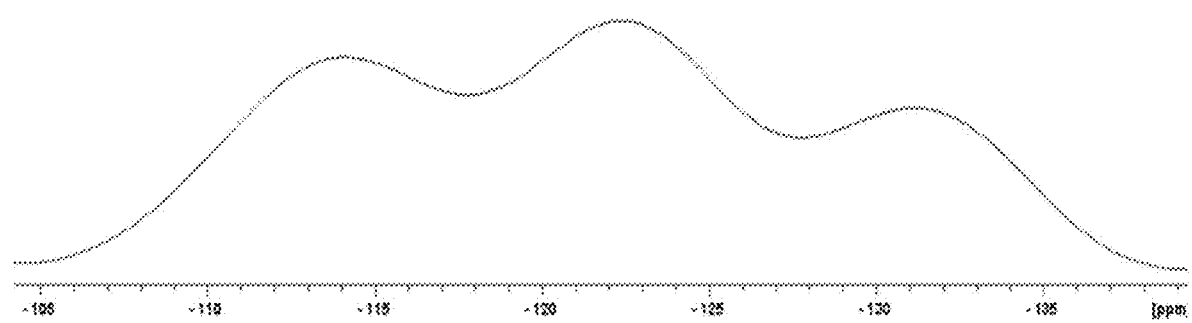
FIG. 36 depicts a $^{19}$F MAS (magnetic angle spinning) spectrum for amorphous form of Compound 2.

The ¹⁹F MAS of the Amorphous Form (FIG. 36) was acquired at 275K with the following parameters: 12.5 kHz spinning; ref. adamantane 29.5 ppm. The peaks are listed in table 29 below. The fluorine peaks highlighted in bold are unique for the Amorphous Form with respect to following forms: Form A, Hydrate A, Hydrate B and amorphous form.

TABLE 29

Peak list from ¹⁹F MAS of the Amorphous Form

| Chem Shift [ppm] | Intensity [rel] |
| --- | --- |
| −114.1 | 10.8 |
| −122.4 | 12.5 |
| −131.1 | 8.3 |

Differential Scanning Calorimetry Analysis

DSC was performed using TA Discovery differential scanning calorimeter (TA Instruments, New Castle, DE). The instrument was calibrated with indium. Samples of approximately 1-10 mg were weighed into hermetic pans that were crimped using lids with one hole. The DSC samples were scanned from 25° C. to 300° C. at a heating rate of 10° C./min. Data was collected and analyzed by Trios Analysis software (TA Instruments, New Castle, DE). The thermogram (FIG. 37) shows a glass transition of ~87° C.

X-Ray Powder Diffraction for Forms of Compound 87

Form A

X-Ray Powder Diffraction:

The X-ray powder diffractogram of Form A (FIG. 38) was acquired at room temperature using a PANalytical Empyrean diffractometer equipped with PIXcel 1D detector. The peaks are listed in table 30 below. stopped here

TABLE 30

Peak list from powder X-ray powder diffraction diffractogram of Form A

| Angle (Degrees 2-Theta ± 0.2) | Intensity % |
| --- | --- |
| 21.0 | 100.0 |
| 14.2 | 95.9 |
| 23.1 | 59.5 |
| 21.2 | 54.2 |
| 4.7 | 49.2 |

TABLE 30-continued

Peak list from powder X-ray powder diffraction diffractogram of Form A

| Angle (Degrees 2-Theta ± 0.2) | Intensity % |
|---|---|
| 9.0 | 46.2 |
| 16.7 | 33.5 |
| 22.9 | 31.2 |
| 24.5 | 24.2 |
| 20.0 | 21.2 |
| 26.1 | 20.1 |
| 26.0 | 18.4 |
| 25.2 | 18.2 |
| 18.9 | 17.6 |
| 9.5 | 16.5 |
| 27.8 | 15.0 |
| 24.3 | 13.6 |
| 25.6 | 12.7 |
| 18.1 | 11.9 |
| 22.1 | 11.8 |
| 17.5 | 9.8 |

Solid State NMR

Figure 39:
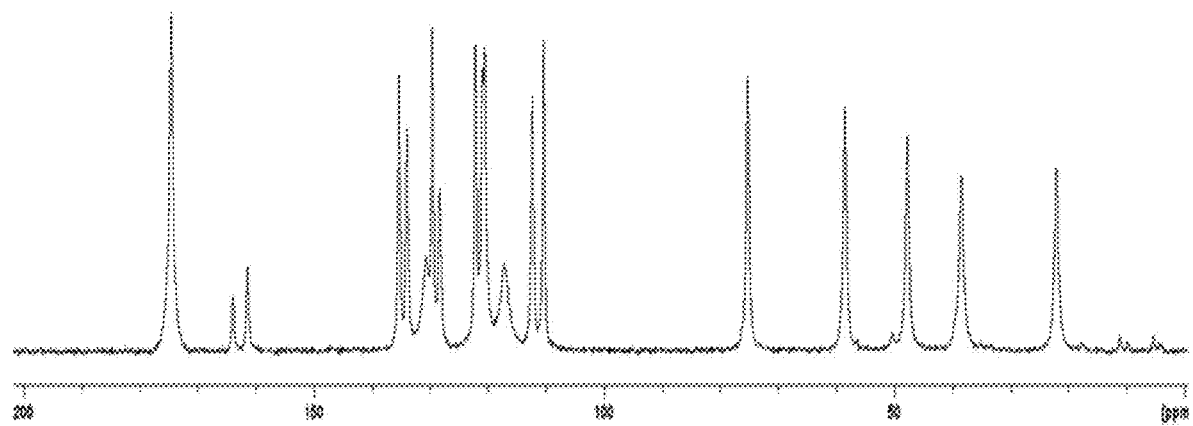
FIG. 39 depicts a solid state $^{13}$C NMR spectrum for Form A of Compound 87.

The $^{13}$C CPMAS of Form A (FIG. 39) was acquired at 275K with the following parameters: 12.5 kHz spinning; ref. adamantane 29.5 ppm. The peaks are listed in table 31 below. The carbon peaks highlighted in bold are unique for Form A with respect to following forms: Hydrate, IPAC solvates and amorphous.

TABLE 31

Peak list from $^{13}$C CPMAS of Form A

| Chem Shift [ppm] | Intensity [rel] |
|---|---|
| 174.5 | 100.0 |
| 163.8 | 16.5 |
| 161.3 | 25.5 |
| 135.3 | 81.6 |
| 133.9 | 66.4 |
| 130.6 | 28.0 |
| 129.5 | 96.0 |
| 128.3 | 48.2 |
| 122.0 | 90.6 |
| 120.8 | 83.3 |
| 120.5 | 89.9 |
| 117.0 | 25.6 |
| 112.2 | 75.4 |
| 110.3 | 91.5 |
| 75.3 | 80.8 |
| 58.4 | 72.4 |
| 47.7 | 63.6 |
| 38.4 | 52.1 |
| 22.0 | 54.3 |

Figure 40:
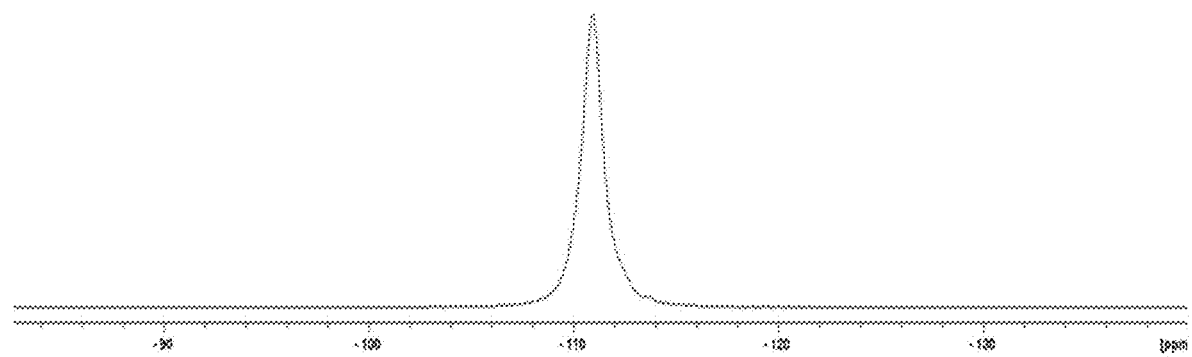
FIG. 40 depicts a $^{19}$F MAS (magnetic angle spinning) spectrum for Form A of Compound 87.

The $^{19}$F MAS of Form A (FIG. 40) was acquired at 275K with the following parameters: 12.5 kHz spinning; ref. adamantane 29.5 ppm. The peaks are listed in table 32 below.

TABLE 32

Peak list from $^{19}$F MAS of Form A

| Chem Shift [ppm] | Intensity [rel] |
|---|---|
| −110.09 | 12.5 |

Thermogravimetric Analysis

Figure 41:
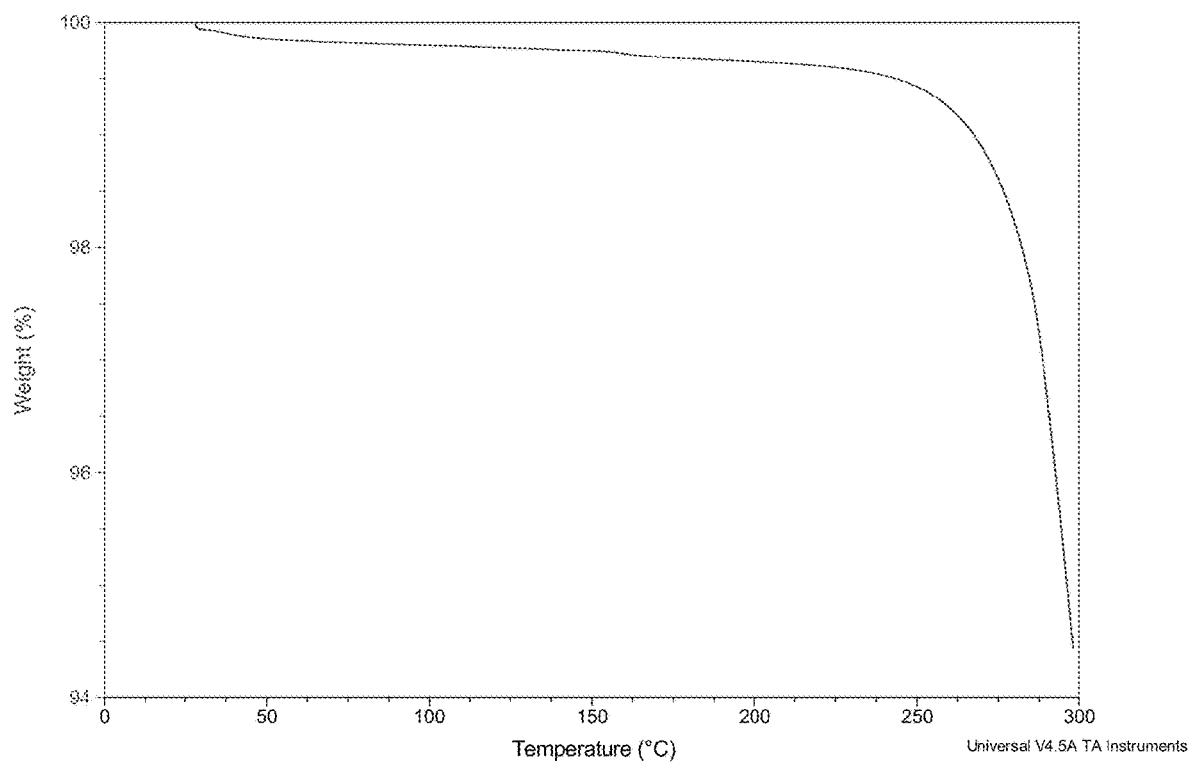
FIG. 41 depicts a TGA thermogram of Form A of Compound 87.

Thermal gravimetric analysis of Form A was measured using a TA Instruments Q5000 TGA. The TGA thermogram (FIG. 41) shows minimal weight loss from ambient temperature up until thermal degradation.

Differential Scanning Calorimetry Analysis

The melting point of Form A was measured using a TA Instruments Discovery DSC. The thermogram (FIG. 42) shows a melting onset of 157° C. with a peak at 160° C.

Hydrate Form

X-Ray Powder Diffraction

X-ray powder diffraction (XRPD) spectra were recorded at room temperature in transmission mode using a PANalytical Empyrean system equipped with a sealed tube source and a PIXcel 1D Medipix-3 detector (Malvern PANalytical Inc, Westborough, Massachusetts). The X-Ray generator operated at a voltage of 45 kV and a current of 40 mA with copper radiation (1.54060 Å). The powder sample was placed on a 96 well sample holder with mylar film and loaded into the instrument. The sample was scanned over the range of about 3° to about 40° 2θ with a step size of 0.0131303° and 49 s per step.

The X-ray powder diffractogram of Hydrate Form (FIG. 43) was acquired at room temperature using a PANalytical Empyrean diffractometer equipped with PIXcel 1D detector. The peaks are listed in Table 33 below.

TABLE 33

Peak list from powder X-ray powder diffraction diffractogram of Hydrate Form

| Angle (Degrees 2-Theta ± 0.2) | Intensity % |
|---|---|
| 12.1 | 100.0 |
| 21.3 | 80.8 |
| 9.3 | 71.5 |
| 10.0 | 68.5 |
| 20.5 | 63.5 |
| 20.0 | 55.6 |
| 20.8 | 50.6 |
| 28.6 | 50.1 |
| 28.7 | 49.4 |
| 23.7 | 43.8 |
| 20.1 | 42.6 |
| 24.8 | 38.6 |
| 15.0 | 37.3 |
| 10.9 | 33.1 |
| 20.9 | 32.1 |
| 18.3 | 29.6 |
| 21.8 | 28.7 |
| 19.3 | 27.5 |
| 26.0 | 26.5 |
| 11.8 | 25.3 |
| 22.7 | 22.2 |
| 26.1 | 20.4 |
| 27.3 | 20.1 |
| 26.4 | 19.1 |
| 26.7 | 18.8 |
| 26.3 | 17.7 |
| 22.8 | 16.6 |
| 15.8 | 12.5 |
| 22.0 | 11.2 |
| 26.8 | 10.3 |

Single Crystal

Single crystals of Compound 87 Hydrate Form were grown from isopropyl alcohol and water. X-ray diffraction data were acquired at 100K on a Bruker diffractometer equipped with Cu Kα radiation (λ=1.54178 Å) and a CMOS detector. The structure was solved and refined using SHELX programs (Sheldrick, G. M., Acta Cryst., (2008) A64, 112-122) and results are summarized in Table 34 below.

TABLE 34

Single Crystal Data

| Crystal System | Orthorhombic |
|---|---|
| Space Group | $P2_12_12_1$ |
| a (Å) | 4.8519 (2) |
| b (Å) | 9.5398 (4) |
| c (Å) | 44.5989 (16) |
| α (°) | 90 |
| β (°) | 90 |
| γ (°) | 90 |
| V (Å$^3$) | 2064.31 (14) |
| Z/Z' | 4/1 |
| Temperature | 100K |

Solid State NMR

Figure 44:
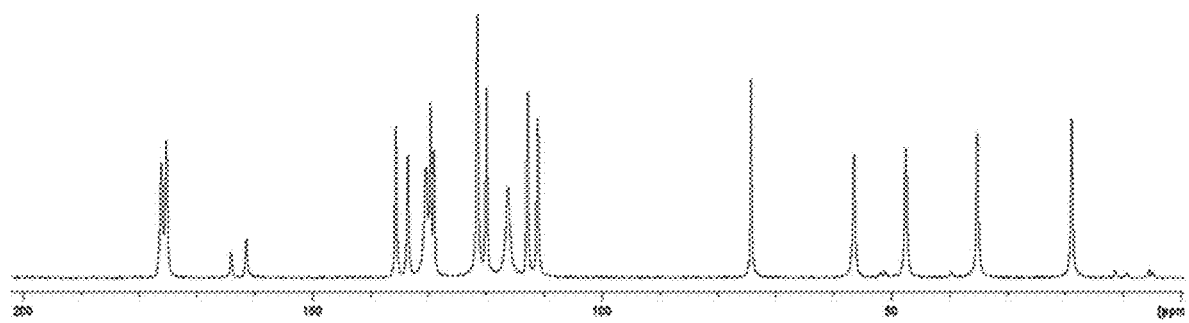
FIG. 44 depicts a solid state $^{13}$C NMR spectrum for Hydrate Form A of Compound 87.

The $^{13}$C CPMAS of Hydrate Form (FIG. 44) was acquired at 275K with the following parameters: 12.5 kHz spinning; ref. adamantane 29.5 ppm. The peaks are listed in Table 35 below. The carbon peaks highlighted in bold are unique for Hydrate Form with respect to following forms: Form A, IPAc solvate and amorphous.

TABLE 35

Peak list from $^{13}$C CPMAS of Hydrate Form

| Chem Shift [ppm] | Intensity [rel] |
|---|---|
| 176.1 | 43.2 |
| 175.2 | 52.9 |
| 163.9 | 9.5 |
| 161.3 | 14.8 |
| 135.5 | 58.5 |
| 133.5 | 46.7 |
| 130.4 | 42.2 |
| 129.6 | 67.2 |
| 129.0 | 49.5 |
| 121.4 | 100.0 |
| 119.8 | 73.4 |
| 116.1 | 34.5 |
| 112.8 | 70.6 |
| 111.0 | 60.2 |
| 74.2 | 75.9 |
| 56.4 | 46.9 |
| 47.4 | 49.4 |
| 35.1 | 55.8 |
| 18.7 | 60.5 |

Figure 45:
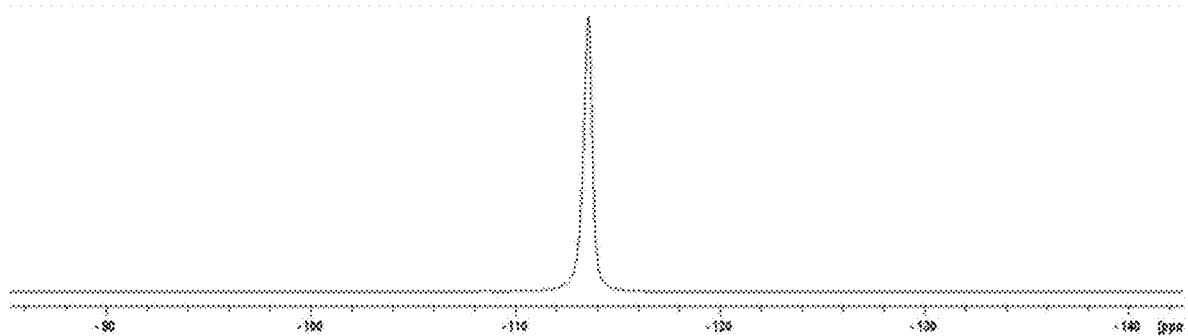
FIG. 45 depicts a $^{19}$F MAS (magnetic angle spinning) spectrum for Hydrate Form A of Compound 87.

The $^{19}$F MAS of Hydrate Form (FIG. 45) was acquired at 275K with the following parameters: 12.5 kHz spinning; ref. adamantane 29.5 ppm. The peak list is in table 36 below.

TABLE 36

Peak list from $^{19}$F MAS of Hydrate Form

| Chem Shift [ppm] | Intensity [rel] |
|---|---|
| −113.6 | 12.5 |

Thermogravimetric Analysis

Figure 46:
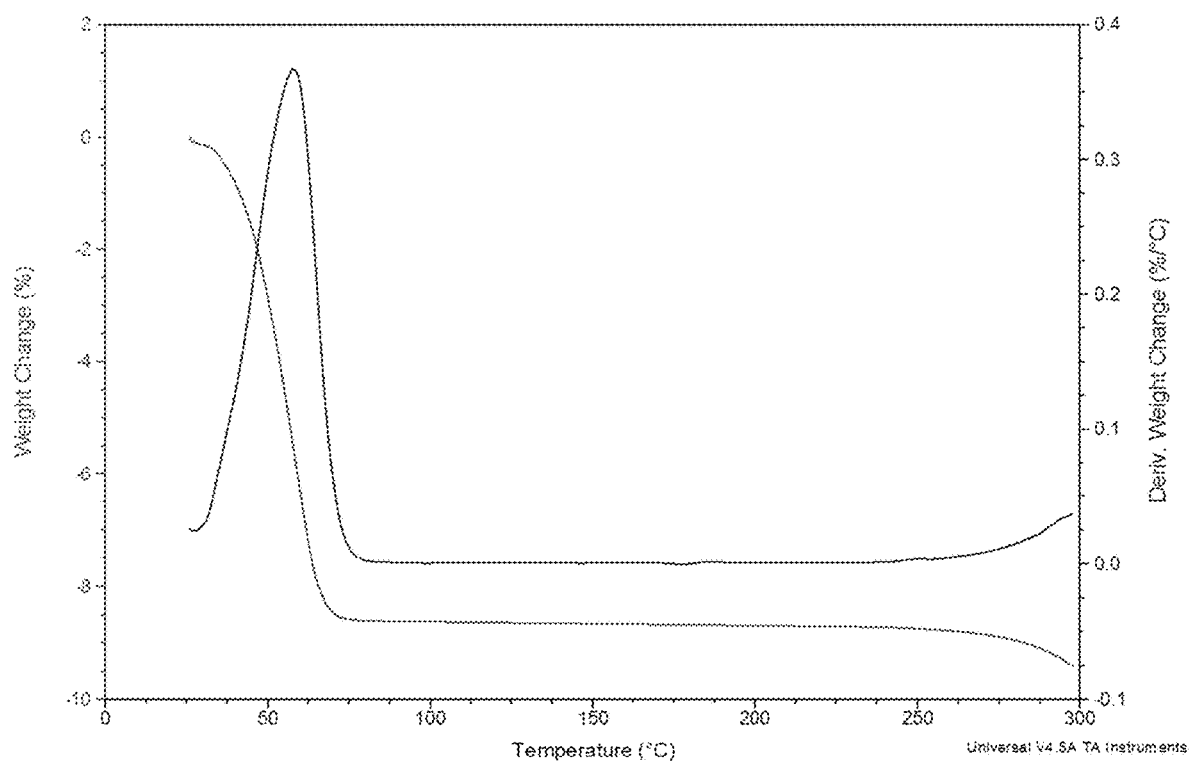
FIG. 46 depicts a TGA thermogram of Hydrate Form A of Compound 87.

TGA data were collected on a TA Discovery Thermogravimetric Analyzer (TA Instruments, New Castle, DE). A sample with weight of approximately 1-10 mg was scanned from 25° C. to 300° C. at a heating rate of 10° C./min. Data were collected and analyzed by Trios Analysis software (TA Instruments, New Castle, DE). The thermogram (FIG. 46) shows ~9% (w/w) weight loss up to ~78° C.

Differential Scanning Calorimetry Analysis:

A MDSC curve was obtained using TA Instruments DSC Q2000. The samples was scanned from 35° C. to 300° C. at a heating rate of 2° C./min with +/−1° C. of modulation within 1 minute. Data was collected and analyzed by Trios Analysis software (TA Instruments, New Castle, DE). The thermogram (FIG. 47) shows two endothermic peaks at ~86° C. and ~158° C.

IPAc Solvate

X-Ray Powder Diffraction

Figure 48:
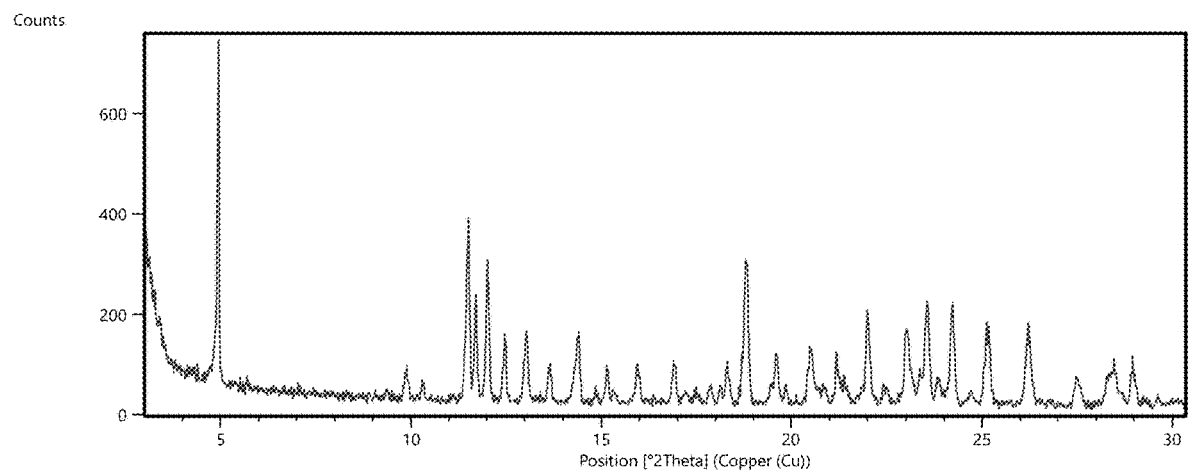
FIG. 48 depicts an XRPD diffractogram of wet sample of IPAc Solvate of Compound 87.

X-ray powder diffraction (XRPD) spectra were recorded at room temperature in transmission mode using a PANalytical Empyrean system equipped with a sealed tube source and a PIXcel 1D Medipix-3 detector (Malvern PANalytical Inc, Westborough, Massachusetts). The X-Ray generator operated at a voltage of 45 kV and a current of 40 mA with copper radiation (1.54060 Å). The powder sample was placed on a 96 well sample holder with mylar film and loaded into the instrument. The sample was scanned over the range of about 3° to about 40° 2θ with a step size of 0.0131303° and 49 s per step. The X-ray powder diffractogram of a wet sample of the IPAc Solvate (FIG. 48) was acquired. The peaks are listed in table 37 below.

TABLE 37

Peak list from powder X-ray powder diffraction diffractogram of a wet sample of the IPAc Solvate

| Angle (Degrees 2-Theta ± 0.2) | Intensity % |
|---|---|
| 5.0 | 100.0 |
| 11.5 | 51.5 |
| 18.8 | 39.5 |
| 12.0 | 34.2 |
| 11.7 | 29.8 |
| 24.2 | 28.4 |
| 23.6 | 28.2 |
| 22.0 | 25.9 |
| 26.2 | 22.5 |
| 14.4 | 20.1 |
| 23.0 | 20.0 |
| 25.2 | 19.3 |
| 13.1 | 18.6 |
| 12.5 | 17.7 |
| 20.5 | 15.2 |
| 21.2 | 14.4 |
| 19.6 | 14.2 |
| 28.9 | 11.5 |
| 16.9 | 10.7 |
| 28.5 | 10.3 |
| 18.3 | 10.2 |

The X-ray powder diffractogram of a vacuum dried sample of the IPAc Solvate (FIG. 49) was acquired. The peaks are listed in table 38 below.

TABLE 38

Peak list from powder X-ray powder diffraction diffractogram of a vacuum dried sample of the IPAc Solvate

| Angle (Degrees 2-Theta ± 0.2) | Intensity % |
|---|---|
| 5.0 | 100.0 |
| 11.5 | 54.6 |
| 18.8 | 50.9 |
| 16.0 | 48.4 |
| 9.9 | 36.4 |
| 12.0 | 29.4 |
| 11.7 | 27.5 |

TABLE 38-continued

Peak list from powder X-ray powder diffraction diffractogram of a vacuum dried sample of the IPAc Solvate

| Angle (Degrees 2-Theta ± 0.2) | Intensity % |
|---|---|
| 22.0 | 26.5 |
| 23.1 | 25.5 |
| 23.6 | 22.6 |
| 24.2 | 19.9 |
| 14.4 | 18.0 |
| 26.2 | 16.9 |
| 25.2 | 16.6 |
| 20.4 | 14.9 |
| 13.0 | 14.7 |
| 27.5 | 13.4 |
| 13.7 | 12.9 |
| 19.9 | 12.5 |
| 16.9 | 11.8 |
| 12.5 | 11.4 |

Solid State NMR

Figure 50:
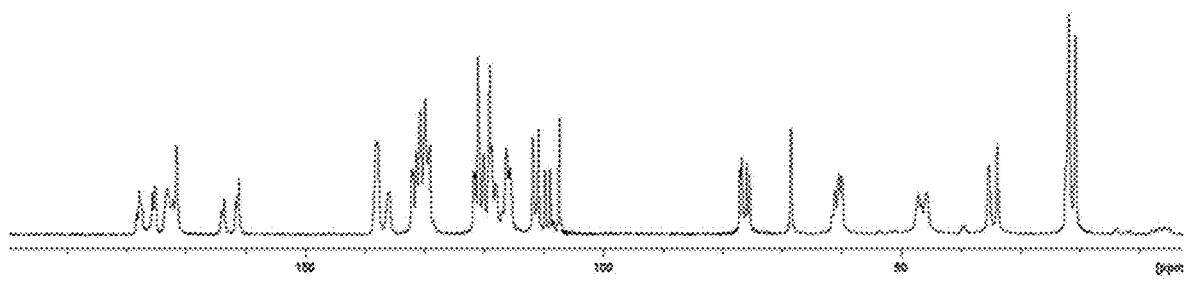
FIG. 50 depicts a solid state $^{13}$C NMR spectrum for IPAc Solvate of Compound 87.

The $^{13}$C CPMAS of IPAc Solvate (FIG. 50) was acquired at 275K with the following parameters: 12.5 kHz spinning; ref. adamantane 29.5 ppm. The peaks are listed in Table 39 below. The carbon peaks highlighted in bold are unique for IPAc Solvate with respect to following forms: Form A, Hydrate and amorphous.

TABLE 39

Peak list from $^{13}$C CPMAS of IPAc Solvate

| Chem Shift [ppm] | Intensity [rel] |
|---|---|
| 178.3 | 9.6 |
| 178.0 | 19.7 |
| 177.5 | 12.2 |
| 175.7 | 19.5 |
| 175.4 | 21.2 |
| 175.2 | 21.2 |
| 173.2 | 20.5 |
| 172.2 | 15.5 |
| 171.5 | 40.2 |
| 164.1 | 10.4 |
| 163.6 | 16.0 |
| 161.7 | 15.2 |
| 161.4 | 16.7 |
| 161.2 | 25.1 |
| 138.1 | 42.0 |
| 137.9 | 41.7 |
| 136.2 | 18.7 |
| 135.9 | 18.9 |
| 132.2 | 30.3 |
| 131.9 | 29.3 |
| 131.4 | 37.4 |
| 130.7 | 55.7 |
| 130.0 | 61.1 |
| 129.2 | 40.3 |
| 121.7 | 28.5 |
| 121.4 | 27.4 |
| 121.0 | 82.7 |
| 120.0 | 36.2 |
| 119.1 | 77.2 |
| 118.7 | 40.2 |
| 118.5 | 24.6 |
| 118.0 | 22.8 |
| 116.9 | 10.8 |
| 116.2 | 39.1 |
| 115.9 | 28.4 |
| 115.6 | 30.2 |
| 111.8 | 44.2 |
| 110.9 | 47.5 |
| 109.8 | 29.5 |

TABLE 39-continued

Peak list from $^{13}$C CPMAS of IPAc Solvate

| Chem Shift [ppm] | Intensity [rel] |
|---|---|
| 108.9 | 29.0 |
| 107.4 | 53.3 |
| 77.1 | 30.5 |
| 76.8 | 34.5 |
| 76.0 | 32.1 |
| 75.5 | 28.3 |
| 68.5 | 47.6 |
| 61.6 | 8.9 |
| 61.1 | 20.0 |
| 60.5 | 27.1 |
| 60.0 | 26.2 |
| 47.2 | 18.4 |
| 46.6 | 14.1 |
| 45.8 | 19.2 |
| 35.4 | 31.0 |
| 33.9 | 40.7 |
| 22.3 | 32.3 |
| 21.9 | 100.0 |
| 20.8 | 91.0 |

Figure 51:
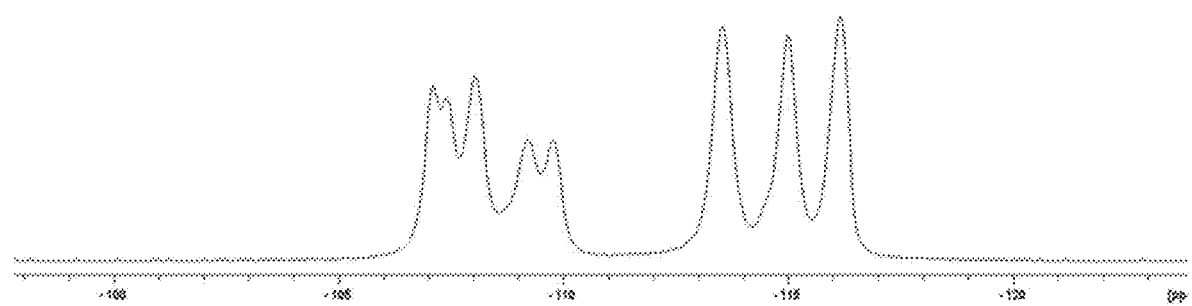
FIG. 51 depicts a $^{19}$F MAS (magnetic angle spinning) spectrum for IPAc Solvate of Compound 87.

The $^{19}$F MAS of IPAc Solvate (FIG. 51) was acquired at 275K with the following parameters: 12.5 kHz spinning; ref. adamantane 29.5 ppm. The peaks are listed in table 40 below. The fluorine peaks highlighted in bold are unique for IPAc Solvate with respect to following forms: Form A, Hydrate and amorphous.

TABLE 40

Peak list from $^{19}$F MAS of Hydrate Form A

| Chem Shift [ppm] | Intensity [rel] | Component |
|---|---|---|
| −107.1 | 9.0 | 2 |
| −107.4 | 8.4 | 3 |
| −108.0 | 9.5 | 1 |
| −109.2 | 6.2 | 3 |
| −109.8 | 6.1 | 2 |
| −113.5 | 12.1 | 2, 3 |
| −114.5 | 3.1 | 4 |
| −115.0 | 11.6 | 1 |
| −116.2 | 12.5 | 3, 2 |

Thermogravimetric Analysis

Figure 52:
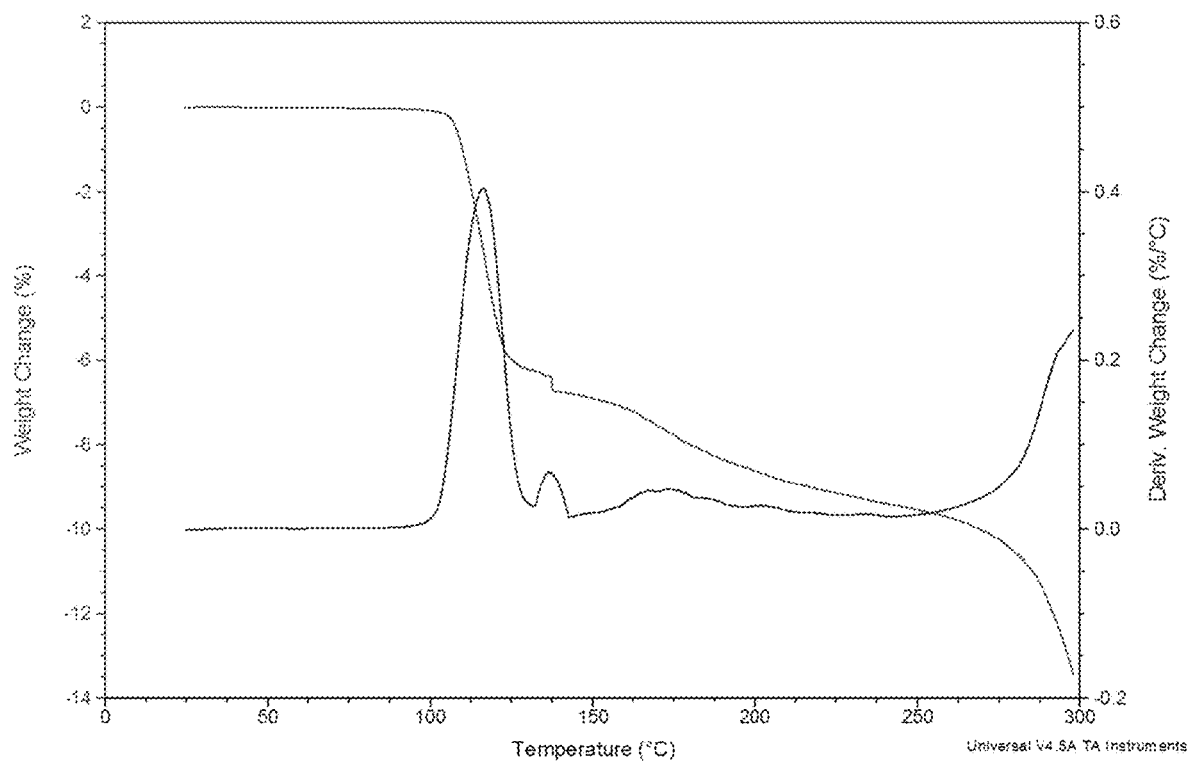
FIG. 52 depicts a TGA thermogram of shortly vacuum dried sample of IPAc Solvate of Compound 87.
Figure 53:
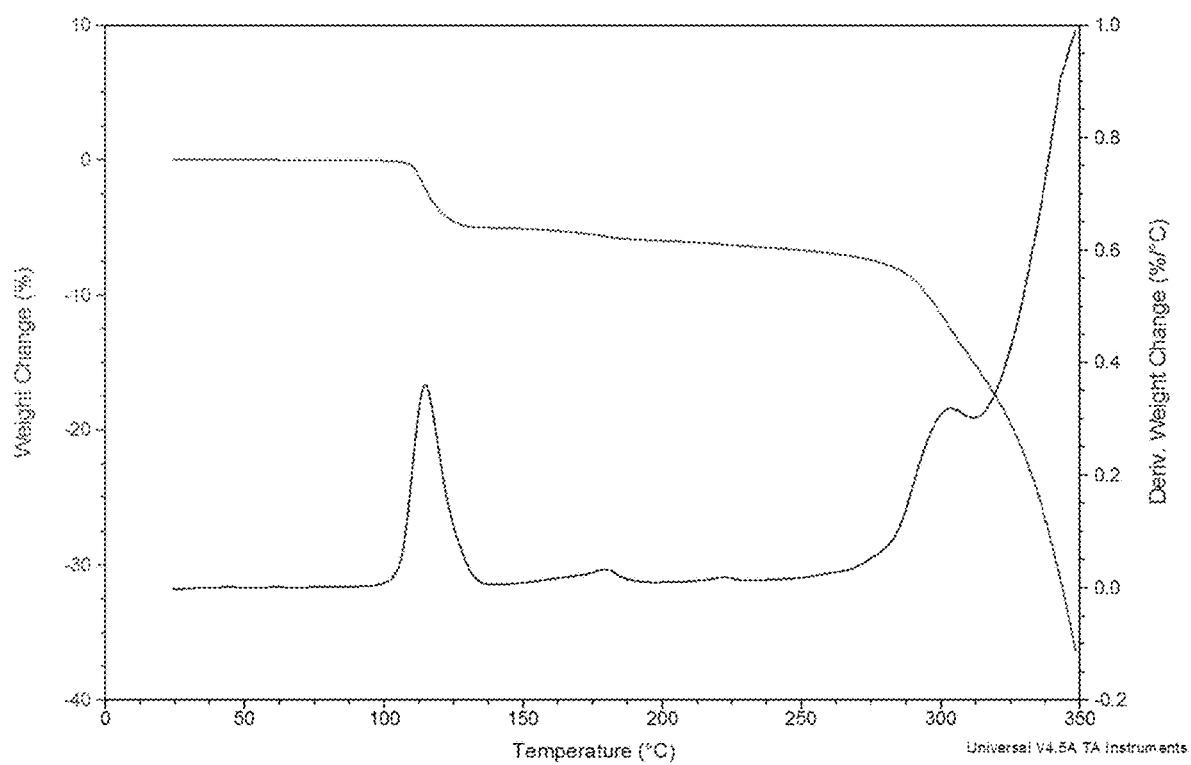
FIG. 53 depicts a TGA thermogram of vacuum dried sample of IPAc Solvate of Compound 87.

Thermal gravimetric analysis of VX-179 Form A was measured using the TA Instruments Q5000 TGA. The thermogram (FIG. 52) of a shortly vacuum dried sample shows ~8% weight loss up to ~200° C. The thermogram (FIG. 53) of a sample vacuum dried for ~1 week shows ~6% weight loss up to ~200° C.

Figure 55:
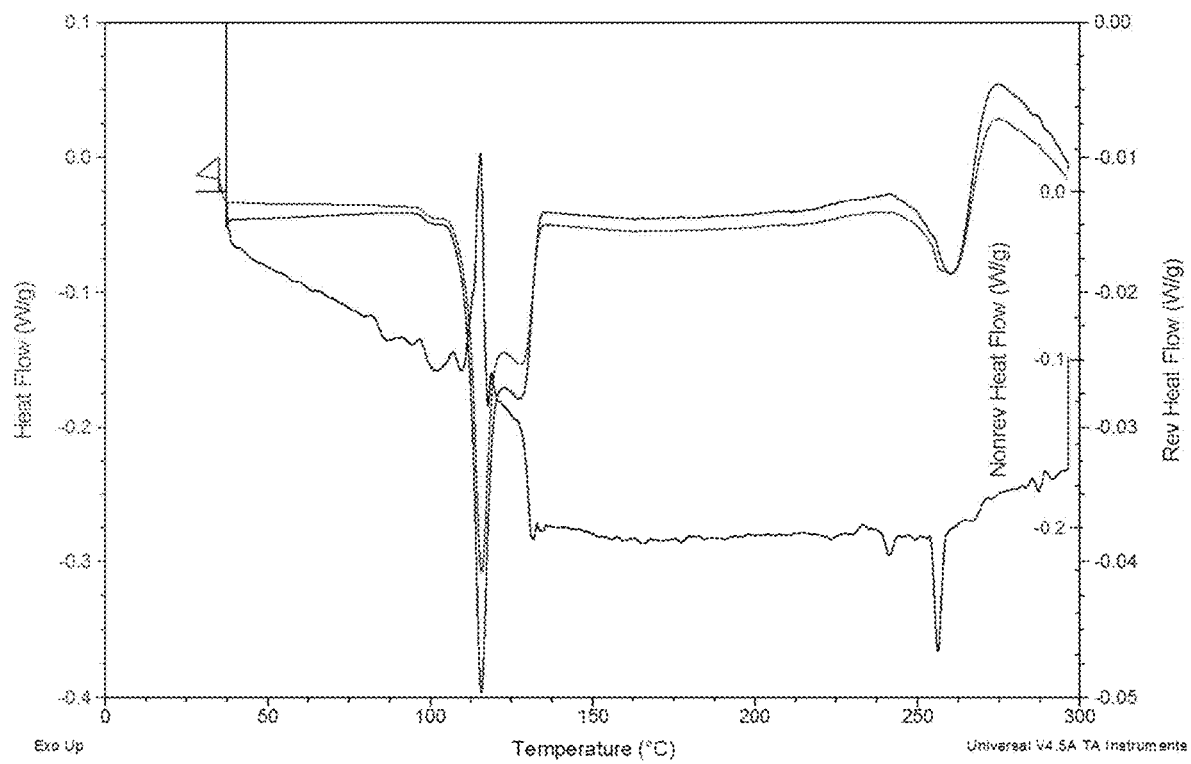
FIG. 55 depicts a DSC curve of vacuum dried sample of IPAc Solvate of Compound 87.

Differential Scanning Calorimetry Analysis:

A MDSC curve was obtained using TA Instruments DSC Q2000. The samples was scanned from 35° C. to 300° C. at a heating rate of 2° C./min with +/−1° C. of modulation within 1 minute. The thermogram of a shortly vacuum dried sample (FIG. 54) shows multiple endothermic peaks including one at ~116° C. The thermogram of a sample vacuum dried for ~1 week (FIG. 55) shows multiple endothermic peaks including one at ~116° C.

Amorphous Form

X-Ray Powder Diffraction:

X-ray powder diffraction (XRPD) spectra were recorded at room temperature in transmission mode using a PANalytical Empyrean system equipped with a sealed tube source and a PIXcel 1D Medipix-3 detector (Malvern PANalytical Inc, Westborough, Massachusetts). The X-Ray generator operated at a voltage of 45 kV and a current of 40 mA with copper radiation (1.54060 Å). The powder sample was placed on a 96 well sample holder with mylar film and loaded into the instrument. The sample was scanned over the range of about 3° to about 40° 2θ with a step size of 0.0131303° and 49 s per step. The X-ray powder diffractogram of the amorphous form (FIG. 56) was acquired.

Solid State NMR

Figure 57:
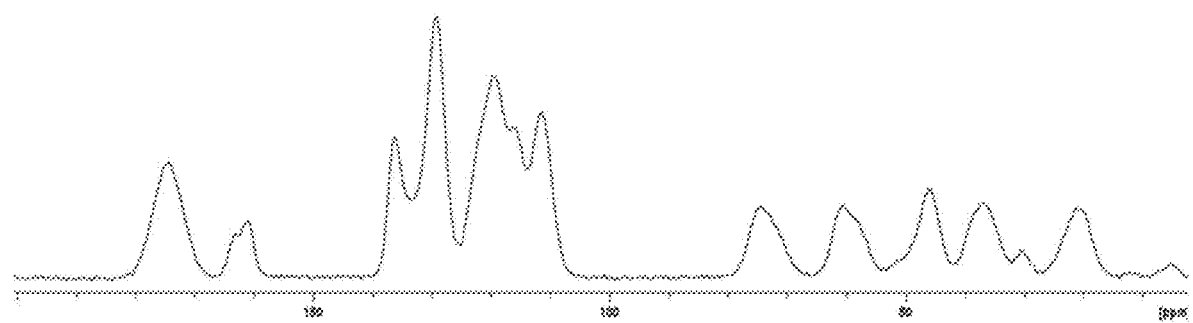
FIG. 57 depicts a solid state $^{13}$C NMR spectrum for amorphous form of Compound 87.

The $^{13}$C CPMAS of the amorphous form (FIG. 57) was acquired at 275K with the following parameters: 12.5 kHz spinning; ref. adamantane 29.5 ppm. The peaks are listed in table 41 below. The carbon peaks in bold are unique to the amorphous form with respect to following forms: Form A, Hydrate Form, and IPAC Solvate.

TABLE 41

Peak list from $^{13}$C CPMAS of the Amorphous Form

| Chem Shift [ppm] | Intensity [rel] |
|---|---|
| 174.5 | 43.9 |
| 163.0 | 16.8 |
| 161.1 | 21.8 |
| 136.3 | 53.5 |
| 129.4 | 100.0 |
| 119.5 | 77.7 |
| 116.0 | 57.6 |
| 111.5 | 63.1 |
| 74.3 | 27.3 |
| 60.6 | 27.9 |
| 46.0 | 34.2 |
| 37.2 | 28.7 |
| 30.5 | 10.7 |
| 21.2 | 26.9 |

Figure 58:
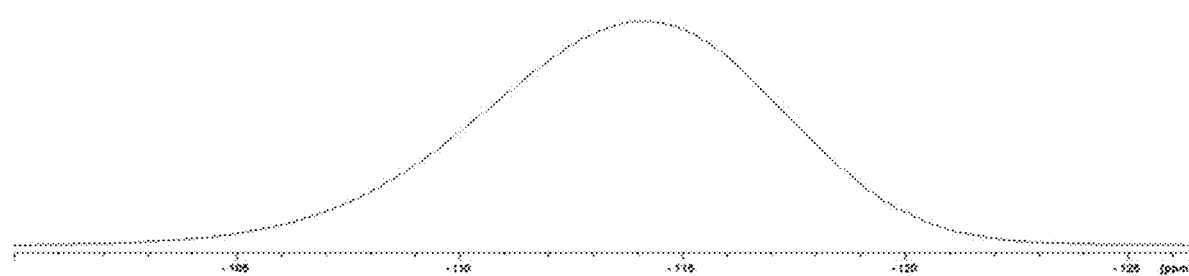
FIG. 58 depicts a $^{19}$F MAS (magnetic angle spinning) spectrum for amorphous form of Compound 87.
Figure 59:
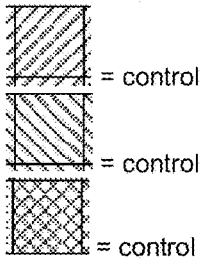
FIG. 59 depicts a plate map used in Example 3.

The $^{19}$F MAS of the amorphous form (FIG. 58) was acquired at 275K with the following parameters: 12.5 kHz spinning; ref. adamantane 29.5 ppm. The peaks are listed in table 42 below. The fluorine peaks highlighted in bold are unique for the amorphous form with respect to following forms: Form A, Hydrate Form, and IPAc Solvate.

TABLE 42

Peak list from $^{19}$F MAS of Hydrate Form C

| Chem Shift [ppm] | Intensity [rel] |
|---|---|
| −114.1 | 12.5 |

Example 3. Assays for Detecting and Measuring APOL1 Inhibitor Properties of Compounds Acute APOL1 Thallium Assay with Inducible Stable Clones of HEK 293 Cells Apolipoprotein L1 (APOL1) proteins form potassium-permeable cation pores in the plasma membrane. APOL1 risk variants (G1 and G2) induce greater potassium flux than G0 in HEK293 cells. This assay exploits the permeability of thallium (Tl+) through ligand-gated potassium channels. The dye produces a bright fluorescent signal upon binding to Tl+ conducted through potassium channels. The intensity of the Tl+ signal is proportional to the number of potassium channels in the open state. Therefore, it provides a functional indication of the potassium channel activities. During the initial dye-loading step, the Tl+ indicator dye as an acetoxymethyl (AM) ester enters the cells through passive diffusion. Cytoplasm esterases cleave the AM ester and relieve its active thallium-sensitive form. The cells are then stimulated with Tl+. The increase of fluorescence in the assay represents the influx of Tl+ into the cell specifically through the potassium channel (i.e. through APOL1 pores), providing a functional measurement of potassium channel/pore activity. The Thallium assay is conducted with cells expressing G1 APOL1.

Reagents and Materials
APOL1 Cell Line (HEK T-Rex Stable Inducible Cell Line)
    HEK T-Rex System
        Tetracycline (Tet) inducible mammalian expression system.
        Stably express the Tet repressor to regulate transcription.
        Expression under the full-length CMV promoter.
    APOL1 stable inducible cell line Clone used: G1 DC3.25
Tissue Culture Media
    Cell Culture Medium
        DMEM+10% FBS+P/S+5 µg/mL blasticidin+1 µg/mL puromycin.
        500 mL DMEM+55 mL FBS+5 mL P/S+280 µL blasticidin S HCl (10 mg/mL)+56 µL puromycin (10 mg/mL).
    Cell Assay Medium
        DMEM with 2% FBS+pen strep.
Reagents:

| | | |
|---|---|---|
| PBS | 7.4 pH no phenol red no sodium pyruvate Concentration: 1X | Gibco Cat. No. 10-010-49 |
| Trypsin | 0.25%/EDTA 2.21 mM in HBSS | Wisent, Cat. No. 325-043-EL |
| DMEM | High Glucose, no sodium pyruvate, with phenol red, with glutamine | GIBCO, Cat. No. 11960-051 |
| FBS | Tet System Approved FBS US Sourced | TakaraCat. No. 631101 |
| HEPES Buffer | 1M | Invitrogen, Cat. No. 15630-080 |
| HBSS | calcium magnesium no phenol red | Life Technologies, Cat. No. 14025-126 |
| DMSO | | |
| Penicillin Streptomycin (P/S) | Sterile filtered for cell culture Concentration: 100X | Wisent, Cat. No. 450-201-EL |
| Puromycin Dihydrochloride | Concentration: 10 mg/mL | Gibco, Cat. No. A11138-03 |
| Blasticidin S HCl | Concentration: 10 mg/mL | Gibco, Cat. No. A11139-03 |
| Ouabain | Prepare 100 mM stock in DMSO aliquot and store at −20° C. | Tocris, Cat. No. 1076 |
| Probenicid | Resuspend in 1 mL HBSS 20 mM HEPES | Invitrogen, Cat. No. P36400 |
| Tetracyclin | Prepare 1 mg/mL stock in H$_2$O aliquot and store at −20° C. | Sigma-Aldrich, Cat. No. T7660 |
| Corning ® BioCoat ™ Poly-D-Lysine 384-well black, transparent, flat bottom tissue culture plates | | Cat. No. 354663, Lot No. 31616006 |
| Corning ® 384-well microplate, clear polypropylene, round bottom, sterile | | Costar Cat. No.: 3656 |

| | |
|---|---|
| FLIPR pipette tips, 384-well | Molecular Devices, Cat. No. 9000-0764 |
| FLIPR Potassium Assay Kit | Molecular Devices, Cat. No. R8223 |

Instruments and Equipment
　Nuaire cell culture hood, Cat. No. 540-600
　37° C./5% CO incubator link to robotic arm, Liconic: STX110
　Molecular Devices FLIPR$^{Tetra}$ High throughput cellular screening system, Cat. No. FT0324, Molecular Devices
　ThermoFisher MultiDrop 384, Cat. No. 5840300
　Biotek Microfill, Cat. No. ASF1000A-4145
　BioRad TC10 cell counter, Cat. No. 145-0010
Assay Procedures
Cells Scaled Up from Frozen Vials
　APOL1 G1 3.25 (HEK293 T-Rex) frozen vials: 5 million cells per vial
　Step 1, Day 1: Defrost frozen vial into T-225.
　Step 2, Day 5: (when 85% confluent): Split one T-225 at $3 \times 10^6$ cells per flask.
　Step 3, Day 8: Splits cells to set up for the assay plates as described below.
Cell Culture
　T-Rex APOL1 HEK cells are split twice per week to keep the confluence state below 85% of the culture flask surface area. Cells can be kept until passage 25.
　Cell Culture Medium
　　DMEM high glucose+10% FBS, +P/S, +5 µg/mL blasticidin, +1 µg/mL puromycin.
　　500 mL DMEM, +55 mL FBS, +5 mL P/S, +280 µL blasticidin 10 mg/mL, +56 µL Puromycin 10 mg/mL.
　Assay Media
　　Opti-MEM reduced serum medium from Invitrogen.
Day 1
Preparation of Cell Assay Plates
　Culture medium is removed from the xcm$^2$ T-flask by aspiration.
　The cell monolayer is rinsed with PBS 1× at room temperature. PBS is removed by aspiration.
　Cells are trypsinized using Trypsin.
　The flasks are incubated at room temperature for 2-3 minutes.
　Complete DMEM medium is then added. Cell suspension is then transferred to a 50 mL Falcon polypropylene tube.
　Cells are then counted using a Biorad TC10 cell counter and the required amount of cells are centrifuged at 1200 RPM for 5 minutes. Required amount is $1.3 \times 10^6$ cells/mL APOL1 T-Rex HEK cells.
　The pellet is suspended in the assay medium.
　Using the MultiDrop, add 20 µL to each well (corresponds to 26000 cells total per well) of a 384-well black, transparent, flat bottom Poly-D coated plate.
　Tetracycline as prepared in the following section is added to the cells before plating to induce APOL1 expression. Plates are left at room temperature for 20 to 30 minutes before incubation at 37° C. and 5% CO$_2$.
Preparation of Tetracyclin
　Tetracyclin stock is prepared at 1 mg/mL in H$_2$O, aliquoted and stored at −20° C.
　On the day the cells are plated for the assay, the tetracycline working concentration is prepared as follows:
　Predilute tetracyclin stock at 100× by transferring 50 µL stock in 5 mL assay media to give 10 µg/mL intermediate stock.
　Prepare tetracycline at 4× if added with Biomek to the cell plates or added directly on cells to give a 1× tetracycline concentration according to Table 43 below.

TABLE 43

Concentration of Tetracycline for cell plate.

| Clones | 1X Tet ng/mL | 5X Tet ng/mL | mL predilution | mL diluted cell suspension |
|---|---|---|---|---|
| G1 DC3.25 | 15 | 75 | 0.3 | 39.7 |

Day 2
Preparation of Thallium Loading Dye and Cells Loading FLIPR@ Potassium Assay Kit R8223
　Preparation of the Loading Buffer:
　　1. Remove one vial each of Component A (Dye) and Component C (Pluronic) from the freezer, and then equilibrate to room temperature.
　　2. For the Bulk Kit, prepare 200 mL of 20 mM HEPES plus 1×HBSS, pH 7.4 as Component B.
　　3. Dissolve the contents of the Component C vial in DMSO, and the mix thoroughly by vortexing.
　　4. Combine the vial of Component A (dye) with 10 mL of the Component B buffer (HBSS 20 mM HEPES).
　　5. Combine the Component C solution from step 3 to the Component A solution from step 4, and then mix by vortexing for 1 to 2 minutes until the contents of the vial are dissolved. Note: It is important that the contents are completely dissolved to ensure reproducibility between experiments.
　　6. For the Bulk Kit only, combine the solution from step 5 with the remaining 190 mL of the prepared Component B buffer, and then mix thoroughly.
　For each 10 mL of prepared dye add: 200 µL Probenecid (equals 2.5 mM final in assay plate) and 20 µL of 100 mM ouabain (equals 100 µM in assay plate).
　Add 25 µL loading dye to each well of assay plate containing 25 µL. Link to robotic arm (with multidrop or microfill).
　Incubate for 30 minutes at room temperature.
Preparation of Drug Plates and Transfer of Compounds to Assay Plates
　The compounds are plated in assay ready plates (ARP). The plate layout in FIG. 1 shows the plate map for ARPs for dose response.
　The compounds are hydrated with 20 µL HBSS with 20 mM HEPES.
　The compounds are transferred to the assay plates 30 minutes after loading thallium sensitive dye as described in Preparation of Thallium Loading Dye described above.
　The compounds are diluted by a 1:500 ratio for the final concentration.
　The compound transfer is done using FLIPR. Mix: 3 strokes, 10 µl with speed @ 5 µl/sec, Height 20 µl. Aspirate: 10 µl with speed @ 5 µl/sec, Height 5 µl; Tip up speed of 20 mm/sec. Dispense: 10 µl with speed @ 5 µl/sec, Height 10 µl; liquid removal speed of 20 mm/sec.
　Incubate for 30 minutes at room temperature.

Preparation of the Thallium Sulfate Source Plate
  Prepare a 5× thallium sulfate solution in 1× chloride buffer.
  For 5 mL of 5× thallium source plate: 1 mL of Chloride Free 5×, 0.5 mL Tl$_2$SO$_4$ 50 mM (2 mM equivalent final), 3.5 mL H2O.
  Dispense in 384-well Corning PP round-bottom plates (Costar, Cat. No. 3656).
  Need 12.5 μL per well for each assay plate+dead volume. Spin briefly.
Start Assay on FLIPR 384-Head
Parameters
  Excitation: 470-495 nm; Emission: 515-575 nm.
  Addition volume: 12.5 μL.
  Aspirate: 12.5 μl with speed @ 20 μl/sec, Height 5 μl; Tip up speed of 20 mm/sec
  Dispense: 12.5 μl with speed @ 20 μl/sec, Height 40 μl; liquid removal speed of 20 mm/sec.
  Read baseline for 10 seconds; transfer 12.5 μL to assay plate.
  Read every second for 60 seconds.
  Keep tips on head for thallium addition.
Data Analysis
  Stat file: Export slope (rate) between 17 and 32 seconds.
  Analyze using (No Tet DMSO) and (Tet DMSO) controls (set up Stimulation and neutral controls, respectively).
  Calculate percent inhibition thallium rate versus controls.
  Data is reported as IC$_{50}$ (half maximum inhibitory concentration) and maximum percent inhibition.

*Trypanosoma brucei* Brucei Lysis Assay Using APOL1 Recombinant Protein

*Trypanosoma brucei* brucei is a blood stream parasite to which human, gorillas and baboon are immune due to the presence of the APOL1 protein in their HDL particles. The protein is uptaken by the parasite via the TbHpHb receptor located in its flagellar pocket and is bonded by the Hpr protein contained in the HDL particles which triggers the receptor endocytosis by the parasite.

Following endocytosis, the formed vesicle containing the HDL particle matures from early to late endosome, and subsequently to lysosome. The concomitant pH change in the lumen of the vesicle triggers the insertion of the APOL1 protein into the membrane of the late endosome/lysosome and hereby triggers lysosomal membrane premeabilisation and as a further downstream event, trypanosome lysis. *Trypanosoma brucei* brucei is sensitive to lysis by all three APOL1 variants (G0, G1, and G2).

The *Trypanosoma brucei* brucei lysis assay is a lysis assay of the parasite using recombinant APOL1 protein variant followed by a fluorescent detection method of viability by the addition of AlamarBlue reagent to the assay well, a general metabolic redox indicator (AlamarBlue assay).

Briefly, the AlamarBlue active compound, the resazurin, a blue, water soluble, non-toxic and cell permeable molecule, which can be followed by absorbance, is reduced by various metabolic pathways into resorufin, a red compound which can be followed by either absorbance or fluorescence. The assay allows the calculation of the percent viability (percent of living Trypanosomes remaining in each well) at the end of a lysis relative to the untreated condition by interpolation of fluorescent values (FLU) on a standard curve with a known amount of seeded trypanosome/well.

Reagents and Materials
*Trypanosoma brucei* brucei (ATCC, Cat. No. PRA-382)
  Lister 427 VSG 221 bloodstream form.
Thaw/Expansion Media (ATCC Medium 2834 Modified HMI-9 Medium)

| IMDM | 250 mL | 76.3% |
| FBS | 25 mL | 7.63% |
| Serum Plus | 25 mL | 7.63% |
| HMI-9 | 25 mL | 7.63% |
| Hypoxanthine | 2.5 mL | 0.763% |
| | 327.5 mL total | |

Assay Media (No Phenol Red/No FBS): Make on Day of Use

| IMDM No Phenol Red | 250 mL | 82.6% |
| Serum Plus | 25 mL | 8.26% |
| HMI-9 | 25 mL | 8.26% |
| Hypoxanthine | 2.5 mL | 0.826% |
| | 302.5 mL total | |

HMI-9 (10×)

| Bathocuproine disulfonic acid | 280 mg |
| Cysteine | 1820 mg |
| Sodium pyruvate (100×) | 100 mL |
| Uracil | 100 mg |
| Cytosine | 100 mg |
| 2-mercaptoethanol | 140 μL |
| Water | 900 mL |
| | 1000 mL total |

Hypoxanthine Stock (100×)-9 (10×)

| Sodium Hydroxide | 0.8 g |
| Hypoxanthine | 2.72 g |
| Water | 200 mL |
| | 200 mL total |

Media Reagents

| IMDM | Phenol Red sodium pyruvate L-glutamine 25 mM HEPES | Life Technologies, Cat. No. 12440 |
| IMDM | NO Phenol Red sodium pyruvate L-glutamine 25 mM HEPES | Life Technologies, Cat. No. 21056 |
| FBS | Heat inactivated | Sigma-Aldrich, Cat. No. F8317-500 mL |
| Serum Plus | medium supplement | Sigma-Aldrich, Cat. No. 14008C |
| Bathocuproine disulfonic acid | | Sigma-Aldrich, Cat. No. B1125-1G |
| Cysteine | | Sigma-Aldrich, Cat. No. C7352-25G |
| Sodium Pyruvate Solution 100× | | Sigma-Aldrich, Cat. No. S8636-100 ml |
| Uracil | | Sigma-Aldrich, Cat. No. U1128-25G |
| Cytosine | | Sigma-Aldrich, Cat. No. C3506-1G |
| 2-mercaptoethanol | | Sigma-Aldrich, Cat. No. M3148-25 ml |
| Hypoxanthine | | Sigma, Cat. No. H9636 |
| Sodium hydroxide | | Sigma-Aldrich, Cat. No. S8045-500G |

Materials

| T75/T175 | Nunc ™ Non-Treated flask | T75 Thermo-Fisher Cat. No. 156800 |
| --- | --- | --- |
| | Non-TC treated Vented/White lids with filter | T175 Thermo-Fisher Cat. No. 159926 |
| Assay Plates | 384 well black clear bottom Non-sterile Non-TC treated | Corning ® Cat. No. 3762 |
| Polypropylene storage plates | | Corning ® Cat. No. 3656 |
| Plate Lids | Clear universal sterile lids | Thermo-Fisher Cat. No. 250002 |
| Bravo Tips | 30 µL tips for 384 well | Axygen Cat. No. VT-384-31UL-R-S |
| E1-Clip Tip pipette 12 channel adjustable 2-125 µL | | Thermo-Fisher Cat. No. 4672070BT |
| Tips | 125 µL E1-Clip steril filter | Thermo-Fisher Cat. No. 94420153 |
| Tips | 125 µL E1-Clip steril (non-filter) | Thermo-Fisher Cat. No. 94410153 |

Equipment
E1-Clip Tip pipette 12 channel adjustable 2-125 µL, Cat. No. 4672070BT
ThermoFisher MultiDrop 384, Cat. No. 5840300
Multidrop
Agilent Bravo, Cat. No. G5409A
Bravo
SpectraMax M5

Assay Ready Plates (ARPs)
ARPs comes in two formats:
10 mM final top concentration with a 2.5 fold dilution down.
5 mM final top concentration with a 3 fold dilution down.
Both have a 10 point Dose response.
0.1% DMSO final in the Black Assay Plate.
Compounds are diluted 1000 fold in the Black Assay Plate.
Each plate is designed for 14 compounds in duplicate.
In the final Black Assay Plate:
Column 1: Media only (no APOL1) (100% viable)
Column 2-23: 0.05 µg/mL APOL1 (~$EC_{90}$) (10% viable with APOL1)
Column 24: 0.1 µg/mL APOL1 ($EC_{100}$) (Approx. 0% viable)

Assay Procedures

*Trypanosoma brucei* Brucei Culture

Protocol A
Step 1, Day 1
That the cells at 35° C. for no more than 2 minutes.
Resuspend one vial gently in 20 mL pre-warmed media and incubate in a T75 flask at 37° C. and 5% $CO_2$.
Do not remove the cryoprotective agent.
Step 2, Day 4
Centrifuge at 800×g for 5 minutes at room temperature.
Resuspend in 1 mL media.
Make a 1:25 fold dilution (10 µL/240 µL media).
Count on a hemocytometer (after adding parasites).
Let sit for 1-2 minutes for the parasites to settle.
Count should be approximately 100 viable motile parasites/16 grid or approximately $25 \times 10^6$ parasites/flask.
Passage the parasites by adding $1 \times 10^6$ parasites/T75 flask in 20 mL media.
Passage the parasites by adding $2.33 \times 10^6$ parasites/T175 flask in 46.6 mL media.
For every T75 flask should make enough for approximately 1.5×384 well assay plates.
For every T175 flask should make enough for approximately 3.8×384 well assay plates.
Step 3, Day 6
Centrifuge at 800×g for 5 minutes.
Resuspend in 3 mL assay media (No phenol red, no FBS) per 75 starting flask.
Resuspend in 7 mL assay media (No phenol red, no FBS) per 175 flask
Make a 1:25 fold dilution.
Count by hemocytometer.
Every T75 flask set up should have approximately $75 \times 10^6$ parasites/flask (verify doubling time=8.7 hrs±1 hr).
Every T175 flask set up should have approximately $175 \times 10^6$ parasites/flask (verify doubling time=8.7 hrs±1 hr).
Require $46 \times 10^6$ parasites per 384 well plate (at 120,000 parasites per well).

Protocol B
Step 1, Day 1
Thaw the cells at 35° C. for not more than 2 minutes.
Resuspend one vial gently in 20 mL of pre-warmed mediate and incubate in a T75 flask at 37° C. and 5% $CO_2$.
Do not remove the cryoprotective agent.
Step 2, Day 2
Centrifuge at 800×g for 5 minutes at room temperature.
Resuspend in 1 mL media.
Make a 1:25 fold dilution (10 µL/240 µL media).
Let sit for 1-2 minutes for the parasites to settle.
Count should be approximately 100 viable motile parasites/16 grid or approximately $8 \times 10^6$ parasites per flask.
Passage the parasites by adding $1.25 \times 10^6$ parasites per T75 flask in 20 mL media.
For every T75 flask set up should have approximately 1.5×384 well assay plates.
For every T175 flask set up should have approximately 3.8×384 well assay plates.
Step 3, Day 5
Centrifuge at 800×g for 5 minutes.
Resuspend in 3 mL assay media (No phenol red, no FBS) per T75 starting flask.
Resuspend in 7 mL assay media (No phenol red, no FBS) per T175 starting flask.
Make a 1:25 fold dilution.
Count by hemocytometer.
Every T75 flask should have approximately $75 \times 10^6$ parasites per flask (verify doubling time: 7.7 hrs±1 hr).
Every T175 flask should have approximately $175 \times 10^6$ parasites per flask (verify doubling time: 7.7 hrs±1 hr).

Lysis Assay Setup

APOL1 G1 Protein
  Remove an aliquot of the 1.2 mg/mL APOL1 protein stock from −70° C.
  Determine amount required for the experiment:
    Need 11.5 mL of 0.1 µg/mL APOL1 per 384 well plate.
    Need 0.5 mL of 0.2 µg/mL APOL1 per 384 well plate for control.
  Make initial 1:10 dilution (10 µL/90 µL) into Assay media (now at 120 µg/mL).
    Using APOL1 at a final concentration of 0.05 µg/mL for an ~$EC_{50}$. Need to determine this value for each new lot of protein used.
    Adding 30 mL/well of 2×APOL1 concentration of 0.1 µg/mL.
      Solution A: Measure 8.33 µL (120 µg/mL) in 10 mL for a 0.1 µg/mL 2× stock.
      Solution B: Measure 16.67 µL (120 µg/mL) in 10 mL for a 0.2 µg/mL 2× stock control.
Multidrop
  Black Assay Plate (384 well black well clear bottom, Cat. No. 3762).
    Column 1: Dispense 30 µL/well of Assay media (no APOL1).
    Column 2-23: Dispense 30 µL/well of Solution A (0.1 µg/mL APOL1).
    Column 24: Dispense 30 µL/well of Solution B (0.2 µg/mL APOL1).
  Storage Plate (Polypropylene storage plate, Corning® Cat. No. 3656).
    Column 1-24: Dispense 80 µL Assay media (no APOL1) per well (30 mL media/plate).
Bravo: Compound Transfer
  Place the storage plate, the Assay Ready Plate (ARP), and Black Assay Plate on the deck.
    Transfer 20 µL from the storage plate to the ARP and mix.
    Transfer 6 µL from the ARP to the Black Assay Plate and mix.
    Black Assay Plates are now ready for Trypanosome addition.
Trypanosome Addition:
  Once the Black Assay Plates have compounds added, begin harvesting the Trypanosomes as described in Step 3 of the *Trypanosoma brucei* brucei Culture section.
    Count the Trypanosomes and prepare at $5\times10^6$/mL in Assay media (No Phenol red and no FBS).
      Requires 9.2 mL of $5\times10^6$ trypanosomes/mL for each 384 well plate ($46\times10^6$/plate).
    Add 24 µL of $5\times10^6$ trypanosomes mix to each well of a 384 well plate using the E1-Clip multichannel 12 channel 2-125 µL adjustable pipette.
    Once addition is complete, tap plate on the surface to ensure liquid is within each well.
    Place plates on the plate shaker for approximately 10 seconds and shake to ensure even distribution and that no drops are left on any edges.
    Place in incubator overnight (16 hrs) at 37° C. and 5% $CO_2$.
  Each well should include 60 µL:
    30 µL 2×APOL1 media, 6 µL of 10× compounds, and 24 µL of trypanosome solution.

AlamarBlue Addition
  After 16 hr overnight in incubator, remove required amount of AlamarBlue (2.3 mL/plate) from the bottle stored in refrigerator, and warm up briefly in a 37° C. water bath.
  Add 6 µL/well using the E1-Clip Multichannel 12 channel 2-125 µL adjustable pipette.
  Protect from light and incubate the plate at 37° C. and 5% $CO_2$ for 2.5 hrs.
  Read on SpectraMax (Softmax Pro 6.4 software, excitation: 555 nm, emission: 585 nm)

Potency Data for Compounds 1 to 135

The compounds of formula (I) are useful as inhibitors of APOL1 activity. Table 9 below illustrates the $IC_{50}$ of the compounds 1 to 135 using procedures described above (assays described above in Example 2A and 2B). In Table 44 below, the following meanings apply. For $IC_{50}$: "+++" means <0.25 µM; "++" means between 0.25 µM and 1.0 µM; "+" means greater than 1.0 µM. N.D.=Not determined.

TABLE 44

Potency data for Compounds 1 to 135

| Compound No. | Thallium Assay ($IC_{50}$) | Trypanosoma Assay ($IC_{50}$) |
|---|---|---|
| 1 | +++ | +++ |
| 2 | +++ | +++ |
| 3 | +++ | +++ |
| 4 | + | N.D. |
| 5 | ++ | ++ |
| 6 | ++ | ++ |
| 7 | + | + |
| 8 | + | + |
| 9 | + | N.D. |
| 10 | + | N.D. |
| 11 | + | N.D. |
| 12 | ++ | N.D. |
| 13 | ++ | +++ |
| 14 | ++ | +++ |
| 15 | ++ | N.D. |
| 16 | ++ | ++ |
| 17 | + | N.D. |
| 18 | N.D. | N.D. |
| 19 | N.D. | N.D. |
| 20 | +++ | +++ |
| 21 | +++ | +++ |
| 22 | +++ | N.D. |
| 23 | +++ | N.D. |
| 24 | +++ | N.D. |
| 25 | +++ | N.D. |
| 26 | +++ | +++ |
| 27 | +++ | +++ |
| 28 | + | + |
| 29 | +++ | +++ |
| 30 | +++ | +++ |
| 31 | ++ | N.D. |
| 32 | +++ | N.D. |
| 33 | ++ | N.D. |
| 34 | +++ | N.D. |
| 35 | +++ | N.D. |
| 36 | +++ | +++ |
| 37 | +++ | +++ |
| 38 | +++ | N.D. |
| 39 | ++ | N.D. |
| 40 | +++ | +++ |
| 41 | ++ | N.D. |
| 42 | +++ | +++ |
| 43 | +++ | +++ |
| 44 | +++ | +++ |
| 45 | +++ | N.D. |
| 46 | +++ | +++ |
| 47 | +++ | +++ |
| 48 | +++ | +++ |
| 49 | ++ | ++ |
| 50 | ++ | ++ |

TABLE 44-continued

Potency data for Compounds 1 to 135

| Compound No. | Thallium Assay (IC$_{50}$) | Trypanosoma Assay (IC$_{50}$) |
|---|---|---|
| 51 | +++ | +++ |
| 52 | +++ | +++ |
| 53 | + | N.D. |
| 54 | ++ | ++ |
| 55 | + | + |
| 56 | + | N.D. |
| 57 | ++ | N.D. |
| 58 | +++ | +++ |
| 59 | +++ | +++ |
| 60 | ++ | N.D. |
| 61 | +++ | +++ |
| 62 | +++ | N.D. |
| 63 | +++ | N.D. |
| 64 | + | N.D. |
| 65 | ++ | N.D. |
| 66 | ++ | N.D. |
| 67 | ++ | N.D. |
| 68 | ++ | N.D. |
| 69 | +++ | N.D. |
| 70 | +++ | +++ |
| 71 | +++ | N.D. |
| 72 | +++ | +++ |
| 73 | +++ | +++ |
| 74 | +++ | N.D. |
| 75 | +++ | +++ |
| 76 | +++ | +++ |
| 77 | + | N.D. |
| 78 | + | + |
| 79 | +++ | N.D. |
| 80 | +++ | +++ |
| 81 | +++ | N.D. |
| 82 | +++ | +++ |
| 83 | +++ | N.D. |
| 84 | +++ | N.D. |
| 85 | +++ | +++ |
| 86 | +++ | +++ |
| 87 | +++ | +++ |
| 88 | +++ | +++ |
| 89 | +++ | +++ |
| 90 | + | N.D. |
| 91 | ++ | N.D. |
| 92 | + | N.D. |
| 93 | + | N.D. |
| 94 | + | N.D. |
| 95 | +++ | +++ |
| 96 | + | N.D. |
| 97 | + | N.D. |
| 98 | +++ | +++ |
| 99 | +++ | +++ |
| 100 | +++ | N.D. |
| 101 | +++ | +++ |
| 102 | +++ | +++ |
| 103 | +++ | +++ |
| 104 | +++ | +++ |
| 105 | +++ | +++ |
| 106 | +++ | N.D. |
| 107 | +++ | ++ |
| 108 | +++ | +++ |
| 109 | +++ | +++ |
| 110 | + | N.D. |
| 111 | +++ | N.D. |
| 112 | ++ | + |
| 113 | +++ | N.D. |
| 114 | +++ | ++ |
| 116 | +++ | +++ |
| 117 | +++ | N.D. |
| 118 | +++ | +++ |
| 119 | ++ | N.D. |
| 120 | +++ | +++ |
| 121 | +++ | +++ |
| 122 | +++ | +++ |
| 123 | +++ | +++ |
| 124 | +++ | +++ |
| 125 | +++ | +++ |
| 126 | +++ | +++ |
| 127 | ++ | ++ |
| 128 | +++ | +++ |
| 129 | +++ | +++ |
| 130 | +++ | N.D. |
| 131 | +++ | +++ |
| 132 | +++ | N.D. |
| 133 | ++ | N.D. |
| 134 | + | N.D. |
| 135 | + | N.D. |

Other Embodiments

This disclosure provides merely exemplary embodiments of the disclosure. One skilled in the art will readily recognize from the disclosure and claims, that various changes, modifications and variations can be made therein without departing from the spirit and scope of the disclosure as defined in the following claims.

The invention claimed is:

1. Form A of Compound 2:

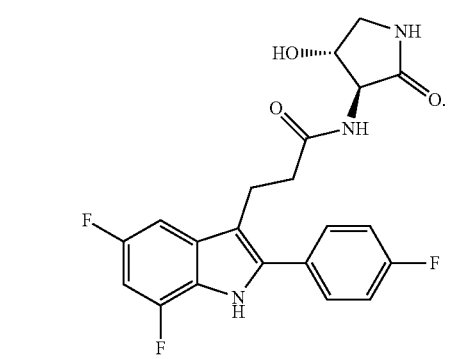

(2)

2. Form A of Compound 2 according to claim 1, characterized by an X-ray powder diffractogram substantially similar to that in FIG. 1.

3. Form A of Compound 2 according to claim 1, characterized by an X-ray powder diffractogram having a signal at at least two two-theta values chosen from 9.5±0.2, 13.2±0.2, 14.4±0.2, 19.2±0.2, 19.5±0.2, 19.8±0.2, 26.3±0.2, 26.7±0.2, and 28.6±0.2.

4. Form A of Compound 2 according to claim 1, characterized by a $^{13}$C NMR spectrum having a signal at at least three ppm values chosen from 178.7±0.2 ppm, 154.4±0.2 ppm, 127.8±0.2 ppm, 125.2±0.2 ppm, 102.0±0.2 ppm, 59.3±0.2 ppm, 38.9±0.2 ppm, and 24.4±0.2 ppm.

5. Form A of Compound 2 according to claim 1, characterized by a $^{19}$F NMR spectrum having a signal at at least one ppm value chosen from −116.0±0.2 ppm, −119.7±0.2 ppm, and −138.1±0.2 ppm.

6. A composition comprising Form A of Compound 2 according to claim 1.

7. Hydrate Form A of Compound 2:

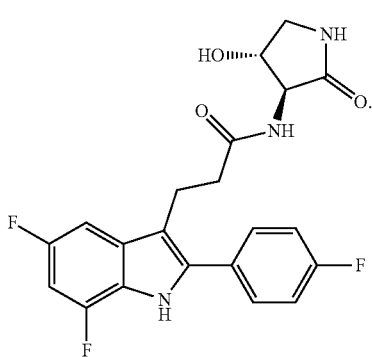

(2)

8. Hydrate Form A of Compound 2 according to claim 7, characterized by an X-ray powder diffractogram substantially similar to that in FIG. 7.

9. Hydrate Form A of Compound 2 according to claim 7, characterized by an X-ray powder diffractogram having a signal at at least two two-theta values chosen from 12.2±0.2, 19.0±0.2, 19.1±0.2, 19.6±0.2, 20.2±0.2, 22.7±0.2, 24.2±0.2, 25.4±0.2, and 25.5±0.2.

10. Hydrate Form A of Compound 2 according to claim 7, characterized by a $^{13}$C NMR spectrum having a signal at at least three ppm values chosen from 177.5±0.2 ppm, 157.7±0.2 ppm, 128.9±0.2 ppm, 95.4±0.2 ppm, 36.9±0.2 ppm, 23.0±0.2 ppm, and 22.3±0.2 ppm.

11. Hydrate Form A of Compound 2 according to claim 7, characterized by a $^{19}$F NMR spectrum having a signal at at least one ppm value chosen from −113.8±0.2 ppm, −125.8±0.2 ppm, and −132.8±0.2 ppm.

12. A composition comprising Hydrate Form A according to claim 7.

13. Hydrate Form B of Compound 2:

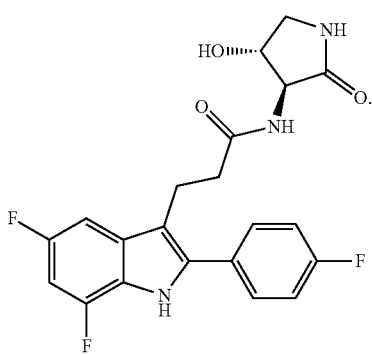

(2)

14. Hydrate Form B of Compound 2 according to claim 13, characterized by an X-ray powder diffractogram substantially similar to that in FIG. 12.

15. Hydrate Form B of Compound 2 according to claim 13, characterized by an X-ray powder diffractogram having a signal at at least two two-theta values chosen from 3.8±0.2, 9.0±0.2, 9.3±0.2, 18.7±0.2, 19.1±0.2, 20.8±0.2, 21.1±0.2, 24.6±0.2, and 26.8±0.2.

16. Hydrate Form B of Compound 2 according to claim 13, characterized by a $^{19}$F NMR spectrum having a signal at at least one ppm value chosen from −117.0±0.2 ppm, −119.1±0.2 ppm, and −137.7±0.2 ppm.

17. A composition comprising Hydrate Form B of Compound 2 according to claim 13.

18. Hydrate Form C of Compound 2:

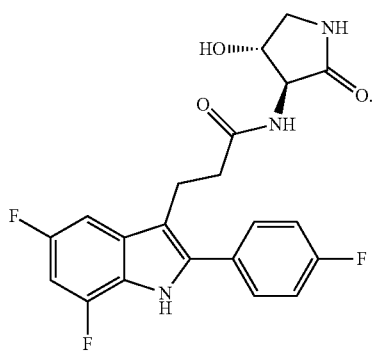

(2)

19. Hydrate Form C of Compound 2 according to claim 18, characterized by an X-ray powder diffractogram substantially similar to that in FIG. 14.

20. Hydrate Form C of Compound 2 according to claim 18, characterized by an X-ray powder diffractogram having a signal at at least two two-theta values chosen from 3.7±0.2, 10.4±0.2, 10.7±0.2, 13.2±0.2, 14.6±0.2, 15.7±0.2, 18.3±0.2, 21.8±0.2, and 24.9±0.2.

21. A composition comprising Hydrate Form C of Compound 2 according to claim 18.

22. Hydrate Form C of Compound 2 according to claim 18, characterized by a $^{13}$C NMR spectrum having a signal at at least three ppm values chosen from 178.2±0.2 ppm, 127.2±0.2 ppm, 116.9±0.2 ppm, 71.6±0.2 ppm, 57.6±0.2 ppm, 49.6±0.2 ppm, 35.5±0.2 ppm, and 20.0±0.2 ppm.

23. Hydrate Form C of Compound 2 according to claim 18, characterized by a $^{19}$F NMR spectrum having a signal at at least one ppm value chosen from −109.9±0.2 ppm, −111.5±0.2 ppm, −113.0±0.2, −120.9±0.2, −121.8±0.2 and −123.4±0.2 ppm.

24. Hydrate Form D of Compound 2:

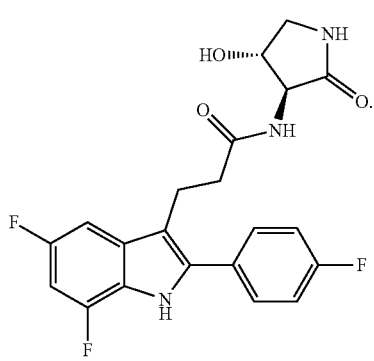

(2)

25. Hydrate Form D of Compound 2 according to claim 24, characterized by an X-ray powder diffractogram substantially similar to that in FIG. 19.

26. Hydrate Form D of Compound 2 according to claim 24, characterized by an X-ray powder diffractogram having a signal at at least two two-theta values chosen from 4.1±0.2, 5.0±0.2, 7.7±0.2, 8.2±0.2, and 15.2±0.2.

27. A composition comprising Hydrate Form D of Compound 2 according to claim 24.

28. Hydrate Form E of Compound 2:

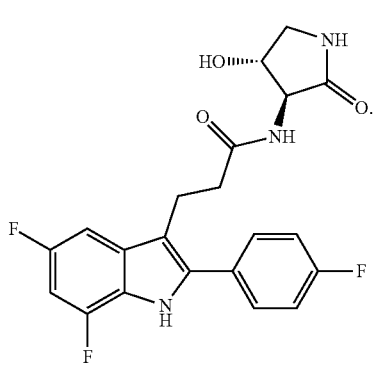
(2)

29. Hydrate Form E of Compound 2 according to claim 28, characterized by an X-ray powder diffractogram substantially similar to that in FIG. 22.

30. Hydrate Form E of Compound 2 according to claim 28, characterized by an X-ray powder diffractogram having a signal at at least two two-theta values chosen from 6.5±0.2, 7.7±0.2, 11.4±0.2, 14.3±0.2, and 18.9±0.2.

31. A composition comprising Hydrate Form E of Compound 2 according to claim 28.

32. Hydrate Form F of Compound 2:

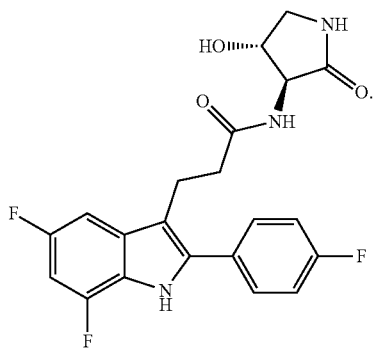
(2)

33. Hydrate Form F of Compound 2 according to claim 32, characterized by an X-ray powder diffractogram substantially similar to that in FIG. 25.

34. Hydrate Form F of Compound 2 according to claim 32, characterized by an X-ray powder diffractogram having a signal at at least two two-theta values chosen from 3.8±0.2, 7.6±0.2, and 11.4±0.2.

35. A composition comprising Hydrate Form F of Compound 2 according to claim 32.

36. MTBE Solvate Form of Compound 2:

(2)

37. MTBE Solvate Form of Compound 2 according to claim 36, characterized by an X-ray powder diffractogram substantially similar to that in FIG. 28.

38. MTBE Solvate Form of Compound 2 according to claim 36, characterized by an X-ray powder diffractogram having a signal at at least two two-theta values chosen from 6.0±0.2, 6.8±0.2, 8.4±0.2, 18.0±0.2, 19.4±0.2, and 20.2±0.2.

39. A composition comprising MTBE Solvate Form of Compound 2 according to claim 36.

40. DMF Solvate Form of Compound 2:

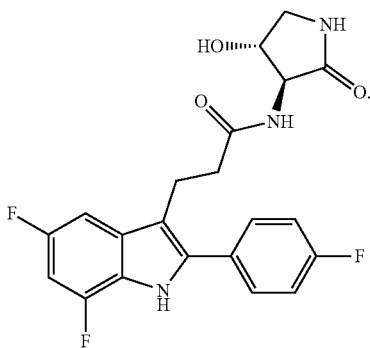
(2)

41. DMF Solvate Form of Compound 2 according to claim 40, characterized by an X-ray powder diffractogram having a signal at at least two two-theta values chosen from 5.6±0.2, 9.3±0.2, 15.3±0.2, 18.0±0.2, and 20.1±0.2.

42. DMF Solvate Form of Compound 2 according to claim 40, characterized by an X-ray powder diffractogram substantially similar to that in FIG. 31.

43. A composition comprising DMF Solvate Form of Compound 2 according to claim 40.

44. Amorphous Form of Compound 2:

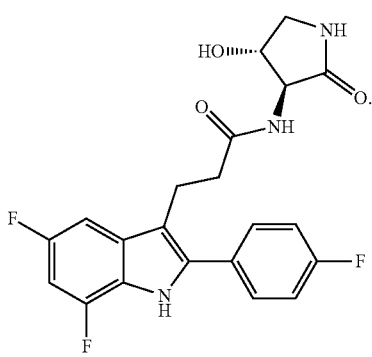

(2)

45. Amorphous Form of Compound 2 according to claim 44, characterized by an X-ray powder diffractogram substantially similar to that in FIG. 34.

46. Amorphous form of Compound 2 according to claim 44, characterized by a $^{13}$C NMR spectrum having a signal at at least three ppm values chosen from 174.7±0.2 ppm, 161.3±0.2 ppm, 130.2±0.2 ppm, 120.9±0.2 ppm, 74.7±0.2 ppm, and 20.5±0.2 ppm.

47. Amorphous form of Compound 2 according to claim 44, characterized by a $^{19}$F NMR spectrum having a signal at at least one ppm value chosen from −122.4±0.2 ppm and −131.1±0.2 ppm.

48. A method of treating focal segmental glomerulosclerosis and/or non-diabetic kidney disease comprising administering to a patient in need thereof at least one entity according to any one of claims 1, 7, 13, 18, 24, 24, 28, 36, 40, or 44.

49. A method of inhibiting APOL1 activity comprising contacting said APOL1 with at least one entity according to any one of claims 1, 7, 13, 18, 24, 28, 32, 36, 40, or 44.

50. At least one entity A compound chosen from compounds of Formula (I):

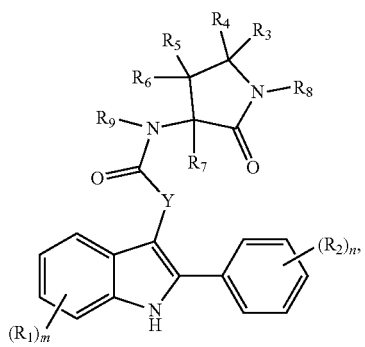

(I)

deuterated derivatives thereof, pharmaceutically acceptable salts of those compounds and deuterated derivatives, and solvates of any of the foregoing, wherein:

(i) each $R_1$ is independently chosen from
halogen groups,
hydroxy,
cyano,
$C_1$-$C_4$ linear, $C_3$-$C_4$ branched, and $C_3$-$C_4$ cyclic alkyl groups,
$C_2$-$C_4$ linear, $C_3$-$C_4$ branched, and $C_3$-$C_4$ cyclic alkenyl groups,
$C_1$-$C_4$ linear, $C_3$-$C_4$ branched, and $C_3$-$C_4$ cyclic hydroxyalkyl groups,
$C_1$-$C_4$ linear, $C_3$-$C_4$ branched, and $C_3$-$C_4$ cyclic alkoxy groups,
$C_1$-$C_4$ linear, $C_3$-$C_4$ branched, and $C_3$-$C_4$ cyclic haloalkyl groups,
$C_1$-$C_4$ linear, $C_3$-$C_4$ branched, and $C_3$-$C_4$ cyclic haloalkoxy groups,
benzyloxy groups,
3 to 6-membered heterocycloalkenyl groups,
3 to 6-membered heterocycloalkyl groups, and
5 and 6-membered heteroaryl groups;

(ii) each $R_2$ is independently chosen from
halogen groups,
cyano,
$C_1$-$C_4$ linear, $C_3$-$C_4$ branched, and $C_3$-$C_4$ cyclic alkoxy groups,
$C_1$-$C_4$ linear, $C_3$-$C_4$ branched, and $C_3$-$C_4$ cyclic haloalkoxy groups,
$C_1$-$C_4$ linear, $C_3$-$C_4$ branched, and $C_3$-$C_4$ cyclic alkyl groups, and
$C_1$-$C_4$ linear, $C_3$-$C_4$ branched, and $C_3$-$C_4$ cyclic haloalkyl groups;

(iii) m is chosen from 0 to, 1, 2, 3, and 4;

(iv) n is chosen from 0 to, 1, 2, 3, 4, and 5;

(v) Y is chosen from divalent $C_1$-$C_8$ linear, $C_3$-$C_8$ branched, and $C_3$-$C_8$ cyclic alkyl groups, wherein the divalent alkyl group is optionally substituted with at least one group chosen from
$C_1$-$C_4$ alkyl groups,
halogen groups, and
hydroxy;

(vi) each of $R_3$ and $R_4$ is independently chosen from
hydrogen,
$C_1$-$C_3$ linear, $C_3$ branched, and $C_3$ cyclic alkyl groups,
$C_1$-$C_3$ linear, $C_3$ branched, and $C_3$ cyclic hydroxyalkyl groups, and
$C_1$-$C_3$ linear, $C_3$ branched, and $C_3$ cyclic haloalkyl groups, or
each $R_3$ and $R_4$, together with the carbon atom to which they are attached, form a $C_3$-$C_6$ cycloalkyl group or carbonyl group;

(vii) each of $R_5$ and $R_6$ is independently chosen from
hydrogen,
hydroxy,
$C_1$-$C_4$ linear, $C_3$-$C_4$ branched, and $C_3$-$C_4$ cyclic alkyl groups,
$C_1$-$C_4$ linear, $C_3$-$C_4$ branched, and $C_3$-$C_4$ cyclic haloalkyl groups, and
—OC(O)$C_1$-$C_4$ linear, $C_3$-$C_4$ branched, and $C_3$-$C_4$ cyclic alkyl groups; and (viii) each of $R_7$, $R_8$, and $R_9$ is independently chosen from
hydrogen,
$C_1$-$C_4$ linear, $C_3$-$C_4$ branched, and $C_3$-$C_4$ cyclic alkyl groups, and
$C_1$-$C_4$ linear, $C_3$-$C_4$ branched, and $C_3$-$C_4$ cyclic haloalkyl groups.

51. The compound, deuterated derivative, pharmaceutically acceptable salt, or solvate according to claim 50, chosen from Compound 2:

(2)

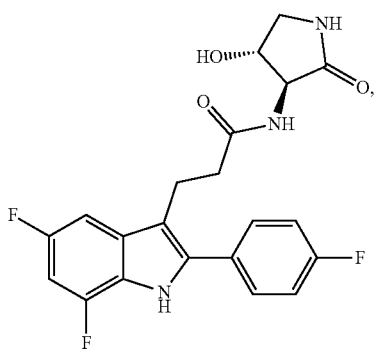

deuterated derivatives thereof, pharmaceutically acceptable salts thereof, and solvates of any of the foregoing.

52. The compound, deuterated derivative, pharmaceutically acceptable salt, or solvate according to claim 50, chosen from Compound 87:

(87)

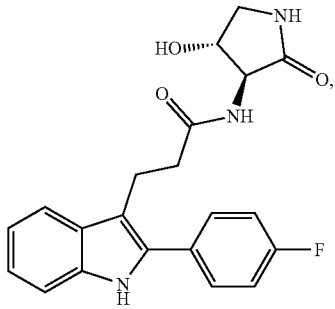

deuterated derivatives thereof, pharmaceutically acceptable salts thereof, and solvates of any of the foregoing.

53. A pharmaceutical composition comprising the compound, deuterated derivative, pharmaceutically acceptable salt, or solvate according to claim 51 or 52, and a pharmaceutically acceptable carrier.

\* \* \* \* \*